United States Patent
Kawano et al.

(10) Patent No.: US 6,924,292 B2
(45) Date of Patent: Aug. 2, 2005

(54) FUROISOQUINOLINE DERIVATIVES, PROCESS FOR PRODUCING THE SAME AND USE THEREOF

(75) Inventors: Yasuhiko Kawano, Suita (JP); Tatsumi Matsumoto, Sakai (JP); Osamu Uchikawa, Kobe (JP); Nobuhiro Fujii, Ibaraki (JP); Naoki Tarui, Nara (JP)

(73) Assignee: Takeda Chemical Industries, Ltd., Osaka (JP)

(*) Notice: Subject to any disclaimer, the term of this patent is extended or adjusted under 35 U.S.C. 154(b) by 227 days.

(21) Appl. No.: 10/239,439

(22) PCT Filed: Mar. 22, 2001

(86) PCT No.: PCT/JP01/02277
§ 371 (c)(1),
(2), (4) Date: Sep. 20, 2002

(87) PCT Pub. No.: WO01/70746
PCT Pub. Date: Sep. 27, 2001

(65) Prior Publication Data
US 2004/0092582 A1 May 13, 2004

(30) Foreign Application Priority Data
Mar. 23, 2000 (JP) .................................. 2000-087121

(51) Int. Cl.[7] .................. A61K 31/4741; C07D 491/02
(52) U.S. Cl. ..................... 514/291; 546/89; 546/22; 540/524; 544/238; 544/331; 544/405; 514/212; 514/253; 514/275
(58) Field of Search ................. 514/291, 212, 514/253, 275; 546/89, 22; 540/524; 544/238, 331, 405

(56) References Cited

U.S. PATENT DOCUMENTS

| | | | |
|---|---|---|---|
| 3,709,909 A | 1/1973 | Habicht et al. | 260/330.5 |
| 4,012,495 A | 3/1977 | Schmiechen et al. | 424/274 |
| 4,193,926 A | 3/1980 | Schmiechen et al. | 260/326.5 |
| 5,177,085 A | 1/1993 | Naef | 514/307 |
| 5,902,824 A | 5/1999 | Ulrich | 514/462 |
| 6,153,406 A | 11/2000 | Tai et al. | 435/69.3 |

FOREIGN PATENT DOCUMENTS

| | | |
|---|---|---|
| GB | 1275 164 | 5/1972 |
| JP | 01246272 | 10/1989 |

OTHER PUBLICATIONS

Yarwood, et al. "The RACK 1 Signaling Scaffold Protein Selectively Interacts with the cAMP–specific Phosphodiesterase PDE4D5 Isoform" The Journal of Biological Chemistry 274(21):14909–14917(1999).

Okumura, et al. "cDNA Cloning and Bacterial Expression of Phospholipase $A_2$ Inhibitor PLIα From The Serum of The chinese Mamuchi, Agkistrodon blomhoffii siniticus" Biochimica et Biophysica Acta 1441 51–60 (1999).

Peter Norman "PDE4 Inhibitors 1999" Exp. Opin. Ther. Patents 9(8): 1101–1118 (1999).

de Souza, et al. "An improved synthesis of 1(2H)–isoquinolinones: Synthesis and biological activity of novel 2H–pyrano[2,3–h]isoquinolin–1,10–diones and 1(2H)–furo [2,3–h] isoquinolinones" Indian Journal of Chemistry 31B:578–582(Sep. 1992).

Christensen, et al. "I,4–Cyclohexanecarboxylates: Potent and Selective Inhibitors of Phosophodiesterase 4 for the Treatment of Asthma" J. Med. Chem 41: 821–835(1998).

de Souza, et al. "Synthesis and biological activity of novel 1(2H)–furo[2,3–h]isoquinolinone, 1(2H)–pyrano[2,3–h]isoquinolinone and 2H–pyrano[2,3–h]isoquinoline–1,8–dione" Indian Journal of Chemistry 33b:552–555 (Jun. 1994).

Némoz et al. "Identification of cyclic AMP–phosphodiesterase variants from the PDE4D gene expressed in human peripheral mononuclear cells" FEBS Letts. 384–97–102(1996).

Fuhrmann, et al. "Identification and Function of Cyclic Nucleotide Phosphodiesterase Isoenzymes in Airway Epithelial Cells" Am. J. Respir. Cell Mol. Biol. 20:292–302 (1999).

*Primary Examiner*—Charanjit S. Aulakh
(74) *Attorney, Agent, or Firm*—Elaine M. Ramesh; Mark Chao

(57) ABSTRACT

A compound having a partial structure represented by Formula:

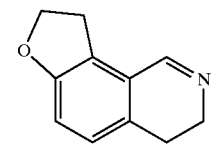

or a salt thereof has an excellent phosphodiesterase (PDE) IV-inhibiting effect, and is useful as a prophylactic or therapeutic agent against inflammatory diseases, for example, bronchial asthma, chronic obstructive pulmonary disease (COPD), rheumatoid arthritis, autoimmune disease, diabetes and the like.

27 Claims, No Drawings

FUROISOQUINOLINE DERIVATIVES, PROCESS FOR PRODUCING THE SAME AND USE THEREOF

This application is the National Phase filing of International Patent Application No. PCT/JP01/02277, filed Mar. 22, 2001.

TECHNICAL FIELD

The present invention relates to a novel furoisoquinoline derivative which has a phosphodiesterase (PDE) IV-inhibiting effect and which is useful as a prophylactic or therapeutic agent against the inflammatory diseases, for example, bronchial asthma, chronic obstructive pulmonary disease (COPD), rheumatoid arthritis, autoimmune disease, diabetes and the like and process for producing the same and use thereof.

BACKGROUND ART

It is known in these days that a large number of hormones and neurotransmitters function to increase or decrease the intracellular level of cyclic adenosine-3',5'-monophosphate (cAMP) which is an intracellular second messenger, whereby regulating the cellular functions. The intracellular cAMP level is regulated by synthesizing and degradating enzymes. Thus, cAMP is produced by adenyl cyclases and degradated by phosphodiesterase (PDE). These degradating enzymes also regulate the degradation of cyclic guanosine-3',5'-monophosphate.

Seven isozymes of the PDE have been found so far [Physiological Reviews, Vol.75, p725 (1995), Endocrine Reviews, Vol.16, p370, (1995)], and each functions, in various cells such as those in central nervous system, circulatory organs, respiratory organs, digestive organs, genital organs, blood cells and tracheal smooth muscles, to regulate intracellular cAMP and cGMP levels, whereby controlling the cellular functions. It is also known that in an inflammatory cell such as an eosinophile, neutrophile, monocyte, T-lymphocyte and macrophage a PDE isozyme referred to as PDE type-IV exists predominantly [Clinical and Experimental Allergy, Vol.22, p337 (1992)].

Pharmaceuticals, which can broadly be classified into three groups, are employed as therapeutic agents against a bronchial asthma. Thus, the three types including bronchodilators (for example, β-adrenaline receptor agonists), antiinflammatory agents (for example, corticosteroids) and xanthine derivatives having both of the bronchodilating effect and antiinflammatory effect (for example, theophylline) are employed. Among these, theophylline has been employed as a therapeutic agent against asthma for a long time. Theophylline is becoming more interesting in these days since its bronchodilating effect has been found to be derived from a PDE-inhibiting effect. However, theophylline is a non-selective PDE inhibitor and sometimes exhibits a cardio-vascular side effect. Then, its blood level should strictly be controlled to reduce the side effect. Accordingly, a medicament for treating an inflammatory disease such as asthma which inhibits the PDE type-VI selectively and which has no effects on other isozymes of the PDE is desired.

A study indicating a possibility that a PDE type-IV-selective inhibitor is an effective therapeutic agent against an inflammatory disease such as asthma was reported [Pulmonary Pharmacology, Vol.7, p1 (1994)]. Thus, it was suggested that a PDE type-IV-selective inhibitor has the both of an antiinflammatory effect and a bronchodilating effect and may exhibit a therapeutic effect on an inflammatory disease such as asthma. In fact, compounds having inhibitory effects selectively on the PDE type-IV are subjected currently to an extensive development all over the world. For example, rolipram (JP-A-50-157360) having the structure represented by Formula:

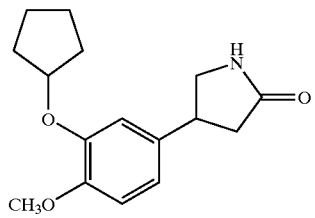

and SB 207499 [The Journal of Pharmacology and Experimental Therapeutics, Vol.287, p988 (1998), Journal of Medicinal Chemistry, Vol.41, p821 (1998)] represented by Formula:

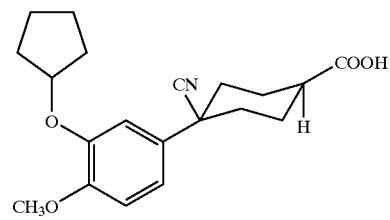

are under development. However, any of those listed above has not been employed clinically, and a further useful agent is desired to be developed.

On the other hand, a method for synthesizing a compound represented by Formula:

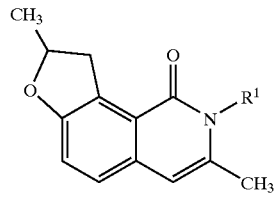

is disclosed in Indian Journal of Chemistry, Section B, Vol.31B, p578 (1992).

Moreover, an antibacterial compound represented by Formula:

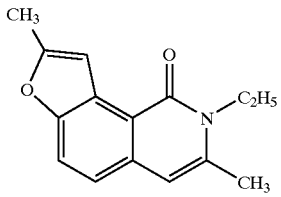

is also disclosed in Indian Journal of Chemistry, Section B, Vol.33B, p552 (1994).

A potent selective PDE type-IV inhibitor having a novel chemical structure is expected to have a sufficient prophylactic or therapeutic effect in a wide range of diseases accompanied with inflammations, and is desired to be developed. The objective of the invention is to provide novel heterocyclic compounds which have selective PDE type-IV-inhibiting effect and increase the intracellular cAMP level whereby exhibiting bronchodilating and antiinflammatory effects and which is also excellent in terms of the safety.

SUMMARY OF THE INVENTION

We made an effort and were finally successful for the first time in synthesizing a novel furoisoquinoline derivative (hereinafter abbreviated sometimes as Compound (I)) having a partial structure represented by Formula:

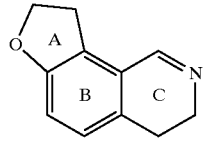

(wherein each of Ring A, Ring B and Ring C may have substituents, especially a novel furoisoquinoline derivative (hereinafter abbreviated sometimes as Compound (I')) whose significant chemical structural characteristics are the substituents introduced in the 1-, 2-, 3-, 4-, 5-, 6-, 8-, 9-positions etc. on the furoisoquinoline backbone, represented by Formula:

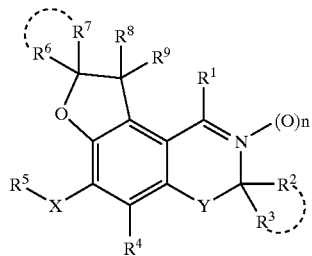

(wherein $R^1$ is a hydrogen atom, optionally substituted hydrocarbon group, optionally substituted heterocyclic group or optionally substituted amino group, each of $R^2$ and $R^3$ is a hydrogen atom, optionally substituted hydrocarbon group or acyl group, and $R^2$ and $R^3$ may be taken together with the adjacent carbon atom to form an optionally substituted 3- to 8-membered ring, $R^4$ is a hydrogen atom, cyano group, optionally substituted hydrocarbon group, acyl group or optionally substituted hydroxy group, $R^5$ is (1) a hydrogen atom, (2) an optionally substituted hydrocarbon group, (3) an acyl group, (4) an optionally substituted heterocyclic group or (5) a halogen atom, each of $R^6$ and $R^7$ is a hydrogen atom or optionally substituted hydrocarbon group, and $R^6$ and $R^7$ are taken together with the adjacent carbon atom to form an optionally substituted 3- to 8-membered ring, each of $R^8$ and $R^9$ is a hydrogen atom or optionally substituted hydrocarbon group, X is a bond, oxygen atom, optionally oxidized sulfur atom or optionally substituted nitrogen atom, Y is an optionally substituted methylene group or carbonyl group and n is 0 to 1), or a salt, prodrug or hydrate thereof, and discovered that such a compound has, on the basis of its specific chemical structure, an unexpectedly excellent phosphodiesterase (PDE) IV-inhibiting effect, and can be used as a prophylactic or therapeutic agent against an inflammation-induced disease, for example, bronchial asthma, chronic obstructive pulmonary disease (COPD), rheumatoid arthritis, autoimmune disease, diabetes and the like. We made a further effort based on these findings, and finally established the present invention.

Thus, the invention provides:

[1] a compound having a partial structure represented by Formula:

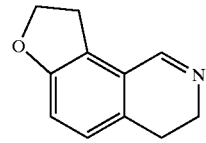

or its salt,

[2] the compound according to the above-mentioned [1] represented by Formula:

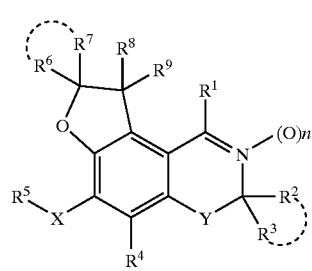

(wherein $R^1$ is a hydrogen atom, optionally substituted hydrocarbon group, optionally substituted heterocyclic group or optionally substituted amino group, each of $R^2$ and $R^3$ is a hydrogen atom, optionally substituted hydrocarbon group or acyl group, and $R^2$ and $R^3$ may be taken together with the adjacent carbon atom to form an optionally substituted 3- to 8-membered ring, $R^4$ is a hydrogen atom, cyano group, optionally substituted hydrocarbon group, acyl group or optionally substituted hydroxy group, $R^5$ is (1) a hydrogen atom, (2) an optionally substituted hydrocarbon group, (3) an acyl group, (4) an optionally substituted heterocyclic group or (5) a halogen atom, each of $R^6$ and $R^7$ is a hydrogen atom or optionally substituted hydrocarbon group, and $R^6$ and $R^7$ are taken together with the adjacent carbon atom to form an optionally substituted 3- to 8-membered ring, each of $R^8$ and $R^9$ is a hydrogen atom or optionally substituted hydrocarbon group, X is a bond, oxygen atom, optionally oxidized sulfur atom or optionally substituted nitrogen atom, Y is an optionally substituted methylene group or carbonyl group, and n is 0 to 1),

[3] the compound according to the above-mentioned [2] wherein each of $R^2$ and $R^3$ is a hydrogen atom, optionally substituted hydrocarbon group or acyl group, $R^2$ and $R^3$ are taken together with the adjacent carbon atom to form an optionally substituted 3- to 8-membered homocyclic or heterocyclic group, $R^4$ is a hydrogen atom or optionally substituted hydrocarbon group, each of $R^6$ and $R^7$ is a hydrogen atom or optionally substituted hydrocarbon group, $R^6$ and $R^7$ may be taken together with the adjacent carbon atom to form an optionally substituted 3- to 8-membered homocyclic group, Y is methylene group which may have a hydroxy group or carbonyl group,

[4] the compound according to the above-mentioned [2] wherein:

$R^1$ is any of the following (i) to (iii):

(i) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from the group (hereinafter referred to as Substituent Group A) consisting of (1) a halogen atom, (2) a $C_{1-3}$ alkylenedioxy group, (3) a nitro group, (4) a cyano group, (5) an optionally halogenated $C_{1-6}$ alkyl group, (6) an optionally halogenated $C_{2-6}$ alkenyl group, (7) an optionally halogenated $C_{2-6}$ alkynyl group, (8) a $C_{3-6}$ cycloalkyl group, (9) a $C_{6-14}$ aryl group, (10) an optionally halogenated $C_{16}$ alkoxy group, (11) an optionally halogenated $C_{1-6}$ alkylthio group, (12) a hydroxy group, (13) an amino group, (14) a mono-$C_{1-6}$ alkylamino group, (15) a mono-$C_{6-14}$ arylamino group, (16) a di-$C_{1-6}$ alkylamino group, (17) a di-$C_{6-14}$ arylamino group, (18) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, (19) an acylamino group selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (20) an acyloxy group selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-arbamoyloxy, di-$C_{1-6}$ alkyl-carbamoyloxy, $C_{6-14}$ aryl-carbamoyloxy and nicotinoyloxy, (21) a 4- to 14-membered heterocyclic group having, in addition to carbon atoms, 1 to 4 heteroatom(s) selected from nitrogen, sulfur and oxygen atoms, (22) a phosphono group, (23) a $C_{6-14}$ aryloxy group, (24) a di-$C_{1-6}$ alkoxy-phosphoryl group, (25) a $C_{6-14}$ arylthio group, (26) a hydrazino group, (27) an imino group, (28) an oxo group, (29) an ureido group, (30) a $C_{1-6}$ alkyl-ureido group, (31) a di-$C_{1-6}$-alkyl-ureido group, (32) an oxide group and (33) a group formed by binding 2 or 3 groups selected from (1) to (32) listed above, (ii) a 5- to 14-membered heterocyclic group having, in addition to carbon atoms, 1 to 4 heteroatom(s) selected from nitrogen, sulfur and oxygen atoms which may have 1 to 5 substituent(s) selected from Substituent Group A described above, (iii) an amino group which may have 1 or 2 substituent(s) selected from the following (ia) to (iiia): (ia) a hydrogen atom, (iia) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (iiia) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above;

each of $R^2$ and $R^3$ is any of the following (i) to (iii):

(i) a hydrogen atom, (ii) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (iii) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{-16}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above;

$R^2$ and $R^3$ may be taken together with the adjacent carbon atom to form a $C_{3-8}$ cycloalkane or 3- to 8-membered heterocyclic ring which may have 1 to 3 substituent(s) selected from $C_{1-6}$ alkyl, $C_{6-14}$ aryl, $C_{7-16}$ aralkyl, amino, mono-$C_{1-6}$ alkylamino, mono-$C_{6-14}$ arylamino, di-$C_{1-6}$ alkylamino, di-$C_{6-14}$ arylamino and 4- to 10-membered aromatic heterocyclic group;

$R^4$ is (i) a hydrogen atom, (ii) a cyano group, (iii) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (iv) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above, or, (v) a group represented by Formula: —$OR^{4'}$
($R^{4'}$ is <1> a hydrogen atom, <2> a $C_{1-6}$ alkyl group, $C_{2-6}$ alkenyl group, $C_{2-6}$ alkynyl group,
$C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, or,
<3> an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbarnoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above);

$R^5$ is any of the following (i) to (v):
(i) a hydrogen atom,
(ii) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above,
(iii) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above,
(iv) a 5- to 14-membered heterocyclic ring containing 1 to 4 heteroatom(s) selected from nitrogen, sulfur and oxygen atoms in addition to carbon atoms which may contain 1 to 5 substituent(s) selected from Substituent Group A described above,
(v) a halogen atom;
each of $R^6$ and $R^7$ is (i) a hydrogen atom, (ii) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, $R^6$ and $R^7$ may be taken together with the adjacent carbon atom to form a $C_{3-8}$ cycloalkane or 3- to 8-membered heterocyclic ring which may have 1 to 3 substituent(s) selected from $C_{1-6}$ alkyl, $C_{6-14}$ aryl, $C_{7-16}$ aralkyl, amino, mono-$C_{1-6}$ alkylamino, mono-$C_{6-14}$ arylamino, di-$C_{1-6}$ alkylamino, di-$C_{6-14}$ arylamino and 4- to 10-membered aromatic heterocyclic group;

each of $R^8$ and $R^9$ is (i) a hydrogen atom, (ii) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above;

X is (i) a bond, (ii) an oxygen atom, (iii) an optionally oxidized sulfur atom, (iv) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (v) a nitrogen atom having an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above, or, (vi) a 5- to 14-membered heterocyclic group containing 1 to 4 heteroatom(s) selected from nitrogen, sulfur and oxygen atoms in addition to carbon atoms which may contain 1 to 5 substituent(s) selected from Substituent Group A described above;

Y is <1> a methylene group which may have 1 to 5 substituent(s) selected from Substituent Group A described above or <2> a carbonyl group;

n is 0 or 1,

[5] the compound according to the above-mentioned [2] or [3] wherein $R^1$ is (1) an optionally substituted aromatic hydrocarbon group, (2) an optionally substituted heterocyclic group, (3) an optionally substituted aliphatic cyclic hydrocarbon group or (4) a group represented by Formula: —L—$R^{1a}$ wherein L is methylene, carbonyl or an optionally substituted nitrogen atom, $R^{1a}$ is a hydrogen atom, optionally substituted aromatic group, optionally substituted hydroxy group or optionally substituted amino group,

[6] the compound according to the above-mentioned [5] wherein $R^1$ is any of the following (i) to (iv):

(i) a $C_{6-14}$ aryl group which may have 1 to 5 substituent(s) selected from Substituent Group A described above, (ii) a 5- to 14-membered heterocyclic group containing 1 to 4 heteroatom(s) selected from nitrogen, sulfur and oxygen atoms in addition to carbon atoms which may contain 1 to 5 substituent(s) selected from Substituent Group A described above, (iii) a $C_{3-6}$ cycloalkyl group which may have 1 to 5 substituent(s) selected from Substituent Group A described above, (iv) a group represented by Formula: —L—$R^{1a}$ wherein L is (a) a methylene, (b) a carbonyl or (c) a nitrogen atom which may be substituted by the following (ia) to (iiia):

(ia) a hydrogen atom, (iia) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (iiia) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above, $R^{1a}$ is (i) a hydrogen atom, (ii) <1> a $C_{6-14}$ aryl group or <2> a 5- to 14-membered aromatic heterocyclic group containing 1 to 4 heteroatom(s) selected from 1 or 2 kind(s) of nitrogen, sulfur and oxygen atoms in addition to carbon atoms, both of which may contain 1 to 5 substituent(s) selected from Substituent Group A described above, (iii) a hydroxy group which may have a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (iv) an amino group which may be substituted by the following (ia) to (iiia):

(ia) a hydrogen atom, (iia) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (iiia) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-34}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl.

[7] the compound according to the above-mentioned [2] wherein $R^1$ is a group represented by Formula:

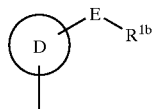

(wherein $R^{1b}$ is a hydrogen atom or an optionally substituted hydrocarbon group or optionally substituted heterocyclic group, Ring D is an optionally substituted aromatic hydrocarbon ring or optionally substituted heterocyclic group, E is a bond, methylene, oxygen atom, optionally oxidized sulfur atom, optionally substituted nitrogen atom or a group represented by Formula: —CS—O—, —CO—O—, —S—CO—, —$(CH_2)_k$—CO—, —$NR^{1C}$—CO—$(CH_2)_m$—, —$NR^{1C}$—$SO_2$—$(CH_2)_m$—, —$SO_2$—$NR^{1C}$—$(CH_2)_m$—, —O—CS—$NR^{1C}$—$(CH_2)_m$—, —$NR^{1C}$—CO—$NR^{1C}$—$(CH_2)_m$—, —$NR^{1C}$—CO—$(CH_2)_m$—$NR^{1C}$— wherein $R^{1C}$ is a hydrogen atom, optionally substituted alkyl group or acyl group, k is 0 or 1, m is an integer of 0 to 3).

[8] the compound according to the above-mentioned [7] wherein $R^{1b}$ is (i) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, or, (ii) a 5- to 14-membered heterocyclic group containing 1 to 4 heteroatom(s) selected from nitrogen, sulfur and oxygen atoms in addition to carbon atoms which may contain 1 to 5 substituent(s) selected from Substituent Group A described above;

Ring D is (i) a $C_{6-14}$ aryl ring which may have 1 to 5 substituent(s) selected from Substituent Group A described above or (ii) a 5- to 14-membered heterocyclic ring containing 1 to 4 heteroatom(s) selected from nitrogen, sulfur and oxygen atoms in addition to carbon atoms which may contain 1 to 5 substituent(s) selected from Substituent Group A described above;

E is any of the following (i) to (viii):

(i) a bond, (ii) methylene, (iii) an oxygen atom, (iv) an optionally oxidized sulfur atom, (v) a nitrogen atom having a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (vi) a nitrogen atom having an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, (vii) a nitrogen atom having a 5- to 14-membered heterocyclic group containing 1 to 4 heteroatom(s) selected from nitrogen, sulfur and oxygen atoms in addition to carbon atoms which may contain 1 to 5 substituent(s) selected from Substituent Group A described above;

(viii) —CS—O—, —CO—O—, —S—CO—, —$(CH_2)_k$—CO—, —$NR^{1C}$—CO—$(CH_2)_m$—, —$NR^{1C}$—$SO_2$—$(CH_2)_m$—, —$SO_2$—$NR^{1C}$—$(CH_2)_m$—, —O—CS—$NR^{1C}$—$(CH_2)_m$—, —$NR^{1C}$—CO—$NR^{1C}$—$(CH_2)_m$—or —$NR^{1C}$—CO—$(CH_2)_m$—$NR^{1C}$— (wherein $R^{1C}$ is (ia) a hydrogen atom, (iia) a $C_{1-6}$ alkyl group which may have 1 to 5 substituent(s) selected from Substituent Group A described above, or, (iiia) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above;

k is 0 or 1, m is an integer of 0 to 3).

[9] the compound according to the above-mentioned [7] wherein $R^{1b}$ is,
(1) a $C_{1-6}$ alkyl group [this $C_{1-6}$ alkyl group may have a substituent selected from a halogen atom, cyano, hydroxy, $C_{1-6}$ alkoxy-carbonyl, di-$C_{1-6}$ alkylamino, optionally halogenated $C_{1-6}$ alkyl-carbonyl-amino, carboxy, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, (5- to 6-membered heterocyclic ring containing 1 to 3 heteroatom(s) selected from nitrogen, sulfur and oxygen atoms in addition to carbon atoms)-$C_{1-6}$ alkyl-carbamoyl, $C_{1-6}$ alkylthio, $C_{1-6}$ alkylsulfinyl, $C_{1-6}$ alkylsulfonylamino, (5- to 6-membered heterocyclic ring containing 1 to 3 heteroatom(s) selected from nitrogen, sulfur and oxygen atoms in addition to carbon atoms)-$C_{1-6}$ alkylcarbamoyl, (5- to 6-membered heterocyclic ring containing 1 to 3 heteroatom(s) selected from nitrogen, sulfur and oxygen atoms in addition to carbon atoms)-amino, sulfamoyl-$C_{6-14}$ aryl, carboxy-$C_{6-14}$ aryl, $C_{1-6}$ alkoxy-carbonyl-$C_{6-14}$ aryl, carbamoyl-$C_{6-14}$ aryl, $C_{1-6}$ alkyl-carbamoyl-$C_{6-14}$ aryl which may have a hydroxy and (4- to 10-membered heterocyclic ring containing 1 to 3 heteroatom(s) selected from nitrogen, sulfur and oxygen atoms in addition to carbon atoms)-carbamoyl-$C_{6-14}$ aryl],
(2) a $C_{3-6}$ cycloalkyl group,
(3) a $C_{6-14}$ aryl group [this $C_{6-14}$ aryl group may have a substituent selected from $C_{1-6}$ alkoxy, amino, carboxy, optionally halogenated $C_{1-6}$ alkyl-carbonylamino, $C_{1-6}$ alkoxy-carbonylamino, formylamino, ureido, $C_{1-6}$ alkylsulfonylamino, ($C_{1-6}$ alkyl)($C_{1-6}$ alkylsulfonyl)amino, $C_{1-6}$ alkoxy-carbonyl-$C_{1-6}$ alkylamino, optionally $C_{1-6}$ alkyl-esterified phosphono-$C_{1-6}$ alkylamino, mono- or di-$C_{1-6}$ alkyl-carbamoyl and $C_{7-16}$ aralkyloxy-carbonylamino] or,
(4) a 5- to 14-membered heterocyclic group containing 1 to 4 heteroatom(s) selected from nitrogen, sulfur and oxygen atoms in addition to carbon atoms [this heterocyclic group may be substituted by 1 or 2 substituent(s) selected from a halogen atom, $C_{1-6}$ alkyl, carboxy-$C_{1-6}$ alkyl, $C_{1-6}$ alkyl-carbonyloxy-$C_{1-6}$ alkyl, $C_{1-6}$ alkoxy-carbonyl, $C_{1-6}$ alkoxy-carbonyl-$C_{1-6}$ alkyl, $C_{1-6}$ alkyl-carbamoyl-$C_{1-6}$ alkyl, carbamoyl, oxo and 4- to 10-membered heterocyclic group containing 1 to 3 heteroatom(s) selected from nitrogen, sulfur and oxygen atoms in addition to carbon atoms];
Ring D is (i) a $C_{6-14}$ aryl ring or (ii) a 5- to 14-membered heterocyclic ring containing 1 to 4 heteroatom(s) selected from nitrogen, sulfur and oxygen atoms in addition to carbon atoms;
E is (i) a bond, (ii) methylene, (iii) O, (iv) S, (v) SO, (vi) $SO_2$, (vii) —NH—, (viii) —N($C_{1-6}$ alkyl)-, (ix) —N($C_{1-6}$ alkyl-carbonyl)-, (x) —N($C_{1-6}$ alkoxy-carbonyl)-, (xi) —N($C_{1-6}$ alkyl-sulfonyl)-, (xii)—CO—O—, (xiii)—S—CO—, (xiv) a group represented by Formula: —($CH_2$)$_k$—CO wherein k is 0 or 1, (xv) —$NR^f$—CO—($CH2$)$_{m1}$— wherein $R^f$ is a hydrogen atom or $C_{1-6}$ alkoxy-carbonyl or $C_{1-6}$ alkyl group which may be substituted by a heterocyclic group containing 1 to 3 heteroatom(s) selected from nitrogen, oxygen and sulfur atoms in addition to carbon atoms, and m1 is an integer of 0 to 3,
(xvi) a group represented by Formula —$NR^g$—$SO_2$—($CH_2$)$_{m2}$— wherein $R^g$ is a hydrogen atom or $C_{1-6}$ alkylsulfonyl group and m2 is 0,
(xvii) a group represented by Formula —$SO_2$—$NR^h$—($CH_2$)$_{m3}$— wherein $R^h$ is a hydrogen atom or $C_{1-6}$ alkyl group and m3 is 0 or 1,
(xviii) a group represented by Formula —O—CS—$NR^i$—($CH_2$)$_{m4}$— wherein $R^i$ is a hydrogen atom or $C_{1-6}$ alkyl group and m4 is 0 or 1,
(xix) a group represented by Formula —$NR^j$—CO—$NR^k$—($CH_2$)$_{m5}$— wherein $R^j$ is a hydrogen atom or $C_{1-6}$ alkyl group, $R^k$ is a hydrogen atom or $C_{1-6}$ alkyl group and m5 is 0 or 1,
(xx) a group represented by Formula —$NR^L$CO—$CH_2$—($CH_2$)$_{m6}$—$NR^m$— wherein $R^L$ is a hydrogen atom or $C_{1-6}$ alkyl group, $R^m$ is a hydrogen atom or $C_{1-6}$ alkyl group and m6 is 0 or 1.
[10] the compound according to the above-mentioned [2] wherein $R^1$ is a group represented by Formula:

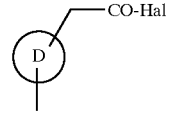

wherein Hal is a halogen atom, Ring D is defined as described in the above-mentioned [7],
[11] the compound according to the above-mentioned [2] wherein $R^1$ is a group represented by Formula:

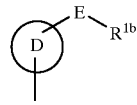

wherein each symbol is defined as described in the above-mentioned [7] or a group represented by Formula:

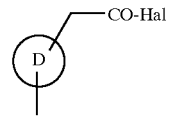

wherein each symbol is defined as described in the above-mentioned [7], each of $R^2$ and $R^3$ is a hydrogen atom or optionally substituted hydrocarbon group, and $R^2$ and $R^3$ may be taken together with the adjacent carbon atom to form an optionally substituted 3- to 8-membered ring, $R^4$ is a hydrogen atom, cyano group, optionally substituted hydrocarbon group, acyl group or a group represented by Formula: —$OR^4$ (wherein $R^4$ is a hydrogen atom, optionally substituted hydrocarbon group or acyl group), $R^5$ is an optionally substituted hydrocarbon group, each of $R^6$ and $R^7$ is an optionally substituted hydrocarbon group, $R^6$ and $R^7$ may be taken together with the adjacent carbon atom to form an optionally substituted 3- to 8-membered ring, each of $R^8$ and $R^9$ is a hydrogen atom, X is an oxygen atom or an optionally oxidized sulfur atom, Y is methylene which may have 1 or 2 $C_{1-6}$ alkyl group(s) and n is 0 or 1.
[12] the compound according to the above-mentioned [2] wherein $R^1$ is,
(i) a $C_{6-14}$ aryl group which may have 1 to 3 substituent(s) selected from the following (1) to (23):
(1) a halogen atom,
(2) a nitro group,
(3) a $C_{1-6}$ alkyl group [this $C_{1-6}$ alkyl group may have a substituent selected from a halogen atom, cyano, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, (5- or 6-membered heterocyclic ring containing 1 to 3 heteroatom(s) selected from nitrogen, sulfur and oxygen atoms in addition to carbon atoms)-$C_{1-6}$ alkyl-carbamoyl, $C_{1-6}$ alkylsulfonylamino, $C_{1-6}$ alkoxy-carbonyl and carboxy], (4) a $C_{3-6}$ cycloalkyl group,
(5) a $C_{6-14}$ aryl group [this $C_{6-14}$ aryl group may have a substituent selected from amino, carboxy, $C_{1-6}$ alkoxy-carbonyl, carbamoyl, mono- or di-$C_{1-6}$ alkylcarbamoyl, formylamino, $C_{1-6}$ alkyl-carbonylamino which may have a halogen atom or carboxy, $C_{6-14}$ aryl-carbonylamino, $C_{1-6}$ alkoxy-carbonylamino, ureido, mono- or di-$C_{1-6}$ alkylureido, $C_{1-6}$ alkylsulfonylamino, ($C_{1-6}$ alkyl) ($C_{1-6}$ alkylsulfonyl) amino, ($C_{1-6}$ alkyl) ($C_{1-6}$ alkyl-carbonyl) amino, $C_{1-6}$ alkoxy-carbonyl-$C_{1-6}$ alkylamino, $C_{6-14}$ aralkyloxy-carbonylamino, $C_{1-6}$ alkyl-carbonylamino-$C_{1-6}$ alkyl-carbonylamino, $C_{1-6}$ alkylthio-$C_{1-6}$ alkyl-carbonylamino, $C_{1-6}$ alkyl-sulfinyl-$C_{1-6}$ alkyl-carbonylamino, $C_{1-6}$ alkyl-sulfonyl-$C_{1-6}$ alkyl-carbonylamino, $C_{6-14}$ aryloxy-carbonylamino and hydroxy-$C_{1-6}$ alkyl-carbamoyl],
(6) a $C_{1-6}$ alkoxy group which may have a halogen atom or $C_{1-6}$ alkoxy-$C_{6-14}$ aryl,
(7) a $C_{6-14}$ aryloxy group,
(8) a $C_{1-6}$ alkylthio group which may have a carbamoyl,
(9) a $C_{1-6}$ alkylsulfinyl group which may have a carbamoyl,
(10) a $C_{6-14}$ arylthio group,
(11) a hydroxy group,
(12) a 5- to 14-membered heterocyclic group containing 1 to 4 heteroatom(s) selected from nitrogen, sulfur and oxygen atoms [this heterocyclic group may have a substituent selected from oxo, carboxy-$C_{1-6}$ alkyl, $C_{1-6}$ alkyl-carbonyloxy-$C_{1-6}$ alkyl, $C_{1-6}$ alkyl, $C_{1-6}$ alkoxy-carbonyl-$C_{1-6}$ alkyl, $C_{1-6}$ alkoxy-carbonyl, carbamoyl-$C_{1-6}$ alkyl and $C_{1-6}$ alkyl-carbamoyl-$C_{1-6}$ alkyl],
(13) a carboxy group,
(14) a group represented by Formula: —CO—Hal (Hal is a halogen atom),
(15) a $C_{1-6}$ alkyl-carbonyl group,
(16) a $C_{1-6}$ alkyl-sulfonyl group,
(17) a $C_{1-6}$ alkoxy-carbonyl group,
(18) a sulfamoyl group [this sulfamoyl group may have 1 or 2 substituent(s) selected from $C_{1-6}$ alkyl, carbamoyl-$C_{1-6}$ alkyl, $C_{1-6}$ alkoxy-carbonyl-$C_{1-6}$ alkyl, (5- to 8-membered heterocyclic ring which may have an oxo group)-$C_{1-6}$ alkyl and $C_{1-6}$ alkyl-carbonylamino-$C_{6-14}$ aryl],
(19) a group represented by Formula: —NR$^a$R$^b$ [each of R$^a$ and R$^b$ is (i) a hydrogen atom, (ii) a $C_{1-6}$ alkyl, (iii) a (5- or 6-membered heterocyclic ring containing 1 to 3 heteroatom(s) selected from nitrogen, sulfur and oxygen atoms in addition to carbon atoms)-$C_{1-6}$ alkyl, (iv) a $C_{1-6}$ alkoxy-carbonyl-$C_{1-6}$ alkyl, (v) a di-$C_{1-6}$ alkylamino-methylene-sulfamoyl-$C_{1-6}$ alkyl, (vi) a carbamoyl-$C_{1-6}$ alkyl, (vii) a sulfamoyl-$C_{1-6}$ alkyl, (viii) a $C_{1-6}$ alkyl-sulfonyl, (ix) a $C_{1-6}$ alkoxy-carbonyl, (x) a di-$C_{1-6}$ alkoxy-carbonyl-$C_{2-6}$ alkenyl, (xi) a $C_{6-14}$ aryl, (xii) a 5- or 6-membered heterocyclic group containing 1 to 3 heteroatom(s) selected from nitrogen, sulfur and oxygen atoms in addition to carbon atoms [this 5- or 6-membered heterocyclic group may have a substituent selected from amino, $C_{1-6}$ alkyl-carboxamido and $C_{1-6}$ alkyl-sulfonylamino], (xiii) an optionally halogenated $C_{1-6}$ alkyl-carbonyl, (xiv) a $C_{1-6}$ alkylthio-$C_{1-6}$ alkyl-carbonyl, (xv) a $C_{1-6}$ alkylsulfinyl-$C_{1-6}$ alkyl-carbonyl, (xvi) a $C_{1-6}$ alkylsulfonyl-$C_{1-6}$ alkyl-carbonyl, (xvii) an amino-$C_{1-6}$ alkyl-carbonyl, (xviii) an optionally halogenated $C_{1-6}$ alkyl-carbonyl-amino-$C_{1-6}$ alkyl-carbonyl, (xix) a $C_{6-14}$ aryl-carbonyl, (xx) a carboxy-$C_{6-14}$ aryl-carbonyl, (xxi) an optionally $C_{1-6}$ alkyl-esterified phosphono-$C_{1-6}$ alkyl-$C_{6-14}$ aryl-carbonyl, (xxii) a (5- or 6-membered heterocyclic ring containing 1 to 3 heteroatom(s) selected from nitrogen, sulfur and oxygen atoms in addition to carbon atoms which may have a halogen atom, oxo or a $C_{1-6}$ alkoxy-carbonyl)-carbonyl, (xxiii) a (5- or 6-membered heterocyclic ring containing 1 to 3 heteroatom(s) selected from nitrogen, sulfur and oxygen atoms in addition to carbon atoms)-$C_{1-6}$ alkyl-carbonyl, (xxiv) a $C_{6-14}$ aryloxy-carbonyl, (xxv) a carboxy-$C_{1-6}$ alkyl, (xxvi) a carbamoyl, (xxvii) an optionally halogenated $C_{1-6}$ alkylcarbamoyl, (xxviii) a $C_{6-14}$ arylcarbamoyl which may have a $C_{1-6}$ alkyl-carbonylamino, (xxix) a (5- or 6-membered heterocyclic ring containing 1 to 3 heteroatom(s) selected from nitrogen, sulfur and oxygen atoms in addition to carbon atoms)-carbamoyl, (xxx) a $C_{2-6}$ alkenyl-carbonyl, (xxxi) a (5- or 6-membered heterocyclic ring containing 1 to 3 heteroatom(s) selected from nitrogen, sulfur and oxygen atoms in addition to carbon atoms which may have an oxo group)-amino-$C_{1-6}$ alkyl-carbonyl, (xxxii) a (5- or 6-membered heterocyclic ring containing 1 to 3 heteroatom(s) selected from nitrogen, sulfur and oxygen atoms in addition to carbon atoms which may have an oxo group)($C_{1-6}$ alkyl) amino-$C_{1-6}$ alkyl-carbonyl, (xxxiii) a (5- or 6-membered heterocyclic ring containing 1 to 3 heteroatom(s) selected from nitrogen, sulfur and oxygen atoms in addition to carbon atoms which may have an oxo group)($C_{1-6}$ alkylcarbonyl) amino-$C_{1-6}$ alkyl-carbonyl, (xxxiv) a $C_{1-6}$ alkylthio-$C_{1-6}$ alkylcarbonyl (sulfur atom may be oxidized), (xxxv) an optionally halogenated $C_{1-6}$ alkylsulfonyl, (xxxvi) a sulfamoyl or (xxxvii) a $C_{1-6}$ alkylsulfamoyl],
(20) a group represented by Formula: —C(=O)NR$^c$R$^d$ [each of R$^c$ and R$^d$ is (i) a hydrogen atom, (ii) a $C_{1-6}$ alkyl, (iii) a (5- or 6-membered heterocyclic ring containing 1 to 3 heteroatom(s) selected from nitrogen, sulfur and oxygen atoms in addition to carbon atoms)-$C_{1-6}$ alkyl, (iv) a carboxy-$C_{1-6}$alkyl, (v) a $C_{1-6}$ alkoxy-carbonyl-$C_{1-6}$ alkyl, (vi) a di-$C_{1-6}$ alkylamino-$C_{1-6}$ alkyl, (vii) a carbamoyl-$C_{1-6}$ alkyl, (viii) a $C_{1-6}$ alkylcarbamoyl-$C_{1-6}$ alkyl, (ix) a (5- or 6-membered heterocyclic group containing 1 to 3 heteroatom(s) selected from nitrogen, sulfur and oxygen atoms in addition to carbon atoms)-$C_{1-6}$ alkylcarbamoyl-$C_{1-6}$ alkyl, (x) a (5- or 6-membered heterocyclic group containing 1 to 3 heteroatom(s) selected from nitrogen, sulfur and oxygen atoms in addition to carbon atoms)-amino-$C_{1-6}$ alkyl, (xi) a sulfamoyl-$C_{6-14}$ aryl-$C_{1-6}$ alkyl, (xii) a $C_{6-14}$ aryl which may have a $C_{1-6}$ alkoxy, (xiii) an optionally $C_{1-6}$ alkyl-esterified phosphono-$C_{1-6}$ alkyl-$C_{6-14}$ aryl, (xiv) a 4- to 10-membered heterocyclic ring containing 1 to 3 heteroatom(s) selected from nitrogen, sulfur and oxygen atoms in addition to carbon atoms [this 4- to 10-membered heterocyclic group may have 1 to 2 substituent(s) selected from a halogen atom, $C_{1-6}$ alkyl and oxo], (xv) a $C_{6-14}$ aryl-carbamoyl-$C_{1-6}$ alkyl, (xvi) a hydroxy-$C_{1-6}$ alkyl or (xvii) a (5- or 6-membered heterocyclic ring containing 1 to 3 heteroatom(s) selected from nitrogen, sulfur and oxygen atoms in addition to carbon atoms which may have a oxo group)-carbamoyl-$C_{1-6}$ alkyl],
(21) a cyano group,
(22) a mono- or di-$C_{1-6}$ alkylcarbamoylthio group,
(23) a mono- or di-$C_{1-6}$ alkylthiocarbamoyloxy group;
(ii) a 5- to 14-membered heterocyclic group containing 1 to 4 heteroatom(s) selected from nitrogen, sulfur and oxygen atoms in addition to carbon atoms which may contain 1 to 3 substituent(s) selected from the following (1) to (8):
(1) a halogen atom,
(2) a $C_{1-6}$ alkyl group [this alkyl may have a substituent selected from carboxy, $C_{1-6}$ alkoxy, $C_{1-6}$ alkoxy-carbonyl, mono-$C_{1-6}$ alkyl-amino, di-$C_{1-6}$ alkyl-amino, carbamoyl, $C_{1-6}$ alkyl-carbamoyl which may have a hydroxy, 4- to 10-membered heterocyclic group containing 1 to 3 heteroatom(s) selected from nitrogen, sulfur and oxygen atoms in addition to carbon atoms which may have oxo, (4- to 10-membered heterocyclic ring containing 1 to 3 heteroatom(s) selected from nitrogen, sulfur and oxygen atoms in addition to carbon atoms)-carbamoyl, carbamoyl-$C_{1-6}$ alkyl-carbamoyl], (3) a $C_{1-6}$ alkoxy group,
(4) a $C_{6-14}$ aryl group,
(5) a $C_{7-16}$ aralkyl group [this $C_{7-16}$ aralkyl group may have a substituent selected from carboxy, $C_{1-6}$ alkoxy-carbonyl, carbamoyl, $C_{1-6}$ alkyl-carbamoyl which may have hydroxy, (4- to 10-membered heterocyclic ring containing 1 to 3 heteroatom(s) selected from nitrogen, sulfur and oxygen atoms in addition to carbon atoms)-carbamoyl],
(6) a 4- to 10-membered heterocyclic group containing 1 to 3 heteroatom(s) selected from nitrogen, sulfur and oxygen atoms in addition to carbon atoms [this 4- to 10-membered heterocyclic group may have a substituent selected from a $C_{1-6}$ alkyl, $C_{1-6}$ alkoxy-carbonyl, carbamoyl, oxo, 4- to 10-membered heterocyclic group containing 1 to 3 heteroatom(s) selected from nitrogen, sulfur and oxygen atoms in addition to carbon atoms],
(7) an oxo group,
(8) an oxide group;
(iii) a $C_{3-6}$ cycloalkyl group; or,
(iv) a group represented by Formula: —L'—$R^{1a'}$ (L' is methylene, carbonyl or an optionally substituted nitrogen atom, $R^{1a'}$ is (1) a hydrogen atom, (2) a $C_{6-14}$ aryl group which may have 1 to 5 substituent(s) selected from a $C_{1-6}$ alkyl and $C_{1-6}$ alkoxy, (3) a hydroxy group which may be substituted by a $C_{1-6}$ alkyl group, (4) a $C_{1-6}$ alkyl-amino group which may be substituted by a 4- to 10-membered heterocyclic ring containing 1 to 3 heteroatom(s) selected from nitrogen, oxygen and sulfur atoms in addition to carbon atoms, (6) a $C_{6-14}$ aryl-amino group or (7) a (4- to 10-membered heterocyclic ring containing 1 to 3 heteroatom(s) selected from nitrogen, oxygen and sulfur atoms in addition to carbon atoms)-amino group), each of $R^2$ and $R^3$ is (1) a hydrogen atom, (2) a $C_{1-6}$ alkyl group which may be substituted by <1> a halogen atom, <2> a hydroxy group which may be substituted by a substituent selected from a $C_{1-6}$ alkyl, $C_{1-6}$ alkyl-carbonyl, $C_{1-6}$ alkyl-sulfonyl and $C_{7-16}$ aralkyl, <3> an amino group which may be substituted by 1 or 2 $C_{1-6}$ alkyl, $C_{1-6}$ alkyl-carbonyl and $C_{6-14}$ aryl-carbonyl, <4> a 4- to 10-membered heterocyclic group containing 1 to 3 heteroatom(s) selected from nitrogen, oxygen and sulfur atoms in addition to carbon atoms, <5> a thio group which may be substituted by a $C_{1-6}$ alkyl, <6> a $C_{1-6}$ alkyl-sulfinyl group or <7> a $C_{1-6}$ alkyl-sulfonyl group, or (3) a $C_{1-6}$ alkoxy-carbonyl group, $R^2$ and $R^3$ may be taken together with the adjacent carbon atom to form a $C_{3-8}$ cycloalkane, $R^4$ is (i) a hydrogen atom, (ii) a cyano group, (iii) a $C_{1-6}$ alkyl group [this $C_{1-6}$ alkyl group may have a substituent selected from (1) a halogen atom, (2) a cyano group, (3) a $C_{1-6}$ alkoxy group, (4) a hydroxy group, (5) an amino group, (6) a mono-$C_{1-6}$ alkylamino group, (7) a di-$C_{1-6}$ alkylamino group, (8) a tri-$C_{1-6}$ alkylammonium group, (8) a 4- to 10-membered heterocyclic group containing 1 to 3 heteroatom(s) selected from nitrogen, sulfur and oxygen atoms in addition to carbon atoms which may have an oxo, (9) a $C_{6-14}$ arylthio, (10) an ureido, (11) a carboxy, (12) a carbamoyl, (13) a $C_{1-6}$ alkoxy-carbonyl, (14) a mono-$C_{1-6}$ alkyl-carbamoyl, (15) a formylamino and (16) a $C_{1-6}$ alkyl-carboxamide], (iv) a $C_{2-6}$ alkenyl group or (v) a formyl group;

X is a bond, oxygen atom, optionally oxidized sulfur atom, —NH— or —N(methyl)-,
$R^5$ is,
when X is a bond, then (i) a hydrogen atom, (ii) a $C_{1-6}$ alkyl group or (iii) a halogen atom,
when X is an oxygen atom, then (i) a hydrogen atom, (ii) a $C_{1-6}$ alkyl group [this $C_{1-6}$ alkyl group may have a substituent selected from (1) a halogen atom, (2) a hydroxy group, (3) an amino group, (4) a carboxy, (5) a carbamoyl, (6) a $C_{1-6}$ alkoxy-carbonyl, (7) a mono-$C_{1-6}$ alkyl-carbamoyl, (8) a di-$C_{1-6}$ alkyl-carbamoyl, (9) a 4- to 10-membered heterocyclic group containing 1 to 3 heteroatom(s) selected from nitrogen, sulfur and oxygen atoms in addition to carbon atoms], (iii) a $C_{2-6}$ alkenyl group [this $C_{2-6}$ alkenyl group may have a $C_{6-14}$ aryl], (iv) a $C_{2-6}$ alkynyl group, (v) a $C_{3-6}$ cycloalkyl group, (vi) a $C_{7-16}$ aralkyl group, (vii) a $C_{1-6}$ alkyl-carbonyl group, (viii) a $C_{6-14}$ aryl-carbonyl group, (ix) a $C_{1-6}$ alkoxy-carbonyl group, (x) a mono- or di-$C_{1-6}$ alkyl-thiocarbamoyl group, (xi) an optionally halogenated $C_{1-6}$ alkyl-sulfonyl group or (xii) a 4- to 10-membered heterocyclic group containing 1 to 4 heteroatom(s) selected from nitrogen, sulfur and oxygen atoms in addition to carbon atoms [this heterocyclic group may have a $C_{6-14}$ aryl],
when X is an optionally oxidized sulfur, then (i) a $C_{1-6}$ alkyl group or (ii) a mono- or di-$C_{1-6}$ alkyl-carbamoyl group,
when X is —NH— or —N(methyl)-, then (i) a hydrogen atom, (ii) a $C_{1-6}$ alkyl group [this $C_{1-6}$ alkyl group may have a $C_{1-6}$ alkoxy-carbonyl], (iii) formyl, (iv) a $C_{1-6}$ alkyl-carbonyl group, (v) a $C_{1-6}$ alkoxy-carbonyl group, (vi) a carbamoyl group, (vii) a mono- or di-$C_{1-6}$ alkyl-carbamoyl group or (viii) a $C_{1-6}$ alkyl-sulfonyl group, each of $R^6$ and $R^7$ is a hydrogen atom or $C_{1-6}$ alkyl group,
$R^6$ and $R^7$ may be taken together with the adjacent carbon atom to form a $C_{3-8}$ cycloalkane,
Each of $R^8$ and $R^9$ is a hydrogen atom or a $C_{1-6}$ alkyl group,
Y is <1> a methylene group which may have 1 or 2 $C_{1-6}$ alkyl or hydroxy group or <2> a carbonyl group,
n is 0 or 1,
[13] the compound according to the above-mentioned [3] wherein $R^1$ is,
(i) a $C_{6-14}$ aryl group which may have 1 to 3 substituent(s) selected from the following (1) to (20):
(1) a halogen atom,
(2) a nitro group,
(3) a $C_{1-6}$ alkyl group [this $C_{1-6}$ alkyl group may have a substituent selected from a halogen atom, cyano, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, (5- or 6-membered heterocyclic ring containing 1 to 3 heteroatom(s) selected from nitrogen, sulfur and oxygen atoms in addition to carbon atoms)-$C_{1-6}$ alkyl-carbamoyl, $C_{1-6}$ alkylsulfonylamino, $C_{1-6}$ alkoxy-carbonyl and carboxy],
(4) a $C_{3-6}$ cycloalkyl group,
(5) a $C_{6-14}$ aryl group [this $C_6C_{14}$ aryl group may have a substituent selected from amino, optionally halogenated $C_{1-6}$ alkyl-carbonylamino, ureido, $C_{1-6}$ alkylsulfonylamino, ($C_{1-6}$ alkyl)($C_{1-6}$ alkylsulfonyl)amino, $C_{1-6}$ alkoxy-carbonyl-$C_{1-6}$ alkylamino],
(6) a $C_{1-6}$ alkoxy group which may have a halogen atom or $C_{1-6}$ alkoxy-$C_{6-14}$ aryl,
(7) a $C_{6-14}$ aryloxy group,
(8) a $C_{1-6}$ alkylthio group,
(9) a $C_{1-6}$ alkylsulfinyl group,

(10) a $C_{6-14}$ arylthio group,
(11) a hydroxy group,
(12) a 5- to 14-membered heterocyclic group containing 1 to 4 heteroatom(s) selected from nitrogen, sulfur and oxygen atoms [this heterocyclic group may have a substituent selected from oxo, carboxy-$C_{1-6}$ alkyl, $C_{1-6}$ alkyl-carbonyloxy-$C_{1-6}$ alkyl, $C_{1-6}$ alkoxy-carbonyl-$C_{1-6}$ alkyl, $C_{1-6}$ alkyl-carbamoyl-$C_{1-6}$ alkyl],
(13) a carboxy group,
(14) a group represented by Formula: —CO—Hal (Hal is a halogen atom),
(15) a $C_{1-6}$ alkyl-carbonyl group,
(16) a $C_{1-6}$ alkyl-sulfonyl group,
(17) a $C_{1-6}$ alkoxy-carbonyl group,
(18) a sulfamoyl group [this sulfamoyl group may have a substituent selected from a $C_{1-6}$ alkyl, carbamoyl-$C_{1-6}$ alkyl, (5- or 6-membered heterocyclic ring containing 1 to 3 heteroatom(s) selected from nitrogen, sulfur and oxygen atoms in addition to carbon atoms)-$C_{1-6}$ alkyl],
(19) a group represented by Formula: —$NR^aR^b$ [each of $R^a$ and $R^b$ is (i) a hydrogen atom, (ii) a $C_{1-6}$ alkyl, (iii) a (5- or 6-membered heterocyclic ring containing 1 to 3 heteroatom(s) selected from nitrogen, sulfur and oxygen atoms in addition to carbon atoms)-$C_{1-6}$ alkyl, (iv) a $C_{1-6}$ alkoxy-carbonyl-$C_{1-6}$ alkyl, (v) a di-$C_{1-6}$ alkylamino-methylene-sulfamoyl-$C_{1-6}$ alkyl, (vi) a carbamoyl-$C_{1-6}$ alkyl, (vii) a sulfamoyl-$C_{1-6}$ alkyl, (viii) a $C_{1-6}$ alkyl-sulfonyl, (ix) a $C_{1-6}$ alkoxy-carbonyl, (x) a di-$C_{1-6}$ alkoxy-carbonyl-$C_{2-6}$ alkenyl, (xi) a $C_{6-14}$ aryl, (xii) a 5- or 6-membered heterocyclic group containing 1 to 3 heteroatom(s) selected from nitrogen, sulfur and oxygen atoms in addition to carbon atoms [this 5- or 6-membered heterocyclic group may have a substituent selected from amino, $C_{1-6}$ alkyl-carboxamido and $C_{1-6}$ alkyl-sulfonylamino], (xiii) an optionally halogenated $C_{1-6}$ alkyl-carbonyl, (xiv) a $C_{1-6}$ alkylthio-$C_{1-6}$ alkyl-carbonyl, (xv) a $C_{1-6}$ alkylsulfinyl-$C_{1-6}$ alkyl-carbonyl, (xvi) a $C_{1-6}$ alkylsulfonyl-$C_{1-6}$ alkyl-carbonyl, (xvii) an amino-$C_{1-6}$ alkyl-carbonyl, (xviii) an optionally halogenated $C_{1-6}$ alkyl-carbonyl-amino-$C_{1-6}$ alkyl-carbonyl, (xix) a $C_{6-14}$ aryl-carbonyl, (xx) a carboxy-$C_{6-14}$ aryl-carbonyl, (xxi) an optionally $C_{1-6}$ alkyl-esterified phosphono-$C_{1-6}$ alkyl-$C_{6-14}$ aryl-carbonyl, (xxii) a (5- or 6-membered heterocyclic ring containing 1 to 3 heteroatom(s) selected from nitrogen, sulfur and oxygen atoms in addition to carbon atoms)-carbonyl, (xxiii) a (5- or 6-membered heterocyclic ring containing 1 to 3 heteroatom(s) selected from nitrogen, sulfur and oxygen atoms in addition to carbon atoms which may have a $C_{1-6}$ alkoxy-carbonyl)-$C_{1-6}$ alkyl-carbonyl, (xxiv) a $C_{6-14}$ aryl-oxy-carbonyl, (xxv) a carboxy-$C_{1-6}$ alkyl or (xxvi) a -carbamoyl],
(20) a group represented by Formula: —C(=O)$NR^cR^d$ [each of $R^c$ and $R^d$ is (i) a hydrogen atom, (ii) a $C_{1-6}$ alkyl, (iii) a (5- or 6-membered heterocyclic ring containing 1 to 3 heteroatom(s) selected from nitrogen, sulfur and oxygen atoms in addition to carbon atoms)-$C_{1-6}$ alkyl, (iv) a carboxy-$C_{1-6}$ alkyl, (v) a $C_{1-6}$ alkoxy-carbonyl-$C_{1-6}$ alkyl, (vi) a di-$C_{1-6}$ alkylamino-$C_{1-6}$ alkyl, (vii) a carbamoyl-$C_{1-6}$ alkyl, (viii) a $C_{1-6}$ alkylcarbamoyl-$C_{1-6}$ alkyl, (ix) a (5- or 6-membered heterocyclic group containing 1 to 3 heteroatom(s) selected from nitrogen, sulfur and oxygen atoms-$C_{1-6}$ alkyl carbamoyl)-$C_{1-6}$ alkyl, (x) a (5- or 6-membered heterocyclic group containing 1 to 3 heteroatom(s) selected from nitrogen, sulfur and oxygen atoms in addition to carbon atoms)-amino-$C_{1-6}$ alkyl, (xi) a sulfamoyl-$C_{6-14}$ aryl-$C_{1-6}$ alkyl, (xii) a $C_{6-14}$ aryl which may have a $C_{1-6}$ alkoxy, (xiii) a $C_{1-6}$ alkyl-$C_{6-14}$ aryl which have an optionally $C_{1-6}$ alkyl-esterified phosphono group, (xiv) a 4- to 10-membered heterocyclic ring containing 1 to 3 heteroatom(s) selected from nitrogen, sulfur and oxygen atoms in addition to carbon atoms [this heterocyclic group may have 1 to 2 substituent(s) selected from a halogen atom, $C_{1-6}$ alkyl and oxo] or (xv) a $C_{6-14}$ aryl-carbamoyl-$C_{1-6}$ alkyl;
(ii) a 5- to 14-membered heterocyclic group containing 1 to 4 heteroatom(s) selected from nitrogen, sulfur and oxygen atoms in addition to carbon atoms which may contain 1 to 3 substituent(s) selected from the following (1) to (8):
(1) a halogen atom,
(2) a $C_{1-6}$ alkyl group [this alkyl may have a substituent selected from carboxy, $C_{1-6}$ alkoxy, $C_{1-6}$ alkoxy-carbonyl, mono-$C_{1-6}$ alkyl-amino, di-$C_{1-6}$ alkyl-amino, carbamoyl, $C_{1-6}$ alkyl-carbamoyl which may have a hydroxy, 4- to 10-membered heterocyclic group containing 1 to 3 heteroatom(s) selected from nitrogen, sulfur and oxygen atoms in addition to carbon atoms which may have oxo, (4- to 10-membered heterocyclic ring containing 1 to 3 heteroatom(s) selected from nitrogen, sulfur and oxygen atoms in addition to carbon atoms)-carbamoyl, carbamoyl-$C_{1-6}$ alkyl-carbamoyl],
(3) a $C_{1-6}$ alkoxy group,
(4) a $C_{6-14}$ aryl group,
(5) a $C_{7-16}$ aralkyl group [this $C_{7-16}$ aralkyl group may have a substituent selected from carboxy, $C_{1-6}$ alkoxy-carbonyl, carbamoyl, $C_{1-6}$ alkyl-carbamoyl which may have a hydroxy, (4- to 10-membered heterocyclic ring containing 1 to 3 heteroatom(s) selected from nitrogen, sulfur and oxygen atoms in addition to carbon atoms)-carbamoyl],
(6) a 4- to 10-membered heterocyclic group containing 1 to 3 heteroatom(s) selected from nitrogen, sulfur and oxygen atoms in addition to carbon atoms [this 4- to 10-membered heterocyclic group may have a substituent selected from a $C_{1-6}$ alkyl, $C_{1-6}$ alkoxy-carbonyl, carbamoyl, oxo, 4- to 10-membered heterocyclic group containing 1 to 3 heteroatom(s) selected from nitrogen, sulfur and oxygen atoms in addition to carbon atoms],
(7) an oxo group,
(8) an oxide group;
(iii) a $C_{3-6}$ cycloalkyl group; or,
(iv) a group represented by Formula: —L'—$R^{1a'}$ (L' is methylene, carbonyl or —NH—, $R^{1a'}$ is (1) a hydrogen atom, (2) a $C_{6-14}$ aryl group which may have 1 to 5 substituent(s) selected from a $C_{1-6}$ alkyl and $C_{1-6}$ alkoxy, (3) a hydroxy group which may be substituted by a $C_{1-6}$ alkyl group, (4) a $C_{1-6}$ alkyl-amino group which may be substituted by a 4- to 10-membered heterocyclic ring containing 1 to 3 heteroatom(s) selected from nitrogen, oxygen and sulfur atoms in addition to carbon atoms, (6) a $C_{6-14}$ aryl-amino group or (7) a (4- to 10-membered heterocyclic ring containing 1 to 3 heteroatom(s) selected from nitrogen, oxygen and sulfur atoms in addition to carbon atoms)-amino group),
each of $R^2$ and $R^3$ is (1) a hydrogen atom, (2) an optionally halogenated $C_{1-6}$ alkyl group or (3) a $C_{1-6}$ alkoxy-carbonyl group,
$R^2$ and R may be taken together with the adjacent carbon atom to form a $C_{3-8}$ cycloalkane,
$R^4$ is (i) a hydrogen atom, (ii) a $C_{1-6}$ alkyl group [this $C_{1-6}$ alkyl group may have a substituent selected from (1) a halogen atom, (2) a cyano group, (3) a $C_{1-6}$ alkoxy group, (4) a hydroxy group, (5) an amino group, (6) a mono-$C_{1-6}$ alkylamino group, (7) a di-$C_{1-6}$ alkylamino group, (8) a tri-$C_{1-6}$ alkylammonium group, (9) a 4- to 10-membered heterocyclic group containing 1 to 3 heteroatom(s) selected from nitrogen, sulfur and oxygen atoms in addition to carbon atoms which may have an oxo, (10) a $C_{6-14}$ arylthio, (11) an ureido, (12) a carboxy, (13) a carbamoyl, (14) a $C_{1-6}$ alkoxy-carbonyl, (15) a mono-$C_{1-6}$ alkyl-carbamoyl, (16) a formylamino, (17) a $C_{1-6}$ alkyl-carboxamido] or (iii) a $C_{2-6}$ alkenyl group;

X is a bond, oxygen atom, sulfur atom, —NH— or —N(methyl)-, $R^5$ is, when X is a bond, then (i) a hydrogen atom, (ii) a $C_{1-6}$ alkyl group or (iii) a halogen atom, when X is an oxygen atom, then (i) a hydrogen atom, (ii) a $C_{1-6}$ alkyl group [this $C_{1-6}$ alkyl group may have a substituent selected from (1) a halogen atom, (2) a hydroxy group, (3) an amino group, (4) a carboxy, (5) a carbamoyl, (6) a $C_{1-6}$ alkoxy-carbonyl, (7) a mono-$C_{1-6}$ alkyl-carbamoyl, (8) a di-$C_{1-6}$ alkyl-carbamoyl, (9) a 4- to 10-membered heterocyclic group containing 1 to 3 heteroatom(s) selected from nitrogen, sulfur and oxygen atoms in addition to carbon atoms which may have an oxo], (iii) a $C_{2-6}$ alkenyl group [this $C_{2-6}$ alkenyl group may have a $C_{6-14}$ aryl], (iv) a $C_{2-6}$ alkynyl group, (v) a $C_{3-6}$ cycloalkyl group, (vi) a $C_{7-16}$ aralkyl group, (vii) a $C_{1-6}$ alkyl-carbonyl group, (viii) a $C_{6-14}$ aryl-carbonyl group, (ix) a $C_{1-6}$ alkoxy-carbonyl group, (x) a mono- or di-$C_{1-6}$ alkyl-thiocarbamoyl group, (xi) an optionally halogenated $C_{1-6}$ alkyl-sulfonyl group or (xii) a 4- to 10-membered heterocyclic group containing 1 to 4 heteroatom(s) selected from nitrogen, sulfur and oxygen atoms in addition to carbon atoms [this heterocyclic group may have a $C_{6-14}$ aryl], when X is a sulfur, then (i) a $C_{1-6}$ alkyl group or (ii) a mono- or di-$C_{1-6}$ alkyl-carbamoyl group, when X is —NH— or —N(methyl)-, then (i) a hydrogen atom, (ii) a $C_{1-6}$ alkyl group [this $C_{1-6}$ alkyl group may have a $C_{1-6}$ alkoxy-carbonyl], (iii) formyl, (iv) a $C_{1-6}$ alkyl-carbonyl group, (v) a $C_{1-6}$ alkoxy-carbonyl group, (vi) a carbamoyl group, (vii) a mono- or di-$C_{1-6}$ alkyl-carbamoyl group or (viii) a $C_{1-6}$ alkyl-sulfonyl group, each of $R^6$ and $R^7$ is a hydrogen atom or $C_{1-6}$ alkyl group, $R^6$ and $R^7$ may be taken together with the adjacent carbon atom to form a $C_{3-8}$ cycloalkane, each of $R^8$ and $R^9$ is a hydrogen atom or a $C_{1-6}$ alkyl group, Y is a methylene group which may have a hydroxy group or carbonyl group, n is 0 or 1.

[14] the compound according to the above-mentioned [2] wherein each of $R^2$ and $R^3$ is a $C_{1-6}$ alkyl group,

[15] the compound according to the above-mentioned [2] wherein $R^4$ is a hydrogen atom,

[16] the compound according to the above-mentioned [2] wherein each of $R^6$ and $R^7$ is a $C_{1-6}$ alkyl group,

[17] the compound according to the above-mentioned [2] wherein each of $R^8$ and $R^9$ is a hydrogen atom,

[18] the compound according to the above-mentioned [2] wherein n is 0,

[19] (i) 2-(Methylsulfinyl)-N-[3-(3,4,8,9-tetrahydro-6-methoxy-3,8,8-tetramethylfuro[2,3-h]isoquinolin-1-yl)phenyl]acetamide, (ii) N-(methylsulfonyl)-N-[3-(3,4,8,9-tetrahydro-6-methoxy-3,3,8,8-tetramethylfuro[2,3-h]isoquinolin-1-yl)phenyl]methanesulfonamide, (iii) N-[2-(4-pyridinyl)ethyl]-3-(3,4,8,9-tetrahydro-6-methoxy-3,3,8,8-tetramethylfuro[2,3-h]isoquinolin-1-yl)benzamide, (iv) N-(2-amino-2-oxoethyl)-3-(3,4,8,9-tetrahydro-6-methoxy-3,3,8,8-tetramethylfuro[2,3-h]isoquinolin-1-yl)benzamide, (v) N-methyl-3-(3,4,8,9-tetrahydro-6-methoxy-3,3,8,8-tetramethylfuro[2,3-h]isoquinolin-1-yl)benzamide, (vi) N-ethyl-3-(3,4,8,9-tetrahydro-6-methoxy-3,3,8,8-tetramethylfuro[2,3-h]isoquinolin-1-yl)benzamide, (vii) N-[3'-(3,4,8,9-tetrahydro-6-methoxy-3,3,8,8-tetramethylfuro[2,3-h]isoquinolin-1-yl)[1,1'-biphenyl]-3-yl]acetamide, (viii) N-(2-amino-1,1-dimethyl-2-oxoethyl)-3-(3,4,8,9-tetrahydro-6-methoxy-3,3,8,8-tetramethylfuro[2,3-h]isoquinolin-1-yl)benzamide, (ix) 3-(6-ethoxy-3,4,8,9-tetrahydro-3,3,8,8-tetramethylfuro[2,3-h]isoquinolin-1-yl)-N-methylbenzamide, (x) N-(2-amino-2-oxoethyl)-3-(6-ethoxy-3,4,8,9-tetrahydro-3,3,8,8-tetramethylfuro[2,3-h]isoquinolin-1-yl)benzamide, (xi) N-(2-amino-1,1-dimethyl-2-oxoethyl)-3-(6-ethoxy-3,4,8,9-tetrahydro-3,3,8,8-tetramethylfuro[2,3-h]isoquinolin-1-yl)benzamide, (xii) N-[3-(6-ethoxy-3,4,8,9-tetrahydro-3,3,8,8-tetramethylfuro[2,3-h]isoquinolin-1-yl)phenyl]methanesulfonamide, (xiii) N-(hydroxymethyl)-3-(3,4,8,9-tetrahydro-6-methoxy-3,3,8,8-tetramethylfuro[2,3-h]isoquinolin-1-yl)benzamide or its salts,

[20] a prodrug of a compound according to the above-mentioned [2],

[21] a process for producing a compound having a partial structure represented by Formula:

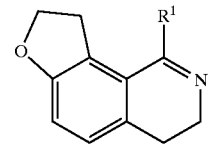

wherein $R^1$ is defined as described in the above mentioned [2], or a salt thereof, comprising:

(1) reacting a compound having a partial structure represented by Formula:

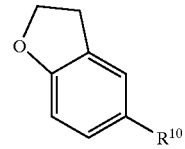

wherein $R^{10}$ is an optionally substituted vinyl group or allyl group, or a salt thereof with a compound represented by Formula: $R^1$—CN or Formula: $R^1$—CONH$_2$ wherein $R^1$ is defined as described above or a salt thereof, or, (2) reacting a compound having a partial structure represented by Formula:

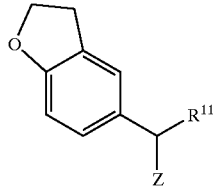

wherein $R^{11}$ is an optionally substituted methyl group, Z is an optionally substituted hydroxy group or halogen atom or a salt thereof with a compound represented by Formula: $R^1$—CN wherein $R^1$ is defined as described above or a salt thereof,

[22] a process for producing a compound according to the above-mentioned [2] comprising:
reacting a compound represented by Formula:

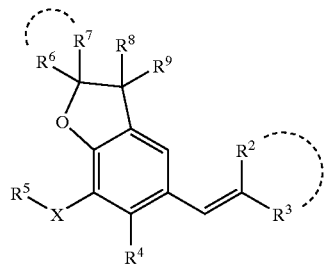

wherein each symbol is defined as described in the above-mentioned [2] or a salt thereof with a compound represented by Formula: $R^1$—CN or Formula: $R^1$—$CONH_2$ wherein $R^1$ is defined as described in the above-mentioned [2] or a salt thereof, or,
reacting a compound represented by Formula:

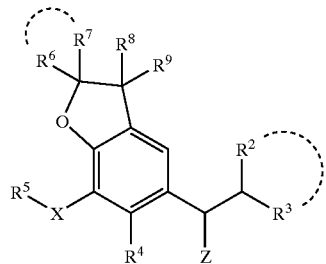

wherein Z is an optionally substituted hydroxy group or halogen atom, and other symbols are defined as described in the above-mentioned [2] or a salt thereof with a compound represented by Formula: $R^1$—CN wherein $R^1$ is defined as described in the above-mentioned [2] or a salt thereof,
[23] a phosphodiesterase IV inhibitor comprising a compound having a partial structure represented by Formula:

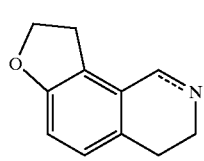

(A-1)

wherein - - - is a single bond or double bond or a salt thereof,
[24] a pharmaceutical composition comprising a compound according to the above-mentioned [1] or a salt thereof,
[25] a pharmaceutical composition comprising a compound according to the above-mentioned [2] or a salt or prodrug thereof,
[26] the pharmaceutical composition according to the above-mentioned [24] or [25] which is a phosphodiesterase IV inhibitor,
[27] the pharmaceutical composition according to the above-mentioned [23] to [26] which is a prophylactic or therapeutic agent against inflammatory diseases,
[28] the pharmaceutical composition according to the above-mentioned [23] to [26] which is a prophylactic or therapeutic agent against asthma, chronic obstructive pulmonary disease (COPD), rheumatoid arthritis, autoimmune disease or diabetes,
[29] a pharmaceutical comprising (1) a compound having a partial structure represented by Formula:

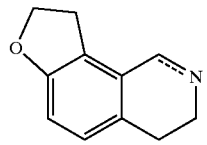

(A-1)

wherein - - - is a single bond or double bond or a salt thereof in combination with (2) a drug selected from antiasthma agents, antiallergic agents, anticholinergic agents, antiinflammatory agents, antibacterial agents, antifungal agents and antidiabetic agents,
[30] a pharmaceutical comprising (1) a compound according to the above-mentioned [1] or a salt thereof in combination with (2) a drug selected from antiasthma agents, antiallergic agents, anticholinergic agents, antiinflammatory agents, antibacterial agents, antifungal agents and antidiabetic agents,
[31] a pharmaceutical comprising (1) a compound according to the above-mentioned [2] or a salt or prodrug thereof in combination with (2) a drug selected from antiasthma agents, antiallergic agents, anticholinergic agents, antiinflammatory agents, antibacterial agents, antifungal agents and antidiabetic agents,
[32] the pharmaceutical according to the above-mentioned [29] to [31] which is a prophylactic or therapeutic agent against inflammatory diseases,
[33] the pharmaceutical according to the above-mentioned [29] to [31] which is a prophylactic or therapeutic agent against asthma, chronic obstructive pulmonary disease (COPD), rheumatoid arthritis, autoimmune disease or diabetes,
[34] *Escherichia coli* BL21/pPDE4D3 (FERM BP-7075),
[35] a method for inhibiting a phosphodiesterase IV comprising administering an effective amount of a compound having a partial structure represented by Formula:

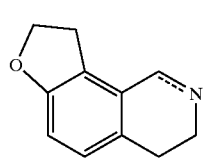

(A-1)

wherein - - - is a single bond or double bond or a salt thereof to a mammal,
[36] a method for preventing or treating inflammatory diseases comprising administering an effective amount of a compound having a partial structure represented by Formula:

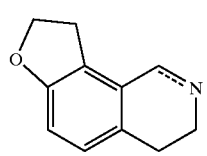

(A-1)

wherein - - - is a single bond or double bond or a salt thereof to a mammal,
[37] a method for preventing or treating asthma, chronic obstructive pulmonary disease (COPD), rheumatoid arthritis, autoimmune disease or diabetes comprising administering an effective amount of a compound having a partial structure represented by Formula:

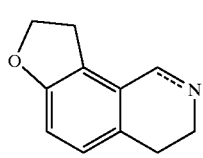

(A-1)

wherein - - - is a single bond or double bond or a salt thereof to a mammal,

[38] a method for inhibiting a phosphodiesterase IV comprising administering an effective amount of the compound according to the above-mentioned [1] or a salt thereof to a mammal,

[39] a method for preventing or treating inflammatory diseases comprising administering an effective amount of the compound according to the above-mentioned [1] or a salt thereof to a mammal,

[40] a method for preventing or treating asthma, chronic obstructive pulmonary disease (COPD), rheumatoid arthritis, autoimmune disease or diabetes comprising administering an effective amount of the compound according to the above-mentioned [1] or a salt thereof to a mammal,

[41] a method for inhibiting a phosphodiesterase IV comprising administering an effective amount of the compound according to the above-mentioned [2] or a salt or prodrug thereof to a mammal,

[42] a method for preventing or treating inflammatory diseases comprising administering an effective amount of the compound according to the above-mentioned [2] or a salt or prodrug thereof to a mammal,

[43] a method for preventing or treating asthma, chronic obstructive pulmonary disease (COPD), rheumatoid arthritis, autoimmune disease or diabetes comprising administering an effective amount of the compound according to the above-mentioned [2] or a salt or prodrug thereof to a mammal,

[44] a method for preventing or treating inflammatory diseases comprising administering (1) an effective amount of a compound having a partial structure represented by Formula:

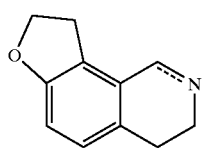

(A-1)

wherein - - - is a single bond or double bond or a salt thereof in combination with (2) an effective amount of a drug selected from antiasthma agents, antiallergic agents, anticholinergic agents, antiinflammatory agents, antibacterial agents, antifungal agents and antidiabetic agents to a mammal,

[45] a method for preventing or treating asthma, chronic obstructive pulmonary disease (COPD), rheumatoid arthritis, autoimmune disease or diabetes comprising administering (1) an effective amount of a compound having a partial structure represented by Formula:

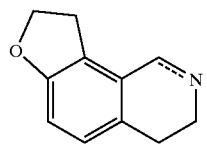

(A-1)

wherein - - - is a single bond or double bond or a salt thereof in combination with (2) an effective amount of a drug selected from antiasthma agents, antiallergic agents, anticholinergic agents, antiinflammatory agents, antibacterial agents, antifungal agents and antidiabetic agents to a mammal,

[46] a method for preventing or treating inflammatory diseases comprising administering (1) an effective amount of the compound according to the above-mentioned [1] or a salt thereof in combination with (2) an effective amount of a drug selected from antiasthma agents, antiallergic agents, anticholinergic agents, antiinflammatory agents, antibacterial agents, antifungal agents and antidiabetic agents to a mammal,

[47] a method for preventing or treating asthma, chronic obstructive pulmonary disease (COPD), rheumatoid arthritis, autoimmune disease or diabetes comprising administering (1) an effective amount of the compound according to the above-mentioned [1] or a salt thereof in combination with (2) an effective amount of a drug selected from antiasthma agents, antiallergic agents, anticholinergic agents, antiinflammatory agents, antibacterial agents, antifungal agents and antidiabetic agents to a mammal,

[48] a method for preventing or treating inflammatory diseases comprising administering (1) an effective amount of the compound according to the above-mentioned [2] or a salt or prodrug thereof in combination with (2) an effective amount of a drug selected from antiasthma agents, antiallergic agents, anticholinergic agents, antiinflammatory agents, antibacterial agents, antifungal agents and antidiabetic agents to a mammal,

[49] a method for preventing or treating asthma, chronic obstructive pulmonary disease (COPD), rheumatoid arthritis, autoimmune disease or diabetes comprising administering (1) an effective amount of the compound according to the above-mentioned [2] or a salt or prodrug thereof in combination with (2) an effective amount of a drug selected from antiasthma agents, antiallergic agents, anticholinergic agents, antiinflammatory agents, antibacterial agents, antifungal agents and antidiabetic agents to a mammal,

[50] a use of a compound having a partial structure represented by Formula:

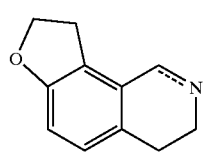

(A-1)

wherein - - - is a single bond or double bond or a salt thereof for producing a phosphodiesterase IV inhibitor,

[51] a use of a compound having a partial structure represented by Formula:

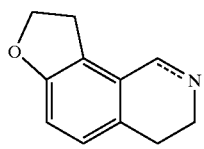
(A-1)

wherein - - - is a single bond or double bond or a salt thereof for producing a prophylactic or therapeutic agent against inflammatory diseases,

[52] a use of a compound having a partial structure represented by Formula:

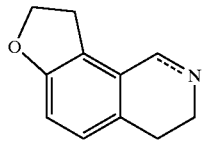
(A-1)

wherein - - - is a single bond or double bond or a salt thereof for producing a prophylactic or therapeutic agent against asthma, chronic obstructive pulmonary disease (COPD), rheumatoid arthritis, autoimmune disease or diabetes,

[53] a use of the compound according to the above-mentioned [1] or a salt thereof for producing a phosphodiesterase IV inhibitor,

[54] a use of the compound according to the above-mentioned [1] or a salt thereof for producing a prophylactic or therapeutic agent against inflammatory diseases,

[55] a use of the compound according to the above-mentioned [1] or a salt thereof for producing a prophylactic or therapeutic agent against asthma, chronic obstructive pulmonary disease (COPD), rheumatoid arthritis, autoimmune disease or diabetes,

[56] a use of the compound according to the above-mentioned [2] or a salt or prodrug thereof for producing a phosphodiesterase IV inhibitor,

[57] a use of the compound according to the above-mentioned [2] or a salt or prodrug thereof for producing a prophylactic or therapeutic agent against inflammatory diseases,

[58] a use of the compound according to the above-mentioned [2] or a salt or prodrug thereof for producing a prophylactic or therapeutic agent against asthma, chronic obstructive pulmonary disease (COPD), rheumatoid arthritis, autoimmune disease or diabetes,

[59] a compound represented by Formula:

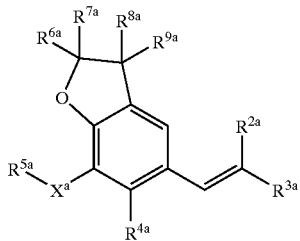

wherein each of $R^{2a}$ and $R^{3a}$ is an optionally substituted aliphatic hydrocarbon group or acyl group, $R^{4a}$ is a hydrogen atom, optionally substituted hydrocarbon group, acyl group or optionally substituted hydroxy group, $R^{5a}$ is an optionally substituted hydrocarbon group, acyl group, optionally substituted heterocyclic group or halogen atom, Each of $R^{6a}$, $R^{7a}$, $R^{8a}$ and $R^{9a}$ is a hydrogen atom or optionally substituted hydrocarbon group, $X^a$ is a bond, oxygen atom, optionally oxidized sulfur atom or optionally substituted nitrogen atom, or by Formula:

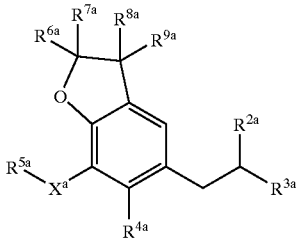

wherein each of $R^{2a}$ and $R^{3a}$ is an optionally substituted aliphatic hydrocarbon group or acyl group, $R^{4a}$ is a hydrogen atom, optionally substituted hydrocarbon group, acyl group or optionally substituted hydroxy group, $R^{5a}$ is an optionally substituted hydrocarbon group, acyl group, optionally substituted heterocyclic group or halogen atom, Each of $R^{6a}$, $R^{7a}$, $R^{8a}$ and $R^{9a}$ is a hydrogen atom or optionally substituted hydrocarbon group, $X^a$ is a bond, oxygen atom, optionally oxidized sulfur atom or optionally substituted nitrogen atom, Z is an optionally substituted hydroxy group or halogen atom, or a salt thereof,

[60] the compound according to the above-mentioned [59] wherein:

each of $R^{2a}$ and $R^{2b}$ is any of the following (i) to (ii):

(i) a $C_{1-6}$ alkyl group or $C_{3-6}$ cycloalkyl group which may have 1 to 5 substituent(s) selected from the group (hereinafter referred to as Substituent Group B) consisting of (1) a halogen atom, (2) a $C_{1-3}$ alkylenedioxy group, (3) a nitro group, (4) an optionally halogenated $C_{1-6}$ alkyl group, (5) a $C_{3-6}$ cycloalkyl group, (6) a $C_{6-14}$ aryl group, (7) an optionally halogenated $C_{1-6}$ alkoxy group, (8) an optionally halogenated $C_{1-6}$ alkylthio group, (9) a hydroxy group, (10) an amino group, (11) a mono-$C_{1-6}$ alkylamino group, (12) a mono-$C_{6-14}$ arylamino group, (13) a di-$C_{1-6}$ alkylamino group, (14) a di-$C_{6-14}$ arylamino group, (15) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl carbamoyl, $C_{6-14}$ aryl-carbamoyl, a (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, a (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, (16) an acylamino group selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (17) an acyloxy group selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (18) a 4- to 14-membered heterocyclic group having, in addition to carbon atoms, 1 to 3 heteroatom(s) selected from nitrogen, sulfur and oxygen atoms, (19) a phosphono group, (20) a $C_{6-14}$ aryloxy group, (21) a di-$C_{1-6}$ alkoxy-phosphoryl group, (22) a $C_{6-14}$ arylthio group, (23) a hydrazino group, (24) an imino group, (25) an oxo group, (26) an ureido group, (27) a $C_{1-6}$ alkyl-ureido group, (28) a di-$C_{1-6}$-alkyl-ureido group, (29) an oxide group and (30) a group formed by binding 2 or 3 groups selected from (1) to (29) listed above, (ii) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered hetero-cycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkylthiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group B described above;

$R^{4a}$ is (i) a hydrogen atom, (ii) a $C_{1-6}$ alkyl group, $C_{3-6}$ cycloalkyl group, $C_{6-14}$ aryl group or $C_{7-16}$ aralkyl group which may have 1 to 5 substituent(s) selected from Substituent Group B described above, (iii) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group B described above;

(iv) a group represented by Formula: —$OR^{4a'}$ ($R^{4a'}$ is <1> a hydrogen atom, <2> a $C_{1-6}$ alkyl group, $C_{3-6}$ cycloalkyl group, $C_{6-14}$ aryl group or $C_{7-16}$ aralkyl group which may have 1 to 5 substituent(s) selected from Substituent Group B described above, or, <3> an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group B described above);

$R^5$ is any of the following (i) to (iv):

(i) a $C_{1-6}$ alkyl group, $C_{3-6}$ cycloalkyl group, $C_{6-14}$ aryl group or $C_{7-16}$ aralkyl group which may have 1 to 5 substituent(s) selected from Substituent Group B described above, (ii) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group B described above, (iii) a 5- to 14-membered heterocyclic ring containing 1 to 4 heteroatom(s) selected from nitrogen, sulfur and oxygen atoms in addition to carbon atoms which may contain 1 to 5 substituent(s) selected from Substituent Group B described above, (iv) a halogen atom;

each of $R^{6a}$, $R^{7a}$, $R^{8a}$ and $R^{9a}$ is (i) a hydrogen atom or (ii) a $C_{1-6}$ alkyl group, $C_{3-6}$ cycloalkyl group, $C_{6-14}$ aryl group or $C_{7-16}$ aralkyl group which may have 1 to 5 substituent(s) selected from Substituent Group B described above, $X^a$ is (i) a bond, (ii) an oxygen atom, (iii) an optionally-oxidized sulfur atom, (iv) a nitrogen atom which may have a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group B described above, (v) a nitrogen atom having an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group B described above, or, (vi) a nitrogen atom having a 5- to 14-membered heterocyclic group containing 1 to 4 heteroatom(s) selected from nitrogen, sulfur and oxygen atoms in addition to carbon atoms which may contain 1 to 5 substituent(s) selected from Substituent Group B described above;

Z is (i) a group represented by Formula: —$OZ^a$ ($Z^a$ is <1> a hydrogen atom, <2> a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group B described above, or, <3> an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above) or (ii) a halogen atom group,

[61] the compound according to the above-mentioned [59] wherein:

each of $R^{2a}$ and $R^{3a}$ is (1) a $C_{1-6}$ alkyl group which may be substituted by <1> a halogen atom, <2> a hydroxy group which may be substituted by a substituent selected from a $C_{1-6}$ alkyl, $C_{1-6}$ alkyl-carbonyl, $C_{1-6}$ alkylsulfonyl and $C_{7-16}$ aralkyl, <3> an amino group which may be substituted by 1 or 2 $C_{1-6}$ alkyl, $C_{1-6}$ alkyl-carbonyl and $C_{6-14}$ aryl-carbonyl, <4> a 4- to 10-membered heterocyclic group containing 1 to 3 heteroatom(s) selected from nitrogen, oxygen and sulfur atoms in addition to carbon atoms, <5> a thio group which may be substituted by $C_{1-6}$ alkyl, <6> a $C_{1-6}$ alkyl-sulfinyl group or <7> a $C_{1-6}$ alkyl-sulfonyl group or (2) a $C_{1-6}$ alkoxy-carbonyl group, $R^{4a}$ is (i) a hydrogen atom, (ii) a $C_{1-6}$ alkyl group [this $C_{1-6}$ alkyl group may have a substituent selected from (1) a halogen atom, (2) a $C_{1-6}$ alkoxy group, (3) a hydroxy group, (4) an amino group, (5) a mono-$C_{1-6}$ alkylamino group, (6) a di-$C_{1-6}$ alkylamino group, (7) a 4- to 10-membered heterocyclic group containing 1 to 3 heteroatom(s) selected from nitrogen, sulfur and oxygen atoms in addition to-carbon atoms which may have an oxo, (8) a $C_{6-14}$ arylthio, (9) an ureido, (10) a carboxy, (11) a carbamoyl, (12) a $C_{1-6}$ alkoxy-carbonyl, (13) a mono-$C_{1-6}$ alkyl-carbamoyl, (14) a formylamino and (15) a $C_{1-6}$ alkyl-carboxamido] or (iii) a formyl group;

$X^a$ is a bond, oxygen atom, optionally oxidized sulfur atom, —NH— or —N(methyl)-, $R^{5a}$ is, when $X^a$ is a bond, then (i) a $C_{1-6}$ alkyl group or (ii) a halogen atom, when $X^a$ is an oxygen atom, then (i) a $C_{1-6}$ alkyl group [this $C_{1-6}$ alkyl group may have a substituent selected from (1) a halogen atom, (2) a hydroxy group, (3) an amino group, (4) a carboxy, (5) a carbamoyl, (6) a $C_{1-6}$ alkoxy-carbonyl, (7) a mono-$C_{1-6}$ alkyl-carbamoyl, (8) a di-$C_{1-6}$ alkyl-carbamoyl, (9) a 4- to 10-membered heterocyclic group containing 1 to 3 heteroatom(s) selected from nitrogen, sulfur and oxygen atoms in addition to carbon atoms], (ii) a $C_{3-6}$ cycloalkyl group, (iii) a $C_{7-16}$ aralkyl group, (iv) a $C_{1-6}$ alkyl-carbonyl group, (v) a $C_{6-14}$ aryl-carbonyl group, (vi) a $C_{1-6}$ alkoxy-carbonyl group, (vii) a mono- or di-$C_{1-6}$ alkyl-thiocarbamoyl group, (viii) an optionally halogenated $C_{1-6}$ alkyl-sulfonyl group or (ix) a 4- to 10-membered heterocyclic group containing 1 to 4 heteroatom(s) selected from nitrogen, sulfur and oxygen atoms in addition to carbon atoms [this heterocyclic group may have a $C_{6-14}$ aryl], when $X^a$ is an optionally oxidized sulfur, then (i) a $C_{1-6}$ alkyl group or (ii) a mono- or di-$C_{1-6}$ alkyl-carbamoyl group, when $X^a$ is —NH— or —N(methyl)-, then (i) a $C_{1-6}$ alkyl group [this $C_{1-6}$ alkyl group may have a $C_{1-6}$ alkoxy-carbonyl], (ii) formyl, (iii) a $C_{1-6}$ alkyl-carbonyl group, (iv) a $C_{1-6}$ alkoxy-carbonyl group, (v) a carbamoyl group, (vi) a mono- or di-$C_{1-6}$ alkyl-carbamoyl group or (vii) a $C_{1-6}$ alkyl-sulfonyl group, each of $R^{6a}$, $R^{7a}$, $R^{8a}$ and $R^{9a}$ is a hydrogen atom or $C_{1-6}$ alkyl group, Z is (i) a hydroxy group which may be substituted by a $C_{1-6}$ alkyl-carbonyl or (ii) a halogen atom,

[62] a use of the compound according to the above-mentioned [59] or a salt thereof for producing the compound according to the above-mentioned [2] or a salt thereof.

Furthermore, the invention also provides:

[63] a compound having a partial structure represented by Formula:

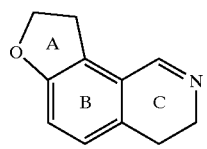

(I)

wherein each of Ring A, Ring B and Ring C may have substituents or a salt thereof,

[64] the compound according to the above-mentioned [63] wherein the substituents on Ring A, Ring B and Ring C are 1 to 5 substituent(s) selected from the group consisting of (1) an optionally substituted hydrocarbon group, (2) an optionally substituted heterocyclic group, (3) an optionally substituted amino group, (4) an acyl group, (5) an optionally substituted hydroxy group, (6) an optionally substituted sulfenyl group, (7) a halogen atom, (8) a lower alkylenedioxy group, (9) a nitro group, (10) a cyano group, (11) an optionally substituted imino group, (12) an oxo group, (13) an optionally substituted ureido group, (14) an azide group, (15) an optionally substituted amidino group, (16) an optionally substituted guanidino group, (17) an optionally substituted hydrazino group and (18) an oxide group,

[65] the compound according to the above-mentioned [64], in which the substituent is a group selected from Substituent Group A,

[66] the pharmaceutical composition according to the above-mentioned [23] wherein Compound (A-1) is a compound represented by Formula:

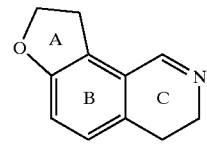

(I-1)

wherein - - - is a single bond or double bond and each of Ring A, Ring B and Ring C may have substituent(s) or a salt thereof,

[67] the pharmaceutical composition according to the above-mentioned [23] wherein Compound (A-1) is a compound represented by Formula:

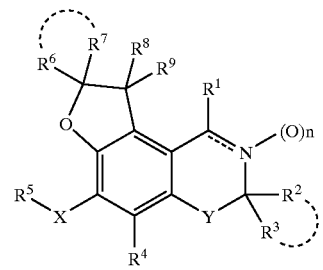

(I'-1)

wherein - - - is a single bond or double bond and other symbols are defined as described in the above-mentioned [2]

Furthermore, when any of Compounds (A), (I), (I'), (A-1), (I-1), (I'-1) or their salts contains asymmetric carbon atom in its structure, any of the optically active forms and racemic forms is encompassed in the invention, and Compounds (A), (I), (I'), (A-1), (I-1), (I'-1) or their salts may be hydrates or anhydrides.

BEST MODE FOR EMBODYING THE INVENTION

A compound according to the invention has a partial structure represented by Formula:

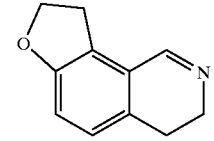

(A)

which is represented typically by Formula:

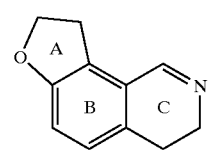

(I)

wherein each symbol is defined as described above.

In the formula shown above, each of Ring A, Ring B and Ring C may have a substitutable number of substituents in any substitutable positions.

Each of such substituents on Ring A, Ring B and Ring C is:

(1) an optionally substituted hydrocarbon group,
(2) an optionally substituted heterocyclic group, (3) an optionally substituted amino group,
(4) an acyl group,
(5) an optionally substituted hydroxy group,
(6) an optionally substituted sulfenyl group,
(7) a halogen atom (for example, fluorine, chlorine, bromine, iodine),
(8) a lower alkylenedioxy group (for example, a $C_{1-3}$ alkylenedioxy group such as methylenedioxy, ethylenedioxy, etc.),
(9) a nitro group,
(10) a cyano group,
(11) an optionally substituted imino group,
(12) an oxo group,
(13) an optionally substituted ureido group,
(14) an azide group,
(15) an optionally substituted amidino group,
(16) an optionally substituted guanidino group,
(17) an optionally substituted hydrazino group,
(18) an oxide group and the like.

A hydrocarbon group in an "optionally substituted hydrocarbon group" employed as a substituent on Ring A, Ring B and Ring C may for example be a linear or cyclic hydrocarbon group such as an alkyl group, alkenyl group, alkynyl group, cycloalkyl group, aryl group and aralkyl group, with a linear (straight or branched) or cyclic hydrocarbon group having 1 to 16 carbon atoms (e.g., aromatic hydrocarbon group, aliphatic cyclic hydrocarbon group) being preferred. Typically, those listed below are employed.

(1) Linear Hydrocarbon Groups:
a) alkyl groups [preferably, lower alkyl groups (for example, $C_{1-6}$ alkyl groups such as methyl, ethyl, propyl, isopropyl, butyl, isobutyl, sec-butyl, tert-butyl, pentyl, hexyl, etc.)],
b) alkenyl groups [preferably, lower alkenyl groups (for example, $C_{2-6}$ alkenyl groups such as vinyl, allyl, isopropenyl, 2-butenyl, 2-methyl-2-propenyl, 4-pentenyl, 5-hexenyl, etc.)],
c) alkynyl groups [preferably, lower alkynyl groups (for example, $C_{2-6}$ alkynyl groups such as propargyl, ethynyl, 2-butynyl, 2-hexynyl)], (2) Aliphatic Cyclic Hydrocarbon Groups:
a) cycloalkyl groups [preferably, lower cycloalkyl group (for example, $C_{3-6}$ cycloalkyl groups such as cyclopropyl, cyclobutyl, cyclopentyl, cyclohexyl, etc.), each of which may be fused with a benzene ring],
b) cycloalkenyl groups [preferably, lower cycloalkenyl group (for example, $C_{3-6}$ cycloalkenyl groups such as 1-cyclopropenyl, 1-cyclobutenyl, 1-cyclopentenyl, 1-cyclohexenyl, etc.), each of which may be fused with a benzene ring], (3) Aromatic Hydrocarbon Groups:
aryl groups (for example, $C_{6-14}$ aryl groups such as phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, preferably phenyl group), (4) Aralkyl Groups:
lower aralkyl groups (for example, $C_{7-16}$ aralkyl groups such as benzyl, phenethyl, diphenylmethyl, 1-naphthylmethyl, 2-naphthylmethyl, 2-phenethyl, 2,2-diphenylethyl, 1-phenylpropyl, 2-phenylpropyl, 3-phenylpropyl, 4-phenylbutyl, 5-phenylpentyl, preferably benzyl group).

A substituent on each of the hydrocarbon groups listed above which is employed preferably may for example be 1 to 5, preferably 1 to 3 group(s) selected from the group (Substituent Group A) consisting of (1) a halogen atom (for example, fluorine, chlorine, bromine, iodine), (2) a lower alkylenedioxy group (for example, a $C_{1-3}$ alkylene dioxy group such as methylenedioxy, ethylenedioxy, etc.), (3) a nitro group, (4) a cyano group, (5) an optionally halogenated lower alkyl group, (6) an optionally halogenated lower alkenyl group, (7) an optionally halogenated lower alkynyl group, (8) a lower cycloalkyl group (for example, a $C_{3-6}$ cycloalkyl group such as cyclopropyl, cyclobutyl, cyclopentyl, cyclohexyl, etc.), (9) a $C_{6-14}$ aryl group (e.g., phenyl, 2-naphthyl, etc.), (10) an optionally halogenated lower alkoxy group, (11) an optionally halogenated lower alkylthio group, (12) a hydroxy group, (13) an amino group, (14) a mono-lower alkylamino group (e.g., mono-$C_{1-6}$ alkylamino group such as methylamino, ethylamino, propylamino, isopropylamino, butylamino, etc.), (15) a mono-$C_{6-14}$ arylamino group (e.g., phenylamino, 2-naphthylamino, etc.), (16) di-lower alkylamino group (e.g., di-Cl6 alkylamino group such as dimethylamino, diethylamino, dipropylamino, dibutylamino, ethylmethylamino, etc.), (17) a di-$C_{6-14}$ arylamino group (e.g., diphenylamino, di(2-naphthyl)amino, etc.), (18) an acyl group, (19) an acylamino group, (20) an acyloxy group, (21) a 4- to 14-membered heterocyclic group (preferably 4- to 10-membered, more preferably 4- to 7-membered, especially 5- or 6-membered heterocyclic group) (e.g., 4- to 10-membered, more preferably 4- to 7-membered, especially 5- or 6-membered heterocyclic group containing 1 to 4 heteroatom(s) selected from nitrogen, sulfur, oxygen atoms and the like in addition to carbon atoms, such as 4-pyridyl, 2-thienyl, 2-furyl, 2-thiazolyl, 3-indolyl, morpholino, piperazin-1-yl, piperidino, pyrrolidin-1-yl, 2-isoindolinyl, etc.), (22) a phosphono group, (23) a $C_{6-14}$ aryloxy group (e.g., phenoxy), (24) a di-$C_{1-6}$ alkoxyphosphoryl group (e.g., dimethoxyphosphoryl, diethoxyphosphoryl, etc.), (25) a $C_{6-14}$ arylthio group (e.g., phenylthio), (26) a hydrazino group, (27) an imino group, (28) an oxo group, (29) an ureido group, (30) a $C_{1-6}$ alkyl-ureido group (e.g., methylureido, ethylureido), (31) a di-$C_{1-6}$ alkyl-ureido group (e.g., dimethylureido, diethylureido, etc.), (32) an oxide group, (33) a group formed by binding 2 or 3 groups selected from (1) to (32) listed above.

An "optionally halogenated lower alkyl group" in Substituent Group A described above may for example be a lower alkyl group which may have 1 to 3 halogen atom(s) (for example, fluorine, chlorine, bromine, iodine) (for example, a $C_{1-6}$ alkyl group such as methyl, ethyl, propyl, isopropyl, butyl, isobutyl, sec-butyl, tert-butyl, pentyl, hexyl, etc.), and those exemplified typically are methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

An "optionally halogenated lower alkenyl group" in Substituent Group A described above may for example be a lower alkenyl group which may have 1 to 3 halogen atom(s) (for example, fluorine, chlorine, bromine, iodine) (for example, a $C_{2-6}$ alkenyl group such as vinyl, allyl, isopropenyl, 2-butenyl, 2-methyl-2-propenyl, 4-pentenyl, 5-hexenyl, etc.).

An "optionally halogenated lower alkynyl group" in Substituent Group A described above may for example be a lower alkynyl group which may have 1 to 3 halogen atom(s) (for example, fluorine, chlorine, bromine, iodine) (for example, a $C_{2-6}$ alkynyl group such as propargyl, ethynyl, 2-butynyl, 2-hexynyl).

An "optionally halogenated lower alkoxy group" in Substituent Group A described above may for example be a lower alkoxy group which may have 1 to 3 halogen atom(s) (e.g., fluorine, chlorine, bromine, iodine) (for example, a $C_{1-6}$ alkoxy group such as methoxy, ethoxy, propoxy, isopropoxy, n-butoxy, isobutoxy, sec-butoxy, tert-butoxy, pentyloxy, isopentyloxy, neopentyloxy, etc.), and those exemplified typically are methoxy, ethoxy, propoxy, isopropoxy, butoxy, isobutoxy, sec-butoxy, tert-butoxy, trichloromethoxy, 3,3,3-trifluoropropoxy, 4,4,4-trifluorobutoxy, 5,5,5-trifluoropentyloxy, 6,6,6-trifluorohexyloxy and the like.

An "optionally halogenated lower alkylthio group" in Substituent Group A described above may for example be a $C_{1-6}$ alkylthio group which may have 1 to 3 halogen atoms (e.g., fluorine, chlorine, bromine, iodine) (for example, a $C_{1-6}$ alkylthio group such as methylthio, ethylthio, propylthio, isopropylthio, butylthio, isobutylthio, sec-butylthio, tert-butylthio, etc.), and those exemplified typically are methylthio, difluoromethylthio, trifluoromethylthio, ethylthio, propylthio, isopropylthio, butylthio, 4,4,4-trifluorobutylthio, pentylthio, hexylthio and the like.

An "acyl group" in Substituent Group A employed preferably may for example be formyl, carboxy, carbamoyl, $C_{1-6}$ alkyl-carbonyl (e.g., acetyl, propionyl, etc.), $C_{3-6}$ cycloalkyl-carbonyl (e.g., cyclopentylcarbonyl, cyclohexylcarbonyl, etc.), $C_{1-6}$ alkoxy-carbonyl (e.g., methoxycarbonyl, ethoxycarbonyl, isopropoxycarbonyl, tert-butoxycarbonyl, etc.), $C_{6-14}$ aryl-carbonyl (e.g., benzoyl, 2-naphthoyl, etc.), $C_{7-16}$ aralkyl-carbonyl (e.g., phenylacetyl, 3-phenylpropionyl, etc.), $C_{6-14}$ aryloxy-carbonyl (e.g., phenoxycarbonyl, 2-naphthyloxycarbonyl), $C_{7-16}$ aralkyloxy-carbonyl (e.g., benzyloxycarbonyl, 2-naphthylmethyloxycarbonyl, etc.), 5- or 6-membered heterocyclic carbonyl (e.g., (5- or 6-membered heterocyclic group containing 1 to 3 heteroatom(s) selected from nitrogen, sulfur, oxygen atoms and the like in addition to carbon atoms)-carbonyl such as 1-pyrrolidinylcarbonyl, 4-piperidylcarbonyl, 1-piperazinylcarbonyl, 2-morpholinylcarbonyl, 4-pyridylcarbonyl, 3-thienylcarbonyl, 2-furylcarbonyl, 2-thiazolylcarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g., dimethylcarbamoyl, diethylcarbamoyl, etc.), $C_{6-14}$ aryl-carbamoyl (e.g., phenylcarbamoyl, 2-naphthylcarbamoyl), 5-or 6-membered heterocyclic carbamoyl (e.g., (5- or 6-membered heterocyclic group containing 1 to 3 heteroatom(s) selected from nitrogen, sulfur, oxygen atoms and the like in addition to carbon atoms)-carbamoyl such as 1-pyrrolidinylcarbamoyl, 4-piperidylcarbamoyl, 1-piperazinylcarbamoyl, 2-morpholinylcarbamoyl, 4-pyridylcarbamoyl, 3-thienylcarbamoyl, 2-furylcarbamoyl, 2-thiazolylcarbamoyl, etc.), $C_{1-6}$ alkyl-thiocarbonyl (e.g., methylthiocarbonyl, etc.), $C_{3-6}$ cycloalkyl-thiocarbonyl (e.g., cyclopentylthiocarbonyl, cyclohexylthiocarbonyl, etc.), $C_{1-6}$ alkoxy-thiocarbonyl (e.g., methoxythiocarbonyl, methoxythiocarbonyl, propoxythiocarbonyl, butoxythiocarbonyl, etc.), $C_{6-14}$ aryl-thiocarbonyl (e.g., phenylthiocarbonyl, 2-naphthylthiocarbonyl, etc.), $C_{7-16}$ aralkyl-thiocarbonyl (e.g., benzylthiocarbonyl, phenethylthiocarbonyl), $C_{6-14}$ aryloxy-thiocarbonyl (e.g., phenoxythiocarbonyl, 2-naphthyloxythiocarbonyl), $C_{7-16}$ aralkyloxy-thiocarbonyl, (e.g., benzyloxythiocarbonyl, 2-naphthylmethyloxythiocarbonyl), 5- or 6-membered heterocyclic thiocarbonyl, (e.g., (5- or 6-membered heterocyclic group containing 1 to 3 heteroatom(s) selected from nitrogen, sulfur, oxygen atoms and the like in addition to carbon atoms)-thiocarbonyl such as 1-pyrrolidinylthiocarbonyl, 4-piperidylthiocarbonyl, 1-piperazinylthiocarbonyl, 2-morpholinylthiocarbonyl, 4-pyridylthiocarbonyl, 3-thienylthiocarbonyl, 2-furylthiocarbonyl, 2-thiazolylthiocarbonyl, etc.), thiocarbamoyl, mono-$C_{1-6}$ alkyl-thiocarbamoyl (e.g., methylthiocarbamoyl, ethylthiocarbamoyl), di-$C_{1-6}$ alkyl-thiocarbamoyl (for example, dimethylthiocarbamoyl, diethylthiocarbamoyl), $C_{6-14}$ aryl-thiocarbamoyl (e.g., phenylthiocarbamoyl, 2-naphthylthiocarbamoyl), sulfamoyl, mono-$C_{1-6}$ alkyl-sulfamoyl (e.g., methylsulfamoyl, ethylsulfamoyl), di-$C_{1-6}$ alkyl-sulfamoyl (e.g., dimethylsulfamoyl, diethylsulfamoyl, etc.), $C_{6-14}$ aryl-sulfamoyl (e.g., phenylsulfamoyl), $C_{1-6}$ alkylsulfonyl (e.g., methylsulfonyl, ethylsulfonyl, etc.), $C_{6-14}$ arylsulfonyl (e.g., phenylsulfonyl, 2-naphthylsulfonyl), $C_{1-6}$ alkylsulfinyl (e.g., methylsulfinyl, ethylsulfinyl), $C_{6-14}$ arylsulfinyl (e.g., phenylsulfinyl, 2-naphthylsulfinyl, etc.), sulfino, sulfo, $C_{1-6}$ alkoxysulfinyl (e.g., methoxysulfinyl, ethoxysulfinyl), $C_{6-14}$ aryloxysulfinyl (e.g., phenoxysulfinyl), $C_{1-6}$ alkoxysulfonyl (e.g., methoxysulfonyl, ethoxysulfonyl) and $C_{6-14}$ aryloxysulfonyl (e.g., phenoxysulfonyl). Among those listed above, a $C_{1-7}$ acyl group such as formyl, carboxy, $C_{1-6}$ alkyl-carbonyl, $C_{1-6}$ alkoxy-carbonyl, carbamoyl, mono-$C_{1-6}$ alkylcarbamoyl, sulfamoyl and mono-$C_{1-6}$ alkyl-sulfamoyl is preferred.

An "acylamino group" in Substituent Group A may for example be formylamino, optionally halogenated $C_{1-6}$ alkyl-carboxamido (e.g., acetamido, propionamido, 2-chloroacetamido, 2,2-dichloroacetamido, 2,2,2-trichloroacetamido, etc.), $C_{6-14}$ aryl-carboxamido (e.g., benzamido, 2-naphthylcarboxamido, etc.), $C_{1-6}$ alkoxy-carboxamido (e.g., methoxycarboxamido, ethoxycarboxamido, isopropoxycarboxamido, tert-butoxycarboxamido, etc.), $C_{1-6}$ alkylsulfonylamino (e.g., methylsulfonylamino, ethylsulfonylamino, etc.), bis($C_{1-6}$ alkylsulfonyl)amino (e.g., bis(methylsulfonyl)amino, bis (ethylsulfonyl)amino), $C_{6-14}$ arylsulfonylamino (e.g., phenylsulfonylamino, 2-naphthylsulfonylamino, etc.) and the like. Among those listed above, a $C_{1-7}$ acylamino group such as formylamino, optionally halogenated $C_{1-6}$ alkyl-carboxamido, $C_{1-6}$ alkoxy-carboxamido, $C_{1-6}$ alkylsulfonylamino and bis($C_{1-6}$ alkylsulfonyl)amino is preferred.

An "acyloxy group" in Substituent Group A described above may for example be a $C_{1-6}$ alkyl-carbonyloxy (e.g., acetyloxy, propionyloxy, etc.), $C_{6-14}$ aryl-carbonyloxy (e.g., benzoyloxy, 2-naphthoyloxy, etc.), $C_{1-6}$ alkoxy-carbonyloxy (e.g., methoxycarbonyloxy, ethoxycarbonyloxy, isopropoxycarbonyloxy, tert-butoxycarbonyloxy, etc.), mono-$C_{1-6}$ alkyl-carbamoyloxy (e.g., methylcarbamoyloxy, ethylcarbamoyloxy, etc.), di-$C_{1-6}$ alkyl-carbamoyloxy (e.g., dimethylcarbamoyloxy, diethylcarbamoyloxy, etc.) and $C_{6-14}$ aryl-carbamoyloxy (e.g., phenylcarbamoyloxy, 2-naphthylcarbamoyloxy, etc.). Among those listed above, a $C_{2-7}$ acyloxy such as a $C_{1-6}$ alkyl-carbonyloxy and $C_{1-6}$ alkoxy-carbonyloxy is preferred.

A group formed by binding 2 or 3 groups selected from (1) to (32) listed above in Substituent Group A described above may for example be:

(33a) a substituted $C_{1-6}$ alkyl group [this $C_{1-6}$ alkyl group has a substituent selected from cyano, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, 5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl, etc.)-$C_{1-6}$ alkyl-carbamoyl, $C_{1-6}$ alkylsulfonylamino, $C_{1-6}$ alkoxy-carbonyl and carboxy, etc.], (33b) a substituted $C_{6-14}$ aryl group [this $C_{6-14}$ aryl group has a substituent selected from amino, optionally halogenated $C_{1-6}$ alkyl-carbonylamino, ureido, $C_{1-6}$ alkylsulfonylamino, $(C_{1-6}$ alkyl)$(C_{1-6}$ alkylsulfonyl) amino and $C_{1-6}$ alkoxy-carbonyl-$C_{1-6}$ alkylamino, etc.], (33c) a $C_{1-6}$ alkoxy-$C_{6-14}$ aryl-$C_{1-6}$ alkoxy group, (33d) a 5- to 14-membered heterocyclic group containing 1 to 4 heteroatom(s) selected from nitrogen, sulfur, oxygen atoms and the like in addition to carbon atoms which has a substituent [this heterocyclic group has a substituent selected from oxo, carboxy-$C_{1-6}$ alkyl, $C_{1-6}$ alkyl-carbonyloxy-$C_{1-6}$ alkyl, $C_{1-6}$ alkyl, $C_{1-6}$ alkoxy-carbonyl-$C_{1-6}$ alkyl and $C_{1-6}$ alkyl-carbamoyl-$C_{1-6}$ alkyl], (33e) a group represented by Formula: —NR$^{12}$R$^{13}$ [each of R$^{12}$ and R$^{13}$ is (i) a 5- or 6-membered heterocyclic ring (e.g., 5- or 6-membered heterocyclic ring containing 1 to 3 heteroatom(s) selected from nitrogen, sulfur, oxygen atoms and the like in addition to carbon atoms)-$C_{1-6}$ alkyl, (ii) a $C_{1-6}$ alkoxy-carbonyl-$C_{1-6}$ alkyl, (iii) a di-$C_{1-6}$ alkylamino-methylene-sulfamoyl-$C_{1-6}$ alkyl, (iv) a carbamoyl-$C_{1-6}$ alkyl, (v) a sulfamoyl-$C_{1-6}$ alkyl, (vi) a $C_{1-6}$ alkyl-sulfonyl, (vii) a $C_{1-6}$ alkoxy-carbonyl, (viii) di-$C_{1-6}$ alkoxy-carbonyl-$C_{2-6}$ alkenyl, (ix) a 5- or 6-membered heterocyclic ring (e.g., 5- or 6-membered heterocyclic group containing 1 to 3 heteroatom(s) selected from nitrogen, sulfur, oxygen atoms and the like in addition to carbon atoms) [this 5- or 6-membered heterocyclic group may have a substituent selected from amino, $C_{1-6}$ alkyl-carboxamido, $C_{1-6}$ alkyl-sulfonylamino and the like], (x) an optionally halogenated $C_{1-6}$ alkyl-carbonyl, (xi) a $C_{1-6}$ alkylthio-$C_{1-6}$ alkyl-carbonyl, (xii) a $C_{1-6}$ alkylsulfinyl-$C_{1-6}$ alkyl-carbonyl, (xiii) a $C_{1-6}$ alkylsulfonyl-$C_{1-6}$ alkyl-carbonyl, (xiv) an amino-$C_{1-6}$ alkyl-carbonyl, (xv) an optionally halogenated $C_{1-6}$ alkyl-carbonyl-amino-$C_{1-6}$ alkyl-carbonyl, (xvi) a $C_{6-14}$ aryl-carbonyl (xvii) a carboxy-$C_{6-14}$ aryl-carbonyl, (xviii) an optionally $C_{1-6}$ alkyl-esterified phosphono-$C_{1-6}$ alkyl-$C_{6-14}$ aryl-carbonyl, (xix) (5- or 6-membered heterocyclic ring (e.g., 5- or 6-membered heterocyclic group containing 1 to 3 heteroatom(s) selected from nitrogen, sulfur, oxygen atoms) which may have a $C_{1-6}$ alkoxy-carbonyl)-carbonyl, (xx) a 5- or 6-membered heterocyclic ring (e.g., 5- or 6-membered heterocyclic group containing 1 to 3 heteroatom(s) selected from nitrogen, sulfur, oxygen atoms and the like in addition to carbon atoms)-$C_{1-6}$ alkyl-carbonyl, (xxi) a $C_{6-14}$ aryl-oxy-carbonyl, (xxii) a carboxy-$C_{1-6}$ alkyl, (xxiii) a carbamoyl and the like], (33f) a group represented by Formula: —CO—Hal (Hal is a halogen atom), (33 g) a substituted sulfamoyl group [this sulfamoyl group has a substituent selected from carbamoyl-$C_{1-6}$ alkyl, (5- or 6-membered heterocyclic ring)-$C_{1-6}$ alkyl], (33h) a group represented by Formula: —C(=O)NR$^{14}$R$^{15}$ [each of R$^{14}$ and R$^{15}$ is (i) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl, imidazolyl, etc.))-$C_{1-6}$ alkyl, (ii) a carboxy-$C_{1-6}$ alkyl, (iii) a $C_{1-6}$ alkoxy-carbonyl-$C_{1-6}$ alkyl-, (iv) a di-$C_{1-6}$ alkylamino-$C_{1-6}$ alkyl, (v) a carbamoyl-$C_{1-6}$ alkyl, (vi) a $C_{1-6}$ alkylcarbamoyl-$C_{1-6}$ alkyl, (vii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-$C_{1-6}$ alkylcarbamoyl-$C_{1-6}$ alkyl, (viii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-amino-$C_{1-6}$ alkyl, (ix) a sulfamoyl-$C_{6-14}$ aryl-$C_{1-6}$ alkyl, (x) a $C_{6-14}$ aryl which may have a $C_{1-6}$ alkoxy, (xi) an optionally $C_{1-6}$ alkyl-esterified phosphono-$C_{1-6}$ alkyl-$C_{6-14}$ aryl, (xii) a 4- to 10-membered heterocyclic group (e.g., 4- to 10-membered heterocyclic ring containing 1 to 3 heteroatom(s) selected from nitrogen, sulfur, oxygen atoms and the like in addition to carbon atoms) [this 4- to 10-membered heterocyclic group may have 1 to 2 substituent(s) selected from a halogen atom, $C_{1-6}$ alkyl, oxo and the like], (xiii) a $C_{6-14}$ aryl-carbamoyl-$C_{1-6}$ alkyl and the like. As R$^{14}$, a hydrogen atom is preferred].

An "optionally substituted heterocyclic group" employed as a substituent on Ring A, Ring B and Ring C may for example be a 4- to 14-membered heterocyclic group containing 1 to 4 (preferably 1 to 3) heteroatom(s) selected from nitrogen, sulfur, oxygen atoms and the like in addition to carbon atoms, and those exemplified typically are (a) a 4- to 14-membered aromatic heterocyclic group, (b) a 4- to 14-membered aliphatic heterocyclic group, (c) a bicyclic or tricyclic fused cyclic group of 4- to 14-membered heterocyclic ring(s) with benzene ring(s) and the like.

Said 4- to 14-membered aromatic heterocyclic group may for example be a 4- to 14-membered aromatic heterocyclic group containing 1 to 4 (preferably 1 to 3) heteroatom(s) selected from nitrogen, sulfur, oxygen atoms and the like in addition to carbon atoms, and those exemplified typically are thiophene, furan, indolizine, pyrrole, imidazole, triazole, thiazole, oxazole, pyrazole, pyridine, pyridine-N-oxide, pyrazine, pyrimidine, pyridazine, purine, 4H-quinolizine, naphthyridine, isothiazole, isoxazole, furazane, etc. Among them, pyridine, thiophene, furan, etc. are preferred.

Said 4- to 14-membered aliphatic heterocyclic group may for example be a 4- to 14-membered aliphatic heterocyclic group containing 1 to 4 (preferably 1 to 3) heteroatom(s) selected from nitrogen, sulfur, oxygen atoms and the like in addition to carbon atoms, and those exemplified typically are pyrrolidine, piperidine, piperazine, morpholine, thiomorpholine, 1,2-dihydropyridine, imidazolidine and the like.

Said bicyclic or tricyclic fused cyclic group of 4- to 14-membered heterocyclic ring(s) with benzene ring(s) may for example be a bicyclic or tricyclic fused cyclic group each containing 1 to 4 (preferably 1 to 3) heteroatom(s) selected from nitrogen, sulfur, oxygen atoms and the like in addition to carbon atoms with benzene rings, and those exemplified typically are benzo[b]thiophene, benzofuran, 1H-benzimidazole, benzoxazole, benzothiazole, 1,2-benzisothiazole, naphtho[2,3-b]thiophene, thianthrene, xanthene, phenoxathiin, indole, isoindole, 1H-indazole, isoquinoline, quinoline, phthalazine, quinoxaline, quinazoline, cinnoline, carbazole, β-carboline, phenanthridine, acridine, phenazine, phenothiazine, phenoxazine, isochroman, dihydrobenzofuran and the like.

Substituents on any of the heterocyclic groups listed above may be 1 to 5, preferably 1 to 3 group(s) selected from Substituent Group A described above.

An "optionally substituted amino group" employed as a substituent on Ring A, Ring B and Ring C may for example be an amino group which may have 1 or 2 substituent(s) selected from an "optionally substituted hydrocarbon group" described above, an "optionally substituted heterocyclic group" described above and an "acyl group" in Substituent Group A (this "acyl group" may further have 1 to 5, preferably 1 to 3 substituent(s) selected from Substituent Group A).

An "acyl group" as a substituent on Ring A, Ring B and Ring C is one similar to an "acyl group" in Substituent Group A described above. Such an "acyl group" may further have 1 to 5, preferably 1 to 3 substituent(s) selected from Substituent Group A.

A substituent on an "optionally substituted hydroxy group", "optionally substituted sulfenyl group", "optionally substituted imino group", "optionally substituted ureido group", "optionally substituted amidino group", "optionally substituted guanidino group" and "optionally substituted hydrazino group" employed as a substituent on Ring A, Ring B and Ring C is an "optionally substituted hydrocarbon group" described above, an "optionally substituted heterocyclic group" described above and an "acyl group" in Substituent Group A (this "acyl group" may further have 1 to 5, preferably 1 to 3 substituent(s) selected from Substituent Group A).

A compound in which each of Ring A, Ring B and Ring C has a substituent is typically a compound represented by Formula:

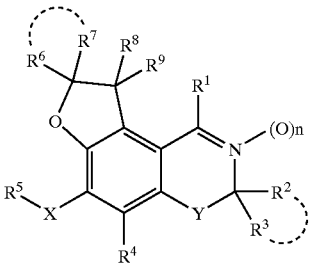

(I')

wherein each symbol is defined as described above.

In the formula shown above, $R^1$ is (1) a hydrogen atom, (2) an optionally substituted hydrocarbon group, (3) an optionally substituted heterocyclic group or (4) an optionally substituted amino group.

An "optionally substituted hydrocarbon group" represented by $R^1$ may be one similar to an "optionally substituted hydrocarbon group" exemplified as a substituent on Ring A.

An "optionally substituted heterocyclic group" represented by $R^1$ may be one similar to an "optionally substituted heterocyclic group" exemplified as a substituent on Ring A.

An "optionally substituted amino group" represented by $R^1$ may be one similar to an "optionally substituted amino group" exemplified as a substituent on Ring A.

Preferably, $R^1$ is (1) an optionally substituted aromatic hydrocarbon group, (2) an optionally substituted heterocyclic group, (3) an optionally substituted alicyclic hydrocarbon group, (4) a group represented by Formula: —L—$R^{1a}$ wherein L is methylene, carbonyl or an optionally substituted nitrogen atom, $R^{1a}$ is a hydrogen atom, optionally substituted aromatic group, optionally substituted hydroxy group or optionally substituted amino group.

Each of an "optionally substituted aromatic hydrocarbon group" and "optionally substituted heterocyclic group" is preferably a group represented by Formula:

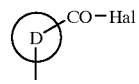

wherein $R^{1b}$ is a hydrogen atom, optionally substituted hydrocarbon group or optionally substituted heterocyclic group, Ring D is an optionally substituted aromatic hydrocarbon ring or optionally substituted heterocyclic ring, E is a bond, methylene, oxygen atom, optionally oxidized sulfur atom, optionally substituted nitrogen atom or group represented by Formula :—CS—O—, —CO—O—, —S—CO—, —(CH$_2$)$_k$—CO—, —NR$^{1c}$—CO—(CH$_2$)$_m$—, —NR$^{1c}$—SO$_2$—(CH$_2$)$_m$—, —SO$_2$—NR$^{1c}$—(CH$_2$)$_m$—, —O—CS—NR$^{1c}$—(CH$_2$)$_m$—, —NR$^{1c}$—CO—NR$^{1c}$—(CH$_2$)$_m$—, —NR$^{1c}$—CO—CH$_2$—(CH$_2$)$_m$—NR$^{1c}$— wherein $R^{1c}$ is a hydrogen atom, optionally substituted alkyl group or acyl group, k is 0 or 1, m is an integer of 0 to 3, or a group represented by Formula:

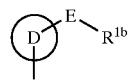

wherein Hal is a halogen atom, Ring D is defined as described above.

An "aromatic hydrocarbon group" as a preferred group of $R^1$ may for example be a monocyclic or fused polycyclic aromatic hydrocarbon group having 6 to 14 carbon atoms (C$_{6-14}$ aryl group). Preferably, a C$_{6-14}$ aryl may for example be phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl and the like, with phenyl, 1-naphthyl and 2-naphthyl, especially phenyl being preferred especially.

As substituents on this "aromatic hydrocarbon group", 1 to 5, preferably 1 to 3 groups selected from Substituent Group A are employed. Among such substituents, one employed preferably is:

(1) a halogen atom,
(2) a nitro group,
(3) a C$_{1-6}$ alkyl group (methyl, isopropyl, tert-butyl and the like), [this C$_{1-6}$ alkyl group may have a substituent selected from a halogen atom, cyano, carbamoyl, C$_{1-6}$ alkyl-carbamoyl, C$_{1-6}$ alkyl-carbonyloxy, C$_{1-6}$ alkoxy-carbonyl-C$_{1-6}$ alkyl-carbamoyl, (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms))-C$_{1-6}$ alkyl-carbamoyl, C$_{1-6}$ alkylsulfonylamino, C$_{1-6}$ alkoxy-carbonyl, carboxy and the like],
(4) a C$_{3-6}$ cycloalkyl group (e.g., cyclohexyl),
(5) a C$_{6-14}$ aryl group (e.g., phenyl), [this C$_{6-14}$ aryl group may have a substituent selected from amino, carboxy, C$_{1-6}$ alkoxy-carbonyl, carbamoyl, mono- or di-C$_{1-6}$ alkylcarbamoyl, formylamino, C$_{1-6}$ alkyl-carbonylamino which may have a halogen atom or carboxy (e.g., acetylamino, propionylamino, trifluoroacetylamino, pivaloylamino), C$_{6-14}$ aryl-carbonylamino (e.g., benzoylamino), C$_{1-6}$ alkoxy-carbonylamino (e.g., methoxycarbonylamino), ureido, mono- or di-C$_{1-6}$ alkylureido, C$_{1-6}$ alkylsulfonylamino (e.g., methylsulfonylamino), (C$_{1-6}$ alkyl)(C$_{1-6}$ alkylsulfonyl)amino (e.g., methyl(methylsulfonyl)amino), (C$_{1-6}$ alkyl)(C$_{1-6}$ alkyl-carbonyl)amino (e.g., methyl(acetyl)amino), C$_{1-6}$ alkoxy-carbonyl-C$_{1-6}$ alkylamino (e.g., 2-ethoxycarbonyl-2-propylamino), C$_{7-15}$ aralkyloxy-carbonylamino (e.g., benzyloxycarbonylamino), C$_{1-6}$ alkyl-carbonylamino-C$_{1-6}$ alkyl-carbonylamino (e.g., acetylaminoacetylamino), C$_{1-6}$ alkylthio-C$_{1-6}$ alkyl-carbonylamino (e.g., methylthioacetylamino), C$_{1-6}$ alkylsulfinyl-C$_{1-6}$ alkyl-carbonylamino (e.g., methylsulfinylacetylamino), C$_{1-6}$ alkyl-sulfonyl-C$_{1-6}$ alkyl-carbonylamino (e.g., methylsulfonylacetylamino), $C_{6-14}$ aryloxy-carbonylamino (e.g., phenoxycarbonylamino), hydroxy-$C_{1-6}$ alkyl-carbamoyl (e.g., hydroxymethylcarbamoyl, hydroxyethylcarbamoyl) and the like, and may have a substituent selected especially from amino, carboxy, $C_{1-6}$ alkoxy-carbonyl, carbamoyl, mono- or di-$C_{1-6}$ alkylcarbamoyl, formylamino, $C_{1-6}$ alkyl-carbonylamino which may have a halogen atom or carboxy (e.g., acetylamino, propionylamino, trifluoroacetylamino, pivaloylamino), $C_{1-6}$ alkoxy-carbonylamino (e.g., methoxycarbonyl-amino), ureido, $C_{1-6}$ alkylsulfonylamino (e.g., methylsulfonylamino), ($C_{1-6}$ alkyl)($C_{1-6}$ alkylsulfonyl) amino (e.g., methyl(methylsulfonyl)amino), ($C_{1-6}$ alkyl) ($C_{1-6}$ alkyl-carbonyl)amino (e.g., methyl(acetyl)amino), $C_{1-6}$ alkoxy-carbonyl-$C_{1-6}$ alkylamino (e.g., 2-ethoxycarbonyl-2-propylamino), $C_{7-15}$ aralkyloxy-carbonylamino (e.g., benzyloxycarbonyl- amino) and the like]

(6) a $C_{1-6}$ alkoxy group which may have a halogen atom or $C_{1-6}$ alkoxy-$C_{6-14}$ aryl (e.g., methoxy, trifluoromethoxy, isopropoxy, 2-(4-methoxyphenyl)ethoxy), (7) a $C_{6-14}$ aryloxy group (e.g., phenoxy), (8) a $C_{1-6}$ alkylthio group which may have a carbamoyl (e.g., methylthio, carbamoylmethylthio), (9) a $C_{1-6}$ alkylsulfinyl group which may have a carbamoyl (e.g., methylsulfinyl, carbamoylmethylsulfinyl),

(10) a $C_{6-14}$ arylthio group (e.g., phenylthio),

(11) a hydroxy group,

(12) a 4- to 14-membered heterocyclic group containing 1 to 4 heteroatom(s) selected from nitrogen, sulfur, oxygen atoms and, the like in addition to carbon atoms (e.g., pyrrolidinyl, piperidyl, isoindolinyl, furyl, thienyl, pyridyl, quinolyl, benzofuranyl, pyrimidinyl, tetrazolyl, imidazolidinyl, isothiazolidinyl, thiadiazolidinyl, azethinyl, etc.), [this heterocyclic group may have a substituent selected from oxo, carboxy-$C_{1-6}$ alkyl, $C_{1-6}$ alkyl-carbonyloxy-$C_{1-6}$ alkyl, $C_{1-6}$ alkyl, $C_{1-6}$ alkoxy-carbonyl-$C_{1-6}$ alkyl, $C_{1-6}$ alkoxy-carbonyl, carbamoyl-$C_{1-6}$ alkyl, $C_{1-6}$ alkyl-carbamoyl-$C_{1-6}$ alkyl, etc.],

(13) a carboxy group,

(14) a group represented by Formula: —CO—Hal (Hal is a halogen atom) (e.g., chloroformyl),

(15) a $C_{1-6}$ alkyl-carbonyl group (e.g., acetyl),

(16) a $C_16$ alkyl-sulfonyl group (e.g., methylsulfonyl),

(17) a $C_{1-6}$ alkoxy-carbonyl group (e.g., methoxycarbonyl),

(18) a sulfamoyl group [this sulfamoyl group may have 1 or 2 substituent(s) selected from $C_{1-6}$ alkyl, carbamoyl-$C_{1-6}$ alkyl, $C_{1-6}$ alkoxy-carbonyl-$C_{1-6}$ alkyl, (5- to 7-membered heterocyclic group which may have an oxo groups (e.g., 5- to 7-membered heterocyclic group containing 1 to 3 heteroatom(s) selected from nitrogen, sulfur, oxygen atoms and the like in addition to carbon atoms such as pyridyl, pyrrolidinyl hexahydroazepinyl))-$C_{1-6}$ alkyl, $C_{1-6}$ alkyl-carbonylamino-$C_{6-14}$ aryl],

(19) a group represented by Formula: —NR$^a$R$^b$ [each of R$^a$ and R$^b$ is (i) a hydrogen atom, (ii) a $C_{1-6}$ alkyl, (iii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-$C_{1-6}$ alkyl, (iv) a $C_{1-6}$ alkoxy-carbonyl-$C_{1-6}$ alkyl, (v) a di-$C_{1-6}$ alkylamino-methylene-sulfamoyl-$C_{1-6}$ alkyl, (vi) a carbamoyl-$C_{1-6}$ alkyl, (vii) a sulfamoyl-$C_{1-6}$ alkyl, (viii) a $C_{1-6}$ alkyl-sulfonyl, (ix) a $C_{1-6}$ alkoxy-carbonyl, (x) a di-$C_{1-6}$ alkoxy-carbonyl-$C_{2-6}$ alkenyl, (xi) a $C_{6-14}$ aryl, (xii) a 5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl), [this 5- or 6-membered heterocyclic group may have a substituent selected from amino, $C_{1-6}$ alkyl-carboxamido and $C_{1-6}$ alkyl-sulfonylamino and the like], (xiii) an optionally halogenated $C_{1-6}$ alkyl-carbonyl, (xiv) a $C_{1-6}$ alkylthio-$C_{1-6}$ alkyl-carbonyl, (xv) a $C_{1-6}$ alkylsulfinyl-$C_{1-6}$ alkyl-carbonyl, (xvi) a $C_{1-6}$ alkylsulfonyl-$C_{1-6}$ alkyl-carbonyl, (xvii) an amino-$C_{1-6}$ alkyl-carbonyl, (xviii) an optionally halogenated $C_{1-6}$ alkyl-carbonyl-amino-$C_{1-6}$ alkyl-carbonyl, (xix) a $C_{6-14}$ aryl-carbonyl, (xx) a carboxy-$C_{6-14}$ aryl-carbonyl, (xxi) an optionally $C_{1-6}$ alkyl-esterified phosphono-$C_{1-6}$ alkyl-$C_{6-14}$ aryl-carbonyl, (xxii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyrrolidinyl, pyridyl) which may have a halogen atom, oxo or a $C_{1-6}$ alkoxy-carbonyl)-carbonyl, (xxiii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-$C_{1-6}$ alkyl-carbonyl, (xxiv) a $C_{6-14}$ aryl-oxy-carbonyl, (xxv) a carboxy-$C_{1-6}$ alkyl, (xxvi) a carbamoyl, (xxvii) an optionally halogenated $C_{1-6}$ alkylcarbamoyl, (xxviii) a $C_{6-14}$ arylcarbamoyl which may have a $C_{1-6}$ alkyl-carbonylamino, (xxix) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-carbamoyl, (xxx) a $C_{2-6}$ alkenyl-carbonyl, (xxxi) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyrrolidinyl) which may have an oxo group)-amino-$C_{1-6}$ alkyl-carbonyl, (xxxii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyrrolidinyl) which may have an oxo group)($C_{1-6}$ alkyl) amino-$C_{1-6}$ alkyl-carbonyl, (xxxiii) a (5- or 6-membered heterocyclic ring (e.g., 5- or 6-membered heterocyclic ring-containing 1 to 3 heteroatom(s) selected from nitrogen, sulfur, oxygen atoms and the like in addition to carbon atoms such as pyrrolidinyl) which may have an oxo group) ($C_{1-6}$ alkylcarbonyl) amino-$C_{1-6}$ alkyl-carbonyl, (xxxiv) a $C_{1-6}$ alkylthio-$C_{1-6}$ alkylcarbonyl (sulfur atom may be oxidized), (xxxv) an optionally halogenated $C_{1-6}$ alkylsulfonyl, (xxxvi) a sulfamoyl, (xxxvii) a $C_{1-6}$ alkylsulfamoyl and the like],

(20) a group represented by Formula: —C(=O)NR$^c$R$^d$ [each of R$^c$ and R$^d$ is (i) a hydrogen atom, (ii) a $C_{1-6}$ alkyl, (iii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl, imidazolyl))-$C_{1-6}$ alkyl, (iv) a carboxy-$C_{1-6}$ alkyl, (v) a $C_{1-6}$ alkoxy-carbonyl-$C_{1-6}$ alkyl, (vi) a di-$C_{1-6}$ alkylamino-$C_{1-6}$ alkyl, (vii) a carbamoyl-$C_{1-6}$ alkyl, (viii) a $C_{1-6}$ alkylcarbamoyl-$C_{1-6}$ alkyl, (ix) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-$C_{1-6}$ alkylcarbamoyl-$C_{1-6}$ alkyl, (x) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-amino-$C_{1-6}$ alkyl, (xi) a sulfamoyl-$C_{6-14}$ aryl-$C_{1-6}$ alkyl, (xii) a $C_{6-14}$ aryl which may have a $C_{1-6}$ alkoxy, (xiii) an optionally $C_{1-6}$ alkyl-esterified phosphono-$C_{1-6}$ alkyl-$C_{6-14}$ aryl, (xiv) a 4- to 10-membered heterocyclic group (e.g., 4- to 10-membered heterocyclic ring containing 1 to 3 heteroatom(s) selected from nitrogen, sulfur, oxygen atoms and the like in addition to carbon atoms such as azethinyl, pyrrolidinyl, piperidinyl, hexahydroazepinyl, pyridyl, pyrimidinyl, pyrazinyl, pyridazinyl, 1-azabicyclo[2.2.2]octo-3-yl) [this 4- to 10-membered heterocyclic group may have 1 to 2 substituent(s) selected from a halogen atom, $C_{1-6}$ alkyl and oxo], (xv) a $C_{6-14}$ aryl-carbamoyl-$C_{1-6}$ alkyl, (xvi) a hydroxy-$C_{1-6}$ alkyl or (xvii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyrrolidinyl, pyridyl) which may have a oxo group)-carbamoyl-$C_{1-6}$ alkyl; and $R^c$ is preferably a hydrogen atom],

(21) a cyano group,
(22) a mono- or di-$C_{1-6}$ alkylcarbamoylthio group (e.g., dimethylcarbamoylthio),
(23) a mono- or di-$C_{1-6}$ alkylthiocarbamoyloxy group (e.g., dimethylthiocarbamoyloxy).

A "heterocyclic group" as a preferred group $R^1$ is preferably pyridyl, thienyl, furyl, imidazolyl, thiazolyl, quinolyl, 1,2-dihydropyridyl, dihydrobenzofuranyl, benzodioxolyl, benzothiazolyl, piperidyl, piperazinyl and the like, with pyridyl and 1,2-dihydropyridyl being preferred especially.

Preferred substituents on this "heterocyclic group" may for example be 1 to 5, preferably 1 to 3 groups selected from:
(1) a halogen atom,
(2) a $C_{1-6}$ alkyl group (e.g., methyl, ethyl, etc.) [this alkyl may have a substituent selected from carboxy, $C_{1-6}$ alkoxy, $C_{1-6}$ alkoxy-carbonyl, mono-$C_{1-6}$ alkyl-amino, di-$C_{1-6}$ alkyl-amino, carbamoyl, $C_{1-6}$ alkyl-carbamoyl which may have a hydroxy, 4- to 10-membered heterocyclic group (e.g., 4- to 10-membered heterocyclic group containing 1 to 3 heteroatom(s) selected from nitrogen, sulfur, oxygen atoms and the like in addition to carbon atoms such as pyridyl, quinolyl, etc.) which may have oxo, (4- to 10-membered heterocyclic group (e.g., 4- to 10-membered heterocyclic group containing 1 to 3 heteroatom(s) selected from nitrogen, sulfur, oxygen atoms and the like in addition to carbon atoms such as pyridyl, quinolyl))-carbamoyl, carbamoyl-$C_{1-6}$ alkyl-carbamoyl, etc.],
(3) a $C_{1-6}$ alkoxy group (e.g., methoxy),
(4) a $C_{6-14}$ aryl group (e.g., phenyl),
(5) a $C_{7-16}$ aralkyl group (e.g., benzyl) [this $C_{7-16}$ aralkyl group may have a substituent selected from carboxy, $C_{1-6}$ alkoxy-carbonyl, carbamoyl, $C_{1-6}$ alkyl-carbamoyl which may have a hydroxy, (4- to 10-membered heterocyclic group (e.g., 4- to 10-membered heterocyclic group containing 1 to 3 heteroatom(s) selected from nitrogen, sulfur, oxygen atoms and the like in addition to carbon atoms such as pyridyl))-carbamoyl and the like],
(6) a 4- to 10-membered heterocyclic group (e.g., 4- to 10-membered heterocyclic group containing 1 to 3 heteroatom(s) selected from nitrogen, sulfur, oxygen atoms and the like in addition to carbon atoms such as pyridyl, quinolyl, isoquinolyl, etc.) [this 4- to 10-membered heterocyclic group may have a substituent selected from a $C_{1-6}$ alkyl, $C_{1-6}$ alkoxy-carbonyl, carbamoyl, oxo, 4- to 10-membered heterocyclic group (e.g., 4- to 10-membered heterocyclic group containing 1 to 3 heteroatom(s) selected from nitrogen, sulfur, oxygen atoms and the like in addition to carbon atoms such as pyridyl, etc.)],
(7) an oxo group,
(8) an oxide group.

A heterocyclic group whose $R^1$ has an oxide group is preferably N-oxidized pyridyl and the like.

An "alicyclic hydrocarbon group" as a preferred group $R^1$ is a $C_{3-6}$ cycloalkyl such as cyclopropyl, cyclobutyl, cyclopentyl and cyclohexyl, etc., with cyclopentyl and cyclohexyl being preferred especially.

This "alicyclic hydrocarbon group" may have a substituent similar to a substituent which may be possessed by a hydrocarbon group represented by $R^1$ described above.

Each of an "optionally substituted aromatic hydrocarbon group" and "optionally substituted heterocyclic group" as a preferred group $R^1$ is preferably a group represented by Formula:

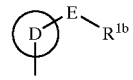

wherein each symbol is defined as described above.

An "optionally substituted hydrocarbon group" represented by $R^{1b}$ is a group similar to an "optionally substituted hydrocarbon group" exemplified as a substituent on Ring A. Among such groups, those employed preferably are:

(1) a $C_{1-6}$ alkyl group (e.g., methyl, isopropyl, tert-butyl, etc.)
[this $C_{1-6}$ alkyl group may have a substituent selected from a halogen atom, cyano, hydroxy, $C_{1-6}$ alkoxy-carbonyl, di-$C_{1-6}$ alkylamino, optionally halogenated $C_{1-6}$ alkyl-carbonyl-amino, carboxy, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl, imidazolyl))-$C_{1-6}$ alkyl-carbamoyl, $C_{1-6}$ alkylthio, $C_{1-6}$ alkylsulfinyl, $C_{1-6}$ alkylsulfonylamino, (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-$C_{1-6}$ alkylcarbamoyl, (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-amino, sulfamoyl-$C_{6-14}$ aryl, carboxy-$C_{6-14}$ aryl, $C_{1-6}$ alkoxy-carbonyl-$C_{6-14}$ aryl, carbamoyl-$C_{6-14}$ aryl, $C_{1-6}$ alkyl-carbamoyl-$C_{6-14}$ aryl which may have a hydroxy, (4- to 10-membered heterocyclic ring (e.g. 4- to 10-membered heterocyclic ring containing 1 to 3 heteroatom(s) selected from nitrogen, sulfur, oxygen atoms and the like in addition to carbon atoms such as pyridyl))-carbamoyl-$C_{6-14}$ aryl],
(2) a $C_{3-6}$ cycloalkyl group (e.g., cyclohexyl),
(3) a $C_{6-14}$ aryl group (e.g., phenyl) [this $C_{6-14}$ aryl group may have a substituent selected from $C_{1-6}$ alkoxy (e.g., methoxy), amino, carboxy, optionally halogenated $C_{1-6}$ alkyl-carbonylamino (e.g., acetylamino, trifluoroacetylamino), $C_{1-6}$ alkoxy-carbonylamino (e.g., methoxycarbonylamino), formylamino, ureido, $C_{1-6}$ alkylsulfonylamino (e.g., methylsufonylamino), ($C_{1-6}$ alkyl)($C_{1-6}$ alkylsulfonyl) amino (e.g., methyl (methylsulfonyl)amino), $C_{1-6}$ alkoxy-carbonyl-$C_{1-6}$ alkylamino (e.g., 2-ethoxycarbonyl-2-propylamino, etc.), optionally $C_{1-6}$ alkyl-esterified phosphono-$C_{1-6}$ alkyl, mono- or di-$C_{1-6}$ alkyl-carbamoyl, $C_{7-16}$ aralkyloxycarbonylamino (e.g., benzyloxycarbonylamino, etc.)].

An "optionally substituted heterocyclic group" represented by $R^{1b}$ is one similar to an "optionally substituted heterocyclic group" exemplified as a substituent on Ring A. Among such groups, those employed preferably are a 5- to 14-membered heterocyclic ring containing 1 to 4 heteroatom(s) selected from nitrogen, sulfur, oxygen atoms and the like in addition to carbon atoms (e.g., azethinyl, pyrrolidinyl, piperidinyl, isothiazolidinyl, thiadiazolidinyl, hexahydroazepinyl, furyl, thienyl, pyridyl, quinolyl, isoquinolyl, benzofuranyl, pyrimidinyl, tetrazolyl, imidazolinyl, pyrazinyl, pyridazinyl and the like) which may be substituted by 1 or 2 substituent(s) selected from a halogen atom, $C_{1-6}$ alkyl, carboxy-$C_{1-6}$ alkyl, $C_{1-6}$ alkoxy-carbonyl-$C_{1-6}$ alkyl, $C_{1-6}$ alkoxy-carbonyl, carbamoyl, oxo, 4- to 10-membered heterocyclic group (4- to 10-membered heterocyclic group containing 1 to 3 heteroatom(s) selected from nitrogen, sulfur, oxygen atoms and the like in addition to carbon atoms such as pyridyl, etc.), (4) $C_{2-6}$ alkenyl group and the like.

An aromatic hydrocarbon ring represented by Ring D may for example be a monocyclic or fused polycyclic aromatic hydrocarbon ring ($C_{6-14}$ aryl ring) having 6 to 14 carbon atoms. Such a $C_{6-14}$ aryl ring may for example be a benzene ring, naphthalene ring, anthracene ring, phenanthrene ring, with a benzene ring and naphthalene ring being preferred and a benzene ring being especially preferred.

Any of these aromatic hydrocarbon groups may have 1 to 5, preferably 1 to 3 substituent(s) selected from Substituent Group A described above.

A heterocyclic ring represented by Ring D may for example be a 5- to 14-membered heterocyclic ring containing 1 to 4 (preferably 1 to 3) heteroatom(s) selected from nitrogen, sulfur and oxygen atoms in addition to carbon atoms, typically, (a) a 5- to 14-membered aromatic heterocyclic ring, (b) a 5- to 14-membered aliphatic heterocyclic ring, (c) a bicyclic or tricyclic fused ring of 5- to 14-membered aromatic heterocyclic ring(s) with benzene ring(s) and the like.

Said 5- to 14-membered aromatic heterocyclic ring may for example be a 5- to 14-membered aromatic heterocyclic ring containing 1 to 4 (preferably 1 to 3) heteroatom(s) selected from nitrogen, sulfur and oxygen atoms in addition to carbon atoms, and those exemplified typically are thiophene, furan, indolizine, pyrrole, imidazole, triazole, thiazole, oxazole, pyrazole, pyridine, pyridine N-oxide, pyrazine, pyrimidine, pyridazine, purine, 4H-quinolizine, naphthyridine, isothiazole, isoxazole, furazane and the like. Among those listed above, pyridine, thiophene and furan are employed preferably.

Said 5- to 14-membered aliphatic heterocyclic ring may for example be a 5- to 14-membered aliphatic heterocyclic ring containing 1 to 4 (preferably 1 to 3) heteroatom(s) selected from nitrogen, sulfur and oxygen atoms in addition to carbon atoms, and those exemplified typically are pyrrolidine, piperidine, piperazine, morpholine, thiomorpholine, 1,2-dihydropyridine, imidazolidine and the like.

Said a bicyclic or tricyclic fused ring of 5- to 14-membered aromatic heterocyclic ring(s) with benzene rings may for example be a bicyclic or tricyclic fused ring of 5- to 14-membered heterocyclic ring containing 1 to 4 (preferably 1 to 3) heteroatom(s) selected from nitrogen, sulfur and oxygen atoms in addition to carbon atoms with benzene ring(s), and those exemplified typically are benzo[b]thiophene, benzofuran, 1H-benzimidazole, benzoxazole, benzothiazole, 1,2-benzisothiazole, naphtho[2,3-b]thiophene, thianthrene, xanthene, phenoxathiin, indole, isoindole, 1H-indazole, isoquinoline, quinoline, phthalazine, quinoxaline, quinazoline, cinnoline, carbazole, β-carboline, phenanthridine, acridine, phenazine, phenothiazine, phenoxazine, isochroman, dihydrobenzofuran and the like.

Among those listed above, a preferred heterocyclic ring represented by Ring D is pyridine, thiophene, furan, imidazole, thiazole, quinoline, pyridine N-oxide, 1,2-dihydropyridine, dihydrobenzofuran, benzodioxole, benzothiazole, piperidine, piperazine and the like, with pyridine, 1,2-dihydropyridine being especially preferred.

Any of these heterocyclic rings may have 1 to 5, preferably 1 to 3 substituent(s) selected from Substituent Group A described above.

An "optionally oxidized sulfur atom" represented by E is S, SO, $SO_2$ and the like.

An optionally substituted nitrogen atom represented by E may for example be a nitrogen atom which may have 1 to 2 group(s) selected from (i) a hydrogen atom, (ii) an optionally substituted hydrocarbon group, (iii) an acyl group and the like.

Said "optionally substituted hydrocarbon group" may be one similar to an "optionally substituted hydrocarbon group" exemplified as a substituent on Ring A.

Said "acyl group" may be one similar to an "acyl group" exemplified as a substituent on Ring A, and this acyl group may further have 1 to 5, preferably 1 to 3 substituent(s) selected from Substituent Group A described above.

In a group represented by Formula: —CS—O—, —CO—O—, —S—CO—, —$(CH_2)_k$—CO—, —$NR^{1c}$ CO—$(CH_2)_m$—, —$NR^{1c}$—$SO_2$—$(CH_2)_m$—, —$SO_2$—$NR^{1c}$—$(CH_2)_m$—, —O—CS—$NR^{1c}$—$(CH_2)_m$—, —$NR^{1c}$—CO—$NR^{1c}$—$(CH_2)_m$—, —$NR^{1c}$—CO—$CH_2$—$(CH_2)_m$—$NR^{1c}$— wherein $R^{1c}$ is a hydrogen atom, optionally substituted alkyl group or acyl group, k is 0 or 1, m is an integer of 0 to 3 which is represented by E, an alkyl group represented by $R^{1c}$ may for example be a $C_{1-6}$ alkyl group such as methyl, ethyl, propyl, isopropyl, butyl, isobutyl, sec-butyl, tert-butyl, pentyl, hexyl and the like.

An alkyl group represented by $R^{1c}$ may have 1 to 5, preferably 1 to 3 substituent(s) selected from Substituent Group A described above.

An acyl group represented by $R^{1c}$ may for example be one similar to an "acyl group" exemplified as a substituent on Ring A, and this acyl group may further have 1 to 5, preferably 1 to 3 substituent(s) selected from Substituent Group A described above.

k is 0 or 1, especially 0.

m is an integer of 0 to 3, especially 0 to 1.

Among those listed above, those preferred as E are:
(i) a bond, (ii) methylene, (iii) 0, (iv) S, (v) SO, (vi) $SO_2$, (vii) —NH—, (viii) —N($C_{1-6}$ alkyl)-(e.g., —N(methyl)-, etc.), (ix) —N($C_{1-6}$ alkyl-carbonyl)-(e.g., —N(acetyl), etc.), (x) —N($C_{1-6}$ alkoxy-carbonyl)-(e.g., —N(ethoxycarbonyl), etc.), (xi) —N($C_{1-6}$ alkyl-sulfonyl)-(e.g., —N(methylsulfonyl)-, etc.), (xii)—CO—O—, (xiii)—S—CO—, (xiv) a group represented by Formula: —$(CH_2)_k$—CO— wherein k is 0 or 1, (xv) —$NR^f$—CO—$(CH_2)_{m1}$—wherein $R^f$ is a hydrogen atom, $C_{1-6}$ alkoxy-carbonyl (e.g., methoxycarbonyl) or $C_{1-6}$ alkyl group which may be substituted by a heterocyclic group containing 1 to 3 heteroatom(s) selected from nitrogen, oxygen, sulfur atoms and the like in addition to carbon atoms (e.g. pyridyl), and m1 is an integer of 0 to 3, (xvi) a group represented by Formula —$NR^g$—$SO_2$—$(CH_2)_{m2}$— wherein $R^g$ is a hydrogen atom or $C_{1-6}$ alkylsulfonyl group (e.g., methylsulfonyl) and m2 is 0, (xvii) a group represented by —$SO_2$—$NR^h$—$(CH_2)_{m3}$— wherein $R^h$ is a hydrogen atom or $C_{1-6}$ alkyl group (e.g., methyl) and m3 is 0 or 1, (xviii) a group represented by —O—CS—$NR^i$—$(CH_2)_{m4}$— wherein $R^i$ is a hydrogen atom or $C_{1-6}$ alkyl group (e.g., methyl) and m4 is 0 or 1, (xix) a group represented by —$NR^j$—CO—$NR^k(CH_2)_{m5}$— wherein $R^j$ is a hydrogen atom or $C_{1-6}$ alkyl group (e.g., methyl), $R^k$ is a hydrogen atom or $C_{1-6}$ alkyl group (e.g., methyl) and m5 is 0 or 1, (xx) a group represented by —$NR^L$—CO—$CH_2$—$(CH_2)_{m6}$—$NR^m$— wherein $R^L$ is a hydrogen atom or $C_{1-6}$ alkyl group (e.g., methyl), $R^m$ is a hydrogen atom or $C_{1-6}$ alkyl group (e.g., methyl) and m6 is 0 or 1.

Each of an "optionally substituted aromatic hydrocarbon group" and "optionally substituted heterocyclic group" exemplified as a preferred $R^1$ may also be a group represented by Formula:

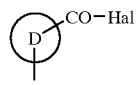

wherein each symbol is defined as described above.

A halogen atom represented by Hal may for example be a fluorine atom, chlorine atom, bromine atom and iodine atom, with a chlorine atom being preferred.

As Ring D, one similar to those described above can be employed.

In a group represented by Formula : —L—$R^{1a}$ wherein each symbol is defined as described above exemplified as a preferred group $R^1$, an "optionally substituted nitrogen atom" represented by L may be one similar to an "optionally substituted nitrogen atom " represented by E. L is preferably methylene, carbonyl, —NH—and the like.

An aromatic group represented by $R^{1a}$ may for example be: <1> a monocyclic or fused polycyclic aromatic hydrocarbon group, typically, a 6- to 14-membered monocyclic or fused polycyclic aromatic hydrocarbon group such as a $C_{6-14}$ aryl group such as phenyl, 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl, (preferably phenyl, 1-naphthyl or 2-naphthyl, especially, phenyl), <2> a 4- to 14-membered aromatic heterocyclic group containing one or more (for example 1 to 4, preferably 1 to 3) heteroatom(s) of 1 or 2 kind(s) selected from nitrogen, sulfur and oxygen atoms in addition to carbon atoms.

Such a 4- to 14-membered aromatic heterocyclic group may for example be a monocyclic heterocyclic group (preferably 5- to 8-membered group) containing one or more (for example 1 to 4, preferably 1 to 3) heteroatom(s) of 1 or 2 kind(s) selected from nitrogen, sulfur and oxygen atoms in addition to carbon atoms or a fused aromatic heterocyclic group thereof, typically, an aromatic heterocyclic ring such as thiophene, benzo[b]thiophene, benzofuran, 1H-benzimidazole, benzoxazole, benzothiazole, 1,2-benzisothiazole, naphtho[2,3-b]thiophene, thianthrene, furan, indolizine, xanthene, phenoxathiin, pyrrole, imidazole, triazole, thiazole, oxazole, pyrazole, pyridine, pyrazine, pyrimidine, pyridazine, indole, isoindole, 1H-indazole, purine, 4H-quinolizine, isoquinoline, quinoline, phthalazine naphthyridine, quinoxaline, quinazoline, cinnoline, carbazole, β-carboline, phenanthridine, acridine, phenazine, isothiazole, phenothiazine, isoxazole, furazane, phenoxazine, isochroman and the like (preferably, pyridine, thiophene or furan, more preferably pyridine) or a fused ring group of one or more (preferably 1 or 2, more preferably 1) of these rings (preferably monocyclic heterocyclic ring) with aromatic rings (for example, aromatic hydrocarbon groups described above, preferably benzene rings).

Substituents on said aromatic group are 1 to 5, preferably 1 to 3 substituent(s) selected from Substituent Group A described above.

An aromatic group which may have a substituent represented by $R^{1a}$ is preferably a $C_{6-14}$ aryl group (e.g., phenyl) which may have 1 to 5 substituent(s) such as a $C_{1-6}$ alkyl and $C_{1-6}$ alkoxy, etc.

An "optionally substituted hydroxy group" represented by $R^{1a}$ is one similar to an "optionally substituted hydroxy group" exemplified as a substituent on Ring A, with a hydroxy group which may have a $C_{1-6}$ alkyl group (e.g., methyl) being preferred.

An "optionally substituted amino group" represented by $R^{1a}$ is one similar to an "optionally substituted amino group" exemplified as a substituent on Ring A.

A preferred "optionally substituted amino group" represented by $R^{1a}$ may for example be an amino group which may have 1 or 2 group(s) such as an optionally substituted alkyl group or optionally substituted aryl group, especially <1> a $C_{1-6}$ alkyl-amino group which may be substituted by a 4- to 10-membered heterocyclic group (4- to 10-membered heterocyclic group containing 1 to 3 heteroatom(s) selected from nitrogen, oxygen, sulfur atoms and the like in addition to carbon atoms, e.g., pyridyl), <2> a $C_{6-14}$ aryl-amino group, <3> a 4- to 10-membered heterocyclic group (4- to 10-membered heterocyclic group containing 1 to 3 heteroatom(s) selected from nitrogen, oxygen, sulfur atoms and the like in addition to carbon atoms, e.g., pyridyl)-amino group and the like.

An "optionally substituted hydrocarbon group" represented by $R^2$ and $R^3$ is one similar to an "optionally substituted hydrocarbon group" exemplified as a substituent on Ring A.

Such an "optionally substituted hydrocarbon group" may for example be a hydrocarbon group (especially $C_{1-6}$ alkyl group) which may be substituted by:

<1> a halogen atom,

<2> an optionally substituted hydroxy group (for example, a hydroxy group which may be substituted by a substituent selected from a $C_{1-6}$ alkyl, $C_{1-6}$ alkyl-carbonyl, $C_{1-6}$ alkylsulfonyl and $C_{7-16}$ aralkyl, etc.), <3> an optionally substituted amino group (for example, an amino group which may be substituted by 1 to 2 $C_{1-6}$ alkyl, $C_{1-6}$ alkyl-carbonyl and $C_{6-14}$ aryl-carbonyl), <4> an optionally substituted 4- to 10-membered heterocyclic group (for example, a 4- to 10-membered heterocyclic group containing 1 to 3 heteroatom(s) selected from nitrogen, oxygen, sulfur atoms and the like in addition to carbon atoms which may have an oxo group (e.g., phthalimido, imidazolinyl, piperidinyl, pyrrolidinyl)), <5> an optionally substituted thio group (for example, a thio group which may be substituted by $C_{1-6}$ alkyl, etc.), <6> a $C_{1-6}$ alkyl-sulfinyl group, <7> a $C_{1-6}$ alkyl-sulfonyl group.

Among those listed above, one employed preferably is a $C_{1-6}$ alkyl group which may be substituted by <1> a halogen atom (especially, bromine atom), <2> a hydroxy, <3> a $C_{1-6}$ alkyl-carbonyloxy (e.g., acetoxy), <4> an amino, <5> a 4- to 10-membered heterocyclic group (4- to 10-membered heterocyclic group containing 1 to 3 heteroatom(s) selected from nitrogen, oxygen, sulfur atoms and the like in addition to carbon atoms (e.g., phthalimido, imidazolinyl, piperidinyl, pyrrolidinyl)) which may have oxo group and the like, and one employed more preferably is a $C_{1-6}$ alkyl group (e.g., methyl, ethyl) which may be halogenated by a halogen atom (especially, bromine atom), with a methyl group being preferred especially.

An "acyl group" represented by $R^2$ and $R^3$ is one similar to an "acyl group" exemplified as a substituent on Ring A, with a $C_{1-6}$ alkoxy-carbonyl group being preferred and a methoxycarbonyl group being more preferred.

A 3- to 8-membered ring formed by $R^2$ and $R^3$ together with the adjacent carbon atom may for example be a 3- to 8-membered homocyclic or heterocyclic ring.

A 3- to 8-membered homocyclic ring formed by $R^2$ and $R^3$ together with the adjacent carbon atom may for example be a 3- to 8-membered cyclic hydrocarbon consisting of carbon atoms, and typically a $C_{3-8}$ cycloalkane (for example, cyclobutane, cyclopentane, cyclohexane, cycloheptane, cyclooctane), $C_{3-8}$ cycloalkene (for example, cyclobutene, cyclopentene, cyclohexene, cycloheptene, cyclooctene) may be exemplified. Among those listed above, a $C_{3-8}$ cycloalkane is preferred, with a 5- or 6-membered homocyclic ring such as cyclopentane and cyclohexane (especially, cyclohexane) being particularly preferred.

A 3- to 8-membered heterocyclic ring formed by $R^2$ and $R^3$ together with the adjacent carbon atom may for example be a 5- to 8-membered aliphatic heterocyclic ring containing one or more (for example 1 to 4, preferably 1 to 3) heteroatom(s) of 1 or 2 kind(s) selected from nitrogen, sulfur and oxygen atoms in addition to carbon atoms.

More specifically, a 5- to 8-membered aliphatic heterocyclic ring containing 1 to 3 heteroatom(s) selected from nitrogen, oxygen and sulfur atoms in addition to carbon atoms and a nitrogen atom such as piperidine, piperazine, morpholine, thiomorpholine, pyrrolidine, imidazolidine ring and the like.

Such a 3- to 8-membered homocyclic or heterocyclic ring formed by $R^2$ and $R^3$ together with the adjacent carbon atom may have 1 to 5, preferably 1 to 3 substituent(s) similar to the substituents which may be possessed by a heterocyclic ring represented by $R^1$ described above. Such substituents are preferably 1 to 3 group(s) selected from a $C_{1-6}$ alkyl, $C_{6-14}$ aryl, $C_{7-16}$ aralkyl, amino, mono-$C_{1-6}$ alkylamino, mono-$C_{6-14}$ arylamino, di-$C_{1-6}$ alkylamino, di-$C_{6-14}$ arylamino, 4- to 10-membered (e.g., 4- to 10-membered (preferably 5- or 6-membered) heterocyclic ring containing 1 to 3 heteroatom(s) selected from nitrogen, oxygen and sulfur atoms in addition to carbon atoms) and the like.

Among those listed above, each of $R^2$ and $R^3$ is preferably a $C_{1-6}$ alkyl group, $C_{1-6}$ alkoxy-carbonyl group each of which may be a halogen atom, with a methyl group and methoxycarbonyl group being preferred.

It is also preferred that $R^2$ and $R^3$ are taken together with the adjacent carbon atom to form a 5- or 6-membered homocyclic ring such as a $C_{3-8}$ cycloalkane, preferably cyclopentane and cyclohexane (especially, cyclohexane).

An "optionally substituted hydrocarbon group" represented by $R^4$ may be one similar to an "optionally substituted hydrocarbon group" exemplified as a substituent on Ring A.

A hydrocarbon group represented by $R^4$ is preferably a $C_{1-6}$ alkyl group (e.g., methyl, ethyl, propyl, isopropyl, etc.), $C_{2-6}$ alkenyl group (e.g., 2-methyl-2-propenyl, etc.), with a $C_{1-3}$ alkyl group such as methyl and isopropyl being preferred especially.

A substituent on said hydrocarbon group is preferably (1) a halogen atom (for example, fluorine, chlorine, bromine, iodine), (2) a cyano group, (3) a lower alkoxy group (e.g., methoxy, ethoxy), (4) a hydroxy group, (5) an amino group, (6) a mono-lower alkylamino group (e.g., mono-$C_{1-6}$ alkylamino group such as methylamino, ethylamino), (7) a di-lower alkylamino group (e.g., di-$C_{1-6}$ alkylamino group such as dimethylamino and diethylamino, etc.), (8) a 4- to 10-membered heterocyclic ring containing 1 to 3 heteroatom (s) selected from nitrogen, oxygen and sulfur atoms in addition to carbon atoms which may have an oxo group (e.g., piperidino, 2-isoindolinyl, etc.), (9) a $C_{6-14}$ arylthio (e.g., phenylthio), (10) an ureido, (11) a carboxy, (12) a carbamoyl, (13) a $C_{1-6}$ alkoxy-carbonyl (e.g., methoxycarbonyl, ethoxycarbonyl, etc.), (14) a mono-$C_{1-6}$ alkyl-carbamoyl (e.g., methylcarbamoyl, ethylcarbamoyl, etc.), (15) a formylamino and (16) a $C_{1-6}$ alkyl-carboxamido (e.g., acetamido, propionamido).

An "acyl group" represented by $R^4$ may be one similar to an "acyl group" exemplified as a substituent on Ring A, and is typically (1) formyl (2) a $C_{1-6}$ alkyl-carbonyl group (e.g., acetyl, propionyl, etc.), (3) a $C_{6-14}$ aryl-carbonyl group (e.g., benzoyl, etc.), (4) a $C_{7-16}$ aralkyl-carbonyl group (e.g., phenylacetyl, etc.) (5) a $C_{1-6}$ alkoxy-carbonyl group (e.g., methoxycarbonyl, ethoxycarbonyl), (6) a carbamoyl group, (7) a mono- or di-$C_{1-6}$ alkyl-carbamoyl group (e.g., methylcarbamoyl, dimethylcarbamoyl, etc.), (8) a mono- or di-$C_{1-6}$ alkyl-thiocarbamoyl group (e.g., methylthiocarbamoyl, dimethylthiocarbamoyl, etc.), (9) a $C_{1-6}$ alkyl-sulfonyl group (e.g., methylsulfonyl, etc.), (10) a $C_{1-6}$ alkyl-sulfinyl group (e.g., methylsulfinyl, etc.) and the like, with formyl being preferred.

An "optionally substituted hydroxy group" represented by $R^4$ may for example be a group represented by Formula: —$OR^{4'}$ ($R^{4'}$ is a hydrogen atom, optionally substituted hydrocarbon group or acyl group).

A hydrocarbon group which may have a substituent represented by $R^{4'}$ may for example be one similar to an "optionally substituted hydrocarbon group" exemplified as a substituent on Ring A, with $C_{1-6}$ alkyl being preferred.

An acyl group represented by $R^{4'}$ may for example be one similar to an "acyl group" exemplified as a substituent on Ring A, with $C_{1-6}$ alkyl-carbonyl being preferred.

$R^4$ is preferably a hydrogen atom, cyano group, $C_{1-6}$ alkyl group which may be substituted by a cyano, formyl and the like, with a hydrogen atom being preferred especially.

An "optionally substituted hydrocarbon group" represented by $R^5$ is one similar to an "optionally substituted hydrocarbon group" exemplified as a substituent on Ring A.

A hydrocarbon group represented by $R^5$ is preferably a $C_{1-6}$ alkyl group (e.g., methyl, ethyl, etc.), $C_{2-6}$ alkenyl group (e.g., allyl, 2-methyl-2-propenyl, etc.), a $C_{2-6}$ alkynyl group (e.g., propargyl, etc.), a $C_{3-6}$ cycloalkyl group (e.g., cyclopentyl, etc.), a $C_{7-16}$ aralkyl group (e.g., benzyl, 3-phenylpropyl, 5-phenylpentyl, etc.) and the like, with a $C_{1-6}$ alkyl group (especially, methyl) being particularly preferred.

A substituent on said hydrocarbon group is preferably (1) a halogen atom (for example, fluorine, chlorine, bromine, iodine), (2) a hydroxy group, (3) an amino group, (4) a carboxy, (5) a carbamoyl, (6) a $C_{1-6}$ alkoxy-carbonyl (e.g., methoxycarbonyl, ethoxycarbonyl, etc.), (7) a mono-$C_{1-6}$ alkyl-carbamoyl (e.g., methylcarbamoyl, ethylcarbamoyl, etc.), (8) a di-$C_{1-6}$ alkyl-carbamoyl (e.g., dimethylcarbamoyl, diethylcarbamoyl, etc.), (9) a 4- to 10-membered heterocyclic group containing 1 to 3 heteroatom(s) selected from nitrogen, sulfur, oxygen atoms and the like in addition to carbon atoms (e.g., pyridyl, isoindolinyl) which may have an oxo, (11) a $C_{6-14}$ aryl group (e.g., phenyl, etc.) and the like.

An "acyl group" represented by $R^5$ is one similar to an "acyl group" exemplified as a substituent on Ring A, and this acyl group may further have 1 to 5, preferably 1 to 3 substituent(s) selected from Substituent Group A described above. Those preferred especially are (1) formyl (2) a $C_{1-6}$ alkyl-carbonyl group (e.g., acetyl, propionyl, etc.), (3) a $C_{6-14}$ aryl-carbonyl group (e.g., benzoyl, etc.), (4) a $C_{7-16}$ aralkyl-carbonyl group (e.g., phenylacetyl, etc.) (5) a $C_{1-6}$ alkoxy-carbonyl group (e.g., methoxycarbonyl, ethoxycarbonyl, etc.), (6) a carbamoyl group, (7) a mono- or di-$C_{1-6}$ alkyl-carbamoyl group (e.g., methylcarbamoyl, dimethylcarbamoyl, etc.), (8) a mono- or di-$C_{1-6}$ alkyl-thiocarbamoyl group (e.g., methylthiocarbamoyl, dimethylthiocarbamoyl, etc.), (9) a $C_{1-6}$ alkyl-sulfonyl group (e.g., methylsulfonyl, etc.), (10) a $C_{1-6}$ alkyl-sulfinyl group (e.g., methylsulfinyl, etc.) and the like.

An "optionally substituted heterocyclic group" represented by $R^5$ is one similar to an "optionally substituted heterocyclic group" exemplified as a substituent on Ring A.

A heterocyclic group represented by $R^5$ is preferably a 4- to 10-membered aromatic heterocyclic ring containing 1 to 4 heteroatom(s) selected from nitrogen, sulfur, oxygen atoms and the like in addition to carbon atoms (e.g., tetrazolyl, etc.), etc.

A substituent on said heterocyclic group is preferably a $C_{6-14}$ aryl group (e.g., phenyl, etc.) and the like.

A halogen atom represented by $R^5$ is a fluorine atom, chlorine atom, bromine atom and iodine atom, with a chlorine atom being preferred.

Depending on $X^5$, $R^5$ is preferably any of those described below:

[X=oxygen atom]
(i) a hydrogen atom,
(ii) a $C_{1-6}$ alkyl group (e.g., methyl, ethyl, isopropyl, butyl, etc.)
[this $C_{1-6}$ alkyl group may have a substituent selected from (1) a halogen atom, (2) a hydroxy group, (3) an amino group, (4) a carboxy, (5) a carbamoyl, (6) a $C_{1-6}$ alkoxy-carbonyl, (7) a mono-$C_{1-6}$ alkyl-carbamoyl, (8) a di-$C_{1-6}$ alkyl-carbamoyl, (9) 4- to 10-membered aromatic heterocyclic group containing 1 to 3 heteroatom(s) selected from nitrogen, sulfur, oxygen atoms and the like in addition to carbon atoms (e.g., pyridyl, 2-isoindolinyl, etc.)],
(iii) a $C_{2-6}$ alkenyl group (e.g., allyl, 2-methyl-propenyl, etc.)[this $C_{2-6}$ alkenyl group may have a $C_{6-14}$ aryl (e.g., phenyl)],
(iv) a $C_{2-6}$ alkenyl group (e.g., propargyl, etc.),
(v) a $C_{3-6}$ cycloalkyl group (e.g., cyclopentyl, etc.),
(vi) a $C_{7-16}$ aralkyl group (e.g., benzyl, 3-phenylpropyl, 5-phenylpentyl, etc.),
(vii) a $C_{1-6}$ alkyl-carbonyl group (e.g., acetyl, etc.),
(viii) a $C_{6-14}$ aryl-carbonyl group (e.g., benzoyl, etc.),
(ix) a $C_{7-16}$ aralkyl-carbonyl group (e.g., phenylacetyl, etc.),
(x) $C_{1-6}$ alkoxy-carbonyl group (e.g., methoxycarbonyl, ethoxycarbonyl, etc.),
(xi) a mono- or di-$C_{1-6}$ alkyl-thiocarbamoyl group (e.g., methylthiocarbamoyl, dimethylthiocarbamoyl, etc.),
(xii) an optionally halogenated $C_{1-6}$ alkyl-sulfonyl group (e.g., methylsulfonyl, etc.),
(xiii) a 4- to 10-membered aromatic heterocyclic group containing 1 to 4 heteroatom(s) selected from nitrogen, sulfur, oxygen atoms and the like in addition to carbon atoms (e.g., tetrazolyl, etc.)
[this heterocyclic ring may have a $C_{6-14}$ aryl (e.g., phenyl)],
[X=nitrogen atom]
<1> a hydrogen atom,
<2> a $C_{1-6}$ alkyl group (e.g., methyl, ethyl, etc.)
[this $C_{1-6}$ alkyl group may have a $C_{1-6}$ alkoxy-carbonyl],
<3> a formyl,
<4> a $C_{1-6}$ alkyl-carbonyl group (e.g., acetyl, propionyl, etc.),
<5> a $C_{1-6}$ alkoxy-carbonyl group (e.g., methoxycarbonyl, ethoxycarbonyl, etc.),
<6> a carbamoyl group,
<7> a mono- or di-$C_{1-6}$ alkyl-carbamoyl group (e.g., methylcarbamoyl, dimethylcarbamoyl, etc.),
<8> a $C_{1-6}$ alkyl-sulfonyl group (e.g., methylsulfonyl),
[X=sulfur atom]
<1> a $C_{1-6}$ alkyl group (e.g., methyl, ethyl, etc.),
<2> a mono- or di-$C_{1-6}$ alkyl-carbamoyl group (e.g., methylcarbamoyl, dimethylcarbamoyl),
[X=bond]
<1> a hydrogen atom,
<2> a $C_{1-6}$ alkyl group (e.g. methyl),
<3> a halogen atom (e.g., chlorine atom).

An "optionally substituted hydrocarbon group" represented by $R^6$ and $R^7$ may be one similar to an "optionally substituted hydrocarbon group" exemplified as a substituent on Ring A, and a $C_{1-6}$ alkyl group (e.g., methyl, ethyl, etc.) is preferred, with a methyl group being preferred especially.

An "optionally substituted 3- to 8-membered ring" formed by $R^6$ and $R^7$ together with the adjacent carbon atom may be one similar to an "optionally substituted 3- to 8-membered ring" formed by $R^2$ and $R^3$ together with the adjacent carbon atom described above, and among such groups an optionally substituted 3- to 8-membered homocyclic ring is preferred, with a $C_{3-8}$ cycloalkane (for example, cyclobutane, cyclopentane, cyclohexane, cycloheptane, cyclooctane) being preferred, and a 5- or 6-membered homocyclic ring such as cyclopentane and cyclohexane (especially cyclopentane) being preferred.

An "optionally substituted hydrocarbon group" represented by $R^8$ and $R^9$ may be one similar to an "optionally substituted hydrocarbon group" exemplified as a substituent on Ring A. Among such groups, those exemplified preferably are a $C_{1-6}$ alkyl group, $C_{1-6}$ alkenyl group or $C_{1-6}$ alkynyl group each of which may have 1 to 5 substituent(s) selected from (1) a halogen atom, (2) an optionally halogenated $C_{1-6}$ alkyl, (3) an optionally halogenated $C_{1-6}$ alkoxy, (4) an optionally halogenated $C_{1-6}$ alkylthio, (5) a hydroxy, (6) an amino, (7) a mono-$C_{1-6}$ alkylamino, (8) a di-$C_{1-6}$ alkylamino and the like, with $C_{1-6}$ alkyl group (e.g., methyl, ethyl, etc.) being preferred especially.

Preferably, each of $R^8$ and $R^9$ may for example be a hydrogen atom, $C_{1-6}$ alkyl group (e.g., methyl, ethyl), with a hydrogen atom being preferred especially.

An optionally oxidized sulfur atom represented by X is S, SO and $SO_2$ with S and SO being preferred.

An "optionally substituted nitrogen atom" represented by X is one similar to an "optionally substituted nitrogen atom" represented by E described above, and those exemplified typically are (1) —NH—, (2) —N($C_{1-6}$ alkyl)-(e.g., —N(methyl)-, —N(ethyl)-, —N(propyl)-, —N(isopropyl)-, etc.), (3) —N($C_{6-14}$ aryl)-(e.g., —N(phenyl)-, —N(2-naphthyl)-, etc.), (4) —N($C_{7-16}$ aralkyl)-(e.g., —N(benzyl)-, —N(phenethyl)-, etc.), with —NH— and —N(methyl)- being preferred especially.

X is preferably a bond, O, S, SO, —NH—, —N(methyl)- and the like.

Y is (1) an optionally substituted methylene group, or (2) a carbonyl group.

A substituent on a methylene group may for example be a group selected from Substituent Group A described above, and among such groups those preferred are one or two $C_{1-6}$ alkyl group(s) (e.g., methyl, ethyl, etc.), hydroxy group(s) and the like.

Y is preferably (1) a methylene group which may have one or two $C_{1-6}$ alkyl group(s) (e.g., methyl, ethyl, ethyl) or (2) a carbonyl group, with a methylene group which may have one or two methyl(s) being preferred, and a methylene group being especially preferred.

n is 0 or 1, with 0 being preferred.

As a compound according to the invention, any one of those listed below is preferred.

[Compound (I)-I]

Compound (I) wherein:

$R^1$ is a group represented by Formula:

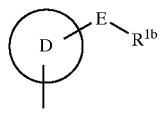

wherein each symbol is defined as described above, or a group represented by Formula:

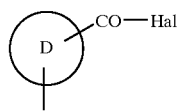

wherein each symbol is defined as described above, each of $R^2$ and $R^3$ is a hydrogen atom or optionally substituted hydrocarbon group, and $R^2$ and $R^3$ may be taken together with the adjacent carbon atom to form an optionally substituted 3- to 8-membered ring, $R^4$ is a hydrogen atom, cyano group, optionally substituted hydrocarbon group, acyl group or optionally substituted hydroxy group, $R^5$ is an optionally substituted hydrocarbon group, each of $R^6$ and $R^7$ is an optionally substituted hydrocarbon group, and $R^6$ and $R^7$ are taken together with the adjacent carbon atom to form an optionally substituted 3- to 8-membered ring, each of $R^8$ and $R^9$ is a hydrogen atom, X is an oxygen atom or optionally oxidized sulfur atom, Y is a methylene group which may have one or two $C_{1-6}$ alkyl groups, and n is 0 or 1.

[Compound (I)-II]

Compound (I) wherein:

$R^1$ is a group represented by Formula:

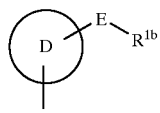

wherein each symbol is defined as described above, or a group represented by Formula:

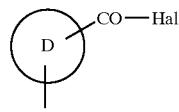

wherein each symbol is defined as described above, each of $R^2$ and $R^3$ is a hydrogen atom or optionally substituted hydrocarbon group, and $R^2$ and $R^3$ may be taken together with the adjacent carbon atom to form an optionally substituted 3- to 8-membered homocyclic or heterocyclic ring, $R^4$ is a hydrogen atom, $R^5$ is an optionally substituted hydrocarbon group, each of $R^6$ and $R^7$ is an optionally substituted hydrocarbon group, and $R^6$ and $R^7$ are taken together with the adjacent carbon atom to form an optionally substituted 3- to 8-membered homocyclic ring, each of $R^8$ and $R^9$ is a hydrogen atom, X is an oxygen atom or sulfur atom, Y is a methylene and n is 0 or 1.

[Compound (I)-III]

Compound (I) wherein $R^1$ is, (i) a $C_{6-14}$ aryl group which may have 1 to 3 substituent(s) selected from the following (1) to (23):
(1) a halogen atom,
(2) a nitro group,
(3) a $C_{1-6}$ alkyl group (e.g., methyl, isopropyl, tert-butyl and the like) [this $C_{1-6}$ alkyl group may have a substituent selected from a halogen atom, cyano, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-$C_{1-6}$ alkyl-carbamoyl, $C_{1-6}$ alkylsulfonylamino, $C_{1-6}$ alkoxy-carbonyl and carboxy, etc.],
(4) a $C_{3-6}$ cycloalkyl group (e.g., cyclohexyl),
(5) a $C_{6-14}$ aryl group (e.g., phenyl)
[this $C_{6-14}$ aryl group may have a substituent selected from amino, carboxy, $C_{1-6}$ alkoxy-carbonyl, carbamoyl, mono- or di-$C_{1-6}$ alkylcarbamoyl, formylamino, $C_{1-6}$ alkyl-carbonylamino which may have a halogen atom or carboxy (e.g., acetylamino, propionylamino, trifluoroacetylamino, pivaloylamino), $C_{6-14}$ arylcarbonylamino (e.g., benzoylamino), $C_{1-6}$ alkoxycarbonylamino (e.g., methoxycarbonylamino), ureido, mono- or di-$C_{1-6}$ alkylureido, $C_{1-6}$ alkylsulfonylamino (e.g., methylsulfonylamino, etc.), ($C_{1-6}$ alkyl) ($C_{1-6}$ alkylsulfonyl) amino (e.g., methyl(methylsulfonyl)amino), ($C_{1-6}$ alkyl) ($C_{1-6}$ alkyl-carbonyl)amino (e.g., methyl(acetyl)amino, etc.), $C_{1-6}$ alkoxy-carbonyl-$C_{1-6}$ alkylamino (e.g., 2-ethoxycarbonyl-2-propylamino, etc.), $C_{6-14}$ aralkyloxy-carbonylamino (e.g., benzyloxycarbonylamino), $C_{1-6}$ alkyl-carbonylamino-$C_{1-6}$ alkyl-carbonylamino (e.g., acetylamino-acetylamino), $C_{1-6}$ alkyloxy-$C_{1-6}$ alkyl-carbonylamino-$C_{1-6}$ alkyl-carbonylamino (e.g., methoxyacetylamino-acetylamino), $C_{1-6}$ alkylthio-$C_{1-6}$ alkyl-carbonylamino (e.g., methylthioacetylamino), $C_{1-6}$ alkyl-sulfinyl-$C_{1-6}$ alkyl-carbonylamino (e.g., methylsulfinylacetylamino), $C_{1-6}$ alkyl-sulfonyl-$C_{1-6}$ alkyl-carbonylamino (e.g., methylsulfonylacetylamino), $C_{6-14}$ aryloxy-carbonylamino (e.g., phenoxycarbonylamino), hydroxy-$C_{1-6}$ alkyl-carbamoyl (e.g., hydroxymethylcarbamoyl, hydroxyethylcarb- amoyl), and may have a substituent selected especially from amino carboxy, $C_{1-6}$ alkoxy-carbonyl, carbamoyl, mono- or di-$C_{1-6}$ alkylcarbamoyl, formylamino, $C_{1-6}$ alkyl-carbonylamino which may have a halogen atom or carboxy (e.g., acetylamino, propionylamino, trifluoroacetylamino, pivaloylamino), $C_{1-6}$ alkoxy-carbonylamino (e.g., methoxycarbonylamino), ureido, $C_{1-6}$ alkylsulfonylamino (e.g., methylsulfonylamino), ($C_{16}$ alkyl) ($C_{1-6}$ alkylsulfonyl) amino (e.g., methyl (methylsulfonyl) amino, etc.), ($C_{1-6}$ alkyl) ($C_{1-6}$ alkyl-carbonyl)amino (e.g., methyl (acetyl) amino, etc.), $C_{1-6}$ alkoxy-carbonyl-$C_{1-6}$ alkylamino (e.g., 2-ethoxycarbonyl-2-propylamino, etc.), $C_{7-16}$ aralkyloxycarbonylamino (e.g., benzyloxycarbonylamino) and the like], (6) a $C_{1-6}$ alkoxy group which may have a halogen atom or $C_{1-6}$ alkoxy-$C_{6-14}$ aryl (e.g., methoxy, trifluoromethoxy, isopropoxy, 2-(4-methoxyphenyl)ethoxy, etc.), (7) a $C_{6-14}$ aryloxy group (e.g., phenoxy), (8) a $C_{1-6}$ alkylthio group which may have a carbamoyl (e.g., methylthio, carbamoylmethylthio), (9) a $C_{1-6}$ alkylsulfinyl group which may have a carbamoyl (e.g., methylsulfinyl, carbamoylmethylsulfinyl),

(10) a $C_{6-14}$ arylthio group (e.g., phenylthio),

(11) a hydroxy group,

(12) a 4- to 14-membered heterocyclic group containing 1 to 4 heteroatom(s) selected from nitrogen, sulfur, oxygen atoms and the like in addition to carbon atoms (e.g., pyrrolidinyl, piperidyl, isoindolinyl, furyl, thienyl, pyridyl, quinolyl, benzofuranyl, pyrimidinyl, tetrazolyl, imidazolidinyl, isothiazolidinyl, thiadiazolidinyl, azethinyl, etc.),

[this heterocyclic group may have a substituent selected from oxo, carboxy-$C_{1-6}$ alkyl, $C_{1-6}$ alkyl-carbonyloxy-$C_{1-6}$ alkyl, $C_{1-6}$ alkyl, $C_{1-6}$ alkoxy-carbonyl-$C_{1-6}$ alkyl, $C_{1-6}$ alkoxy-carbonyl, carbamoyl-$C_{1-6}$ alkyl, $C_{1-6}$ alkyl-carbamoyl-$C_{1-6}$ alkyl, etc.],

(13) a carboxy group,

(14) a group represented by Formula: —CO—Hal (Hal is a halogen atom) (e.g., chloroformyl),

(15) a $C_{1-6}$ alkyl-carbonyl group (e.g., acetyl, etc.),

(16) a $C_{1-6}$ alkyl-sulfonyl group (e.g., methylsulfonyl, etc.),

(17) a $C_{1-6}$ alkoxy-carbonyl group (e.g., methoxycarbonyl, etc.),

(18) a sulfamoyl group

[this sulfamoyl group may have 1 or 2 substituent(s) selected from $C_{1-6}$ alkyl, carbamoyl-$C_{1-6}$ alkyl, $C_{1-6}$ alkoxy-carbonyl-$C_{1-6}$ alkyl, (5- to 7-membered heterocyclic group which may have an oxo group (e.g., 5- to 7-membered heterocyclic group containing 1 to 3 heteroatom(s) selected from nitrogen, sulfur, oxygen atoms and the like in addition to carbon atoms such as pyridyl, pyrrolidinyl hexahydroazepinyl))-$C_{1-6}$ alkyl, $C_{1-6}$ alkyl-carbonylamino-$C_{6-14}$ aryl],

(19) a group represented by Formula: —NR$^a$R$^b$

[each of R$^a$ and R$^b$ is (i) a hydrogen atom, (ii) a $C_{1-6}$ alkyl, (iii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-$C_{1-6}$ alkyl, (iv) a $C_{1-6}$ alkoxy-carbonyl-$C_{1-6}$ alkyl, (v) a di-$C_{1-6}$ alkylamino-methylene-sulfamoyl-$C_{1-6}$ alkyl, (vi) a carbamoyl-$C_{1-6}$ alkyl, (vii) a sulfamoyl-$C_{1-6}$ alkyl, (viii) a $C_{1-6}$ alkyl-sulfonyl, (ix) a $C_{1-6}$ alkoxy-carbonyl, (x) a di-$C_{1-6}$ alkoxy-carbonyl-$C_{2-6}$ alkenyl, (xi) a $C_{6-14}$ aryl, (xii) a 5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl), [this 5- or 6-membered heterocyclic group may have a substituent selected from amino, $C_{1-6}$ alkyl-carboxamido and $C_{1-6}$ alkyl-sulfonylamino and the like], (xiii) an optionally halogenated $C_{1-6}$ alkyl-carbonyl, (xiv) a $C_{1-6}$ alkylthio-$C_{1-6}$ alkyl-carbonyl, (xv) a $C_{1-6}$ alkylsulfinyl-$C_{1-6}$ alkyl-carbonyl, (xvi) a $C_{1-6}$ alkylsulfonyl-$C_{1-6}$ alkyl-carbonyl, (xvii) an amino-$C_{1-6}$ alkyl-carbonyl, (xviii) an optionally halogenated $C_{1-6}$ alkyl-carbonyl-amino-$C_{1-6}$ alkyl-carbonyl, (xix) a $C_{6-14}$ aryl-carbonyl, (xx) a carboxy-$C_{6-14}$ aryl-carbonyl, (xxi) an optionally $C_{1-6}$ alkyl-esterified phosphono-$C_{1-6}$ alkyl-$C_{6-14}$ aryl-carbonyl, (xxii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyrrolidinyl, pyridyl) which may have a halogen atom, oxo or a $C_{1-6}$ alkoxy-carbonyl)-carbonyl, (xxiii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-$C_{1-6}$ alkyl-carbonyl, (xxiv) a $C_{6-14}$ aryl-oxy-carbonyl, (xxv) a carboxy-$C_{1-6}$ alkyl, (xxvi) a carbamoyl, (xxvii) an optionally halogenated $C_{1-6}$ alkylcarbamoyl, (xxviii) a $C_{6-14}$ arylcarbamoyl which may have a $C_{1-6}$ alkyl-carbonylamino, (xxix) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-carbamoyl, (xxx) a $C_{2-6}$ alkenyl-carbonyl, (xxxi) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyrrolidinyl) which may have an oxo group)-amino-$C_{1-6}$ alkyl-carbonyl, (xxxii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyrrolidinyl) which may have an oxo group)($C_{1-6}$ alkyl) amino-$C_{1-6}$ alkyl-carbonyl, (xxxiii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyrrolidinyl) which may have an oxo group) ($C_{1-6}$ alkylcarbonyl) amino-$C_{1-6}$ alkyl-carbonyl, (xxxiv) a $C_{1-6}$ alkylthio-$C_{1-6}$ alkylcarbonyl (sulfur atom may be oxidized), (xxxv) an optionally halogenated $C_{1-6}$ alkylsulfonyl, (xxxvi) a sulfamoyl, (xxxvii) a $C_{1-6}$ alkylsulfamoyl and the like],

(20) a group represented by Formula: —C(=O)NR$^c$R$^d$

[each of R$^c$ and R$^d$ is (i) a hydrogen atom, (ii) a $C_{1-6}$ alkyl, (iii) a 5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl, imidazolyl)-$C_{1-6}$ alkyl, (iv) a carboxy-$C_{1-6}$alkyl, (v) a $C_{1-6}$ alkoxy-carbonyl-$C_{1-6}$ alkyl, (vi) a di-$C_{1-6}$ alkylamino-$C_{1-6}$ alkyl, (vii) a carbamoyl-$C_{1-6}$ alkyl, (viii) a $C_{1-6}$ alkylcarbamoyl-$C_{1-6}$ alkyl, (ix) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-$C_{1-6}$ alkylcarbamoyl-$C_{1-6}$ alkyl, (x) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyridyl))-amino-$C_{1-6}$ alkyl, (xi) a sulfamoyl-$C_{6-14}$ aryl-$C_{1-6}$ alkyl, (xii) a $C_{6-14}$ aryl which may have $C_{1-6}$ alkoxy, (xiii) an optionally $C_{1-6}$ alkyl-esterified phosphono-$C_{1-6}$ alkyl-$C_{6-14}$ aryl, (xiv) a 4- to 10-membered heterocyclic group (e.g., 4- to 10-membered heterocyclic ring containing 1 to 3 heteroatom(s) selected from nitrogen, sulfur, oxygen atoms and the like in addition to carbon atoms such as azethinyl, pyrrolidinyl, piperidinyl, hexahydroazepinyl, pyridyl, pyrimidinyl, pyrazinyl, pyridazinyl, 1-azabicyclo [2.2.2]octo-3-yl, etc.) [this 4- to 10-membered heterocyclic group may have 1 to 2 substituent(s) selected from a halogen atom, $C_{1-6}$ alkyl and oxo, etc.], (xv) a $C_{6-14}$ aryl-carbamoyl-$C_{1-6}$ alkyl, (xvi) a hydroxy-$C_{1-6}$ alkyl or (xvii) a (5- or 6-membered heterocyclic ring (e.g., 5- or 6-membered heterocyclic ring containing 1 to 3 heteroatom(s) selected from nitrogen, sulfur, oxygen atoms and the like in addition to carbon atoms such as pyrrolidinyl, pyridyl) which may have a oxo group)-carbamoyl-$C_{1-6}$ alkyl; and $R^c$ is preferably a hydrogen atom],

(21) a cyano group,

(22) a mono- or di-$C_{1-6}$ alkylcarbamoylthio group (e.g., dimethylcarbamoylthio),

(23) a mono- or di-$C_{1-6}$ alkylthiocarbamoyloxy group (e.g., dimethylthiocarbamoyloxy);

(ii) a 4- to 14-membered heterocyclic group containing 1 to 4 heteroatom(s) selected from nitrogen, sulfur and oxygen atoms in addition to carbon atoms which may contain 1 to 3 substituent(s) selected from the following (1) to (8):

(1) a halogen atom, (2) a $C_{1-6}$ alkyl group [this alkyl may have a substituent selected from carboxy, $C_{1-6}$ alkoxy, $C_{1-6}$ alkoxy-carbonyl, mono-$C_{1-6}$ alkyl-amino, di-$C_{1-6}$ alkyl-amino, carbamoyl, $C_{1-6}$ alkyl-carbamoyl which may have a hydroxy, 4- to 10-membered heterocyclic group containing 1 to 3 heteroatom(s) selected from nitrogen, sulfur and oxygen atoms in addition to carbon atoms which may have oxo, (4- to 10-membered heterocyclic ring containing 1 to 3 heteroatom(s) selected from nitrogen, sulfur and oxygen atoms in addition to carbon atoms)-carbamoyl, carbamoyl-$C_{1-6}$ alkyl-carbamoyl], (3) a $C_{1-6}$ alkoxy group, (4) a $C_{6-14}$ aryl group, (5) a $C_{7-16}$ aralkyl group [this $C_{7-16}$ aralkyl group may have a substituent selected from carboxy, $C_{1-6}$ alkoxy-carbonyl, carbamoyl, $C_{1-6}$ alkyl-carbamoyl which may have hydroxy, (4- to 10-membered heterocyclic ring containing 1 to 3 heteroatom(s) selected from nitrogen, sulfur and oxygen atoms in addition to carbon atoms)-carbamoyl], (6) a 4- to 10-membered heterocyclic group containing 1 to 3 heteroatom(s) selected from nitrogen, sulfur and oxygen atoms in addition to carbon atoms [this 4- to 10-membered heterocyclic group may have a substituent selected from a $C_{1-6}$ alkyl, $C_{1-6}$ alkoxy-carbonyl, carbamoyl, oxo, 4- to 10-membered heterocyclic group containing 1 to 3 heteroatom(s) selected from nitrogen, sulfur and oxygen atoms in addition to carbon atoms], (7) an oxo group, (8) an oxide group;

(iii) a $C_{3-6}$ cycloalkyl group; or, (iv) a group represented by Formula: —L'—$R^{1a'}$ (L' is methylene, carbonyl or an optionally substituted nitrogen atom, $R^{1a'}$ is (1) a hydrogen atom, (2) a $C_{6-14}$ aryl group which may have 1 to 5 substituent(s) selected from a $C_{1-6}$ alkyl and $C_{1-6}$ alkoxy, (3) a hydroxy group which may be substituted by a $C_{1-6}$ alkyl group, (4) a $C_{1-6}$ alkyl-amino group which may be substituted by a 4- to 10-membered heterocyclic ring containing 1 to 3 heteroatom(s) selected from nitrogen, oxygen and sulfur atoms in addition to carbon atoms, (6) a $C_{6-14}$ aryl-amino group or (7) a (4- to 10-membered heterocyclic ring containing 1 to 3 heteroatom(s) selected from nitrogen, oxygen and sulfur atoms in addition to carbon atoms)-amino group), each of $R^2$ and $R^3$ is (1) a hydrogen atom, (2) a $C_{1-6}$ alkyl group which may be substituted by <1> a halogen atom, <2> an optionally substituted hydroxy group (for example, a hydroxy group which may be substituted by a substituent selected from a $C_{1-6}$ alkyl, $C_{1-6}$ alkyl-carbonyl, $C_{1-6}$ alkylsulfonyl and $C_{7-16}$ aralkyl), <3> an optionally substituted amino group (for example, an amino group which may be substituted by 1 or 2 $C_{1-6}$ alkyl, $C_{1-6}$ alkyl-carbonyl and $C_{6-14}$ aryl-carbonyl, etc.), <4> an optionally substituted 4- to 10-membered heterocyclic group (for example, a 4- to 10-membered heterocyclic group containing 1 to 3 heteroatom(s) selected from nitrogen, oxygen, sulfur atoms and the like in addition to carbon atoms which may have an oxo group (e.g., phthalimido, imidazolinyl, piperidinyl, pyrrolidinyl)), <5> an optionally substituted thio group (for example, a thio group which may have a $C_{1-6}$ alkyl), <6> a $C_{1-6}$ alkyl-sulfinyl group or <7> a $C_{1-6}$ alkyl-sulfonyl group, or (3) a $C_{1-6}$ alkoxy-carbonyl group, $R^2$ and $R^3$ may be taken together with the adjacent carbon atom to form a $C_{3-8}$ cycloalkane, $R^4$ is (i) a hydrogen atom, (ii) a cyano group, (iii) a $C_{1-6}$ alkyl group [this $C_{1-6}$ alkyl group may have a substituent selected from (1) a halogen atom, (2) a cyano group, (3) a $C_{1-6}$ alkoxy group, (4) a hydroxy group, (5) an amino group, (6) a mono-$C_{1-6}$ alkylamino group, (7) a di-$C_{1-6}$ alkylamino group, (8) a tri-$C_{1-6}$ alkylammonium group, (8) a 4- to 10-membered heterocyclic group containing 1 to 3 heteroatom(s) selected from nitrogen, sulfur and oxygen atoms in addition to carbon atoms which may have an oxo, (9) a $C_{6-14}$ arylthio, (10) an ureido, (11) a carboxy, (12) a carbamoyl, (13) a $C_{1-6}$ alkoxy-carbonyl, (14) a mono-$C_{1-6}$ alkyl-carbamoyl, (15) a formylamino and (16) a $C_{1-6}$ alkyl-carboxamido], (iv) a $C_{2-6}$ alkenyl group or (v) a formyl group;

X is a bond, oxygen atom, optionally oxidized sulfur atom, —NH— or —N(methyl)-, $R^5$ is, when X is a bond, then (i) a hydrogen atom, (ii) a $C_{1-6}$ alkyl group or (iii) a halogen atom, when X is an oxygen atom, then (i) a hydrogen atom, (ii) a $C_{1-6}$ alkyl group [this $C_{1-6}$ alkyl group may have a substituent selected from (1) a halogen atom, (2) a hydroxy group, (3) an amino group, (4) a carboxy, (5) a carbamoyl, (6) a $C_{1-6}$ alkoxy-carbonyl, (7) a mono-$C_{1-6}$ alkyl-carbamoyl, (8) a di-$C_{1-6}$ alkyl-carbamoyl, (9) a 4- to 10-membered heterocyclic group containing 1 to 3 heteroatom(s) selected from nitrogen, sulfur and oxygen atoms in addition to carbon atoms], (iii) a $C_{2-6}$ alkenyl group [this $C_{2-6}$ alkenyl group may have a $C_{6-14}$ aryl], (iv) a $C_{2-6}$ alkynyl group, (v) a $C_{3-6}$ cycloalkyl group, (vi) a $C_{7-16}$ aralkyl group, (vii) a $C_{1-6}$ alkyl-carbonyl group, (viii) a $C_{6-14}$ aryl-carbonyl group, (ix) a $C_{1-6}$ alkoxy-carbonyl group, (x) a mono- or di-$C_{1-6}$ alkyl-thiocarbamoyl group, (xi) an optionally halogenated $C_{1-6}$ alkyl-sulfonyl group or (xii) a 4- to 10-membered heterocyclic group containing 1 to 4 heteroatom(s) selected from nitrogen, sulfur and oxygen atoms in addition to carbon atoms [this heterocyclic group may have a $C_{6-14}$ aryl], when X is an optionally oxidized sulfur, then (i) a $C_{1-6}$ alkyl group or (ii) a mono- or di-$C_{1-6}$ alkyl-carbamoyl group, when X is —NH— or —N(methyl)-, then (i) a hydrogen atom, (ii) a $C_{1-6}$ alkyl group [this $C_{1-6}$ alkyl group may have a $C_{1-6}$ alkoxy-carbonyl], (iii) formyl, (iv) a $C_{1-6}$ alkyl-carbonyl group, (v) a $C_{1-6}$ alkoxy-carbonyl group, (vi) a carbamoyl group, (vii) a mono- or di-$C_{1-6}$ alkyl-carbamoyl group or (viii) a $C_{1-6}$ alkyl-sulfonyl group, each of $R^6$ and $R^7$ is a hydrogen atom or $C_{1-6}$ alkyl group, $R^6$ and $R^7$ may be taken together with the adjacent carbon atom to form a $C_{3-8}$ cycloalkane, Each of $R^8$ and $R^9$ is a hydrogen atom or a $C_{1-6}$ alkyl group, Y is <1> a methylene group which may have 1 or 2 $C_{1-6}$ alkyl or hydroxy group or <2> a carbonyl group, n is 0 or 1.

[Compound (I)-IV]

Compound (I) wherein $R^1$ is, (i) a $C_{6-14}$ aryl group which may have 1 to 3 substituent(s) selected from the following (1) to (20):
(1) a halogen atom,
(2) a nitro group,
(3) a $C_{1-6}$ alkyl group [this $C_{1-6}$ alkyl group may have a substituent selected from a halogen atom, cyano, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, (5- or 6-membered heterocyclic ring containing 1 to 3 heteroatom(s) selected from nitrogen, sulfur and oxygen atoms in addition to carbon atoms)-$C_{1-6}$ alkyl-carbamoyl, $C_{1-6}$ alkylsulfonylamino, $C_{1-6}$ alkoxy-carbonyl and carboxy],
(4) a $C_{3-6}$ cycloalkyl group,
(5) a $C_{6-14}$ aryl group [this $C_{6-14}$ aryl group may have a substituent selected from amino, optionally halogenated $C_{1-6}$ alkyl-carbonylamino, ureido, $C_{1-6}$ alkylsulfonylamino, ($C_{1-6}$ alkyl)($C_{1-6}$ alkylsulfonyl)amino, $C_{1-6}$ alkoxy-carbonyl-$C_{1-6}$ alkylamino],
(6) a $C_{1-6}$ alkoxy group which may have a halogen atom or $C_{1-6}$ alkoxy-$C_{6-14}$ aryl,
(7) a $C_{6-14}$ aryloxy group,
(8) a $C_{1-6}$ alkylthio group,
(9) a $C_{1-6}$ alkylsulfinyl group,
(10) a $C_{6-14}$ arylthio group,
(11) a hydroxy group,
(12) a 5- to 14-membered heterocyclic group containing 1 to 4 heteroatom(s) selected from nitrogen, sulfur and oxygen atoms [this heterocyclic group may have a substituent selected from oxo, carboxy-$C_{1-6}$ alkyl, $C_{1-6}$ alkyl-carbonyloxy-$C_{1-6}$ alkyl, $C_{1-6}$ alkoxy-carbonyl-$C_{1-6}$ alkyl, $C_{1-6}$ alkyl-carbamoyl-$C_{1-6}$ alkyl],
(13) a carboxy group,
(14) a group represented by Formula: —CO—Hal (Hal is a halogen atom),
(15) a $C_{1-6}$ alkyl-carbonyl group,
(16) a $C_{1-6}$ alkyl-sulfonyl group,
(17) a $C_{1-6}$ alkoxy-carbonyl group,
(18) a sulfamoyl group [this sulfamoyl group may have a substituent selected from a $C_{1-6}$ alkyl, carbamoyl-$C_{1-6}$ alkyl, (5- or 6-membered heterocyclic ring containing 1 to 3 heteroatom(s) selected from nitrogen, sulfur and oxygen atoms in addition to carbon atoms)-$C_{1-6}$ alkyl],
(19) a group represented by Formula: $NR^aR^b$ [each of $R^a$ and $R^b$ is (i) a hydrogen atom, (ii) a $C_{1-6}$ alkyl, (iii) a (5- or 6-membered heterocyclic ring containing 1 to 3 heteroatom(s) selected from nitrogen, sulfur and oxygen atoms in addition to carbon atoms)-$C_{1-6}$ alkyl, (iv) a $C_{1-6}$ alkoxy-carbonyl-$C_{1-6}$ alkyl, (v) a di-$C_{1-6}$ alkylamino-methylene-sulfamoyl-$C_{1-6}$ alkyl, (vi) a carbamoyl-$C_{1-6}$ alkyl, (vii) a sulfamoyl-$C_{1-6}$ alkyl, (viii) a $C_{1-6}$ alkyl-sulfonyl, (ix) a $C_{1-6}$ alkoxy-carbonyl, (x) a di-$C_{1-6}$ alkoxy-carbonyl-$C_{2-6}$ alkenyl, (xi) a $C_{6-14}$ aryl, (xii) a 5- or 6-membered heterocyclic group containing 1 to 3 heteroatom(s) selected from nitrogen, sulfur and oxygen atoms in addition to carbon atoms [this 5- or 6-membered heterocyclic group may have a substituent selected from amino, $C_{1-6}$ alkyl-carboxamido and $C_{1-6}$ alkyl-sulfonylamino], (xiii) an optionally halogenated $C_{1-6}$ alkyl-carbonyl, (xiv) a $C_{1-6}$ alkylthio-$C_{1-6}$ alkyl-carbonyl, (xv) a $C_{1-6}$ alkylsulfinyl-$C_{1-6}$ alkyl-carbonyl, (xvi) a $C_{1-6}$ alkylsulfonyl-$C_{1-6}$ alkyl-carbonyl, (xvii) an amino-$C_{1-6}$ alkyl-carbonyl, (xviii) an optionally halogenated $C_{1-6}$ alkyl-carbonyl-amino-$C_{1-6}$ alkyl-carbonyl, (xix) a $C_{6-14}$ aryl-carbonyl, (xx) a carboxy-$C_{6-14}$ aryl-carbonyl, (xxi) an optionally $C_{1-6}$ alkyl-esterified phosphono-$C_{1-6}$ alkyl-$C_{6-14}$ aryl-carbonyl, (xxii) a 5-or 6-membered heterocyclic ring containing 1 to 3 heteroatom(s) selected from nitrogen, sulfur and oxygen atoms in addition to carbon atoms, (xxiii) a (5- or 6-membered heterocyclic ring containing 1 to 3 heteroatom(s) selected from nitrogen, sulfur and oxygen atoms in addition to carbon atoms which may have a $C_{1-6}$ alkoxy-carbonyl)-$C_{1-6}$ alkyl-carbonyl, (xxiv) a $C_{6-14}$ aryl-oxy-carbonyl, (xxv) a carboxy-$C_{1-6}$ alkyl or (xxvi) a carbamoyl],
(20) a group represented by Formula: —C(=O)$NR^cR^d$ [each of $R^c$ and $R^d$ is (1) a hydrogen atom, (ii) a $C_{1-6}$ alkyl, (iii) a (5- or 6-membered heterocyclic ring containing 1 to 3 heteroatom(s) selected from nitrogen, sulfur and oxygen atoms in addition to carbon atoms)-$C_{1-6}$ alkyl, (iv) a carboxy-$C_{1-6}$ alkyl, (v) a $C_{1-6}$ alkoxy-carbonyl-$C_{1-6}$ alkyl, (vi) a di-$C_{1-6}$ alkylamino-$C_{1-6}$ alkyl, (vii) a carbamoyl-$C_{1-6}$ alkyl, (viii) a $C_{1-6}$ alkylcarbamoyl-$C_{1-6}$ alkyl, (ix) a (5- or 6-membered heterocyclic group containing 1 to 3 heteroatom(s) selected from nitrogen, sulfur and oxygen atoms)-$C_{1-6}$ alkyl-carbamoyl-$C_{1-6}$ alkyl, (x) a (5- or 6-membered heterocyclic group containing 1 to 3 heteroatom(s) selected from nitrogen, sulfur and oxygen atoms in addition to carbon atoms)-amino-$C_{1-6}$ alkyl, (xi) a sulfamoyl-$C_{6-14}$ aryl-$C_{1-6}$ alkyl, (xii) a $C_{6-14}$ aryl which may have a $C_{1-6}$ alkoxy, (xiii) a $C_{1-6}$ alkyl-$C_{6-14}$ aryl which may have an optionally $C_{1-6}$ alkyl-esterified phosphono group, (xiv) a 4- to 10-membered heterocyclic ring containing 1 to 3 heteroatom(s) selected from nitrogen, sulfur and oxygen atoms in addition to carbon atoms [this heterocyclic group may have 1 or 2 substituent(s) selected from a halogen atom, $C_{1-6}$ alkyl and oxo] or (xv) a $C_{6-14}$ aryl-carbamoyl-$C_{1-6}$ alkyl;

(ii) a 5- to 14-membered heterocyclic group containing 1 to 4 heteroatom(s) selected from nitrogen, sulfur and oxygen atoms in addition to carbon atoms which may contain 1 to 3 substituent(s) selected from the following (1) to (8):
(1) a halogen atom,
(2) a $C_{1-6}$ alkyl group [this alkyl may have a substituent selected from carboxy, $C_{1-6}$ alkoxy, $C_{1-6}$ alkoxy-carbonyl, mono-$C_{1-6}$ alkyl-amino, di-$C_{1-6}$ alkyl-amino, carbamoyl, $C_{1-6}$ alkyl-carbamoyl which may have a hydroxy, 4- to 10-membered heterocyclic group containing 1 to 3 heteroatom(s) selected from nitrogen, sulfur and oxygen atoms in addition to carbon atoms which may have oxo, (4- to 10-membered heterocyclic ring containing 1 to 3 heteroatom(s) selected from nitrogen, sulfur and oxygen atoms in addition to carbon atoms)-carbamoyl, carbamoyl-$C_{1-6}$ alkyl-carbamoyl],
(3) a $C_{1-6}$ alkoxy group, (4) a $C_{6-14}$ aryl group, (5) a $C_{7-16}$ aralkyl group [this $C_{7-16}$ aralkyl group may have a substituent selected from carboxy, $C_{1-6}$ alkoxy-carbonyl, carbamoyl, $C_{1-6}$ alkyl-carbamoyl which may have a hydroxy, (4- to 10-membered heterocyclic ring containing 1 to 3 heteroatom(s) selected from nitrogen, sulfur and oxygen atoms in addition to carbon atoms)-carbamoyl], (6) a 4- to 10-membered heterocyclic group containing 1 to 3 heteroatom(s) selected from nitrogen, sulfur and oxygen atoms in addition to carbon atoms [this 4- to 10-membered heterocyclic group may have a substituent selected from a $C_{1-6}$ alkyl, $C_{1-6}$ alkoxy-carbonyl, carbamoyl, oxo, 4- to 10-membered heterocyclic group containing 1 to 3 heteroatom(s) selected from nitrogen, sulfur and oxygen atoms in addition to carbon atoms], (7) an oxo group, (8) an oxide group;

(iii) a $C_{3-6}$ cycloalkyl group; or, (iv) a group represented by Formula: —L'—$R^{1a'}$ (L' is methylene, carbonyl or an optionally substituted nitrogen atom, $R^{1a'}$ is (1) a hydrogen atom, (2) a $C_{6-14}$ aryl group which may have 1 to 5 substituent(s) selected from a $C_{1-6}$ alkyl and $C_{1-6}$ alkoxy, (3) a hydroxy group which may be substituted by a $C_{1-6}$ alkyl group, (4) a $C_{1-6}$ alkyl-amino group which may be substituted by a 4- to 10-membered heterocyclic ring containing 1 to 3 heteroatom(s) selected from nitrogen, oxygen and sulfur atoms in addition to carbon atoms, (6) a $C_{6-14}$ aryl-amino group or (7) a (4- to 10-membered heterocyclic ring containing 1 to 3 heteroatom(s) selected from nitrogen, oxygen and sulfur atoms in addition to carbon atoms)-amino group), each of $R^2$ and $R^3$ is (1) a hydrogen atom, (2) an optionally halogenated $C_{1-6}$ alkyl group or (3) a $C_{1-6}$ alkoxy-carbonyl group, $R^2$ and $R^3$ may be taken together with the adjacent carbon atom to form a $C_{3-8}$ cycloalkane, $R^4$ is (i) a hydrogen atom, (ii) a $C_{1-6}$ alkyl group [this $C_{1-6}$ alkyl group may have a substituent selected from (1) a halogen atom, (2) a cyano group, (3) a $C_{1-6}$ alkoxy group, (4) a hydroxy group, (5) an amino group, (6) a mono-$C_{1-6}$ alkylamino group, (7) a di-$C_{1-6}$ alkylamino group, (8) a tri-$C_{1-6}$ alkylammonium group, (9) a 4- to 10-membered heterocyclic group containing 1 to 3 heteroatom(s) selected from nitrogen, sulfur and oxygen atoms in addition to carbon atoms which may have an oxo, (10) a $C_{6-14}$ arylthio, (11) an ureido, (12) a carboxy, (13) a carbamoyl, (14) a $C_{1-6}$ alkoxy-carbonyl, (15) a mono-$C_{1-6}$ alkyl-carbamoyl, (16) a formylamino, (17) a $C_{1-6}$ alkyl-carboxamido] or (iii) a $C_{2-6}$ alkenyl group;

X is a bond, oxygen atom, sulfur atom, —NH— or —N(methyl)-, $R^5$ is, when X is a bond, then (i) a hydrogen atom, (ii) a $C_{1-6}$ alkyl group or (iii) a halogen atom, when X is an oxygen atom, then (i) a hydrogen atom, (ii) a $C_{1-6}$ alkyl group [this $C_{1-6}$ alkyl group may have a substituent selected from (1) a halogen atom, (2) a hydroxy group, (3) an amino group, (4) a carboxy, (5) a carbamoyl, (6) a $C_{1-6}$ alkoxy-carbonyl, (7) a mono-$C_{1-6}$ alkyl-carbamoyl, (8) a di-$C_{1-6}$ alkyl-carbamoyl, (9) a 4- to 10-membered heterocyclic group containing 1 to 3 heteroatom(s) selected from nitrogen, sulfur and oxygen atoms in addition to carbon atoms], (iii) a $C_{2-6}$ alkenyl group [this $C_{2-6}$ alkenyl group may have a $C_{6-14}$ aryl], (iv) a $C_{2-6}$ alkynyl group, (v) a $C_{3-6}$ cycloalkyl group, (vi) a $C_{7-16}$ aralkyl group, (vii) a $C_{1-6}$ alkyl-carbonyl group, (viii) a $C_{6-14}$ aryl-carbonyl group, (ix) a $C_{1-6}$ alkoxy-carbonyl group, (x) a mono- or di-$C_{1-6}$ alkyl-thiocarbamoyl group, (xi) an optionally halogenated $C_{1-6}$ alkyl-sulfonyl group or (xii) a 4- to 10-membered heterocyclic group containing 1 to 4 heteroatom(s) selected from nitrogen, sulfur and oxygen atoms in addition to carbon atoms [this heterocyclic group may have a $C_{6-14}$ aryl], when X is a sulfur atom, then (i) a $C_{1-6}$ alkyl group or (ii) a mono- or di-$C_{1-6}$ alkyl-carbamoyl group, when X is —NH— or —N(methyl)-, then (i) a hydrogen atom, (ii) a $C_{1-6}$ alkyl group [this $C_{1-6}$ alkyl group may have a $C_{1-6}$ alkoxy-carbonyl], (iii) formyl, (iv) a $C_{1-6}$ alkyl-carbonyl group, (v) a $C_{1-6}$ alkoxy-carbonyl group, (vi) a carbamoyl group, (vii) a mono- or di-$C_{1-6}$ alkyl-carbamoyl group or (viii) a $C_{1-6}$ alkyl-sulfonyl group, each of $R^6$ and $R^7$ is a hydrogen atom or $C_{1-6}$ alkyl group, $R^6$ and $R^7$ may be taken together with the adjacent carbon atom to form a $C_{3-8}$ cycloalkane, each of $R^8$ and $R^9$ is a hydrogen atom or a $C_{1-6}$ alkyl group, Y is (1) a methylene group which may have a hydroxy group or (2) a carbonyl group, n is 0 or 1.

[Compound (I)-V]

Compounds produced in Examples 1 to 588 or salts thereof.

[Compound (I)-VI]

Compounds produced in Examples 1 to 438 or salts thereof.

[Compound (I)-VII]

(i) 2-(Methylsulfinyl)-N-[3-(3,4,8,9-tetrahydro-6-methoxy-3,3,8,8-tetramethylfuro[2,3-h]isoquinolin-1-yl)phenyl]acetamide, (ii) N-(methylsulfonyl)-N-[3-(3,4,8,9-tetrahydro-6-methoxy-3,3,8,8-tetramethylfuro[2,3-h]isoquinolin-1-yl)phenyl]methanesulfonamide, (iii) N-[2-(4-pyridinyl)ethyl]-3-(3,4,8,9-tetrahydro-6-methoxy-3,3,8,8-tetramethylfuro[2,3-h]isoquinolin-1-yl)benzamide, (iv) N-(2-amino-2-oxoethyl)-3-(3,4,8,9-tetrahydro-6-methoxy-3,3,8,8-tetramethylfuro[2,3-h]isoquinolin-1-yl)benzamide, (v) N-methyl-3-(3,4,8,9-tetrahydro-6-methoxy-3,3,8,8-tetramethylfuro[2,3-h]isoquinolin-1-yl)benzamide, (vi) N-ethyl-3-(3,4,8,9-tetrahydro-6-methoxy-3,3,8,8-tetramethylfuro[2,3-h]isoquinolin-1-yl)benzamide, (vii) N-[3'-(3,4,8,9-tetrahydro-6-methoxy-3,3,8,8-tetramethylfuro[2,3-h]isoquinolin-1-yl)[1,1'-biphenyl]-3-yl]acetamide, (viii) N-(2-amino-1,1-dimethyl-2-oxoethyl)-3-(3,4,8,9-tetrahydro-6-methoxy-3,3,8,8-tetramethylfuro[2,3-h]isoquinolin-1-yl)benzamide, (ix) 3-(6-ethoxy-3,4,8,9-tetrahydro-3,3,8,8-tetramethylfuro[2,3-h]isoquinolin-1-yl)-N-methylbenzamide, (x) N-[2-amino-2-oxoethyl]-3-(6-ethoxy-3,4,8,9-tetrahydro-3,3,8,8-tetramethylfuro[2,3-h]isoquinolin-1-yl)benzamide, (xi) N-(2-amino-1,1-dimethyl-2-oxoethyl)-3-(6-ethoxy-3,4,8,9-tetrahydro-3,3,8,8-tetramethylfuro[2,3-h]isoquinolin-1-yl)benzamide, (xii) N-[3-(6-ethoxy-3,4,8,9-tetrahydro-3,3,8,8-tetramethylfuro[2,3-h]isoquinolin-1-yl)phenyl]methanesulfonamide, (xiii) N-(hydroxymethyl)-3-(3,4,8,9-tetrahydro-6-methoxy-3,3,8,8-tetramethylfuro[2,3-h]isoquinolin-1-yl)benzamide or its salts.

[Compound (I)-VIII]

(i) 2-(Methylsulfinyl)-N-[3-(3,4,8,9-tetrahydro-6-methoxy-3,3,8,8-tetramethylfuro[2,3-h]isoquinolin-1-yl)phenyl]acetamide, (ii) N-(methylsulfonyl)-N-[3-(3,4,8,9-tetrahydro-6-methoxy-3,3,8,8-tetramethylfuro[2,3-h]isoquinolin-1-yl)phenyl]methanesulfonamide, (iii) N-[2-(4-pyridinyl)ethyl]-3-(3,4,8,9-tetrahydro-6-methoxy-3,3, 8,8-tetramethylfuro[2,3-h]isoquinolin-1-yl)benzamide, (iv) N-(2-amino-2-oxoethyl)-3-(3,4,8,9-tetrahydro-6-methoxy-3,3,8,8-tetramethylfuro[2,3-h]isoquinolin-1-yl)benzamide, (v)N-methyl-3-(3,4,8,9-tetrahydro-6-methoxy-3,3,8,8-tetramethylfuro[2,3-h]isoquinolin-1-yl)benzamide, (vi) N-ethyl-3-(3,4,8,9-tetrahydro-6-methoxy-3,3,8,8-tetramethylfuro[2,3-h]isoquinolin-1-yl)benzamide, (vii) N-[3'-(3,4,8,9-tetrahydro-6-methoxy-3,3,8,8-tetramethylfuro[2,3-h]isoquinolin-1-yl)[1,1'-biphenyl]-3-yl]acetamide or its salts.

A compound having a partial structure represented by Formula:

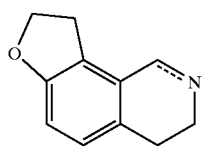

(A-1)

wherein --- is a single bond or double bond employed in a pharmaceutical composition according to the invention is typically a compound represented by Formula:

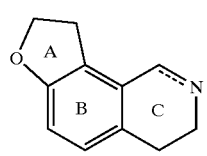

(I-1)

wherein each of Ring A, Ring B and Ring C may have a substituent similar to that described above, more typically a compound represented by Formula:

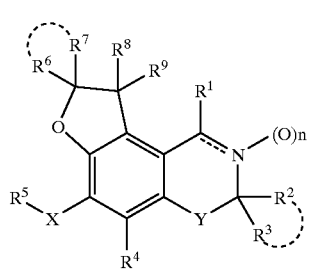

(I'-1)

wherein --- is a single bond or double bond and other symbols are defined as descried above.

When --- is a single bond, then N may have a hydrogen atom or a substituent described above.

As Compound (A-1), (I-1) or (I'-1) according to the invention, a compound produced in any of Examples 1 to 588 and Reference Example 10 to 12, 112, 134, 135, 138 and 139 is specifically employed.

A process for producing Compound (I) or (I') according to the invention is described below. It should be understood that Compound (Ia), (Ib) and (Ic) are encompassed in Compound (I).

Compound (I) and (I') according to the invention can be obtained for example by the methods represented by Schemes 1 to 17 shown below or analogous methods.

Compounds (A), (A-1), (I-1) and (I'-1) can be produced also in accordance with the production methods described below.

Unless otherwise specified, each symbol in a compound shown in a formula in the following schemes is defined as described above. In the schemes, Compounds (II') to (LII'), (LIII) to (LXII) and (LXIII') to (LXIX') encompass their respective salt forms, and such a salt may for example be one similar to a salt of Compound (I) or (I').

Compounds (II'), (III'), (VI'), (VIb'), (VII'), (VIIa'), (IX'), (XI'), (XII'), (XIII'), (XVIII'), (XVIIIa'), (XX'), (XXI'), (XXVII'), (XXIX'), (XXXI'), (XXXIII'), (XXXIIIa'), (XXXVII'), (XXXVIII'), (XL'), (XLI'), (XLVII'), (L'), (LI'), (LIII), (LVI), (LVIII), (LXIII'), (LXV') and (LXVII') may readily be available commercially, or may be produced by a method known per se or an analogous method.

Solvent referred to as general names employed in the following reactions are, unless otherwise specified, alcohol including methanol, ethanol, 1-propanol, 2-propanol and tert-butyl alcohol, etc., ether including diethyl ether, diisopropyl ether, diphenyl ether, tetrahydrofuran, 1,4-dioxane and 1,2-dimethoxyethane, etc., hydrocarbon including benzene, toluene, cyclohexane and hexane, etc., amide including N,N-dimethylformamide, N,N-dimethylacetamide and hexamethylphosphoric triamide, etc., halogenated hydrocarbon including dichloromethane, chloroform, carbon tetrachloride and 1,2-dichloroethane, etc., nitrile including acetonitrile and propionitrile, etc., ketone including acetone and ethyl methyl ketone, etc., organic acid including formic acid, acetic acid, propionic acid, trifluoroacetic acid and methanesulfonic acid, etc., aromatic amine including pyridine, 2,6-lutidine and quinoline, etc., sulfoxide including dimethyl sulfoxide, etc.

Bases referred to as general names employed in the following reactions are, unless otherwise specified, inorganic base including sodium hydroxide, potassium hydroxide, lithium hydroxide and barium hydroxide, etc., basic salt including sodium carbonate, potassium carbonate, cesium carbonate, sodium hydrogen carbonate, sodium acetate and ammonium acetate, etc., aromatic amine including pyridine and lutidine, etc., tertiary amine including triethylamine, tripropylamine, tributylamine, N-ethyldiisopropylamine, cyclohexyldimethylamine, 4-dimethylaminopyridine, N,N-dimethylaniline, N-methylpiperidine, N-methylpyrrolidine and N-methylmorpholine, etc., alkaline metal hydride including sodium hydride and potassium hydride, etc., metal amide including sodium amide, lithium diisopropylamide and lithium hexamethyldisilazide, etc., alkyl metal including butyllithium and tert-butyllithium, etc., aryl metal including phenyllithium, etc., metal alkoxide including sodium methoxide, sodium ethoxide, sodium tert-butoxide and potassium tert-butoxide, etc.

While a product can be used as a reaction solution or a crude material in the next reaction, it can be isolated from the reaction mixture according to a standard method, and can readily be purified by an ordinary separation procedure (e.g., recrystallization, distillation, chromatography, etc.).

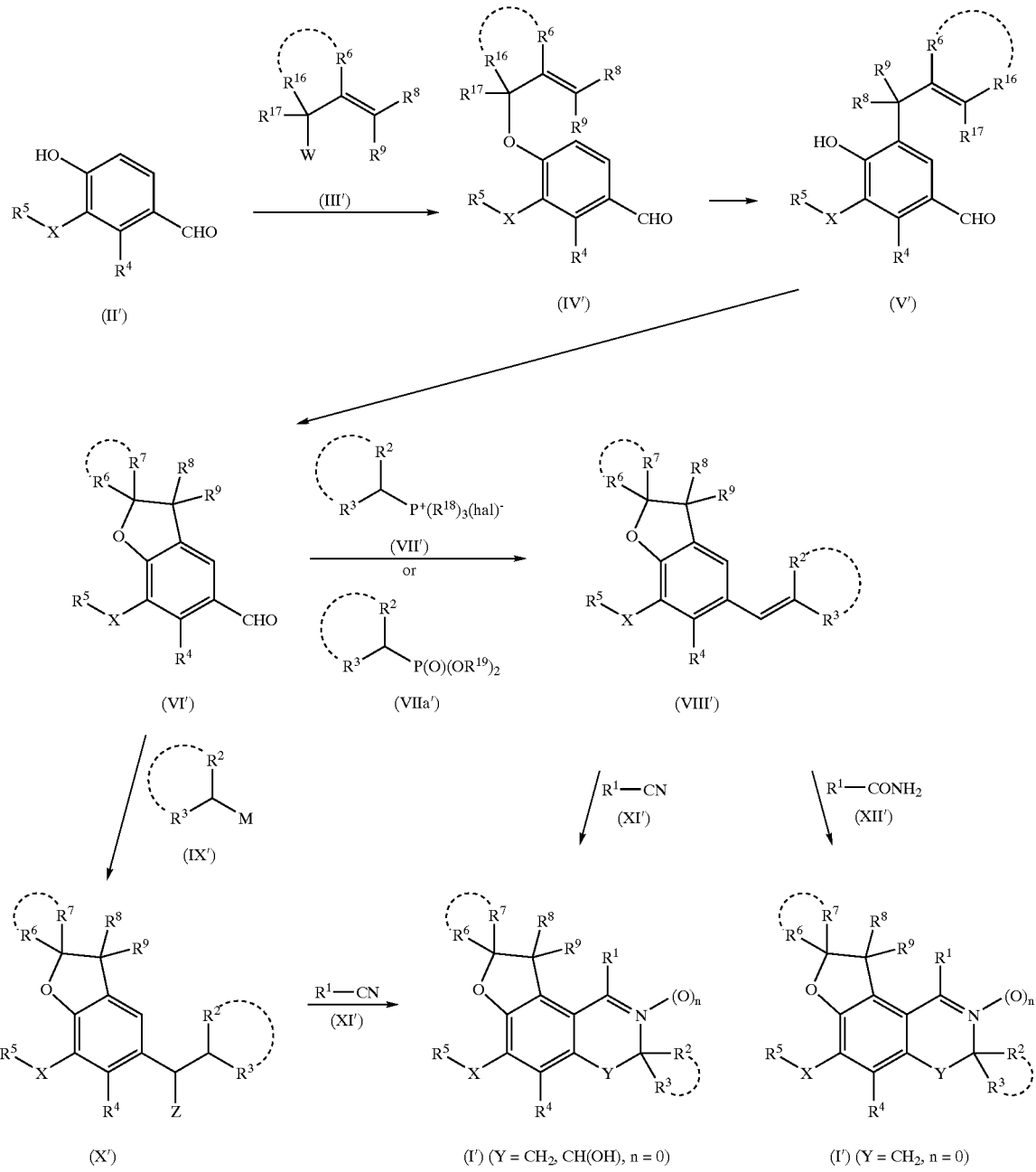

Scheme 1

Compound (IV') can be produced by reacting Compound (II') and Compound (III') wherein $R^{16}$ and $R^{17}$ are optionally substituted hydrocarbon groups which form a part of $R^7$, and may be those similar to $R^7$, and when $R^{16}$ forms a homocyclic ring with $R^6$ then it may have a substituent similar to a substituent which may be possessed by a "3- to 8-membered homocyclic ring" and W is a leaving group, if desired in the presence of a base.

Said "leaving group" may for example be a hydroxy, halogen atom (for example, fluorine, chlorine, bromine, iodine, etc.), optionally halogenated $C_{1-5}$ alkylsulfonyloxy (for example, methanesulfonyloxy, ethanesulfonyloxy, trichloromethanesulfonyloxy, etc.), optionally substituted $C_{6-10}$ arylsulfonyloxy and the like. An "optionally substituted $C_{6-10}$ arylsulfonyloxy" may for example, a $C_{6-10}$ arylsulfonyloxy (e.g., phenylsulfonyloxy, naphthylsulfonyloxy, etc.) which may have 1 to 3 substituent (s) selected from a $C_{1-6}$ alkyl (e.g. methyl, ethyl, etc.), $C_{1-6}$ alkoxy (e.g., methoxy, ethoxy, etc.) and nitro, and those exemplified typically are phenylsulfonyloxy, m-nitrophenylsulfonyloxy, p-toluenesulfonyloxy and the like.

The amount of Compound (III') employed is about 1 to about 5 moles, preferably about 1 to about 2 moles per mole of Compound (II').

Said "base" may for example be an inorganic base, basic salt, aromatic amine, tertiary amine, metal hydride, metal amide and metal alkoxide, etc. The amount of a base employed is about 1 to about 5 moles, preferably about 1 to about 2 moles per mole of Compound (II').

This reaction is conducted advantageously using a solvent which is inert to the reaction. While such a solvent is not limited particularly as long as the reaction is proceeded, it may for example be a solvent such as an alcohol, ether, hydrocarbon, amide, halogenated hydrocarbon, nitrile, ketone and sulfoxide as well as a mixture thereof.

The reaction time is usually about 30 minutes to about 48 hours, preferably about 1 hour to about 24 hours. The reaction temperature is usually about −20 to about 150° C., preferably about 0 to about 100° C.

In addition to the reaction described above, Mitsunobu reaction (Synthesis, 1981, p1–27) can also be employed.

Said reaction allows Compound (II') and Compound (III') wherein W is OH to react with each other in the presence of an azodicarboxylate (e.g., diethylazodicarboxylate, etc.) and a phosphine (e.g., triphenylphosphine, tributylphosphine, etc.).

The amount of Compound (III') wherein W is OH is about 1 to about 5 moles, preferably about 1 to about 2 moles per mole of Compound (II').

The amount of each of said "azodicarboxylate" and "phosphine" employed is about 1 to about 5 moles, preferably about 1 to about 2 moles per mole of Compound (II').

This reaction is conducted advantageously using a solvent which is inert to the reaction. While such a solvent is not limited particularly as long as the reaction is proceeded, it may for example be a solvent such as an ether, hydrocarbon, amide, halogenated hydrocarbon, nitrile, ketone and sulfoxide as well as a mixture thereof.

The reaction time is usually about 5 minutes to about 48 hours, preferably about 10 minutes to about 24 hours. The reaction temperature is usually about −20 to about 200° C., preferably about 0 to about 100° C.

Compound (V') is produced by subjecting Compound (IV') to a Claisen rearrangement.

This reaction is conducted advantageously without using a solvent or with using a solvent which is inert to the reaction. While such a solvent is not limited particularly as long as the reaction is proceeded, it may for example be a solvent such as an alcohol, hydrocarbon, organic acid, ether, aniline (e.g., N,N-dimethylaniline, N,N-diethylaniline, etc.), phenol (e.g., 2,6-dimethylphenol, etc.) and halogenated hydrocarbon as well as a mixture thereof.

This reaction may be conducted also using an acid catalyst if desired. Such an acid catalyst may be a Lewis acid such as aluminum chloride and boron tribromide, etc. The amount of an acid catalyst, for example, when using a Lewis acid, is about 0.1 to about 20 moles, preferably about 0.1 to about 5 moles per mole of Compound (IV'). The reaction time is usually about 30 minutes to about 24 hours, preferably about 1 hour to about 6 hours. The reaction temperature is usually about −70 to about 300° C., preferably about 150 to about 250° C.

Compound (VI') can be produced by subjecting Compound (V') to a ring closure reaction in the presence of a protonic acid, Lewis acid or iodine. Such a protonic acid may for example be mineral acid such as hydrochloric acid, hydrobromic acid, sulfuric acid, etc., sulfonic acid such as methanesulfonic acid, trifluoromethanesulfonic acid, fluorosulfonic acid. Such a Lewis acid may for example be aluminum chloride, aluminum bromide, titanium (IV) chloride, tin (IV) chloride, zinc chloride, boron trichloride, boron tribromide and boron trifluoride, etc. While a protonic acid or Lewis acid is employed usually each alone, the both may be combined if necessary. When a protonic acid is employed, it is used in an amount of about 1 to about 200 moles, preferably about 1 to about 100 moles per mole of Compound (V'). When a Lewis acid is employed, it is used in an amount of about 1 to about 5 moles, preferably about 1 to about 3 moles per mole of Compound (V'). When iodine is employed, it is used in an amount of about 0.05 to about 1 moles, preferably about 0.1 to about 0.5 moles per mole of Compound (V').

This reaction is conducted advantageously using a solvent which is inert to the reaction. While such a solvent is not limited particularly as long as the reaction is proceeded, it may for example be a solvent such as an ether, hydrocarbon, amide, halogenated hydrocarbon, nitrile, ketone and sulfoxide as well as a mixture thereof.

The reaction temperature is usually about −20 to about 150° C., preferably about 0 to about 120° C. The reaction time is usually about 5 minutes to about 24 hours, preferably about 10 minutes to about 5 hours.

Compound (VIII') is produced by reacting Compound (VI') with Compound (VII') wherein $R^{18}$ is a hydrocarbon group and hal is a halogen, if desired in the presence of a base.

Said "hydrocarbon group" may for example be a linear or cyclic hydrocarbon group (e.g., $C_{1-6}$ alkyl (for example, methyl, ethyl, propyl, isopropyl, butyl, isobutyl, sec-butyl, tert-butyl, pentyl, hexyl, etc.), $C_{3-6}$ cycloalkyl (for example, cyclopropyl, cyclobutyl, cyclopentyl, cyclohexyl, etc.), $C_{6-14}$ aryl (for example, phenyl, 1-naphthyl, 2-naphthyl, biphenylyl, 2-anthryl, etc.), and the like.

The amount of Compound (VII') is about 1 to about 5 moles, preferably about 1 to about 2 moles per mole of Compound (VI').

Said "base" may for example be an inorganic base, basic salt, aromatic amine, tertiary amine, alkaline metal hydride, alkyl metal, aryl metal, metal amide, metal alkoxide and the like. The amount of such a base employed is about 1 to about 5 moles, preferably about 1 to about 2 moles per mole of Compound (VI').

This reaction is conducted advantageously using a solvent which is inert to the reaction. While such a solvent is not limited particularly as long as the reaction is proceeded, it may for example be a solvent such as an alcohol, ether, hydrocarbon, amide, halogenated hydrocarbon, nitrile, sulfoxide, water as well as a mixture thereof.

The reaction time is usually about 30 minutes to about 48 hours, preferably about 1 hour to about 24 hours. The reaction temperature is usually about −100 to about 200° C., preferably about −80 to about 150° C.

Compound (VIII') is produced by reacting Compound (VI') with Compound (VIIa') wherein $R^{19}$ is an optionally substituted hydrocarbon group, if desired in the presence of a base.

Said "hydrocarbon group" may for example be a linear or cyclic hydrocarbon group (e.g., $C_{1-6}$ alkyl (for example, methyl, ethyl, propyl, isopropyl, butyl, isobutyl, sec-butyl, tert-butyl, pentyl, hexyl, etc.), $C_{3-6}$ cycloalkyl (for example, cyclopropyl, cyclobutyl, cyclopentyl, cyclohexyl, etc.), $C_{6-14}$ aryl (for example, phenyl, 1-naphthyl, 2-naphthyl, biphenylyl, 2-anthryl), $C_{7-16}$ aralkyl (for example, benzyl, 1-naphthylmethyl)) and the like.

A "substituent" on said "optionally substituted hydrocarbon group" may for example be a halogen atom (e.g., fluorine, chlorine, bromine, iodine, etc.) and an optionally halogenated $C_{1-6}$ alkyl, etc.

The amount of Compound (VIIa') is about 1 to about 3 moles, preferably about 1 to about 1.5 moles per mole of Compound (VI').

Said "base" may for example be an inorganic base, basic salt, aromatic amine, tertiary amine, metal hydride, alkyl metal, aryl metal, metal amide, metal alkoxide and the like. The amount of such a base employed is about 1 to about 5 moles, preferably about 1 to about 2 moles per mole of Compound (VI').

This reaction is conducted advantageously using a solvent which is inert to the reaction. While such a solvent is not limited particularly as long as the reaction is proceeded, it may for example be a solvent such as alcohol, ether, hydrocarbon, amide, halogenated hydrocarbon, nitrile, sulfoxide, water as well as mixture thereof.

The reaction time is usually about 30 minutes to about 48 hours, preferably about 1 hour to about 24 hours. The reaction temperature is usually about −100 to about 200° C., preferably about −80 to about 150° C.

Compound (X') wherein Z is an optionally substituted hydroxy group or halogen can be produced by reacting Compound (VI') and Compound (IX') wherein M is a metal provided that a salt is included when M is polyvalent, followed if necessary by an acylation or halogenation.

Z representing said "optionally substituted hydroxy group" may for example be hydroxy, optionally halogenated $C_{1-6}$ alkylcarbonyloxy (e.g., acetyloxy, trifluoroacetyloxy, propionyloxy, etc.), optionally halogenated $C_{1-6}$ alkylsulfonyloxy (e.g., methanesulfonyloxy, trifluoromethanesulfonyloxy, ethanesulfonyloxy, etc.), optionally substituted $C_{6-10}$ arylsulfonyloxy and the like. An "optionally substituted $C_{6-10}$ arylsulfonyloxy" may for example, a $C_{6-10}$ arylsulfonyloxy (e.g., phenylsulfonyloxy, naphthylsulfonyloxy, etc.) which may have 1 to 3 substituent (s) selected from a halogen, $C_{1-6}$ alkyl, $C_{1-6}$ alkoxy and nitro, and those exemplified typically are phenylsulfonyloxy, p-chlorophenylsulfonyloxy, m-nitrophenylsulfonyloxy, p-toluenesulfonyloxy and the like.

Said "metal" may for example be a magnesium halide (e.g., magnesium bromide, magnesium chloride, etc.), lithium and the like.

The amount of Compound (IX') is about 1 to about 3 moles, preferably about 1 to about 1.5 moles per mole of Compound (VI').

This reaction may employ additives if desired.

Said "additives" may for example be cerium (III) chloride, copper (I) iodide and the like. The amount of an additive employed is usually about 0.1 to about 5 moles, preferably about 0.1 to about 2 moles per mole of Compound (VI').

This reaction is conducted advantageously using a solvent which is inert to the reaction. While such a solvent is not limited particularly as long as the reaction is proceeded, it may for example be a solvent such as an ether and hydrocarbon, as well as a mixture thereof.

The reaction time is usually about 10 minutes to about 48 hours, preferably about 30 minutes to about 24 hours. The reaction temperature is usually about −100 to about 150° C., preferably about −80 to about 100° C.

A resultant alcohol form is subjected to an acylation if necessary.

Compound (X') wherein Z is a hydroxy group and an acylating agent are reacted if desired in the presence of a base or acid.

Said "acylating agent" may for example be a corresponding carboxylic acid or a reactive derivative thereof (for example, acid halide, acid anhydride, ester, etc.), etc. Such an acylating agent is employed in an amount of about 1 to about 5 moles, preferably about 1 to about 2 moles per mole of Compound (X').

This reaction is conducted advantageously without using a solvent or with using a solvent which is inert to the reaction. While such a solvent is not limited particularly as long as the reaction is proceeded, it may for example be a solvent such as an ether, hydrocarbon, amide, halogenated hydrocarbon, nitrile, ketone, sulfoxide, aromatic amine and water as well as a mixture thereof.

A base employed if desired may for example be an inorganic base, basic salt, aromatic amine, tertiary amine and the like.

An acid employed if desired may for example be methanesulfonic acid, p-toluenesulfonic acid, camphorsulfonic acid and the like.]

The reaction temperature is usually about −20 to about 200° C., preferably about 0 to about 150° C. The reaction time is usually about 5 minutes to about 48 hours, preferably about 10 minutes to about 24 hours.

A resultant alcohol form is subjected to a halogenation if necessary.

Compound (X') wherein Z is a hydroxy group is reacted with a halogenating agent if desired in the presence of a base.

Said "halogenating agent" may for example be a thionyl halide such as thionyl chloride and thionyl bromide, etc., a phosphoryl halide such as phosphoryl chloride and phosphoryl bromide, etc., a phosphorus halide such as phosphorus pentachloride, phosphorus trichloride, phosphorus pentabromide and phosphorus tribromide, etc., an oxalyl halide such as oxalyl chloride, etc., phosgene and the like. Such a halogenating agent is employed in an amount of about 1 to about 30 moles, preferably about 1 to about 10 moles per mole of Compound (X').

Said "base" may for example be a tertiary amine.

This reaction is conducted advantageously without using a solvent or with using a solvent which is inert to the reaction. While such a solvent is not limited particularly as long as the reaction is proceeded, it may for example be a solvent such as a hydrocarbon, ether, amide, halogenated hydrocarbon as well as a mixture thereof.

The reaction time is usually about 10 minutes to about 12 hours, preferably about 10 minutes to about 5 hours. The reaction temperature is usually about −10 to about 200° C., preferably about −10 to about 120° C.

Compound (I') wherein Y is $CH_2$ or CH(OH) and n is 0 is produced by reacting Compound (VIII') with Compound (XI') in the presence of an acid or halogenating agent.

The amount of Compound (XI') is about 0.5 to about 5 moles, preferably about 0.5 to about 2 moles per mole of Compound (VIII'). Compound (XI') may be employed also as a solvent, and in such a case the amount used is about 0.5 to about 10 mL, preferably about 1 to about 5 mL per gram of Compound (VIII').

Said "acid" may for example be a mineral acid such as sulfuric acid, hydrogen chloride, hydrogen bromide, hydrogen iodide and perchloric acid or a Lewis acid such as boron trifluoride diethyl ether complex, zinc chloride and aluminum chloride. The amount of an acid employed is about 1 to about 5 moles, preferably about 1 to about 3 moles per mole of Compound (VIII').

Said "halogenating agent" may for example be a halogen such as bromine, chlorine and iodine, an imide such as N-bromosuccinimide, a halogen adduct such as benzyltrimethylammonium dichloroiodate and benzyltrimethylammonium tribromide and the like. The amount of a halogenating agent is about 1 to about 5 moles, preferably about 1 to about 2 moles per mole of Compound (VIII').

This reaction is conducted advantageously using a solvent which is inert to the reaction. While such a solvent is not limited particularly as long as the reaction is proceeded, it may for example be a solvent such as a hydrocarbon, organic acid and halogenated hydrocarbon as well as a mixture thereof.

The reaction time is usually about 10 minutes to about 48 hours, preferably about 15 minutes to about 24 hours. The reaction temperature is usually about −20 to about 150° C., preferably about 0 to about 100° C.

Compound (I') wherein Y is $CH_2$ and n is 0 is produced also by reacting Compound (VIII') with Compound (XII') in the presence of phosphoryl chloride.

The amount of Compound (XII') employed is about 0.5 to about 5 moles, preferably about 0.5 to about 3 moles per mole of Compound (VIII').

The amount of phosphoryl chloride employed is about 0.5 to about 5 moles, preferably about 0.5 to about 3 moles per mole of Compound (VIII'). Phosphoryl chloride may be employed also as a solvent, and in such a case the amount used is about 0.5 to about 20 mL, preferably about 1 to about 10 mL per gram of Compound (VIII').

This reaction is conducted advantageously using a solvent which is inert to the reaction. While such a solvent is not limited particularly as long as the reaction is proceeded, it may for example be a solvent such as a hydrocarbon and halogenated hydrocarbon as well as a mixture thereof.

The reaction time is usually about 10 minutes to about 48 hours, preferably about 15 minutes to about 24 hours. The reaction temperature is usually about −20 to about 150° C., preferably about 0 to about 100° C.

Compound (I') wherein Y is $CH_2$ or CH(OH) and n is 0 is produced also from Compound (X') and Compound (XI') similarly to the production of Compound (I') from Compound (VIII') and Compound (XI').

Compound (I') is produced also by a process shown in Scheme 2.

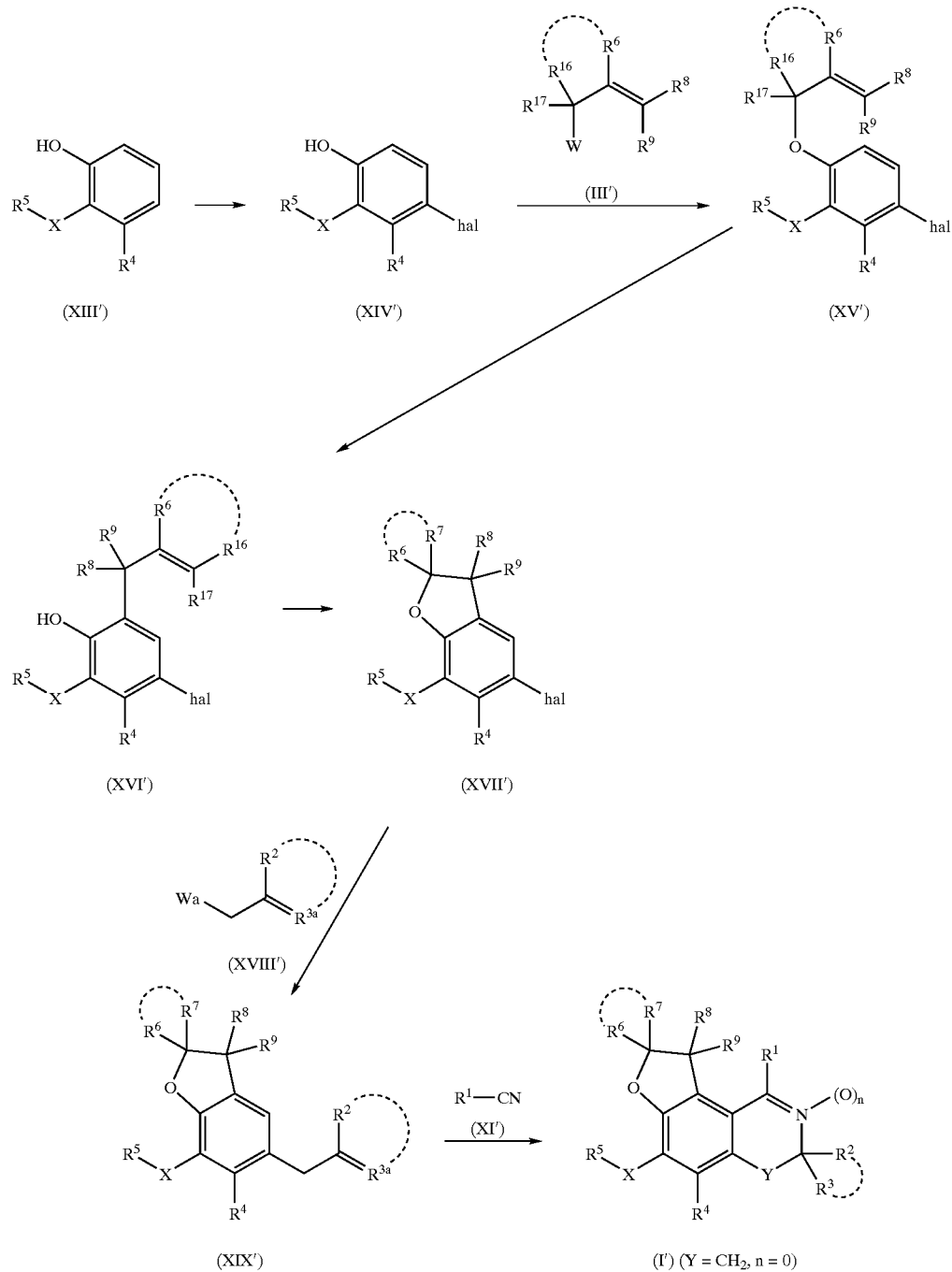

Compound (XIV'), wherein hal is a halogen, is produced by reacting Compound (XIII') with a halogenating agent.

Said "halogenating agent" may for example be a halogen such as bromine, chlorine and iodine, etc., an imide such as N-bromosuccinimide, etc., a halogen adduct such as benzyltrimethylammonium dichloroiodate and benzyltrimethylammonium tribromide and the like. The amount of a halogenating agent is about 1 to about 5 moles, preferably about 1 to about 2 moles per mole of Compound (XIII').

This reaction is conducted advantageously using a solvent which is inert to the reaction. While such a solvent is not limited particularly as long as the reaction is proceeded, it may for example be a solvent such as a hydrocarbon, organic acid and halogenated hydrocarbon as well as a mixture thereof.

The reaction time is usually about 10 minutes to about 48 hours, preferably about 15 minutes to about 24 hours. The reaction temperature is usually about −20 to about 150° C., preferably about 0 to about 100° C.

The process from Compound (XIV') to Compound (XVII') is conducted in accordance with the process for producing Compound (VI') from Compound (II') in Scheme 1.

Compound (XIX') is produced by reacting Compound (XVII') with Compound (XVIII'), wherein $R^{3a}$ is a divalent group formed by removing one hydrogen atom from $R^3$ and Wa is a leaving group, in the presence of a base.

The amount of Compound (XVIII') is about 1 to about 3 moles, preferably about 1 to about 1.5 moles per mole of Compound (XVII').

Said "leaving group" may for example be a halogen atom (for example, fluorine, chlorine, bromine, iodine, etc.), optionally halogenated $C_{1-5}$ alkylsulfonyloxy (for example, methanesulfonyloxy, ethanesulfonyloxy, trichloromethanesulfonyloxy, etc.), optionally substituted $C_{6-10}$ arylsulfonyloxy and the like. An "optionally substituted $C_{6-10}$ arylsulfonyloxy" may for example, a $C_{6-10}$ arylsulfonyloxy (e.g., phenylsulfonyloxy, naphthylsulfonyloxy) which may have 1 to 3 substituent(s) selected from a $C_{1-6}$ alkyl (e.g. methyl, ethyl, etc.), $C_{1-6}$ alkoxy (e.g., methoxy, ethoxy, etc.) and nitro, and those exemplified typically are phenylsulfonyloxy, m-nitrophenylsulfonyloxy, p-toluenesulfonyloxy and the like.

Said "base" may for example be metal amide, alkyl metal, aryl metal and the like. The amount of a base employed is about 1 to about 5 moles, preferably about 1 to about 2 moles per mole of Compound (XVII').

This reaction may employ additives if desired.

Said "additives" may for example be cerium (III) chloride, copper (I) iodide and the like. The amount of an additive employed is usually about 0.1 to about 5 moles, preferably about 0.1 to about 2 moles per mole of Compound (XVII').

This reaction is conducted advantageously using a solvent which is inert to the reaction. While such a solvent is not limited particularly as long as the reaction is proceeded, it may for example be a solvent such as an ether and hydrocarbon, as well as a mixture thereof.

The reaction time is usually about 10 minutes to about 48 hours, preferably about 30 minutes to about 24 hours. The reaction temperature is usually about −100 to about 150° C., preferably about −80 to about 100° C.

Compound (I'), wherein Y is $CH_2$ and n is 0, is produced also from Compound (XIX') and Compound (XI') similarly to the production of Compound (I') from Compound (VIII') and Compound (XI').

Compound (I') is produced also by a process shown in Scheme 3.

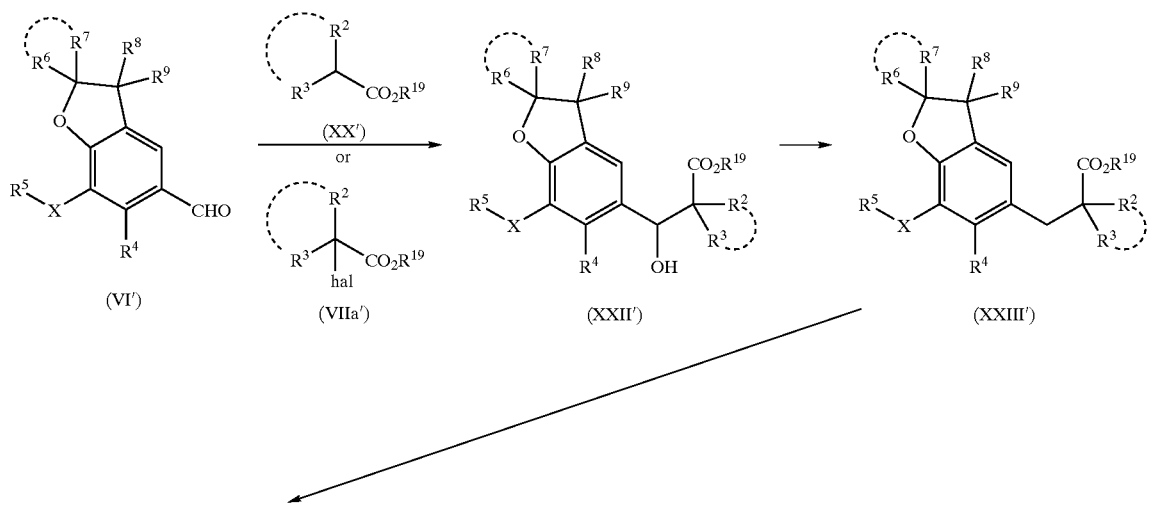

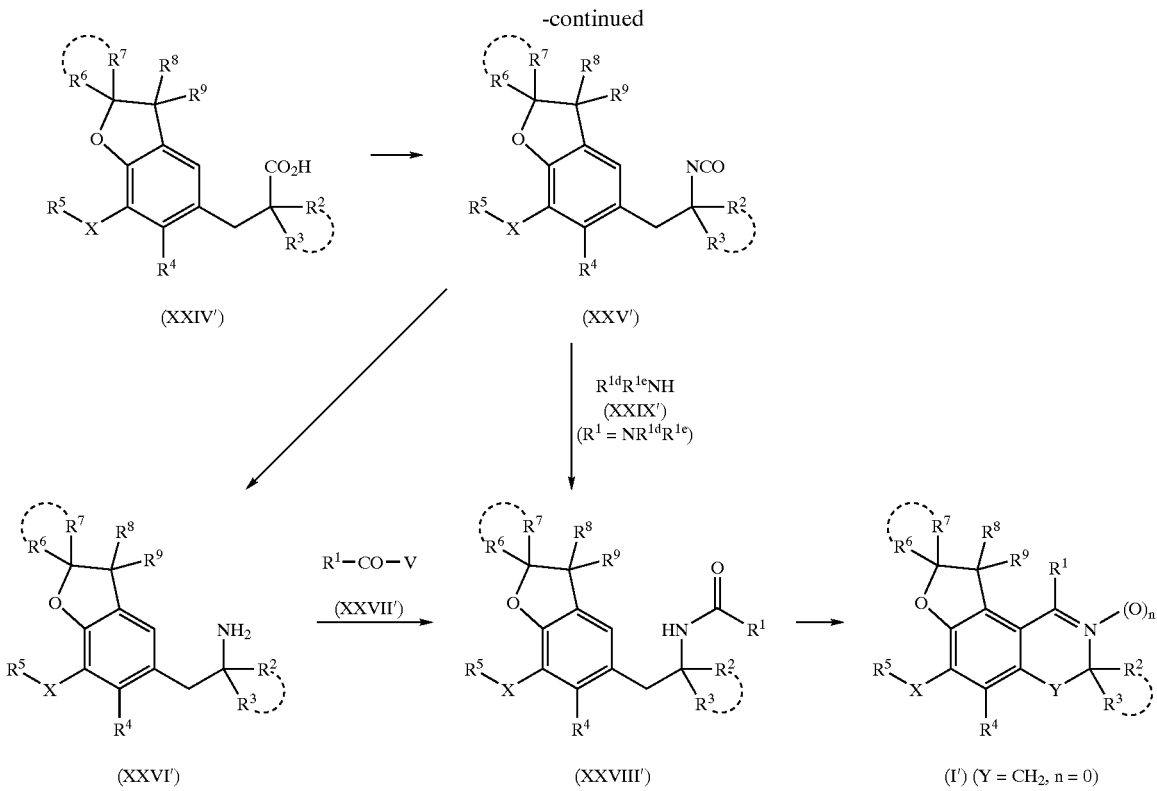

Compound (XXII') is produced by reacting Compound (VI') and Compound (XX'), wherein $R^{19}$ is an optionally substituted hydrocarbon group, in the presence of a base.

Said "hydrocarbon group" may for example be a linear or cyclic hydrocarbon group (e.g., $C_{1-6}$ alkyl (for example, methyl, ethyl, propyl, isopropyl, butyl, isobutyl, sec-butyl, tert-butyl, pentyl, hexyl, etc.), $C_{3-6}$ cycloalkyl (for example, cyclopropyl, cyclobutyl, cyclopentyl, cyclohexyl, etc.), $C_{6-14}$ aryl (for example, phenyl, 1-naphthyl, 2-naphthyl, biphenylyl, 2-anthryl, etc.), $C_{7-16}$ aralkyl (for example, benzyl, 1-naphthylmethyl, etc.) and the like.

A "substituent" on said "optionally substituted hydrocarbon group" may for example be a halogen atom (e.g., fluorine, chlorine, bromine, iodine, etc.) and an optionally halogenated $C_{1-6}$ alkyl, etc.

The amount of Compound (XX') is about 1 to about 5 moles, preferably about 1 to about 2 moles per mole of Compound (VI').

Said "base" may for example be an alkaline metal hydride, alkyl metal, aryl metal, metal amide and the like. The amount of such a base employed is about 1 to about 5 moles, preferably about 1 to about 2 moles per mole of Compound (VI').

This reaction is conducted advantageously using a solvent which is inert to the reaction. While such a solvent is not limited particularly as long as the reaction is proceeded, it may for example be a solvent such as ether and hydrocarbon as well as a mixture thereof.

The reaction time is usually about 30 minutes to about 48 hours, preferably about 1 hour to about 24 hours. The reaction temperature is usually about −100 to about 150° C., preferably about −80 to about 100° C.

Compound (XXII') is produced by reacting Compound (VI') with Compound (XXI'), wherein $R^{19}$ and hal are defined as described above, in the presence of zinc.

The amount of each of Compound (XXI') and zinc employed is about 1 to about 5 moles, preferably about 1 to about 2 moles per mole of Compound (VI').

This reaction is conducted advantageously using a solvent which is inert to the reaction. While such a solvent is not limited particularly as long as the reaction is proceeded, it may for example be a solvent such as ether, hydrocarbon and nitrile as well as a mixture thereof.

The reaction time is usually about 30 minutes to about 48 hours, preferably about 1 hour to about 24 hours. The reaction temperature is usually about 0 to about 200° C., preferably about 0 to about 150° C.

Compound (XXIII') is produced by reducing Compound (XXII').

A reducing agent employed in such a reduction may for example be a silane such as triethylsilane, etc., a metal hydride such as tributyltin hydride, aluminum hydride and diisobutylaluminum hydride, etc., a metal hydrogen complex such as lithium aluminum hydride and sodium borohydride, etc., a borane complex such as borane tetrahydrofuran complex and borane dimethylsulfide complex, etc., an alkylborane such as thexylborane and disiamylborane, etc., diborane, metal such as zinc, aluminum, tin and iron, etc., an alkaline metal such as sodium and lithium/liquid ammonia (Birch reduction) and the like.

The amount of a reducing agent is about 1 to about 10 moles, preferably about 1 to about 3 moles per mole of Compound (XXII') when a silane, metal hydride or metal hydrogen complex is employed, about 1 to about 10 moles, preferably about 1 to about 5 moles per mole of Compound (XXII') when a borane complex, alkyl borane or diborane is employed, and about 1 to about 20 equivalents, preferably about 1 to about 5 equivalents when metal or alkaline metal is employed. This reaction may employ a Lewis acid if desired. Said "Lewis acids" may for example be aluminum chloride, aluminum bromide, titanium (IV) chloride, tin (II) chloride, zinc chloride, boron trichloride, boron tribromide, boron trifluoride and the like. The amount of a Lewis acid employed is about 1 to about 5 moles, preferably about 1 to about 2 moles per mole of Compound (XXII').

A hydrogenation reaction may also serve for the reduction, and in such a case a catalyst such as Pd/C, platinum (IV) oxide, Raney nickel and Raney cobalt, etc. may be employed. The amount of a catalyst employed is about 5 to about 1000% by weight, preferably about 10 to about 300% by weight, based on Compound (XXII').

This reaction is conducted advantageously using a solvent which is inert to the reaction. While such a solvent is not limited particularly as long as the reaction is proceeded, it may for example be solvent such as alcohol, ether, hydrocarbon, halogenated hydrocarbon, amide and organic acid as well as a mixture thereof.

The reaction time is usually about 1 hour to about 100 hours, preferably about 1 hour to about 50 hours, although it may vary depending on the type and the amount of the reducing agent employed and the activity and the amount of the catalyst. The reaction temperature is usually about −20 to about 120° C., preferably about 0 to about 80° C. When a hydrogenation catalyst is employed, the pressure of hydrogen is usually about 1 to about 100 atm.

Compound (XXIV') is produced by hydrolyzing the ester group of Compound (XXIII') using acid or base.

The acidic hydrolysis usually employs mineral acid such as hydrochloric acid and sulfuric acid, a Lewis acid such as boron trichloride and boron tribromide, a combination of a Lewis acid and a thiol or sulfide, an organic acid such as trifluoroacetic acid and p-toluenesulfonic acid, etc.

The basic hydrolysis usually employs an inorganic base, basic salt, metal alkoxide and the like.

The amount of each of the acid and base employed is about 0.5 to about 10 moles, preferably about 0.5 to about 5 moles per mole of Compound (XXIII').

This reaction is conducted advantageously using a solvent which is inert to the reaction. While such a solvent is not limited particularly as long as the reaction is proceeded, it may for example be a solvent such as an alcohol, hydrocarbon, organic acid, ether, amide, halogenated hydrocarbon, nitrile, ketone, sulfoxide and water as well as a mixture thereof.

The reaction time is usually about 10 minutes to about 48 hours, preferably about 15 minutes to about 24 hours. The reaction temperature is usually about −20 to about 150° C., preferably about 0 to about 100° C.

Compound (XXV') is produced by subjecting Compound (XXIV') to a rearrangement directly or after converting into a reactive derivative thereof (for example, acid halide, acid amide, acid anhydride, ester, etc.).

Said "rearrangement" may for example be a Curtius rearrangement, Hofmann rearrangement, Schmidt rearrangement and the like.

A case employing diphenylphosphoryl azide is described below.

The amount of diphenylphosphoryl azide is about 1 to about 3 moles, preferably about 1 to about 1.5 moles per mole of Compound (XXIV').

This reaction is conducted if desired in the presence of a base.

Said "base" is preferably tertiary amine, aromatic amine and the like.

This reaction is conducted advantageously using a solvent which is inert to the reaction. While such a solvent is not limited particularly as long as the reaction is proceeded, it may for example be a solvent such as a hydrocarbon, halogenated hydrocarbon and ether as well as a mixture thereof.

The reaction time is usually about 10 minutes to about 48 hours, preferably about 15 minutes to about 24 hours. The reaction temperature is usually about −20 to about 200° C., preferably about 0 to about 150° C.

Other reaction conditions are those described in JIKKEN-KAGAKUKOZA 20, 4th edition (Ed. by Japanese Association of Chemistry), pages 304, 477 to 479.

Compound (XXVI') is produced by subjecting Compound (XXV') to the acidic hydrolysis.

The acidic hydrolysis usually employs a mineral acid such as hydrochloric acid and sulfuric acid, etc., a Lewis acid such as boron trichloride and boron tribromide, etc., a combination of a Lewis acid and a thiol or sulfide, an organic acid such as trifluoroacetic acid and p-toluenesulfonic acid, etc.

The amount of such an acid employed is about 0.5 to about 10 moles, preferably about 0.5 to about 5 moles per mole of Compound (XXV').

This reaction is conducted advantageously using a solvent which is inert to the reaction. While such a solvent is not limited particularly as long as the reaction is proceeded, it may for example be a solvent such as a hydrocarbon, ether, halogenated hydrocarbon, ketone, sulfoxide and water as well as a mixture thereof.

The reaction time is usually about 10 minutes to about 48 hours, preferably about 15 minutes to about 24 hours. The reaction temperature is usually about −20 to about 200° C., preferably about 0 to about 150° C.

Compound (XXVIII') is produced by reacting Compound (XXVI') and Compound (XXVII'), wherein V is an optionally substituted hydroxy group, halogen and the like, if desired in the presence of a base or acid.

V, which represents said "optionally substituted hydroxy groups" may for example be a hydroxy, optionally halogenated $C_{1-6}$ alkylcarbonyloxy (e.g., acetyloxy, trifluoroacetyloxy, propionyloxy, etc.), optionally halogenated $C_{1-6}$ alkylsulfonyloxy (e.g., methanesulfonyloxy, trifluoromethanesulfonyloxy, ethanesulfonyloxy, etc.), optionally substituted $C_{6-10}$ arylsulfonyloxy, or a group represented by Formula: $R^1$—$CO_2$ and the like. An "optionally substituted $C_{6-10}$ arylsulfonyloxy" may for example, a $C_{6-10}$ arylsulfonyloxy (e.g., phenylsulfonyloxy, naphthylsulfonyloxy, etc.) which may have 1 to 3 substituent (s) selected from a halogen, $C_{1-6}$ alkyl, $C_{1-6}$ alkoxy and nitro, and those exemplified typically are phenylsulfonyloxy, p-chlorophenylsulfonyloxy, m-nitrophenylsulfonyloxy, p-toluenesulfonyloxy and the like.

Compound (XXVII') is employed in an amount of about 1 to about 5 moles, preferably about 1 to about 2 moles per mole of Compound (XXVI').

This reaction is conducted advantageously without using a solvent or with using a solvent which is inert to the reaction. While such a solvent is not limited particularly as long as the reaction is proceeded, it may for example be a solvent such as ether, hydrocarbon, amide, halogenated hydrocarbon, nitrile, ketone, sulfoxide, aromatic amine and water as well as a mixture thereof.

A base employed if desired may for example be an inorganic base, basic salt, aromatic amine, tertiary amine and the like.

An acid employed if desired may for example be methanesulfonic acid, p-toluenesulfonic acid, camphorsulfonic acid and the like.

The reaction temperature is usually about −20 to about 200° C., preferably about 0 to about 150° C. The reaction time is usually about 5 minutes to about 48 hours, preferably about 10 minutes to about 24 hours.

Compound (XXVIII') is produced also by reacting Compound (XXV') and Compound (XXIX'), wherein $R^{1d}$ and $R^{1e}$ are substituents forming a part of $R^1$ and each is a hydrogen atom or optionally substituted hydrocarbon group, if desired in the presence of a base or acid.

Said "hydrocarbon group" may for example be a linear or cyclic hydrocarbon group (e.g., $C_{1-6}$ alkyl (for example, methyl, ethyl, propyl, isopropyl, butyl, isobutyl, sec-butyl, tert-butyl, pentyl, hexyl, etc.), $C_{3-6}$ cycloalkyl (for example, cyclopropyl, cyclobutyl, cyclopentyl, cyclohexyl, etc.), $C_{6-14}$ aryl (for example, phenyl, 1-naphthyl, 2-naphthyl, biphenylyl, 2-anthryl, etc.), $C_{71-6}$ aralkyl (for example, benzyl, 1-naphthylmethyl, etc.), and the like.

The "substituent" on said optionally substituted hydrocarbon group may for example be a halogen atom (e.g., fluorine, chlorine, bromine, iodine, etc.) and an optionally halogenated $C_{1-6}$ alkyl, etc.

The amount of Compound. (XXIX') is about 1 to about 3 moles, preferably about 1 to about 2 moles per mole of Compound (XXV').

This reaction is conducted advantageously using a solvent which is inert to the reaction. While such a solvent is not limited particularly as long as the reaction is proceeded, it may for example be a solvent such as an ether, hydrocarbon, amide, halogenated hydrocarbon, nitrile and sulfoxide as well as a mixture thereof.

The reaction time is usually about 30 minutes to about 48 hours, preferably about 1 hour to about 24 hours. The reaction temperature is usually about −20 to about 150° C., preferably about 0 to about 100° C.

Compound (I'), wherein Y is $CH_2$ and n is 0, is produced by subjecting Compound (XXVIII') to an intramolecular cyclization using a halogenating agent and the like.

Said "halogenating agent" may for example be phosphoryl chloride, phosphorus pentachloride, phosphorus pentoxide, aluminum chloride and the like.

The amount of said "halogenating agent" is about 1 to about 20 moles, preferably about 1 mole to about 5 moles per mole of Compound (XXVIII'). Said "halogenating agent" may be used also as a solvent, and in such a case the amount used is about 0.5 to about 20 mL, preferably about 1 to about 10 mL pert gram of Compound (XXVIII').

This reaction is conducted advantageously using a solvent which is inert to the reaction. While such a solvent is not limited particularly as long as the reaction is proceeded, it may for example be a solvent such as a hydrocarbon, nitrile and halogenated hydrocarbon as well as a mixture thereof.

The reaction temperature is usually about −20 to about 200° C, preferably about 0 to about 150° C. The reaction time is usually about 5 minutes to about 48 hours, preferably about 10 minutes to about 24 hours.

Compound (I') is produced also by a process shown in Scheme 4.

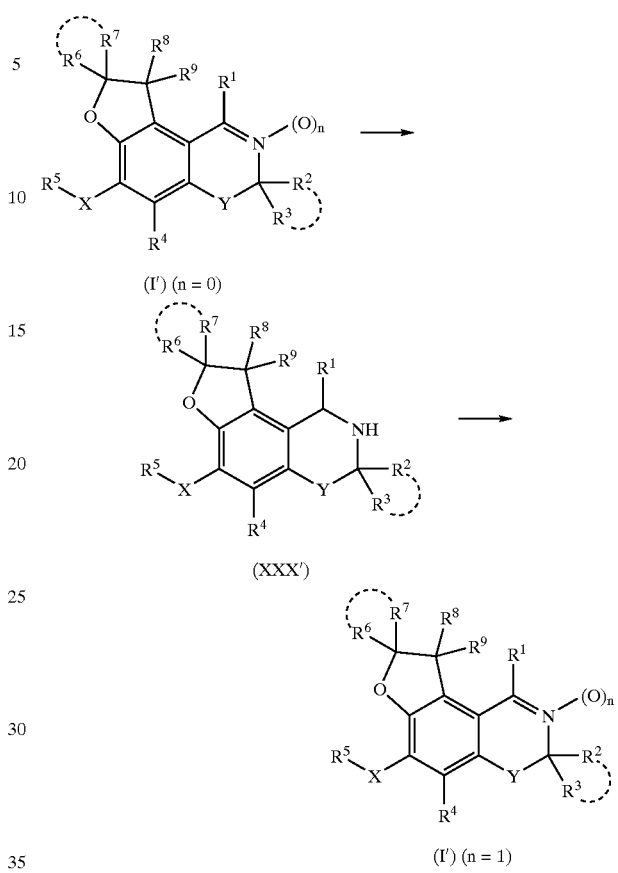

Scheme 4

Compound (XXX') is produced by reducing Compound (I') wherein n is 0.

The reducing agent employed in such a reduction may for example be a metal hydride such as tributyltin hydride, aluminum hydride and diisobutylaluminum hydride, etc., a metal hydrogen complex such as lithium aluminum hydride and sodium borohydride, etc., a borane complex such as borane tetrahydrofuran complex and borane dimethylsulfide complex, an alkylborane such as thexylborane and disiamylborane, etc., diborane, a metal such as zinc, aluminum, tin and iron, etc., an alkaline metal such as sodium and lithium/liquid ammonia (Birch reduction) and the like.

The amount of a reducing agent is about 1 to about 10 moles, preferably about 1 to about 3 moles per mole of Compound (I') when a metal hydride or metal hydrogen complex is employed, about 1 to about 10 moles, preferably about 1 to about 5 moles per mole of Compound (I') when a borane complex, alkyl borane or diborane is employed, and about 1 to about 20 equivalents, preferably about 1 to about 5 equivalents when a metal or alkaline metal is employed. This reaction may employ a Lewis acid if desired. Said "Lewis acid" may for example be aluminum chloride, aluminum bromide, titanium (IV) chloride, tin (II) chloride, zinc chloride, boron trichloride, boron tribromide, boron trifluoride and the like. The amount of a Lewis acid employed is about 1 to about 5 moles, preferably about 1 to about 2 moles per mole of Compound (I').

A hydrogenation reaction may also serve for the reduction, and in such a case a catalyst such as Pd/C, platinum (IV) oxide, Raney nickel and Raney cobalt may be employed. The amount of a catalyst employed is about 5 to about 1000% by weight, preferably about 10 to about 300% by weight, based on Compound (I').

This reaction is conducted advantageously using a solvent which is inert to the reaction. While such a solvent is not limited particularly as long as the reaction is proceeded, it may for example be a solvent such as an alcohol, ether, hydrocarbon, amide and organic acid as well as a mixture thereof.

The reaction time is usually about 1 hour to about 100 hours, preferably about 1 hour to about 50 hours, although it may vary depending on the type and the amount of the reducing agent employed and the activity and the amount of the catalyst. The reaction temperature is usually about −20 to about 120° C., preferably about 0 to about 80° C. When a hydrogenation catalyst is employed, the pressure of hydrogen is usually about 1 to about 100 atm.

Compound (I') wherein n is 1 is produced by oxidizing Compound (XXX').

An oxidizing agent employed in such an oxidation may for example be hydrogen peroxide, etc. The amount of an oxidizing agent employed is about 1 to about 20 moles, preferably about 1 to about 5 moles per mole of Compound (XXX'), In this reaction, it is preferable to use a catalyst such as sodium tungstate (VI). The amount of such a catalyst is about 0.05 to about 1 moles, preferably about 0.05 to about 0.5 moles per mole of Compound (XXX').

This reaction is conducted advantageously using a solvent which is inert to the reaction. While such a solvent is not limited particularly as long as the reaction is proceeded, it may for example be a solvent such as an alcohol, hydrocarbon, amide, halogenated hydrocarbon and water as well as a mixture thereof.

The reaction time is usually about 30 minutes to about 48 hours, preferably about 1 hour to about 24 hours. The reaction temperature is usually about −20 to about 150° C., preferably about 0 to about 100° C.

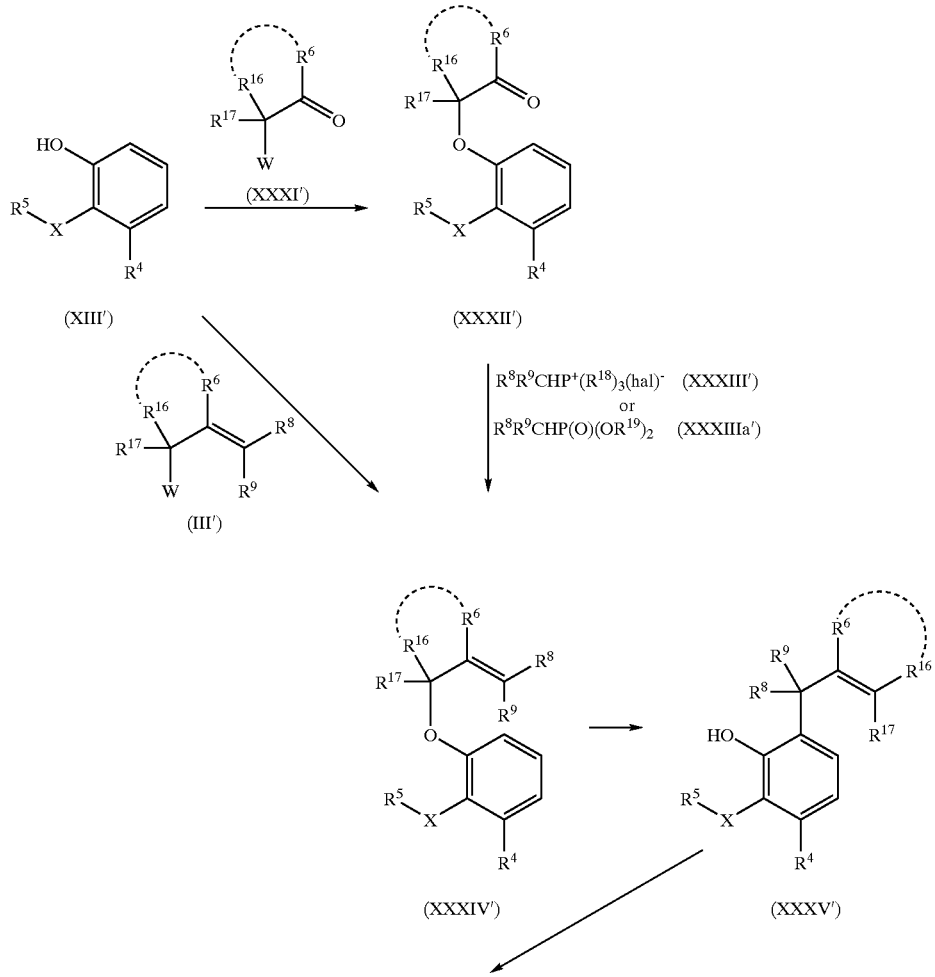

Scheme 5

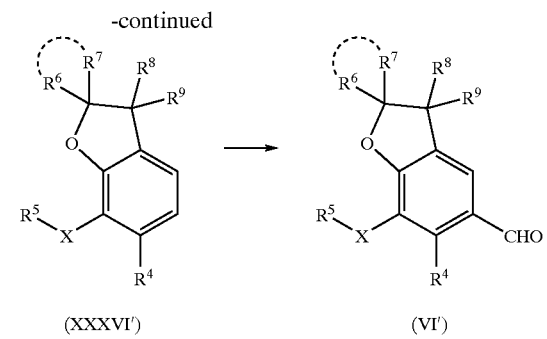

(XXXVI') → (VI')

Compound (XXXII') is produced from Compound (XIII') and Compound (XXXI'), wherein $R^{16}$, $R^{17}$ and W are defined as described above, similarly to the production of Compound (IV') from Compound (II') and Compound (III').

Compound (XXXIV') is produced from Compound (XXXII') and Compound (XXXIII'), wherein $R^{18}$ and hal are defined as described above, similarly to the production of Compound (VIII') from Compound (VI') and Compound (VII').

Compound (XXXIV') is also produced from Compound (XXXII') and Compound (XXXIIIa'), wherein $R^{19}$ is defined as described above, similarly to the production of Compound (VIII') from Compound (VI') and Compound (VIIa').

Compound (XXXIV') is also produced from Compound (XIII') and Compound (III') similarly to the production of Compound (IV') from Compound (II') and Compound (III').

The process from Compound (XXXIV') to Compound (XXXVI') is conducted in accordance with the process for producing Compound (VI') from Compound (IV') in Scheme 1.

Compound (VI') is produced by reacting Compound (XXXVI') with a formamide in the presence of an acid catalyst.

Said "formamide" may for example be dimethylformamide and N-methylformanilide, etc. The formamide is used in an amount of about 1 to about 10 moles, preferably about 1 to about 5 moles per mole of Compound (XXXVI').

Said "acid catalysts" may for example be phosphoryl chloride and thionyl chloride. Such an acid catalyst is employed usually in an amount of about 1 to about 10 moles, preferably about 1 to about 5 moles per mole of Compound (XXXVI').

This reaction is conducted advantageously using a solvent which is inert to the reaction. While such a solvent is not limited particularly as long as the reaction is proceeded, it may for example be a solvent such as an amide, ether, hydrocarbon, halogenated hydrocarbon and nitrile as well as a mixture thereof.

The reaction time is usually about 10 minutes to about 48 hours, preferably about 30 minutes to about 24 hours. The reaction temperature is usually about −20 to about 150° C., preferably about 0 to about 100° C.

Compound (VI') is produced also by reacting Compound (XXXVI') with a dichloromethylalkyl ether in the presence of an acid catalyst.

Said "dichloromethylalkyl ether" may for example be dichloromethylmethyl ether and dichloromethylbutyl ether, etc. The dichloromethylalkyl-ether is used in an amount of about 1 to 5 moles, preferably about 1 to 3 moles per mole of Compound (XXXVI').

Said "acid catalyst" may for example be titanium (IV) chloride, aluminum chloride or tin (IV) chloride. An acid catalyst is used in an amount of about 1 to 5 moles, preferably about 1 to 3 moles per mole of Compound (XXXVI').

This reaction is conducted advantageously using a solvent which is inert to the reaction. While such a solvent is not limited particularly as long as the reaction is proceeded, it may for example be a solvent such as an ether, hydrocarbon, halogenated hydrocarbon and nitrile as well as a mixture thereof.

The reaction time is usually about 10 minutes to about 48 hours, preferably about 30 minutes to about 24 hours. The reaction temperature is usually about −20 to about 100° C., preferably about 0 to about 80° C.

Scheme 6

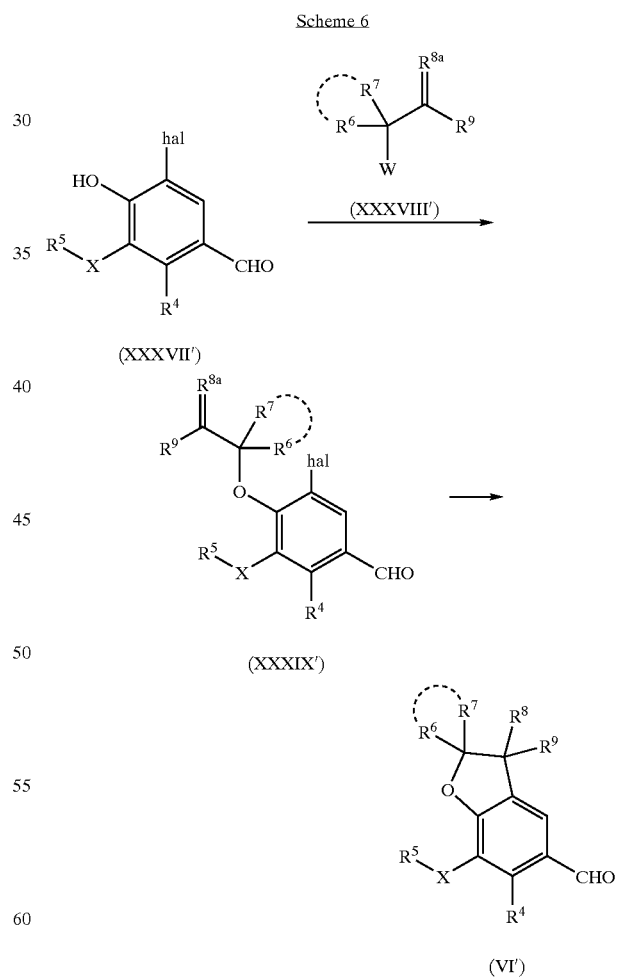

Compound (XXXIX') is produced by reacting Compound (XXXVII') wherein hal is a halogen with Compound (XXXVIII') wherein $R^{8a}$ is a divalent group formed by removing one hydrogen atom from $R^8$ and W is defined as described above similarly to the production of Compound (IV') from Compound (II') and Compound (III').

Compound (VI') is produced by subjecting Compound (XXXIX') to a ring closure in the presence of a catalyst or in the presence of a radical initiator.

In a case of a ring closure using a catalyst, said "catalyst" may for example be a palladium such as palladium (II) acetate and palladium (II) chloride, etc. The amount of a catalyst employed is about 0.01 to about 0.5 mole, preferably about 0.01 to about 0.2 moles per mole of Compound (XXXIX').

This reaction preferably employs additives. Said "additives" may for example be a quaternary ammonium salt such as tetrabutylammonium chloride, etc., tetramethylammonium chloride and tetraethylammonium chloride, a metal halide such as lithium chloride, etc., triphenylphosphine and the like. The amount of additives employed is usually about 1 to about 5 moles, preferably about 1 to about 2 moles per mole of Compound (XXXIX').

This reaction preferably employs a base if desired. Said "base" may for example be an inorganic base, basic salt, aromatic amine, tertiary amine, metal alkoxide and the like. The amount of such a base employed is about 1 to about 5 moles, preferably about 1 to about 2 moles per mole of Compound (XXXIX').

In addition, it is preferable to add a formate such as sodium formate in this reaction. The amount of such a formate employed is about 1 to about 5 moles, preferably about 1 to about 2 moles per mole of Compound (XXXIX').

This reaction is conducted advantageously using a solvent which is inert to the reaction. While such a solvent is not limited particularly as long as the reaction is proceeded, it may for example be a solvent such as an alcohol, ether, hydrocarbon, amide and ketone as well as a mixture thereof.

The reaction time is usually about 10 minutes to about 48 hours, preferably about 30 minutes to about 24 hours. The reaction temperature is usually about 0 to about 150° C., preferably about 0 to about 120° C.

In a case of a ring closure using a radical initiator, said "radical initiator" may for example be benzoyl peroxide, 2,2'-azobis(isobutyronitrile) and the like. The amount of a radical initiator employed is about 0.01 to about 1 moles, preferably about 0.0.1 to about 0.1 moles per mole of Compound (XXXIX').

This reaction employs a radical source and the like. Said "radical source" may for example be hypophosphorous acid, tris(trimethylsilyl)silane, tributyltin hydride and the like. The amount of a radical source employed is about 1 to about 100 moles, preferably about 1 to about 50 moles per mole of Compound (XXXIX').

This reaction preferably employs a base if desired. Said "base" may for example be inorganic base, basic salt, aromatic amine, tertiary amine, metal alkoxide and the like. The amount of such a base employed is about 1 to about 5 moles, preferably about 1 to about 2 moles per mole of Compound (XXXIX').

This reaction is conducted advantageously using a solvent which is inert to the reaction. While such a solvent is not limited particularly as long as the reaction is proceeded, it may for example be a solvent such as an alcohol, ether, hydrocarbon, amide and ketone as well as a mixture thereof.

The reaction time is usually about 10 minutes to about 48 hours, preferably about 30 minutes to about 24 hours. The reaction temperature is usually about 0 to about 200° C. preferably about 0 to about 150° C.

Scheme 7

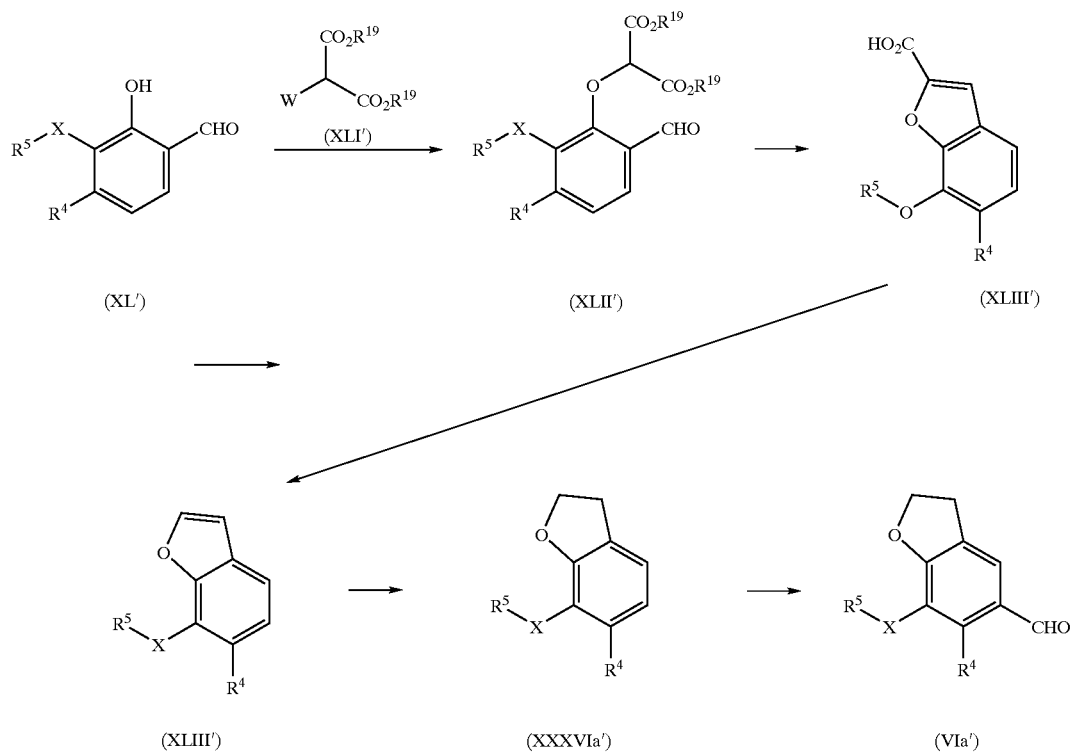

Compound (XLII') is produced by reacting Compound (XL') with Compound (XLI'), wherein $R^{19}$ and W is defined as described above, similarly to the production of Compound (IV') from Compound (II') and Compound (III').

Compound (XLIII') is produced by subjecting Compound (XLII') to a ring closure in the presence of a base. Said "base" may for example be an inorganic salt. The amount of a base employed is about 1 to about 10 moles, preferably about 1 to about 5 moles per mole of Compound (XLII').

This reaction is conducted advantageously using a solvent which is inert to the reaction. While such a solvent is not limited particularly as long as the reaction is proceeded, it may for example be a solvent such as an alcohol, ether, hydrocarbon and water as well as a mixture thereof.

The reaction time is usually about 10 minutes to about 48 hours, preferably about 30 minutes to about 24 hours. The reaction temperature is usually about 0 to about 150° C., preferably about 0 to about 120° C.

Compound (XLIV') is produced by subjecting Compound (XLIII') to a decarboxylation in the presence of copper.

The amount of copper employed is about 0.1 to about 5 moles, preferably about 0.5 to about 3 moles per mole of Compound (XLIII').

This reaction is conducted advantageously using a solvent which is inert to the reaction. While such a solvent is not limited particularly as long as the reaction is proceeded, it may for example be a solvent such as a hydrocarbon including tetrahydronaphthalene, etc., ether including diphenyl ether, etc., aromatic amine including quinoline, etc. and a tertiary amine including N,N-diethylaniline, etc. as well as a mixture thereof.

The reaction time is usually about 10 minutes to about 24 hours, preferably about 15 minutes to about 12 hours. The reaction temperature is usually about 100 to about 300° C., preferably about 100 to about 250° C.

Compound (XXXVIa') is produced by subjecting Compound (XLIV') to a hydrogenation. In this reaction, a hydrogenation catalyst such as Pd/C, platinum (IV) oxide, Raney nickel and Raney cobalt, etc. may be employed. The amount of the catalyst employed is about 5 to about 1000% by weight, preferably about 10 to about 300% by weight, based on Compound (XLIV').

This reaction is conducted advantageously using a solvent which is inert to the reaction. While such a solvent is not limited particularly as long as the reaction is proceeded, it may for example be a solvent such as alcohol, ether, hydrocarbon, amide and organic acid as well as a mixture thereof.

The reaction time is usually about 1 hour to about 100 hours, preferably about 1 hour to about 50 hours, although it may vary depending on the activity and the amount of the catalyst employed. The reaction temperature is usually about −20 to about 120° C., preferably about 0 to about 80° C. The pressure of hydrogen is usually about 1 to about 100 atm.

Compound (VIa') is produced from Compound (XXXVIa') similarly to the production of Compound (VI') from Compound (XXXVI').

Scheme 8

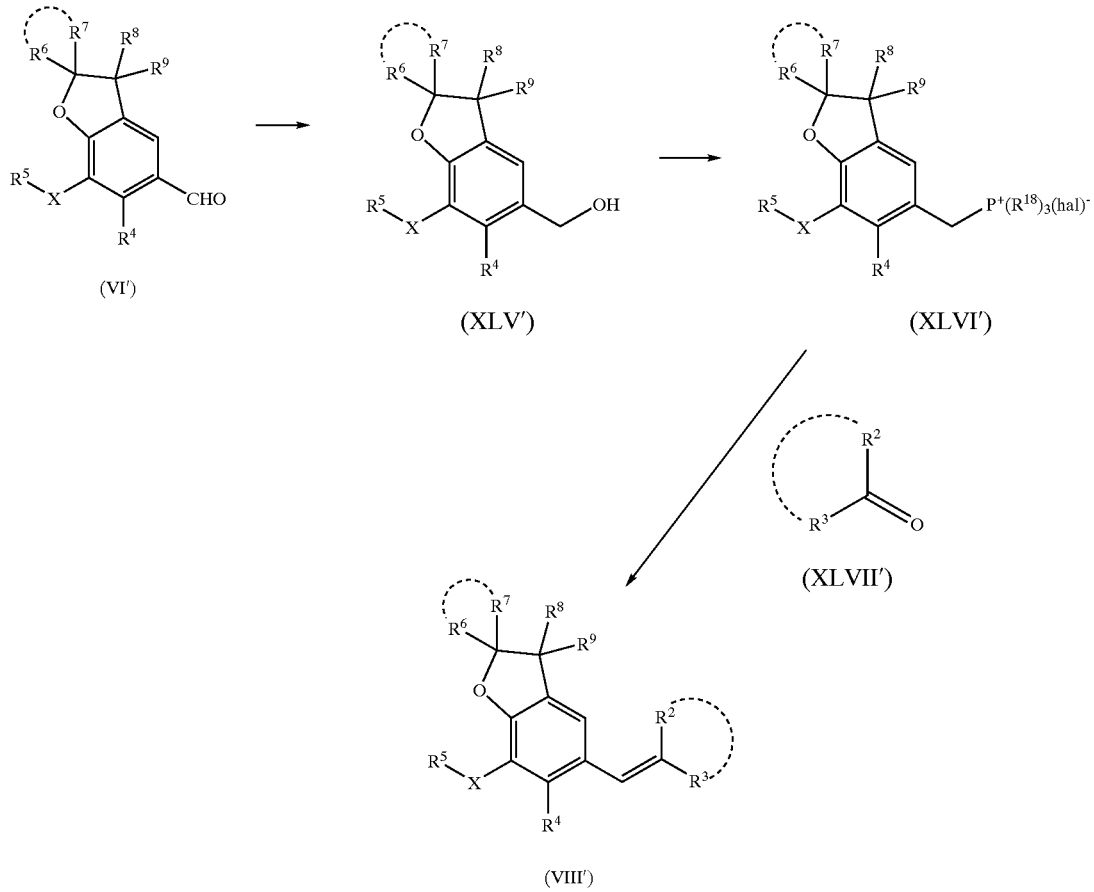

Compound (XLV') is produced from Compound (VI') similarly to the production of Compound (XXX') from Compound (I').

Compound (XLVI'), wherein $R^{18}$ and hal are defined as described above, is produced by halogenating Compound (XLV') followed by a reaction with a corresponding phosphine.

The halogenating agent employed in such a halogenation may for example be thionyl halide such as thionyl chloride and thionyl bromide, etc., a phosphoryl halide such as phosphoryl chloride and phosphoryl bromide, etc., a phosphorus halide such as phosphorus pentachloride, phosphorus trichloride, phosphorus pentabromide and phosphorus tribromide, etc., an oxalyl halide such as oxalyl chloride, etc., phosgene and the like. Such a halogenating agent is employed in an amount of about 0.1 to about 30 moles, preferably about 0.2 to about 10 moles per mole of Compound (XLV').

This reaction is conducted if desired in the presence of a base. Said "base" is preferably a tertiary amine, and the like.

This reaction is conducted advantageously without using a solvent or with using a solvent which is inert to the reaction. While such a solvent is not limited particularly as long as the reaction is proceeded, it may for example be a solvent such as a hydrocarbon, ether, amide and halogenated hydrocarbon as well as a mixture thereof.

The reaction time is usually about 10 minutes to about 12 hours, preferably about 10 minutes to about 5 hours. The reaction temperature is usually about −10 to about 200° C., preferably about −10 to about 120° C.

The phosphine employed in the subsequent reaction with the phosphine may for example be triphenylphosphine, tri-o-tolylphosphine, tributylphosphine and the like. The phosphine is employed in an amount of about 1 to about 3 moles, preferably about 1 to about 1.5 moles per mole of Compound (XLV').

This reaction is conducted advantageously without using a solvent or with using a solvent which is inert to the reaction. While such a solvent is not limited particularly as long as the reaction is proceeded, it may for example be a solvent such as an ether, hydrocarbon, halogenated hydrocarbon and nitrile as well as a mixture thereof.

The reaction temperature is usually about −20 to about 200° C., preferably about 0 to about 150° C. The reaction time is usually about 5 minutes to about 48 hours, preferably about 10 minutes to about 24 hours.

Compound (VIII') is also produced from Compound (XLVI') and Compound (XLVII') similarly to the production of Compound (VIII') from Compound (VI') and Compound (VII').

Compound (VIII') is also produced by a process shown in Scheme 9.

Scheme 9

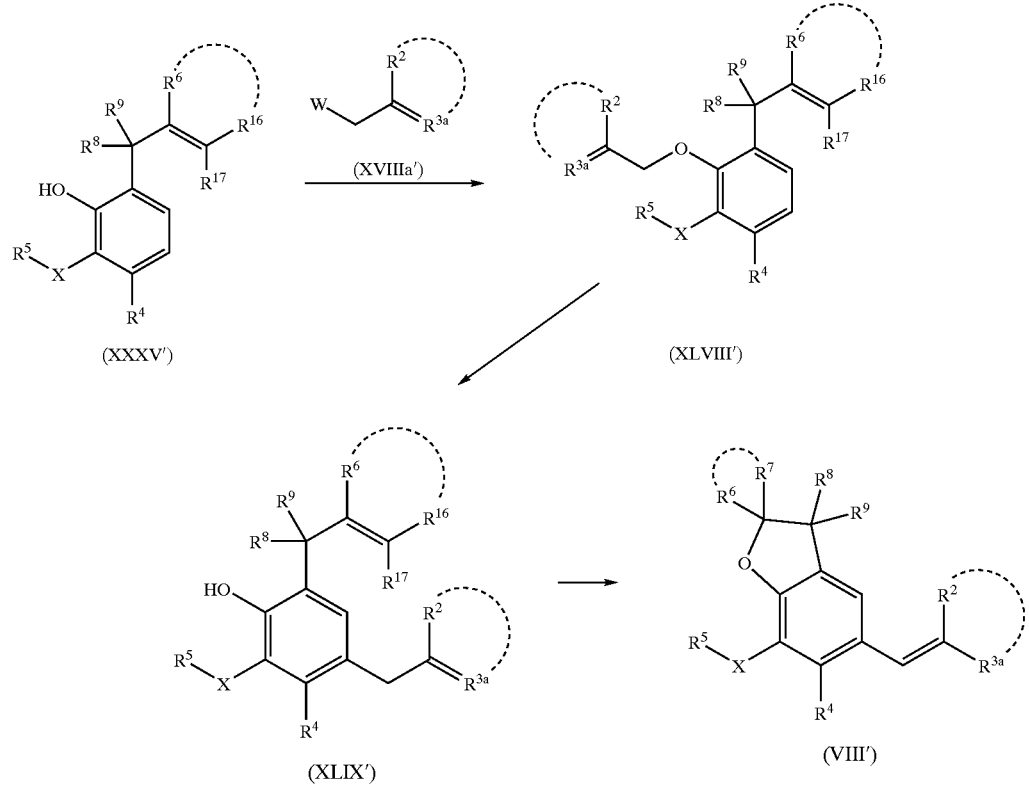

The process from Compound (XXXV') to Compound (VIII'), wherein $R^{3a}$ and W are defined as described above, is conducted in accordance with the process for producing Compound (VI') from Compound (II') in Scheme 1.

Such "additives" may for example be N,N,N',N'-tetramethylethylenediamine and the like. The amount of additives is about 1 to about 15 moles, preferably about 1 to about 10 moles per mole of Compound (VIIIa').

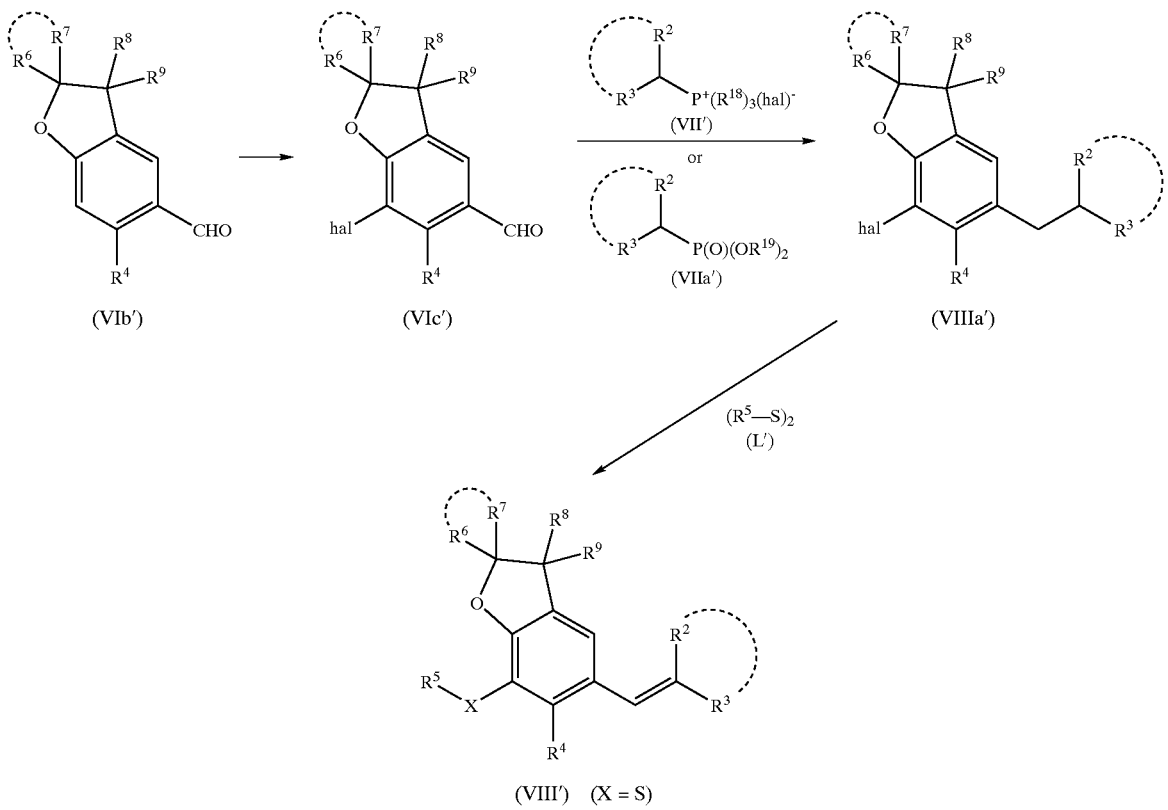

Scheme 10

Compound (VIc'), wherein hal is a halogen, is produced from Compound (VIb') similarly to the production of Compound (XIV') from Compound (VIb').

Compound (VIIIa') is produced from Compound (VIc') and Compound (VII'), wherein $R^{18}$ and hal are defined as described above, similarly to the production of Compound (VIII') from Compound (VI') and Compound (VII').

Compound (VIIIa') is produced from Compound (VIc'), and Compound (VIIa'), wherein $R^{19}$ is defined as described above, similarly to the production of Compound (VIII') from Compound (VI') and Compound (VIIa').

Compound (VIII'), wherein X is a sulfur atom, is produced by reacting Compound (VIIIa') with a disulfide compound (L') in the presence of a base. The amount of Compound (L') employed is about 1 to about 30 moles, preferably about 1 to about 15 moles per mole of Compound (VIIIa').

Said "base" may for example be an alkyl metal, aryl metal and the like.

The amount of a base employed is about 1 to about 15 moles, preferably about 1 to about 10 moles per mole of Compound (VIIIa').

This reaction employs additives if desired.

This reaction is conducted advantageously using a solvent which is inert to the reaction. While such a solvent is not limited particularly as long as the reaction is proceeded, it may for example be a solvent such as an ether and hydrocarbon as well as a mixture thereof.

The reaction time is usually about 30 minutes to about 48 hours, preferably about 1 hour to about 24 hours. The reaction temperature is usually about −100 to about 100° C., preferably about −80 to about 60° C.

Scheme 11

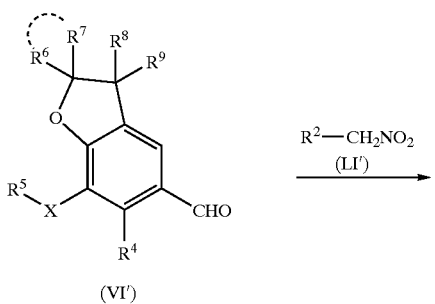

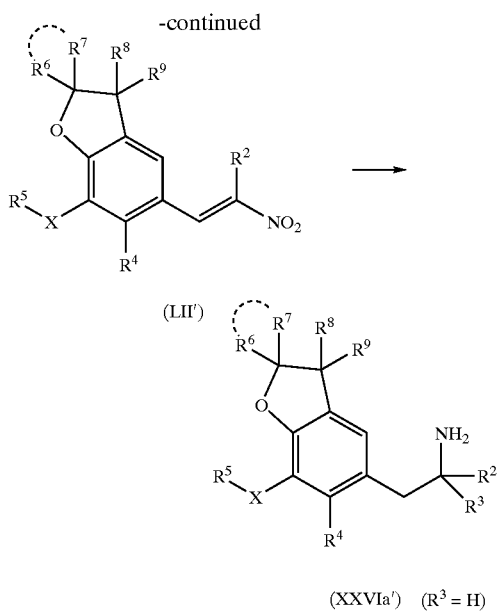

(LII')

(XXVIa')  (R³ = H)

Compound (LII') is produced by reacting Compound (VI') and Compound (LI') if desired in the presence of a base.

The amount of Compound (LI') employed is about 1 to about 5 moles, preferably about 1 to about 2 moles per mole of Compound (VI'). Compound (LI') may be also employed as a solvent, and in such a case the amount used is about 0.5 to about 20 mL, preferably about 1 to about 10 mL per gram of Compound (VI').

Said "base" may for example be an inorganic base, basic salt, aromatic amine, primary amine (n-butylamine, etc.), tertiary amine, metal hydride, metal amide and metal alkoxide, etc. The amount of a base employed is about 0.1 to about 10 moles, preferably about 0.5 to about 5 moles per mole of Compound (VI').

This reaction is conducted advantageously using a solvent which is inert to the reaction. While such a solvent is not limited particularly as long as the reaction is proceeded, it may for example be a solvent such as an alcohol, ether, hydrocarbon, amide, halogenated hydrocarbon and water as well as a mixture thereof.

The reaction time is usually about 30 minutes to about 12 hours, preferably about 1 hour to about 6 hours. The reaction temperature is usually about −20 to about 200° C. preferably about 0 to about 150° C.

Compound (XXVIa') is produced by reducing Compound (LII'). The reducing agent employed in such a reduction may for example be metal hydride such as aluminum hydride and diisobutylaluminum-hydride, etc., metal hydrogen complex such as lithium aluminum hydride and sodium borohydride, etc., a metal such as zinc, aluminum, tin and iron, etc. The amount of the reducing agent employed is about 1 to about 10 moles, preferably about 1 to about 5 moles per mole of Compound (LII') when a metal hydride or metal hydrogen complex is employed, while it was about 1 to about 20 equivalents, preferably about 1 to about 5 equivalents when a metal is employed. In this reaction, a Lewis acid may be employed if desired. Said "Lewis acid" may for example be aluminum chloride, aluminum bromide, titanium (IV) chloride, tin (II) chloride, zinc chloride, boron trichloride, boron tribromide, boron trifluoride and the like. The amount of a Lewis acid employed is about 1 to about 10 moles, preferably about 1 to about 5 moles per mole of Compound (LII').

A hydrogenation reaction may also serve for the reduction, and in such a case the catalyst such as Pd/C, platinum (IV) oxide, Raney nickel and Raney cobalt, etc. may be employed. The amount of the catalyst employed is about 5 to about 1000% by weight, preferably about 10 to about 300% by weight, based on Compound (LII'). In such a case, various hydrogen sources may be employed instead of gaseous hydrogen. Said "hydrogen source" may for example be formic acid, ammonium formate, triethylammonium formate, sodium phosphinate, hydrazine and the like. The amount of such a hydrogen source is about 1 to about 10 moles, preferably about 1 to about 5 moles, per mole of Compound (LII').

This reaction is conducted advantageously using a solvent which is inert to the reaction. While such a solvent is not limited particularly as long as the reaction is proceeded, it may for example be a solvent such as an alcohol, ether, hydrocarbon, amide and organic acid as well as a mixture thereof.

The reaction time is usually about 1 hour to about 100 hours, preferably about 1 hour to about 50 hours, although it may vary depending on the type and the amount of the reducing agent employed and the activity and the amount of the catalyst. The reaction temperature is usually about −20 to about 120° C., preferably about 0 to about 80° C. When a hydrogenation catalyst is employed, the pressure of hydrogen is usually about 1 to about 100 atm.

Compound (Ia), wherein Ring C'' may have a substituent other than R¹, R² and R³, is produced by a process shown in Scheme 12.

Scheme 12

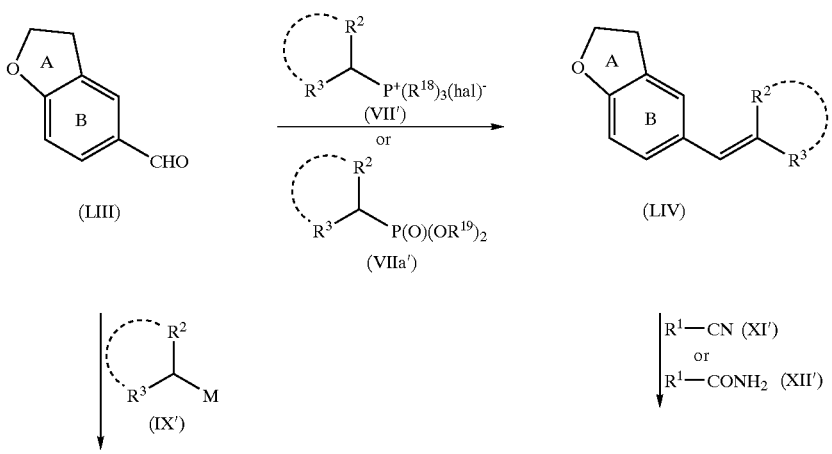

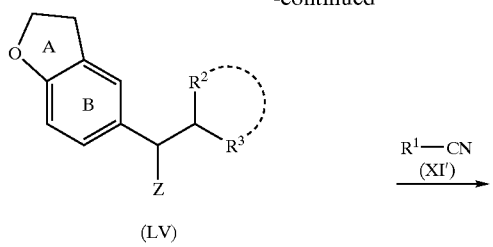

(LV) → (Ia)

Compound (LIV) is produced from Compound (LIII) and Compound (VII'), wherein $R^{18}$ and hal are defined as described above, similarly to the production of Compound (VIII') from Compound (VI') and Compound (VII').

Compound (LIV) is also produced from Compound (LIII) and Compound (VIIa'), wherein $R^{19}$ is defined as described above, similarly to the production of Compound(VIII') from Compound (VI') and Compound (VIIa').

Compound (LV), wherein Z is defined as described above, is produced from Compound (LIII) and Compound (IX'), wherein M is defined as described above, similarly to the production of Compound(X') from Compound (VI') and Compound (IX').

Compound (Ia) is produced from Compound (LIV) and Compound (XI') similarly to the production of Compound (I') from Compound (VIII') and Compound (XI').

Compound (Ia) is also produced from Compound (LIV) and Compound (XII') similarly to the production of Compound (I') from Compound (VIII') and Compound (XII').

Compound (Ia) is also produced from Compound (LV) and Compound (XI') similarly to the production of Compound (I') from Compound (X') and Compound (XI').

Compound (Ia'), wherein Ring C" is defined as described above, is also produced by the process shown in Scheme 13.

Scheme 13

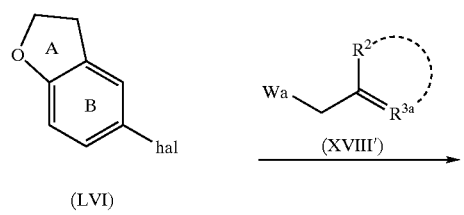

Compound (LVII) is produced from Compound (LVI), wherein hal is a halogen, and Compound (XVIII'), wherein $R^{3a}$ and Wa are defined as described above, similarly to the production of Compound (XIX') from Compound (XVII') and Compound (XVIII').

Compound (Ia) is also produced from Compound (LVII) and Compound (XI') similarly to the production of Compound (I') from Compound (XIX') and Compound (XI').

Compound (Ia), wherein Ring C" is defined as described above, is also produced by a process shown in Scheme 14.

Scheme 14

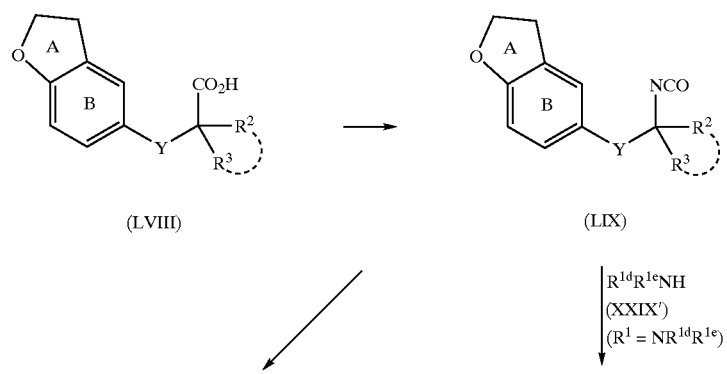

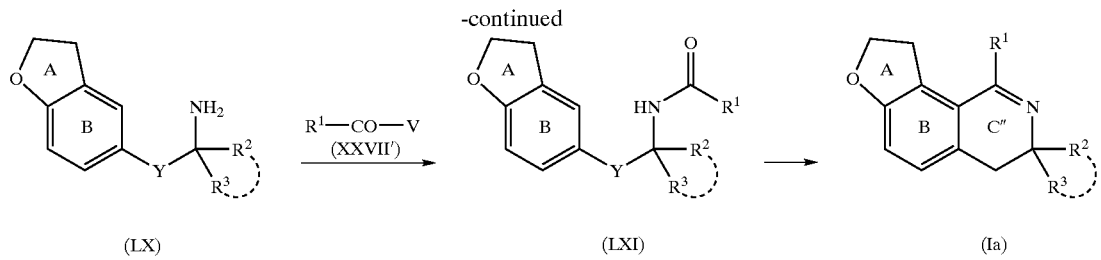

Compound (LIX), wherein Y is a methylene group which may have 1 or 2 substituent(s) is produced from Compound (LVIII) similarly to the production of Compound (XXV') from Compound (XXIV').

The "substituent" on said "methylene group which may have substituent(s)" may for example be a $C_{1-6}$ alkyl group.

Compound (LX) is produced from Compound (LIX) similarly to the production of Compound (XXVI') from Compound (XXV').

Compound (LXI) is produced from Compound (LX) and Compound (XXVII'), wherein V is defined as described above, similarly to the production of Compound (XXVIII') from Compound (XXVI') and Compound (XXVII').

Compound (LXI) is also produced from Compound (LIX) and Compound (XXIX'), wherein $R^{1d}$ and $R^{1e}$ are defined as described above, similarly to the production of Compound (XXVIII') from Compound (XXV') and Compound (XXIX').

Compound (Ic) wherein Ring $C^a$ may have a substituent in the position except for a nitrogen atom is produced also by a process shown in Scheme 15.

Scheme 15

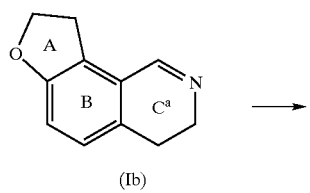

Compound (LXII) is produced from Compound (Ib), wherein Ring $C^a$ is defined as described above, similarly to the production of Compound (XXX') from Compound (I').

Compound (Ic) is produced from Compound (LXII) similarly to the production of Compound (I') from Compound (XXX').

Compound (Ia) is also produced from Compound (LXI) similarly to the production of Compound (I') from Compound (XXVIII').

Scheme 16

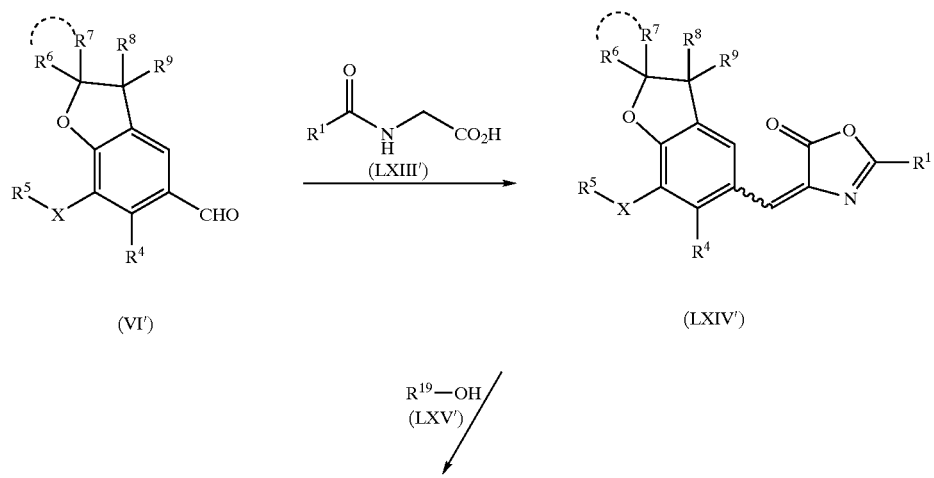

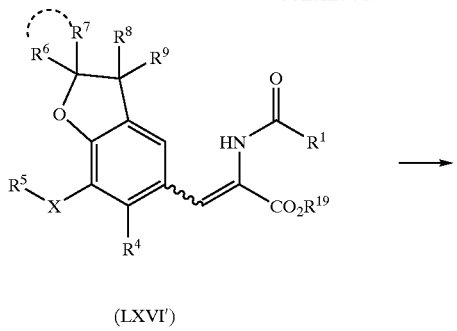

(LXVI')

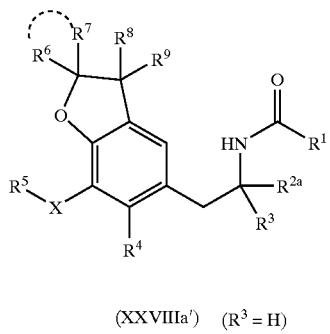

(XXVIIIa') (R³ = H)

Compound (LXIV') is produced by reacting Compound (VI') and Compound (LXIII') in the presence of an acid anhydride and a base.

The amount of Compound (LXIII') is about 1 to about 5 moles, preferably about 1 to about 2 moles per mole of Compound (VI').

Said "acid anhydride" may for example be acetic anhydride and the like. The amount of such an acid anhydride is about 1 to about 20 moles, preferably about 1 to about 10 moles per mole of Compound (VI').

Said "base" may for example be inorganic base, basic salt, aromatic amine, tertiary amine, potassium fluoride/alumina and the like. The amount of the base employed is about 1 to about 5 moles, preferably about 1 to about 2 moles per mole of Compound (VI').

This reaction is conducted advantageously without using a solvent or using a solvent which is inert to the reaction. While such a solvent is not limited particularly as long as the reaction is proceeded, it may for example be a solvent such a hydrocarbon and halogenated hydrocarbon as well as a mixture thereof.

The reaction time is usually about 10 minutes to about 12 hours, preferably about 15 minutes to about 6 hours. The reaction temperature is usually about −20 to about 150° C., preferably about 0 to about 120° C.

Compound (LXVI') is produced by reacting Compound (LXIV') and Compound (LXV'), wherein $R^{19}$ is defined as described above, in the presence of a base.

The amount of Compound (LXV') is about 1 to about 10 moles, preferably about 1 to about 5 moles per mole of Compound (LXIV'). Compound (LXV') may be employed also as a solvent, and in such a case the amount used is about 0.5 to about 50 mL, preferably about 1 to about 20 mL per gram of Compound (LXIV').

Said "base" may for example be an inorganic base, basic salt, aromatic amine, tertiary amine and the like. The amount of such a base employed is about 0.01 to about 1 mole, preferably about 0.01 to about 0.1 moles per mole of Compound (LXIV').

This reaction is conducted advantageously without using a solvent or with using a solvent which is inert to the reaction. While such a solvent is not limited particularly as long as the reaction is proceeded, it may for example be a solvent such as an alcohol, ether, hydrocarbon, amide, halogenated hydrocarbon, nitrile, ketone and sulfoxide as well as a mixture thereof.

The reaction time is usually about 10 minutes to about 12 hours, preferably about 15 minutes to about 6 hours. The reaction temperature is usually about −20 to about 150° C., preferably about 0 to about 100° C.

Compound (XXVIIIa'), wherein $R^{2a}$ is an optionally substituted hydrocarbon group or acyl group and may be same to those represented by $R^2$, is produced by reducing Compound (LXVI').

A reducing agent employed in such a reduction may for example be a metal hydride such as aluminum hydride and diisobutylaluminum hydride, etc., a metal hydrogen complex such as lithium aluminum hydride and sodium borohydride, etc., a metal such as zinc, aluminum, tin and iron, etc. The amount of a reducing agent employed is about 1 to about 10 moles, preferably about 1 to about 5 moles per mole of Compound (LXVI') when a metal hydride or metal hydrogen complex is employed, while it was about 1 to about 20 equivalents, preferably about 1 to about 5 equivalents when a metal is employed. In this reaction, a Lewis acid may be employed if desired. Said "Lewis acid" may for example be aluminum chloride, aluminum bromide, titanium (IV) chloride, tin (II) chloride, zinc chloride, boron trichloride, boron tribromide, boron trifluoride and the like. The amount of a Lewis acid employed is about 1 to about 10 moles, preferably about 1 to about 5 moles per mole of Compound (LXVI').

A hydrogenation reaction may also serve for the reduction, and in such a case a catalyst such as Pd/C, platinum (IV) oxide, Raney nickel and Raney cobalt may be employed. The amount of a catalyst employed is about 5 to about 1000% by weight, preferably about 10 to about 300% by weight, based on Compound (LXVI'). In such a case, various hydrogen sources may be employed instead of gaseous hydrogen. Said "hydrogen source" may for example be formic acid, ammonium formate, triethylammonium formate, sodium phosphinate, hydrazine and the like. The amount of such a hydrogen source is about 1 to about 10 moles, preferably about 1 to about 5 moles, per mole of Compound (LXVI').

This reaction is conducted advantageously using a solvent which is inert to the reaction. While such a solvent is not limited particularly as long as the reaction is proceeded, it may for example be solvent such as alcohol, ether, hydrocarbon, amide and organic acid as well as a mixture thereof.

The reaction time is usually about 1 hour to about 100 hours, preferably about 1 hour to about 50 hours, although it may vary depending on the type and the amount of the reducing agent employed and the activity and the amount of the catalyst. The reaction temperature is usually about −20 to about 120° C., preferably about 0 to about 80° C. When a hydrogenation catalyst is employed, the pressure of hydrogen is usually about 1 to about 100 atm.

Scheme 17

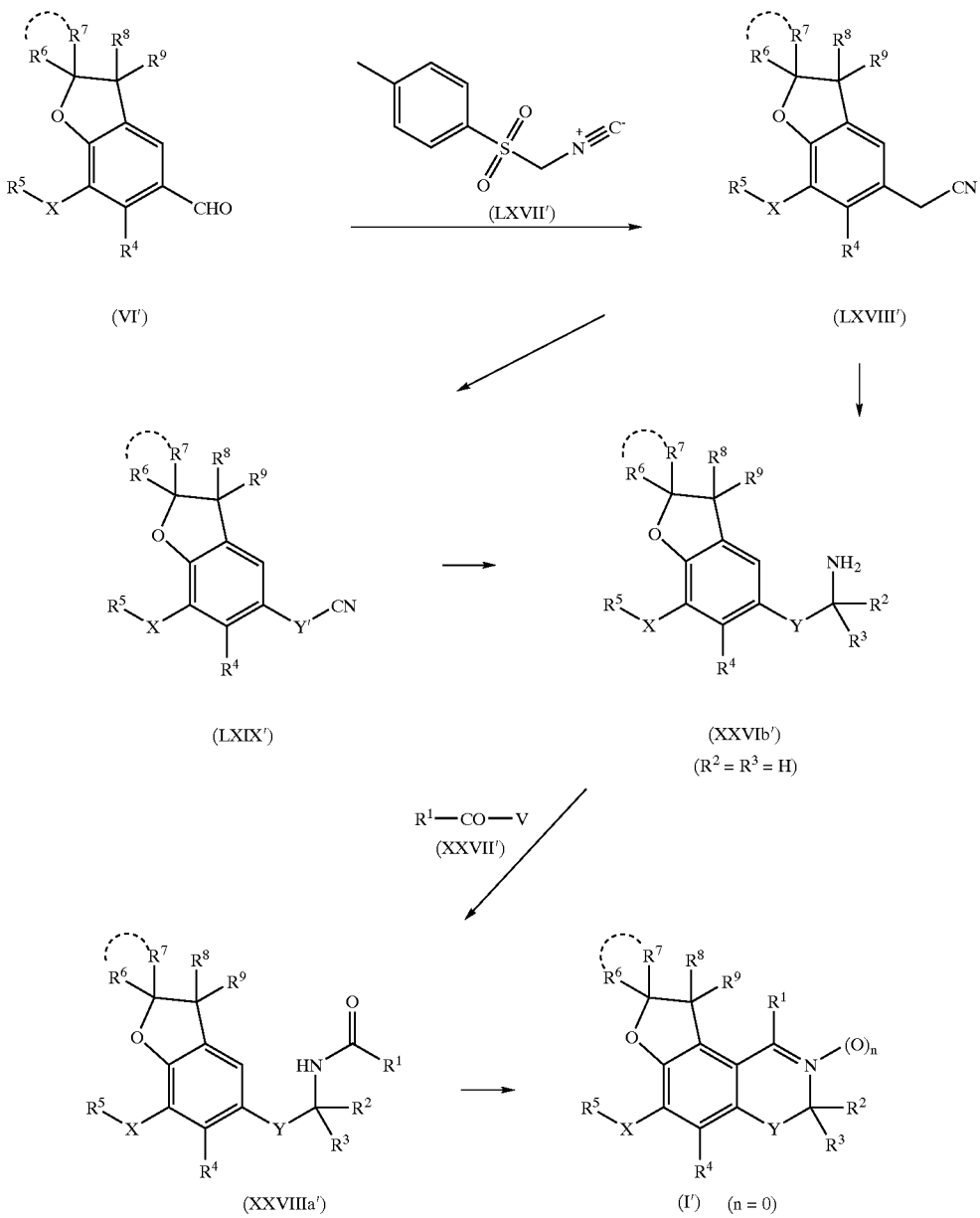

Compound (LXVIII') is produced by reacting Compound (VI') and Compound (LXVII') in the presence of a base followed by a reaction with alcohol.

The amount of Compound (LXVII') employed is about 1 to about 5 moles, preferably about 1 to about 2 moles per mole of Compound (VI').

Said "base" may for example be an inorganic base, basic salt, aromatic amine, tertiary amine, metal hydride, metal amide and metal alkoxide, etc. The amount of a base employed is about 1 to about 5 moles, preferably about 1 to about 3 moles per mole of Compound (VI').

This reaction is conducted advantageously using a solvent which is inert to the reaction. While such a solvent is not limited particularly as long as the reaction is proceeded, it may for example be a solvent such as ether, hydrocarbon, amide, halogenated hydrocarbon, nitrile and sulfoxide as well as a mixture thereof.

The reaction time is usually about 10 minutes to about 6 hours, preferably about 15 minutes to about 3 hours. The reaction temperature is usually about −100 to about 50° C., preferably about −80 to about 50° C.

The amount of an alcohol employed subsequently is about 1 to about 30 mL, preferably about 2 to about 20 mL per gram of Compound (VI').

The reaction time is usually about 10 minutes to about 12 hours, preferably about 15 minutes to about 6 hours. The reaction temperature is usually about −100 to about 150° C., preferably about −80 to about 100° C.

Compound (LXIX'), wherein Y' is a methylene group having 1 or 2 substituent(s) is produced by alkylating Compound (LXVIII') in the presence of a base.

The "substituent" on said "methylene group which has substituents" may for example be a $C_{1-6}$ alkyl group, etc.

Said "base" may for example be an inorganic base, basic salt, aromatic amine, tertiary amine, metal hydride, metal amide, and metal alkoxide, etc. The amount of a base employed is about 1 to about 5 moles, preferably about 1 to about 3 moles per mole of Compound (LXVII').

An alkylating agent may for example be a hydrocarbon having a leaving group.

Said "leaving group" may for example be a halogen atom (for example, fluorine, chlorine, bromine, iodine, etc.), optionally halogenated $C_{1-5}$ alkylsulfonyloxy (for example, methanesulfonyloxy, ethanesulfonyloxy, trichloromethanesulfonyloxy, etc.), optionally substituted $C_{6-10}$ arylsulfonyloxy and the like. An "optionally substituted $C_{6-10}$ arylsulfonyloxy" may for example, a $C_{6-10}$ arylsulfonyloxy (e.g., phenylsulfonyloxy, naphthylsulfonyloxy, etc.) which may have 1 to 3 substituent (s) selected from a $C_{1-6}$ alkyl (e.g. methyl, ethyl, etc.), $C_{1-6}$ alkoxy (e.g., methoxy, ethoxy, etc.) and nitro, and those exemplified typically are phenylsulfonyloxy, m-nitrophenylsulfonyloxy, p-toluenesulfonyloxy and the like.

Said hydrocarbon may for example be a $C_{1-6}$ alkyl group, etc.

The amount of an alkylating agent employed in this reaction is about 1 to about 10 moles, preferably about 1 to about 3-moles per mole of Compound (LXVIII').

This reaction is conducted advantageously using a solvent which is inert to the reaction. While such a solvent is not limited particularly as long as the reaction is proceeded, it may for example be a solvent such as alcohol, ether, hydrocarbon, amide, halogenated hydrocarbon, nitrile, sulfoxide and water as well as a mixture thereof.

The reaction time is usually about 30 minutes to about 12 hours, preferably about 1 hour to about 6 hours. The reaction temperature is usually about –50 to about 150° C., preferably about –20 to about 100° C.

Compound (XXVIb'), wherein Y is a methylene which may have 1 or 2 substituent(s), is produced by hydrolyzing the nitrile of Compound (LXIX') to form an acid amide followed by a reduction.

The "substituent" on said "methylene group which may have substituents" may for example be a $C_{1-6}$ alkyl group.

Said "hydrolyzing" reaction is conducted using a base in the presence of hydrogen peroxide. The amount of hydrogen peroxide employed is about 1 to about 5 mole, preferably about 1 to about 3 moles per mole of Compound (LXIX').

Said "base" may for example be an inorganic base, basic salt and the like. The amount of the base employed is about 1 to about 5 moles, preferably about 1 to about 3 moles per mole of Compound (LXIX').

This reaction is conducted advantageously using a solvent which is inert to the reaction. While such a solvent is not limited particularly as long as the reaction is proceeded, it may for example be a solvent such as alcohol, ether, hydrocarbon, amide, halogenated hydrocarbon, sulfoxide and water as well as a mixture thereof.

The reaction time is usually about 30 minutes to about 36 hours, preferably about 1 hour to about 24 hours. The reaction temperature is usually about –20 to about 100° C., preferably about 0 to about 80° C.

Other hydrolysis reaction conditions are those described in JIKKENKAGAKUKOZA 22, 4th edition (Ed. by Japanese Association of Chemistry), pages 151 to 153.

A reducing agent employed in a subsequent reduction may for example be metal hydride such as aluminum hydride and diisobutylaluminum hydride, etc., a metal hydrogen complex such as lithium aluminum hydride and sodium borohydride, etc., a metal such as zinc, aluminum, tin and iron, etc. The amount of a reducing agent employed is about 1 to about 10 moles, preferably about 1 to about 5 moles per mole of Compound (LXIX') when a metal hydride or metal hydrogen complex is employed, while it was about 1 to about 20 equivalents, preferably about 1 to about 5 equivalents when a metal is employed. In this reaction, a Lewis acid may be employed if desired. Said "Lewis acid" may for example be aluminum chloride, aluminum bromide, titanium (IV) chloride, tin (II) chloride, zinc chloride, boron trichloride, boron tribromide, boron trifluoride and the like. The amount of a Lewis acid employed is about 1 to about 10 moles, preferably about 1 to about 5 moles per mole of Compound (LXIX').

This reaction is conducted advantageously using a solvent which is inert to the reaction. While such a solvent is not limited particularly as long as the reaction is proceeded, it may for example be a solvent such as an alcohol, ether, hydrocarbon, amide and organic acid as well as a mixture thereof.

The reaction time is usually about 1 hour to about 100 hours, preferably about 1 hour to about 50 hours, although it may vary depending on the type and the amount of the reducing agent employed. The reaction temperature is usually about –20 to about 120° C., preferably about 0 to about 80° C.

Compound (XXVIb') is produced also by reducing Compound (LXIX') directly.

The reducing agent employed in such a reduction may for example be a metal hydride such as aluminum hydride and diisobutylaluminum hydride, etc., a metal hydrogen complex such as lithium aluminum hydride and sodium borohydride, a metal such as zinc, aluminum, tin and iron. The amount of a reducing agent employed is about 1 to about 10 moles, preferably about 1 to about 5 moles per mole of Compound (LXIX') when a metal hydride or metal hydrogen complex is employed, while it was about 1 to about 20 equivalents, preferably about 1 to about 5 equivalents when a metal is employed. In this reaction, a Lewis acid may be employed if desired. Said "Lewis acid" may for example be aluminum chloride, aluminum bromide, titanium (IV) chloride, tin (II) chloride, zinc chloride, boron trichloride, boron tribromide, boron trifluoride and the like. The amount of a Lewis acid employed is about 1 to about 10 moles, preferably about 1 to about 5 moles per mole of Compound (LXIX').

A hydrogenation reaction may also serve for the reduction, and in such a case a catalyst such as Pd/C, platinum (IV) oxide, Raney nickel and Raney cobalt, etc. may be employed. The amount of a catalyst employed is about 5 to about 1000% by weight, preferably about 10 to about 300% by weight, based on Compound (LXIX'). This reaction may employ an amine such as ammonia, etc. if desired. The amount of the amine employed is about 1 to about 50 moles, preferably about 1 to about 20 moles per mole of Compound (LXIX'). It is also possible that various hydrogen sources may be employed instead of gaseous hydrogen. Said "hydrogen source" may for example be formic acid, ammonium formate, triethylammonium formate, sodium phosphinate, hydrazine and the like. The amount of such a hydrogen source is about 1 to about 10 moles, preferably about 1 to about 5 moles, per mole of Compound (LXIX').

This reaction is conducted advantageously using a solvent which is inert to the reaction. While such a solvent is not limited particularly as long as the reaction is proceeded, it may for example be a solvent such as an alcohol, ether, hydrocarbon, amide and organic acid as well as a mixture thereof.

The reaction time is usually about 1 hour to about 100 hours, preferably about 1 hour to about 50 hours, although it may vary depending on the type and the amount of the reducing agent employed and the activity and the amount of the catalyst. The reaction temperature is usually about −20 to about 120° C., preferably about 0 to about 80° C. When a hydrogenation catalyst is employed, the pressure of hydrogen is usually about 1 to about 100 atm.

Compound (XXVIb') is produced also from Compound (LXVIII') similarly to the production of Compound (XXVIb') from Compound (LXIX').

Compound (XXVIIIa') is produced from Compound (XXVIb') and Compound (XXVII') similarly to the production of Compound (XXVIII') from Compound (XXVI') and Compound (XXVII').

Compound (I') is produced from Compound (XXVIIIa') similarly to the production of Compound (I') from Compound (XXVIII').

In each of the reactions described above, a starting compound having an amino, carboxy or hydroxy as its substituent may be present as a compound in which a protective group employed ordinarily in a peptide chemistry has been introduced into such a substituent, and an intended compound can be obtained by deprotection if necessary after the reaction.

A protective group for an amino may for example be a formyl or each optionally substituted $C_{1-6}$ alkyl-carbonyl (for example, acetyl, propionyl, etc.), benzoyl, $C_{1-6}$ alkoxy-carbonyl (for example, methoxycarbonyl, ethoxycarbonyl, etc.), phenyloxycarbonyl, $C_{7-10}$ aralkyloxy-carbonyl (for example, benzyloxycarbonyl, etc.), trityl, phthaloyl and the like. Its substituent may for example be a halogen atom (for example, fluorine, chlorine, bromine, iodine, etc.), $C_{1-6}$ alkyl-carbonyl (for example, acetyl, propionyl, valeryl, etc.), nitro and the like, and the number of the substituents may be 1 to 3.

A protective group for a carboxy may for example be each optionally substituted $C_{1-6}$ alkyl (for example, methyl, ethyl, propyl, isopropyl, butyl, tert-butyl, etc.), phenyl, trityl, silyl and the like. Its substituent may for example be a halogen atom (for example, fluorine, chlorine, bromine, iodine, etc.), formyl, $C_{1-6}$ alkyl-carbonyl (for example, acetyl, propionyl, butylcarbonyl, etc.), nitro, $C_{1-6}$ alkyl (for example, methyl, ethyl, tert-butyl, etc.) and $C_{6-10}$ aryl (for example, phenyl, naphthyl, etc.), and the number of the substituents may be 1 to 3.

A protective group for a hydroxy may for example be a formyl or each optionally substituted $C_{1-6}$ alkyl (for example, methyl, ethyl, propyl, isopropyl, butyl, tert-butyl, etc.), phenyl, $C_{7-11}$ aralkyl (for example, benzyl, etc.), $C_{1-6}$ alkyl-carbonyl (for example, acetyl, propionyl, etc.), phenyloxycarbonyl, $C_{7-11}$ aralkyloxy-carbonyl (for example, benzyloxycarbonyl, etc.), tetrahydropyranyl, tetrahydrofuranyl, silyl and the like. Its substituent may for example be a halogen atom (for example, fluorine, chlorine, bromine, iodine, etc.), $C_{1-6}$ alkyl (for example, methyl, ethyl, tert-butyl, etc.), $C_{7-11}$ aralkyl (for example, benzyl, etc.), $C_{6-10}$ aryl (for example, phenyl, naphthyl, etc.), nitro, etc., and the number of the substituents may be 1 to 3.

A deprotection method may be a method known per se such as a treatment with an acid, base, UV, hydrazine, phenylhydrazine, sodium N-methyldithiocarbamate, tetrabutylammonium fluoride, Palladium (II) acetate and the like, as well as a reduction.

In any case, a deprotection, acylation, alkylation, hydrogenation, oxidation, reduction, carbon chain elongation and substituent exchange reaction are further employed if necessary alone or in combination with each other to synthesize Compound (A), (I), (I'), (A-1), (I-1) or (I'-1). These reactions may employ the methods described for example in SINJIKKENKAGAKUKOZA, Vols. 14 and 15, 1977 (MARUZEN) and the like.

When an objective product is obtained in a free form by a reaction described above, then it may be converted in accordance with an ordinary method into a salt, and when it is obtained as a salt then it may be converted in accordance with an ordinary method into a free form or another salt. Compound (A), (I), (I'), (A-1), (I-1) or (I'-1) thus obtained can be isolated and purified from a reaction solution by a known method such as a partition, concentration, solvent extraction, fraction distillation, crystallization, recrystallization, chromatography and the like.

When Compound (A), (I), (I'), (A-1), (I-1) or (I'-1) is present as a configuration isomer, diastereomer, conformer and the like, then it can be isolated if desired by a separation or purification procedure described above. When Compound (A), (I), (I'), (A-1), (I-1) or (I'-1) is present as a racemate, it can be resolved into S form and R form by an ordinary optical resolution method.

When Compound (A), (I), (I'), (A-1), (I-1) or (I'-1) has its stereoisomers, then individual isomers or a mixture thereof may also encompassed in the invention.

Compound (A), (I), (I'), (A-1), (I-1) or (I'-1) may be a hydrate or anhydrous substance.

Compound (A), (I), (I'), (A-1), (I-1) or (I'-1) may be labeled with an isotope (for example, $^3H$, $^{14}C$, $^{35}S$) and the like.

A compound represented by Formula:

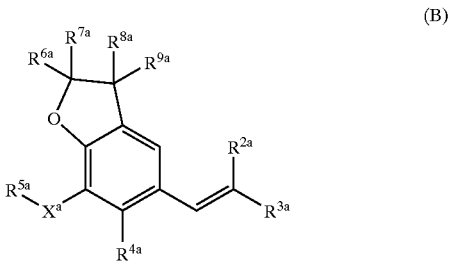

(B)

(wherein each of $R^{2a}$ and $R^{3a}$ is an optionally substituted aliphatic hydrocarbon group or acyl group, $R^{4a}$ is a hydrogen atom, optionally substituted hydrocarbon group, acyl group or optionally substituted hydroxy group, $R^{5a}$ is an optionally substituted hydrocarbon group, acyl group, optionally substituted heterocyclic group or halogen atom, Each of $R^{6a}$, $R^{7a}$, $R^{8a}$ and $R^{9a}$ is a hydrogen atom or optionally substituted hydrocarbon group, $X^a$ is a bond, oxygen atom, optionally oxidized sulfur atom or optionally substituted nitrogen atom), or by Formula:

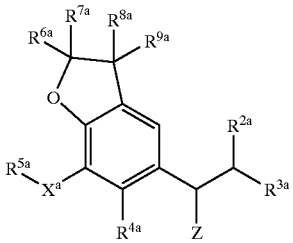

(wherein each of $R^{2a}$ and $R^{3a}$ is an optionally substituted aliphatic hydrocarbon group or acyl group, $R^{4a}$ is a hydrogen atom, optionally substituted hydrocarbon group, acyl group or optionally substituted hydroxy group, $R^{5a}$ is an optionally substituted hydrocarbon group, acyl group, optionally substituted heterocyclic group or halogen atom, Each of $R^{6a}$, $R^{7a}$, $R^{8a}$ and $R^{9a}$ is a hydrogen atom or optionally substituted hydrocarbon group, $X^a$ is a bond, oxygen atom, optionally oxidized sulfur atom or optionally substituted nitrogen atom, Z is an optionally substituted hydroxy group or halogen atom, or a salt thereof, is a novel compound.

An "aliphatic hydrocarbon group" of an "optionally substituted aliphatic hydrocarbon group" represented by $R^{2a}$ and $R^{3a}$ may for example be a linear hydrocarbon or alicyclic hydrocarbon group such as an alkyl group, alkenyl group, alkynyl group, cycloalkyl group and the like, with a linear (straight or branched) or alicyclic hydrocarbon group having 1 to 16 carbon atoms being preferred. Specifically, those listed below are employed.

(1) Linear Hydrocarbon Groups:

alkyl groups [preferably, a lower alkyl group (for example, a $C_{1-6}$ alkyl group such as methyl, ethyl, propyl, isopropyl, butyl, isobutyl, sec-butyl, tert-butyl, pentyl, hexyl and the like)], (2) Alicyclic Hydrocarbon Groups:

cycloalkyl groups [preferably, a lower cycloalkyl group (for example, a $C_{3-6}$ cycloalkyl group such as cyclopropyl, cyclobutyl, cyclopentyl, cyclohexyl and the like) and this lower cycloalkyl group may be fused with benzene ring.], and a substituent on such a "aliphatic hydrocarbon group" may for example be a group selected from the group (hereinafter referred to as Substituent Group B) consisting of (1) a halogen atom, (2) a $C_{1-3}$ alkylenedioxy group, (3) a nitro group, (4) an optionally halogenated $C_{1-6}$ alkyl group, (5) a $C_{3-6}$ cycloalkyl group, (6) a $C_{6-14}$ aryl group, (7) an optionally halogenated $C_{1-6}$ alkoxy group, (8) an optionally halogenated $C_{1-6}$ alkylthio group, (9) a hydroxy group, (10) an amino group, (11) a mono-$C_{1-6}$ alkylamino group, (12) a mono-$C_{6-14}$ arylamino group, (13) a di-$C_{1-6}$ alkylamino group, (14) a di-$C_{6-14}$ arylamino group, (15) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered-heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, (16) an acylamino group selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylamino, (17) an acyloxy group selected from $C_{1-6}$ aLkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (18) a 4- to 14-membered heterocyclic group having, in addition to carbon atoms, 1 to 3 heteroatom(s) selected from nitrogen, sulfur and oxygen atoms, (19) a phosphono group, (20) a $C_{6-14}$ aryloxy group, (21) a di-$C_{1-6}$ alkoxy-phosphoryl group, (22) a $C_{6-14}$ arylthio group, (23) a hydrazino group, (24) an imino group, (25) an oxo group, (26) an ureido group, (27) a $C_{1-6}$ alkyl-ureido group, (28) a di-$C_{1-6}$-alkyl-ureido group, (29) an oxide group and (30) a group formed by binding 2 or 3 groups selected from (1) to (29) listed above. Those exemplified typically as these substituents are those exemplified with regard to Substituent Group A described above.

An "acyl group" represented by $R^{2a}$ and $R^{3a}$ is one similar to an "acyl group" represented by $R^2$ and $R^3$.

Any of "optionally substituted hydrocarbon group", "acyl group" and "optionally substituted hydroxy group" represented by $R^{4a}$ is one similar to any of "optionally substituted hydrocarbon group", "acyl group" and "optionally substituted hydroxy group" represented by $R^4$.

Any of "optionally substituted hydrocarbon group", "acyl group", "optionally substituted heterocyclic group" and "halogen atom" represented by $R^{5a}$ is one similar to any of "optionally substituted hydrocarbon group", "acyl group", "optionally substituted heterocyclic group" and "halogen atom" represented by $R^5$.

An "optionally substituted hydrocarbon group" represented by $R^{6a}$, $R^{7a}$, $R^{8a}$ and $R^{9a}$ is one similar to an "optionally substituted hydrocarbon group" represented by $R^{61}$, $R^7$, $R^8$ and $R^9$.

Any of "optionally oxidized sulfur atom" and "optionally substituted nitrogen atom" represented by $X^a$ is one similar to an "optionally-oxidized sulfur atom" or "optionally substituted nitrogen atom" represented by X.

An "optionally substituted hydroxy group" represented by Z may for example be a group represented by Formula: —$OZ^a$ wherein $Z^a$ is a hydrogen atom, optionally substituted hydrocarbon group or acyl group.

Any of "optionally substituted hydrocarbon group" and "acyl group" represented by $Z^a$ is one similar to any of "optionally substituted hydrocarbon group" and "acyl group" represented by $R^2$.

A halogen atom represented by Z is a fluorine atom, chlorine atom, bromine atom and iodine atom.

Compounds (B) and (C) are preferably those listed below.
(1) Compounds (B) and (C) wherein each of $R^{2a}$ and $R^{3a}$ is
(1) a $C_{1-6}$ alkyl group which may be substituted by <1> a halogen atom, <2> a hydroxy group which may be substituted by a substituent selected from a $C_{1-6}$ alkyl, $C_{1-6}$ alkyl-carbonyl, $C_{1-6}$ alkylsulfonyl and $C_{7-16}$ aralkyl, <3> an amino group which may be substituted by 1 or 2 $C_{1-6}$ alkyl, $C_{1-6}$ alkyl-carbonyl and $C_{6-14}$ aryl-carbonyl, <4> a 4- to 10-membered heterocyclic group containing 1 to 3 heteroatom(s) selected from nitrogen, oxygen and sulfur atoms in addition to carbon atoms, <5> a thio group which may be substituted by $C_{1-6}$ alkyl, <6> a $C_{1-6}$ alkyl-sulfinyl group or <7> a $C_{1-6}$ alkyl-sulfonyl group or (2) a $C_{1-6}$ alkoxy-carbonyl group, $R^{4a}$ is (i) a hydrogen atom, (ii) a $C_{1-6}$ alkyl group [this $C_{1-6}$ alkyl group may have a substituent selected from (1) a halogen atom, (2) a $C_{1-6}$ alkoxy group, (3) a hydroxy group, (4) an amino group, (5) a mono-$C_{1-6}$ alkylamino group, (6) a di-$C_{1-6}$ alkylamino group, (7) a 4- to 10-membered heterocyclic group containing 1 to 3 heteroatom(s) selected from nitrogen, sulfur and oxygen atoms in addition to carbon atoms which may have an oxo, (8) a $C_{6-14}$ arylthio, (9) an ureido, (10) a carboxy, (11) a carbamoyl, (12) a $C_{1-6}$ alkoxy-carbonyl, (13) a mono-$C_{1-6}$ alkyl-carbamoyl, (14) a formylamino and (15) a $C_{1-6}$ alkyl-carboxamido] or (iii) a formyl group;

$X^a$ is a bond, oxygen atom, optionally oxidized sulfur atom, —NH— or —N(methyl)-, $R^{5a}$ is, when $X^a$ is a bond, then (i) a $C_{1-6}$ alkyl group or (ii) a halogen atom, when $X^a$ is an oxygen atom, then (i) a $C_{1-6}$ alkyl group [this $C_{1-6}$ alkyl group may have a substituent selected from (1) a halogen atom, (2) a hydroxy group, (3) an amino group, (4) a carboxy, (5) a carbamoyl, (6) a $C_{1-6}$ alkoxy-carbonyl, (7) a mono-$C_{1-6}$ alkyl-carbamoyl, (8) a di-$C_{1-6}$ alkyl-carbamoyl, (9) a 4- to 10-membered heterocyclic group containing 1 to 3 heteroatom(s) selected from nitrogen, sulfur and oxygen atoms in addition to carbon atoms], (ii) a $C_{3-6}$ cycloalkyl group, (iii) a $C_{7-16}$ aralkyl group, (iv) a $C_{1-6}$ alkyl-carbonyl group, (v) a $C_{6-14}$ aryl-carbonyl group, (vi) a $C_{1-6}$ alkoxy-carbonyl group, (vii) a mono- or di-$C_{1-6}$ alkyl-thiocarbamoyl group, (viii) an optionally halogenated $C_{1-6}$ alkyl-sulfonyl group or (ix) a 4- to 10-membered heterocyclic group containing 1 to 4 heteroatom(s) selected from nitrogen, sulfur and oxygen atoms in addition to carbon atoms [this heterocyclic group may have a $C_{6-14}$ aryl], when $X^a$ is an optionally oxidized sulfur, then (i) a $C_{1-6}$ alkyl group or (ii) a mono- or di-$C_{1-6}$ alkyl-carbamoyl group, when $X^a$ is —NH— or —N(methyl)-, then (i) a $C_{1-6}$ alkyl group [this $C_{1-6}$ alkyl group may have a $C_{1-6}$ alkoxy-carbonyl], (ii) formyl, (iii) a $C_{1-6}$ alkyl-carbonyl group, (iv) a $C_{1-6}$ alkoxy-carbonyl group, (v) a carbamoyl group, (vi) a mono- or di-$C_{1-6}$ alkyl-carbamoyl group or (vii) a $C_{1-6}$ alkyl-sulfonyl group, each of $R^{6a}$, $R^{7a}$, $R^{8a}$ and $R^{9a}$ is a hydrogen atom or $C_{1-6}$ alkyl group, Z is (i) a hydroxy group which may be substituted by a $C_{1-6}$ alkyl-carbonyl or (ii) a halogen atom.

(2) Compounds (B) produced in Reference Examples 5, 6, 26, 27, 30, 57, 60, 63, 95 and 137.

(3) Compounds (C) produced in Reference Examples 7, 8 and 115.

A prodrug for an inventive Compound (I), (I'), (I-1) or (I'-1) is a compound which is converted into Compound (I), (I'), (I-1) or (I'-1) under a physiological condition as a result of a reaction with an enzyme or gastric acid, thus a compound undergoing an enzymatic oxidation, reduction or hydrolysis to form Compound (I), (I'), (I-1) or (I'-1) and a compound hydrolyzed by gastric acid to form Compound (I), (I'), (I-1) or (I'-1). A prodrug for Compound (I), (I'), (I-1) or (I'-1) may for example be a compound obtained by subjecting an amino group in Compound (I), (I'), (I-1) or (I'-1) to an acylation, alkylation or phosphorylation (e.g., a compound obtained by subjecting an amino group in Compound (I), (I'), (I-1) or (I'-1) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in Compound (I), (I'), (I-1) or (I'-1) to an acylation, alkylation, phosphorylation or boration (e.g., a compound obtained by subjecting an hydroxy in Compound (I), (I'), (I-1) or (I'-1) to an acetylation, palmitoylation, propanoylation, pivaloylation, succinylation, fumarylation, alanylation, dimethylaminomethylcarbonylation, etc.); a compound obtained by subjecting a carboxy group in Compound (I), (I'), (I-1) or (I'-1) to an esterification or amidation (e.g., a compound obtained by subjecting a carboxy group in Compound (I), (I'), (I-1) or (I'-1) to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethylesterification and methylamidation, etc.) and the like. Any of these compounds can be produced from Compound (I), (I'), (I-1) or (I'-1) by a method known per se.

A prodrug for Compound (I), (I'), (I-1) or (I'-1) may also be one which is converted into Compound (I), (I'), (I-1) or (I'-1) under a physiological condition, such as those described in "IYAKUHIN no KAIHATSU (Development of Pharmaceuticals)", Vol. 7, Design of Molecules, p. 163–198, Published by HIROKAWA SHOTEN (1990).

As a salt of Compound (A), (I), (I'), (A-1), (I-1), (I'-1), (B) or (C) may for example be a physiologically acceptable salt. For example, a salt with an inorganic base, ammonium, organic base, inorganic acid, organic acid, basic or acidic amino acid may be employed. A salt with an inorganic base may for example be an alkaline metal salt such as sodium and potassium salts, etc., an alkaline earth metal salt such as calcium and magnesium salts, etc., aluminum and the like. A salt with an organic base may for example be a salt with. trimethylamine, triethylamine, pyridine, picoline, 2,6-lutidine, ethanolamine, diethanolamine, triethanolamine, cyclohexylamine, dicyclohexylamine or N,N'-dibenzylethylenediamine, etc. A salt with an inorganic acid may for example be a salt with hydrochloric acid, hydrobromic acid, nitric acid, sulfuric acid or phosphoric acid, etc. A salt with an organic salt may for example be a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid, etc. A salt with a basic amino acid may for example be a salt with arginine, lysine or ornithine, etc., and a salt with acidic amino acid may for example be a salt with aspartic acid or glutamic acid, etc.

Among those listed above, a pharmacologically acceptable salt is preferred, including, a salt with an inorganic acid such as hydrochloric acid, hydrobromic acid, nitric acid, sulfuric acid and phosphoric acid, etc., a salt with an organic acid such as acetic acid, phthalic acid, fumaric acid, oxalic acid, tartaric acid, maleic acid, citric acid, methanesulfonic acid and p-toluenesulfonic acid, etc. when Compound (I) or (I') has a basic functional group, as well as an alkaline metal salt such as sodium salt and potassium salt, etc., an alkaline earth metal salt such as calcium salt and magnesium salt, etc., and an ammonium salt when Compound (I) or (I') has a acidic functional group.

Since Compound (A), (I), (I'), (A-1), (I-1), (I'-1) according to the invention or a salt thereof (including a prodrug for Compound (I), (I-1), (I'), (I'-1)) (hereinafter abbreviated as an inventive compound) has an excellent phosphodiesterase (PDE) IV-inhibiting effect and a low toxicity and also is safe, it can be employed as a prophylactic or therapeutic agent in mammals (for example, human, mouse, dog, rat, cattle, etc.) against inflammatory diseases, for example, bronchial asthma, chronic obstructive pulmonary disease (COPD), rheumatoid arthritis, autoimmune disease, diabetes, graft versus host disease, multiple sclerosis, sepsis, psoriasis, osteoporosis, depression, central dysfunction after cerebrovascular occlusion, cerebrovascular dementia, Alzheimer dementia, obesity, cardiac insufficiency, atopic dermatitis and the like, as well as a phosphodiesterase (PDE) IV inhibitor. The administration route may be oral or parenteral.

A specific dosage form may for example be a tablet (including sugar-coated and film-coated tablets), pill, capsule (including microcapsule), granule, fine powder, powder, syrup, emulsion, injection formulation, inhalation formulation, ointment, eye drop, aerosol, ophthalmic ointment, hard ointment, suppository, troche, poulitic, liniment and the like. Any of these formulations can be prepared in accordance with an ordinary method (for example a method described in Japanese Pharmacopoeia).

The amount of an inventive compound in a formulation according to the invention may vary depending on the dosage form, and it is usually 0.01 to 100% by weight based on the entire formulation, preferably 0.1 to 50% by weight, more preferably 0.5 to 20% by weight.

Specifically, a tablet is produced by mixing a medicament as it is with an excipient, binder, disintegrant or other suitable additives to form a homogenous mass, granulating by a suitable method, combining with a lubricant and the like, and then compressing into a tablet, or by mixing a medicament as it is with an excipient, binder, disintegrant or other suitable additives to form a homogenous mass and then compressing directly into a tablet, or by preparing a granule first and then compressing into a tablet directly or after mixing with suitable additives to form a homogenous mass. The formulation can further contain colorants, seasonings and the like, if necessary. The formulation can further be film-coated by a suitable coating.

In a method for producing an injection formulation, a certain amount of a medicament is dissolved, suspended or emulsified in a water for injection, physiological saline and Ringer's solution when the medicament is water-soluble, or usually in a vegetable oil when the medicament is water-insoluble, whereby obtaining a certain quantity, or a certain amount of the medicament is enclosed in a vial for an injection formulation.

An oral formulation carrier is a material employed customarily in the pharmaceutical field, such as starch, mannitol, crystalline cellulose, sodium carboxymethylcellulose and the like. A vehicle for injection may for example be distilled water, physiological saline, glucose solution, infusion solution and the like. Other additives generally employed in a formulation may also be added properly.

While the dose of such a formulation may vary depending on the age, body weight, condition, administration route, administration frequency and the like, a daily dose in an adult having asthma is usually 0.01 to 100 mg/kg as an active ingredient (inventive compound), preferably 0.01 to 50 mg/kg, more preferably 0.05 to 10 mg/kg, which is given orally once or in two portions a day.

While the compound of the invention can exhibit an excellent phosphodiesterase (PDE) IV-inhibiting activity even when being given alone, it can be used also in combination (multimedicament combination) with pharmaceutical components other than inventive compounds (hereinafter referred to as concomitant medicaments).

Such a concomitant medicament may for example be an antiasthma agent (for example, fluticasone propionate, beclomethasone propionate, theophylline, procaterol, ketotifen, azelastine, seratrodast, etc.), anti-allergic agent (for example, fexofenadine, epinastine, ebastine, etc.), anti-cholinergic agent (for example ipratropium bromide, flutropium bromide, oxitropium bromide, etc.), anti-inflammatory agent (for example, diclofenac sodium, ibuprofen, indomethacin, loxoprofen sodium, etc.), antibacterial agent (for example, cefixime, cefdinir, ofloxacin, tosufloxacin tosilate, levofloxacin, etc.), antifungal agent (for example, fluconazole, itraconazole, etc.), diabetes-treating agent (for example, pioglitazone, nateglinide, voglibose, acarbose, etc.), etc.

When using an inventive compound in combination with a concomitant medicament, the timings of the administration of the inventive compound and the concomitant medicament are not particularly limited, and the inventive compound and the concomitant medicament can be given to a subject simultaneously or at a certain time interval. The dose of the concomitant medicament may be in accordance with a dose employed clinically, and selected appropriately depending on the target, route, disease, combination and the like.

The administration mode of an inventive compound and a concomitant medicament are not particularly limited, provided that the inventive compound and the concomitant medicament are combined upon administration. Such an administration mode may for example be (1) an administration of a single formulation obtained by formulating an inventive compound and a concomitant medicament simultaneously, (2) a simultaneous administration via an identical route of two formulations obtained by formulating an inventive compound and a concomitant medicament separately, (3) a sequential and intermittent administration via an identical route of two formulations obtained by formulating an inventive compound and a concomitant medicament separately, (4) a simultaneous administration via different routes of two formulations obtained by formulating an inventive compound and a concomitant medicament separately, (5) a sequential and intermittent administration via different routes of two formulations obtained by formulating an inventive compound and a concomitant medicament separately (for example, inventive compound followed by concomitant medicament, or inverse order) and the like. These administration modes are hereinafter referred to as an inventive concomitant preparation.

An inventive concomitant preparation has a low toxicity, and thus an inventive compound and/or a concomitant medicament described above are mixed with a pharmacologically acceptable carrier in accordance with a method known per se to form a. pharmaceutical composition, for example, a tablet (including sugar-coated and film-coated tablets), powder, granule, capsule (including softcapsule), solution, injection formulation, suppository, sustained release formulation and the like, which can safely be given orally or parenteraly.(e.g., topically, rectally, intravenously). An injection formulation may be given intravenously, intramuscularly, subcutaneously, into an organ, intranasally, intradermally, via eye drop, intracerebrally, rectally, vaginally and intraperitoneally, or into a tumor, or proximal to the tumor, or directly into a lesion.

A pharmacologically acceptable carrier which may be employed for producing an inventive concomitant preparation may for example be one similar to those employed in an inventive pharmaceutical composition described above.

The ratio between an inventive compound and a concomitant medicament in an inventive concomitant preparation may be selected appropriately on the basis of the target, route and disease, etc.

For example, the amount of an inventive compound contained in an inventive concomitant preparation is usually about 0.01 to 100% by weight based on the entire formulation, preferably about 0.1 to about 50% by weight, more preferably about 0.5 to about 20% by weight, although it may vary depending on the dosage form.

The amount of an concomitant medicament contained in an inventive concomitant preparation is usually about 0.01 to 100% by weight based on the entire formulation, preferably about 0.1 to about 50% by weight, more preferably about 0.5 to about 20% by weight, although it may vary depending on the dosage form.

The amount of an additive such as a carrier contained in an inventive concomitant preparation is usually about 1 to about 99.99% by weight based on the entire formulation, preferably about 10 to about 90% by weight, although it may vary depending on the dosage form.

Similar amounts may be employed also when an inventive compound and a concomitant medicament are formulated separately.

Such a formulation can be produced by a method known per se which is employed usually in a pharmaceutical process.

For example, an inventive compound and a concomitant medicament can be formulated with a dispersant (e.g., Tween 80 (ATLAS POWDER, USA), HCO60 (NIKKO CHEMICALS), polyethylene. glycol, carboxymethyl cellulose, sodium alginate hydroxypropylmethyl cellulose, dextrin, etc.), a stabilizer (e.g., ascorbic acid, sodium pyrosulfite, etc.), a surfactant (e.g., polysorbate 80, macrogol, etc.), a solubilizing agent (e.g., glycerin, ethanol, etc.), buffer agent (e.g., phosphoric acid and its alkali metal salts, citric acid and its alkali metal salt, etc.), an osmotic agent (e.g., sodium chloride, potassium chloride, mannitol, sorbitol, glucose, etc.), a pH modifier (e.g., hydrochloric acid, sodium hydroxide, etc.), a preservative (e.g., ethyl p-hydroxybenzoate, benzoic acid, methylparabene, propylparabene, benzyl alcohol, etc.), a solubilizer (e.g., concentrated glycerin, meglumine, etc.), a solubilizing aid (e.g., propylene glycol, sugar, etc.), a painkiller (e.g., glucose, benzyl alcohol, etc.), etc. into an aqueous formulation for injection, or dissolved, suspended or emulsified in a vegetable oil such as olive oil, sesame oil, cottonseed oil and corn oil, etc. and in a solubilizing aid such as propylene glycol, etc. to form an oily formulation, whereby producing an injection formulation.

In order to obtain an oral dosage form, a method known per se is employed to compress an inventive compound or a concomitant medicament for example with an excipient (e.g., lactose, sugar, starch, etc.), a disintegrant (e.g., starch, calcium carbonate, etc.), a binder (e.g., starch, gum arabic, carboxymethyl cellulose, polyvinyl pyrrolidone, hydroxypropyl cellulose, etc.) or a glidant (e.g., talc, magnesium stearate, polyethylene glycol 6000, etc.) into a desired shape, which is then subjected to a taste masking, covered with an enteric coating or imparted with a sustained release performance if necessary by means of a coating method known per se, whereby obtaining an oral dosage form. Such a coating may for example be hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (Rohm, German, methacrylic/acrylic acid copolymer) and a colorant (e.g., iron oxide red, titanium dioxide, etc.). An oral dosage form may be an instantaneous release formulation or a sustained release formulation.

In order to obtain for example a suppository, a method known per se is employed to convert an inventive compound or concomitant medicament into an oily or aqueous solid, semi-solid or liquid suppository. The oily base employed in a composition described above may for example be a higher fatty acid glyceride [e.g., cocoa butter, UITEPSOL (DYNAMITE NOVEL, Germany), etc.], a medium fatty acid [e.g., MIGRIOL (DYNAMITE NOVEL, Germany), etc.], or a vegetable oil (e.g., sesame oil, soybean oil, cottonseed oil, etc.), etc. The aqueous base may for example be polyethylene glycol and propylene glycol, and the aqueous gel base may for example be natural gums, cellulose derivatives, vinyl polymers and acrylic acid polymers, etc.

A sustained release formulation described above may for example be a sustained-release microcapsule, etc.

While a sustained-release microcapsule can be obtained by a method known per se, a sustained release formulation shown in Section [2] described below is formed and administered in a preferred case.

The inventive compound is preferably formulated as an oral dosage form such as a solid formulation (e.g., powder, granule, tablet, capsule, etc.), or as a rectal formulation such as a suppository, etc. The oral dosage form is particularly preferred.

A concomitant medicament can be formulated into a dosage form described above based on the type of the medicament.

The followings are the descriptions with regard to [1] the injection formulation of the inventive compound and the concomitant medicament and the method for producing the same, [2] the sustained-release or immediate release formulation of the medicament of the inventive compound and the concomitant medicament and the method for producing the same and [3] the sublingual, buccal or instant oral disintegration formulations employing of the inventive compound and the concomitant medicament and the method for producing the same.

[1] Injection Formulation and Method for Producing the Same

The solution obtained by dissolving the inventive compound and the concomitant medicament in water is employed preferably. Such injection formulation may contain a benzoate and/or a salicylate.

Said injection formulation is obtained by dissolving the inventive compound and the concomitant medicament in water together with a benzoate and/or a salicylate in water as desired.

The benzoate and/or a salicylate described above may be an alkali metal salt such as sodium and potassium salts, etc., an alkaline earth metal salt such as calcium and magnesium salts, etc., an ammonium salt, a meglumine salt as well as a salt of an organic acid such as trometamol, etc.

The concentration of an inventive compound or a concomitant medicament in an injection formulation is about 0.5 to about 50 w/v %, preferably about 3 to about 20 w/v %. The concentration of a benzoate and/or a salicylate is about 0.5 to about 50 w/v %, preferably about 3 to about 20 w/v %.

The formulation may contain additives employed customarily in a injection formulation, such as a stabilizer (ascorbic acid, sodium pyrosulfite and the like), a surfactant (polysorbate 80, macrogol and the like), a solubillzing agent (glycerin, ethanol and the like), a buffer agent (phosphoric acid and its alkali metal salt, citric acid and its alkali metal salt and the like), an osmotic agent (sodium chloride, potassium chloride and the like), a dispersing agent (hydroxypropylmethyl cellulose, dextrin), a pH modifier (hydrochloric acid, sodium hydroxide and the like), a preservative (ethyl p-hydroxybenzoate, benzoic acid and the like), a solubilizer (concentrated glycerin, meglumine and the like), a solubilizing aid (propylene glycol, sugar and the like), a painkiller (glucose, benzyl alcohol and the like) properly. Any of these additives are added in an amount employed customarily in a formulation for injection.

The pH of the injection formulation is adjusted at 2 to 12, preferably 2.5 to 8.0 with a pH modifier.

An injection formulation is obtained by dissolving an inventive compound and a concomitant medicament if desired together with a benzoate and/or sallcylate in water if desired together with the additives listed above. These components may be dissolved in any order as appropriate similarly to a customary preparation of a formulation for injection.

An injection formulation is preferably warmed, and given as a formulation for injection after sterilizing by filtration or autoclave similarly to a customary formulation for injection.

An injection formulation is preferably autoclaved at 100 to 121° C. for 5 to 30 minutes.

A formulation may be present as a solution imparted with an antibacterial activity for the purpose of using several times in divided doses.

[2] Sustained-release or Immediate Release Formulation and Method for Producing the Same A sustained release formulation obtained by coating a core containing an inventive compound or a concomitant medicament with a water-insoluble material or a swelling polymer as desired is employed preferably. For example, a sustained-release oral formulation of a single daily dose is preferred.

A water-insoluble material employed as a coating may for example be cellulose ether such as ethyl cellulose and butyl cellulose, etc., cellulose ester such as cellulose acetate and cellulose propionate, etc., polyvinyl ester such as polyvinyl acetate and polyvinyl butyrate, etc., acrylic acid-based polymer such as acrylic acid/methacrylic acid copolymer, methyl methacrylate copolymer, ethoxyethyl methacrylate/cinnamoethyl methacrylate/aminoalkyl methacrylate copolymer, polyacrylic acid, polymethacrylic acid, metacrylic acid alkylamide copolymer, poly(methyl methacrylate), polymethacrylate, polymethacrylamide, aminoalkyl methacrylate copolymer, poly(methacrylic anhydride), glycidyl methacrylate copolymer, especially, a series of Eudragit such as Eudragit RS-100, RL-100, RS-30D, RL-30D, RL-PO, RS-PO (ethyl acrylate/methyl methacrylate/chlorotrimethyl methacrylate/ethyl ammonium copolymer) and Eudragit NE-30D (methyl methacrylate/ethyl acrylate copolymer), hydrogenated oils such as a hydrogenated castor oil (e.g., Lubri wax (Freund Industrial Co.,Ltd.), waxes such as carnauba wax, a fatty acid glycerin ester and paraffin and a polyglycerin fatty acid ester, etc.

As a swelling polymer, a polymer having an acidic cleavable group and exhibiting a pH-dependent swelling is preferred, and an acidic cleavable group-bearing polymer which undergoes a less swelling at an acidic pH such as in stomach but is swollen extensively at a neutral pH such as in small and large intestines is preferred.

Such polymer having an acidic cleavable group and exhibiting a pH-dependent swelling may for example be a crosslinked polyacrylic acid polymer such as Carbomers 934P, 940, 941, 974P, 980, 1342 and the like, Polycarbophil and Calcium Polycarbophil (BF GOODRICH), HIGHVIS Wakos 103, 104, 105 and 304 (Wako Pure Chemical).

A coating employed in a sustained release formulation may further contain a hydrophilic material.

Such hydrophilic material may for example be a polysaccharide which may have a sulfate group such as pullulan, dextrin and alkali metal alginates, a polysaccharide having a hydroxyalkyl group or a carboxyalkyl group such as hydroxypropyl cellulose, hydroxypropylmethyl cellulose and sodium carboxymethyl cellulose as well as methyl cellulose, polyvinyl pyrrolidone, polyvinyl alcohol and polyethylene glycol, etc.

The water-insoluble material content in a coating of a sustained release formulation is about 30 to about 90% (w/w), preferably about 35 to about 80% (w/w), more preferably about 40 to about 75% (w/w), and the swelling polymer content is about 3 to about 30% (w/w), preferably about 3 to about 15% (w/w). A coating may further contain a hydrophilic material, the content of which in the coating is about 50% (w/w) or less, preferably about 5 to about 40% (w/w), more preferably about 5 to about 35% (w/w). Percent (w/w) referred here means a % by weight based on the coating composition which is the rest of the coating solution after deleting any solvent (e.g., water and a lower alcohol such as methanol and ethanol, etc.).

A sustained release formulation is produced, as exemplified below, by preparing a core containing a medicament followed by coating a resultant core with a coating solution obtained by melting a water-insoluble material or a swelling polymer or by dissolving or dispersing such material in a solvent.

I. Drug-containing Core Preparation

While a coated medicament-containing core (hereinafter sometimes referred to simply as a core) may be in any non-limiting shape, it is formed preferably as a particle such as a granule or a fine particle.

When a core is a granule or a fine particle, it has a mean particle size preferable of about 150 to 2,000 μm, more preferably about 500 to 1,400 μm.

The core can be prepared by a standard method. For example, a medicament is combined with suitable excipient, binder, disintegrant, glidant, stabilizer and the like, and then subjected to a wet extrusion granulation or a fluidized bed granulation.

The medicament content in a core is about 0.5 to about 95% (w/w), preferably about 5.0 to about 80% (w/w), more preferably about 30 to about 70% (w/w).

The excipient contained in a core may for example be a saccharide such as sucrose, lactose, mannitol and glucose, etc., starch, crystalline cellulose, calcium phosphate and corn starch. Among these, crystalline cellulose and corn starch are preferred.

A binder may for example be polyvinyl alcohol, hydroxypropyl cellulose, polyethylene glycol, polyvinyl pyrrolidone, Pluronic F68, gum arabic, gelatin and starch, etc. A disintegrant may for example be calcium carboxymethyl cellulose (ECG505), sodium croscarmellose (Ac-Di-Sol), crosslinked polyvinyl pyrrolidone (crospovldone) and a low-substituted hydroxypropyl cellulose (L-HPS), etc. Among these, hydroxypropyl cellulose, polyvinyl pyrrolidone and a low-substituted hydroxypropyl cellulose are preferred. A glidanxt and an anticoagulant may for example be talc, magnesium stearate, etc., and a lubricant may for example be polyethylene glycol, etc. A stabilizer may for example be an acid such as tartaric acid, citric acid, succinic acid, fumaric acid and maleic acid, etc.

In addition to the methods described above, other methods can be employed to form a core, such as an agitating granulation method wherein an inert carrier particle as a seed for the core is sprayed with a binder dissolved in a suitable solvent such as water and a lower alcohol (e.g., methanol and ethanol) with being supplemented portionwise with a medicament or a mixture thereof with an excipient and a glidant as well as a pan coating method, a fluidized bed coating method and a melting granulation method. An inert carrier particle may for example be one prepared from sugar, lactose, starch, crystalline cellulose and waxes, and has a mean particle size preferably of about 100 µm to about 1,500 µm.

In order to separate a medicament contained in a core from a coating, the surface of the core may be covered with a protective material. Such protective material may for example be a hydrophilic material described above and a water-insoluble material. A preferred protective material is polyethylene glycol or a polysaccharide having a hydroxyalkyl group or a carboxyalkyl group, more preferably, hydroxypropylmethyl cellulose and hydroxypropyl cellulose. The protective material may contain, as a stabilizer, an acid such as tartaric acid, citric acid, succinic acid, fumaric acid and maleic acid, as well as a glidant such as talc, etc. A protective material, when employed, is coated at a rate of about 1 to about 15% (w/w), preferably about 1 to about 10% (w/w), more preferably about 2 to about 8% (w/w) based on a core.

A protective material can be coated by a standard coating method, and typically a core is sprayed with the protective material by a fluidized bed coating method and a pan coating method.

II. Coating of Core with Coating Agent

A core obtained as described above in Section I is coated with a coating solution containing a water-insoluble material, a pH-dependent swelling polymer and a hydrophilic material being melted therein by heating or being dissolved or dispersed in a solvent to obtain a sustained release formulation.

A method for coating a core with a coating solution may for example be a spray coating.

The ratio between a water-insoluble material, a swelling polymer and a hydrophilic material in a coating solution may be selected appropriately in such a manner that respective contents in the coating become those specified above.

The coating rate is about 1 to about 90% (w/w) based on the core (excluding the protective material coating), preferably about 5 to about 50% (w/w), more preferably about 5 to about 35% (w/w).

The solvent for a coating solution is water or an organic solvent, which may be employed alone or in combination with each other. The ratio between water and the organic solvent when being employed in combination (water/organic solvent: weight ratio) may vary from 1 to 100%, and is preferably 1 to about 30%. While said organic solvent is not limited particularly as long as it can dissolve a water-insoluble material, it may for example be a lower alcohol such as methyl alcohol, ethyl alcohol, isopropyl alcohol and n-butyl alcohol, etc., a lower alkanone such as acetone, etc., as well as acetonitrile, chloroform, methylene chloride and the like. Among those listed above, a lower alcohol is preferred, with ethyl alcohol and isopropyl alcohol being especially preferred. Water and a mixture of water and an organic solvent are employed preferably as solvents for a coating. In such a case, an acid such as tartaric acid, citric acid, succinic acid, fumaric acid and maleic acid may be added to the coating solution for the purpose of stabilizing the coating solution.

An operation when the coating is effected by a spray coating, a standard coating method can be employed, and typically a core is sprayed with a coating by a fluidized bed coating method and a pan coating method. During this process, a lubricant such as talc, titanium oxide, magnesium stearate, calcium stearate and light silicic anhydride, etc. and a plasticizer such as glycerin fatty acid ester, hardened castor oil, triethyl citrate, cetyl alcohol and stearyl alcohol, etc. may also be added.

After coating with the coating agent, an antistatic agent such as a talc may also be incorporated if necessary.

An instantaneous release formulation may be a liquid (solution, suspension, emulsion, etc.) or a solid (particle, pill, tablet, etc.). While an oral formulation and a parenteral formulation such as an injection formulation may be employed, an oral formulation is preferred.

An instantaneous release formulation may usually contain, a carrier, additive and excipient (hereinafter sometimes abbreviated as excipient) which are employed customarily in the pharmaceutical field, in addition to a medicament which is an active ingredient. Such a formulation excipient is not limited particularly as long as it is an excipient employed usually as a formulation excipient. For example, an excipient for an oral solid formulation may be lactose, starch, corn starch, crystalline cellulose (Asahi Kasei, Avicel PH101 and the like), powder sugar, granulated sugar, mannitol, light silicic anhydride, magnesium carbonate, calcium carbonate, L-cysteine and the like, with corn starch and mannitol being preferred. Any of these excipients may be employed alone or in combination with each other. The amount of an excipient may for example be about 4.5 to about 99.4 w/w %, preferably about 20 to about 98.5 w/w %, more preferably about 30 to about 97 w/w %, based on the entire amount of an instantaneous release formulation.

The medicament content in an instantaneous release formulation may be selected within the range from about 0.5 to about 95%, preferably about 1 to about 60%, based on the entire amount of an instantaneous release formulation.

An oral solid instantaneous release formulation contains a disintegrant in addition to the ingredients described above. Such a disintegrant may for example be calcium carboxymethyl cellulose (GOTOKUYAKUHIN, ECG505), sodium croscarmellose (for example, Asahi Kasei, Ac-Di-Sol), crospovidone (for example, BASF, COLIDON CL), low-substituted hydroxypropyl cellulose (SHINETSU KAGAKU), carboxymethyl starch (MATSUTANI KAGAKU), sodium carboxymethyl starch (KIMURASANGYO, EXORITAB), partial a starch (Asahi Kasei, PCS) and the like, any of which may for example be brought into contact with water to effect water absorption or swelling, or to make a channel between a core-forming active ingredient and an excipient, whereby, disintegrating a granule. Any of these disintegrants may be employed alone or in combination with each other. While the amount of a disintegrant to be incorporated may be selected appropriately based on the type and the amount of the medicament employed and the preparation design for releasing, it may for example be about 0.05 to about 30 w/w %, preferably about 0.5 to about 15 w/w % based on the entire amount of an instantaneous release formulation.

An oral solid instantaneous release formulation contains additives employed customarily in a solid formulation if desired in addition to the components described above. Such additives may for example be binders (for example, sucrose, gelatin, powdery gum arabic, methyl cellulose, hydroxypropyl cellulose, hydroxypropylmethyl cellulose, carboxymethyl cellulose, polyvinylpyrrolidone, pulluran, dextrin, etc.), lubricants (polyethylene glycol, magnesium stearate, talc, light silicic anhydride (for example, aerosil (NIPPON AEROSIL)), surfactants (for example, anionic surfactants such as sodium alkylsulfate, nonionic surfactants such as polyoxyethylene fatty acid ester and polyoxyethylene sorbitan fatty acid ester, polyoxyethylene castor oil derivatives, etc.), colorants (for example, tar-based colorants, caramel, red ocher, titanium oxide, ribofravin, etc.), if necessary together with seasonings (for example, sweetener and flavor), adsorbents, preservatives, wetting agents, antistatic agents and the like. As a stabilizer, an organic acid such as tartaric acid, citric acid, succinic acid and fumaric acid may also be added.

Binders described above are preferably hydroxypropyl cellulose, polyethylene glycol and polyvinylpyrrolidone, etc.

An instantaneous formulation can be prepared based on an ordinary formulation technology by mixing the components described above and kneading if necessary and then molding. Such a mixing may be accomplished by an ordinary method, such as mixing and kneading. Typically, when an instantaneous release formulation is formed as a particle, then a method similar to that for preparing a core of a sustained release formulation described above is employed to mix the materials using a vertical granulator, multipurpose kneader (HATAKE TEKKOSHO), fluidized bed granulator FD-5S (Powrex Corporation) and the like, after which a granulation is effected using a wet extrusion granulation or a fluidized bed granulation.

Each of an instantaneous release formulation and a sustained release formulation thus obtained may be formulated separately by a standard method as it is or in combination with an excipient properly and then provided as a final formulation for simultaneous administration or intermittent sequential administration, or the both may be formulated in a single oral formulation (e.g., granule., fine powder, tablet, capsule, etc.) as they are or in combination with an excipient properly. The both formulation may be formulated also as granules or fine powders, which are then filled in a single capsule for oral administration.

[3] Sublingual, Buccal or Instant Oral Disintegration Formulations and Method for Producing the Same Any of sublingual, buccal or instant oral disintegration formulations may be a solid formulation such as a tablet, etc., or may be an oral mucosa plaster (film).

Each of sublingual, buccal or instant oral disintegration formulations is preferably a formulation containing an inventive compound or a concomitant medicament together with an excipient. An auxiliary agent may also be contained such as a lubricant, osmotic agent, hydrophilic carrier, water-dispersible polymer and stabilizer. For the purpose of promoting the absorption and enhancing the bioavailability, β-cyclodextrin or β-cyclodextrin derivatives (e.g., hydroxypropyl-β-cyclodextrin, etc.), etc. may also be. contained.

Such an excipient may for example be lactose, sugar, D-mannitol, starch, crystalline cellulose, light silicic anhydride and the like. A lubricant may for example be magnesium stearate, calcium stearate, talc, colloidal silica and the like, with magnesium stearate and colloidal silica being preferred. An osmotic agent may for example be sodium chloride, glucose, fructose, mannitol, sorbitol, lactose, saccharose, glycerin and urea, with mannitol being preferred especially. A hydrophilic carrier may for example be a swelling hydrophilic carrier such as a crystalline cellulose, ethyl cellulose, crosslinked polyvinyl pyrrolidone, light silicic anhydride, silicic acid, dicalcium phosphate, calcium carbonate and the like, with a crystalline cellulose (e.g., microcrystalline cellulose) being preferred. A water-dispersible polymer may for example be a gum (e.g., tragacanth gum, acacia gum, guar gum), alginate (e.g., sodium alginate), cellulose derivative (e.g., methyl cellulose, carboxymethyl cellulose, hydroxymethyl cellulose, hydroxypropyl cellulose, hydroxypropylmethyl cellulose), gelatin, water-soluble starch, polyacrylic acid (e.g., carbomer), polymethacrylic acid, polyvinyl alcohol, polyethylene glycol, polyvinylpyrrolidone, polycarbophil, ascorbate palmitate ester and the like, with hydroxypropylmethyl cellulose, polyacrylic acid, alginate, gelatin, carboxymethyl cellulose, polyvinylpyrrolidone and polyethylene glycol, etc. being preferred. Hydroxypropylmethyl cellulose is especially preferred. A stabilizer may for example be cysteine, thiosorbitol, tartaric acid, citric acid, sodium carbonate, ascorbic acid, glycine and sodium sulfite, with citric acid and ascorbic acid being preferred especially.

Each of sublingual, buccal or instant oral disintegration formulations can be produced by mixing an inventive compound or concomitant medicament with an excipient by a method known per se. If desired, an auxiliary agent described above, such as lubricant, osmotic agent, hydrophilic carrier, water-dispersible polymer, stabilizer, colorant, sweeteners and preservative, may also be incorporated. After mixing the components described above simultaneously or at a certain time interval, the mixture is compressed and molded into each of sublingual, buccal or instant oral disintegration formulations. For the purpose of obtaining a suitable hardness, a solvent such as water and alcohol may be employed to hydrate the mixture before or after the tablet impaction, and then dried finally.

When an oral mucosa plaster (film) is to be molded, an inventive compound or concomitant medicament and a water-dispersible polymer (preferably, hydroxypropyl cellulose, hydroxypropylmethyl cellulose) and excipient described above are dissolved in a solvent such as water, and then the resultant solution is casted into a film. Additives may also be added such as plasticizers, stabilizers, antioxidants, preservatives, colorants, buffering agents and sweeteners. A glycol such as polyethylene glycol or propylene glycol may be added for the purpose of imparting a film with an appropriate elasticity, and a bioadhesive polymer (e.g., polycarbophile, carbopol) may be added for the purpose of enhancing the adhesion of the film to the oral mucosal lining. The casting may be accomplished by pouring a solution onto a non-adhesive surface, spreading the solution using a coater such as a doctor blade, etc. into a uniform thickness (preferably about 10 to 1000 microns), and then drying the solution to form a film. The film thus formed is dried at room temperature or with arming, and then cut into pieces each having a desired surface area.

A preferred instant oral disintegration formulation may for example be a rapid diffusion formulation in the form of a solid network consisting of an inventive compound or concomitant medicament together with a water-soluble or water-diffusible carrier which is inert to the inventive compound or concomitant medicament. Said network is obtained by sublimating a solvent from a solid composition consisting of a solution of an inventive compound or concomitant medicament in a suitable solvent.

In addition to an inventive compound or concomitant medicament, a matrix-forming agent and a secondary component are contained preferably in the composition of said instant oral disintegration formulation.

Said matrix-forming agents may for example be an animal or vegetable protein such as a gelatin, dextrin and soybean, wheat and psyllium seed proteins; a gummy material such as gum arabic, guar gum, agar and xanthane gum; polysaccharide; alginate; carboxymethyl cellulose; carrageenan; dextran; pectin; synthetic polymer such as polyvinylpyrrolidone; a material derived from a gelatin-gum arabic complex. Those which are also included are saccharides such as mannitol, dextrose, lactose, galactose and trehalose, etc.; cyclic saccharides such as cyclodextrin, etc.; inorganic salts such as sodium phosphate, sodium chloride and aluminum silicate, etc.; amino acids having 2 to 12 carbon atoms such as glycine, L-alanine, L-aspartic acid, L-glutamic acid, L-hydroxyproline, L-isoleucine, L-leucine and L-phenylalanine, etc.

One or more matrix-forming agents may be introduced into a solution or suspension before solidification. Such a matrix-forming agent may be present in addition to a surfactant, or may be present in the absence of the surfactant. The matrix-forming agent serves not only to form a matrix itself, but also to aid in maintaining the inventive compound or concomitant medicament as being diffused in the solution or suspension.

A secondary agent may be contained in a composition such as a preservative, antioxidant, surfactant, thickening agent, colorant, pH modifier, flavor, sweetener or taste masking agent, etc. A suitable colorant may for example be iron oxide red, black and yellow, FD&C dyes available from ERIS AND EVERALD such as FD&C Blue No.2 and FD&C Red No.40. A suitable flavor may for example be mint, raspberry, licorice, orange, lemon, grape fruit, caramel, vanilla, cherry and grape flavor as well as a combination thereof. A suitable pH modifier may for example be citric acid, tartaric acid, phosphoric acid, hydrochloric acid and maleic acid. A suitable sweetener may for example be aspartame, acesulfame K and thaumatine. A suitable taste masking agent may for example be sodium bicarbonate, ion exchange resin, cyclodextrin inclusion compound, adsorbent and microencapsulated apomorphine.

A formulation contains an inventive compound or concomitant medicament in an amount usually of about 0.1 to about 50% by weight, preferably about 0.1 to about 30% by weight, and is preferably a formulation (sublingual or buccal formulation described above) which allows 90% or more of the inventive compound or concomitant medicament to be dissolved. (in water) within a time period of about 1 to about 60 minutes, preferably about 1 minutes to about 15 minutes, more preferably about 2 minutes to about 5 minutes, or a instant oral disintegration formulation which disintegrates within about 1 to about 60 seconds, preferably about 1 to about 30 seconds, more preferably about 1 to about 10 seconds after being placed in the oral cavity.

The amount of an excipient described above based on the entire formulation is about 10 to about 99% by weight, preferably about 30 to about 90% by weight. The amount of β-cyclodextrin or β-cyclodextrin derivative based on the entire formulation is about 0 to about 30% by weight. The amount of a lubricant based on the entire formulation is about 0.1 to about 10% by weight, preferably about 1 to about 5% by weight. The amount of an osmotic agent based on the entire formulation is about 0.01 to about 90% by weight, preferably about 10 to about 70% by weight. The amount of a hydrophilic carrier based on the entire formulation is about 0.1 to about 50% by weight, preferably about 10 to about 30% by weight. The amount of a water-dispersible polymer based on the entire formulation is about 0.1 to about 30% by weight, preferably about 10 to about 25% by weight. The amount of a stabilizer based on the entire formulation is about 0.1 to about 10% by weight, preferably about 1 to about 5% by weight. The formulation described above may further contain additives if desired such as colorants, sweeteners and preservatives, etc.

While the dose of an inventive concomitant preparation may vary depending on the type of the inventive compound, the subject's age, body weight, condition, and the dosage form as well as administration mode and duration, the daily dose for example in a patient having a breast cancer (adult, body weight: about 60 kg) is about 0.01 to about 1000 mg/kg as an inventive compound and concomitant medicament, preferably about 0.01 to about 100 mg/kg, more preferably about 0.1 to about 100 mg/kg, particularly about 0.1 to about 50 mg/kg, especially about 1.5 to about 30 mg/kg, which is given intravenously at once or in several portions. It is a matter of course that the dose may vary depending on various factors as described above, and a less amount may sometimes be sufficient and an excessive amount should sometimes be required.

A concomitant medicament may be employed in any amount within the range causing no problematic side effects. The daily dose of a concomitant medicament is not limited particularly and may vary depending on the severity of the disease, the subject's age, sex, body weight and susceptibility as well as time and interval of the administration and the characteristics, preparation, type and active ingredient of the pharmaceutical formulation, and the daily oral dose per kg body weight in a mammal is about 0.001 to 2000 mg, preferably about 0.01 to 500 mg, more preferably about 0.1 to about 100 mg as medicaments, which is given usually in 1 to 4 portions.

When the inventive concomitant preparation is administered, it may be administered at the same time, but it is also possible that the concomitant medicament is first administered and then the inventive compound is administered, or that the inventive compound is first administered and then the concomitant medicament is administered. When such an intermittent administration is employed, the time interval may vary depending on the active ingredient administered, the dosage form and the administration mode, and when the concomitant medicament is first administered, the inventive compound may be administered within 1 minute to 3 days, preferably 10 minutes to 1 day, more preferably 15 minutes to 1 hour after the administration of the concomitant medicament. When the inventive compound is first administered, then the concomitant medicament may be administered within 1 minutes to 1 day, preferably 10 minutes to 6 hours, more preferably 15 minutes to 1 hour after the administration of the inventive compound.

The present invention is further detailed in the following Reference Examples, Examples, Formulation Examples and Experiment Examples, any of which serves only a practice and is not intended to restrict the invention and can be modified without departing from the scope of the invention.

In the following Reference Examples and Examples, the term "room temperature " usually means a temperature from about 10 to about 35° C. A % means a mol/mol % when employed for a yield and a % by volume when employed for a chromatographic solvent, and otherwise it is a % by weight. A basic silica gel employed was NH-DM1020 manufactured by FUJI SILYSIA CHEMICAL LTD. Any unidentifiable broad peak such as those of OH and NH protons in each proton NMR spectrum are not included in the data.

Abbreviations shown below are employed here.
s: Singlet
d: Doublet
t: Triplet
q: Quartet
m: Multiplet
br: Broad
J: Coupling constant
Hz: Hertz
$CDCl_3$: chloroform-d
$DMSO-d_6$: dimethylsulfoxide-$d_6$
$^1$H NMR: Proton nuclear magnetic resonance A transformant *Escherichia coli* BL21/pPDE4D3 obtained in Experiment Example 1 described below was deposited on Mar. 8, 2000 to National Institute of Bioscience and Human-Technology Agency of Industrial Science and. Technology (NIBH) under the deposition No.FERM BP-7075 and on Feb. 24, 2000 to Institution for Fermentation, Osaka (IFO) under the deposition No.IFO 16383.

The gene engineering operations employing *Escherichia coli* was in accordance with Molecular Cloning.

The Sequence ID Nos. in the sequence listing in this specification indicate the following sequences.

[Sequence ID No.1]
Sequence ID No.1 indicates the base sequence of a primer employed in Experiment Example 1.

[Sequence ID No.2]
Sequence ID No.2 indicates the base sequence of a primer employed in Experiment Example.

[Sequence ID No.3]
Sequence ID No.3 indicates the cDNA base sequence possessed by *Escherichia coli* BL21/pPDE4D3 obtained in Experiment Example 1.

[Sequence ID No.4]
Sequence ID No.4 indicates the amino acid sequence encoded by the cDNA base sequence possessed by *Escherichia coli* BL21/pPDE4D3 obtained in Experiment Example 1.

EXAMPLES

Reference Example 1
4-Hydroxy-3-methoxy-5-(2-methyl-2-propenyl) benzaldehyde

To a solution of vanillin (25.6 g, 0.168 mol) in N,N-dimethylformamide (150 mL), 3-chloro-2-methyl-1-propene (19.9 mL, 0.202 mol) and potassium carbonate (30.2 g, 0.219 mol) was added and the mixture was stirred at 75° C. for 2.5 hours under nitrogen atmosphere. Water was added to the reaction mixture and the mixture was extracted three times with ethyl acetate. The combined organic layer was washed twice with water, and then concentrated under reduced pressure. The residue was subjected to a column chromatography on a silica gel (hexane/ethyl acetate, 5:1) to obtain 3-methoxy-4-(2-methyl-2-propenyloxy)benzaldehyde (35.4 g) as an oil.

This 34.3 g of the material was dissolved in N,N-diethylaniline (80 mL), and stirred at 200° C. for 5 hours under nitrogen atmosphere. The reaction mixture was dissolved in diisopropyl ether, washed with 1 M hydrochloric acid (twice) and brine, dried over magnesium sulfate, treated with activated charcoal, filtered, and concentrated under reduced pressure. The residue was crystallized from diisopropyl ether-hexane to obtain the title compound (27.1 g, yield: 79%).

Melting point: 53–54° C.
$^1$H NMR ($CDCl_3$) δ 1.75 (3H, s), 3.42 (2H, s), 3.97 (3H, s), 4.69–4.75 (1H, m), 4.82–4.97 (1H, m), 6.31 (1H, s), 7.31 (2H, s), 9.81 (1H, s).

Reference Example 2
4-Hydroxy-3-ethoxy-5-(2-methyl-2-propenyl)benzaldehyde

To a solution of 3-ethoxy-4-hydroxybenzaldehyde (25.6 g, 0.154 mol) in N,N-dimethylformamide (150 mL), 3-chloro-2-methyl-1-propene (16.7 mL, 0.169 mol) and potassium carbonate (24.5 g, 0.177 mol) were added, and the mixture was stirred at 80° C. for 3 hours under nitrogen atmosphere. Water was added to the reaction mixture and the reaction mixture was extracted twice with ethyl acetate. The combined organic layer was washed twice with water, and then concentrated under reduced pressure to obtain 3-ethoxy-4-(2-methyl-2-propenyloxy)benzaldehyde (35.5 g) as an oil.

This was dissolved in N,N-diethylaniline (25 mL), and stirred at 210° C. for 5 hours under nitrogen atmosphere. The reaction mixture was dissolved in ethyl acetate, washed twice with 1 M hydrochloric acid and twice with water, and then concentrated under reduced pressure. The residue was crystallized from diisopropyl ether-hexane to obtain the title compound (26.7 g, yield: 79%).

Melting Point: 85–86° C.
$^1$H NMR ($CDCl_3$) δ 1.48 (3H, t, J=7.0 Hz), 1.75 (3H, s), 3.42 (2H, s), 4.20 (2H, q, J=7.0 Hz), 4.68–4.73 (1H, m), 4.82–4.87 (1H, m), 6.34 (1H, s), 7.29 (2H, s), 9.80 (1H, s).

Reference Example 3
2,3-Dihydro-7-methoxy-2,2-dimethyl-5-benzofurancarboxaldehyde To a solution of 4-hydroxy-3-methoxy-5-(2-methyl-2-propenyl)benzaldehyde (26.2 g, 0.127 mol) in toluene (130 mL), boron trifluoride diethyl ether complex (17.2 mL, 0.140 mol) was added, and the mixture was stirred at 110° C. for 1 hour.

The reaction mixture was washed with water and saturated aqueous solution of sodium hydrogen carbonate, dried through sodium sulfate and a silica gel (eluted with hexane/ethyl acetate 3:1), and then concentrated under reduced pressure. The residue was crystallized from diisopropyl ether-hexane to obtain the title compound (17.1 g, yield: 65%).

Melting point: 58–59° C.
$^1$H NMR ($CDCl_3$) δ 1.56 (6H, s), 3.11 (2H, s), 3.94 (3H, s), 7.28–7.35 (2H, m), 9.80 (1H, s).

(Alternative Synthetic Method)
A suspension of 4-hydroxy-3-methoxy-5-(2-methyl-2-propenyl)benzaldehyde (88.4 g, 0.429 mol) and Amberlyst 15 (trade name) (17 g) in toluene (300 mL) was stirred at 100° C. for 1.5 hours. The reaction mixture was filtered, and washed with ethyl acetate. The filtrate was washed with 0.5 M aqueous solution of sodium hydroxide and water (twice), and concentrated under reduced pressure. The residue was crystallized from diisopropyl ether-hexane to obtain the title compound (72.1 g, yield: 82%).

Reference Example 4
7-Ethoxy-2,3-dihydro-2,2-dimethyl-5-benzofurancarboxaldehyde To a solution of 3-ethoxy-4-hydroxy-5-(2-methyl-2-propenyl)benzaldehyde (28.9 g, 0.131 mol) in toluene (150 mL), boron trifluoride diethyl ether complex (17.8 mL, 0.145 mol) was added, and the mixture was stirred at 100° C. for 1 hour. The reaction mixture was washed with water, saturated aqueous solution of sodium hydrogen carbonate and brine, dried through sodium sulfate and a silica gel (eluted with hexane/ethyl acetate 5:1), and then concentrated under reduced pressure to obtain the title compound (26.8 g, yield: 93%).

Melting point: 33–36° C.

$^1$H NMR (CDCl$_3$) δ 1.47 (3H, t, J=7.0 Hz), 1.56 (6H, s), 3.09 (2H, s), 4.19 (2H, q, J=7.0 Hz), 7.26–7.35 (2H, m), 9.78 (1H, s).

Reference Example 5

2,3-Dihydro-7-methoxy-2,2-dimethyl-5-(2-methyl-1-propenyl)benzofuran

To a suspension of 2,3-dihydro-7-methoxy-2,2-dimethyl-5-benzofurancarboxaldehyde (1.50 g, 7.27 mmol) and isopropyltriphenylphosphonium iodide (3.77 g, 8.73 mmol) in tetrahydrofuran (20 mL), sodium hydride (66% suspension in oil) (397 mg, 11 mmol) was added, and the mixture was heated under reflux for 1.5 hours. The reaction mixture was poured into a 10% aqueous solution of ammonium chloride, and extracted twice with ethyl acetate. The combined organic layer was washed with water and brine, dried over magnesium sulfate, filtered, and then concentrated under reduced pressure. The residue was subjected to a column chromatography on a silica gel (hexane/ethyl acetate, 50:1 followed by 30:1) to obtain the title compound (1.22 g, yield: 72%). An oil.

$^1$H NMR (CDCl$_3$) δ 1.51 (6H, s), 1.867 (3H, d, J=1.4 Hz), 1.874 (3H, d, J=1.4 Hz), 3.02 (2H, s), 3.85 (3H, s), 6.20 (1H, s), 6.61 (1H, s), 6.65 (1H, s).

(Alternative Synthetic Method)

To a solution of guaiacol (124 g, 1.00 mol) in N,N-dimethylformamide (500 mL), 3-chloro-2-methyl-1-propene (128 mL, 1.30 mol) and potassium carbonate (166 g, 1.20 mol) were added, and the mixture was stirred at 80° C. for 5 hours under nitrogen atmosphere. Water was added to the reaction mixture and the mixture was extracted twice with hexane. The combined organic layer was washed each twice with 0.5 M aqueous solution of sodium hydroxide and water, and then concentrated under reduced pressure to obtain 1-methoxy-2-[(2-methyl-2-propenyl)oxy]benzene (178 g) as an oil.

This was dissolved in N,N-diethylaniline (250 mL), and stirred at 205° C. for 5 hours under nitrogen atmosphere. The reaction mixture was cooled with ice, combined with 2 M hydrochloric acid (850 mL), and extracted with ethyl acetate. The organic layer was washed twice with water, and concentrated under reduced pressure to obtain 2-methoxy-6-(2-methyl-2-propenyl)phenol (178 g) as an oil.

This was dissolved in N,N-dimethylformamide (600 ml). 3-chloro-2-methyl-1-propene (128 mL, 1.30 mol) and potassium carbonate (166 g, 1.20 mol) were added to the mixture and the mixture was stirred at 80° C. for 7 hours under nitrogen atmosphere. Water was added to the reaction mixture and the mixture was extracted twice with hexane. The combined organic layer was washed each twice with water, an aqueous solution of sodium hydroxide and water, and then concentrated under reduced pressure to obtain 1-methoxy-3-(2-methyl-2-propenyl)-2-[(2-methyl-2-propenyl)oxy]benzene (231 g) as an oil.

This was dissolved in N,N-diethylaniline (250 mL), and stirred at 205° C. for 5 hours under nitrogen atmosphere. The reaction mixture was cooled with ice, combined with 2 M hydrochloric acid (850 mL), and extracted twice with ethyl acetate. The combined organic layer was washed twice with water, and concentrated under reduced pressure. The residue was distilled under reduced pressure to obtain 2-methoxy-4,6-bis(2-methyl-2-propenyl)phenol (186 g, yield: 80%). Boiling point: 104–115° C./0.11 kPa (0.8 mmHg).

164 g (0.706 mol) of this material was dissolved in ethanol (300 mL) conc. hydrochloric acid (75 mL) and ethanol (75 mL) were added to the reaction mixture and the mixture was heated under reflux for 13 hours. The reaction mixture was combined with hexane and water, and the organic layer was separated, and then the aqueous layer was extracted with hexane. The combined organic layer was washed with water, 5 M aqueous solution of sodium hydroxide and water (twice), treated with activated charcoal, filtered, and then concentrated under reduced pressure to obtain the title compound (163 g) as an oil. This was used in the next reaction without further purification.

Reference Example 6

7-Ethoxy-2,3-dihydro-2,2-dimethyl-5-(2-methyl-1-propenyl)benzofuran

The title compound was obtained from 7-ethoxy-2,3-dihydro-2,2-dimethyl-5-benzofurancarboxaldehyde by the method similar to that in Reference Example 5. Yield: 91%. An oil.

$^1$H NMR (CDCl$_3$) δ 1.42 (3H, t, J=6.9 Hz), 1.51 (6H, s), 1.83–1.89 (6H, m), 3.00 (2H, s), 4.11 (2H, q, J=6.9 Hz), 6.18 (1H, br s), 6.61 (1H, s), 6.64 (1H, s).

Reference Example 7

1-(2,3-Dihydro-7-methoxy-2,2-dimethyl-5-benzofuranyl)-2-methyl-1-propanol

To a 15% solution of isopropylmagnesium bromide/tetrahydrofuran (101 g, 0.10 mol), a solution of 2,3-dihydro-7-methoxy-2,2-dimethyl-5-benzofurancarboxaldehyde (20.2 g, 97.9 mmol) in tetrahydrofuran (100 mL) was added dropwise, and the mixture was stirred at room temperature for 40 minutes. The reaction mixture was poured into a saturated aqueous solution of ammonium chloride, and extracted twice with ethyl acetate. The combined organic layer was washed twice with water, treated with activated charcoal, filtered, and concentrated under reduced pressure. The residue was recrystallized from ethyl acetate-hexane to obtain the title compound (17.4 g, yield: 71%).

Melting point: 113–116° C.

$^1$H NMR (CDCl$_3$) δ 0.78 (3H, d, J=7.0 Hz), 1.03 (3H, d, J=6.6 Hz), 1.51 (6H, s), 1.92 (1H, sixtet, J=6.9 Hz), 3.02 (2H, s), 3.87 (3H, s), 4.23 (1H, d, J=7.6 Hz), 6.71 (2H, s).

Reference Example 8

1-(2,3-Dihydro-7-methoxy-2,2-dimethyl-5-benzofuranyl)-2-methyl-1-propoyl Acetate To a solution of 1-(2,3-dihydro-7-methoxy-2,2-dimethyl-5-benzofuranyl)-2-methyl-1-propanol (937 mg, 3.74 mol) in pyridine (5 mL), acetic anhydride (0.35 mL, 3.7 mmol) was added dropwise with cooling in ice, and the mixture was stirred at 60° C. for 2 hours. The reaction mixture was dissolved in diisopropyl ether, washed with water, 1 M hydrochloric acid (twice), a saturated aqueous solution of sodium hydrogen carbonate and water, and then concentrated under reduced pressure. The residue was subjected to a column chromatography on a silica gel (hexane/ethyl acetate, 20:1 followed by 10:1) to obtain the title compound (915 mg, yield: 84%).

An oil.

$^1$H NMR (CDCl$_3$) δ 0.78 (3H, d, J=6.6 Hz), 0.98 (3H, d, J=6.6 Hz), 1.50 (6H, s), 1.95–2.17 (1H, m), 2.06 (3H, s), 3.01 (2H, s), 3.86 (3H, s), 5.35 (1H, d, J=8.4 Hz), 6.66 (1H, s), 6.71 (1H, s).

Reference Example 9
2,3-Dihydro-7-methoxy-2,2-dimethyl-5-(2-methyl-2-propenyl)benzofuran To a solution of guaiacol (12.5 g, 0.101 mol) in dichloromethane (50 mL), a solution of bromine (5.3 mL, 0.10 mol) in dichloromethane (10 mL) was added dropwise at −10° C. over 50 minutes, and the mixture was stirred at room temperature for 1 hour. The reaction mixture was combined with water, the organic layer was separated, and the aqueous layer was extracted with dichloromethane. The combined organic layer was washed with a saturated aqueous solution of sodium hydrogen carbonate and brine, dried over magnesium sulfate, filtered, and concentrated under reduced pressure to obtain an oil.

This was dissolved in N,N-dimethylformamide (80 mL). 3-Chloro-2-methyl-1-propene (11 mL, 0.11 mol) and potassium carbonate (16.6 g, 0.120 mol) were added to the mixture and the mixture was stirred at 80° C. for 3 hours under nitrogen atmosphere. The reaction mixture was combined with water, and extracted twice with ethyl acetate/hexane (1:1). The combined organic layer was washed with 0.5 M aqueous solution of sodium hydroxide and water (twice), treated with activated charcoal, filtered, and concentrated under reduced pressure to obtain an oil.

This was dissolved in N,N-diethylaniline (20 mL), and stirred at 205° C. for 5 hours under nitrogen atmosphere. The reaction mixture was dissolved in diisopropyl ether, washed with 1 M hydrochloric acid (twice) and water, treated with activated charcoal, filtered, and concentrated under reduced pressure to obtain an oil.

This was dissolved in ethanol (40 mL). Conc. hydrochloric acid (10 mL) and ethanol (10 mL) were added to the mixture and the mixture was heated under reflux for 2.5 hours. The reaction mixture was combined with hexane, the organic layer was separated, and the aqueous layer was extracted with hexane and diisopropyl ether. The combined organic layer was washed with 2 M aqueous solution of sodium hydroxide (twice) and water, and concentrated under reduced pressure. The residue was subjected to a column chromatography on a silica gel (hexane/ethyl acetate, 20:1) to obtain an oil (15.7 g).

2.57 g of this material was dissolved in tetrahydrofuran (10 mL), a 1.6 M solution of n-butyllithium/hexane (7.5 mL, 12 mmol) was added dropwise to the mixture at −40° C., and the mixture was stirred at the same temperature for 1 hour. To this, copper (I) iodide (1.14 g, 5.99 mmol) was added, and the mixture was stirred at −40° C. for 20 minutes. To the resultant mixture, 3-chloro-2-methyl-1-propene (1.1 mL, 11 mmol) was added dropwise, and the mixture was stirred at room temperature for 1 hour. The reaction mixture was poured into ice water, the insolubles were filtered off, and washed with ethyl acetate. The organic layer was separated, and the aqueous layer was extracted with ethyl acetate. The combined organic layer was washed with water and brine, dried over magnesium sulfate, filtered, and concentrated under reduced pressure. The residue was subjected to a column chromatography on a silica gel (hexane/ethyl acetate, 50:1) to obtain the title compound (1.77 g, yield: 46%).

An oil.
$^1$H NMR (CDCl$_3$) δ 1.50 (6H, s), 1.69 (3H, s), 3.00 (2H, s), 3.24 (2H, s), 3.85 (3H, s), 4.74 (1H, br s), 4.79 (1H, br s), 6.55 (1H, s), 6.59 (1H, s).

Reference Example 10
6-Ethoxy-1,2,3,4,8,9-hexahydro-3,3,8,8-tetramethyl-1-phenylfuro[2,3-h]isoquinoline To a solution of 6-ethoxy-3,4,8,9-tetrahydro-3,3,8,8-tetramethyl-1-phenylfuro[2,3-h]isoquinoline (2.27 g, 6.50 mmol) in methanol (30 mL), 0.8 M solution of hydrogen chloride/methanol (9.7 mL) was added dropwise. The resultant mixture was cooled with ice, treated portionwise with sodium borohydride (90%) (0.28 g, 7.8 mmol), and stirred at room temperature for 10 minutes. The reaction mixture was combined with water, and extracted twice with ethyl acetate. The combined organic layer was washed with water and brine, dried over sodium sulfate, filtered, and concentrated under reduced pressure to obtain the title compound (2.20 g, yield: 96%).

A gum.
$^1$H NMR (CDCl$_3$) δ 1.16 (3H, s), 1.21 (3H, s), 1.24 (3H, s), 1.34 (3H, s), 1.43 (3H, t, J=7.0 Hz), 1.76 (1H, d, J=15.7 Hz), 2.43 (1H, d, J=15.7 Hz), 2.54 (1H, d, J=15.0 Hz), 2.80 (1H, d, J=15.0 Hz), 4.11 (2H, q, J=7.0 Hz), 4.93 (1H, s), 6.49 (1H, s), 7.16–7.38 (5H, m).

Reference Example 11
1,2,3,4,8,9-Hexahydro-6-methoxy-3,3,8,8-tetramethyl-1-phenylfuro[2,3-h]isoquinoline The title compound was obtained from 3,4,8,9-tetrahydro-6-methoxy-3,3,8,8-tetramethyl-1-phenylfuro[2,3-h]isoquinoline by the method similar to that in Reference Example 10.

Quantitative Amorphous.
$^1$H NMR (CDCl$_3$) δ 1.17 (3H, s), 1.21 (3H, s), 1.24 (3H, s), 1.34 (3H, s), 1.76 (1H, d, J=15.8 Hz), 2.44 (1H, d, J=15.8 Hz), 2.55 (1H, d, J=15.0 Hz), 2.81 (1H, d, J=15.0 Hz), 3.86 (3H, s), 4.93 (1H, s), 6.49 (1H, s), 7.13–7.38 (5H, m).

Reference Example 12
4-(6-Ethoxy-1,2,3,4,8,9-hexahydro-3,3,8,8-tetramethylfuro[2,3-h]isoquinolin-1-yl)benzamide The title compound was obtained from 4-(6-ethoxy-3,4,8,9-tetrahydro-3,3,8,8-tetramethylfuro[2,3-h]isoquinolin-1-yl)benzamide by the method similar to that in Reference Example 10. Yield: 96%.

Melting point: 157–163° C. (ethyl acetate-hexane).
$^1$H NMR (CDCl$_3$) δ 1.17 (3H, s), 1.22 (3H, s), 1.24 (3H, s), 1.34 (3H, s), 1.43 (3H, t, J=7.0 Hz), 1.76 (1H, d, J=15.5 Hz), 2.42 (1H, d, J=15.5 Hz), 2.54 (1H, d, J=15.4 Hz), 2.82 (1H, d, J=15.4 Hz), 4.11 (2H, q, J=7.0 Hz), 5.00 (1H, s), 5.45–6.40 (2H, m), 6.50 (1H, s), 7.33 (2H, d, J=8.2 Hz), 7.75 (2H, d, J=8.2 Hz).

Reference Example 13
3-(2,3-Dihydro-7-methoxy-2,2-dimethyl-5-benzofuranyl)-3-hydroxy-2,2-dimethylpropionic Acid Ethyl Ester To a solution of 1,1,1,3,3,3-hexamethyldisilazane (1.88 g, 11.6 mmol) in tetrahydrofuran (40 mL), a 1.53 M solution of n-butyllithium/hexane (7.61 mL, 11.6 mmol) was added dropwise at −78° C., and the mixture was stirred at the same temperature for 15 minutes. To the reaction mixture, a solution of ethyl isobutyrate (1.35 g, 11.6 mmol) in tetrahydrofuran (1 mL) was added dropwise, and the mixture was stirred with cooling in ice for 30 minutes. The reaction mixture was cooled at −78° C. again, and treated dropwise with a solution of 2,3-dihydro-7-methoxy-2,2-dimethyl-5-benzofurancarboxaldehyde (2.00 g, 9.70 mmol) in tetrahydrofuran (3 mL). The reaction mixture was stirred for 1 hour, combined with an aqueous solution of ammonium chloride, and then extracted with ethyl acetate. The extract was washed with water, and then concentrated under reduced pressure. The residue was subjected to a column chromatography on a silica gel (hexane/ethyl acetate, 4:1 to 13:7) to obtain the title compound (1.56 g, yield: 50%).

An oil.
$^1$H NMR (CDCl$_3$) δ1.11 (3H, s), 1.16 (3H, s), 1.28 (3H, t, J=7.2 Hz), 1.50 (6H, s), 3.01 (2H, s), 3.86, (3H, s), 4.18 (2H, q, J=7.2 Hz), 4.80 (1H, s), 6.70 (1H, s), 6.71 (1H, s).

(Alternative Synthetic Method)

To a mixture of zinc (powder, 11 g, 170 mmol) and toluene (300 mL), a solution of 2,3-dihydro-7-methoxy-2,2-dimethyl-5-benzofurancarboxaldehyde (17 g, 82 mmol) and 2-bromoisobutyric acid ethyl ester (35 g, 180 mmol) in toluene (300 mL) was added at 100° C. The reaction mixture was heated under reflux for 3 hours. The reaction mixture was cooled to room temperature, and then the insolubles were filtered off. The filtrate was washed with 1 M hydrochloric acid and brine, dried over magnesium sulfate, and then the solvent was distilled off under reduced pressure. The resultant residue was purified by a column chromatography on a silica gel (hexane/ethyl acetate, 5:1) to obtain the title compound (17 g, yield: 62%).

Reference Example 14

3-(2,3-Dihydro-7-methoxy-2,2-dimethyl-5-benzofuranyl)-2,2-dimethylpropionic Acid Ethyl Ester To a solution of 3-(2,3-dihydro-7-methoxy-2,2-dimethyl-5-benzofuranyl)-3-hydroxy-2,2-dimethylpropionic acid ethyl ester (1.50 g, 4.65 mmol) and triethylsilane (0.817 mL, 5.12 mmol) in dichloromethane (15 mL), boron trifluoride diethyl ether complex (0.648 mL, 5.12 mmol) was added with cooling in ice, and the mixture was stirred with cooling in ice for 1 hour. The reaction mixture was combined with a saturated aqueous solution of sodium hydrogen carbonate, and extracted with ethyl acetate. The extract was washed with water, and concentrated under reduced pressure. The residue was subjected to a column chromatography on a silica gel (hexane/ethyl acetate, 9:1) to obtain the title compound (1.30 g, yield: 91%).

An oil.

$^1$H NMR (CDCl$_3$) δ 1.17 (6H, s), 1.24 (3H, t, J=7.4 Hz), 1.49 (6H, s), 2.77 (2H, s), 2.98 (2H, s), 3.83 (3H, s), 4.11 (2H, q, J=7.4 Hz), 6.49 (1H, s), 6.52 (1H, s).

Reference Example 15

3-(2,3-Dihydro-7-methoxy-2,2-dimethyl-5-benzofuranyl)-2,2-dimethylpropionic Acid To a solution of 3-(2,3-dihydro-7-methoxy-2,2-dimethyl-5-benzofuranyl)-2,2-dimethylpropionic acid ethyl ester (1.25 g, 4.08 mmol) in methanol (10 mL), 2 M aqueous solution of sodium hydroxide was added, and the mixture was stirred for 1.5 hours. The reaction mixture was acidified with 1 M hydrochloric acid, and extracted with ethyl acetate. The extract was washed with water, and then concentrated under reduced pressure. The residue was subjected to a column chromatography on a silica gel (hexane/ethyl acetate, 3:2), and then recrystallized from hexane-ethyl acetate to obtain the title compound (0.87 g, yield: 69%).

Melting point: 88–89° C.

$^1$H NMR (CDCl$_3$) δ 1.21 (6H, s), 1.50 (6H, s), 2.81 (2H, s), 2.99 (2H, s), 3.82 (3H, s), 6.55 (2H, s).

Reference Example 16

N-[2-(2,3-dihydro-7-methoxy-2,2-dimethyl-5-benzofuranyl)-1,1-dimethylethyl]-N'-phenylurea To a solution of 3-(2,3-dihydro-7-methoxy-2,2-dimethyl-5-benzofuranyl)-2,2-dimethylpropionic acid (0.80 g, 2.87 mmol) and diphenylphosphoryl azide (0.650 mL, 3.01 mmol) in toluene (5 mL), triethylamine (0.421 mL, 3.01 mmol) was added, and the mixture was stirred at 70° C. for 1 hour. The reaction mixture was allowed to cool to room temperature. Aniline (0.275 mL, 3.01 mmol) was added to the mixture and the mixture was stirred at 80° C. for 1 hour. The reaction mixture was diluted with ethyl acetate washed with water followed by 1 M hydrochloric acid and water, and then concentrated under reduced pressure. The residue was subjected to a column chromatography on a silica gel (hexane/ethyl acetate, 7:3) to obtain the title compound (0.69 g, yield: 65%).

Amorphous.

$^1$H NMR (CDCl$_3$) δ 1.34 (6H, s), 1.48 (6H, s), 2.96 (4H, s), 3.73 (3H, s), 4.54 (1H, br s), 6.28 (1H, br s), 6.55 (2H, s), 7.04 (1H, t, J=7.0 Hz), 7.18–7.30 (4H, m).

Reference Example 17

N-[2-(2,3-Dihydro-7-methoxy-2,2-dimethyl-5-benzofuranyl)-1,1-dimethylethyl]-N'-(4-methoxyphenyl)urea The title compound was obtained employing 4-methoxyaniline by the method similar to that in Reference Example 16. Yield: 88%.

An oil.

$^1$H NMR (CDCl$_3$) δ 1.32 (6H, s), 1.49 (6H, s), 2.93 (2H, s), 2.97 (2H, s), 3.77 (3H, s), 3.78 (3H, s), 4.37 (1H, br s), 6.01 (1H, br s), 6.53 (2H, s), 6.80 (2H, d, J=8.8 Hz), 7.04 (2H, d, J=8.8 Hz).

Reference Example 18

N-[2-(2,3-Dihydro-7-methoxy-2,2-dimethyl-5-benzofuranyl)-1,1-dimethylethyl]-1-piperidinecarboxamide The title compound was obtained employing piperidine by the method similar to that in Reference Example 16.

Melting Point: 133–134° C. (ethyl acetate-hexane).

$^1$H NMR (CDCl$_3$) δ 1.34 (6H, s), 1.48–1.60 (6H, m), 1.50 (6H, s), 2.93 (2H, s), 2.99 (2H, s), 3.21–3.28 (4H, m), 3.83 (3H, s), 4.11 (1H, br s), 6.53 (1H, s), 6.55 (1H, s).

Reference Example 19

Cyclohexyltriphenylphosphonium Bromide

A mixture of cyclohexyl bromide (10.0 g, 61.3 mmol) and triphenylphosphine (16.1 g, 61.3 mmol) was stirred at 140–150° C. for 72 hours. The reaction solution was cooled, and then crystallized from ethyl acetate to obtain the title compound (19.1 g, yield: 73%). This was used in the next reaction without further purification.

Reference Example 20

5-(Cyclohexylidenemethyl)-2,3-dihydro-7-methoxy-2,2-dimethylbenzofuran

A suspension of cyclohexyltriphenylphosphonium bromide (7.42 g, 17.4 mmol) in tetrahydrofuran (70 mL) was cooled at −78° C., to this, a 1.53 M solution of n-butyllithium in hexane (11.4 mL, 17.4 mmol) was added dropwise, and the mixture was stirred with cooling in ice for 1 hour. To this, 2,3-dihydro-7-methoxy-2,2-dimethyl-5-benzofurancarboxaldehyde (3.00 g, 14.5 mmol) was added, and the mixture was allowed to stir with cooling in ice further for 1 hour. The reaction solution was combined with water, and extracted with ethyl acetate. The extract was washed with water, and then concentrated under reduced pressure. The residue was subjected to a column chromatography on a silica gel (hexane/ethyl acetate, 19:1) to obtain the title compound (0.87 g, yield: 22%).

An oil.

$^1$H NMR (CDCl$_3$) δ 1.51 (6H, s), 1.59 (6H, br s), 2.20–2.26 (2H, m), 2.35–2.42 (2H, m), 3.02 (2H, s), 3.85 (3H, s), 6.16 (1H, s), 6.58 (1H, s), 6.63 (1H, s).

Reference Example 21

3-Formyl-α,α-dimethylbenzeneacetic Acid Ethyl Ester

To a solution of 3-methylbenzeneacetic acid ethyl ester (10.0 g, 56.1 mmol) in N,N-dimethylformamide (80 mL), sodium hydride (66% suspension in oil) (4.29 g, 118 mmol) was added with cooling in ice, and the mixture was stirred at room temperature for 3 hours. A solution of iodomethane (7.34 mL, 118 mmol) in N,N-dimethylformamide (20 mL) was added dropwise with cooling in ice, and the mixture was stirred at room temperature for 3.5 hours. Ice water was poured into the reaction mixture, and the mixture was extracted twice with ethyl acetate. The combined organic layer was washed with a dilute aqueous solution of sodium chloride twice, and brine, dried over magnesium sulfate, filtered, and concentrated under reduced pressure to obtain the mixture (13.3 g) containing α,α,3-trimethylbenzeneacetic acid ethyl ester as an oil.

This was dissolved in ethyl acetate (100 mL). N-bromosuccinimide (10.5 g, 58.9 mmol) and 2,2'-azobis(isobutyroflitrile) (92 mg, 0.561 mmol) were added to the mixture and the mixture was stirred at 60° C. for 9 hours. Ice water was poured into the reaction mixture, and the mixture was washed with brine, dried over magnesium sulfate, filtered, and concentrated under reduced pressure. The residue was subjected to a column chromatography on a silica gel (hexane/ethyl acetate, 50:1 followed by 10:1) to obtain the mixture (15.6 g) containing 3-(bromomethyl)-α,α-dimethylbenzeneacetic acid ethyl ester as an oil.

This was dissolved in acetic acid (35 mL) and water (35 mL). Hexamethylenetetramine (15.7 g, 112 mmol) was added to the mixture and the mixture was heated under reflux at 90° C. for 1 hour. Ethyl acetate was poured into the reaction mixture, and the mixture was washed with water, a saturated aqueous solution of sodium hydrogen carbonate and brine, dried over magnesium sulfate, filtered, and concentrated under reduced pressure. The residue was subjected to a column chromatography on a silica gel (hexane/ethyl acetate, 50:1 followed by 30:1) to obtain the title compound (5.84 g, yield: 47%).

An oil.

$^1$H NMR (CDCl$_3$) δ 1.91 (3H, t, J=7.1 Hz), 1.63 (6H, s), 4.14 (2H, q, J=7.1 Hz), 7.46–7.65 (2H, m), 7.74–7.89 (2H, m), 10.02 (1H, s).

Reference Example 22
3-Cyano-α,α-dimethylbenzeneacetic Acid Ethyl Ester

3-Formyl-α,α-dimethylbenzeneacetic acid ethyl ester (5.49 g, 24.9 mmol) was dissolved in ethanol (30 mL). Hydroxylamine hydrochloride (3.46 g, 49.9 mmol) and sodium acetate (4.09 g, 49.9 mmol) were added to the mixture and the mixture was heated under reflux for 40 hours. Ethanol was distilled off under reduced pressure, ethyl acetate was poured into the residue, and the mixture was washed with water and brine, dried over sodium sulfate, filtered, and concentrated under reduced pressure. The residue was dissolved in acetic anhydride (30 mL), and stirred at 130° C. for 15 hours. 5 M aqueous solution of sodium hydroxide was poured into the reaction mixture, and the mixture was extracted with ethyl acetate. The organic layer was washed with a saturated aqueous solution of sodium hydrogen carbonate, water, and brine, dried over magnesium sulfate, filtered, and concentrated under reduced pressure. The residue was subjected to a column chromatography on a silica gel (hexane/ethyl acetate, 40:1 followed by 20:1) to obtain the title compound (4.21 g, yield: 78%).

An oil.

$^1$H NMR (CDCl$_3$) δ 1.19 (3H, t, J=7.1 Hz), 1.59 (6H, s), 4.13 (2H, q, J=7.1 Hz), 7.39–7.65 (4H, m).

Reference Example 23
4-Hydroxy-3-(2-methyl-2-propenyl)benzaldehyde

The title compound was obtained from p-hydroxybenzaldehyde by the method similar to that in Reference Example 1. Yield: 59%.

An oil.

$^1$H NMR (CDCl$_3$) δ 1.75 (3H, s), 3.45 (2H, s), 4.89 (1H, s), 4.98 (1H, s), 6.19 (1H, br s), 6.96 (1H, d, J=8.1 Hz), 7.70 (1H, d, J=8.1 Hz), 7.74 (1H, s), 9.86 (1H, s).

Reference Example 24
2,3-Dihydro-2,2-dimethyl-5-benzofurancarboxaldehyde

To a solution of 4-hydroxy-3-(2-methyl-2-propenyl)benzaldehyde (8.52 g, 4.84 mmol) in toluene (40 mL), boron trifluoride diethyl ether complex (6.74 mL, 53.2 mmol) was added, and the mixture was stirred at 110° C. for 1 hour. The reaction mixture was washed with water, a saturated aqueous solution of sodium hydrogen carbonate, and brine, dried over magnesium sulfate, filtered, and concentrated under reduced pressure. The residue was subjected to a column chromatography on a silica gel (hexane/ethylacetate, 20:1 followed by 10:1) to obtain the title compound (6.41 g, yield: 75%).

An oil.

$^1$H NMR (CDCl$_3$) δ 1.51 (6H, s), 3.06 (2H, s), 6.82 (1H, d, J=8.4 Hz), 7.64–7.71 (2H, m), 9.82 (1H, s).

Reference Example 25
7-Bromo-2,3-dihydro-2,2-dimethyl-5-benzofurancarboxaldehyde To a solution of 2,3-dihydro-2,2-dimethyl-5-benzofurancarboxaldehyde (5.90 g, 33.5 mmol) in acetic acid (20 mL), a solution of bromine (2.07 mL, 40.2 mmol) in acetic acid (5 mL) was added, and the mixture was stirred at room temperature for 5 hours. An aqueous solution of sodium thiosulfate was poured into the reaction mixture, and the mixture was extracted twice with ethyl acetate. The combined organic layer was washed with brine, dried over magnesium sulfate, filtered, and concentrated under reduced pressure. The residue was subjected to a column chromatography on a silica gel (hexane/ethyl acetate, 10:1) to obtain the title compound (8.08 g, yield: 94%).

An oil.

$^1$H NMR (CDCl$_3$) δ 1.57 (6H, s), 3.16 (2H, s), 7.63 (1H, d, J=1.6 Hz), 7.83 (1H, d, J=1.8 Hz), 9.77 (1H, s).

Reference Example 26
7-Bromo-2,3-dihydro-2,2-dimethyl-5-(2-methyl-1-propenyl)benzofuran The title compound was obtained from 5-bromo-2,3-dihydro-2,2-dimethyl-5-benzofurancarboxaldehyde by the method similar to that in Reference Example 5. Yield: 81%.

$^1$H NMR (CDCl$_3$) δ 1.52 (6H, s), 1.83 (3H, d, J=1.1 Hz), 1.86 (3H, d, J=1.1 Hz), 3.07 (2H, s), 6.12 (1H, s), 6.91 (1H, s), 7.13 (1H, s).

Reference Example 27
7-Ethylthio-2,3-dihydro-2,2-dimethyl-5-(2-methyl-1-propenyl)benzofuran To a solution of 1.54 M solution of tert-butyllithium/pentane (3.45 mL, 5.34 mmol) in tetrahydrofuran (1 mL), a solution of N,N,N',N'-tetramethylethylenediamine (0.81 mL, 5.34 mmol) and 7-bromo-2,3-dihydro-2,2-dimethyl-5-(2-methyl-1-propenyl)benzofuran (300 mg, 1.07 mmol) in tetrahydrofuran (1 mL) was added, and the mixture was stirred at −78° C. for 30 minutes. A solution of diethyl disulfide (1.32 mL, 10.7 mmol) in tetrahydrofuran was added to the mixture and the mixture was warmed gradually from −78° C. to room temperature, and then stirred for 15 hours. Water was poured into the reaction mixture, and the mixture was extracted twice with ethyl acetate. The combined organic layer was washed with brine, dried over magnesium sulfate, filtered, and concentrated under reduced pressure. The residue was subjected to a column chromatography on a silica gel (hexane followed by hexane/ethyl acetate, 50:1) to obtain the title compound (264 mg, yield: 94%).

An oil.

$^1$H NMR (CDCl$_3$) δ 1.26 (3H, t, J=7.3 Hz), 1.50 (6H, s), 1.84 (3H, s), 1.87 (3H, s), 2.90 (2H, q, J=7.3 Hz), 6.15 (1H, s), 6.89 (1H, s), 7.00 (1H, s).

Reference Example 28

2,3-Dihydro-2,2,7-trimethylbenzofuran

To a solution of o-cresol (19.1 mL, 184 mol) in N,N-dimethylformamide (100 mL), 3-chloro-2-methyl-1-propene (20.1 mL, 203 mmol) and potassium carbonate (30.5 g, 221 mmol) were added, and the mixture was stirred at 80° C. for 3 hours. Ice water was poured into the reaction mixture, and the mixture was extracted twice with ethyl acetate. The combined organic layer was washed with water (twice) and brine, dried over magnesium sulfate, filtered, and concentrated under reduced pressure to obtain 1-methyl-2-[(2-methyl-2-propenyl)oxy]benzene (30.8 g) as an oil.

This was dissolved in N,N-diethylaniline (27 mL), and stirred at 210° C. for 5 hours under nitrogen atmosphere. Ethyl acetate was poured into the reaction mixture, and the mixture was washed with 1 M hydrochloric acid, 2 M hydrochloric acid and brine, dried over magnesium sulfate, filtered, and concentrated under reduced pressure to obtain 2-methyl-6-(2-methyl-2-propenyl)phenol (34.3 g) as an oil.

1.20 g of this material was dissolved in ethanol (6 mL). conc. Hydrochloric acid (1.5 mL) was added to the mixture and the mixture was heated under reflux for 2 hours. Ethanol was distilled off under reduced pressure, ethyl acetate was poured into the residue, and the mixture was washed with water and brine, dried over magnesium sulfate, filtered, and concentrated under reduced pressure. The residue was subjected to a column chromatography on a silica gel (hexane) to obtain the title compound (710 mg, yield: 59%).

An oil.

$^1$H NMR (CDCl$_3$) δ 1.47 (6H, s), 2.19 (3H, s), 3.00 (2H, s), 6.69–6.76 (1H, m), 6.91–6.98 (2H, m).

Reference Example 29

2,3-Dihydro-2,2,7-trimethyl-5-benzofurancarboxaldehyde

To a solution of phosphorus oxychloride (0.78 mL, 8.38 mmol) in N,N-dimethylformamide (0.71 mL, 9.22 mmol), a solution of 2,3-dihydro-2,2,7-trimethylbenzofuran (680 mg, 4.19 mmol) in N,N-dimethylformamide (2 mL) was added, and the mixture was stirred at 80° C. for 15 hours. Ice water was poured into the reaction mixture, and the mixture was neutralized with 5 M aqueous solution of sodium hydroxide, and extracted twice with ethyl acetate. The combined organic layer was washed with water (twice) and brine, dried over magnesium sulfate, filtered, and concentrated under reduced pressure. The residue was subjected to a column chromatography on a silica gel (hexane/ethyl acetate, 30:1 followed by 10:1) to obtain the title compound (640 mg, yield: 80%).

An oil.

$^1$H NMR (CDCl$_3$) δ 1.51 (6H, s), 2.23 (3H, s), 3.05 (2H, s), 7.50 (1H, d, J=0.8 Hz), 7.53 (1H, d, J=0.8 Hz), 9.78 (1H, s).

Reference Example 30

2,3-Dihydro-2,2,7-trimethyl-5-(2-methyl-1-propenyl)benzofuran

The title compound was obtained from 2,3-dihydro-2,2,7-trimethyl-5-benzofurancarboxaldehyde by the method similar to that in Reference Example 5. Yield: 93%.

An oil.

$^1$H NMR (CDCl$_3$) δ 1.47 (6H, s), 1.85 (6H, s), 2.17 (3H, s), 2.99 (2H, s), 6.16 (1H, s), 6.80 (1H, s), 6.85 (1H, s).

Reference Example 31

4-Cyclohexylbenzaldehyde

To a mixture of phenylcyclohexane (24.9 g, 155 mmol) and aluminum chloride (20.9 g, 157 mmol) in nitromethane (200 mL), a solution of dichloromethylmethyl ether (18.0 g, 157 mmol) in nitromethane (50 mL) was added dropwise at 0° C. over 40 minutes, and the mixture was stirred at 0° C. for 40 minutes. The reaction mixture was poured into ice water, and the organic material was extracted with diethyl ether. The extract was washed with brine, dried over magnesium sulfate, and then the solvent was distilled off under reduced pressure to obtain the mixture (27.8 g) containing the title compound. This was used in the next reaction without further purification.

An oil.

Reference Example 32

4-Cyclohexylbenzonitrile

A solution of 4-cyclohaxylbenzaldehyde (13.4 g, 71.1 mmol) and hydroxylamine hydrochloride (6.82 g, 98.1 mmol) in formic acid (200 mL) was heated under reflux for 2 hours. The reaction solution was cooled to room temperature, and then poured into ice water, and the solution was basified with potassium hydroxide. The organic material was extracted with hexane. The extract was washed with brine, dried over sodium sulfate, and then the solvent was distilled off under reduced pressure. The resultant residue was purified by a column chromatography on a silica gel (hexane/ethyl acetate, 20:1 followed by 10:1) to obtain the title compound (5.75 g, yield: 44%).

An oil.

$^1$H NMR (CDCl$_3$) δ 1.26–1.52 (4H, m), 1.74–1.89 (6H, m), 2.56 (1H, br), 7.27–7.39 (2H, m), 7.50–7.62. (2H, m).

Reference Example 33

4-Phenoxybenzaldehyde

A suspension of 4-fluorobenzaldehyde (30.5 g, 246 mmol), phenol (23.5 g, 249 mmol), and potassium carbonate (34.8 g, 252 mmol) in N,N-dimethylformamide (500 mL) was heated under reflux for 11.5 hours. The reaction solution was cooled to room temperature, and then the solvent was distilled off under reduced pressure. The resultant residue was combined with water, and the organic material was extracted with ethyl acetate. The extract was washed with brine, dried over magnesium sulfate, and then the solvent was distilled off under reduced pressure to obtain the mixture (48.1 g) containing the title compound. This was used in the next reaction without further purification.

An oil.

Reference Example 34

4-Phenoxybenzonitrile

The title compound was obtained from 4-phenoxybenzaldehyde by the method similar to that in Reference Example 32. Yield: 80%.

$^1$H NMR (CDCl$_3$) δ 6.97–7.19 (4H, m), 7.20–7.28 (1H, m), 7.37–7.46 (2H, m), 7.57–7.64 (2H, m).

Reference Example 35

4-(1-Piperidinyl)benzonitrile

A suspension of 4-fluorobenzonitrile (6.0 g, 50 mmol), piperidine (4.0 g, 47 mmol), and potassium carbonate (8.5 g, 62 mmol) in N,N-dimethylformamide (100 mL) was stirred at 95° C. for 37 hours. The reaction solution was cooled to room temperature, and the solvent was distilled off under reduced pressure. The resultant residue was combined with water, and the organic material was extracted with ethyl acetate. The extract was washed with brine, dried over magnesium sulfate, and then the solvent was distilled off under reduced pressure. The resultant residue was purified by a column chromatography on a silica gel (hexane/ethyl acetate, 20:1 followed by 5:1) to obtain the title compound (8.3 g, yield: 90%).

$^1$H NMR (CDCl$_3$) δ 1.66 (6H, s), 3.33 (4H, s), 6.84 (2H, d, J=8.8 Hz), 7.46 (2H, d, J=8.8 Hz).

Reference Example 36
3,5-Bis(1,1-dimethylethyl)-4-hydroxybenzonitrile

The title compound was obtained from 3,5-bis(1,1-dimethylethyl)-4-hydroxybenzaldehyde by the method similar to that in Reference Example 32. Yield: 45%.

$^1$H NMR (CDCl$_3$) δ 1.44 (18H, s), 5.74 (1H, s), 7.47 (2H, s).

Reference Example 37
4-Methyl-2-phenyl-1H-imidazole-5-carbonitrile

The title compound was obtained from 4-methyl-2-phenyl-1H-imidazole-5-carboxaldehyde by the method similar to that in Reference Example 32. Yield: 54%.

$^1$H NMR (DMSO-d$_6$) δ 2.41 (3H, s), 3.19 (1H, s), 7.42–7.54 (3H, m), 7.92 (2H, dd, J=7.8, 1.4 Hz).

Reference Example 38
4-(1-Methylethoxy)benzonitrile

A solution of 2-propanol (4.4 g, 73 mmol) and sodium hydride (60% in oil, 2.9 g, 73 mmol) in N,N-dimethylformamide (100 mL) was stirred at 0° C. for 10 minutes. A solution of 4-fluorobenzonitrile (7.1 g, 59 mmol) in N,N-dimethylformamide (25 mL) was added to the reaction mixture at 0° C., and stirred at the same temperature for 3 hours, and at room temperature further for 15.5 hours. The reaction solution was poured into water, and extracted with ethyl acetate. The extract was washed with brine, dried over magnesium sulfate, and then the solvent was distilled off under reduced pressure. The resultant residue was crystallized from hexane to obtain the title compound (7.4 g, yield: 85%).

$^1$H NMR (CDCl$_3$) δ 1.36 (6H, d, J=6.2 Hz), 4.52–4.64 (1H, m), 6.91 (2H, d, J=8.6 Hz), 7.57 (2H, d, J=8.6 Hz).

Reference Example 39
4-Cyanobenzyl Acetate

A mixture of 4-cyanobenzylbromide (12.6 g, 64 mmol) and sodium acetate (10.6 g, 129 mmol) in N,N-dimethylformamide (50 mL) was stirred at 80° C. for 25 hours. The solvent was distilled off under reduced pressure, the resultant residue was combined with water, and the organic material was extracted with ethyl acetate. The extract was washed with brine, dried over magnesium sulfate, and then the solvent was distilled off under reduced pressure. The resultant residue was purified by a column chromatography on a silica gel (hexane/ethyl acetate, 20:1 followed by 2:1) to obtain the title compound (8.9 g, yield; 80%).

$^1$H NMR (CDCl$_3$) δ 2.14 (3H, s), 5.16 (2H, s), 7.47 (2H, d, J=8.4 Hz), 7.68 (2H, d, J=8.4 Hz).

Reference Example 40
4-[2-(4-Methoxyphenyl)ethoxy]benzonitrile

The title compound was obtained from 4-methoxyphenethyl alcohol and 4-fluorobenzonitrile by the method similar to that in Reference Example 38. Yield 93%.

$^1$H NMR (CDCl$_3$) δ 3.06 (2H, t, J=7.0 Hz), 3.80 (3H, s), 4.17 (2H, t, J=7.0 Hz), 6.87 (2H, t, J=8.7 Hz), 6.93 (2H, d, J=9.0 Hz), 7.19 (2H, d, J=8.7 Hz), 7.57 (2H, d, J=9.0 Hz).

Reference Example 41
2,3-Dihydro-7-methoxy-5-benzofurancarbonitrile

The title compound was obtained from 7-methoxy-2,3-dihydro-5-benzofurancarboxaldehyde by the method similar to that in Reference Example 32. Yield 77%.

$^1$H NMR (CDCl$_3$) δ 3.28 (2H, t, J=8.8 Hz), 3.89 (3H, s), 4.73 (2H, t, J=8.8 Hz), 7.00 (1H, s), 7.16 (1H, s).

Reference Example 42
4-[(1,3-Dihydro-1,3-dioxo-2H-isoindol-2-yl)methyl]benzonitrile A mixture of 4-cyanobenzylbromide (4.0 g, 20 mmol) and potassium phthalimide (3.8 g, 21 mmol) in N,N-dimethylformamide (40 mL) was stirred at room temperature for 20 hours. The reaction solution was concentrated under reduced pressure, the resultant residue was combined with water, and the organic material was extracted with ethyl acetate. The extract was washed with brine, dried over magnesium sulfate, and then the solvent was distilled off under reduced pressure to obtain the mixture (4.6 g) containing the title compound. This was used in the next reaction without further purification.

Reference Example 43
4-(Aminomethyl)benzonitrile

A solution of 4-[(1,3-dihydro-1,3-dioxo-2H-isoindol-2-yl)methyl]benzonitrile (4.6 g, 18 mmol) and hydrazine monohydrate (8.9 g, 180 mmol) in ethanol (90 mL) was heated under reflux for 33 hours. The reaction solution was cooled to room temperature, and concentrated under reduced pressure. The residue was combined with water, basified with potassium hydroxide, and then extracted with diethyl ether. The extract was washed with brine, dried over magnesium sulfate, and then the solvent was distilled off under reduced pressure to obtain the title compound (1.9 g, yield: 81%).

An oil.

$^1$H NMR (CDCl$_3$) δ 3.96 (2H, s), 7.45 (2H, d, J=8.0 Hz), 7.63 (2H, d, J=8.0 Hz).

Reference Example 44
N-[(4-cyanophenyl)methyl]methanesulfonamide

To a solution of 4-(aminomethyl)benzonitrile (1.9 g, 14 mmol) and triethylamine (3.0 mL, 22 mmol) in tetrahydrofuran (30 mL), methanesulfonyl chloride (1.1 mL, 14 mmol) was added dropwise at 0° C. The reaction solution was stirred at room temperature for 9 hours. The reaction solution was poured into water, and the organic material was extracted with ethyl acetate. The extract was washed with brine, dried over magnesium sulfate, and then the solvent was distilled under reduced pressure to obtain crude crystals. The resultant crude crystals were washed with hexane-diethylether to obtain the title compound (2.0 g, yield: 66%).

$^1$H NMR (CDCl$_3$) δ 2.94 (3H, s), 4.40 (2H, d, J=6.6 Hz), 5.01 (1H, br), 7.50 (2H, d, J=8.6 Hz), 7.67 (2H, d, J=8.6 Hz).

Reference Example 45
6-Methoxy-3-pyridinecarbonitrile

A solution of sodium methoxide (2.42 g, 44.8 mmol) and 6-chloronicotinonitrile (3.04 g, 21.9 mmol) in N,N-dimethylformamide (50 mL) was stirred at room temperature for 10 hours. The reaction solution was poured into water, and the organic material was extracted with ethyl acetate. The extract was washed with brine, dried over magnesium sulfate, and then the solvent was distilled off under reduced pressure. The resultant residue was purified by a column chromatography on a silica gel (hexane/ethyl acetate, 2:1) to obtain the title compound (2.28 g, yield: 78%).

$^1$H NMR (CDCl$_3$) δ 4.00 (3H, s), 6.83 (1H, dd, J=8.8, 0.8 Hz), 7.78 (1H, dd, J=8.6, 2.4 Hz), 8.50 (1H, d, J=1.4 Hz).

Reference Example 46
3-(1-Methylethoxy)benzonitrile

The title compound was objected from 2-propanol and 3-fluorobenzonitrile by the method similar to that in Reference Example 38. Yield: 78%.

$^1$H NMR (CDCl$_3$) δ 1.35 (6H, d, J=6.0 Hz), 4.51–4.63 (1H, m), 7.07–7.13 (2H, m), 7.21 (1H, dt, J=7.6, 1.2 Hz), 7.36 (1H, td, J=7.6, 1.4 Hz).

Reference Example 47
4-Pyridinecarboxamide 1-oxide

A solution of isonicotinamide (52 g, 430 mmol) and a 30% aqueous solution of hydrogen peroxide (65 mL, 570 mol) in acetic acid (170 mL) was stirred at 80° C. for 12 hours. The reaction solution was cooled to room temperature, precipitated crystals were recovered by filtration, and washed with water and hexane to obtain the title compound (30 g, yield: 50%).

$^1$H NMR (DMSO-d$_6$) δ 7.66 (1H, br), 7.82–7.87 (2H, m), 8.17 (1H, br), 8.26–8.33 (2H, m).

Reference Example 48
4-Methylquinoline 1-oxide

The title compound was obtained from 4-methylquinoline by the method similar to that in Reference Example 47. Yield: 75%.

$^1$H NMR (CDCl$_3$) δ 2.67 (3H, s), 7.14 (1H, d, J=6.2 Hz), 7.65–7.84 (2H, m), 7.96–8.01 (1H, m), 8.45 (1H, d, J=6.4 Hz), 8.79–8.84 (1H, m).

Reference Example 49
3-Methylquinoline 1-oxide

The title compound was obtained from 3-methylquinoline by the method similar to that in Reference Example 47. Yield: 91%.

$^1$H NMR (CDCl$_3$) δ 2.46 (3H, s), 7.53–7.81 (4H, m), 8.43 (1H, s), 8.69 (1H, d, J=8.8 Hz).

Reference Example 50
7-Methylquinoline 1-oxide

The title compound was obtained from 7-methylquinoline by the method similar to that in Reference Example 47. Yield: 46%.

$^1$H NMR (CDCl$_3$) δ 2.61 (3H, s), 7.20–7.27 (1H, m), 7.46–7.51 (1H, m), 7.69–7.79 (2H, m), 8.50–8.56 (2H, m).

Reference Example 51
4-Pyridinecarboxylic Acid Ethyl Ester 1-oxide

The title compound was obtained from isonicotinic acid ethyl ester by the method similar to that in Reference Example 47. Yield: 80%.

$^1$H NMR (CDCl$_3$) δ 1.39 (3H, t, J=7.0 Hz), 4.42 (2H, q, J=7.0 Hz), 7.92–7.97 (2H, m), 8.33–8.39 (2H, m).

Reference Example 52
6-Methylquinoline 1-oxide

The title compound was obtained from 6-methylquinoline by the method similar to that in Reference Example 47. Yield: 87%.

$^1$H NMR (CDCl$_3$) δ 2.55 (3H, s), 7.22–7.29 (1H, m), 7.56–7.68 (3H, m), 8.47 (1H, d, J=6.0 Hz) 8.64 (1H, d, J=8.8 Hz).

Reference Example 53
7-Methoxy-2-benzofurancarboxylic Acid

A solution of o-vanillin (51 g, 340 mmol), bromomalonic acid diethyl ester (73 g, 310 mmol), and potassium carbonate (82 g, 590 mmol) in 2-butanone (200 mL) was heated under reflux for 3.5 hours. The reaction solution was cooled to room temperature, and then the solvent was distilled off under reduced pressure. The resultant residue was combined with water, and the organic material was extracted with diethyl ether. The extract was washed with brine, dried over magnesium sulfate, and then the solvent was distilled off under reduced pressure. The solution of the resultant residue and potassium hydroxide (43 g, 740 mmol) in ethanol (400 mL) was heated under reflux for 1 hour. The reaction solution was cooled to room temperature, poured into water, and then acidified by the addition of 6 M hydrochloric acid. The organic material was extracted with ethyl acetate, the extract was washed with brine, dried over magnesium sulfate, and then the solvent was distilled off under reduced pressure. The resultant residue was crystallized from diisopropyl ether to obtain the title compound (26 g, yield: 45%).

$^1$NMR (DMSO-d$_6$) δ 3.97 (3H, s), 5.71 (1H, s), 7.09 (1H, dd, J=7.4, 1.5 Hz), 7.27 (1H, t, J=7.8 Hz), 7.33 (1H, dd, J=7.8, 1.5 Hz), 7.65 (1H, s).

Reference Example 54
7-Methoxybenzofuran

A suspension of 7-methoxy-2-benzofurancarboxylic acid (23 g, 120 mmol) and copper (powder, 5.8 g, 92 mmol) in quinoline (70 mL) was heated under reflux for 12 hours. The reaction solution was cooled to room temperature. The insolubles were filtered off, filtrate was poured into water, and acidified by the addition of 2 M hydrochloric acid. The organic material was extracted with ethyl acetate, the extract was washed with brine, dried over magnesium sulfate, and then the solvent was distilled off under reduced pressure. The resultant residue was purified by a column chromatography on a silica gel (hexane/ethyl acetate, 10:1) to obtain the title compound (8.0 g, yield 46%).

$^1$H NMR (CDCl$_3$) δ 4.02 (3H, s), 6.77 (1H, d, J=2.2 Hz), 6.81 (1H, dd, J=6.8, 2.2 Hz), 7.12–7.22 (2H, m), 7.63 (1H, d, J=2.2 Hz).

Reference Example 55
2,3-Dihydro-7-methoxybenzofuran

To a solution of 7-methoxybenzofuran (8.0 g, 54 mmol) in acetic acid (55 mL), 10% palladium on carbon (3.9 g, 49% hydrate) was added, and the mixture was stirred at room temperature for 8 hours under hydrogen atmosphere. The reaction solution was filtered to remove the catalyst, and then the filtrate was concentrated under reduced pressure. The resultant residue was neutralized by the addition of 8 M aqueous solution of sodium hydroxide, and the organic material was extracted with diethyl ether. The extract was washed with brine, dried over magnesium sulfate, and then the solvent was distilled off under reduced pressure to obtain the title compound (7.2 g, yield: 90%).

An oil.

$^1$H NMR (CDCl$_3$) δ 3.17 (2H, t, J=8.6 Hz), 3.82 (3H, s), 4.56 (2H, t, J=8.6 Hz), 6.65–6.72 (1H, m), 6.72–6.78 (2H, m).

Reference Example 56
2,3-Dihydro-7-methoxy-5-benzofurancarboxaldehyde

To N,N-dimethylformamide (8.0 mL), phosphorus oxychloride (8.0 mL, 86 mmol) was added dropwise at 0° C. A solution of 2,3-dihydro-7-methoxybenzofuran (6.7 g, 44 mmol) in N,N-dimethylformamide (26 mL) was added to the reaction mixture and the mixture was stirred at 80° C. for 1 hour. The reaction solution was cooled to room temperature, and then poured into water. The solution was basified by the addition of 8 M aqueous solution of sodium hydroxide, and then extracted with diethyl ether. The extract was washed with brine, dried over magnesium sulfate, and then the solvent was distilled off under reduced pressure. The resultant residue was purified by a column chromatography on a silica gel (hexane/ethyl acetate, 10:1 followed by 5:2) to obtain the title compound (3.5 g, yield: 44%).

$^1$H NMR (CDCl$_3$) δ 3.32 (2H, t, J=8.8 Hz), 3.94 (3H, s), 4.77 (2H, t, J=8.8 Hz), 7.32 (1H, d, J=1.2 Hz), 7.38 (1H, d, J=1.2 Hz), 9.82 (1H, s).

Reference Example 57
2,3-Dihydro-7-methoxy-5-(2-methyl-1-propenyl)benzofuran

To a suspension of 2,3-dihydro-7-methoxy-5-benzofurancarboxaldehyde (3.5 g, 20 mmol) and isopropyltriphenylphosphonium iodide (10 g, 24 mmol) in tetrahydrofuran (60 mL), sodium hydride (60% in oil, 1.1 g, 28 mmol) was added at 0° C., and the mixture was heated under reflux for 2.5 hours. The reaction solution was cooled to room temperature, and poured into water. The organic material was extracted with ethyl acetate, the extract was washed with brine, dried over magnesium sulfate, and then the solvent was distilled off under reduced pressure. The resultant residue was purified by a column chromatography on a silica gel (hexane/ethyl acetate, 50:1 followed by 10:1) to obtain the title compound (2.0 g, yield: 50%).

An oil.

$^1$H NMR (CDCl$_3$) δ 1.86–1.88 (6H, m), 3.22 (2H, t, J=8.6 Hz), 3.86 (3H, s), 4.62 (2H, t, J=8.6 Hz), 6.20 (1H, br s), 6.61 (1H, s), 6.71 (1H, s).

Reference Example 58
3-Iodo-5-methoxy-4-[(2-methyl-2-propenyl)oxy]benzaldehyde

A suspension of 5-iodovanillin (20 g, 72 mmol), 3-chloro-2-methyl-1-propene (13 g, 140 mmol), and potassium carbonate (20 g, 140 mmol) in N,N-dimethylformamide (100 mL) was stirred at 80° C. for 6 hours. The reaction solution was cooled to room temperature, and then the solvent was distilled off under reduced pressure. The residue was combined with water, and the organic material was extracted with ethyl acetate. The extract was washed with brine, dried over magnesium sulfate, and then the solvent was distilled off under reduced pressure. The resultant residue was purified by a column chromatography on a silica gel (hexane/ethyl acetate, 10:1 followed by 5:1) to obtain the title compound (22 g, yield: 93%).

An oil.

$^1$H NMR (CDCl$_3$) δ 1.94 (3H, s), 3.91 (3H, s), 4.54 (2H, s), 5.01 (1H, s), 5.17 (1H, s), 7.41 (1H, d, J=1.8 Hz), 7.87 (1H, d, J=1.8 Hz), 9.83 (1H, s).

Reference Example 59
2,3-Dihydro-7-methoxy-3,3-dimethyl-5-benzofurancarboxaldehyde A suspension of 3-iodo-5-methoxy-4-[(2-methyl-2-propenyl)oxy]benzaldehyde (22 g, 66 mmol), palladium(II) acetate (0.60 g, 27 mmol), potassium carbonate (9.0 g, 65 mmol), sodium formate (4.3 g, 63 mmol), and tetrabutylammonium bromide (18 g, 55 mmol) in N,N-dimethylformamide (300 mL) was stirred at 100° C. for 2.5 hours. The reaction solution was cooled to room temperature, and then the solvent was distilled off under reduced pressure. The residue was combined with water, and the organic material was extracted with ethyl acetate. The extract was washed with brine, dried over magnesium sulfate, and then the solvent was distilled off under reduced pressure. The resultant residue was purified by a column chromatography on a silica gel (hexane/ethyl acetate, 10:1 followed by 2:1) to obtain the title compound (7.7 g, yield: 57%).

An oil.

$^1$H NMR (CDCl$_3$) δ 1.40 (6H, s), 3.95 (3H, s), 4.43 (2H, s), 7.31–7.32 (2H, m), 9.84 (1H, s).

Reference Example 60
2,3-Dihydro-7-methoxy-3,3-dimethyl-5-(2-methyl-1-propenyl)benzofuran The title compound was obtained from 2,3-dihydro-7-methoxy-3,3-dimethyl-5-benzofurancarboxaldehyde and isopropyltriphenylphosphonium iodide by the method similar to that in Reference Example 57. Yield 59%.

An oil.

$^1$H NMR (CDCl$_3$) δ 1.33 (6H, s), 1.87–1.89 (6H, m), 3.87 (3H, s), 4.29 (2H, s), 6.23 (1H, br s), 6.61 (1H, s), 6.62 (1H, s).

Reference Example 61
2,3-Dihydro-7-methoxy-2,2-dimethyl-5-benzofuranmethanol

A solution of 2,3-dihydro-7-methoxy-2,2-dimethyl-5-benzofurancarboxaldehyde (7.5 g, 36 mmol) and sodium borohydride (0.72 g, 19 mmol) in methanol (60 mL) was stirred at 0° C. for 3 hours. The reaction solution was concentrated under reduced pressure, and the resultant residue was combined with water. The solution was acidified by the addition of 1 M hydrochloric acid, and then the organic material was extracted with ethyl acetate. The extract was washed with brine, dried over magnesium sulfate, and then the solvent was distilled off under reduced pressure. The resultant residue was purified by a column chromatography on a silica gel (hexane/ethyl acetate, 5:1 followed by 2:1) to obtain the title compound (5.8 g, yield:77%).

An oil.

$^1$H NMR (CDCl$_3$) δ 1.50 (6H, s), 2.20 (1H, br), 3.01 (2H, s), 3.86 (3H, s), 4.57 (2H, s), 6.76 (2H, s).

Reference Example 62
[(2,3-Dihydro-7-methoxy-2,2-dimethyl-5-benzofuranyl)methyl]triphenylphosphonium Bromide To a solution of 2,3-dihydro-7-methoxy-2,2-dimethyl-5-benzofuranmethanol (5.8 g, 28 mmol) in diethyl ether (90 mL), phosphorus tribromide (0.90 mL, 9.5 mmol) was added dropwise at 0° C. The reaction solution was stirred at 0° C. for 30 minutes, and then poured into water. The organic layer was washed with brine, dried over magnesium sulfate, and then the solvent was distilled off under reduced pressure. The solution of the resultant residue (7.2 g) and triphenylphosphine (7.5 g, 29 mmol) in toluene (70 mL) was stirred at 80° C. for 10 hours. The reaction solution was cooled to room temperature, and precipitated crystals were recovered by filtration and washed with diethyl ether to obtain the title compound (12 g, yield: 84%).

$^1$H NMR (CDCl$_3$) δ 1.45 (6H, s), 2.83 (2H, s), 3.49 (3H, s), 5.33 (2H, d, J=13.6 Hz), 6.50 (1H, s), 6.58 (1H, s), 7.59–7.81 (15H, m).

Reference Example 63
5-(2-Ethyl-1-butenyl)-2,3-dihydro-7-methoxy-2,2-dimethylbenzofuran To a suspension of [(2,3-dihydro-7-methoxy-2,2-dimethyl-5-benzofuranyl)methyl]triphenylphosphonium bromide (5.6 g, 10 mmol) in tetrahydrofuran (50 mL), potassium tert-butoxide (1.3 g, 11 mmol) was added at 0° C. 3-pentanone (2.2 mL, 21 mmol) was added to the reaction mixture and the mixture was heated under reflux for 20 hours. The reaction solution-was cooled to room temperature, and then poured into water. The solution was acidified by the addition of 1 M hydrochloric acid, and then the organic material was extracted with ethyl acetate. The extract was washed with brine, dried over magnesium sulfate, and then the solvent was distilled off under reduced pressure. The resultant residue was purified by a column chromatography on a silica gel (hexane/ethyl acetate, 50:1 followed by 5:1) to obtain the title compound (2.4 g, yield: 87%).

An oil.
$^1$H NMR (CDCl$_3$) δ 1.09 (6H, td, J=7.6, 1.8 Hz), 1.51 (6H, s), 2.12–2.34 (4H, m), 3.02 (2H, s), 3.85 (3H, s), 6.16 (1H, s), 6.61 (1H, s), 6.64 (1H, s).

Reference Example 64
2,3-Dihydro-5-benzofurancarbonitrile

A solution of 2,3-dihydro-5-benzofurancarboxaldehyde (5.00 g, 33.7 mmol) and hydroxylamine hydrochloride (3.52 g, 50.6 mmol) in formic acid (70 mL) was heated under reflux for 2 hours. The reaction mixture-was poured into ice water, and neutralized with potassium hydroxide to recover precipitated crystals. The resultant crystals were dissolved in ethyl acetate, dried over magnesium sulfate, filtered, and concentrated under reduced pressure. The residue was recrystallized from ethyl acetate-hexane to obtain the title compound (3.03 g, yield: 62%).

Melting point: 69–70° C.
$^1$H NMR (CDCl$_3$) δ 3.26 (2H, d, J=8.8 Hz), 4.67 (2H, d, J=8.8 Hz), 6.82 (1H, dd, J=8.8, 1.0 Hz), 7.42–7.46 (2H, m).

Reference Example 65
2,3-Dihydro-7-methoxy-2,2-dimethyl-5-benzofurancarbonitrile A solution of 2,3-dihydro-7-methoxy-2,2-dimethyl-5-benzofurancarboxaldehyde (8.40 g, 40.7 mmol) and hydroxylamine hydrochloride (4.25 g, 61.1 mmol) in formic acid (100 mL) was heated under reflux for 3 hours. The reaction mixture was poured into ice water, neutralized with potassium hydroxide to recover precipitated crystals. The resultant crystals were dissolved in ethyl acetate, dried over magnesium sulfate, filtered, and concentrated under reduced pressure. The residue was subjected to a column chromatography on a silica gel (hexane/ethyl acetate, 5:1) to obtain the title compound (6.73 g, yield: 81%).

Melting point: 73–74° C.
$^1$H NMR (CDCl$_3$) δ 1.54 (6H, s), 3.07 (2H, s), 3.89 (3H, s), 7.00 (1H, br s), 7.12 (1H, br s).

Reference Example 66
4-(Phenylthio)benzonitrile

To a solution of 4-fluorobenzonitrile (5.00 g, 41.3 mmol) in N,N-dimethylformamide (100 mL), thiophenol (4.55 g, 41.3 mol) and potassium carbonate (5.71 g, 41.3 mmol) were added, and the mixture was stirred at 150° C. for 2.5 days under nitrogen atmosphere. The reaction solution was cooled to room temperature, the reaction solvent was concentrated and distilled off under reduced pressure, and the residue was poured into water. The organic material was extracted with ethyl acetate, the extract was washed with brine, dried over magnesium sulfate, filtered, and concentrated under reduced pressure. The residue was subjected to a column chromatography on a silica gel (hexane followed by hexane/ethyl acetate, 20:1) to obtain the title compound (6.03 g, yield: 69%).

An oil.
$^1$H NMR (CDCl$_3$) δ 7.15–7.20 (2H, m), 7.42–7.55 (7H, m).

Reference Example 67
4-(1-Methylethyl)benzonitrile

The title compound was obtained employing 4-(1-methylethyl)benzaldehyde by the method similar to that in Reference Example 65. Yield: 77%.

An oil.
$^1$H NMR (CDCl$_3$) δ 1.26 (6H, d, J=7.0 Hz), 2.89–3.03 (1H, m), 7.00 (2H, ddd, J=8.4, 2.0, 1.6 Hz), 7.12 (2H, ddd, J=8.4, 2.0, 1.6 Hz).

Reference Example 68
5-Methyl-2-thiophene Carbonitrile

The title compound was obtained employing 5-methyl-2-thiophenecarboxaldehyde by the method similar to that in Reference Example 65. Yield: 60%.

An oil.
H NMR (CDCl$_3$) δ 2.46 (3H, s), 6.95 (1H, d, J=5.0 Hz), 7.47 (1H, d, J=5.0 Hz).

Reference Example 69
4-(Trifluoromethoxy)benzonitrile

The title compound was obtained employing 4-(trifluoromethoxy)benzaldehyde by the method similar to that in Reference Example 65. Yield: 71%.

An oil.
$^1$H NMR (CDCl$_3$) δ 7.33 (2H, d, J=8.6 Hz), 7.76 (2H, d, J=8.6 Hz).

Reference Example 70
3,5-Dichloro-4-pyridinecarboxaldehyde

To a solution of diisopropylamine (24.9 mL, 177 mmol) in tetrahydrofuran (150 mL), 1.6 M solution of n-butyllithium/hexane (116 mL, 186 mmol) was added dropwise at −78° C. over 20 minutes under nitrogen atmosphere, and then a solution of 3,5-dichloropyridine (25.0 g, 169 mmol) in tetrahydrofuran (100 mL) was added dropwise over 15 minutes, and the mixture was stirred further for 20 minutes. N,N-dimethylformamide (18.3 mL, 237 mmol) was added to the mixture, and the mixture was stirred at room temperature for 18 hours. The reaction solution was poured into a solution of conc. hydrochloric acid (60 mL) in water (400 mL), and stirred at room temperature for 24 hours. The aqueous layer was separated, and the organic material was extracted with diethyl ether. The extract was washed with brine, dried over sodium sulfate, filtered, and concentrated under reduced pressure. The residue was subjected to a column chromatography on a silica gel (hexane/ethyl acetate, 10:1 followed by 5:1) to obtain the title compound (7.96 g, yield: 27%).
$^1$H NMR CDCl$_3$) δ 8.64 (2H, s), 10.46 (1H, s).

Reference Example 71
3,5-Dichloro-4-pyridinecarbonitrile

The title compound was obtained employing 3,5-dichloro-4-pyridinecarboxaldehyde by the method similar to that in Reference Example 64. Yield: 86%.

Melting point: 114–115° C.
$^1$H NMR (CDCl$_3$) δ 8.69 (2H, s).

Reference Example 72
3-Methyl-2-thiophene Carbonitrile

The title compound was obtained employing 3-methyl-2-thiophenecarboxaldehyde by the method similar to that in Reference Example 65. Yield: 59%.

¹H NMR (CDCl₃) δ 2.55 (3H, d, J=1.0 Hz), 6.78 (1H, dd, J=4.0, 1.0 Hz), 7.44 (1H, d, J=4.0 Hz).

Reference Example 73
4-(Methylsulfinyl)benzonitrile

To a mixture solution of 4-(methylthio)benzonitrile (5.00 g, 33.5 mmol) in methanol (200 mL), tetrahydrofuran (50 mL) and water (50 mL), sodium metaperiodate (7.89 g, 36.9 mmol) was added, and the mixture was heated under reflux for 2 hours. The reaction solution was cooled to room temperature, and then precipitated crystals were recovered by filtration, washed with water, and air-dried to obtain the title compound (4.39 g, yield: 79%).

Melting point: 87–90° C.
¹H NMR (CDCl₃) δ 2.81 (3H, s), 7.89 (2H, dd, J=8.4, 2.0 Hz), 8.07 (2H, dd, J=8.4, 2.0 Hz).

Reference Example 74
4-(Methylsulfonyl)benzonitrile

To a solution of 4-(methylthio)benzonitrile (5.00 g, 33.5 mmol) in dichloromethane (150 mL), m-chloroperbenzoic acid (15.0 g, 73.7 mmol) was added, and the mixture was stirred at 0° C. for 30 minutes, and at room temperature further for 5 hours. The reaction solution was poured into 2 M aqueous solution of sodium hydroxide, and extracted with dichloromethane. The extract was washed with a mixture aqueous solution of sodium hydroxide, sodium thiosulfate, and sodium iodide, and brine, dried over magnesium sulfate, filtered, and concentrated under reduced pressure. The residue was recrystallized from ethyl acetate-hexane to obtain the title compound (4.53 g, yield: 75%).

Melting point: 142–144° C.
¹H NMR (CDCl₃) δ 3.10 (3H, s), 7.90 (2H, d, J=8.8 Hz), 8.10 (2H, d, J=8.8 Hz).

Reference Example 75
3,4,5-Trimethoxybenzonitrile

The title compound was obtained employing 3,4,5-trimethoxybenzaldehyde by the method similar to that in Reference Example 65. Yield: 60%.

Melting point: 93–94° C.
¹H NMR (CDCl₃) δ 3.89 (6H, s), 3.91 (3H, s), 6.87 (2H, s).

Reference Example 76
2,2'-Bipyridyl 1-oxide

To a solution of 2,2'-bipyridyl (25.0 g, 160 mmol) in chloroform (400 mL), m-chloroperbenzoic acid (38.4 g, 160 mmol) was added with cooling in ice, and the mixture was stirred at room temperature for 12 hours. The reaction solution was washed with a 5% aqueous solution of sodium carbonate, and the aqueous layer was extracted with dichloromethane. The combined organic layer was washed with brine, dried over magnesium sulfate, filtered and concentrated under reduced pressure. The residue was subjected to a basic column chromatography on a silica gel (hexane/ethyl acetate 1:1 followed by ethyl acetate), and the precipitated crystals were washed with diethyl ether to obtain the title compound (16.1 g, yield: 58%).

Melting point: 58–60° C.
¹H NMR (CDCl₃) δ 7.45–7.52 (3H, m), 7.89–7.98 (1H, m), 8.09–8.14 (1H, m), 8.35–8.39 (1H, m), 8.73–8.78 (2H, m).

Reference Example 77
1-[2,2'-Bipyridin]-6-yl-1,6-dihydro-6-oxo-3-pyridinecarboxamide To a solution of 6-chloronicotinamide (4.70 g, 30.0 mmol, and 2,2'-bipyridyl-1-oxide (10.3 g, 60.0 mmol) in xylene (90 mL) and acetic acid (18 mL), a 25% solution of hydrogen bromide/acetic acid (12 mL) was added, and the mixture was heated under reflux for 10 hours. The reaction mixture was poured into an aqueous solution of sodium hydroxide, and precipitated crystals were recovered, and air-dried to obtain the title compound (3.20 g, yield: 36%).

¹H NMR (CDCl₃) δ 6.60 (1H, d, J=10.0 Hz), 7.39–7.66 (3H, m), 7.83–8.03 (3H, m), 8.14–8.51 (3H, m), 8.68–8.75 (2H, m).

Reference Example 78
1-[2,2'-Bipyridin]-6-yl-1,6-dihydro-6-oxo-3-pyridinecarbonitrile To a solution of N,N-dimethylformamide (2.04 mL, 26.4 mmol) in acetonitrile (30 mL), oxalyl chloride (2.09 mL, 24.0 mmol) was added dropwise with cooling on ice, and the mixture was stirred at the same temperature for 15 minutes. 1-[2,2'-bipyridin]-6-yl-1,6-dihydro-6-oxo-3-pyridinecarboxamide (3.50 g, 12.0 mmol) was added to the mixture, triethylamine (7.36 mL. 52.8 mmol) was added dropwise to the mixture with cooling in ice, and then the mixture was stirred at room temperature for 24 hours. The reaction solvent was concentrated and distilled off under reduced pressure, and the residue was poured into water. The precipitated crystals were recovered, and dissolved in chloroform. This was dried over sodium sulfate, filtered, and concentrated under reduced pressure. The residue was washed with diethyl ether to obtain the title compound (2.06 g, yield: 63%).

¹H NMR (CDCl₃) δ 6.69 (1H, d, J=9.6 Hz), 7.51 (1H, ddd, J=7.4, 4.8, 1.0 Hz), 7.82 (1H, dd, J=9.6, 2.2 Hz), 7.83 (1H, d, J=7.6 Hz), 7.99 (1H, td, J=7.6, 1.8 Hz), 8.19 (1H, t, J=7.6 Hz), 8.42 (1H, d, J=7.6 Hz), 8.49 (1H, d, J=7.6 Hz), 8.74 (1H, dd, J=4.8, 0.6 Hz), 8.97 (1H, d, J=2.2 Hz).

Reference Example 79
1,6-Dihydro-1-(8-methyl-2-quinolinyl)-6-oxo-3-pyridinecarbonitrile To a solution of 6-chloronicotinamide (5.90 g, 37.7 mmol) and 8-methylquinoline 1-oxide (9.00 g, 56.5 mmol) in xylene (90 mL) and acetic acid (18 mL), a 25% solution of hydrogen bromide/acetic acid (12 mL) was added, and the mixture was heated under reflux for 6 hours. The reaction mixture was poured into an aqueous solution of sodium hydroxide and a precipitated crystals were recovered, and air-dried to obtain 1,6-dihydro-1-(8-methyl-2-quinolinyl)-6-oxo-3-pyridinecarboxamide (9.03 g, yield: 86%).

To a solution of N,N-dimethylformamide (7.48 mL 96.6 mmol) in acetonitrile (200 mL), oxalyl chloride was then added dropwise with cooling in ice, and the mixture was stirred at the same temperature for 15 minutes. 1,6-dihydro-1-(8-methyl-2-quinolyl)-6-oxo-3-pyridinecarboxamide (9.00 g, 32.2 mmol) was added to the mixture, and then triethylamine (26.9 mL, 193 mmol) was added dropwise to the mixture with cooling in ice, and the mixture was stirred at room temperature for 20 hours. The reaction solvent was concentrated and distilled off under reduced pressure, and the residue was poured into an aqueous solution of sodium hydroxide. The organic material was extracted with ethyl acetate and chloroform, washed with brine, dried over sodium sulfate, filtered, and concentrated under reduced pressure. The residue was subjected to a column chromatography on a basic silica gel (hexane/ethyl acetate, 2:1), and precipitated crystals were washed with diethyl ether to obtain the title compound (2.04 g, yield: 25%).

Melting point 269–271° C.
¹H NMR (CDCl₃) δ 2.73 (3H, s), 6.70 (1H, dd, J=9.6, 0.6 Hz), 7.62 (1H, dd, J=7.6, 7.0 Hz), 7.73 (1H, d, J=7.0 Hz), 7.84 (1H, d, J=8.8 Hz), 7.84 (1H, dd, J=9.6, 2.6 Hz), 7.93 (1H, d, J=7.6 Hz), 8.55 (1H, d, J=8.8 Hz), 8.93 (1H, d, J=2.6 Hz).

Reference Example 80
1,6-Dihydro-1-(4-methyl-2-pyridinyl)-6-oxo-3-pyridinecarboxamide To a solution of 6-chloronicotinamide (6.68 g, 42.7 mmol) and 4-methylpyridine 1-oxide (9.32 g, 85.4 mmol) in xylene (120 mL) and acetic acid (25 mL), a 25% solution of hydrogen bromide/acetic acid (15 mL) was added, and the mixture was heated under reflux for 3 hours. The reaction mixture was poured into an aqueous solution of sodium hydroxide, and precipitated crystals were recovered by filtration, and air-dried to obtain the title compound (5.14 g, yield: 56%).

$^1$H NMR (CDCl$_3$) δ 2.42 (3H, s), 6.55 (1H, d, J=9.4 Hz), 7.33 (1H, br s), 7.36–7.40 (1H, m), 7.61–7.62 (1H, m), 7.86 (1H, br s), 7.96 (1H, dd, J=9.4, 2.6 Hz), 8.49 (1H, d, J=2.6 Hz), 8.51 (1H, s).

Reference Example 81
1,6-Dihydro-1-(4-methyl-2-pyridinyl)-6-oxo-3-pyridinecarbonitrile To a solution of N,N-dimethylformamide (2.30 mL, 29.7 mmol) in acetonitrile (70 mL), oxalyl chloride (2.36 mL, 27.0 mmol) was added dropwise with cooling in ice, and the mixture was stirred at the same temperature for 15 minutes. 1,6-dihydro-1-(4-methyl-2-pyridinyl)-6-oxo-3-pyridinecarboxamide (2.88 g, 13.5 mmol) was added to the mixture, triethylamine (4.14 mL, 29.7 mmol) was added dropwise to the mixture with cooling in ice, and then the mixture was stirred at room temperature for 12 hours. The reaction solvent was concentrated and distilled off under reduced pressure, and the residue was poured into an aqueous solution of sodium hydroxide. The organic material was extracted with ethyl acetate, washed with brine, dried over sodium sulfate, filtered, and concentrated under reduced pressure. The residue was subjected to a column chromatography on a basic silica gel (hexane/ethyl acetate, 2:1 followed by 1:1), and precipitated crystals were washed with diethyl ether to obtain the title compound (2.02 g, yield: 71%).

Melting point: 166–168° C.
$^1$H NMR (CDCl$_3$) δ 2.47 (3H, s), 6.68 (1H, dd, J=9.4, 0.8 Hz), 7.20–7.24 (1H, m), 7.45 (1H, dd, J=9.4, 2.6 Hz), 7.71–7.73 (1H, m), 8.43 (1H, d, J=5.0 Hz), 8.46 (1H, d, J=0.8 Hz).

Reference Example 82
2-Chlorocyclopentanone

To a solution of cyclopentanone (84.1 g, 1.00 mol) and N-chlorosuccinimide (134 g, 1.00 mol) in carbon tetrachloride (250 mL), 2,2'-azobis(isobutyronitrile) (1.64 g, 0.10 mol) was added, and the mixture was stirred under a light irradiation for 6 hours. The reaction solution was filtered, and concentrated under reduced pressure. The residue was distilled under reduced pressure to obtain the title compound (59.2 g, yield: 50%).

Boiling point: 80–86° C./1.7 kPa (13 mmHg).
$^1$H NMR (CDCl$_3$) δ 1.84–2.72 (6H, m), 4.12 (1H, t, J=6.8 Hz).

Reference Example 83
2-(2-Methoxyphenoxy)cyclopentanone

To a solution of guaiacol (31.0 g, 250 mmol) in N,N-dimethylformamide (400 mL), sodium hydride (60% suspension in oil) (12.0 g, 300 mmol) was added, and the mixture was stirred. at 0° C. for 30 minutes. A solution of 2-chlorocyclopentanone (59.2 g, 499 mmol) in N,N-dimethylformamide (100 mL) was added dropwise to the mixture, and the mixture was stirred at 0° C. further for 1 hour. The reaction solvent was concentrated and distilled off under reduced pressure, and the residue was poured into water. The organic material was extracted with ethyl acetate, the extract was washed with brine, dried over magnesium sulfate, filtered, and concentrated under reduced pressure. The residue was subjected to a column chromatography on a silica gel (hexane/ethyl acetate, 4:1) to obtain the title compound (28.4 g, yield: 55%).

An oil.
$^1$H NMR (CDCl$_3$) δ 1.62–2.51 (6H, m), 3.86 (3H, s), 4.61 (1H, td, J=7.8, 1.4 Hz), 6.84–7.04 (4H, m).

Reference Example 84
1-Methoxy-2-[(2-methylenecyclopentyl)oxy]benzene

To a solution of methyltriphenylphosphonium bromide (103 g, 289 mmol) in tetrahydrofuran (600 mL), potassium tert-butoxide (30.9 g, 275 mmol) was added, and the mixture was stirred at 0° C. for 3 hours. A solution of 2-(2-methoxyphenoxy)cyclopentanone (28.4 g, 138 mmol) in tetrahydrofuran (200 mL) was added dropwise, and the mixture was stirred at 0° C. further for 1 hour. The reaction solution was combined with water, and the organic layer was separated. The aqueous layer was extracted with ethyl acetate, and the combined organic layer was washed with brine, dried over magnesium sulfate, filtered, and concentrated under reduced pressure. The residue was subjected to a column chromatography on a silica gel (hexane/ethyl acetate, 20:1) to obtain the title compound (22.4 g, yield: 79%).

An oil.
$^1$H NMR (CDCl$_3$) δ 1.60–2.55 (6H, m), 3.85 (3H, s), 4.89–4.93 (1H, m), 5.07–5.17 (2H, m), 6.83–7.00 (4H, m).

Reference Example 85
2-(1-Cyclopenten-1-ylmethyl)-6-methoxyphenol

1-Methoxy-2-[(2-methylenecyclopentyl)oxy]benzene (22.4 g, 110 mmol) was dissolved in N,N-diethylaniline (30 mL), and stirred at 180° C. for 3 hours under nitrogen atmosphere. The reaction mixture was cooled with ice, combined with 2 M hydrochloric acid, and extracted with ethyl acetate. The organic layer was washed with brine, dried over magnesium sulfate, filtered, and concentrated under reduced pressure. The residue was subjected to a column chromatography on a silica gel (hexane/ethyl acetate, 50:1) to obtain the title compound (19.3 g, yield: 86%).

An oil.
$^1$H NMR (CDCl$_3$) δ 1.78–1.94 (2H, m), 2.24–2.36 (4H, m), 3.42 (2H, s), 3.88 (3H, s), 5.30–5.32 (1H, m), 5.68 (1H, s), 6.70–6.83 (3H, m).

Reference Example 86
7-Methoxyspiro[benzofuran-2 (3H),1'-cyclopentane]

To a solution of 2-(1-cyclopentan-1-ylmethyl)-6-methoxyphenol (22.4 g, 110 mmol) in methanol (200 mL), conc. sulfuric acid (20 mL) was added dropwise with cooling in ice, and the mixture was heated under reflux for 4 hours. The reaction solvent was concentrated and distilled under reduced pressure, and the residue was poured into ice water. The organic material was extracted with ethyl acetate, washed with brine, dried over magnesium sulfate, filtered, and concentrated under reduced pressure. The residue was subjected to a column chromatography on a silica gel (hexane/ethyl acetate, 50:1) to obtain the title compound (17.0 g, 88%).

An oil.

$^1$H NMR (CDCl$_3$) δ 1.67–2.21 (8H, m), 3.19 (2H, s), 3.86 (3H, s), 6.70–6.80 (3H, m).

Reference Example 87
7-Methoxyspiro[benzofuran-2 (3H), 1'-cyclopentane]-5-carboxaldehyde Phosphorus oxychloride (15.5 mL, 166 mmol) was added dropwise to N,N-dimethylformamide (6.44 mL, 166 mmol), a solution of 7-methoxyspiro[benzofuran-2(3H),1'-cyclopentane] (17.0 g, 83.2 mmol) in N,N-dimethylformamide (30 mL) was added dropwise with cooling in ice, and then the mixture was stirred at 80° C. for 6 hours. The reaction mixture was poured into ice water, neutralized with 8 M aqueous solution of sodium hydroxide, and then extracted with ethyl acetate. The extract was washed with brine, dried over sodium sulfate, filtered, concentrated under reduced pressure. The residue was subjected to a column chromatography on a silica gel (hexane/ethyl acetate, 10:1), and crystallized from diethyl ether-hexane to obtain the title compound (11.0 g, yield: 57%).

Melting point: 54° C.

$^1$H NMR (CDCl$_3$) δ 1.70–2.26 (8H, m), 3.26 (2H, s), 3.93 (3H, s), 7.31–7.34 (2H, m), 9.80 (1H, s).

Reference Example 88
7-Methoxy-5-(2-methyl-1-propenyl)spiro[benzofuran-2 (3H),1'-cyclopentane]

To a suspension of 7-methoxyspiro[benzofuran-2(3H),1'-cyclopentane]-5-carboxaldehyde (10.5 g, 45.2 mmol) and isopropyltriphenylphosphonium iodide (31.4 g, 72.6 mmol) in tetrahydrofuran (150 mL), sodium hydride (60% suspension in oil) (3.26 g, 81.4 mmol) was added, and the mixture was heated under reflux for 1 hour. The reaction mixture was poured into a 10% aqueous solution of ammonium chloride, and extracted twice with ethyl acetate. The combined organic layer was washed with water and brine, dried over magnesium sulfate, filtered, and concentrated under reduced pressure. The residue was subjected to a column chromatography on a silica gel (hexane/ethyl acetate, 20:1) to obtain the title compound (11.0 g, yield: 94%).

An oil.

$^1$H NMR (CDCl$_3$) δ 1.54–2.20 (14H, s), 3.17 (2H, s), 3.85 (3H, s), 6.20 (1H, s), 6.60 (1H, s), 6.66 (1H, s).

Reference Example 89
2-Bromo-3-pentanone

To a solution of 3-pentanone (172 g, 2.00 mol) in methanol (500 mL), bromine (51.1 mL, 1.00 mol) was added dropwise, and the mixture was stirred at room temperature for 3 hours. The reaction solvent was concentrated and distilled off under reduced pressure, and the residue was treated with an aqueous solution of sodium thiosulfate, and extracted with ethyl acetate. The extract was washed with brine, dried over magnesium sulfate, filtered, and concentrated under reduced pressure. The residue was distilled under reduced pressure to obtain the title compound (72.3 g, yield: 44%).

Boiling point: 65° C./3.3 kPa (25 mmHg)

$^1$H NMR (CDCl$_3$) δ 1.12 (3H, t, J=7.4 Hz), 1.75 (3H, t, J=7.0 Hz), 2.61 (1H, dq, J=18.0, 7.4 Hz), 2.87 (1H, dq, J=18.0, 7.4 Hz), 4.42 (1H, q, J=7.0 Hz).

Reference Example 90
2-(2-Methoxyphenoxy)-3-pentanone

The title compound was obtained from 2-bromo-3-pentanone by the method similar to that in Reference Example 83.

Quantitative.

An oil.

$^1$H NMR (CDCl$_3$) δ 1.07 (3H, t, J=7.4 Hz), 1.51 (3H, t, J=6.8 Hz), 2.59 (1H, dq, J=18.0, 7.4 Hz), 2.75 (1H, dq, J=18.0, 7.4 Hz), 3.87 (3H, s), 4.62 (1H, q, J=6.8 Hz), 6.75–6.99 (4H, m).

Reference Example 91
1-Methoxy-2-(1-methyl-2-methylenebutoxy)benzene.

The title compound was obtained from 2-(2-methoxyphenoxy)-3-pentanone by the method similar to that in Reference Example 84. Yield: 79%.

An oil.

$^1$H NMR (CDCl$_3$) δ 1.07 (3H, t, J=7.2 Hz), 1.50 (3H, t, J=6.6 Hz), 2.13 (2H, q, J=7.2 Hz), 3.86 (3H, s), 4.74 (1H, q, J=6.6 Hz), 4.88 (1H, d, J=1.4 Hz), 5.07–5.08 (1H, m), 6.78–6.91 (4H, m).

Reference Example 92
2-(2-Ethyl-2-butenyl)-6-methoxyphenol

The title compound was obtained from 1-methoxy-2-(1-methyl-2-methylenebutoxy)benzene by the method similar to that in Reference Example 85. Yield: 97%.

An oil.

$^1$H NMR (CDCl$_3$) δ 0.98 (3H, t, J=7.6 Hz), 1.61 (3H, d, J=7.0 Hz), 2.04 (2H, q, J=7.6 Hz), 3.35 (2H, s), 3.88 (3H, s), 5.19 (1H, q, J=7.0 Hz), 5.68 (1H, s), 6.69–6.83 (3H, m).

Reference Example 93
2,2-Diethyl-2,3-dihydro-7-methoxybenzofuran

The title compound was obtained from 2-(2-ethyl-2-butenyl)-6-methoxyphenol by the method similar to that in Reference Example 86. Yield: 86%.

An oil.

$^1$H NMR (CDCl$_3$) δ 0.94 (6H, t, J=7.4 Hz), 1.78 (4H, q, J=7.4 Hz), 3.01 (2H, s), 3.87 (3H, s), 6.71–6.78 (3H, m).

Reference Example 94
2,2-Diethyl-2,3-dihydro-7-methoxy-5-benzofurancarboxaldehyde The title compound was obtained from 2,2-diethyl-2,3-dihydro-7-methoxybenzofuran by the method similar to that in Reference Example 87. Yield: 59%.

An oil.

$^1$H NMR (CDCl$_3$) δ 0.95 (6H, t, J=7.4 Hz), 1.82 (4H, q, J=7.4 Hz), 3.08 (2H, s), 3.93 (3H, s), 7.30, (1H, br s), 7.31 (1H, br s), 9.79 (1H, s).

Reference Example 95
2,2-Diethyl-2,3-dihydro-7-methoxy-5-(2-methyl-1-propenyl)benzofuran The title compound was obtained from 2,2-diethyl-2,3-dihydro-7-methoxy-5-benzofurancarboxaldehyde by the method similar to that in Reference Example 88. Quantitative.

An oil.

$^1$H NMR (CDCl$_3$) δ 0.94 (6H, t, J=7.4 Hz), 1.77 (4H, q, J=7.4 Hz), 1.87 (6H, s), 2.99 (2H, s), 3.85 (3H, s), 6.19 (1H, s), 6.59 (1H, s), 6.64 (1H, s).

Reference Example 96
2,3-Dihydro-7-methoxy-α,α,2,2-tetramethyl-5-benzofuranethanamine A mixture of 3-(2,3-dihydro-7-methoxy-2,2-dimethyl-5-benzofuranyl)-2,2-dimethylpropionic acid (5.0 g, 18 mmol), diphenylphosphoryl azide (5.6 g, 20 mmol), and triethylamine (2.8 mL, 20 mmol) in toluene (100 mL) was heated under reflux for 1 hour. The reaction solution was cooled to room temperature, and then washed with water and brine, dried over magnesium sulfate, and then the solvent was distilled off under reduced pressure. 6 M Hydrochloric acid (30 mL) was added to the resultant residue and the mixture was stirred at 60° C. for 1.5 hours. The reaction solution was cooled to room temperature, basified by the addition of 8 M aqueous solution of sodium hydroxide, and then the organic material was extracted with diethyl ether. The extract was washed with brine, dried over magnesium sulfate, and then the solvent was distilled off under reduced pressure to obtain the title compound (3.6 g, yield: 80%).

An oil.

$^1$H NMR (CDCl$_3$) δ 1.13 (6H, s), 1.51 (6H, s), 2.58 (2H, s), 3.02 (2H, s), 3.86 (3H, s), 6.55 (1H, s), 6.59 (1H, s).

Reference Example 97

6-Chloro-N-[2-(2,3-dihydro-7-methoxy-2,2-dimethyl-5-benzofuranyl)-1,1-dimethylethyl]-3-pyridinecarboxamide A mixture of 2,3-dihydro-7-methoxy-α,α,2,2-tetramethyl-5-benzofuranethanamine (3.7 g, 15 mmol), 6-chloronicotinoyl chloride hydrochloride-(3.9 g, 18 mmol), sodium hydrogen carbonate (4.7 g, 56 mmol), tetrahydrofuran (30 mL), toluene (60 mL) and water (30 mL) was stirred at room temperature for 14.5 hours. The reaction solution was concentrated under reduced pressure, and the residue was combined with water. The organic material was extracted with ethyl acetate. The extract was washed with brine, dried over magnesium sulfate, and then the solvent was distilled off under reduced pressure. The resultant residue was recrystallized from ethyl acetate-hexane to obtain the title compound (4.9 g, yield: 86%).

Melting point: 118–119° C.

$^1$H NMR (CDCl$_3$) δ 1.48 (6H, s), 1.49 (6H, s), 2.97 (2H, s), 3.04 (2H, s), 3.73 (3H, s), 5.72 (1H, br), 6.51 (1H, s), 6.56 (1H, s), 7.38 (1H, d, J=8.4 Hz), 7.96 (1H, dd, J=8.4, 2.1 Hz), 8.62 (1H, d, J=2.1 Hz).

Reference Example 98

N-[2-(2,3-Dihydro-7-methoxy-2,2-dimethyl-5-benzofuranyl)-1,1-dimethylethyl]-1,6-dihydro-1-(6-methyl-2-quinolinyl)-6-oxo-3-pyridinecarboxamide A solution of 6-chloro-N-[2-(2,3-dihydro-7-methoxy-2,2-dimethyl-5-benzofuranyl)-1,1-dimethylethyl]-3-pyridinecarboxamide (1.5 g, 3.9 mmol), 6-methylquinoline 1-oxide (3.9 g, 24 mmol), a 25% solution of hydrogen bromide/acetic acid (1.6 mL), and acetic acid (2.4 mL) in toluene (13 mL) was heated under reflux for 19.5 hours. The reaction solution was cooled to room temperature, and then the reaction mixture was poured into water. The mixture was weak-alkalized by the addition of 8 M aqueous solution of sodium hydroxide, and then the organic material was extracted with ethyl acetate. The extract was washed with brine, and then dried over sodium sulfate, and the solvent was distilled off under reduced pressure. The resultant residue was purified by a column chromatography on a basic silica gel (hexane/chloroform/ethyl acetate, 1:1:1 followed by 1:1:2), and crystallized from hexane-diisopropyl ether to obtain the title compound (1.2 g, yield: 59%).

Melting point: 192–193° C.

$^1$H NMR (CDCl$_3$) δ 1.45 (12H, s), 2.57 (3H, s), 2.92 (2H, s), 3.03 (2H, s), 3.75 (3H, s), 5.60 (1H, br s), 6.54 (2H, d, J=7.4 Hz), 6.65 (1H, d, J=9.4 Hz), 7.58–7.70 (3H, m), 7.86 (1H, d, J=8.8 Hz), 7.97 (1H, d, J=8.4 Hz), 8.20 (1H, d, J=8.8 Hz), 8.51 (1H, d, J=2.2 Hz).

Reference Example 99

5-(3-Cyanophenyl)-1H-tetrazole-1-acetic Acid Methyl Ester 3-(1H-tetrazol-5-yl)benzonitrile (1.77 g, 10 mmol) was dissolved in N,N-dimethylformamide (20 mL). Sodium carbonate (1.65 g, 12 mmol) and methyl bromoacetate (1.84 g, 12 mmol) were added to the mixture with cooling in ice. The reaction mixture was allowed to warm to room temperature, and stirred for 1 hour. The reaction mixture was combined with ice water, and extracted twice with ethyl acetate. The extract was washed with an aqueous solution of sodium chloride, dried over magnesium sulfate, filtered, and concentrated under reduced pressure. The residue was subjected to a column chromatography on a silica gel eluted with hexane/ethyl acetate (2:1), and the objective fraction was collected to concentrate, and recrystallized from hexane to obtain the title compound (1.98 g, yield: 81%).

Melting point: 67–69° C.

$^1$H NMR (CDCl$_3$) δ 3.86 (3H, s), 5.51 (2H, s), 7.5–8.6 (4H, m).

Reference Example 100

2,3-Dihydro-7-methoxy-2,2-dimethyl-5-(2-nitroethenyl)benzofuran

A mixture of 2,3-dihydro-7-methoxy-2,2-dimethyl-5-benzofurancarboxaldehyde (17.5 g, 84.9 mmol), and ammonium acetate (4.36 g, 56.6 mmol) in nitromethane (85 mL) was stirred at 100–105° C. for 1.5 hours. The reaction mixture was dissolved in ethyl acetate, washed with water and brine, dried over magnesium sulfate, filtered, and concentrated under reduced pressure. The residue was recrystallized from ethyl acetate-diisopropyl ether to obtain the title compound (17.1 g, yield: 81%).

Melting point: 154–156° C.

$^1$H NMR (CDCl$_3$) δ 1.55 (6H, s), 3.08 (2H, s), 3.92 (3H, s), 6.91 (1H, s), 7.04 (1H, s), 7.51 (1H, d, J=13.6 Hz), 7.96 (1H, d, J=13.6 Hz).

Reference Example 101

N-[2-(2,3-Dihydro-7-methoxy-2,2-dimethyl-5-benzofuranyl)ethyl]benzamide

To a solution of 2,3-dihydro-7-methoxy-2.2-dimethyl-5-(2-nitroethenyl)benzofuran (16.3 g, 65.4 mmol) in tetrahydrofuran (250 mL), lithium aluminum hydride (7.44 g, 0.196 mol) was added in portions, and the mixture was heated under reflux for 4 hours. The reaction mixture-was cooled with ice, combined with Hyflo Super-Cell (trade name) (37 g), and ethyl acetate (100 mL) was added dropwise, followed by water (15 mL). The resultant mixture was stirred at the same temperature for 10 minutes, filtered, and concentrated under reduced pressure to obtain the mixture (12.9 g) containing 2,3-dihydro-7-methoxy-2,2-dimethyl-5-benzofuranethanamine. 2.22 g of this material was dissolved in tetrahydrofuran (10 mL). A solution of sodium carbonate (1.38 g, 13.0 mmol) in water (10 mL) was added to the reaction mixture, and then benzoyl chloride (1.28 mL, 11.0 mmol) was added dropwise to the mixture with cooling in ice. The mixture was stirred at the same temperature for 20 minutes. The reaction mixture was combined with water, and extracted twice with ethyl acetate. The combined organic layer was washed with brine, dried over sodium sulfate, filtered, and concentrated under reduced pressure. The residue was subjected to a column chromatography on a silica gel (hexane/ethyl acetate, 10:1 followed by 3:1), and recrystallized from ethyl acetate-hexane to obtain the title compound (929 mg, yield 25%).

Melting point: 137–138° C.

$^1$H NMR (CDCl$_3$) δ 1.51 (6H, s), 2.86 (2H, t, J=6.8 Hz), 3.01 (2H, s), 3.61–3.75 (2H, m), 3.83. (3H, s), 6.08–6.22 (1H, m), 6.59 (1H, s), 6.65 (1H, s), 7.35–7.55 (3H, m), 7.67–7.75 (2H, m).

Reference Example 102
2,3-Dihydro-7-methoxy-2,2-dimethyl-5-(2-nitro-1-propenyl)benzofuran A solution of 2,3-dihydro-7-methoxy-2,2-dimethyl-5-benzofurancarboxaldehyde (20.0 g, 97.0 mmol), nitroethane (7.70 mL, 107 mmol), piperidine (2.00 mL, 20.2 mmol) and acetic acid (5.60 mL, 97.8 mmol) in toluene (37 mL) was heated under reflux for 5 hours using Dean-Stark water separator. The reaction solution was cooled to room temperature. The mixture was separated into water and ethyl acetate. The organic layer was washed with brine, dried over magnesium sulfate, and then distilled off under reduced pressure. The resultant residue was crystallized from diisopropyl ether to obtain the title compound (20.9 g, yield: 82%).

Melting point: 120–121° C.
$^1$H NMR (CDCl$_3$) δ 1.55 (6H, s), 2.50 (3H, s), 3.09 (2H, s), 3.91 (3H, s), 6.85 (1H, s), 6.96 (1H, s), 8.08 (1H, s).

Reference Example 103
2,3-Dihydro-7-methoxy-α,2,2-trimethyl-5-benzofuranethanamine To a solution of 2,3-dihydro-7-methoxy-2,2-dimethyl-5-(2-nitro-1-propenyl)benzofuran (10.9 g, 41.4 mmol) in tetrahydrofuran (150 mL), lithium aluminum hydride (3.35 g, 88.3 mmol) was added at 0° C. in portions. The reaction solution was stirred at 0° C. for 15 minutes, and heated under reflux for 1 hour. The reaction solution was cooled with ice, water was added in portions, and the insolubles were filtered off. The filtrate was dried over sodium sulfate, and then the solvent was distilled off under reduced pressure to obtain the title compound (9.00 g, yield: 92%).

An oil.
$^1$H NMR (CDCl$_3$) δ 1.12 (3H, d, J=6.4 Hz), 1.50 (6H, s), 2.40 (1H, dd, J=13.2, 8.4 Hz), 2.66 (1H, dd, J=13.2, 5.2 Hz), 3.01 (2H, s), 3.07–3.17 (1H, m), 3.85 (3H, s), 6.56 (1H, s), 6.59 (1H, s).

Reference Example 104
N-[2-(2,3-dihydro-7-methoxy-2,2-dimethyl-5-benzofuranyl)-1-methylethyl]benzamide To a solution of 2,3-dihydro-7-methoxy-α,2,2-trimethyl-5-benzofuranethanamine (3.00 g, 12.7 mmol) and triethylamine (2.10 mL, 15.1 mmol) in tetrahydrofuran (50.0 mL) and ethyl acetate (50.0 mL), benzoyl chloride (1.50 mL, 12.9 mmol) was added dropwise at 0° C. The reaction solution was stirred at room temperature for 4 hours, and then the solvent was distilled off. The resultant residue was combined with water, and the organic material was extracted with ethyl acetate. The extract was washed with brine, dried over magnesium sulfate, and then the solvent was distilled off under reduced pressure. The resultant residue was recrystallized from ethyl acetate-isopropyl ether to obtain the title compound (1.94 g, yield: 45%).

Melting point: 141–142° C.
$^1$H NMR (CDCl$_3$) δ 1.24 (3H, d, J=6.6 Hz), 1.50 (6H, s), 2.76 (1H, dd, J=13.4, 7.0 Hz), 2.88 (1H, dd, J=13.8, 5.6 Hz), 3.00 (2H, s), 3.80 (3H, s), 4.34–4.48 (1H, m), 5.93 (1H, br), 6.58 (1H, s), 6.63 (1H, s), 7.37–7.53 (3H, m), 7.71 (2H, dd, J=8.6, 2.0 Hz).

Reference Example 105
N-[2-(2,3-dihydro-7-methoxy-2,2-dimethyl-5-benzofuranyl)-1-methylethyl]-4-pyridinecarboxamide The title compound was obtained from 2,3-dihydro-7-methoxy-α,2,2-trimethyl-5-benzofuranethanamine and isonicotinoyl chloride hydrochloride by the method similar to that in Reference Example 97. Yield: 75%.

Melting point 159–160° C. (ethyl acetate-diisopropyl ether)
$^1$H NMR (CDCl$_3$) δ 1.26 (3H, d, J=6.6 Hz), 1.51 (6H, s), 2.71–2.93 (2H, m), 3.00 (2H, s), 3.82 (3H, s), 4.34–4.47 (1H, m), 6.00 (1H, br d, J=8.4 Hz), 6.56 (1H, s), 6.61 (1H, s), 7.52–7.55 (2H, m), 8.71–8.74 (2H, m).

Reference Example 106
2-(Benzoylamino)-3-(2,3-dihydro-7-methoxy-2,2-dimethyl-5-benzofuranyl)-2-propenoic Acid Methyl Ester A suspension of 2,3-dihydro-7-methoxy-2,2-dimethyl-5-benzofurancarboxaldehyde (12.8 g, 62.1 mmol), hippuric acid (12.2 g, 68.1 mmol) and sodium acetate (5.60 g, 68.3 mmol) in acetic anhydride (65 mL) was stirred at 100° C. for 1.5 hours. The reaction mixture was cooled to room temperature, combined with diethyl ether, and crystals were recovered by filtration to obtain a mixture (16.9 g) containing 4-[(2,3-dihydro-7-methoxy-2,2-dimethyl-5-benzofuranyl)methylene]-2-phenyl-5 (4H)-oxazolone. The mother liquor was concentrated again, and crystals were washed with diisopropyl ether to obtain the same mixture (3.72 g). These were suspended in methanol (100 mL). Sodium carbonate (0.20 g, 1.9 mmol) was added to the suspension and the mixture heated under reflux for 3 hours. The reaction mixture was concentrated under reduced pressure and the residue was partitioned between ethyl acetate and water. The aqueous layer was separated, the organic layer was washed and concentrated under reduced pressure. The residue was crystallized from methanol-diisopropyl ether to obtain the title compound (10.5 g, yield: 44%).

Melting point: 184–186° C.
$^1$H NMR (CDCl$_3$) δ 1.50 (6H, s), 2.99 (2H, s), 3.66 (3H, s), 3.85 (3H, s), 7.00 (2H, s), 7.43–7.64 (4H, m), 7.67 (1H, br s), 7.86–7.95 (2H, m).

Reference Example 107
α-(Benzoylamino)-2,3-dihydro-7-methoxy-2,2-dimethyl-5-benzofuranpropanoic Acid Methyl Ester To a solution of 2-(benzoylamino)-3-(2,3-dihydro-7-methoxy-2,2-dimethyl-5-benzofuranyl)-2-propenoic acid methyl ester (11.5 g, 30.2 mmol) in tetrahydrofuran (100 mL), 10% palladium on carbon (50% hydrate) (1.2 g) was added, and the mixture was stirred at 50° C. for 4 hours under hydrogen atmosphere. The catalyst was filtered off and filtrate was concentrated under reduced pressure. The resultant crystals were washed with diisopropyl ether to obtain the title compound (10.1 g, yield: 87%).

Melting point: 160–162° C.
$^1$H NMR (CDCl$_3$) δ 1.50 (6H, s), 2.98 (2H, s), 3.15 (1H, dd, J=13.9, 5.1 Hz), 3.23 (1H, dd, J=13.9, 5.9 Hz), 3.75 (3H, s), 3.78 (3H, s), 5.04 (1H, dt, J=7.5, 5.5 Hz), 6.48 (1H, s), 6.53 (1H, s), 6.59 (1H, br d, J=7.5 Hz), 7.36–7.57 (3H, m), 7.71–7.79 (2H, m).

Reference Example 108
2-Amino-5-(4,4,5,5-tetramethyl-1,3,2-dioxaborolane-2-yl)benzoic Acid Methyl Ester To a solution of methyl 5-iodoanthranilate (2.87 g, 10.0 mmol) and triethylamine (4.2 mL. 30 mmol) in 1,4-dioxane (20 mL), [1,1'-bis(diphenylphosphino)ferrocene] dichloropalladium (II) dichloromethane complex (82 mg, 0.10 mmol) was added and 4,4,5,5-tetramethyl-1,3,2-dioxaborolane (3.7 mL, 25 mmol) was added dropwise. The resultant mixture was stirred at 80° C. for 14 hours under nitrogen atmosphere. The reaction mixture was combined with water, and extracted twice with ethyl acetate. The combined organic layer was washed with water and brine, filtered through a silica gel (eluting with ethyl acetate), and concentrated under reduced pressure. The residue was subjected to a column chromatography on a silica gel (hexane/ethyl acetate, 5:1), and recrystallized from ethyl acetate-hexane to obtain the title compound (1.45 9 yield: 52%).

Melting point: 110–112° C.

$^1$H NMR (CDCl$_3$) δ 1.33 (12H, s), 3.86 (3H, s), 5.96 (2H, br s), 6.63 (1H, d, J=8.3 Hz), 7.67 (1H, dd, J=8.3, 1.5 Hz), 8.33 (1H, d, J=1.5 Hz).

Reference Example 109

4-(4,4,5,5-Tetramethyl-1,3,2-dioxaborolane-2-yl)benzoic Acid Ethyl Ester

To a solution of ethyl 4-iodobenzoate (2.76 g, 10.0 mmol) and triethylamine (4.2 mL, 30 mmol) in 1,4-dioxane (20 mL), [1,1'-bis(diphenylphosphino)ferrocene]dichloropalladium(II) dichloromethane complex (82 mg, 0.10 mmol) was added, and 4,4,5,5-tetramethyl-1,3,2-dioxaborolane (3.2 mL, 22 mmol) was added dropwise. The resultant mixture was stirred at 80° C. for 14 hours under nitrogen atmosphere, and at 100° C. for 3 hours. The reaction mixture was combined with water, and extracted twice with ethyl acetate. The combined organic layer was washed with water and brine, dried through sodium sulfate-silica gel (eluting with ethyl acetate), and concentrated under reduced pressure. The residue was subjected to a column chromatography on a silica gel (hexane/ethyl acetate, 20:1) to obtain the title compound (2.26 g, yield: 82%).

An oil.

$^1$H NMR (CDCl$_3$) δ 1.36 (12H, s), 1.40 (3H, t, J=7.1 Hz), 4.39 (2H, q, J=7.1 Hz), 7.86 (2H, d, J=8.4 Hz), 8.03 (2H, d, J=8.4 Hz).

Reference Example 110

β-(Benzoylamino)-2,3-dihydro-7-methoxy-2,2-dimethyl-5-benzofuranpropanol

To a suspension of α-(benzoylamino)-2,3-dihydro-7-methoxy-2,2-dimethyl-5-benzofuranpropanoic acid methyl ester (3.84 g, 10.0 mmol) in tetrahydrofuran (30 mL), sodium borohydride (90%) (1.26 g, 30 mmol) was added. Methanol (5 mL) was added dropwise to the resultant mixture while heating under reflux over 30 minutes, and then the mixture was heated under reflux for 5 minutes. The reaction mixture was allowed to cool, combined with water, and extracted twice with ethyl acetate. The combined organic layer was washed twice with water and concentrated under reduced pressure. The residue was recrystallized from methanol-diisopropyl ether to obtain the title compound (2.65 g, yield: 75%).

Melting point: 155–158° C.

$^1$H NMR (CDCl$_3$) δ 1.50 (6H, s), 2.91 (2H, d, J=7.2 Hz), 3.00 (2H, s), 3.66–3.87 (2H, m), 3.82 (3H, s), 4.20–4.38 (1H, m), 6.37–6.48 (1H, m), 6.63 (1H, s), 6.67 (1H, s), 7.35–7.55 (3H, m), 7.65–7.73 (2H, m).

Reference Example 111

2-(Benzoylamino)-3-(2,3-dihydro-7-methoxy-2,2-dimethyl-5-benzofuranyl)propyl Acetate To a suspension of β-(Benzoylamino)-2,3-dihydro-7-methoxy-2,2-dimethyl-5-benzofuranpropanol (3.13 g, 8.81 mmol) and 4-(dimethylamino)pyridine (108 mg, 0.884 mmol) in tetrahydrofuran (30 mL), triethylamine (1.84 mL, 13.2 mmol) and acetic anhydride (1.16 mL, 12.3 mmol) was added dropwise, and the mixture was stirred at room temperature for 20 minutes. The reaction mixture was combined with water and extracted twice with ethyl acetate. The combined organic layer was washed twice with water and concentrated under reduced pressure. The residue was recrystallized from methanol-diisopropyl ether to obtain the title compound (3.26 g, yield: 93%).

Melting point: 141–142° C.

$^1$H NMR (CDCl$_3$) δ 1.50 (6H, s), 2.11 (3H, s), 2.79 (1H, dd, J=13.7, 8.3 Hz), 2.93–3.05 (1H, m), 3.00 (2H, s), 3.82 (3H, s), 4.15 (1H, dd, J=11.4, 4.1 Hz), 4.28 (1H, dd, J=11.4, 6.2 Hz), 4.47–4.64 (1H, m), 6.43 (1H, br d, J=8.4 Hz), 6.61 (1H, s), 6.64 (1H, s), 7.38–7.57 (3H, m), 7.70–7.78 (2H, m).

Reference Example 112

N-[3'-(1,2,3,4,8,9-Hexahydro-6-methoxy-3,3,8,8-tetramethylfuro[2,3-h]isoquinolin-1-yl)[1,1'-biphenyl]-3-yl]acetamide The title compound was obtained from N-[3'-(3,4,8,9-tetrahydro-6-methoxy-3,3,8,8-tetramethylfuro[2,3-h]isoquinolin-1-yl)[1,1'-biphenyl]-3-yl]acetamide by the method similar to that in Reference Example 10. Yield: 84%.

Melting point: 162–165° C. (ethyl acetate-hexane)

$^1$H NMR (CDCl$_3$) δ 1.18 (3H, s), 1.21 (3H, s), 1.25 (3H, s), 1.34 (3H, s), 1.85 (1H, d, J=15.8 Hz), 2.20 (3H, s), 2.47 (1H, d, J=15.8 Hz), 2.56 (1H, d, J=15.4 Hz), 2.83 (1H, d, J=15.4 Hz), 3.87 (3H, s), 5.00 (1H, s), 6.50 (1H, s), 7.15–7.66 (9H, m).

Reference Example 113

3-Cyano-N-(3,5-dichloro-4-pyridinyl)benzamide

A mixture of 3-cyanobenzoic acid (2.71 g, 18.4 mmol) and thionyl chloride (10 mL) was heated under reflux for 1.5 hours. The reaction solution was concentrated under reduced pressure, and the residue was combined with toluene and concentrated under reduced pressure again. A suspension of 4-amino-3,5-dichloropyridine (2.50 g, 15.3 mmol) in tetrahydrofuran (30 mL) was cooled with ice. Then sodium hydride (66% suspension in oil) (1.34 g, 36.7 mmol) followed by the concentrated residue prepared previously were added to the suspension. The mixture was stirred at room temperature for 2 hours, poured into ice water, and then extracted with ethyl acetate. The extract was washed with water and concentrated under reduced pressure. The residue was recrystallized from ethyl acetate-hexane to obtain the title compound (0.45 g, yield: 11%). The mother liquor was concentrated, the residue was subjected to a column chromatography on a basic silica gel (ethyl acetate/methanol, 19:1),and then recrystallized from ethyl acetate-hexane to obtain the additional title compound (0.66 g, yield: 15%).

Melting point: 242–244° C.

$^1$H NMR (CDCl$_3$+DMSO-d$_6$) δ 7.65 (1H, t, J=8.0 Hz), 7.87 (1H, dd, J=1.4, 8.0 Hz), 8.34 (1H, dd, J=1.4, 8.0 Hz), 8.49 (1H, s), 8.58 (2H, s), 10.24 (1H, br s).

Reference Example 114

3-Cyano-N-(3,5-dichloro-1-oxido-4-pyridinyl)benzamide

A suspension of 3-cyano-N-(3,5-dichloro-4-pyridinyl)benzamide (1.06 g, 3.78 mmol) and m-chloroperbenzoic acid (70%) (2.80 g, 11.3 mmol) in ethyl acetate (20 mL) was stirred at 50° C. for 15 hours under nitrogen atmosphere. The reaction mixture was combined with water and an aqueous solution of sodium thiosulfate, and extracted with ethyl acetate. The extract was washed with water and then concentrated under reduced pressure. The residue was subjected to a column chromatography on a silica gel (ethyl acetate/methanol, 49:1 to 23:2) and recrystallized from ethyl acetate-hexane to obtain the title compound (0.88 g, yield: 79%).

Melting point: 234–235° C.

$^1$H NMR (CDCl$_3$+DMSO-d$_6$) δ 7.65 (1H, t, J=8.0 Hz), 7.87 (1H, d, J=8.0 Hz), 8.26 (2H, s), 8.32 (1H, d, J=8.0 Hz), 8.47 (1H, s), 10.16 (1H, br s).

Reference Example 115
1-(7-Ethoxy-2,3-dihydro-2,2-dimethyl-5-benzofuranyl)-2-methyl-1-propanol A solution of 7-ethoxy-2,3-dihydro-2,2-dimethyl-5-benzofurancarboxaldehyde (30.0 g, 0.136 mol) in tetrahydrofuran (50 mL) was cooled with ice, to this a suspension of the Grignard reagent prepared from 2-bromopropane (25.1 g, 0.204 mol) and magnesium (4.97 g, 0.204 mol) in tetrahydrofuran (50 mL) was added, and the mixture was stirred at room temperature for 1 hour. The reaction solution was poured into ice water and extracted with ethyl acetate. The extract was, washed with water and concentrated under reduced pressure. The residue was crystallized from ethyl acetate-hexane to obtain the title compound (29.8 g, yield: 83%).

Melting point: 100–101° C.

$^1$H NMR (CDCl$_3$) δ 0.77 (3H, d, J=6.6 Hz), 1.02 (3H, d, J=6.6 Hz), 1.42 (3H, t, J=7.0 Hz), 1.51 (6H, s), 1.77 (1H, d, J=6.6 Hz), 1.80–1.99 (1H, m), 3.00 (2H, s), 4.12 (2H, q, J=7.0 Hz), 4.21 (1H, dd, J=2.8 Hz, 7.2 Hz), 6.70 (2H, s).

Reference Example 116
1-Ethoxy-2-(2-methyl-2-propenyloxy)benzene

A suspension of 2-ethoxyphenol(5.00 g, 36.2 mmol), 3-chloro-2-methyl-1-propene (3.93 mL, 39.8 mmol), potassium carbonate (5.75 g, 41.6 mmol) and potassium iodide (0.60 g, 3.62 mmol) in N,N-dimethylformamide (25 mL) was stirred at 90° C. for 1.5 hours under nitrogen atmosphere. The reaction mixture was allowed to cool to room temperature, combined with water, and then extracted with ethyl acetate. The extract was washed with 1 M aqueous solution of sodium hydroxide and water, and then concentrated under reduced pressure to obtain the title compound (5.90 g, yield: 85%).

An oil.

$^1$H NMR (CDCl$_3$) δ 1.44 (3H, t, J=6.9 Hz), 1.84 (3H, s), 4.09 (2H, q, J=6.9 Hz), 4.50 (2H, s), 4.97 (1H, s), 5.10 (1H, s), 6.88–6.91 (4H, m).

Reference Example 117
2-Ethoxy-6-(2-methyl-2-propenyl)phenol

A solution of 1-ethoxy-2-(2-methyl-2-propenyloxy)benzene (5.80 g, 30.2 mmol) in N,N-diethylaniline (12 mL) was stirred at 205° C. for 3.5 hours under nitrogen atmosphere. The reaction mixture was allowed to cool to room temperature, cooled with ice, combined with 2 M hydrochloric acid (39 mL), and then extracted with ethyl acetate. The extract was washed with water and then concentrated under reduced pressure to obtain the title compound (5.60 g, yield: 97%).

An oil.

$^1$H NMR (CDCl$_3$) δ 1.44 (3H, t, J=7.0 Hz), 1.75 (3H, s), 3.36 (2H, s), 4.10 (2H, q, J=7.0 Hz), 4.69 (1H, s), 4.80 (1H, s), 6.65–6.79 (3H, m).

Reference Example 118
7-Ethoxy-2,3-dihydro-2,2-dimethylbenzofuran

To a solution of 2-ethoxy-6-(2-methyl-2-propenyl)phenol (5.50 g, 28.6 mmol) in toluene (30 mL), boron trifluoride diethyl ether complex (3.99 mL, 31.5 mmol) was added, and the mixture was stirred at 100° C. for 1.5 hours under nitrogen atmosphere. The reaction solution was allowed to cool to room temperature, combined with 1 M aqueous solution of sodium hydroxide (30 mL), and then extracted with hexane. The extract was washed with 1 M aqueous solution of sodium hydroxide and water, and then concentrated under reduced pressure. The residue was subjected to a column chromatography on a silica gel to obtain the title compound (2.90 g, yield: 53%).

An oil.

$^1$H NMR (CDCl$_3$) δ 1.43 (3H, t, J=7.0 Hz), 1.51(6H, s), 3.02 (2H, s), 4.12 (2H, q, J=7.0 Hz), 6.71–6.78 (3H, m).

Reference Example 119
5-Bromo-7-ethoxy-2,3-dihydro-2,2-dimethylbenzofuran

A solution of 7-ethoxy-2,3-dihydro-2,2-dimethylbenzofuran (10.0 g, 52.0 mmol) in toluene (50 mL) was cooled to −40° C., and bromine (8.72 g, 54.6 mmol) was added dropwise. The reaction solution was stirred at the same temperature for 20 minutes, combined with an aqueous solution of sodium thiosulfate, and then extracted with hexane. The extract was washed with water and then concentrated under reduced pressure. The residue was subjected to a column chromatography on a silica gel (hexane/ethyl acetate, 19:1) to obtain the title compound (13.6 g, yield: 96%).

Melting point: 55–58 °C. (pentane)

$^1$H NMR (CDCl$_3$) δ 1.43 (3H, t, J=7.0 Hz), 1.50 (6H, s), 3.00 (2H, s), 4.09 (2H, q, J=7.0 Hz), 6.83–6.85 (1H, m), 6.86–6.88 (1H, m).

Reference Example 120
7-Ethoxy-2,3-dihydro-2,2-dimethyl-5-(2-methyl-2-propenyl)benzofuran A solution of 5-bromo-7-ethoxy-2,3-dihydro-2,2-dimethylbenzofuran (3.60 g, 13.3 mmol) in tetrahydrofuran (30 mL) was cooled to −78° C., a 1.57 M solution of n-butyllithium in hexane (9.30 mL, 14.6 mmol) was added dropwise, and the mixture was stirred at the same temperature for 15 minutes. To this copper (I) iodide (1.39 g, 7.32 mmol) was added, and the mixture was stirred under ice cooling for 15 minutes. After cooling the mixture to −40° C., 3-chloro-2-methyl-1-propene (1.44 mL, 14.6 mmol) was added dropwise, and the mixture was stirred under ice cooling for 15 minutes. The reaction mixture was combined with water and extracted with ethyl acetate. The extract was washed with water and then concentrated under reduced pressure. The residue was subjected to a column chromatography on a silica gel (hexane/ethyl acetate, 19:1) to obtain the title compound (2.34 g, yield: 71%).

An oil.

$^1$H NMR (CDCl$_3$) δ 1.41 (3H, t, J=7.0 Hz), 1.50 (6H, s), 1.68 (3H, s), 2.99 (2H, s), 3.22 (2H, s), 4.11 (2H, q, J=7.0 Hz), 4.73 (1H, s), 4.78 (1H, s), 6.56 (1H, s), 6.58 (1H, s).

Reference Example 121
3-Cyano-N-methylbenzenesulfonamide

To a suspension of methylamine hydrochloride (1.67 g, 24.8mmol) in pyridine (6 mL), 3-cyanobenzenesulfonyl chloride (5.00 g, 24.8 mmol) was added with cooling in ice, and the mixture was stirred at room temperature for 3 hours. The reaction mixture was poured into ice water, acidified with 1 M hydrochloric acid, and extracted twice with ethyl acetate. The combined organic layer was washed with 1 M hydrochloric acid, water and brine, dried over magnesium sulfate, and concentrated under reduced pressure to obtain the title compound (4.49 g, yield: 92%) as crystals.

$^1$H NMR (CDCl$_3$) δ 2.73 (3H, d, J=5.4 Hz), 4.51 (1H, br), 7.69 (1H, t, J=7.8 Hz), 7.88 (1H, dt, J=7.8, 1.5, Hz), 8.00 (1H, dt, J=7.8, 1.5 Hz), 8.17 (1H, t, J=1.5 Hz).

Reference 122
N-[3-[[(3-Cyanophenyl)sulfonyl]amino]phenyl]acetamide

To a solution of 3'-aminoacetanilide (745 mg, 4.96 mmol) in tetrahydrofuran (10 mL), triethylamine (0.76 mL, 5.46 mmol) and 3-cyanobenzenesulfonyl chloride (1.00 g, 4.96 mmol) were added, and the mixture was stirred at room temperature for 3 hours. Water was poured into the reaction mixture, which was then extracted twice with ethyl acetate. The combined organic layer was washed with brine, dried over magnesium sulfate, filtered, and concentrated under reduced pressure. The residue was subjected to a column chromatography on a silica gel (hexane/ethyl acetate, 1:1 followed by 1:2) to obtain the title compound (1.39 g, yield: 89%) as crystals.

$^1$H NMR (CDCl$_3$) δ 2.23 (3H, s), 6.97–7.03 (2H, m), 7.21 (1H, d, J=8.2 Hz), 7.51–7.64 (2H, m), 7.73–7.81 (2H, m), 7.96–8.10 (2H, m).

Reference Example 123
2-[[(3-Cyanobenzene)sulfonyl]amino]acetamide

To a solution of 3-cyanobenzensulfonyl chloride (538 mg, 2.67 mmol) in pyridine (3 mL), glycinamide hydrochloride (301 mg, 2.67 mmol) was added, and the mixture was stirred at room temperature for 1 hour, at 60° C. for 2 hours, and at 90° C. for 4 hours. Water was poured into the reaction mixture, which was then extracted twice with ethyl acetate. The combined organic layer was washed with 1 M hydrochloric acid and brine, dried over sodium sulfate, filtered, and concentrated under reduced pressure to obtain the title compound (180 mg, yield: 28%) as crystals.

$^1$H NMR (CDCl$_3$) δ 3.57 (2H, d, J=5.7 Hz), 6.25 (1H, br s), 7.00 (1H, br s), 7.68 (1H, t, J=7.8 Hz), 7.76 (1H, t, J=5.7 Hz), 7.87 (1H, dd, J=7.8, 1.4 Hz), 8.12 (1H, dd, J=7.8, 1.4 Hz), 8.14 (1H, t, J=1.4 Hz).

Reference Example 124
3-Cyano-N-(hexahydro-2-oxo-1H-azepin-3-yl)benzenesulfonamide To a solution of 3-aminohexahydro-2H-azepin-2-one (305 mg, 2.38 mmol) in tetrahydrofuran (3 mL), 1 M aqueous solution of sodium hydroxide (2 mL) and 3-cyanobenzenesulfonyl chloride (400 mg, 1.98 mmol) was added, and the mixture was stirred at room temperature for 3 hours. Diisopropyl ether was poured into the reaction mixture, and precipitated crystals were filtered off and washed with water and diisopropyl ether to obtain the title compound (360 mg, yield: 62%) as crystals.

$^1$H NMR (CDCl$_3$) δ 1.34–1.90 (4H, m), 2.02–2.16 (2H, m), 3.11–3.25 (2H, m), 3.87–3.92 (1H, m), 5.99 (1H, br s), 6.25 (1H, br s), 7.65 (1H, dd, J=8.4, 7.8 Hz), 7.84 (1H, ddd, J=7.8, 1.6, 1.4 Hz), 8.04 (1H, ddd, J=8.4, 1.6, 1.4 Hz), 8.15 (1H, dd, J=1.6, 1.4 Hz).

Reference Example 125
2,3-Dihydro-7-methoxy-2,2-dimethyl-5-benzofuranacetonitrile Potassium tert-butoxide (11.8 g, 105 mmol) was suspended in dimethoxyethane (75 mL), cooled at a temperature not higher than −70° C. Then toluenesulfonylmethyl isocyanide (10.2 g, 52.5 mmol) was added to the mixture and the mixture was stirred at a temperature not higher than −70° C. for 30 minutes. A solution of 2,3-dihydro-7-methoxy-2,2-dimethyl-5-benzofurancarboxaldehyde (10.4 g, 50 mmol) in dimethoxyethane (25 mL) was added dropwise to the reaction mixture for 10 minutes. After stirring at a temperature not higher than −70° C. for 30 minutes, the mixture was combined with methanol (75 mL), allowed to warm to room temperature, and heated under reflux further for 2 hours. The reaction solution was concentrated under reduced pressure, and iced water was poured into the residue, which was then extracted twice with ethyl acetate. The extract was washed with brine, dried over magnesium sulfate, filtered, and concentrated under reduced pressure. Diethyl ether was poured into the residue, and precipitated crystals were recovered by-filtration, washed with diethyl ether, and dried to obtain the title compound (6.85 g, yield: 63%).

$^1$H NMR (CDCl$_3$) δ 1.51 (6H, s), 3.03 (2H, s), 3.67 (2H, s), 3.87 (3H, s), 6.66 (1H, s), 6.74 (1H, s).

Reference Example 126
2-(2,3-Dihydro-7-methoxy-2,2-dimethyl-5-benzofuranyl)-2-methylpropanenitrile A 60% sodium hydride in oil (2.92 g, 73 mmol) was suspended in N,N-dimethylformamide (75 mL), and 2,3-dihydro-7-methoxy-2,2-dimethyl-5-benzofuranacetonitrile (7.95 g, 36.5 mmol) was added thereto in portions with cooling in ice. The mixture was stirred at room temperature for 30 minutes, and iodomethane (13 g, 92 mmol) was added dropwise with cooling in ice again over 5 minutes. After stirring at room temperature for 3 hours, the reaction mixture was poured into ice water, and extracted twice with ethyl acetate. The extract was washed with brine, dried over magnesium sulfate, filtered, and concentrated under reduced pressure. The residue was subjected to a column chromatography on a silica gel eluting with hexane/ethyl acetate (5:1), and the desired fraction was collected and concentrated to obtain the title compound (8.6 g, yield 96%).

An oil.

$^1$H NMR (CDCl$_3$) δ 1.52 (6H, s), 1.71 (6H, s), 3.04 (2H, s), 3.90 (3H, s), 6.82 (1H, s), 6.87 (1H, s).

Reference Example 127
2-(2,3-Dihydro-7-methoxy-2,2-dimethyl-5-benzofuranyl)-2-methylpropanamide 2-(2,3-Dihydro-7-methoxy-2,2-dimethyl-5-benzofuranyl)-2-methylpropanenitrile (8.6 g, 35 mmol) was dissolved in methanol (105 mL). 1 M aqueous solution of sodium hydroxide (52 mL) and 30% aqueous solution of hydrogen peroxide (7.94 mL) were added to the mixture and the mixture was stirred at room temperature for 18 hours. Methanol was distilled off under reduced pressure, and the residue was extracted twice with ethyl acetate. The extract was washed with brine, dried over magnesium sulfate, filtered, and concentrated under reduced pressure. The residue was combined with diethyl ether, and crystallized to obtain the title compound (7.73 g, yield: 84%).

Melting point: 112–113° C.

$^1$H NMR (CDCl$_3$) δ 1.51 (6H, s), 1.56 (6H, s), 3.03 (2H, s), 3.87 (3H, s), 5.30 (1H, br), 5.45 (1H, br), 6.73 (1H, s), 6.81 (1H, s).

Reference Example 128
N-[2-(2,3-Dihydro-7-methoxy-2,2-dimethyl-5-benzofuranyl)-2-methylpropyl]benzamide To a suspension of lithium aluminum hydride (0.285 g, 7.5 mmol) in tetrahydrofuran (15 mL), 2-(2,3-dihydro-7-methoxy-2,2-dimethyl-5-benzofuranyl)-2-methylpropanamide (0.791 g, 3 mmol) was added in nitrogen flow. After stirring at room temperature for 30 minutes, the mixture was heated under reflux further for 1 hour. The mixture was combined with ethyl acetate (15 mL) with cooling in ice stirred for 30 minutes, and combined with ice water (15 mL), the insolubles were removed using Celite, and the filtrate was extracted twice with ethyl acetate. The extract was washed with brine, dried over magnesium sulfate, filtered, and concentrated under reduced pressure. The residue was dissolved in tetrahydrofuran (10 mL). Pyridine (0.73 mL, 9 mmol) and benzoyl chloride (0.53 mL, 4.5 mmol) were added to the mixture and the mixture was stirred at room temperature for 15 hours. The reaction solution was combined with ethyl acetate (20 mL), washed with water and an aqueous solution of sodium chloride, dried over magnesium sulfate, filtered, and concentrated under reduced pressure. The residue was subjected to a column chromatography on a silica gel eluting with hexane/ethyl acetate (3:1), and the desired fraction was collected and concentrated to obtain the title compound (0.572 g, yield: 53%), which was then recrystallized from diethyl ether/hexane (1:1).

Melting point: 109–110° C.

$^1$H NMR (CDCl$_3$) δ 1.38 (6H, s), 1.53 (6H, s), 3.04 (2H, s), 3.61 (2H, d, J=6 Hz), 3.88 (3H, s), 5.80 (1H, br), 6.76 (1H, s), 6.81 (1H, s), 7.3–7.7 (5H, m).

Reference Example 129
3-Cyano-N-[2-(2,3-dihydro-7-methoxy-2,2-dimethyl-5-benzofuranyl)-2-methylpropyl]benzamide To a suspension of lithium aluminum (0.475 g, 12.5 mmol) in tetrahydrofuran (33 mL), 2-(2,3-dihydro-7-methoxy-2,2-dimethyl-5-benzofuranyl)-2-methylpropanamide (1.32 g, 5 mmol) was added in nitrogen flow. After stirring at room temperature for 30 minutes, the mixture was heated under reflux further for 1 hour. The mixture was combined with ethyl acetate (25 mL) with cooling in ice, stirred for 30 minutes, combined with ice water (15 mL), the insolubles were removed using Celite, and the filtrate was extracted twice with ethyl acetate. The extract was washed with an aqueous solution of sodium chloride, dried over magnesium sulfate, filtered, and concentrated under reduced pressure. The residue was dissolved in tetrahydrofuran (10 mL), added to a solution of activated ester which had been prepared by stirring 3-cyanobenzoic acid (0.883 g, 6 mmol) and N,N'-carbonyldiimidazole. (0.892 g, 5.5 mmol) at room temperature for 30 minutes, and stirred at room temperature for 15 hours. The reaction solution was combined with ethyl acetate (33 mL), washed with water and an aqueous solution of sodium chloride, dried over magnesium sulfate, filtered, and concentrated under reduced pressure. The residue was subjected to a column chromatography on a silica gel eluting with hexane/ethyl acetate (2:1), and the desired fraction was collected and concentrated under reduced pressure to obtain the title compound (0.955 g, yield: 50%).

An oil.

$^1$H NMR (CDCl$_3$) δ 1.39 (6H, s), 1.52 (6H, s), 3.06 (2H, s), 3.62 (2H, d, J=6 Hz), 3.88 (3H, s), 5.80 (1H, br), 6.75 (1H, s), 6.81 (1H, s), 7.4–8.0 (4H, m).

Reference Example 130
[[2-(2,3-Dihydro-7-methoxy-2,2-dimethyl-1-benzofuran-5-yl)-2-methylpropyl]amino]oxoacetic Acid Ether Ester To a suspension of lithium aluminum hydride (0.285 g, 7.5 mmol) in tetrahydrofuran (20 mL), 2-(2,3-dihydro-7-methoxy-2,2-dimethyl-5-benzofuranyl)-2-methylpropanamide (0.791 g, 3 mmol) was added in nitrogen flow. After stirring at room temperature for 30 minutes, the mixture was heated under reflux further for 1 hour. The mixture was combined with ethyl acetate (15 mL) with cooling in ice, stirred for 30 minutes, combined with ice water (15 mL), the insolubles were removed using Celite, and the filtrate was extracted twice with ethyl acetate. The extract was washed with an aqueous solution of sodium chloride, dried over magnesium sulfate, filtered, and concentrated under reduced pressure. The residue was dissolved in tetrahydrofuran (10 mL). Pyridine (0.73 mL, 9 mmol) and ethyl chloroglyoxylate (0.615 g, 4.5 mmol) were added to the mixture and the mixture was stirred at room temperature for 15 hours. The reaction solution was combined with ethyl acetate (20 mL), washed with water and an aqueous solution of sodium chloride, dried over magnesium sulfate, filtered, and concentrated under reduced pressure. The residue was subjected to a column chromatography on a silica gel eluting with hexane/ethyl acetate (2:1), and the desired fraction was collected and concentrated to obtain the title compound (0.51 g, yield: 49%).

An oil.

$^1$H NMR (CDCl$_3$) δ 1.26 (3H, t, J=7 Hz), 1.34 (6H, s), 1.52 (6H, s), 3.03 (2H, s), 3.48 (2H, d, J=6 Hz), 3.88 (3H, s), 4.13 (2H, q, J=7 Hz), 6.69 (1H, s), 6.74 (1H, s), 6.92 (1H, br).

Reference Example 131
3-Bromo-N-[2-(2,3-dihydro-7-methoxy-2,2-dimethyl-5-benzofuranyl)-2-methylpropyl]benzamide To a solution of 2-(2,3-dihydro-7-methoxy-2,2-dimethyl-5-benzofuranyl)-2-methylpropanamide (1.00 g, 3.80 mmol) in tetrahydrofuran (10 mL), lithium aluminum hydride (80%) (0.36 g, 7.6 mmol) was added with cooling in ice, and the mixture was heated under reflux for 1 hour. The reaction mixture was cooled with ice, Hyflo Super-Cell (trade name) (1.5 g) was added thereto, ethyl acetate (1 mL) and water (0.5 mL) were added dropwise thereto slowly, and ethyl acetate was added to suspend, and the mixture was filtered and concentrated under reduced pressure to obtain 2-(2,3-dihydro-7-methoxy-2,2-dimethyl-5-benzofuranyl)-2-methylpropanamine.

This was dissolved in tetrahydrofuran (8 mL) and triethylamine (0.64 mL, 4.6 mmol) was added to the mixture. The resultant mixture was cooled with ice, 3-bromobenzoyl chloride (0.55 mL, 4.2 mmol) was added dropwise thereto, and the mixture was stirred at the same temperature for 10 minutes. The reaction mixture was combined with water and extracted twice with chloroform. The combined organic layer was washed with brine, dried over magnesium sulfate, filtered, and concentrated under reduced pressure. The residue was crystallized from chloroform-diisopropyl ether to obtain the title compound (1.41 g, yield: 86%).

Melting point: 157–163° C.

$^1$H NMR (CDCl$_3$) δ 1.38 (6H, s), 1.53 (6H, s), 3.06 (2H, s), 3.58 (2H, d, J=5.8 Hz), 3.89 (3H, s), 5.65–5.80 (1H, m), 6.76 (1H, s), 6.80 (1H, s), 7.21–7.31 (1H, m), 7.51 (1H, dt, J=7.8, 2.5 Hz), 7.59 (1H, ddd, J=7.8, 2.0, 1.1 Hz), 7.73 (1H, t, J=1.8 Hz).

Reference Example 132
(4-Iodophenyl)carbamic Acid Phenylmethyl Ester

To a solution of 4-iodoaniline (4.38 g, 20.0 mmol) in tetrahydrofuran, a solution of sodium carbonate (2.65 g, 25.0 mmol) in water (15 mL) was added, benzyl chloroformate (3.1 mL, 22 mmol) was added dropwise with cooling in ice, and the mixture was stirred at the same temperature for 15 minutes. The reaction mixture was combined with water and extracted twice with ethyl acetate. The combined organic layer was washed with water and brine, dried over magnesium sulfate, treated with activated charcoal, filtered, and concentrated under reduced pressure. The residue was recrystallized from diisopropyl ether to obtain the title compound (4.71 g, yield: 67%).

Melting point: 132–134° C.

$^1$H NMR (CDCl$_3$) δ 5.20 (2H, s), 6.64 (1H, br s), 7.18 (2H, d, J=8.8 Hz), 7.33–7.45 (5H, m), 7.60 (2H, d, J=8.8 Hz).

Reference Example 133
[4-(4,4,5,5-Tetramethyl-1,3,2-dioxaborolan-2-yl)phenyl]carbamic Acid Phenylmethyl Ester To a solution of (4-iodophenyl)carbamic acid phenylmethyl ester (6.50 g, 18.4 mmol) and triethylamine (7.7 mL, 55 mmol) in 1,4-dioxane (35 mL), [1,1'-bis(diphenylphosphino)ferrocene]dichloropalladium(II) dichloromethane complex (150 mg, 0.184 mmol) was added, and 4,4,5,5-tetramethyl-1,3,2-dioxaborolane (5.9 mL, 41 mmol) was added dropwise. The resultant mixture was stirred at 85° C. for 2.5 hours under nitrogen atmosphere. The reaction mixture was cooled with ice, combined with water, and extracted twice with ethyl acetate. The combined organic layer was washed with water and brine, dried through sodium sulfate silica gel (eluting with ethyl acetate), and concentrated under reduced pressure. The residue was subjected to a column chromatography on a silica gel (hexane/ethyl acetate, 10:1 followed by 4:1) to obtain the title compound (5.47 g, yield: 84%).

An oil.

$^1$H NMR (CDCl$_3$) δ 1.33 (12H, s), 5.20 (2H, s), 6.76 (1H, br s), 7.25–7.52 (7H, m), 7.75 (2H, d, J=8.4 Hz).

Reference Example 134

N-[3'-(1,2,3,4,8,9-Hexahydro-6-methoxy-3,3,8,8-tetramethylfuro[2,3-h]isoquinolin-1-yl)[1,1'-biphenyl]-4-yl]acetamide The title compound was obtained from N-[3'-(3,4,8,9-tetrahydro-6-methoxy-3,3,8,8-tetramethylfuro[2,3-h]isoquinolin-1-yl)[1,1'-biphenyl]-4-yl]acetamide by the method similar to that in Reference Example 10. Yield: 88%.

Amorphous.

$^1$H NMR (CDCl$_3$) δ 1.19 (3H, s), 1.20 (3H, s), 1.25 (3H, s), 1.35 (3H, s), 1.85 (1H, d, J=15.7 Hz), 2.19 (3H, s), 2.48 (1H, d, J=15.7 Hz), 2.57 (1H, d, J=15.6 Hz), 2.83 (1H, d, J=15.6 Hz), 3.87 (3H, s), 5.00 (1H, s), 6.50 (1H, s), 7.17 (1H, d, J=7.4 Hz), 7.30–7.60 (8H, m).

Reference Example 135

3'-(1,2,3,4,8,9-Hexahydro-6-methoxy-3,3,8,8-tetramethylfuro[2,3-h]isoquinolin-1-yl)[1,1'-biphenyl]-4-amine The title compound was obtained from 3'-(3,4,8,9-tetrahydro-6-methoxy-3,3,8,8-tetramethylfuro[2,3-h]isoquinolin-1-yl)[1,1'-biphenyl]-4-amine by the method similar to that in Reference Example 10. Yield: 91%.

Amorphous.

$^1$H NMR (CDCl$_3$) δ 1.18 (3H, s), 1.20 (3H, s), 1.25 (3H, s), 1.34 (3H, s), 1.87 (1H, d, J=15.4 Hz), 2.43–2.60 (2H, m), 2.82. (1H, d, J=15.4 Hz), 3.72 (2H, br s), 3.87 (3H, s), 4.98 (1H, s), 6.49 (1H, s), 6.73 (2H, d, J=8.4 Hz), 7.11 (1H, dt, J=7.3, 1.5 Hz), 7.25–7.47 (5H, m).

Reference Example 136

3-Cyano-N-methylbenzamide

A solution of 3-cyanobenzoic acid (2.00 g, 13.6 mmol) in tetrahydrofuran (10 mL) was cooled with ice, N,N'-carbonyldiimidazole (2.42 g, 15.0 mmol) was added to this, and the mixture was stirred with cooling in ice for 30 minutes. 40% Solution of methylamine/methanol (2 mL) was added to the mixture and the mixture was stirred further for 30 minutes. The reaction solution was concentrated under reduced pressure, the residue was combined with water and extracted with ethyl acetate. The extract was washed with 1 M hydrochloric acid, 1 M aqueous solution of sodium hydroxide and water, and then concentrated under reduced pressure. The residue was crystallized from ethyl acetate-hexane to obtain the title compound (1.66 g, yield: 76%).

Melting point: 132–133° C.

$^1$H NMR (CDCl$_3$) δ 3.04 (3H, d, J=4.8 Hz), 6.33 (1H, br s), 7.58 (1H, t, J=7.8 Hz), 7.78 (1H, d, J=7.8 Hz), 8.00–8.08 (2H, m).

Reference Example 137

2,3-Dihydro-6,7-dimethoxy-2,2-dimethyl-5-(2-methyl-1-propenyl)benzofuran

4-Hydroxy-2,3-dimethoxy-5-(2-methyl-2-propenyl)benzaldehyde was obtained from 4-hydroxy-2,3-dimethoxybenzaldehyde by the method similar to that in Reference Example 1. This was converted to 2,3-dihydro-6,7-dimethoxy-2,2-dimethyl-5-benzofurancarboxaldehyde by the method similar to that in Reference Example 3 and converted to the title compound by the method similar to that in Reference Example 5. Yield: 48%.

An oil.

$^1$H NMR (CDCl$_3$) δ 1.50 (6H, s), 1.79 (3H, d, J=1.2 Hz), 1.89 (3H, d, J=1.2 Hz), 2.97 (2H, s), 3.73 (3H, s), 3.93 (3H, s), 6.22 (1H, s), 6.69 (1H, s).

Reference Example 138

1-(1,2,3,4,8,9-Tetrahydro-6-methoxy-3,3,8,8-tetramethyl-1-phenylfuro[2,3-h]isoquinolin-2-yl)ethanone To a solution of 1,2,3,4,8,9-tetrahydro-6-methoxy-3,3,8,8-tetramethyl-1-phenylfuro[2,3-h]isoquinolin (503 mg, 1.49 mmol) in tetrahydrofuran (5 mL), triethylamine (0.23 mL, 1.64 mmol) and acetyl chloride (0.12 mL. 1.64 mmol) were added, and the mixture was stirred at room temperature for 1 hour. Ice water was poured into the reaction mixture, which was then extracted twice with ethyl acetate. The combined organic layer was washed with brine, dried over magnesium sulfate, filtered, and concentrated under, reduced pressure. The precipitated crystals were recovered by filtration, and washed with diethyl ether to obtain the title compound (380 mg, yield: 67%).

Melting point: 193–195° C.

$^1$H NMR (CDCl$_3$) δ 1.25 (3H, s), 1.59 (3H, s), 1.61 (3H, s), 1.72 (3H, s), 2.17 (1H, d, J=14.6 Hz), 2.54 (1H, d, J=14.6 Hz), 2.27 (3H, s), 3.12 (2H, s), 3.88 (3H, s), 5.81 (1H, br s), 6.56 (1H, s), 7.03 (5H, m).

Reference Example 139

Phenyl(1,2,3,4,8,9-tetrahydro-6-methoxy-3,3,8,8-tetramethyl-1-phenylfuro[2,3-h]isoquinolin-2-yl)methanone To a solution of 1,2,3,4,8,9-tetrahydro-6-methoxy-3,3,8,8-tetramethyl-1-phenylfuro[2,3-h]isoquinoline (420 mg, 1.24 mmol) in tetrahydrofuran (5 mL), triethylamine (0.19 mL, 1.37 mmol) and acetyl chloride (0.16 mL, 1.37 mmol) were added, and the mixture was stirred at room temperature for 3 hours. The reaction mixture was poured into ice water and extracted twice with ethyl acetate. The combined organic layer was washed with brine, dried over magnesium sulfate, filtered, and concentrated under reduced pressure. The precipitated crystals were recovered by filtration and washed with hexane to obtain the title compound (415 mg, yield: 76%).

Melting point: 190–225° C.

$^1$H NMR (CDCl$_3$) δ 1.42 (3H, s), 1.50 (3H, s), 1.57 (3H, s), 1.75 (3H, s), 2.29 (1H, d, J=14.5 Hz), 2.60 (1H, d, J=14.5 Hz), 2.71 (2H, s), 3.92 (3H, s), 5.85 (1H, s), 6.65 (1H, s), 7.07 (2H, d, J=8.6 Hz), 7.23–7.27 (3H, m), 7.36 (5H, m).

Example 1

3,4,8,9-Tetrahydro-6-methoxy-3,3,8,8-tetramethyl-1-phenylfuro[2,3-h]isoquinoline A solution of 2,3-dihydro-7-methoxy-2,2-dimethyl-5-(2-methyl-1-propenyl)benzofuran (2.09 g, 9.00 mmol) and benzonitrile (1.24 g, 12.0 mmol) in acetic acid (3 mL) was treated dropwise with conc. sulfuric acid (1.0 mL) at 10° C., and stirred at room temperature for 40 minutes. The reaction mixture was poured into ice water and washed with diisopropyl ether. The aqueous layer was neutralized with conc. aqueous ammonia and extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate, 15:1 followed by 10:1), and crystallized from hexane to obtain the title compound (1.55 g, yield: 51%).

Melting point: 128–129° C.

$^1$H NMR (CDCl$_3$) δ 1.25 (6H, s), 1.30 (6H, s), 2.19 (2H, s), 2.69 (2H, s), 3.92 (3H, s), 6.61 (1H, s), 7.38 (5H, s).

Example 2
3,4,8,9-Tetrahydro-6-methoxy-3,3,8,8-tetramethyl-1-(1-naphthyl)furo[2,3-h]isoquinoline The title compound was obtained using 1-naphthonitrile by the method similar to that in Example 1. Yield: 49%.

Melting point: 162–164° C. (ethyl acetate-hexane)

$^1$H NMR (CDCl$_3$) δ 0.92 (3H, s), 1.17 (3H, s), 1.28 (3H, s), 1.29 (1H, d, J=16.3 Hz), 1.46 (3H, s), 1.91 (1H, d, J=16.3 Hz), 2.78 (1H, d, J=15.6 Hz), 2.90 (1H, d, J=15.6 Hz), 3.93 (3H, s), 6.65 (1H, s), 7.30–7.55 (4H, m), 7.61–7.68 (1H, m), 7.81–7.91 (2H, m).

Example 3
4-(3,4,8,9-Tetrahydro-6-methoxy-3,3,8,8-tetramethylfuro[2,3-h]isoquinolin-1-yl)phenol The title compound was obtained using 4-cyanophenol by the method similar to that in Example 1. Yield: 48%.

Melting point: 236–239° C. (methanol-diisopropyl ether)

$^1$H NMR (CDCl$_3$) δ 1.29 (6H, s), 1.30 (6H, s), 2.26 (2H, s), 2.72 (2H, s), 3.92 (3H, s), 6.50 (2H, d, J=8.4 Hz), 6.60 (1H, s), 7.05 (2H, d, J=8.4 Hz).

Example 4
3,4,8,9-Tetrahydro-6-methoxy-1-(4-methoxyphenyl)-3,3,8,8-tetramethylfuro[2,3-h]isoquinoline The title compound was obtained using 4-methoxybenzonitrile by the method similar to that in Example 1. Yield: 49%.

Melting point: 151–152° C. (ethyl acetate-hexane)

$^1$H NMR (CDCl$_3$) δ 1.23 (6H, s), 1.33 (6H, s), 2.28 (2H, s), 2.67 (2H, s), 3.85 (3H, s), 3.92 (3H, s), 6.60 (1H, s), 6.91 (2H, d, J=8.8 Hz), 7.34 (2H, d, J=8.8 Hz).

Example 5
3,4,8,9-Tetrahydro-6-methoxy-1-(2-methoxyphenyl)-3,3,8,8-tetramethylfuro[2,3-h]isoquinoline The title compound was obtained using 2-methoxybenzonitrile by the method similar to that in Example 1. Yield: 51%.

Melting point: 124–1–25° C. (ethyl acetate-hexane)

$^1$H NMR (CDCl$_3$) δ 1.13 (3H, s), 1.27 (3H, s), 1.30 (3H, s), 1.42 (3H, s), 2.07 (1H, d, J=16.2 Hz), 2.17 (1H, d, J=16.2 Hz), 2.61 (1H, d, J=15.6 Hz), 2.83 (1H, d, J=15.6 Hz), 3.68 (3H, s), 3.91 (3H, s), 6.57 (1H, s), 6.85 (1H, d, J=8.0 Hz), 7.00 (1H, td, J=7.5, 1.0 Hz), 7.21–7.28 (1H, m), 7.34 (1H, ddd, J=8.3, 7.6, 1.9 Hz).

Example 6
(3,4-Dimethoxyphenyl)-3,4,8,9-tetrahydro-1–6-methoxy-3,3,8,8-tetramethylfuro[2,3-h]isoquinoline The title compound was obtained using 3,4-dimethoxybenzonitrile by the method similar to that in Example 1. Yield: 42%.

Melting point: 121–122° C. (diisopropyl ether-hexane)

$^1$H NMR (CDCl$_3$) δ 1.24 (6H, s), 1.33 (6H, s), 2.30 (2H, s), 2.68 (2H, s), 3.89 (3H, s), 3.91 (3H, s), 3.92 (3H, s), 6.61 (1H, s), 6.87 (1H, d, J=8.1 Hz), 6.93 (1H, d, J=1.8 Hz), 6.97 (1H, dd, J=8.1, 1.8 Hz).

Example 7
3,4,8,9-Tetrahydro-6-methoxy-3,3,8,8-tetramethyl-1-(phenylmethyl)furo[2,3-h]isoquinoline The title compound was obtained using phenylacetonitrile by the method similar to that in Example 1. Yield: 16%.

Melting point: 77–79° C. (hexane)

$^1$H NMR (CDCl$_3$) δ 1.25 (6H, s), 1.34 (6H, s), 2.65 (2H, s), 3.06 (2H, s), 3.87 (3H, s), 4.01% (2H, s), 6.54 (1H, s), 7.06–7.27 (5H, m).

Example 8
Phenyl(3,4,8,9-tetrahydro-6-methoxy-3,3,8,8-tetramethylfuro[2,3-h]isoquinolin-1-yl)methanone The mother liquor after filtration of the desired material in Example 7 was concentrated under reduced pressure, the residue was allowed to stand at room temperature, and then crystallized from diisopropyl ether-hexane to obtain the title compound. Yield: 7.8%.

Melting point: 135–137° C.

$^1$H NMR (CDCl$_3$) δ 1.33 (6H, s), 1.35 (6H, s), 2.66 (2H, s), 2.75 (2H, s), 3.92 (3H, s), 6.60 (1H, s), 7.42–7.53 (2H, m), 7.56–7.67 (1H, m), 7.96–8.02 (2H, m).

Example 9
1-[1,1'-Biphenyl]-4-yl-3,4,8,9-tetrahydro-6-methoxy-3,3,8,8-tetramethylfuro[2,3-h]isoquinoline The title compound was obtained using 4-cyanobiphenyl by the method similar to that in Example 1. Yield: 33%.

Amorphous.

$^1$H NMR (CDCl$_3$) δ 1.26 (6H, s), 1.33 (6H, s), 2.32 (2H, s), 2.70 (2H, s), 3.93 (3H, s), 6.63 (1H, s) 7.32–7.52 (5H, m), 7.60–7.69 (4H, m).

Example 10
3,4,8,9-Tetrahydro-6-methoxy-3,3,8,8-tetramethyl-1-(4-methylphenyl)furo[2,3-h]isoquinoline The title compound was obtained using 4-methylbenzonitrile by the method similar to that in Example 1. Yield: 51%.

Melting point: 158–161° C. (ethyl acetate-hexane)

$^1$H NMR (CDCl$_3$) δ 1.23 (6H, s), 1.32 (6H, s), 2.25 (2H, s), 2.39 (3H, s), 2.67 (2H, s), 3.92 (3H, s), 6.60 (1H, s), 7.18 (2H, d, J=8.0 Hz), 7.24–7.32 (2H, m).

Example 11
3,4,8,9-Tetrahydro-6-methoxy-3,3,8,8-tetramethyl-1-(2-methylphenyl)furo[2,3-h]isoquinoline Hydrochloride A free base of the title compound was obtained using 2-methylbenzonitrile by the method similar to that in Example 1. This was dissolved in methanol, combined with 10% solution of hydrogen chloride/methanol, and concentrated under reduced pressure to obtain the title compound. Yield: 54%.

Amorphous.

$^1$H NMR (CDCl$_3$) δ 1.28 (3H, s), 1.30 (3H, s), 1.52 (3H, s), 1.56 (3H, s), 2.01 (2H, s), 2.21 (3H, s), 2.92 (2H, s), 3.96 (3H, s), 6.68 (1H, s), 7.15–7.48 (4H, m).

Example 12
1-(4-Bromophenyl)-3,4.8.9-tetrahydro-6-methoxy-3,3,8,8-tetramethylfuro[2,3-h]isoquinoline Hydrochloride The title compound was obtained using 4-bromobenzonitrile by the method similar to that in Example 11. Yield: 40%.

Melting point: 140–145° C. (ethyl acetate-diethyl ether).

¹H NMR (DMSO-d₆) δ 1.25 (6H, s), 1.43 (6H, s), 2.25 (2H, s), 3.15 (2H, s), 3.94 (3H, s), 7.10 (1H, s), 7.59 (2H, d, J=8.6 Hz), 7.89 (2H, d, J=8.6 Hz).

Example 13

3,4,8,9-Tetrahydro-6-methoxy-1-(3-methoxyphenyl)-3,3,8,8-tetramethylfuro[2,3-h]isoquinoline Hydrochloride The title compound was obtained using 3-methoxybenzonitrile by the method similar to that in Example 11. Yield: 49%.
Amorphous.
¹H NMR (CDCl₃) δ 1.34 (6H, s), 1.48 (6H, br s), 2.30 (2H, s), 2.86 (2H, br s), 3.91 (3H, s), 3.97 (3H, s), 6.67 (1H, s), 6.99–7.10 (2H, m), 7.21 (1H, br s), 7.35 (1H, t, J=7.9 Hz).

Example 14

3,4,8,9-Tetrahydro-6-methoxy-1,3,3,8,8-pentamethylfuro[2,3-h]isoquinoline

A solution of 2,3-dihydro-7-methoxy-2,2-dimethyl-5-(2-methyl-1-propenyl)benzofuran (697 mg, 3.00 mL) in acetonitrile (0.9 mL) was treated dropwise with conc. sulfuric acid (0.45 mL) with cooling in ice, and stirred at room temperature for 22 hours. The reaction mixture was poured into ice water and washed with diisopropyl ether. The aqueous layer was neutralized with 2 M solution of sodium hydroxide and extracted twice with ethyl acetate. The combined organic layer was washed with brine, dried over magnesium sulfate, filtered, and concentrated under reduced pressure. The residue was subjected to a column chromatography on a basic silica gel (hexane/ethyl acetate, 5:1) and crystallized from diisopropyl ether-hexane to obtain the title compound (431 mg, yield: 53%).
Melting point: 112–113° C.
¹H NMR (CDCl₃) δ 1.17 (6H, s), 1.53 (6H, s), 2.30 (3H, s), 2.58 (2H, s), 3.27 (2H, s), 3.90 (3H, s), 6.53 (1H, s).

Example 15

3,4,8,9-Tetrahydro-6-methoxy-3,3,8,8-tetramethyl-1-(4-pyridinyl)furo[2,3-h]isoquinoline A solution of 4-cyanopyridine (312 mg, 3.00 mmol) in toluene (1.5 mL) was treated dropwise with conc. sulfuric acid (1.2 mL) with cooling in ice. Ice bath was removed a solution of 2,3-dihydro-7-methoxy-2,2-dimethyl-5-(2-methyl-1-propenyl)benzofuran (697 mg, 3.00 mmol) in toluene (0.5 mL) was added to the mixture, and the mixture was stirred at 80° C. for 45 minutes. The reaction mixture was combined with ice and diluted with water and toluene. The organic layer was separated, and the aqueous layer was neutralized with conc. aqueous ammonia and extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate, 3:1) and crystallized from ethyl acetate-hexane to obtain the title compound (294 mg, yield: 29%).
Melting point: 173–175° C.
¹H NMR (CDCl₃) δ 1.26 (6H, s), 1.33 (6H, s), 2.23 (2H, s), 2.70 (2H, s), 3.93 (3H, s), 6.63 (1H, s), 7.35 (2H, d, J=6.0 Hz), 8.67 (2H, d, J=6.0 Hz).

Example 16

1-(2-Fluorophenyl)-3,4,8,9-tetrahydro-6-methoxy-3,3,8,8-tetramethylfuro[2,3-h]isoquinoline Hydrochloride A free base of the title compound was obtained using 2-fluorobenzonitrile by the method similar to that in Example 15. This was dissolved in ethyl acetate, combined with 0.8 M solution of hydrogen chloride/methanol, and concentrated under reduced pressure to obtain the title compound. Yield: 50%.
Amorphous.
¹H NMR (CDCl₃) δ 1.33 (3H, s), 1.38 (3H, s), 1.61 (3H, s), 1.81 (3H, s), 2.20 (1H, d, J=17.0 Hz), 2.32–2.45 (1H, m), 2.95 (1H, d, J=16.2 Hz), 3.18 (1H, d, J=16.2 Hz), 4.02 (3H, s), 6.74 (1H, s), 7.15–7.28 (1H, m), 7.41 (1H, t, J=7.7 Hz), 7.59–7.76 (2H, m)).

Example 17

3,4,8,9-Tetrahydro-6-methoxy-3,3,8,8-tetramethyl-1-(3-pyridinyl)furo[2,3-h]isoquinoline Conc. sulfuric acid (0.60 mL) was added to a solution of 3-cyanopyridine (312 mg, 3.00 mmol) in toluene (1 mL) and acetic acid (1 mL) with cooling in ice and then a solution of 2,3-dihydro-7-methoxy-2,2-dimethyl-5-(2-methyl-1-propenyl)benzofuran (697 mg, 3.00 mmol) in toluene (0.5 mL) was added to the mixture. The mixture was stirred at 80° C. for 1 hour. The reaction mixture was poured into ice water and washed with diisopropyl ether, and the aqueous layer was neutralized with conc. aqueous ammonia and extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate, 5:1) and crystallized from diisopropyl ether-hexane to obtain the title compound (301 mg, yield: 30%).
Melting point: 113–114° C.
¹H NMR (CDCl₃) δ 1.26 (6H, s), 1.32 (6H, s), 2.21 (2H, s), 2.71 (2H, s), 3.93 (3H, s), 6.63 (1H, s), 7.34 (1H, ddd, J=7.7, 4.9, 0.8 Hz), 7.75 (1H, dt, J=7.7, 1.9 Hz), 8.63 (H, d, J=0.8 Hz), 8.65 (1H, dd, J=4.9, 1.9 Hz).

Example 18

3,4,8,9-Tetrahydro-6-methoxy-3,3,8,8-tetramethyl-1-(2-pyridinyl)furo[2,3-h]isoquinoline The title compound was obtained using 2-cyanopyridine by the method similar to that in Example 17. Yield: 27%.
Melting point: 146–147° C. (diisopropyl ether-hexane)
¹H NMR (CDCl₃) δ 1.28 (6H, s), 1.32 (6H, s), 2.15 (2H, s), 2.73 (2H, s), 3.91 (3H, s), 6.60 (1H, s), 7.33 (1H, ddd, J=7.6, 4.9, 1.4 Hz), 7.56–7.63 (1H, m), 7.99 (1H, td, J=7.6, 1.8 Hz), 8.63 (1H, ddd, J=4.9, 1.8, 1.0 Hz).

Example 19

1-(4-Fluorophenyl)-3,4,8,9-tetrahydro-6-methoxy-3,3,8,8-tetramethylfuro[2,3-h]isoquinoline The title compound was obtained using 4-fluorobenzonitrile by the method similar to that in Example 17. Yield: 44%.
Melting point: 131–132° C. (hexane)
¹H NMR (CDCl₃) δ 1.24 (6H, s), 1.33 (6H, s), 2.22 (2H, s), 2.68 (2H, s), 3.92 (3H, s), 6.61 (1H, s), 7.08 (2H, t, J=8.8 Hz), 7.39 (2H, dd, J=8.8, 5.4 Hz).

Example 20

1-(3-Bromophenyl)-3,4,8,9-tetrahydro-6-methoxy-3,3,8,8-tetramethylfuro[2,3-h]isoquinoline The title compound was obtained using 3-bromobenzonitrile by the method similar to that in Example 17. Yield: 51%.
Melting point: 108–109° C. (hexane)
¹H NMR (CDCl₃) δ 1.24 (6H, s), 1.34 (6H, s), 2.24 (2H, s), 2.68 (2H, s), 3.92, (3H, s), 6.61 (1H, s), 7.25 (1H, t, J=7.6 Hz), 7.34 (1H, dt, J=7.6, 1.6 Hz), 7.52 (1H, dt, J=7.6, 1.6 Hz), 7.57 (1H, t, J=1.6 Hz).

Example 21
4-(3,4,8,9-Tetrahydro-6-methoxy-3,3,8,8-tetramethylfuro[2,3-h]isoquinolin-1-yl)benzenesulfonamide The title compound was obtained using 4-cyanobenzenesulfonamide by the method similar to that in Example 17. Yield: 55%.

Melting point: 153–168° C. (decomposition) (ethyl acetate-hexane).

$^1$H NMR (DMSO-d$_6$) δ 1.15 (6H, s), 1.22 (6H, s), 2.22 (2H, s), 2.65 (2H, s), 3.82 (3H, s), 6.83 (1H, s), 7.54 (2H, d, J=8.4 Hz), 7.86 (2H, d, J=8.4 Hz).

Example 22
6-Ethoxy-3,4,8,9-tetrahydro-3,3,8,8-tetramethyl-1-phenylfuro[2,3-h]isoquinoline The title compound was obtained from 7-ethoxy-2,3-dihydro-2,2-dimethyl-5-(2-methyl-1-propenyl)benzofuran and benzonitrile by the method similar to that in Example 17. Yield: 65%.

Gummy.

$^1$H NMR (CDCl$_3$) δ 1.24 (6H, s), 1.30 (6H, s), 1.46 (3H, t, J=7.0 Hz), 2.17 (2H, s), 2.67 (2H, s), 4.18 (2H, q, J=7.0 Hz), 6.60 (1H, s), 7.38 (5H, s).

Example 23
6-Ethoxy-3,4,8,9-tetrahydro-1-(4-methoxyphenyl)-3,3,8,8-tetramethylfuro[2,3-h]isoquinoline The title compound was obtained using 7-ethoxy-2,3-dihydro-2,2-dimethyl-5-(2-methyl-1-propenyl)benzofuran and 4-methoxybenzonitrile by the method similar to that in Example 17. Yield: 55%.

Melting point: 140–142° C.(hexane).

$^1$H NMR (CDCl$_3$) δ 1.22 (6H, s), 1.32 (6H, s), 1.46 (3H, t, J=7.0 Hz), 2.26 (2H, s), 2.65 (2H, s), 3.84 (3H, s), 4.18 (2H, q, J=7.0 Hz), 6.59 (1H, s), 6.90 (2H, d, J=8.4 Hz), 7.34 (2H, d, J=8.4 Hz).

Example 24
3-(3,4,8,9-Tetrahydro-6-methoxy-3,3,8,8-tetramethylfuro[2,3-h]isoquinolin-1-yl)benzoic Acid Methyl Ester Conc. sulfuric acid (1.8 mL) was added to a solution of methyl 3-cyanobenzoate (2.42 g, 15.0 mmol) in toluene (15 mL) and acetic acid (8 mL) with cooling in ice and then a solution of 2,3-dihydro-7-methoxy-2,2-dimethyl-5-(2-methyl-1-propenyl)benzofuran-(3.49 g, 15.0 mmol) in toluene (15 mL) was added to the mixture. The mixture was stirred at 80° C. for 1 hour. The reaction mixture was cooled with ice, combined with an aqueous solution containing sodium acetate (6.69 g, 81.6 mmol), and then neutralized with conc. aqueous ammonia and extracted twice with ethyl acetate. The combined organic layer was washed with water and extracted with 1 M hydrochloric acid 3 times. The combined aqueous layer was neutralized with conc. aqueous ammonia and extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate 10:1) and crystallized from ethyl acetate-hexane to obtain the title compound (2.18 g, Yield: 37%).

Melting point: 137–138° C.

$^1$H NMR (CDCl$_3$) δ 1.26 (6H, s), 1.30 (6H, s), 2.16 (2H, s), 2.70 (2H, s), 3.92 (3H, s), 3.93 (3H, s), 6.63 (1H, s), 7.48 (1H, t, J=7.8 Hz), 7.62 (1H, dt, J=7.8, 1.5 Hz), 8.05–8.12 (2H, m).

Example 25
4-(3,4,8,9-Tetrahydro-6-methoxy-3,3,8,8-tetramethylfuro[2,3-h]isoquinolin-1-yl)benzoic Acid Methyl Ester The title compound was obtained using methyl 4-cyanobenzoate by the method similar to that in Example 24. Yield: 48%.

Melting point: 150–152° C. (diisopropyl ether-hexane).

$^1$H NMR (CDCl$_3$) δ 1.26 (6H, s), 1.30 (6H, s), 2.17 (2H, s), 2.70 (2H, s), 3.92 (3H, s), 3.95 (3H, s), 6.62 (1H, s), 7.48 (2H, d, J=8.6 Hz), 8.07 (2H, d, J=8.6 Hz).

Example 26
4-(6-Ethoxy-3,4,8,9-tetrahydro-3,3,8,8-tetramethylfuro[2,3-h]isoquinolin-1-yl)benzoic Acid Methyl Ester The title compound was obtained-from 7-ethoxy-2,3-dihydro-2,2-dimethyl-5-(2-methyl-1-propenyl)benzofuran and methyl 4-cyanobenzoate by the method similar to that in Example 24. Yield: 43%.

Melting point: 81–85° C. (hexane).

$^1$H NMR (CDCl$_3$) δ 1.25 (6H, s), 1.30 (6H, s), 1.46 (3H, t, J=7.0 Hz), 2.15 (2H, s), 2.68 (2H, s), 3.95 (3H, s), 4.18 (2H, q, J=7.0 Hz), 6.61 (1H, s), 7.48 (2H, d, J=8.3 Hz), 8.07 (2H, d, J=8.3 Hz).

Example 27
4-(3,4,8,9-Tetrahydro-6-methoxy-3,3,8,8-tetramethylfuro[2,3-h]isoquinolin-1-yl)benzenamine Conc. sulfuric acid (3.6 mL) was added to a suspension of N-(4-cyanophenyl)-2,2,2-trifluoroacetamide (6.43 g, 30.0 mmol) in toluene (30 mL) and acetic acid (15 mL) with cooling in ice and then a solution of 2,3-dihydro-7-methoxy-2,2-dimethyl-5-(2-methyl-1-propenyl)benzofuran (10.5 g, 45.2 mmol) in toluene (20 mL) was added to the mixture. The mixture was stirred at 80° C. for 1 hour. The reaction mixture was cooled with ice and combined with water and a small amount of methanol, and the organic layer was separated, and the aqueous layer was washed with diisopropyl ether, neutralized with conc. aqueous ammonia, and extracted twice with ethyl acetate. The combined organic layer was washed with water and concentrated under reduced pressure. The residue was dissolved in ethanol (30 mL), combined with 2 M aqueous solution of sodium hydroxide (15 mL, 30 mmol), and heated under reflux for 40 minutes. The reaction mixture was concentrated under reduced pressure, and the residue was combined with water and extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate 1:1) and recrystallized from ethanol-diisopropyl ether to obtain the title compound (6.32 g, Yield: 60%).

Melting point: 192–195° C.

$^1$H NMR (CDCl$_3$) δ 1.21 (6H, s), 1.33 (6H, s), 2.36 (2H, s), 2.65 (2H, s), 3.45–3.95 (2H, br), 3.91 (3H, s), 6.59 (1H, s), 6.68 (2H, d, J=8.5 Hz), 7.21 (2H, d, J=8.5 Hz).

Example 28
3-(3,4,8,9-Tetrahydro-6-methoxy-3,3,8,8-tetramethylfuro[2,3-h]isoquinolin-1-yl)benzenamine A solution of 3-aminobenzonitrile (9.48 g, 80.2 mmol) in toluene (100 mL) and acetic acid (80 mL) was cooled with ice, conc. sulfuric acid (16 mL) was added dropwise thereto, and then 1-(2,3-dihydro-7-methoxy-2,2-dimethyl-5-benzofuranyl)-2-methyl-1-propanol (22.1 g, 88.3 mmol) was added in portions thereto. The resultant mixture was stirred at 85° C. for 1 hour. Ethanol was added dropwise to the reaction mixture, which was then stirred at the same temperature for 45 minutes. The resultant mixture was cooled and then combined with water to separate an aqueous layer, and the organic layer was extracted with water. The combined aqueous layer was neutralized with conc. aqueous ammonia and extracted twice with ethyl acetate. The combined organic layer was washed with water, and then extracted twice with a 10% aqueous solution of acetic acid. The combined aqueous layer was neutralized with conc. aqueous ammonia and extracted twice with ethyl acetate. The combined organic layer was washed twice with water and concentrated. under reduced pressure. The residue was subjected to a column chromatography on a basic silica gel (hexane/ethyl acetate, 4:1 followed by 1:1) and crystallized from ethyl acetate-hexane to obtain the title compound (12.7 g, Yield: 45%).

Melting point: 131–134° C.

$^1$H NMR (CDCl$_3$) δ 1.26 (6H, br s), 1.33 (6H, s), 2.33 (2H, s), 2.67 (2H, s), 3.69 (2H, br s), 3.91 (3H, s), 6.59 (1H, s), 6.66–6.77 (3H, m), 7.09–7.19 (1H, m).

(Alternative Synthetic Method)

A solution of 1-(2,3-Dihydro-7-methoxy-2,2-dimethyl-5-benzofuranyl)-2-methyl-1-propyl acetate (907 mg, 3.10 mmol) and 3-aminobenzonitrile (440 mg, 3.72 mmol) in toluene (5 mL) was heated at 85° C., a solution of conc. sulfuric acid (0.56 mL) in acetic acid (3 mL) was added dropwise thereto, and the mixture was stirred at the same temperature for 1.5 hours. Ethanol was added dropwise to the reaction mixture, which was then stirred at the same temperature for 1 hour. The resultant mixture was cooled with ice and combined with water to separate an aqueous layer, and the organic layer was extracted with water. The combined aqueous layer was neutralized with conc. aqueous ammonia and extracted twice with ethyl acetate. The combined organic layer was washed with water, and then extracted twice with a 10% aqueous solution of acetic acid. The combined aqueous layer was neutralized with conc. aqueous ammonia and extracted twice with ethyl acetate. The combined organic layer was washed twice with water and concentrated under reduced pressure. The residue was crystallized from diethyl ether-hexane to obtain the title compound (373 mg, Yield: 34%).

Example 29

3-(3,4,8,9-Tetrahydro-6-methoxy-3,3,8,8-tetramethylfuro[2,3-h]isoquinolin-1-yl)benzenamine Dihydrochloride 3-(3,4,8,9-Tetrahydro-6-methoxy-3,3,8,8-tetramethylfuro[(2,3-h]isoquinolin-1-yl)benzenamine (351 mg, 1.00 mmol) was dissolved in ethyl acetate (10 mL), combined with 0.8 M hydrogen chloride/methanol (3 mL), and concentrated under reduced pressure. The residue was recrystallized from ethanol-diisopropyl ether to obtain the title compound (401 mg, Yield: 95%).

Melting point: 176–180° C.

$^1$H NMR (DMSO-d$_6$) δ 1.26 (6H, br s), 1.43 (6H, s), 2.23–2.38 (2H, m), 3.15 (2H, br s), 3.94 (3H, s), 6.80–7.22 (3H, m), 7.09 (1H, s), 7.30–7.48 (1H, m).

Example 30

N-[3-(3,4,8,9-Tetrahydro-6-methoxy-3,3,8,8-tetramethylfuro[2,3-h]isoquinolin-1-yl)phenyl]acetamide A solution of 3-(3,4,8,9-tetrahydro-6-methoxy-3,3,8,8-tetramethylfuro[2,3-h]isoquinolin-1-yl)benzenamine (351 mg, 1.00 mmol) and triethylamine (0.17 mL, 1.2 mmol) in tetrahydrofuran (3 mL) was treated dropwise with acetyl chloride (78 μL, 1.1 mmol) with cooling in ice, and stirred at the same temperature for 10 minutes. The reaction mixture was combined with water and a saturated aqueous solution of sodium hydrogen carbonate and extracted twice with ethyl acetate. The combined organic layer was washed with water and brine, dried over sodium sulfate, filtered and concentrated under reduced pressure. The resultant crystals were washed with diisopropyl ether to obtain the title compound (305 mg, Yield: 78%).

Melting point: 246–247° C.

$^1$H NMR (DMSO-d$_6$) δ 1.13 (6H, s), 1.21 (6H, s), 2.02 (3H, s), 2.28 (2H, s), 2.62 (2H, s), 3.81 (3H, s), 6.80 (1H, s), 6.96–7.04 (1H, m), 7.31 (1H, t, J=7.9 Hz), 7.55–7.67 (2H, m), 9.99 (1H, br s).

Example 31

2,2,2-Trifluoro-N-[3-(3,4,8,9-tetrahydro-6-methoxy-3,3,8,8-tetramethylfuro[2,3-h]isoquinolin-1-yl)phenyl]acetamide The title compound was obtained using trifluoroacetic anhydride by the method similar to that in Example 30. Yield: 86%.

Melting point: 241–242° C. (ethyl acetate-diisopropyl ether).

$^1$H NMR (DMSO-d$_6$) δ 1.14 (6H, s), 1.21 (6H, s), 2.28 (2H, s), 2.63 (2H, s), 3.82 (3H, s), 6.82 (1H, s), 7.17–7.25 (1H, m), 7.45 (1H, t, J=7.7 Hz), 7.65–7.78 (2H, m), 11.31 (1H, br s).

Example 32

N-[3-(3,4,8,9-Tetrahydro-6-methoxy-3,3,8,8-tetramethylfuro[2,3-h]isoquinolin-1-yl)phenyl]methanesulfonamide The title compound was obtained from 3-(3,4,8,9-tetrahydro-6-methoxy-3,3,8,8-tetramethylfuro[2,3-h]isoquinolin-1-yl)benzenamine and methanesulfonyl chloride by the method similar to that in Example 30. Yield: 58%.

Melting point: 245–247° C. (ethanol).

$^1$H NMR (CDCl$_3$) δ 1.27 (6H, br s), 1.33 (6H, s), 2.24 (2H, s), 2.71 (2H, s), 2.88 (3H, s), 3.92 (3H, s), 6.61 (1H, s), 7.15 (1H, dt, J=6.3, 1.9 Hz), 7.19–7.23 (1H, m), 7.26–7.40 (2H, m).

Example 33

2,2,2-Trifluoro-N-[4-(3,4,8,9-tetrahydro-6-methoxy-3,3,8,8-tetramethylfuro[2,3-h]isoquinolin-1-yl)phenyl]acetamide The title compound was obtained from 4-(3,4,8,9-tetrahydro-6-methoxy-3,3,8,8-tetramethylfuro[2,3-h]isoquinolin-1-yl)benzenamine and trifluoroacetic anhydride by the method similar to that in Example 30. Yield: 89%.

Melting point: 117–123° C. (ethyl acetate-diisopropyl ether).

$^1$H NMR (CDCl$_3$) δ 1.25 (6H, s), 1.32 (6H, s), 2.23 (2H, s), 2.69 (2H, s), 3.92 (3H, s), 6.62 (1H, s), 7.39 (2H, d, J=8.6 Hz), 7.56 (2H, d, J=8.6 Hz), 8.30–8.60 (1H, br).

Example 34

N-[4-(3,4,8,9-Tetrahydro-6-methoxy-3,3,8,8-tetramethylfuro[2,3-h]isoquinolin-1-yl)phenyl]acetamide The title compound was obtained from 4-(3,4,8,9-tetrahydro-6-methoxy-3,3,8,8-tetramethylfuro[2,3-h]isoquinolin-1-yl)benzenamine and acetyl chloride by the method similar to that in Example 30. Yield: 90%.

Melting point: 119–123° C. (ethyl acetate-diisopropyl ether).

$^1$H NMR (CDCl$_3$) δ 1.23 (6H, s), 1.32 (6H, s), 2.19 (3H, s), 2.27 (2H, s), 2.68 (2H, s), 3.92 (3H, s), 6.61 (1H, s), 7.35 (2H, d, J=8.5 Hz), 7.44 (1H, br s), 7.54 (2H, d, J=8.5 Hz).

Example 35
3-(3,4,8,9-Tetrahydro-6-methoxy-3,3,8,8-tetramethylfuro[2,3-h]isoquinolin-1-yl)phenylcarbamic Acid Phenyl Ester The title compound was obtained using phenyl chloroformate by the method similar to that in Example 30. Yield: 88%.

Melting point: 155–164° C. (ethyl acetate-hexane).

$^1$H NMR (CDCl$_3$) δ 1.26 (6H, br s), 1.32 (6H, s), 2.30 (2H, s), 2.69 (2H, br s), 3.92 (3H, s), 6.60 (1H, s), 7.05–7.11 (1H, m), 7.13–7.57 (9H, m).

Example 36
N-[3-(3,4,8,9-Tetrahydro-6-methoxy-3,3.8,8-tetramethylfuro[2,3-h]isoquinolin-1-yl)phenyl]benzamide The title compound was obtained from benzoyl chloride by the method similar to that in Example 30. Yield: 93%.

Melting point: 124–130, 174–176° C. (ethyl acetate-hexane).

$^1$H NMR (CDCl$_3$) δ 1.21 (6H, br s), 1.33 (6H, s), 2.35 (2H, s), 2.65 (2H, s), 3.92 (3H, s), 6.60 (1H, s), 7.12 (1H, dt, J=7.8, 1.3 Hz), 7.38 (1H, t, J=7.8 Hz), 7.41–7.60 (4H, m), 7.82–7.98 (3H, m), 8.26 (1H, br s).

Example 37
2-Chloro-N-[3-(3,4,8,9-tetrahydro-6-methoxy-3,3,8,8-tetramethylfuro[2,3-h]isoquinolin-1-yl)phenyl]acetamide The title compound was obtained using chloroacetyl chloride by the method similar to that in Example 30. Yield: 86%.

Melting point: 205–207° C. (ethyl acetate-diethyl ether).

$^1$H NMR (CDCl$_3$) δ 1.24 (6H, br s), 1.32 (6H, s), 2.28 (2H, s), 2.68 (2H, s), 3.92. (3H, s), 4.18 (2H, s), 6.61 (1H, s), 7.12–7.19 (1H, m), 7.37 (1H, t, J=7.9 Hz), 7.46 (1H, t, J=1.7 Hz), 7.73–7.80 (1H, m), 8.37 (1H, br s).

Example 38
2-(Methylthio)-N-[3-(3,4,8,9-tetrahydro-6-methoxy-3,3,8,8-tetramethylfuro[2,3-h]isoquinolin-1-yl)phenyl]acetamide A suspension of 2-chloro-N-[3-(3,4,8,9-tetrahydro-6-methoxy-3,3,8,8-tetramethylfuro[2,3-h]isoquinolin-1-yl)phenyl]acetamide (2.20 g, 5.15 mmol) in N,N-dimethylformamide (15 mL) was treated dropwise with a 15% aqueous solution of methylmercaptan sodium salt (3.1 g, 6.6 mmol) slowly, and stirred at 60° C. for 40 minutes. The reaction mixture was combined with water, and extracted twice with ethyl acetate. The combined organic layer was washed twice with water, and concentrated under reduced pressure. The residue was crystallized from ethyl acetate-diethyl ether to obtain the title compound (1.92 g, yield: 85%).

Melting point: 139–141° C.

$^1$H NMR (CDCl$_3$) δ 1.25 (6H, br s), 1.32 (6H, s), 2.19 (3H, s), 2.29 (2H, s), 2.69 (2H, s), 3.34 (2H, s), 3.92 (3H, s), 6.61 (1H, s), 7.12 (1H, dt, J=7.9, 1.1 Hz), 7.36 (1H, t, J=7.9 Hz), 7.44 (1H, t, J=2.0 Hz), 7.84 (1H, ddd, J=7.9, 2.0, 1.1 Hz), 8.81 (1H, br s).

Example 39
2-(Methylsulfinyl)-N-[3-(3,4,8,9-tetrahydro-6-methoxy-3,3,8,8-tetramethylfuro[2,3-h]isoquinolin-1-yl)phenyl]acetamide A suspension of 2-(methylthio)-N-[3-(3,4,8–9-tetrahydro-6-methoxy-3,3,8,8-tetramethylfuro[2,3-h]isoquinolin-1-yl)phenyl]acetamide (1.37 g, 3.12 mmol) in methanol (15 mL) was treated dropwise with a solution of sodium metaperiodate (1.67 g, 7.81 mmol) in water(10 mL) slowly, and stirred at room temperature for 15 minutes. The reaction mixture was combined with water and as saturated aqueous solution of sodium hydrogen carbonate, and extracted twice with ethyl acetate. The combined organic layer was washed twice with water, and concentrated under reduced pressure. The residue was subjected to a column chromatography on a basic silica gel (hexane/ethyl acetate, 1:1 followed by ethyl acetate/methanol 10:1) and crystallized from ethyl acetate-diethyl ether to obtain the title compound (1.02 g, Yield: 72%).

Melting point: 198–201° C.

$^1$H NMR (CDCl$_3$) δ1.23 (6H, br s), 1.32 (6H, s), 2.28 (2H, s), 2.68 (2H, s), 2.76 (3H, s), 3.38 (1H, d, J=14.6 Hz), 3.87 (1H, d, J=14.6 Hz), 3.92 (3H, s), 6.60 (1H, s), 7.12 (1H, dt, J=7.8, 1.3 Hz), 7.33 (1H, t, J=7.8 Hz), 7.48–7.53 (1H, m), 7.66–7.75 (1H, m), 9.21 (1H, br s).

Example 40
2-(Methylsulfonyl)-N-[3-(3,4,8,9-tetrahydro-6-methoxy-3,3,8,8-tetramethylfuro[2,3-h]isoquinolin-1-yl)phenyl]acetamide A suspension of 2-(methylthio)-N-[3-(3,4,8,9-tetrahydro-6-methoxy-3,3,8,8-tetramethylfuro[2,3-h]isoquinolin-1-yl)phenyl]acetamide (877 mg, 2.00 mmol) in methanol (15 mL) was treated dropwise with a solution of sodium metaperiodate (1.43 g, 6.69 mmol) in water (10 mL) and heated under reflux for 24 hours. The reaction mixture was combined with water and a saturated aqueous solution of sodium hydrogen carbonate, and extracted twice with chloroform. The combined organic layer was washed with water and brine, dried over sodium sulfate, filtered and concentrated under reduced pressure. The residue was subjected to a column chromatography on a basic silica gel (hexane/ethyl acetate, 1:1, 1:3 followed by 1:20) and crystals were washed with a mixture of ethyl acetate and diethyl ether to obtain the title compound (239 mg, Yield: 25%).

Melting point: 135–140° C.

$^1$H NMR (DMSO-d$_6$) δ 1.14 (6H, s), 1.22 (6H, s), 2.29 (2H, s), 2.63 (2H, s), 3.16 (3H, s), 3.81 (3H, s), 4.27 (2H, s), 6.81 (1H, s), 7.10 (1H, d, J=7.7 Hz), 7.38 (1H, t, J=7.7 Hz), 7.59 (1H, d, J=7.7 Hz), 7.66 (1H, s), 10.54 (1H, br s).

Example 41
3-(Methylthio)-N-[3-(3,4,8,9-tetrahydro-6-methoxy-3,3,8,8-tetramethylfuro[2,3-h]isoquinolin-1-yl)phenyl]propanamide The title compound was obtained using 3-methylthiopropionyl chloride by the method similar to that in Example 30. Yield: 99%.

Melting point: 195–197° C. (ethyl acetate-diethyl ether).

$^1$H NMR (CDCl$_3$) δ 1.25 (6H, br s), 1.32 (6H, s), 2.16 (3H, s), 2.29 (2H, s), 2.61 (2H, t, J=7.0 Hz), 2.68 (2H, br s), 2.86 (2H, t, J=7.0 Hz), 3.92 (3H, s), 6.60 (1H, s), 7.07 (1H, d, J=7.4 Hz), 7.25–7.37 (1H, m), 7.42 (1H, s), 7.72 (1H, d, J=7.6 Hz), 7.97 (1H, br s).

Example 42
3-(Methylsulfinyl)-N-[3-(3,4,8,9-tetrahydro-6-methoxy-3,3,8,8-tetramethylfuro[2,3-h]isoquinolin-1-yl)phenyl]propanamide The title compound was obtained from 3-(methylthio)-N-[3-(3,4,8,9-tetrahydro-6-methoxy-3,3,8,8-tetramethylfuro[2,3-h]isoquinolin-1-yl)phenyl]propanamide by the method similar to that in Example 39. Yield: 83%.

Melting point: 178–179° C. (ethyl acetate-diethyl ether).

$^1$H NMR (CDCl$_3$) δ 1.23 (6H, br s), 1.31 (6H, s), 2.25 (2H, s), 2.65 (3H, s), 2.67 (2H, br s), 2.87–3.03 (3H, m), 3.15–3.34 (1H, m), 3.92 (3H, s), 6.59 (1H, s), 7.03 (1H, d, J=7.2 Hz), 7.21–7.32 (1H, m), 7.43 (1H, s), 7.72 (1H, d, J=8.0 Hz), 9.27 (1H, br s).

Example 43
N-[4-(3,4,8,9-Tetrahydro-6-methoxy-3,3,8,8-tetramethylfuro[2,3-h]isoquinolin-1-yl)phenyl]methanesulfonamide A solution of 4-(3,4,8,9-tetrahydro-6-methoxy-3,3,8,8-tetramethylfuro[2,3-h]isoquinolin-1-yl)benzenamine (1.05 g, 3.00 mmol) in pyridine (7 mL) was treated dropwise with methanesulfonyl chloride (0.50 mL, 6.5 mmol) with cooling in ice, and stirred at the same temperature for 1 hour and at room temperature for 80 minutes. The reaction mixture was combined with water and a saturated aqueous solution of sodium hydrogen carbonate and extracted twice with ethyl acetate. The combined organic layer was washed with water and brine, dried over sodium sulfate, filtered, and concentrated under reduced pressure. The residue was suspended in toluene, concentrated under reduced pressure, and then recrystallized from ethanol-diethyl ether to obtain the title compound (500 mg, Yield: 39%).

Melting point: 235–237° C.
$^1$H NMR (CDCl$_3$) δ 1.25 (6H, s), 1.33 (6H, s), 2.24 (2H, s), 2.69 (2H, s), 3.00 (3H, s), 3.92 (3H, s), 6.61 (1H, s), 7.21 (2H, d, J=8.8 Hz), 7.38 (2H, d, J=8.8 Hz).

Example 44
N-(Methylsulfonyl)-N-[4-(3,4,8,9-tetrahydro-6-methoxy-3,3,8,8-tetramethylfuro[2,3-h]isoquinolin-1-yl)phenyl]methanesulfonamide A suspension of N-[4-(3,4,8,9-tetrahydro-6-methoxy-3,3,8,8-tetramethylfuro[2,3-h]isoquinolin-1-yl)phenyl]methanesulfonamide (564 mg, 1.32 mmol) and triethylamine (0.55 mL, 3.9 mmol) in tetrahydrofuran (6 mL) was treated dropwise with methanesulfonyl chloride (0.20 mL, 2.6 mmol), and stirred at 70° C. for 30 minutes. The reaction mixture was combined with water and a saturated aqueous solution of sodium hydrogen carbonate, and extracted twice with ethyl acetate. The combined organic layer was washed twice with water, and concentrated under reduced pressure. The residue was subjected to a column chromatography on a basic silica gel (hexane/ethyl acetate, 3:1 followed by 1:1) and recrystallized from ethyl acetate-ethyl ether to obtain the title compound (454 mg, Yield: 68%).

Melting point: 223–225° C.
$^1$H NMR (CDCl$_3$) δ 1.26 (6H, s), 1.30 (6H, s), 2.14 (2H, s), 2.70 (2H, s), 3.41 (6H, s), 3.92 (3H, s), 6.62 (1H, s), 7.39 (2H, d, J=8.6 Hz), 7.50 (2H, d, J=8.6 Hz).

Example 45
N-(Methylsulfonyl)-N-[3-(3.4,8,9-tetrahydro-6-methoxy-3,3,8,8-tetramethylfuro[2,3-h]isoquinolin-1-yl)phenyl]methanesulfonamide The title compound was obtained from 3-(3,4,8,9-tetrahydro-6-methoxy-3,3,8,8-tetramethylfuro[2,3-h]isoquinolin-1-yl)benzenamine by the method similar to that in Example 44. Yield: 63%.

Melting point: 192–195° C. (acetone-hexane).
$^1$H NMR (CDCl$_3$) δ 1.25 (6H, br s), 1.32 (6H, s), 2.05–2.55 (2H, m), 2.70 (2H, br s), 3.41 (6H, s), 3.92 (3H, s), 6.61 (1H, s), 7.29 (1H, t, J=1.7 Hz), 7.38 (1H, dt, J=7.5, 1.7 Hz), 7.53 (1H, t, J=7.5 Hz), 7.61 (1H, dt, J=7.5, 1.7 Hz).

Example 46
N-[4-(3,4,8,9-Tetrahydro-6-methoxy-3,3,8,8-tetramethylfuro[2,3-h]isoquinolin-1-yl)phenyl]-3-pyridinecarboxamide Nicotinoyl chloride hydrochloride (712 mg, 4.00 mmol) was added to a solution of 4-(3,4,8,9-tetrahydro-6-methoxy-3,3,8,8-tetramethylfuro[2,3-h]isoquinolin-1-yl)benzenamine (701 mg, 2.00 mmol) and 4-dimethylaminopyridine (611 mg, 5.00 mol) in N,N-dimethylformamide (10 mL) and the mixture was stirred at room temperature for 20 minutes. The reaction mixture was combined with water and a saturated aqueous solution of sodium hydrogen carbonate, and extracted twice with ethyl acetate. The combined organic layer was washed twice with water, and concentrated under reduced pressure. The residue was subjected to a column chromatography on a basic silica gel (hexane/ethyl acetate, 2:1 followed by 1:3) and crystallized from ethyl acetate-hexane to obtain the title compound (181 mg, Yield: 20%).

Melting point: 130–137° C.
$^1$H NMR (CDCl$_3$) δ 1.25 (6H, s), 1.33 (6H, s), 2.31 (2H, s), 2.69 (2H, s), 3.93 (3H, s), 6.62 (1H, s), 7.38–7.51 (1H, m), 7.42 (2H, d, J=8.6 Hz), 7.70 (2H, d, J=8.6 Hz), 8.21 (1H, br s), 8.25 (1H, dt, J=8.0, 2.0 Hz), 8.79 (1H, dd, J=4.8, 1.4 Hz), 9.14 (1H, dd, J=2.6, 0.8 Hz).

Example 47
N-[3-(3,4,8,9-tetrahydro-6-methoxy-3,3,8,8-tetramethylfuro[2,3-h]isoquinolin-1-yl)phenyl]-4-pyridinecarboxamide The title compound was obtained from 3-(3,4,8,9-tetrahydro-6-methoxy-3,3,8,8-tetramethylfuro[2,3-h]isoquinolin-1-yl)benzenamine and isonicotinoyl chloride hydrochloride by the method similar to that in Example 46. Yield: 83%.

Melting point: 233–236° C. (ethyl acetate-diethyl ether).
$^1$H NMR (CDCl$_3$) δ 1.17 (6H, br s), 1.33 (6H, s), 2.33 (2H, s), 2.60 (2H, s), 3.92 (3H, s), 6.59.(1H, s), 7.13 (1H, d, J=7.7 Hz), 7.36 (1H, t, J=7.7 Hz), 7.51–7.56 (1H, m), 7.71 (2H, d, J=6.1 Hz), 7.86–7.93 (1H, m), 8.76 (2H, d, J=6.1 Hz), 8.98 (1H, br s).

Example 48
N-[3-(3,4,8,9-Tetrahydro-6-methoxy-3,3,8,8-tetramethylfuro[2,3-h]isoquinolin-1-yl)phenyl]-2-pyridinecarboxamide The title compound was obtained from 3-(3,4,8,9-tetrahydro-6-methoxy-3,3,8,8-tetramethylfuro[2,3-h]isoquinolin-1-yl)benzenamine and picolinoyl chloride hydrochloride by the method similar to that in Example 46. Yield: 86%.

Melting point: 179–183° C. (ethyl acetate-hexane).
$^1$H NMR (CDCl$_3$) δ 1.26 (6H, br s), 1.32 (6H, s), 2.32 (2H, s), 2.70 (2H, s), 3.92 (3H, s), 6.61 (1H, s), 7.15 (1H, d, J=7.8 Hz), 7.41 (1H, t, J=8.1 Hz), 7.44 (1H, m), 7.71 (1H, t, J=1.8 Hz), 7.86–7.96 (1H, m), 7.97–8.04 (1H, m), 8.26–8.32 (1H, m), 8.60 (1H, dt, J=4.7, 0.7 Hz), 10.12 (1H, br s).

Example 49
N-[4-(3,4,8,9-Tetrahydro-6-methoxy-3,3,8,8-tetramethylfuro[2,3-h]isoquinolin-1-yl)phenyl]-4-pyridinecarboxamide The title compound was obtained using isonicotinoyl chloride hydrochloride by the method similar to that in Example 46. Yield: 90%.

Melting point: 159–163° C. (ethyl acetate-diethyl ether).
$^1$H NMR (CDCl$_3$) δ 1.25 (6H, s), 1.33 (6H, s), 2.30 (2H, s), 2.69 (2H, s), 3.93 (3H, s), 6.62 (1H, s), 7.42 (2H, d, J=8.4 Hz), 7.69 (2H, d, J=8.4 Hz), 7.75 (2H, d, J=6.2 Hz), 8.21 (1H, br s), 8.81 (2H, d, J=6.2 Hz).

Example 50
N-[3-(3,4,8,9-Tetrahydro-6-methoxy-3,3,8,8-tetramethylfuro[2,3-h]isoquinolin-1-yl)phenyl]-3-pyridinecarboxamide A solution of sodium carbonate (466 mg, 4.40 mmol) in water (4 mL) was added to a solution of 3-(3,4,8,9-tetrahydro-6-methoxy-3,3,8,8-tetramethylfuro[2,3-h]isoquinolin-1-yl)benzenamine (701 mg, 2.00 mmol) in tetrahydrofuran (4 mL). Nicotinoyl chloride hydrochloride (392 mg, 2.20 mmol) was added to the mixture with cooling in ice, and the mixture was stirred at room temperature for 20 minutes. Furthermore a solution of sodium carbonate (466 mg, 4.40 mmol) in water (2 mL) and nicotinoyl chloride hydrochloride (392 mg, 2.20 mmol) were added to the mixture and the mixture was stirred at room temperature for 15 minutes. The reaction mixture was combined with water and extracted twice with ethyl acetate. The combined organic layer was washed with water and brine, dried over sodium sulfate, filtered, and concentrated under reduced pressure. The residue was crystallized from ethyl acetate-hexane to obtain the title compound (783 mg, Yield:86%).

Melting point: 213–219° C.

$^1$H NMR (CDCl$_3$) δ 1.16 (6H, br s), 1.33 (6H, s), 2.34 (2H, s), 2.60 (2H, br s), 3.92 (3H, s), 6.58 (1H, s), 7.09–7.18 (1H, m), 7.30–7.46 (2H, m), 7.52–7.58 (1H, m), 7.88–7.97 (1H, m), 8.19 (1H, dt, J=7.9, 1.9 Hz), 8.75 (1H, dd, J=5.0, 1.6 Hz), 8.88–9.10 (1H, m), 9.08 (1H, d, J=1.6 Hz).

Example 51
N-(3-Pyridinecarbonyl)-N-[3-(3,4,8,9-tetrahydro-6-methoxy-3,3,8,8-tetramethylfuro[2,3-h]isoquinolin-1-yl)phenyl]glycine Methyl Ester Sodium hydride.(66% suspension in oil) (0.22 g, 6.1 mmol) was added to a solution of N-[3-(3,4,8,9-tetrahydro-6-methoxy-3,3,8,8-tetramethylfuro[2,3-h]isoquinolin-1-yl)phenyl]-3-pyridinecarboxamide (1.37 g, 3.01 mmol) in N,N-dimethylformamide (10 mL) with cooling in ice, and the mixture was stirred at room temperature for 10 minutes. Methyl bromoacetate (0.62 mL, 6.5 mmol) was added to the mixture and the mixture was stirred at room temperature for 30 minutes. The reaction mixture was poured into a saturated aqueous solution of ammonium chloride, and extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate 2:1, 1:1 followed by 1:2) to obtain the title compound (1.12 g, Yield: 71%).

Amorphous.

$^1$H NMR (CDCl$_3$) δ 1.23 (6H, br s), 1.36 (6H, s), 2.09 (2H, br s), 2.67 (2H, br s), 3.79 (3H, s), 3.92 (3H, s), 4.66 (2H, br s), 6.00 (1H, s), 7.10–7.30 (4H, m), 7.36 (1H, br s), 7.82 (1H, dt, J=8.0, 2.0 Hz), 8.49 (1H, dd, J=4.9, 1.7 Hz), 8.55 (1H, d, J=2.0 Hz).

Example 52
N-Methyl-N-[3-(3,4,8,9-tetrahydro-6-methoxy-3,3,8,8-tetramethylfuro[2,3-h]isoquinolin-1-yl)phenyl]-3-pyridinecarboxamide The title compound was obtained using iodomethane by the method similar to that in Example 51. Yield: 69%.

Melting point: 151–153° C. (ethyl acetate-hexane).

$^1$H NMR (CDCl$_3$) δ 1.23 (6H, br s), 1.36 (6H, s), 2.08 (2H, br s), 2.67 (2H, br s), 3.54 (3H, s), 3.92 (3H, s), 6.61 (1H, s), 6.99–7.07 (1H, m), 7.13–7.37 (4H, m), 7.76 (1H, dt, J=7.9, 1.8 Hz), 8.47 (1H, dd, J=4.9, 1.8 Hz), 8.50–8.54 (1H, m).

Example 53
N-(3-Pyridinylmethyl)-N-[3-(3,4,8,9-tetrahydro-6-methoxy-3,3,8,8-tetramethylfuro[2,3-h]isoquinolin-1-yl)phenyl]benzamide The title compound was obtained from N-[3-(3,4,8,9-tetrahydro-6-methoxy-3,3,8,8-tetramethylfuro[2,3-h]isoquinolin-1-yl)phenyl]benzamide and 3-chloromethylpyridine by the method similar to that in Example 51. Yield: 95%.

Melting point: 98–104° C. (ethyl acetate-hexane).

$^1$H NMR (CDCl$_3$) δ 1.22 (6H, br s), 1.30 (6H, s), 2.02 (2H, s), 2.65 (2H, s), 3.91 (3H, s), 5.17 (2H, br s), 6.60 (1H, s), 6.81 (1H, dt, J=6.4, 2.5 Hz), 7.05–7.32 (7H, m), 7.37–7.45 (2H, m), 7.77 (1H, dt, J=7.9, 1.9 Hz), 8.52 (1H, dd, J=4.7, 1.9 Hz), 8.59 (1H, d, J=1.8 Hz).

Example 54
N-(3-pyridinylmethyl)-3-(3,4,8,9-tetrahydro-6-methoxy-3,3,8,8-tetramethylfuro[2,3-h]isoquinolin-1-yl)benzenamine Trihydrochloride 5 M aqueous solution of sodium hydroxide (1.9 mL, 9.5 mmol) was added to a solution of N-(3-pyridinylmethyl)-N-[3-(3,4,8,9-tetrahydro-6-methoxy-3,3,8,8-tetramethylfuro[2,3-h]isoquinolin-1-yl)phenyl]benzamide (1.05 g, 1.92 mmol) in methanol (5 mL) and the mixture was heated under reflux for 8 hours. The reaction mixture was combined with water, and extracted twice with ethyl acetate. The combined organic layer was washed with water and brine, dried over sodium sulfate, filtered, and concentrated under reduced pressure to obtain a free base of the title compound. This was dissolved in methanol (5 mL), combined with 0.8 M solution of hydrogen chloride/methanol (10 mL), and concentrated under reduced pressure. The residue was crystallized from ethanol-diethyl ether to obtain the title compound (826 mg, Yield: 78%).

Melting point: 156–159° C.

$^1$H NMR (DMSO-d$_6$) δ 1.23 (6H, s), 1.43 (6H, s), 2.25 (2H, s), 3.14 (2H, s), 3.93 (3H, s), 4.62 (2H, s), 6.71–6.79 (1H, m), 6.84 (1H, s), 6.98 (1H, dd, J=8.4, 1.4 Hz), 7.09 (1H, s), 7.33 (1H, t, J=7.9 Hz), 8.07 (1H, dd, J=8.0, 5.5 Hz), 8.60 (1H, d, J=8.4 Hz), 8.86 (1H, d, J=5.5 Hz), 8.91 (1H, s).

Example 55
N-(Methylsulfonyl)-N-[3-(3,4,8,9-tetrahydro-6-methoxy-3,3,8,8-tetramethylfuro[2,3-h]isoquinolin-1-yl)phenyl]glycine Methyl Ester The title compound was synthesized from N-[3-(3,4,8,9-tetrahydro-6-methoxy-3,3,8,8-tetramethylfuro[2,3-h]isoquinolin-1-yl)phenyl]methanesulfonamide by the method similar to that in Example 51. Yield: 98%.

Amorphous.

$^1$H NMR (CDCl$_3$) δ 1.25 (6H, br s), 1.32 (6H, s), 2.23 (2H, br s), 2.70 (2H, br s), 3.16 (3H, s), 3.75 (3H, s), 3.92 (3H, s), 4.51 (2H, br s), 6.61 (1H, s), 7.39–7.58 (4H, m).

Example 56
N-[(Dimethylamino)methylene]-3-[(methylsulfonyl)[3-(3,4,8,9-tetrahydro-6-methoxy-3,3,8,8-tetramethylfuro[2,3-h]isoquinolin-1-yl)phenyl]amino]propanesulfonamide N,N-dimethylformamide dimethylacetal (0.73 mL, 5.5 mmol) was added to a suspension of 3-chloro-1-propanesulfonamide (788 mg, 5.00 mmol) in toluene (10 mL), and the mixture was stirred at 60° C. for 30 minutes. The reaction mixture was concentrated under reduced pressure to obtain the mixture (1.15 g) containing 3-chloro-N-[(dimethylamino)methylene]-1-propanesulfonamide.

Sodium hydride (66% suspension in oil)(77 mg, 2.1 mmol) was added to a solution of N-[3-(3,4,8,9-tetrahydro- 6-methoxy-3,3,8,8-tetramethylfuro[2,3-h]isoquinolin-1-yl)phenyl]methanesulfonamide (757 mg, 1.77 mmol) and sodium iodide (69 mg, 0.46 mmol) in N,N-dimethylformamide (4 mL) and the mixture was stirred at room temperature for 15 minutes. A solution of the mixture (528 mg) containing 3-chloro-N-[(dimethylamino)methylene]-1-propansulfonamide in N,N-dimethylformamide (0.5 mL) was added to the reaction mixture, and the reaction mixture was stirred at 60° C. for 19 hours. The reaction mixture was combined with water, and extracted with ethyl acetate 3 times. The combined organic layer was washed with water and brine, dried over sodium sulfate, filtered, and concentrated under reduced pressure. The residue was subjected to a column chromatography on a silica gel (ethyl acetate followed by ethyl acetate/methanol 10:1) to obtain the title compound (879 mg, Yield: 82%).

Amorphous.

$^1$H NMR (CDCl$_3$) δ 1.25 (6H, br s), 1.32 (6H, s), 1.91–2.08 (2H, m), 2.23 (2H, s), 2.70 (2H, s), 2.92 (3H, s), 3.02–3.13 (2H, m), 3.03 (3H, s), 3.13 (3H, s), 3.82 (2H, t, J=6.9 Hz), 3.92 (3H, s), 6.61 (1H, s), 7.27–7.52 (4H, m), 8.00 (1H, s).

Example 57

3-[(Methylsulfonyl)[3-(3,4,8,9-tetrahydro-6-methoxy-3,3,8,8-tetramethylfuro[2,3-h]isoquinolin-1-yl)phenyl]amino]propanesulfonamide Hydrochloride N-[(dimethylamino)methylene]-3-[(methylsulfonyl)[3-(3,4,8,9-tetrahydro-6-methoxy-3,3,8,8-tetramethylfuro[2,3-h]isoquinolin-1-yl)phenyl]amino]propanesulfonamide (625 mg, 1.03 mmol) was dissolved in 2 M hydrochloric acid (2 mL), and heated under reflux for 30 minutes. The reaction mixture was neutralized with sodium hydrogen carbonate, diluted with water, and extracted twice with ethyl acetate. The combined organic layer was washed with water and brine, dried over sodium sulfate, filtered, and concentrated under reduced pressure to obtain a free base of the title compound. This was dissolved in methanol (2 mL), and concentrated under reduced pressure to obtain the title compound (582 mg, Yield: 96%).

Amorphous.

$^1$H NMR (DMSO-d$_6$) δ 1.20 (3H, s), 1.23 (3H, s), 1.45 (3H, s), 1.48 (3H, s), 1.70–1.90 (2H, m), 2.05 (1H, d, J=16.6 Hz), 2.31 (1H, d, J=16.6 Hz), 2.95–3.20 (2H, m), 3.11 (3H, s), 3.18 (2H, br s), 3.81 (2H, t, J=6.1 Hz), 3.94 (3H, s), 6.84 (2H, br s), 7.10 (1H, s), 7.50–7.82 (4H, m), 12.80–12.95 (1H, br).

Example 58

2-[(Methylsulfonyl)[3-(3,4,8,9-tetrahydro-6-methoxy-3,3,8,8-tetramethylfuro[2,3-h]isoquinolin-1-yl)phenyl]amino]acetamide Potassium tert-butoxide (90%) (225 mg, 1.8 mmol) was added to a solution of N-[3-(3,4,8,9-tetrahydro-6-methoxy-3,3,8,8-tetramethylfuro[2,3-h]isoquinolin-1-yl)phenyl]methanesulfonamide (643 mg, 1.50 mmol) in tetrahydrofuran (5 mL) and the mixture was stirred at room temperature for 5 minutes. 2-Bromoacetamide (290 mg, 2.10 mmol) was added to the resultant mixture and the mixture was stirred at 60° C. for 1 hour. Potassium tert-butoxide (90%) (56 mg, 0.45 mmol) and 2-bromoacetamide (62 mg, 0.45 mmol) were added to the mixture and the mixture was stirred at 60° C. for 30 minutes. The reaction mixture was cooled with ice, combined with water, and extracted twice with ethyl acetate. The combined organic layer was washed with water and brine, dried over sodium sulfate, filtered, and concentrated under reduced pressure. The residue was subjected to a column chromatography on a basic silica gel (ethyl acetate), and crystallized from ethyl acetate-diethyl ether to obtain the title compound (469 mg. Yield: 64%).

Melting point: 190–191° C.

$^1$H NMR (CDCl$_3$) δ 1.25 (6H, br s), 1.32 (6H, s), 2.26 (2H, br s), 2.70 (2H, s), 3.09 (3H, s), 3.92 (3H, s), 4.32 (2H, s), 5.36–5.58 (1H, br), 6.08–6.28 (1H, br), 6.61 (1H, s), 7.38–7.56 (4H, m).

Example 59

2-[[[3-(3,4,8,9-Tetrahydro-6-methoxy-3,3,8,8-tetramethylfuro[2,3-h]isoquinolin-1-yl)phenyl]amino]carbonyl]benzoic Acid A solution of phthalic anhydride (222 mg, 1.50 mmol) in tetrahydrofuran (2 mL) was added to a solution of 3-(3,4,8,9-tetrahydro-6-methoxy-3,3,8,8-tetramethylfuro[2,3-h]isoquinolin-1-yl)benzenamine (526 mg, 1.50 mmol) in tetrahydrofuran (3 mL), and stirred at room temperature for 15 minutes. The reaction mixture was combined with diisopropyl ether, and crystals were recovered by filtration and recrystallized from ethanol-ethyl acetate to obtain the title compound(630 mg, Yield: 84%).

Melting point: 194–197° C.

$^1$H NMR (DMSO-d$_6$) δ 1.15 (6H, s), 1.24 (6H, s), 2.35 (2H, br s), 2.66 (2H, br s), 3.82 (3H, s), 6.82 (1H, s), 7.08 (1H, d, J=7.6 Hz), 7.37 (1H, t, J=7.7 Hz), 7.50–7.65 (3H, m), 7.67 (1H, d, J=7.8 Hz), 7.81 (1H, s), 7.83–7.90 (1H, m), 10.46 (1H, br s).

Example 60

2-[3-(3,4,8,9-Tetrahydro-6-methoxy-3,3,8,8-tetramethylfuro[2,3-h]isoquinolin-1-yl)phenyl]-1H-isoindole-1,3(2H)-dione A mixture of 3-(3,4,8,9-tetrahydro-6-methoxy-3,3,8,8-tetramethylfuro[2,3-h]isoquinolin-1-yl)benzenamine (491 mg, 1.40 mmol) and phthalic anhydride (208 mg, 1.40 mmol) in xylene (3 mL) was heated under reflux for 10 minutes. The reaction mixture was dissolved in ethyl acetate, washed with water, a saturated aqueous solution of sodium hydrogen carbonate and brine, dried over sodium sulfate, filtered, and concentrated under reduced pressure. The residue was subjected to a column chromatography on a silica gel (hexane/ethyl acetate 2:1 followed by 1:2), and crystallized from ethyl acetate-hexane to obtain the title compound (439 mg, Yield: 65%).

Melting point: 162–168° C.

$^1$H NMR (CDCl$_3$) δ 1.25 (6H, s), 1.37 (6H, s), 2.10–2.80 (2H, br), 2.68 (2H, s), 3.92 (3H, s), 6.60 (1H, s), 7.44–7.61 (4H, m), 7.73–7.84 (2H, m), 7.88–7.99 (2H, m).

Example 61

6-[3-(3,4,8,9-Tetrahydro-6-methoxy-3,3,8,8-tetramethylfuro[2,3-h]isoquinolin-1-yl)phenyl]-5H-pyrrolo[3,4-b]pyridine-5,7(6H)-dione A mixture of 3-(3,4,8,9-tetrahydro-6-methoxy-3,3,8,8-tetramethylfuro[2,3-h]isoquinolin-1-yl)benzenamine (701 mg, 2.00 mmol) and 2,3-pyridinedicarboxylic anhydride (298 mg, 2.00 mmol) in tetrahydrofuran (4 mL) was stirred at room temperature for 15 minutes. The reaction mixture was combined with diethyl ether, and crystals were recovered by filtration. This was suspended in acetic anhydride (4 mL), and stirred at 100° C. for 1 hour. The reaction mixture was concentrated under reduced pressure, and the residue was combined with ethyl acetate and a saturated aqueous solution of sodium hydrogen carbonate, stirred vigorously, and diluted with water, and then the organic layer was separated, and the aqueous layer was extracted with ethyl acetate. The combined organic layer was washed with water and brine, dried over sodium sulfate, filtered, and concentrated under reduced pressure. The residue was subjected to a column chromatography on a silica gel (hexane/ethyl acetate 1:3) to obtain the title compound (724 mg, 75%). Amorphous.

$^1$H NMR (CDCl$_3$) δ 1.26 (6H, s), 1.38 (6H, s), 2.25–2.60 (2H, br), 2.69 (2H, s), 3.93 (3H, s), 6.61 (1H, s), 7.46–7.60 (4H, m), 7.70 (1H, dd, J=7.7, 4.8 Hz), 8.26 (1H, dd, J=7.7, 1.5 Hz), 9.05 (1H, dd, J=4.8, 1.5 Hz).

Example 62

2-[3-(3,4,8,9-Tetrahydro-6-methoxy-3,3,8,8-tetramethylfuro[2,3-h]isoquinolin-1-yl)phenyl]-1H-pyrrolo[3,4-c]pyridine-1,3(2H)-dione The title compound was obtained using 3,4-pyridinedicarboxylic anhydride by the method similar to that in Example 61. Yield: 77%.

Melting point: 123–129° C. (decomposition) (ethyl acetate-hexane).

$^1$H NMR (CDCl$_3$) δ 1.26 (6H, s), 1.38 (6H, s), 2.15–2.70 (2H, br), 2.69 (2H, s), 3.92 (3H, s), 6.61 (1H, s), 7.42–7.63 (4H, m), 7.84 (1H, dd, J=4.8, 0.8 Hz), 9.14 (1H, d, J=4.8 Hz), 9.24 (1H, d, J=0.8 Hz).

Example 63

4-[[[3-(3,4,8,9-Tetrahydro-6-methoxy-3,3,8,8-tetramethylfuro[2,3-h]isoquinolin-1-yl)phenyl]amino]carbonyl]-1-piperidinecarboxylic acid 1,1-dimethylethyl Ester 1-ethyl-3-(3-dimethylaminopropyl)carbodiimide hydrochloride (1.00 g, 5.22 mmol) was added to a solution of N-(tert-butoxycarbonyl)isonipecotic acid (1.01 g, 4.41 mmol) and 1-hydroxy-1H-benzotriazole monohydrate (678 mg, 4.43 mmol) in N,N-dimethylformamide (15 mL) and the mixture was stirred at room temperature for 1 hour. 3-(3,4,8,9-Tetrahydro-6-methoxy-3,3,8,8-tetramethylfuro[2,3-h]isoquinolin-1-yl)benzenamine (1.41 g, 4.02 mmol) was added to the resultant mixture and the mixture was stirred at room temperature for 4 hours. The reaction mixture was combined with a saturated sodium hydrogen carbonate and water, and extracted twice with ethyl acetate. The combined organic layer was washed with water and brine, dried over sodium sulfate, filtered, and concentrated under reduced pressure. The residue was subjected to a column chromatography on a silica gel-(hexane/ethyl acetate 3:1, 1:1 followed by 1:2). This was dissolved in ethyl acetate and washed with a 2% aqueous solution of acetic acid (twice), water and a saturated aqueous solution of sodium hydrogen carbonate, dried over sodium sulfate, filtered, and concentrated under reduced pressure to obtain the title compound (1.83 g, Yield; 81%).

Amorphous.

$^1$H NMR (CDCl$_3$) δ 1.23 (6H, br s), 1.32 (6H, s), 1.46 (9H, s), 1.60–1.92 (4H, m), 2.22–2.42 (1H, m), 2.30 (2H, s), 2.62–2.85 (2H, m), 2.68 (2H, br s), 3.92 (3H, s), 4.06–4.29 (2H, m), 6.60 (1H, s), 7.05 (1H, d, J=7.6 Hz), 7.25–7.36 (1H, m), 7.48 (1H, s), 7.63–7.85 (2H, m).

Example 64

N-[3-(3,4,8,9-Tetrahydro-6-methoxy-3,3,8,8-tetramethylfuro[2,3-h]isoquinolin-1-yl)phenyl]-4-piperidinecarboxamide Dihydrochloride 4 M solution of hydrogen chloride/ethyl acetate (2.0 mL) was added to a solution of 4-[[[3-(3,4,8,9-tetrahydro-6-methoxy-3,3,8,8-tetramethylfuro[2,3-h]isoquinolin-1-yl)phenyl]amino]carbonyl]-1-piperidinecarboxylic acid 1,1-dimethylethyl ester (1.44 g, 2.56 mmol) in ethyl acetate (15 mL) and the mixture was stirred at room temperature for 1.5 hours, and then at 60° C. for 1 hour. Ethanol (3 mL) was added to the resultant mixture and the mixture was stirred at 60° C. for 1 hour. The reaction mixture was cooled, and the crystals were recovered by filtration to obtain the title compound (774 mg, 57%).

Melting point: 217–224° C.

$^1$H NMR (DMSO-d$_6$) δ 1.23 (6H, s), 1.44 (6H, br s), 1.68–2.07 (4H, m), 2.10–2.50 (2H, m), 2.65–3.40 (7H, m), 3.95 (3H, s), 7.11 (1H, s), 7.31 (1H, d, J=8.2 Hz), 7.59 (1H, t, J=8.2 Hz), 7.86 (1H, d, J=8.2 Hz), 8.03 (1H, s), 8.70–9.35 (2H, m), 10.78–10.90 (1H, m), 12.50–12.80 (1H, br).

Example 65

N-[3-(3,4,8,9-Tetrahydro-6-methoxy-3,3,8,8-tetramethylfuro[2,3-h]isoquinolin-1-yl)phenyl]-4-pyridineacetamide Triethylamine (0.77 mL, 5.5 mol.) and 1-ethyl-3-(3-dimethylaminopropyl)carbodiimide hydrochloride (537 mg, 2.80 mmol) were added to a solution of 3-(3,4,8,9-tetrahydro-6-methoxy-3,3,8,8-tetramethylfuro[2,3-h]isoquinolin-1-yl)benzenamine (701 mg, 2.00 mmol), 4-pyridineacetic acid hydrochloride (417 mg, 2.40 mmol) and 1-hydroxy-1H-benzotriazole monohydrate (368 mg, 2.40 mmol) in N,N-dimethylformamide (10 mL) and the mixture was stirred at room temperature for 1 hour. The mixture was combined with water and a saturated aqueous solution of sodium hydrogen carbonate, and extracted twice with a mixture of ethyl acetate/methanol (5:1). The combined organic layer was washed twice with water, and concentrated under reduced pressure. The residue was recrystallized from ethanol-diethyl ether to obtain the title compound (523 mg, yield: 56%).

Melting point: 124–128° C.

$^1$H NMR (CDCl$_3$) δ 1.23 (6H, br s), 1.30 (6H, s), 2.27 (2H, s), 2.67 (2H, br s), 3.67 (2H, s), 3.92 (3H, s), 6.60 (1H, s), 7.03–7.10 (1H, m), 7.24–7.40 (4H, m), 7.67–7.74 (1H, m), 7.91 (1H, br s), 8.60 (2H, d, J=5.8 Hz).

Example 66

N-[3-(3,4,8,9-Tetrahydro-6-methoxy-3,3,8,8-tetramethylfuro[2,3-h]isoquinolin-1-yl)phenyl]-3-pyridineacetamide.

The title compound was obtained using 3-pyridineacetic acid hydrochloride by the method similar to that in Example 65. Yield: 70%.

Melting point: 122–127° C. (ethanol-diethyl ether).

$^1$H NMR (CDCl$_3$) δ 1.23 (6H, br s), 1.30 (6H, s), 2.26 (2H, s), 2.67 (2H, s), 3.67 (2H, s), 3.91 (3H, s), 6.59 (1H, s), 7.06 (1H, d, J=7.4 Hz), 7.24–7.37 (3H, m), 7.64–7.80 (3H, m), 8.52–8.58 (2H, m).

Example 67

N-[3-(3,4,8,9-Tetrahydro-6-methoxy-3,3,8,8-tetramethylfuro[2,3-h]isoquinolin-1-yl)phenyl]-2-pyridineacetamide The title compound was obtained using 2-pyridineacetic acid hydrochloride by the method similar to that in Example 65. Yield: 75%.

Melting point: 176–177° C. (ethanol-diethyl ether).

$^1$H NMR (CDCl$_3$) δ 1.24 (6H, br s), 1.29 (6H, s), 2.27 (2H, s), 2.68 (2H, s), 3.87 (2H, s), 3.92 (3H, s), 6.60 (1H, s), 7.07 (1H, dt, J=7.7, 1.3 Hz), 7.21–7.37 (3H, m), 7.42 (1H, t, J=1.6 Hz), 7.71 (1H, td, J=7.7, 1.9 Hz), 7.80 (1H, ddd, J=8.2, 2.0, 0.8 Hz), 8.63 (1H, ddd, J=4.9, 1.8, 1.1 Hz), 9.82 (1H, br s).

Example 68
[[4-[[[3-(3,4,8,9-Tetrahydro-6-methoxy-3,3,8,8-tetramethylfuro[2,3-h]isoquinolin-1-yl)phenyl]amino]carbonyl]phenyl]methyl]phosphonic Acid Diethyl Ester Hydrochloride 1-Ethyl-3-(3-dimethylaminopropyl)carbodimide hydrochloride (1.55 g, 8.09 mmol) and triethylamine (1.0 mL, 7.2 mmol) were added to a solution of 3-(3,4,8,9-tetrahydro-6-methoxy-3,3,8,8-tetramethylfuro[2,3-h]isoquinolin-1-yl)benzenamine (2.18 g, 6.22 mmol), 4-[(diethoxyphosphinyl)methyl]benzoic acid (1.86 g, 6.83 mmol) and 1-hydroxy-1H-benzotriazole monohydrate (1.05 g, 6.86 mmol) in N,N-dimethylformamide (30 mL) and the mixture was stirred at room temperature for 17 hours. The reaction mixture was combined with water and a saturated aqueous solution of sodium hydrogen carbonate, and extracted with ethyl acetate 3 times. The combined organic layer was washed with water and brine, dried over sodium sulfate, filtered, and concentrated under reduced pressure. The residue was subjected to a column chromatography on a basic silica gel (hexane/ethyl acetate 2:1, 1:1, 1:3, followed by 1:10) to obtain a free base of the title compound. This was dissolved in ethyl acetate (20 mL), combined with 0.8 M solution of hydrogen chloride/methanol (8.5 mL), and concentrated under reduced pressure. The residue was recrystallized from ethanol-ethyl acetate to obtain the title compound (3.23 g, Yield: 81%).

Melting point: 196–200° C. (decomposition).

$^1$H NMR (DMSO-d$_6$) δ 1.18 (6H, t, J=7.1 Hz), 1.25 (6H, br s), 1.37–1.58 (6H, m), 2.16–2.57 (2H, m), 3.05–3.35 (2H, m), 3.35 (2H, d, J=22.0 Hz), 3.89–4.05 (4H, m), 3.96 (3H, s), 7.12 (1H, s), 7.34–7.48 (3H, m), 7.65 (1H, t, J=8.1 Hz), 7.97 (2H, d, J =8.0 Hz), 8.05–8.16 (2H, m), 10.69 (1H, br s), 12.60–12.80 (1H, br).

Example 69
[[4-[[[3-(3,4,8,9-Tetrahydro-6-methoxy-3,3,8,8-tetramethylfuro[2,3-h]isoquinolin-1-yl)phenyl]amino]carbonyl]phenyl]methyl]phosphonic Acid A solution of [[4-[[[3-(3,4,8,9-tetrahydro-6-methoxy-3,3,8,8-tetramethylfuro[2,3-h]isoquinolin-1-yl)phenyl]amino]carbonyl]phenyl]methyl]phosphonic acid diethyl ester hydrochloride (1.60 g, 2.50 mmol) in dichloromethane (10 mL) was treated dropwise with trimethylsilyl bromide (1.0 mL, 7.6 mmol), and stirred at room temperature for 22 hours. The reaction mixture was concentrated under reduced pressure, and the residue was dissolved in methanol (7.5 mL) and diethyl ether (10 mL). Propylene oxide (7.5 mL) was added to the resultant solution and the mixture was stirred at room temperature. The precipitated crystals were recovered by filtration to obtain the title compound (1.31 g, Yield: 96%).

Melting point: 237–241° C.

$^1$H NMR (DMSO-d$_6$) δ 1.20 (6H, s), 1.22 (6H, s), 2.34 (2H, br s), 2.73 (2H, br s), 3.00 (2H, d, J=21.2 Hz), 3.84 (3H, s), 6.86 (1H, s), 7.11 (1H, d, J=7.8 Hz), 7.33–7.46 (3H, m), 7.82–7.97 (4H, m), 10.32 (1H, br 8).

Example 70
2-Methyl-N-[3-(3,4,8,9-tetrahydro-6-methoxy-3,3,8,8-tetramethylfuro[2,3-h]isoquinolin-1-yl)phenyl]-2-[(2,2,2-trifluoroacetyl)amino]propanamide Hydrochloride The title compound was obtained using 2-methyl-2-[(2,2,2-trifluoroacetyl)amino]propionic acid by the method similar to that in Example 68. Yield: 89%.

Melting point: 210–217° C. (decomposition) (methanol-ethyl acetate).

$^1$H NMR (DMSO-d$_6$) δ 1.23 (6H, s), 1.30–1.60 (6H, m), 1.53 (6H, s), 2.10–2.53 (2H, m), 3.00–3.35 (2H, m), 3.95 (3H, s), 7.11 (1H, s), 7.35 (1H, d, J=8.0 Hz), 7.59 (1H, t, J=8.0 Hz), 7.91 (1H, s), 7.98 (1H, d, J=8.0 Hz), 9.44 (1H, br s), 10.16 (1H, br s), 12.60–12.80 (1H, br s).

Example 71
2-Amino-2-methyl-N-[3-(3,4,8,9-tetrahydro-6-methoxy-3,3,8,8-tetramethylfuro[2,3-h]isoquinolin-1-yl)phenyl]propanamide 1-Ethyl-3-(3-dimethylaminopropyl)carbodiimide hydrochloride (4.98 g, 26.0 mmol) was added to a solution of 3-(3,4,8,9-tetrahydro-6-methoxy-3,3,8,8-tetramethylfuro[2,3-h]isoquinolin-1-yl)benzenamine (7.01 g, 20.0 mmol), 2-methyl-2-[(2,2,2-trifluoroacetyl)amino]propionic acid (4.38 g, 22.0 mmol) and 1-hydroxy-1H-benzotriazole monohydrate (3.37 g, 22.0 mmol) in N,N-dimethylformamide (75 mL) and the mixture was stirred at room temperature for 4.5 hours, and then at 45° C. for 30 minutes. The reaction mixture was combined with water and a saturated aqueous solution of sodium hydrogen carbonate, and extracted twice with ethyl acetate. The combined organic layer was washed twice with water, and concentrated under reduced pressure. The residue was dissolved in ethanol (40 mL), combined with 2 M aqueous solution of sodium hydroxide (25 mL, 50 mmol), and heated under reflux for 1.5 hours. The reaction mixture was concentrated under reduced pressure, and the residue was combined with water, and extracted twice with ethyl acetate. The combined organic layer was washed twice with water, treated with activated charcoal, filtered, and concentrated under reduced pressure. The residue was crystallized from ethyl acetate-hexane to obtain the title compound (7.28 g, Yield: 84%).

Melting point: 175–177° C.

$^1$H NMR (CDCl$_3$) δ 1.24 (6H, br s), 1.32 (6H, s), 1.45 (6H, s), 2.30 (2H, s), 2.67 (2H, br s), 3.92 (3H, s), 6.60 (1H, s), 7.04–7.10 (1H, m), 7.33 (1H, t, J=8.1 Hz), 7.55 (1H, t, J=2.0 Hz), 7.83 (1H, ddd, J=8.1, 2.0, 1.0 Hz), 9.93 (1H, br s).

Example 72
5,5-Dimethyl-3-[3-(3,4,8,9-tetrahydro-6-methoxy-3,3,8,8-tetramethylfuro[2,3-h,]isoquinolin-1-yl)phenyl]-2,4-imidazolidinedione N,N'-carbonyldiimidazole (426 mg, 2.63 mmol) was added to a solution of 2-amino-2-methyl-N-[3-(3,4,8,9-tetrahydro-6-methoxy-3,3,8,8-tetramethylfuro[2,3-h]isoquinolin-1-yl)phenyl]propanamide (1.09 g, 2.50 mmol) in N,N-dimethylformamide (10 mL) and the mixture was stirred at room temperature for 2 hours. The reaction mixture was combined with water and a saturated aqueous solution of sodium hydrogen carbonate, and extracted twice with ethyl, acetate. The combined organic layer was washed twice with water, and concentrated under reduced pressure. The residue was crystallized from ethyl acetate-diethyl ether to obtain the title compound (686 mg, Yield: 59%).

Melting point:289–294° C.

$^1$H NMR (CDCl$_3$) δ 1.28 (6H, br s), 1.33 (12H, s), 2.36 (2H, br s), 2.70 (2H, s), 3.92 (3H, s), 6.61 (1H, s), 7.16 (1H, br s), 7.30–7.51 (3H, m), 7.56–7.60 (1H, m).

Example 73
3-[3-(3,4,8,9-Tetrahydro-6-methoxy-3,3,8,8-tetramethylfuro[2,3-h]isoquinolin-1-yl)phenyl]-2,4-imidazolidinedione 3-(3,4,8,9-Tetrahydro-6-methoxy-3,3,8,8-tetramethylfuro[2,3-h]isoquinolin-1-yl)benzenamine (3.51 g, 10.0 mmol) was added to a solution of ethyl isocyanatoacetate (1.42 g, 11.0 mmol) in tetrahydrofuran (15 mL) and the mixture was heated under reflux for 15 minutes. The reaction mixture was concentrated under reduced pressure, and the residue was dissolved in 5 M hydrochloride (20 mL). The resultant mixture was stirred at 80° C. for 2 hours. The mixture was cooled with ice, neutralized with conc. aqueous ammonia, and extracted twice with ethyl acetate. The combined organic layer was washed twice with water, and concentrated under reduced pressure. The residue was recrystallized from ethyl acetate-hexane, and furthermore recrystallized from methanol-acetate-hexane to obtain the title compound (2.50 g, Yield: 58%).

Melting point: 214–216 C.

$^1$H NMR (CDCl$_3$) δ 1.25 (6H, s), 1.33 (6H, s), 2.37 (2H, br s), 2.68 (2H, s), 3.92 (3H, s), 4.04 (2H, s), 6.22 (1H, br s), 6.60 (1H, s), 7.39–7.57 (4H, m).

Example 74

1-Methyl-3-[3-(3,4,8,9-tetrahydro-6-methoxy-3,3,8,8-tetramethylfuro[2,3-h]isoquinolin-1-yl)phenyl]-2,4-imidazolidinedione Sodium hydride (66% suspension in oil) (80 mg, 2.2 mmol) was added to a solution of 3-[3-(3,4,8,9-tetrahydro-6-methoxy-3,3,8,8-tetramethylfuro[2,3-h]isoquinolin-1-yl)phenyl]-2,4-imidazolidinedione (867 mg, 2.00 mmol) in N,N-dimethylformamide (4 mL) with cooling in ice, and the mixture was stirred at room temperature for 15 minutes. The resultant mixture was cooled with ice, treated dropwise with iodomethane (0.19 mL, 3.1 mmol), and stirred at room temperature for 45 minutes. The reaction mixture was combined with water, and extracted twice with ethyl acetate. The combined organic layer was washed twice with water, and concentrated under reduced pressure. The residue was subjected to a column chromatography on a basic silica gel (hexane/ethyl acetate 2:1 followed by 1:2) to obtain the title compound (724 mg, Yield: 81%).

Amorphous.

$^1$H NMR (CDCl$_3$) δ 1.24 (6H, s), 1.33 (6H, s), 2.38 (2H, br s), 2.67 (2H, s), 3.07 (3H, s), 3.91 (3H, s), 4.01 (2H, s), 6.59 (1H, s), 7.39–7.55 (4H, m).

Example 75

2,4-Dioxo-3-[3-(3,4,8,9-tetrahydro-6-methoxy-3,3,8,8-tetramethylfuro[2,3-h]isoquinolin-1-yl)phenyl]-1-imidazolidineacetic Acid Methyl Ester The title compound was obtained using methyl bromoacetate by the method similar to that in Example 74. Yield: 77%.

Amorphous.

$^1$H NMR (CDCl$_3$) δ 1.24 (6H, s), 1.33 (6H, s), 2.37 (2H, br s), 2.67 (2H, s), 3.79 (3H, s), 3.92 (3H, s), 4.16 (2H, s), 4.24 (2H, s), 6.60 (1H, s), 7.40–7.56 (4H, m).

Example 76

N-methyl-3-[3-(3,4,8,9-tetrahydro-6-methoxy-3,3,8,8-tetramethylfuro[2,3-h]isoquinolin-1-yl)phenyl]-2,4-dioxo-1-imidazolidineacetamide 5 M aqueous solution of sodium hydroxide (1.5 mL) was added to a solution of 3-[3-(3,4,8,9-tetrahydro-6-methoxy-3,3,8,8-tetramethylfuro[2,3-h]isoquinolin-1-yl)phenyl]-2,4-dioxo-1-imidazolidineacetic acid methyl ester (1.87 g, 3.70 mmol) in methanol (10 mL) and the mixture was stirred at room temperature for 15 minutes. 2 M hydrochloric acid was added to the reaction mixture and the reaction mixture was concentrated under reduced pressure. The residue was combined with ethanol, and the insolubles were filtered off, and filtrate was concentrated under reduced pressure. The same procedure was repeated twice, and then suspended in ethanol-ethyl acetate, filtered, and concentrated under reduced pressure to obtain an amorphous material (2.08 g) containing 3-[3-(3,4,8,9-tetrahydro-6-methoxy-3,3,8,8-tetramethylfuro[2,3-h]isoquinolin-1-yl)phenyl]-2,4-dioxo-1-imidazolidineacetic acid.

1-Ethyl-3-(3-dimethylaminopropyl)carbodiimide hydrochloride (312 mg, 1.63 mmol) and 40% solution of methylamine/methanol (0.27 mL, 6.6 mmol) were added to a solution of 700 mg of the material and 1-hydroxy-1H-benzotoriazole monohydrate (211 mg, 1.38 mmol) in N,N-dimethylformamide (10 mL) with cooling in ice and the mixture was stirred at room temperature for 43 hours. The reaction mixture was combined with water and a saturated aqueous solution of sodium hydrogen carbonate, and extracted twice with ethyl acetate. The combined organic layer was washed twice with water, and concentrated under reduced pressure. The residue was subjected to a column chromatography on a basic silica gel (hexane/ethyl acetate 1:1 followed by ethyl acetate) to obtain the title compound (289 mg, Yield: 46%).

Amorphous.

$^1$H NMR (CDCl$_3$) δ 1.24 (6H, s), 1.33 (6H, s), 2.37 (2H, br s), 2.67 (2H, s), 2.81 (3H, d, J=5.2 Hz), 3.92 (3H, s), 4.00 (2H, s), 4.18 (2H, s), 6.10–6.25 (1H, m), 6.60 (1H, s), 7.38–7.56 (4H, m).

Example 77

1-[1,1'-Biphenyl]-3-yl-3,4,8,9-tetrahydro-6-methoxy-3,3,8,8-tetramethylfuro[2,3-h]isoquinoline A solution of phenylboronic acid (219 mg, 1.80 mmol) in ethanol (2 mL), a solution of sodium carbonate (210 mg, 1.98 mmol) in water (2 mL) and tetrakis(triphenylphosphine)palladium(0) (58 mg, 0.050 mmol) were added to a solution of 1-(3-bromophenyl)-3,4,8,9-tetrahydro-6-methoxy-3,3,8,8-tetramethylfuro[2,3-h]isoquinoline (497 mg, 1.20 mmol) in 1,2-dimethoxyethane (6 mL) and the mixture was stirred at 80° C. for 15 hours under nitrogen atmosphere. The reaction mixture was combined with water, and extracted twice with ethyl acetate. The combined organic layer was washed with water and brine, dried over sodium sulfate, filtered, and concentrated under reduced pressure. The residue as subjected to a column chromatography on a basic silica gel (hexane/ethyl acetate 10:1), and crystallized from hexane to obtain the title compound (353 mg, Yield: 71%).

Melting point: 141–142° C.

$^1$H NMR (CDCl$_3$) δ 1.27 (6H, s), 1.30 (6H, s), 2.26 (2H, s), 2.71 (2H, s), 3.93 (3H, s), 6.63 (1H, s), 7.28–7.51 (5H, m), 7.57–7.66 (4H, m).

Example 78

3,4,8,9-Tetrahydro-6-methoxy-3,3,8,8-tetramethyl-1-[3-(4-pyridinyl)phenyl]furo[2,3-h]isoquinoline The title compound was obtained using 4-pyridinylboronic acid by the method similar to that in Example 77. Yield: 69%.

Melting point: 148–150° C. (diisopropyl ether-hexane).

$^1$H NMR (CDCl$_3$) δ 1.28 (6H, s), 1.30 (6H, s), 2.23 (2H, s), 2.72 (2H, s), 3.93 (3H, s), 6.64 (1H, s), 7.44–7.57 (4H, m), 7.64–7.72 (2H, m), 8.66 (2H, d, J=6.2 Hz).

Example 79

3,4,8,9-Tetrahydro-6-methoxy-3,3,8,8-tetramethyl-1-[3-(2-quinolinyl)phenyl]furo[2,3-h]isoquinoline Hexamethylditin (879 mg, 2.68 mmol) was added to a suspension of 1-(3-bromophenyl)-3,4,8,9-tetrahydro-6-methoxy-3,3,8,8-tetramethylfuro[2,3-h]isoquinoline (1.04 g, 2.51 mmol), 2-quinolinyl trifluoromethanesulfonate (731 mg, 2.64 mmol), lithium chloride (319 mg, 7.53 mmol) and tetrakis(triphenylphosphine)palladium(0) (145 mg, 0.125 mmol) in 1,4-dioxane (15 mL), and stirred at 100° C. for 15.5 hours under nitrogen atmosphere. The reaction mixture was poured into a mixture of a 10% aqueous solution of potassium fluoride (25 mL)/ethyl acetate (25 mL), and stirred at room temperature for 2 hours. The insolubles were filtered off, and the organic layer was separated, and the aqueous layer was extracted with ethyl acetate. The combined organic layer was washed with brine, dried over sodium sulfate, filtered, and concentrated under reduced pressure. The residue-was subjected to a column chromatography on a basic silica gel (hexane/ethyl acetate 20:1, 5:1 followed by 3:1), and crystallized from ethyl acetate-hexane to obtain the title compound (529 mg, Yield: 46%).

Melting point: 167–169° C.

$^1$H NMR (CDCl$_3$) δ 1.28 (6H, s), 1.29 (6H, s), 2.34 (2H, s), 2.74 (2H, s), 3.94 (3H, s), 6.65 (1H, s), 7.48–7.62 (3H, m), 7.73 (1H, ddd, J=8.4, 6.9, 1.5 Hz), 7.80–7.87 (1H, m), 7.93 (1H, d, J=8.4 Hz), 8.13–8.26 (3H, m), 8.29 (1H, dt, J=7.0, 1.8 Hz).

Example 80
3-(3,4,8,9-Tetrahydro-6-methoxy-3,3,8,8-tetramethylfuro[2,3-h]isoquinolin-1-yl)benzoic Acid Hydrochloride 5 M aqueous solution of sodium hydroxide (2.0 mL, 10 mmol) was added to a suspension of 3-(3,4,8,9-tetrahydro-6-methoxy-3,3,8,8-tetramethylfuro[2,3-h]isoquinolin-1-yl)benzoic acid methyl ester (1.81 g, 4.60 mmol) in ethanol (5 mL) and the mixture was stirred at room temperature for 4 hours. 1 M hydrochloric acid (10 mL, 20 mmol) was added to the reaction mixture and the resultant mixture was concentrated under reduced pressure. The residue was combined with ethanol, and the insolubles were filtered off using Hyflo Super-Cell (trade name), and the filtrate was concentrated under reduced pressure. The same procedure was repeated twice, and then the residue was recrystallized from ethanol-ethyl acetate to obtain the title compound (1.92 g, quantitative).

Melting point: 184–191° C.

$^1$H NMR (DMSO-d$_6$) δ 1.21 (6H, br s), 1.46 (6H, br s), 2.05–2.25 (2H, m), 3.17 (2H, br s), 3.95 (3H, s), 7.11 (1H, s), 7.77 (1H, t, J=7.6 Hz), 7.86 (1H, d, J=7.6 Hz), 8.17 (1H, s), 8.27 (1H, s).

Example 81
4-(3,4,8,9-Tetrahydro-6-methoxy-3,3,8,8-tetramethylfuro[2,3-h]isoquinolin-1-yl)benzoic Acid Hydrochloride The title compound was obtained from 4-(3,4,8,9-tetrahydro-6-methoxy-3,3,8,8-tetramethylfuro[2,3-h]isoquinolin-1-yl)benzoic acid methyl ester by the method similar to that in Example 80. Yield: 83%.

Melting point: 195–204° C. (ethanol-ethyl acetate).

$^1$H NMR (DMSO-d$_6$) δ 1.31 (6H, s), 1.74 (6H, s), 2.15 (2H, s), 3.10 (2H, s), 4.03 (3H, s), 6.76 (1H, s), 7.66 (2H, d, J=8.3 Hz), 8.11 (2H, d, J=8.3 Hz).

Example 82
4-(6-Ethoxy-3,4,8,9-tetrahydro-3,3,8,8-tetramethylfuro[2,3-h]isoquinolin-1-yl)benzoic Acid Hydrochloride The title compound was obtained from 4-(6-ethoxy-3,4,8,9-tetrahydro-3,3,8,8-tetramethylfuro[2,3-h]isoquinolin-1-yl)benzoic acid methyl ester by the method similar to that in Example 80. Yield: 99%.

Melting point: 206–217° C. (ethanol-ethyl acetate).

$^1$H NMR (DMSO-d$_6$) δ 1.23 (6H, s), 1.37 (3H, t, J=6.9 Hz), 1.46 (6H, s), 2.16 (2H, s), 3.17 (2H, s), 4.25 (2H, q, J=6.9 Hz), 7.10 (1H, s), 7.75 (2H, d, J=8.3 Hz), 8.16 (2H, d, J=8.3 Hz).

Example 83
N-(4-Methoxyphenyl)-4-(3,4,8,9-tetrahydro-6-methoxy-3,3,8,8-tetramethylfuro[2,3-h]isoquinolin-1-yl)benzamide 1-Ethyl-3-(3-dimethylaminopropyl)carbodiimide hydrochloride (300 mg, 1.56 mmol) was added to a solution of 4-(3,4,8,9-tetrahydro-6-methoxy-3,3,8,8-tetramethylfuro[2,3-h]isoquinolin-1-yl)benzoic acid hydrochloride (500 mg, 1.20 mmol) and 1-hydroxy-1H-benzotriazole-monohydrate (202 mg, 1.32 mmol) in N,N-dimethylformamide (3 mL) with cooling in ice and the mixture was stirred for 20 minutes. 4-Methoxyaniline (177 mg, 1.44 mmol) was added to the resultant mixture at the same temperature, and the mixture was stirred at room temperature for 2 hours. The reaction mixture was combined with water, and extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate 2:1 followed by 1:1), and recrystallized from ethyl acetate-hexane to obtain the title compound (442 mg, Yield: 76%).

Melting point: 120–122° C.

$^1$H NMR (CDCl$_3$) δ 1.26 (6H, s), 1.32 (6H, s), 2.22 (2H, s), 2.71 (2H, s), 3.83 (3H, s), 3.93 (3H, s), 6.63 (1H, s), 6.93 (2H, d, J=8.8 Hz), 7.52 (2H, d, J=8.6 Hz), 7.57 (2H, d, J=9.2 Hz), 7.84 (1H, br s), 7.90 (2H, d, J=8.4 Hz).

Example 84
4-(3,4,8,9-Tetrahydro-6-methoxy-3,3,8,8-tetramethylfuro[2,3-h]isoquinolin-1-yl)benzamide.

The title compound was obtained using 4 M solution of ammonia/methanol by the method similar to that in Example 83. Yield: 74%.

Melting point: 229–231° C. (ethyl acetate-hexane).

$^1$H NMR (CDCl$_3$) δ 1.26 (6H, s), 1.31 (6H, s), 2.19 (2H, s), 2.70 (2H, s), 3.93 (3H, s), 5.50–6.50 (2H, m), 6.62 (1H, s), 7.49 (2H, d, J=8.4 Hz), 7.84 (2H, d, J=8.4 Hz).

Example 85
N-Methyl-4-(3,4,8,9-tetrahydro-6-methoxy-3,3,8,8-tetramethylfuro[2,3-h]isoquinolin-1-yl)benzamide The title compound was obtained using a 40% aqueous solution of methylamine by the method similar to that in Example 83. Yield: 77%.

Melting point: 168–169° C. (ethyl acetate-hexane).

$^1$H NMR (CDCl$_3$) δ 1.26 (6H, s), 1.30 (6H, s), 2.17 (2H, s), 2.70 (2H, s), 3.04 (3H, d, J=5.2 Hz), 3.92 (3H, s), 6.32–6.43 (1H, m), 6.62 (1H, s), 7.45 (2H, d, J=8.3 Hz), 7.78 (2H, d, J=8.3 Hz).

Example 86
3-(3,4,8,9-Tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 4 M solution of ammonia/methanol by the method similar to that in Example 83. Yield: 67%.

Melting point: 219–220° C. (methanol-diisopropyl ether).

$^1$H NMR (CDCl$_3$) δ 1.25 (6H, br s), 1.30 (6H, s), 2.17 (2H, s), 2.69 (2H, s), 3.93 (3H, s), 5.30–6.60 (2H, m), 6.62 (1H, s), 7.45–7.57 (2H, m), 7.84–7.87 (1H, m), 7.90 (1H, dt, J=6.9, 2.1 Hz).

Example 87
4-(6-Ethoxy-3,4,8,9-tetrahydro-3,3,8,8-tetramethylfuro[2,3-h]isoquinolin-1-yl)benzamide The title compound was obtained from 4-(6-ethoxy-3,4,8,9-tetrahydro-3,3,8,8-tetramethylfuro[2,3-h]isoquinolin-1-yl)benzoic acid hydrochloride and 4 M solution of ammonia/methanol by the method similar to that in Example 83. Yield: 71%.

Melting point: 179–182° C. (ethyl acetate-hexane).

$^1$H NMR (CDCl$_3$) δ 1.25 (6H, s), 1.30 (6H, s), 1.46 (3H, t, J=6.9 Hz), 2.17 (2H, s), 2.68 (2H, s), 4.19 (2H, q, J=6.9 Hz), 5.50–6.50 (2H, m), 6.61 (1H, s), 7.28 (2H, d, J=8.6 Hz), 7.84 (2H, d, J=8.6 Hz).

Example 88

N-Phenyl-4-(3,4,8,9-tetrahydro-6-methoxy-3,3,8,8-tetramethylfuro[2,3-h]isoquinolin-1-yl)benzamide Hydrochloride 1-Ethyl-3-(3-dimethylaminopropyl)carbodiimide hydrochloride (300 mg, 1.56 mmol) was added to a solution of 4-(3,4,8,9-tetrahydro-6-methoxy-3,3,8,8-tetramethylfuro[2,3-h]isoquinolin-1-yl)benzoic acid hydrochloride (500 mg, 1.20 mmol) and 1-hydroxy-1H-benzotriazole monohydrate (202 mg, 1.32 mmol) in N,N-dimethylformamide (3 mL) with cooling in ice and the mixture was stirred for 25 minutes Aniline (0.13 mL, 1.4 mmol) was added to the resultant mixture at the same temperature, and the mixture was stirred at room temperature for 2 hours. The reaction mixture was combined with water and a saturated aqueous solution of sodium hydrogen carbonate, and extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate 2:1 followed by 1:1) to obtain a free base of the title compound. This was dissolved in ethyl acetate (5 mL), combined with 0.8 M solution of hydrogen chloride/methanol (2.1 mL), and concentrated under reduced pressure to obtain the title compound (537 mg, Yield: 91%).

Amorphous.

$^1$H NMR (CDCl$_3$) δ 1.31 (6H, s), 1.64 (6H, s), 2.24 (2H, s), 3.07 (2H, s), 4.01 (3H, s), 6.72 (1H, s), 7.11 (1H, t, J=7.4 Hz), 7.33 (2H, t, J=7.9 Hz), 7.60 (2H, d, J=8.0 Hz), 7.92 (2H, d, J=7.6 Hz), 8.18 (2H, d, J=7.6 Hz), 9.96 (1H, br s).

Example 89

N,N-Dimethyl-4-(3,4,8,9-tetrahydro-6-methoxy-3,3,8,8-tetramethylfuro[2,3-h]isoquinolin-1-yl)benzamide Hydrochloride The title compound was obtained using a 50% aqueous solution of dimethylamine by the method similar to that in Example 88. Yield: 88%.

Amorphous.

$^1$H NMR (CDCl$_3$) δ 1.36 (6H, s), 1.69 (6H, s), 2.35 (2H, s), 3.01 (3H, br s), 3.05 (2H, s), 3.13 (3H, br s), 4.03 (3H, s), 6.75 (1H, s), 7.61 (2H, d, J=8.4 Hz), 7.72 (2H, d, J=8.4 Hz), 14.20–14.60 (1H, br).

Example 90

[[4-[[3-(3,4,8,9-Tetrahydro-6-methoxy-3,3,8,8-tetramethylfuro[2,3-h]isoquinolin-1-yl)benzoyl]amino]phenyl]methyl]phosphonic Acid Diethyl Ester 1-Ethyl-3-(3-dimethylaminopropyl)carbodiimide hydrochloride (748 mg, 3.90 mmol) and triethylamine (1.0 mL, 7.2 mmol) were added to a solution of 3-(3,4,8,9-tetrahydro-6-methoxy-3,3,8,8-tetramethylfuro[2,3-h]isoquinolin-1-yl)benzoic acid hydrochloride (137 g, 3.29 mmol), diethyl 4-aminobenzylphosphonate (730 mg, 3.00 mmol) and 1-hydroxy-1H-benzotriazole monohydrate (506 mg, 3.30 mmol) in N,N-dimethylformamide (15 mL) and the mixture was stirred at room temperature for 18 hours. The reaction mixture was combined with water and a saturated aqueous solution of sodium hydrogen carbonate, and extracted twice with ethyl acetate. The combined organic layer was washed twice with water and concentrated under reduced pressure. The residue was subjected to a column chromatography on a basic silica gel (hexane/ethyl acetate 1:1 followed by 1:5) to obtain the title compound (1.16 g, Yield: 64%).

Amorphous.

$^1$H NMR (CDCl$_3$) δ 1.25 (6H, s), 1.25 (6H, t, J=7.1 Hz), 1.31 (6H, s), 2.22 (2H, s), 2.68 (2H, s), 3.14 (2H, d, J=21.6 Hz), 3.92–4.10 (4H, m), 3.93 (3H, s), 6.63 (1H, s), 7.24–7.34 (2H, m), 7.46–7.53 (2H, m), 7.64 (2H, d, J=8.0 Hz), 7.94–8.02 (2H, m), 8.63 (1H, br s).

Example 91

3,4,8,9-Tetrahydro-3,3,8,8-tetramethyl-1-phenyl-6-furo[2,3-h]isoquinolinol Hydrobromide 48% Hydrobromic acid (7.5 mL) was added to 3,4,8,9-tetrahydro-6-methoxy-3,3,8,8-tetramethyl-1-phenylfuro[2,3-h]isoquinoline (500 mg, 1.49 mmol) and the mixture was stirred at 105° C. for 18 hours. The reaction mixture was cooled, and the precipitated crystals were recovered by filtration, washed with water, and then air-dried overnight to obtain the title compound (463 mg, Yield: 77%).

$^1$H NMR (DMSO-d$_6$) δ 1.23 (6H, s), 1.42 (6H, s), 2.15 (2H, s), 3.09 (2H, s), 6.79(1H, s), 7.57–7.80 (5H, m), 11.2–11.4 (1H, br), 12.1–12.4 (1H, br).

Example 92

3,4,8,9-Tetrahydro-3,3,8,8-tetramethyl-1-phenyl-6-furo[2,3-h]isoquinolinol.

4.8% Hydrobromic acid (45 mL) was added to 3,4,8,9-tetrahydro-6-methoxy-3,3,8,8-tetramethyl-1-phenylfuro[2,3-h]isoquinoline (3.02 g, 9.00 mmol) and the mixture was heated under reflux for 16 hours. The reaction mixture was cooled with ice, neutralized with conc. aqueous ammonia, diluted with water, and extracted with ethyl acetate 3 times. The combined organic layer was washed with brine, dried over sodium sulfate, treated with activated charcoal, filtered and concentrated under reduced pressure. The residue was crystallized from ethyl acetate-diisopropyl ether to obtain the title compound (2.70 g, Yield: 93%).

Melting point: 208–210° C.

$^1$H NMR (CDCl$_3$) δ 1.26 (6H, s), 1.28 (6H, s), 2.16 (2H, s), 2.66 (2H, s), 6.54 (1H, s), 7.38 (5H, m).

Example 93

3,4,8,9-Tetrahydro-1-(4-hydroxyphenyl)-6-methoxy-3,3,8,8-tetramethyl-6-furo[2,3-h]isoquinolinol Hydrobromide The title compound was obtained from 3,4,8,9-tetrahydro-6-methoxy-1-(4-methoxyphenyl)-3,3,8,8-tetramethylfuro[2,3-h]isoquinoline by the method similar to that in Example 91. Yield: 77%.

Melting point: 194–200° C.

$^1$H NMR (DMSO-d$_6$) δ 1.27 (6H, s), 1.38 (6H, s), 2.34 (2H, s), 3.03 (2H, s), 6.77 (1H, s), 6.99 (2H, d, J=8.4 Hz), 7.46 (2H, d, J=8.4 Hz), 10.59 (1H, s), 11.17 (1H, br s), 11.80–11.95 (1H, br).

Example 94

1-(3-Bromophenyl)-3,4,8,9-tetrahydro-3,3,8,8-tetramethyl-6-furo[2,3-h]isoquinolinol The title compound was obtained from 1-(3-bromophenyl)-3,4,8,9-tetrahydro-6-methoxy-3,3,8,8-tetramethylfuro[2,3-h]isoquinoline by the method similar to that in Example 92. Yield: 91%.

Melting point: 202–208° C. (ethyl acetate-diisopropyl ether).

$^1$H NMR (CDCl$_3$) δ 1.25 (6H, s), 1.32 (6H, s), 2.22 (2H, s), 2.63 (2H, s), 6.52 (1H, s), 7.24 (1H, t, J=7.6 Hz), 7.34 (1H, dt, J=7.6, 1.4 Hz), 7.47–7.54 (1H, m), 7.57 (1H, t, J=1.4 Hz).

Example 95
Trifluoromethanesulfonic acid (3,4,8,9-tetrahydro-3,3,8,8-tetramethyl-1-phenylfuro[2,3-h]isoquinolin-6-yl)ester A solution of 3,4,8,9-tetrahydro-3,3,8,8-tetramethyl-1-phenyl-6-furo[2,3-h]isoquinolinol (1.03 g, 3.20 mmol) in pyridine (10 mL) was treated dropwise with trifluoromethanesulfonic anhydride (0.60 mL, 3.6 mmol) with cooling in ice, and stirred for 10 minutes. The reaction mixture was combined with water and a saturated aqueous solution of sodium hydrogen carbonate, and extracted twice with ethyl acetate. The combined organic layer was washed twice with water, and concentrated under reduced pressure. The residue was subjected to a column chromatography on a basic silica gel (hexane/ethyl acetate 10:1) to obtain the title compound (1.37 g, Yield: 94%).

An oil.

$^1$H NMR (CDCl$_3$) δ 1.25 (6H, s), 1.30 (6H, s), 2.23 (2H, s), 2.70 (2H, s), 6.94 (1H, s), 7.41 (5H, s).

Example 96
Trifluoromethanesulfonic acid (3,4,8,9-tetrahydro-6-methoxy-3,3,8,8-tetramethylfuro[2,3-h]isoquinolin-6-yl)ester Hydrochloride The title compound was obtained from trifluoromethanesulfonic acid (3,4,8,9-tetrahydro-3,3,8,8-tetramethyl-1-phenylfuro[2,3-h]isoquinolin-6-yl)ester by the method similar to that in Example 29. Yield: 84%.

Melting point: 152–160° C. (methanol-ethyl acetate).

$^1$H NMR (DMSO-d$_6$) δ 1.28 (6H, s), 1.43 (6H, br s), 2.32 (2H, s), 3.17 (2H, br s), 7.56 (1H, s), 7.57–7.83 (5H, m).

Example 97
3,4,8,9-Tetrahydro-3,3,8,8-tetramethyl-1-phenylfuro[2,3-h]isoquinoline Hydrochloride Formic acid (0.17 mL, 4.5 mmol) was added to a solution of trifluoromethanesulfonic acid (3,4,8,9-tetrahydro-3,3,8,8-tetramethyl-1-phenylfuro[2,3-h]isoquinolin-6-yl)ester (1.00 g, 2.21 mmol), triethylamine (0.92 mL, 6.6 mmol), palladium(II) acetate (9.9 mg, 0.044 mmol) and triphenylphosphine (23.1 mg, 0.0881 mmol) in N,N-dimethylformamide (4 mL) and the mixture was stirred at 60° C. for 3.5 hours under nitrogen atmosphere. The reaction mixture was combined with water, and extracted twice with ethyl acetate. The combined organic layer was extracted twice with 1 M hydrochloric acid. The combined aqueous layer was neutralized with conc. aqueous ammonia, and extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 15:1) to obtain a free base of the title compound. The mixture was dissolved in ethyl acetate (3 mL), and combined with 0.8 M solution of hydrogen chloride/methanol (3.0 mL). The resultant mixture was concentrated under reduced pressure, and the residue was crystallized from ethyl acetate-diisopropyl ether to obtain the title compound (705 mg, Yield: 93%).

Melting point: 167–179° C.

$^1$H NMR (DMSO-d$_6$) δ 1.23 (6H, s), 1.46 (6H, s), 2.19 (2H, s), 3.16 (2H, s), 7.17 (1H, d, J=8.1 Hz), 7.30 (1H, d, J=8.1 Hz), 7.62–7.84 (5H, m).

Example 98
3,4,8,9-Tetrahydro-3,3,8,8-tetramethyl-1-[3-(4-pyridinyl)phenyl]-6-furo[2,3-h]isoquinolinol A solution of sodium carbonate (480 mg, 4.53 mmol) in water (5 mL) and tetrakis(triphenylphosphine)palladium(0) (105 mg, 0.0909 mmol) were added to a suspension of 1-(3-bromophenyl)-3,4,8,9-tetrahydro-3,3,8,8-tetramethyl-6-furo[2,3-h]isoquinolinol (725 mg, 1.81 mmol) and 4-pyridinylboronic acid (334 mg, 2.72 mmol) in toluene (10 mL) and ethanol (3 mL) and the mixture was stirred at 90° C. for 15 hours under nitrogen atmosphere. The reaction mixture was cooled and combined with 1 M hydrochloric acid, and the insolubles were filtered off, and the organic layer was separated. The aqueous layer was neutralized with conc. aqueous ammonia, and extracted twice with ethyl acetate. The combined organic layer was washed with brine, dried over sodium sulfate, filtered, and concentrated under reduced pressure. The residue was subjected to a column chromatography on a basic silica gel (ethyl acetate followed by ethyl acetate/methanol 20:1), and crystallized from ethyl acetate-diisopropyl ether to obtain the title compound (294 mg, Yield: 41%).

Melting point: 141–149° C.

$^1$H NMR (CDCl$_3$) δ 1.27 (12H, s), 2.21 (2H, s), 2.67 (2H, s), 6.58 (1H, s), 7.43–7.58 (4H, m), 7.64–7.73 (2H, m), 8.66 (2H, d, J=6.2 Hz).

Example 99
3,4,8,9-Tetrahydro-3,3,8,8-tetramethyl-6-propoxy-1-[3-(4-pyridinyl)phenyl]furo[2,3-h]isoquinoline Sodium hydride (66% suspension in oil) (95 mg, 2.6 mmol) was added to a solution of 3,4,8,9-tetrahydro-3,3,8,8-tetramethyl-1-[3-(4-pyridinyl)phenyl]-6-furo[2,3-h]isoquinolinol (812 mg, 2.00 mmol) and 1-iodopropane (0.59 mL, 6.0 mmol) in N,N-dimethylformamide (4 mL) and the mixture was stirred at room temperature for 30 minutes. The reaction mixture was poured into water, and extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate 10:1 followed by 2:1), and recrystallized from ethyl acetate-hexane to obtain the title compound (614 mg, Yield: 70%).

Melting point: 132–134° C.

$^1$H NMR (CDCl$_3$) δ 1.04 (3H, t, J=7.5 Hz), 1.27 (6H, s), 1.30 (6H, s), 1.87 (2H, sixtet, J=7.2 Hz), 2.21 (2H, s), 2.70 (2H, s), 4.07 (2H, t, J=6.9 Hz), 6.63 (1H, s), 7.43–7.57 (4H, m), 7.64–7.71 (2H, m), 8.66 (2H, d, J=6.0 Hz).

Example 100
2-[[3,4,8,9-Tetrahydro-3,3,8,8-tetramethyl-1-[3-(4-pyridinyl)phenyl]furo[2,3-h]isoquinolin-6-yl]oxy]acetamide The title compound was obtained using 2-bromoacetamide by the method similar to that in Example 99. Yield: 63%.

Melting point: 120–125° C. (ethyl acetate-hexane).

$^1$H NMR (CDCl$_3$) δ 1.28 (6H, s), 1.30 (6H, s), 2.24 (2H, s), 2.71 (2H, s), 4.63 (2H, s), 5.55–5.85 (1H, br), 6.65 (1H, s), 6.70–6.95 (1H, br), 7.43–7.59 (4H, m), 7.64–7.73 (2H, m), 8.67 (2H, d, J=6.4 Hz).

Example 101
1-(3-Bromophenyl)-6-ethoxy-3,4,8,9-tetrahydro-3,3,8,8-tetramethylfuro[2,3-h]isoquinoline The title compound was obtained from 1-(3-bromophenyl)-3,4,8,9-tetrahydro-3,3,8,8-tetramethyl-6-furo[2,3-h]isoquinolinol and iodomethane by the method similar to that in Example 99. Quantitative.

Amorphous.

$^1$H NMR (CDCl$_3$) δ 1.23 (6H, s), 1.34 (6H, s), 1.46 (3H, t, J=7.1 Hz), 2.22 (2H, s), 2.66 (2H, s), 4.18 (2H, q, J=7.1 Hz), 6.60 (1H, s), 7.25 (1H, t, J=7.5 Hz), 7.33 (1H, dt, J=7.5, 1.7 Hz), 7.52 (1H, dt, J=7.5, 1.7 Hz), 7.57 (1H, t, J=1.7 Hz).

Example 102
1-(3-Bromophenyl)-6-ethoxy-3,4,8,9-tetrahydro-3,3,8,8-tetramethylfuro[2,3-h]isoquinoline Hydrochloride The title compound was obtained from 1-(3-bromophenyl)-6-ethoxy-3,4,8,9-tetrahydro-3,3,8,8-tetramethylfuro[2,3-h]isoquinoline by the method similar to that in Example 29. Yield: 74%.

Melting point: 219–223° C. (sealed tube) (methanol-ethyl acetate-diethyl ether).

$^1$H NMR (DMSO-d$_6$) δ 1.25 (6H, s), 1.37 (3H, t, J=7.0 Hz), 1.44 (6H, br s), 2.22 (2H, s), 3.12 (2H, br s), 4.24 (2H, q, J=7.0 Hz), 7.08 (1H, s), 7.52–7.65 (2H, m), 7.88–7.99 (2H, m).

Example 103
1-(3-Bromophenyl)-6-butoxy-3,4,8,9-tetrahydro-3,3,8,8-tetramethylfuro[2,3-h]isoquinoline The title compound was obtained from 1-(3-bromophenyl)-3,4,8,9-tetrahydro-3,3,8,8-tetramethyl-6-furo[2,3-h]isoquinolinol and 1-iodobutane by the method similar to that in Example 99. Yield: 84%.

Gummy.

$^1$H NMR (CDCl$_3$) δ 0.98 (3H, t, J=7.2 Hz), 1.23 (6H, s), 1.33 (6H, s), 1.38–1.59 (2H, m), 1.74–1.90 (2H, m), 2.21 (2H, s), 2.66 (2H, s), 4.10 (2H, t, J=6.8 Hz), 6.60 (1H, s), 7.20–7.29 (1H, m), 7.34 (1H, dt, J=7.5, 1.5 Hz), 7.48–7.55 (1H, m), 7.57 (1H, t, J=1.5 Hz).

Example 104
1-(3-Bromophenyl)-6-butoxy-3,4,8,9-tetrahydro-3,3,8,8-tetramethylfuro[2,3-h]isoquinoline Hydrochloride The title compound was obtained from 1-(3-Bromophenyl)-6-butoxy-3,4,8,9-tetrahydro-3,3,8,8-tetramethylfuro[2,3-h]isoquinoline by the method similar to that in Example 29. Yield: 75%.

Melting point: 201–205° C. (sealed tube) (methanol-ethyl acetate-diethyl ether).

$^1$H NMR (DMSO-d$_6$) δ 0.94 (3H, t, J=7.2 Hz), 1.20–1.60 (8H, m), 1.25 (6H, s), 1.65–1.82 (2H, m), 2.21 (2H, s), 3.12 (2H, br s), 4.18 (2H, t, J=6.5 Hz), 7.10 (1H, s), 7.48–7.66 (2H, m), 7.90–7.99 (2H, m), 12.50–13.00 (1H, br).

Example 105
6-Butoxy-3,4,8,9-tetrahydro-3,3,8,8-tetramethyl-1-[3-(4-pyridinyl)phenyl]furo[2,3-h]isoquinoline A solution of sodium carbonate (5.10 g, 48.1 mmol) in water (45 mL) and tetrakis(triphenylphosphine)palladium (0) (1.69 g, 1.46 mmol) were added to a suspension of 1-(3-bromophenyl)-6-butoxy-3,4,8,9-tetrahydro-3,3,8,8-tetramethylfuro[2,3-h]isoquinoline (18.2 g, 39.9 mmol) and 4-pyridinylboronic acid (5.38 g, 43.8 mmol) in N,N-dimethylformamide (75 mL) and the mixture was stirred at 120° C. for 1.5 hours under nitrogen atmosphere. The reaction mixture was cooled and combined with water and ethyl acetate, and the organic layer was separated, and the aqueous layer was extracted with ethyl acetate. The combined organic layer was washed twice with water, and concentrated under reduced pressure. The residue was subjected to a column chromatography on a basic silica gel (hexane/ethyl acetate 10:1 followed by 2:1), and recrystallized from diethyl ether-hexane to obtain the title compound (9.12 g, Yield: 50%).

Melting point: 114–116° C.

$^1$H NMR (CDCl$_3$) δ 0.98 (3H, t, J=7.3 Hz), 1.27 (6H, s), 1.29 (6H, s), 1.39–1.60 (2H, m), 1.75–1.92 (2H, m), 2.21 (2H, s), 2.70 (2H, s), 4.11 (2H, t, J=6.9 Hz), 6.63 (1H, s), 7.45–7.57 (4H, m), 7.64–7.72 (2H, m), 8.66 (2H, d, J=6.2 Hz).

Example 106
6-Ethoxy-3,4,8,9-tetrahydro-3,3,8,8-tetramethyl-1-[3-(4-pyridinyl)phenyl]furo[2,3-h]isoquinoline The title compound was obtained from 1-(3-bromophenyl)-6-ethoxy-3,4,8,9-tetrahydro-3,3,8,8-tetramethylfuro[2,3-h]isoquinoline by the method similar to that in Example 105. Yield: 59%.

Melting point: 102–104° C. (diethyl ether-hexane).

$^1$H NMR (CDCl$_3$) δ 1.27 (6H, s), 1.30 (6H, s), 1.47 (3H, t, J=7.0 Hz), 2.22 (2H, s), 2.70 (2H, s), 4.19 (2H, q, J=7.0 Hz), 6.63 (1H, s), 7.42–7.58 (4H, m), 7.65–7.71 (2H, m), 8.66 (2H, d, J=6.0 Hz).

Example 107
6-Ethoxy-3,4,8,9-tetrahydro-3,3,8,8-tetramethyl-1-phenylfuro[2,3-h]isoquinoline Hydrochloride A free base of the title compound was obtained from 3,4,8,9-tetrahydro-3,3,8,8-tetramethyl-1-phenyl6-furo[2,3-h]isoquinolinol and iodomethane by the method similar to that in Example 99. This was dissolved in ethyl acetate, combined with 0.8 M solution of hydrogen chloride/methanol, and concentrated under reduced pressure to obtain the title compound. Quantitative.

Amorphous.

$^1$H NMR (CDCl$_3$) δ 1.33 (6H, s), 1.51 (3H, t, J=7.0 Hz), 1.69 (6H, s), 2.23 (2H, s), 3.02 (2H, s), 4.28 (2H, q, J=7.0 Hz), 6.73 (1H, s), 7.50–7.75 (5H, m).

Example 108
3,4,8,9-Tetrahydro-6-methoxy-3,3,8,8-tetramethyl-1-phenyl-4-furo[2,3-h]isoquinolinol Aluminum chloride (0.68 g, 5.1 mmol) was added to a solution of 2,3-dihydro-7-methoxy-2,2-dimethyl-5-(2-methyl-1-propenyl)benzofuran (1.17 g, 5.04 mmol) in benzonitrile (10 mL) at −10° C. and the mixture was stirred at the same temperature for 5 minutes. The resultant mixture was treated dropwise with bromine (0.26 mL, 5.0 mmol), and stirred at room temperature for 20 minutes and then at 60° C. for 2 hours. The reaction. mixture was cooled, combined with water and diisopropyl ether, stirred, and then the organic layer was separated. The aqueous layer was neutralized with conc. aqueous ammonia, combined with ethyl acetate, and then the insolubles were filtered off. The aqueous layer was separated, and the organic layer was washed with brine, dried over sodium sulfate, filtered, and concentrated under reduced pressure. The residue was recrystallized from tetrahydrofuran diethyl ether to obtain the title compound (722 mg, Yield: 41%)

Melting point: 207–212° C.

$^1$H NMR (CDCl$_3$) δ 1.25 (3H, s) 1.31 (6H, s), 1.32 (3H, s), 2.21 (2H, s), 3.96 (3H, s), 4.48 (1H, br s), 6.96 (1H, s), 7.40 (5H, s).

Example 109
3-(Bromomethyl)-3,4,8,9-tetrahydro-6-methoxy-3,8,8-triethyl-1-phenylfuro[2,3-h]isoquinoline Aluminum chloride (1.01 g, 7.57 mmol) was added to a solution of 2,3-dihydro-7-methoxy-2,2-dimethyl-5-(2-methyl-2-propenyl)benzofuran (1.76 g, 7.58 mmol) in benzonitrile (15 mL) at −5° C. and the mixture was stirred at the same temperature for 5 minutes. The resultant mixture was treated dropwise with bromine (0.39 mL, 7.6 mmol), and stirred at room temperature for 25 minutes and then at 60° C. for 30 minutes. The reaction mixture was cooled, combined with water and diisopropyl ether, stirred, and then the aqueous layer was separated, and the organic layer was extracted twice with 1 M hydrochloric acid. The combined aqueous layer was neutralized with conc. aqueous ammonia with cooling in ice, and extracted twice with ethyl acetate. The combined organic layer was washed with water and brine, dried over sodium sulfate, filtered, and concentrated under reduced pressure. The residue was subjected to a column chromatography on a silica gel (hexane-ethyl acetate 10:1), and crystallized from diethyl ether-hexane to obtain the title compound (297 mg, Yield: 9.5%).

Melting point: 108–110° C.

$^1$H NMR (CDCl$_3$) δ 1.31 (6H, s), 1.34 (3H, s), 2.20 (2H, s), 2.80 (1H, d, J=15.8 Hz), 2.96 (1H, d, J=15.8 Hz), 3.41 (1H, d, J =9.9 Hz), 3.57 (1H, d, J=9.9 Hz), 3.93 (3H, s), 6.60 (1H, s), 7.40 (5H, s).

Example 110

6-Ethoxy-3,4,8,9-tetrahydro-3,3,8,8-tetramethyl-1-phenylfuro[2,3-h]isoquinoline 2-oxide A solution of sodium tungstate(VI) dihydrate (310 mg, 0.940 mol) in water (3 mL) was added to a solution of 6-ethoxy-1,2,3,4,8,9-hexahydro-3,3,8,8-tetramethyl-1-phenylfuro[2,3-h]isoquinoline (1.65 g, 4.69 mmol) in methanol (10 mL). This was cooled, treated dropwise with 30% aqueous hydrogen peroxide (1.6 g, 14 mmol), and stirred at room temperature for 15 hours. The reaction mixture was combined with water, and extracted with ethyl acetate 3 times. The combined organic layer was washed with water, a 10% aqueous solution of sodium thiosulfate and brine, dried over magnesium sulfate, filtered, and concentrated under reduced pressure. The residue was subjected to a column chromatography on a basic silica gel (hexane/ethyl acetate 5:1 followed by 1:1), and crystallized from diisopropyl ether-hexane to obtain the title compound (1.33 g, Yield: 78%).

Melting point: 125–126° C.

$^1$H NMR (CDCl$_3$) δ 1.27 (6H, s), 1.45 (3H, t, J=7.0 Hz), 1.48 (6H, s), 1.98 (2H, s), 3.04 (2H, s), 4.16 (2H, q, J=7.0 Hz), 6.62 (1H, s), 7.32–7.47 (5H, m).

Example 111

3,4,8,9-Tetrahydro-6-methoxy-3,3,8,8-tetramethyl-1-phenylfuro[2,3-h]isoquinoline 2-oxide The title compound was obtained from 1,2,3,4,8,9-hexahydro-6-methoxy-3,3,8,8-tetramethyl-1-phenylfuro[2,3-h]isoquinoline by the method similar to that in Example 110. Yield: 84%.

Melting point: 177–180° C. (diisopropyl ether).

$^1$H NMR (CDCl$_3$) δ 1.28 (6H, s), 1.49 (6H, s), 1.99 (2H, s), 3.06 (2H, s), 3.91 (3H, s), 6.63 (1H, s), 7.27–7.47 (5H, m).

Example 112

4-(6-Ethoxy-3,4,8,9-tetrahydro-3,3,8,8-tetramethyl-2-oxidefuro[2,3-h]isoquinolin-1-yl)benzamide The title compound was obtained from 4-(6-ethoxy-1,2,3,4,8,9-hexahydro-3,3,8,8-tetramethylfuro[2,3-h]isoquinolin-1-yl)benzamide by the method similar to that in Example 110. Yield: 83%.

Melting point: 134–136, 218–219° C. (ethyl acetate-diisopropyl ether).

$^1$H NMR (CDCl$_3$), δ 1.28 (6H, s), 1.46 (3H, t, J=7.1 Hz), 1.48 (6H, s), 2.00 (2H, s), 3.06 (2H, s), 4.17 (2H, q, J=7.1 Hz), 5.40–6.50 (2H, m), 6.64 (1H, s), 7.55 (2H, d, J=8.4 Hz), 7.89 (2H, d, J=8.4 Hz).

Example 113

5-[(Dimethylamino)methyl]-3,4,8,9-tetrahydro-3,3,8,8-tetramethyl-1-phenyl-6-furo[2,3-h]isoquinolinol A mixture of 3,4,8,9-tetrahydro-3,3,8,8-tetramethyl-1-phenyl-6-furo[2,3-h]isoquinolinol (1.50 g, 4.67 mmol), paraformaldehyde (94%) (0.298 g, 9.34 mmol), a 2 M solution of dimethylamine/tetrahydrofuran (7.00 mL, 14.0 mmol) and ethanol (7 mL) was stirred at 60° C. for 20 minutes. The reaction solution was concentrated under reduced pressure, and the residue was subjected to a column chromatography on a basic silica gel (hexane/ethyl acetate 3:1), and recrystallized from hexane-ethyl acetate to obtain the title compound (1.38 g, Yield: 78%)

Melting point: 164–166° C.

$^1$H NMR (CDCl$_3$) δ 1.23 (6H, s), 1.30 (6H, s), 2.14 (2H, s), 2.38 (6H, s), 2.58 (2H, s), 3.74 (2H, s), 7.37 (5H, s).

Example 114

3,4,8,9-Tetrahydro-6-methoxy-N,N,3,3,8,8-hexamethyl-1-phenyl-5-furo[2,3-h]isoquinolinemethanamine Diisopropyl azodicarboxylate (0.624 mL, 3.18 mmol) was added to a solution of 5-[(dimethylamino)methyl]-3,4,8,9-tetrahydro-3,3,8,8-tetramethyl-1-phenyl-6-furo[2,3-h]isoquinolinol (0.40 g, 1.06 mmol), methanol (0.128 mL, 3.18 mmol) and triphenylphosphine (0.832 g, 3.18 mmol) in tetrahydrofuran (3 mL) with cooling in ice, and the mixture was stirred at room temperature for 30 minutes. The reaction solution was combined with 1 M hydrochloric acid, and washed with ethyl acetate. The aqueous layer was basified with 1 M aqueous solution of sodium hydroxide, and then extracted with ethyl acetate. The extract was washed with water, and then concentrated under reduced pressure. The residue was subjected to a column chromatography on a basic silica gel (hexane/ethyl acetate 9:1) to obtain the title compound (0.40 g, Yield: 96%). An aliquot was recrystallized from hexane.

Melting point: 124–125° C.

$^1$H NMR (CDCl$_3$) δ 1.23 (6H, s), 1.27 (6H, s), 2.13 (2H, s), 2.25 (6H, s), 2.77 (2H, s), 3.45 (2H, s), 3.92 (3H, s), 7.38 (5H, s).

Example 115

3,4,8,9-Tetrahydro-6-methoxy-N,N,N,3,3,8,8-heptamethyl-1-phenyl-5-furo[2,3-h]isoquinolinemethanaminium Iodide Iodomethane (0.309 mL, 4.97 mmol) was added to a solution of 3,4,8,9-tetrahydro-6-methoxy-N,N,3,3,8,8-hexamethyl-1-phenyl-5-furo[2,3-h]isoquinolinemethanamine (1.50 g, 3.82 mmol) in toluene (10 mL) and the mixture was stirred at room temperature for 15 hours. The reaction solution was combined with hexane, and the precipitated crystals were recovered by filtration, dried, and then recrystallized from ethanol-ethyl acetate-hexane to obtain the title compound (1.90 g, Yield: 93%).

Melting point: 174–178° C.

$^1$H NMR (DMSO-d$_6$) δ 1.17 (6H, s), 1.26 (6H, s), 2.21 (2H, s), 2.78 (2H, s), 3.07 (9H, s), 3.94 (3H, s), 4.60 (2H, s), 7.37–7.46 (5H, m).

Example 116

3,4,8,9-Tetrahydro-6-methoxy-3,3,8,8-tetramethyl-1-phenyl-5-[(phenylthio)methyl]furo[2,3-h]isoquinoline Hydrochloride Sodium hydride (66% suspension in oil) (68.0 mg, 1.87 mmol) was added to a solution of thiophenol (0.192 mL, 1.87 mmol) in N,N-dimethylformamide (3 mL) with cooling in ice, and the mixture was stirred at room temperature for 30 minutes. 3,4,8,9-Tetrahydro-6-methoxy-N,N,N,3,3,8,8-heptamethyl-1-phenyl-5-furo[2,3-h]isoquinolinemethanaminium iodide (0.40 g, 0.748 mmol) was added to the mixture, and the mixture was stirred at 70° C. for 1 hour. The reaction solution was combined with water, and extracted with ethyl acetate. The extract was washed with 1 M aqueous solution of sodium hydroxide and water, and then concentrated under reduced pressure. The residue was subjected to a column chromatography on a silica gel (hexane/ethyl acetate 7:3) to obtain a free base (0.31 g, Yield: 91%) of the title compound as an oil.

¹H NMR (CDCl₃) δ 1.23 (6H, s), 1.28 (6H, s), 2.13 (2H, s), 2.67 (2H, s), 3.92 (3H, s), 4.24 (2H, s), 7.18–7.45 (10H, m).

This was converted into a hydrochloride with 4 M solution of hydrogen chloride/ethyl acetate, and then concentrated under reduced pressure to obtain the title compound (0.31 g, Yield: 84%).

Amorphous.

¹H NMR (DMSO-d₆) δ 1.25 (6H, s), 1.43 (6H, s), 2.15 (2H, s), 3.15 (2H, s), 3.90 (3H, s), 4.29 (2H, s), 7.25–7.45 (5H, m), 7.62–7.80 (5H, m).

Example 117
6-Ethoxy-3,4,8,9-tetrahydro-N,N,3,3,8,8-hexamethyl-1-phenyl 5-furo[2,3-h]isoquinolinemethanamine The title compound was obtained using ethanol by the method similar to that in Example 114. Yield: 89%.

Melting point: 106–107° C. (hexane).

¹H NMR (CDCl₃) δ 1.23 (6H, s), 1.25 (6H, s), 1.36 (3H, t, J=7.2 Hz), 2.12 (2H, s), 2.25 (6H, s), 2.77 (2H, s), 3.46 (2H, s), 4.19 (2H, q, J=7.2 Hz), 7.37 (5H, s).

Example 118
5-[(Dimethylamino)methyl]-3,4,8,9-tetrahydro-3,3,8,8-tetramethyl-1-phenylfuro[2,3-h]isoquinolin-6-yl Acetate Acetic anhydride (82.3 µL, 0.872 mmol) was added to a solution of 5-[(dimethylamino)methyl]-3,4,8,9-tetrahydro-3,3,8,8-tetramethyl-1-phenyl-6-furo[2,3-h]isoquinolinol (0.30 g, 0.793 mmol) in pyridine (3 mL), and the mixture was stirred at room temperature for 1 hour. The reaction solution was combined with water, and extracted with ethyl acetate. The extract was washed with water, and then concentrated under reduced pressure. The residue was recrystallized from hexane to obtain the title compound (0.24 g, Yield: 72%).

Melting point: 125–126° C.

¹H NMR (CDCl₃) δ 1.25 (12H, s), 2.17 (2H, s), 2.21 (6H, s), 2.31 (3H, s), 2.79 (2H, s), 3.33 (2H, s), 7.38 (5H, s).

Example 119
3,4,8,9-Tetrahydro-3,3,8,8-tetramethyl-1-phenyl-5-[(1-pyridinyl)methyl]-6-furo[2,3-h]isoquinolinol The title compound was obtained using piperidine by the method similar to that in Example 113. Yield: 85%.

Melting point: 164–165° C.

¹H NMR (CDCl₃) δ 1.22 (6H, s), 1.29 (6H, s), 1.40–1.72 (6H, m), 2.14 (2H, s), 2.40–2.79 (4H, m), 2.56 (2H, s), 3.76 (2H, s), 5.32 (1H, br s), 7.37 (5H, s).

Example 120
3,4,8,9-Tetrahydro-6-methoxy-3,3,8,8-tetramethyl-1-phenyl-5-[(1-piperidinyl)methyl]furo[2,3-h]isoquinoline Dihydrochloride A free base of the title compound was obtained as an oil from 3,4,8,9-tetrahydro-3,3,8,8-tetramethyl-1-phenyl-5-[(1-piperidinyl)methyl]-6-furo[2,3-h]isoquinolinol by the method similar to that in Example 114. Yield: 85%.

¹H NMR (CDCl₃) δ 1.23 (6H, s), 1.28 (6H, s), 1.37–1.60 (6H, m), 2.13 (2H, s), 2.37–2.44 (4H, m), 2.82 (2H, s), 3.48 (2H, s), 3.89 (3H, s), 7.38 (5H, s).

This free base was converted into a hydrochloride with 4 M solution of hydrogen chloride/ethyl acetate, and then concentrated under reduced pressure to obtain the title compound. Yield: 80%.

Amorphous.

¹H NMR (DMSO-d₆) δ 1.27 (6H, s), 1.47 (6H, s), 1.55–1.86 (6H, m), 1.90–2.10 (2H, m), 2.19 (2H, s), 2.90–3.10 (2H, m), 3.80–3.88 (2H, m), 3.96 (3H, s), 4.37 (2H, br s), 7.60–7.82 (5H, m).

Example 121
6-Ethoxy-3,4,8,9-tetrahydro-3,3,8,8-tetramethyl-1-phenyl-5-[(1-piperidinyl)methyl]furo[2,3-h]isoquinoline The title compound was obtained from 3,4,8,9-tetrahydro-3,3,8,8-tetramethyl-1-phenyl-5-[(1-piperidinyl)methyl]-6-furo[2,3-h]isoquinolinol and ethanol by the method similar to that in Example 114. Yield: 87%.

Melting point: 75–77° C. (ethyl acetate-hexane).

¹H NMR (CDCl₃) δ 1.23 (6H, s), 1.26 (6H, s), 1.36 (3H, t, J=7.0 Hz), 1.40–1.58 (6H, m), 2.12 (2H, s), 2.37–2.43 (4H, m), 2.82 (2H, s), 3.49 (2H, s), 4.16 (2H, q, J=7.0 Hz), 7.35–7.42 (5H, m).

Example 122
3,4,8,9-Tetrahydro-3,3,8,8-tetramethyl-1-phenyl-5-[(1-piperidinyl)methyl]furo[2,3-h]isoquinolin-6-yl Acetate Dihydrochloride.

A free base of the title compound was obtained from 3,4,8,9-tetrahydro-3,3,8–8-tetramethyl-1-phenyl-5-[(1-piperidinyl)methyl]-6-furo[2,3-h]isoquinolinol by the method similar to that in Example 118. This was converted into a hydrochloride with 4 M solution of hydrogen chloride/ethyl acetate, and then concentrated under reduced pressure to obtain the title compound. Yield: 96%.

Amorphous.

¹H NMR (DMSO-d₆) δ 1.22 (6H, s), 1.49 (6H, s), 1.61–1.82 (4H, m), 1.93–2.45 (7H, m), 2.95–3.10 (2H, m), 3.38–3.64 (4H, m), 4.40–4.48 (2H, m), 7.60–7.83 (5H, m).

Example 123
3,4,8,9-Tetrahydro-6-methoxy-3,3,8,8-tetramethyl-1-(3-nitrophenyl)furo[2,3-h]isoquinoline Conc. sulfuric acid (2.75 mL. 51.6 mmol) was added to a solution of 2,3-dihydro-7-methoxy-2,2-dimethyl-5-(2-methyl-1-propenyl)benzofuran (6.00 g, 25.8 mmol), 3-nitrobenzonitrile (3.83 g, 25.8 mmol) and acetic acid (18 mL) in toluene (24 mL), and the mixture was stirred at 80° C. for 1 hour. The reaction solution was combined with excessive aqueous ammonia, and extracted with ethyl acetate. The extract was washed with water, and concentrated under reduced pressure. The residue was subjected to a column chromatography on a basic silica gel (hexane/ethyl acetate 17:3) to obtain the title compound (4.28 g, Yield: 44%).

Amorphous.

¹H NMR (CDCl₃) δ 1.26 (6H, s), 1.32 (6H, s), 2.19 (2H, s), 2.71 (2H, s), 3.94 (3H, s), 6.65 (1H, s), 7.59 (1H, t, J=7.8 Hz), 7.73–7.79 (1H, m), 8.22–8.32 (2H, m).

Example 124
3,4,8,9-Tetrahydro-3,3,8,8-tetramethyl-1-(3-nitrophenyl)-6-furo[2,3-h]isoquinolinol Under nitrogen atmosphere, a mixture of 3,4,8,9-tetrahydro-6-methoxy-3,3,8,8-tetramethyl-1-(3-nitrophenyl)furo[2,3-h]isoquinoline (4.20 g, 11.0 mmol) and hydrobromic acid (42 mL) was stirred at 100° C. for 20 hours. The reaction solution was cooled, combined with aqueous ammonia, and then extracted with ethyl acetate. The extract was washed with water, and then concentrated under reduced pressure. The residue was subjected to a column chromatography on a silica gel (hexane/ethyl acetate 1:1), and recrystallized from ethyl acetate-hexane to obtain the title compound (2.50 g, Yield: 62%).

Melting point: 239–241° C.

$^1$H NMR (CDCl$_3$) δ 1.26 (6H, s), 1.30 (6H, s), 2.18 (2H, s), 2.67 (2H, s), 6.62 (1H, s), 7.58 (1H, t, J=7.8 Hz), 7.73–7.80 (1H, m), 8.22–8.31 (2H, m).

Example 125
3,4,8,9-Tetrahydro-3,3,8,8-tetramethyl-1-(3-nitrophenyl)-5-[(1-piperidinyl)methyl]-6-furo[2,3-h]isoquinolinol The title compound was obtained from 3,4,8,9-tetrahydro-3,3,8,8-tetramethyl-1-(3-nitrophenyl)-6-furo[2,3-h]isoquinolinol and piperidine by the method similar to that in Example 113. Yield: 78%.

Amorphous.

$^1$H NMR (CDCl$_3$) δ 1.24 (6H, s), 1.31 (6H, s), 1.46–1.72 (6H, m), 2.13 (2H, s), 2.40–2.80 (4H, m), 2.58 (2H, s), 3.78 (2H, s), 6.30 (1H, s), 7.56 (1H, t, J=8.0 Hz), 7.72–7.78 (1H, m), 8.22–8.31 (2H, m).

Example 126
6-Ethoxy-3,4,8,9-tetrahydro-3,3,8,8-tetramethyl-1-(3-nitrophenyl)-5-[(1-piperidinyl)methyl]furo[2,3-h]isoquinoline The title compound was obtained from 3,4,8,9-tetrahydro-3,3,8,8-tetramethyl-1-(3-nitrophenyl)-5-[(1-piperidinyl)methyl]-6-furo[2,3-h]isoquinolinol and ethanol by the method similar to that in Example 114. Yield: 97%.

Amorphous.

$^1$H NMR (CDCl$_3$) δ 1.24 (6H, s), 1.28 (6H, s), 1.37 (3H, t, J=7.0 Hz), 1.40–1.60 (6H, m), 2.11 (2H, s), 2.36–2.44 (4H, m), 2.84 (2H, s), 3.49 (2H, s), 4.18 (2H, q, J=7.0 Hz), 7.57 (1H, t, J=8.0 Hz), 7.78 (1H, d, J=8.0 Hz), 8.22–8.31 (2H, m).

Example 127
3-[6-Ethoxy-3,4,8,9-tetrahydro-3,3,8,8-tetramethyl-5-[(1-piperidinyl)methyl]furo[2,3-h]isoquinolin-1-yl]benzenamine 20% aqueous solution of titanium trichloride (9.13 mL, 14.2 mmol) was added to a solution of 6-ethoxy-3,4,8,9-tetrahydro-3,3,8,8-tetramethyl-1-(3-nitrophenyl)-5-[(1-piperidinyl)methyl]furo[2,3-h]isoquinoline (1.00 g, 2.03 mmol) in acetic acid (5 mL) and the mixture was stirred at room temperature for 30 minutes. The reaction solution was poured into an excessive saturated aqueous solution of sodium hydrogen carbonate, and extracted with ethyl acetate. Tie extract was washed with water, and then concentrated under reduced pressure to obtain the title compound (0.90 g, Yield: 96%).

Amorphous.

$^1$H NMR (CDCl$_3$) δ 1.21 (6H, s), 1.28 (6H, s), 1.36 (3H, t, J=7.2 Hz), 1.42–1.58 (6H, m), 2.27 (2H, s), 2.38–2.45 (2H, m), 2.80 (2H, s), 3.48 (2H, s), 3.77 (2H, br s), 4.16 (2H, q, J=7.2 Hz), 6.66–6.76 (3H, m), 7.13 (1H, t, J=7.4 Hz).

Example 128
2-[[[3-[6-Ethoxy-3,4,8,9-tetrahydro-3,3,8,8-tetramethyl-5-[(1-piperidinyl)methyl]furo[2,3-h]isoquinolin-1-yl]phenyl]amino]carbonyl]benzoic Acid A solution of phthalic anhydride (0.314 g, 2.12 mmol) in tetrahydrofuran (3 mL) was added to a solution of 3-[6-ethoxy-3,4,8,9-tetrahydro-3,3,8,8-tetramethyl-5-[(1-piperidinyl)methyl]furo[2,3-h]isoquinolin-1-yl]benzenamine (0.98 g, 2.12 mmol) in tetrahydrofuran (3 mL), and the mixture was stirred at room temperature for 4 hours. The reaction solution was combined with diisopropyl ether, and the precipitated crystals were recovered by filtration and dried to obtain the title compound (1.20 g, Yield: 93%).

Melting point: 155–157° C.

$^1$H NMR (DMSO-d$_6$) δ 1.13 (6H, s), 1.26 (6H, s), 1.28 (3H, t, J=7.0 Hz), 1.40–1.60 (6H, m), 2.34 (2H, s), 2.42–2.56 (4H, m), 2.78 (2H, s), 3.60 (2H, s), 4.12 (2H, q, J=7.0 Hz), 7.08 (1H, d, J=7.8 Hz), 7.36 (1H, t, J=7.8 Hz), 7.58–7.84 (7H, m), 10.77 (1H, br s).

Example 129
2-[3-[6-Ethoxy-3,4,8,9-tetrahydro-3,3,8,8-tetramethyl-5-[(1-piperidinyl)methyl]furo[2,3-h]isoquinolin-1-yl]phenyl]-1H-isoindole-1,3(2H)-dione A mixture of 2-[[[3-[6-ethoxy-3,4,8,9-tetrahydro-3,3,8,8-tetramethyl-5-[(1-piperidinyl)methyl]furo[2,3-h]isoquinolin-1-yl]phenyl]amino]carbonyl]benzoic acid and acetic anhydride (5 mL) was stirred at 100° C. for 1 hour. The reaction solution was combined with an excessive saturated aqueous solution of sodium hydrogen carbonate, and extracted with ethyl acetate. The extract was washed with water, and then concentrated under reduced pressure. The residue was subjected to a column chromatography on a silica gel (ethyl acetate), and recrystallized from methanol-diisopropyl ether to obtain the title compound (0.50 g, Yield: 52%).

Melting point: 176–177° C.

$^1$H NMR (DMSO-d$_6$) δ 1.18 (6H, br s), 1.23 (3H, t, J=7.0 Hz), 1.27 (6H, s), 1.43 (6H, br s), 2.35 (4H, br s), 2.62–2.83 (4H, m), 3.42 (2H, s), 4.11 (2H, q, J=7.0 Hz), 7.38–7.40 (1H, m), 7.43–7.61 (3H, m), 7.84–7.96 (4H, m).

Example 130
N-[3-[6-Ethoxy-3,4,8,9-tetrahydro-3,3,8,8-tetramethyl-5-[(1-piperidinyl)methyl]furo[2,3-h]isoquinolin-1-yl]phenyl]methanesulfonamide Methanesulfonyl chloride (0.352 mL, 4.56 mmol) was added to a solution of 3-[6-ethoxy-3,4,8,9-tetrahydro-3,3,8,8-tetramethyl-5-[(1-piperidinyl)methyl]furo[2,3-h]isoquinolin-1-yl]benzenamine (0.70 g, 1.52 mmol) in pyridine (4 mL) and the mixture was stirred at room temperature for 3 hours. The reaction solution was combined with an excessive saturated aqueous solution of sodium hydrogen carbonate, and extracted with ethyl acetate. The extract was washed with water, and then concentrated under reduced pressure. The residue was recrystallized from methanol-diisopropyl ether to obtain the title compound (0.52 g, Yield: 63%).

Melting point: 230–231° C.

$^1$H NMR (DMSO-d$_6$) δ 1.12 (6H, s), 1.24 (6H, s), 1.28 (3H, t, J=7.0 Hz), 1.42 (6H, br s), 2.22 (2H, s), 2.34 (4H, br s), 2.74 (2H, s), 2.99 (3H, s), 3.44 (2H, br s), 4.09 (2H, q, J=7.0 Hz), 7.10–7.15 (2H, m), 7.28–7.43 (2H, m), 9.72 (1H, br s).

Example 131
N-[3-[6-Ethoxy-3,4,8,9-tetrahydro-3,3,8,8-tetramethyl-5-[(1-piperidinyl)methyl]furo[2,3-h]isoquinolin-1-yl]phenyl]-N-(methylsulfonyl)methanesulfonamide Methanesulfonyl chloride (0.184 mL, 2.38 mmol) was added to a solution of N-[3-[6-ethoxy-3,4,8,9-tetrahydro-3,3,8,8-tetramethyl-5-[(1-piperidinyl)methyl]furo[2,3-h]isoquinolin-1-yl]phenyl]methanesulfonamide (0.64 g, 1.19 mmol) and triethylamine (0.496 mL, 3.57 mmol) in tetrahydrofuran (5 mL) and the mixture was heated under reflux for 20 minutes. The reaction mixture was cooled, poured into a saturated aqueous solution of sodium hydrogen carbonate, and then extracted with ethyl acetate. The extract was washed with water, and then concentrated under reduced pressure. The residue was subjected to a column chromatography on a basic silica gel (hexane/ethyl acetate 2:1), and then recrystallized from methanol-diisopropyl ether to obtain the title compound (0.45 g, Yield: 61%).

Melting point: 118–119° C.
¹H NMR (DMSO-$d_6$) δ 1.10–1.31 (15H, m), 1.42 (6H, br s), 2.35 (4H, br s), 2.60–2.83 (4H, m), 3.43 (2H, s), 3.55 (6H, s), 4.08 (2H, q, J=7.0 Hz), 7.42 (1H, s), 7.50–7.60 (3H, m).

Example 132

3,4,8,9-Tetrahydro-3,3,8,8-tetramethyl-5-(2-methylethyl)-1-phenyl-6-furo[2,3-h]isoquinolinol A mixture of 3,4,8,9-tetrahydro-3,3,8,8-tetramethyl-1-phenyl-6-furo[2,3-h]isoquinolinol (0.30 g, 0.933 mmol), 2-propanol (0.357 mL, 4.67 mmol) and conc. sulfuric acid (0.995 mL, 18.7 mmol) was stirred at 55° C. for 1 hour. The reaction solution was poured into an excessive saturated aqueous solution of sodium hydrogen carbonate, and extracted with ethyl acetate. The extract was washed with water, and then concentrated under reduced pressure. The residue was subjected to a column chromatography on a basic silica gel (hexane/ethyl acetate 3:1), and then recrystallized from ethyl acetate-hexane to obtain the title compound (0.18 g, Yield: 53%).
Amorphous.
¹H NMR (CDCl₃) δ 1.24 (6H, s), 1.27 (6H, s), 1.38 (6H, d, J=7.2 Hz), 2.15 (2H, s), 2.70 (2H, s), 3.25–3.46 (1H, m), 7.37 (5H, m).

Example 133

3,4,8,9-Tetrahydro-6-methoxy-3,3,8,8-tetramethyl-5-(1-methylethyl)-1-phenylfuro[2,3-h]isoquinoline Hydrochloride A free base of the title compound was obtained as an oil from 3,4,8,9-tetrahydro-3,3,8,8-tetramethyl-5-(1-methylethyl)-1-phenyl-6-furo[2,3-h]isoquinolinol by the method similar to that in Example 114. Yield: 69%. This free base was converted into a hydrochloride with 4 M solution of hydrogen chloride/ethyl acetate, and then concentrated under reduced pressure to obtain the title compound. Yield: 65%.
Amorphous.
¹H NMR (DMSO-$d_6$) δ 1.25 (6H, s), 1.30 (6H, d, J=7.0 Hz), 1.45 (6H, s), 2.12 (2H, s), 3.17 (2 Hz s), 3.23–3.45 (1H, m), 3.97 (3H, s), 7.52–7.78 (5H, m).

Example 134

6-Ethoxy-3,4,8,9-tetrahydro-3,3,8,8-tetramethyl-5-(1-methylethyl)-1-phenylfuro[2,3-h]isoquinoline Hydrochloride A free base of the title compound was obtained as an oil from 3,4,8,9-tetrahydro-3,3,8,8-tetramethyl-5-(1-methylethyl)-1-phenyl-6-furo[2,3-h]isoquinolinol and ethanol by the method similar to that in Example 114. Yield: 40%. This free base was converted into a hydrochloride with 4 M solution of hydrogen chloride/ethyl acetate, and then concentrated under reduced pressure to obtain the title compound. Yield: 39%.
Amorphous.
¹H NMR (DMSO-$d_6$) δ 1.23 (6H, s), 1.32 (6H, d, J=7.0 Hz), 1.34 (3H, t, J=7.0 Hz), 1.45 (6H, s), 2.11 (2H, s), 3.17 (2H, s), 3.31–3.46 (1H, m), 4.33 (2H, q, J=7.0 Hz), 7.52–7.78 (5H, m).

Example 135

3,4,8,9-Tetrahydro-3,3,8,8-tetramethyl-5-(1-methylethyl)-1-phenylfuro[2,3-h]isoquinolin-6-yl Acetate Hydrochloride A free base of the title compound was obtained as an oil from 3,4,8,9-tetrahydro-3,3,8,8-tetramethyl-5-(1-methylethyl)-1-phenyl-6-furo[2,3-h]isoquinolinol by the method similar to that in Example 118. Yield: 93%. This was converted into a hydrochloride with 4 M solution of hydrogen chloride/ethyl acetate, and then concentrated under reduced pressure to obtain the title compound. Yield: 87%.
Amorphous.
¹H NMR (DMSO-$d_6$) δ 1.19 (6H, s), 1.26 (6H, d, J=7.0 Hz), 1.48 (6H, s), 2.17 (2H, s), 2.35 (3H, s), 3.23 (2H, s), 3.35 (1H, septet, J=7.0 Hz), 7.60–7.80 (5H, m).

Example 136

3,4,8,9-Tetrahydro-3,3,8,8-tetramethyl-6-[(2-methyl-2-propenyl)oxy]-1-phenylfuro[2,3-h]isoquinoline Hydrochloride Under nitrogen atmosphere, a suspension of 3,4,8,9-tetrahydro-3,3,8,8-tetramethyl-1-phenyl-6-furo[2,3-h]isoquinolinol (0.80 g, 2.49 mmol), 3-chloro-2-methyl-1-propene (0.258 mL, 2.61 mmol) and potassium carbonate (0.361 g, 2.61 mmol) in N,N-dimethylformamide (4 mL) was stirred at 80° C. for 2 hours. The reaction mixture was combined with water and extracted with ethyl acetate. The extract was washed with water, and then concentrated under reduced pressure. The residue was subjected to a column chromatography on a basic silica gel (hexane/ethyl acetate 9:1) to obtain a free base (0.93 g, quantitative) of the title compound as an oil. An aliquot was converted into a hydrochloride salt with 4 M solution of hydrogen chloride/ethyl acetate, and then concentrated under reduced pressure to obtain the title compound.
Amorphous.
¹H NMR (DMSO-$d_6$) δ 1.23 (6H, s), 1.46 (6H, s), 1.78 (3H, s), 2.17 (2H, s), 3.15 (2H, s), 4.70 (2H, s), 5.02 (1H, s), 5.08 (1H, s), 7.11 (1H, s), 7.61–7.80 (5H, m).

Example 137

3,4,8,9-Tetrahydro-3,3,8,8-tetramethyl-5-(2-methyl-2-propenyl)-1-phenyl-6-furo[2,3-h]isoquinolinol Under nitrogen atmosphere, a solution of 3,4,8,9-tetrahydro-3,3,8,8-tetramethyl-6-[(2-methyl-2-propenyl)oxy]-1-phenylfuro[2,3-h]isoquinoline (0.78 g, 2.08 mmol) in N,N-diethylaniline (4 mL) was stirred at 205° C. for 4.5 hours. The reaction solution was cooled, and then combined with hexane, and the precipitated crystals were recovered by filtration. Recrystallization from ethyl acetate-hexane gave the title compound (0.41 g, Yield: 53%).
Melting point: 196–198° C.
¹H NMR (CDCl₃) δ 1.22 (6H, s), 1.28 (6H, s), 1.84 (3H, s), 2.17 (2H, s), 2.59 (2H, s), 3.37 (2H, s), 4.51 (1H, s), 4.80 (1H, s), 7.37 (5H, s).

Example 138

3,4,8,9-Tetrahydro-3,3,8,8-tetramethyl-1-phenyl-6-[(2-propynyl)oxy]furo[2,3-h]isoquinoline Hydrochloride Under nitrogen atmosphere, a mixture of 3,4,8,9-tetrahydro-3,3,8,8-tetramethyl-1-phenyl-6-furo[2,3-h]isoquinolinol (1.00 g, 3.11 mmol), propargyl bromide (0.305 mL, 3.42 mmol), potassium carbonate (0.473 g, 3.42 mmol) and N,N-dimethylformamide (10 mL) was stirred at 60° C. for 2 hours. The reaction mixture was combined with water, and extracted with ethyl acetate. The extract was washed with water, and then concentrated under reduced pressure. The residue was subjected to a column chromatography on a silica gel (hexane/ethyl acetate 1:1) to obtain a free base (1.11 g, quantitative) of the title compound as an oil.
¹H NMR (CDCl₃) δ 1.25 (6H, s), 1.30 (6H, s), 2.19 (2H, s), 2.55 (1H, t, J=2.4 Hz), 2.70 (2H, s), 4.83 (2H, d, J=2.4 Hz), 6.77 (1H, s), 7.39 (5H, s).

An aliquot was converted into a hydrochloride salt with 4 M solution of hydrogen chloride/ethyl acetate, and then concentrated under reduced pressure to obtain the title compound.
Amorphous.
¹H NMR (DMSO-$d_6$) δ 1.23 (6H, s), 1.46 (6H, s), 2.18 (2H, s), 3.17 (2H, s), 3.76 (1H, s), 5.02 (2H, s), 7.14 (1H, s), 7.62–7.80 (5H, m).

Example 139
4-(3,4,8,9-Tetrahydro-6-methoxy-3,3,8,8-tetramethylfuro[2,3-h]isoquinolin-1-yl)benzoyl Chloride Hydrochloride A mixture of 4-(3,4,8,9-tetrahydro-6-methoxy-3,3,8,8-tetramethylfuro[2,3-h]isoquinolin-1-yl)benzoic acid hydrochloride (0.30 g, 0.721 mmol) and thionyl chloride (1 mL) was stirred at 70° C. for 1 hour. The reaction solution was concentrated under reduced pressure to obtain the title compound (0.30 g, Yield: 96%). This was used in the next reaction without further purification.

Example 140
3-(3,4,8,9-Tetrahydro-6-methoxy-3,3,8,8-tetramethylfuro[2,3-h]isoquinolin-1-yl)benzoyl Chloride Hydrochloride The title compound was obtained as an amorphous material using 3-(3,4,8,9-tetrahydro-6-methoxy-3,3,8,8-tetramethylfuro[2,3-h]isoquinolin-1-yl)benzoic acid hydrochloride by the method similar to that in Example 139. Yield: 96%. This compound was used in the next reaction without further purification.

Example 141
N-(4-Pyridinyl)-4-(3,4,8,9-tetrahydro-6-methoxy-3,3,8,8-tetramethylfuro[2,3-h]isoquinolin-1-yl)benzamide Dihydrochloride 4-(3,4,8,9-Tetrahydro-6-methoxy-3,3,8,8-tetramethylfuro[2,3-h]isoquinolin-1-yl)benzoyl chloride hydrochloride (0.30 g, 0.691 mmol) was added to a solution of 4-aminopyridine (71.5 mg, 0.760 mmol) and triethylamine (0.116 mL, 0.829 mmol) in N,N-dimethylformamide (1 mL) with cooling in ice, and the mixture was stirred at room temperature for 1 hour. The reaction mixture was combined with a saturated aqueous solution of sodium hydrogen carbonate, and extracted with ethyl acetate. The extract was washed with water, and then concentrated under reduced pressure. The residue was subjected to a column chromatography on a silica gel (ethyl acetate/methanol 19:1) to obtain a free base (0.31 g, Yield: 98%) of the title compound as an oil. This was converted into a hydrochloride salt with 4 M solution of hydrogen chloride/ethyl acetate, concentrated under reduced pressure, and then recrystallized from methanol-ethyl acetate to obtain the title compound (0.29 g, Yield: 74%).

Melting point: 194–198° C.
$^1$H NMR (DMSO-$d_6$) δ 1.24 (6H, s), 1.49 (6H, s), 2.22 (2H, s), 3.20 (2H, s), 3.96 (3H, s), 7.13 (1H, s), 7.84 (2H, d, J=8.0 Hz), 8.45 (2H, d, J=8.0 Hz), 8.63 (2H, d, J=7.0 Hz), 8.82 (2H, d, J=7.0 Hz), 12.55 (1H, s).

Example 142
N-(3-Pyridinyl)-4-(3,4,8,9-tetrahydro-6-methoxy-3,3,8,8-tetramethylfuro[2,3-h]isoquinolin-1-yl)benzamide Dihydrochloride The title compound was obtained using 3-aminopyridine by the method similar to that in Example 141. Yield: 85%.
Amorphous.
$^1$H NMR (DMSO-$d_6$) δ 1.24 (6H, s), 1.49 (6H, s), 2.23 (2H, s), 3.20 (2H, s), 3.96 (3H, s), 7.14 (1H, s), 7.84 (2H, d, J=8.0 Hz), 8.08–8.17 (1H, m), 8.46 (2H, d, J=8.0 Hz), 8.71 (1H, d, J=5.4 Hz), 9.10 (1H, d, J=7.6 Hz), 9.56 (1H, s), 12.15 (1H, s).

Example 143
N-(2-Pyridinyl)-4-(3,4,8,9-tetrahydro-6-methoxy-3,3,8,8-tetramethylfuro[2,3-h]isoquinolin-1-yl)benzamide Dihydrochloride The title compound was obtained using 2-aminopyridine by the method similar to that in Example 141. Yield: 74%. Amorphous.
$^1$H NMR (DMSO-$d_6$) δ 1.24 (6H, s), 1.49 (6H, s), 2.22 (2H, s), 3.20 (2H, s), 3.96 (3H, s), 7.13 (1H, s), 7.38–7.46 (1H, m), 7.83 (2H, d, J=7.8 Hz), 7.91–7.99 (1H, m), 8.12–8.20 (1H, m), 8.37 (2H, d, J=7.8 Hz), 8.53 (1H, d, J=4.4 Hz), 12.04 (1H, s).

Example 144
N-(4-Pyridinylmethyl)-4-(3,4,8,9-tetrahydro-6-methoxy-3,3,8,8-tetramethylfuro[2,3-h]isoquinolin-1-yl)benzamide Dihydrochloride The title compound was obtained using 4-(aminomethyl)pyridine by the method similar to that in Example 141. Yield: 75%.

Melting point: 220–225° C. (methanol-ethyl acetate).
$^1$H NMR (DMSO-$d_6$) δ 1.24 (6H, s), 1.48 (6H, s), 2.22 (2H, s), 3.19 (2H, s), 3.95 (3H, s), 4.77 (2H, d, J=5.4 Hz), 7.13 (1H, s), 7.78 (2H, d, J=8.4 Hz), 7.98 (2H, d, J=6.2 Hz), 8.23 (2H, d, J=8.4 Hz), 8.87 (2H, d, J=6.2 Hz), 9.96–10.03 (1H,

Example 145
N-(3-Pyridinylmethyl)-4-(3,4,8,9-tetrahydro-6-methoxy-3,3,8,8-tetramethylfuro[2,3-h]isoquinolin-1-yl)benzamide Dihydrochloride The title compound was obtained using 3-(aminomethyl)pyridine by the method similar to that in Example 141. Quantitative.
Amorphous.
$^1$H NMR (DMSO-$d_6$) δ 1.23 (6H, s), 1.47 (6H, s), 2.22 (2H, s), 3.18 (2H, s), 3.95 (3H, s), 4.70 (2H, d, J=4.0 Hz), 7.12 (1H, s), 7.77 (2H, d, J=8.0 Hz), 8.01–8.08 (1H, m), 8.22 (2H, d, J=8.0 Hz), 8.58 (1H, d, J=7.4 Hz), 8.85 (1H, d, J=5.2 Hz), 8.95 (1H, s), 9.95–10.04 (1H, m).

Example 146
N-(2-Pyridinylmethyl)-4-(3,4,8,9-tetrahydro-6-methoxy-3,3,8,8-tetramethylfuro[2,3-h]isoquinolin-1-yl)benzamide Dihydrochloride The title compound was obtained using 2-(aminomethyl)pyridine by the method similar to that in Example 141. Yield: 75%.
Amorphous.
$^1$H NMR (DMSO-$d_6$) δ 1.24 (6H, s), 1.48 (6H, s), 2.21 (2H, s), 3.19 (2H, s), 3.95 (3H, s), 4.90 (2H, s), 7.13 (1H, s), 7.78 (2H, d, J=7.2 Hz), 7.90–8.04 (2H, m), 8.24 (2H, d, J=7.2 Hz), 8.46–8.55 (1H, m), 8.85 (1H, d, J=4.8 Hz), 10.05 (1H, s).

Example 147
N-[2-(4-Pyridinyl)ethyl]-4-(3,4,8,9-tetrahydro-6-methoxy-3,3,8,8-tetramethylfuro[2,3-h]isoquinolin-1-yl)benzamide Dihydrochloride The title compound was obtained using 4-(2-aminoethyl)pyridine by the method similar to that in Example 141. Yield: 83%.
Amorphous.
$^1$H NMR (DMSO-$d_6$) δ 1.23 (6H, s), 1.47 (6H, s), 2.18 (2H, s), 3.16–3.27 (4H, m), 3.65–3.76 (2H, m), 3.95 (3H, s), 7.12 (1H, s), 7.72 (2H, d, J=7.6 Hz), 7.96–8.12 (4H, m), 8.84 (2H, d, J=5.6 Hz), 9.25 (1H, br s).

Example 148
N-(4-Pyridinylmethyl)-3-(3,4,8,9-tetrahydro-6-methoxy-3,3,8,8-tetramethylfuro[2,3-h]isoquinolin-1-yl)benzamide 3-(3,4,8,9-Tetrahydro-6-methoxy-3,3,8,8-tetramethylfuro[2,3-h]isoquinolin-1-yl)benzoyl chloride hydrochloride (0.50 g, 1.15 mmol) was added to a solution of 4-(aminomethyl)pyridine (0.129 mL, 1.27 mmol) and triethylamine (0.193 mL, 1.38 mmol) in N,N-dimethylformamide (5 mL) with cooling in ice, and the mixture was stirred with cooling in ice for 30 minutes. The reaction mixture was combined with a saturated aqueous solution of sodium hydrogen carbonate, and extracted with ethyl acetate. The extract was washed with water, and then concentrated under reduced pressure. The residue was recrystallized from ethyl acetate-diisopropyl ether to obtain the title compound (0.32 g, Yield: 59%).

Melting point: 197–198° C.

$^1$H NMR (CDCl$_3$) δ 1.19 (6H, s), 1.30 (6H, s), 2.18 (2H, s), 2.63 (2H, s), 3.93 (3H, s), 4.59 (2H, d, J=6.0 Hz), 6.61 (1H, s), 7.19 (2H, d, J=5.8 Hz), 7.41–7.53 (3H, m), 7.93–8.01 (2H, m), 8.51–8.56 (2H, m).

Example 149

N-[2-(4-Pyridinyl)ethyl]-3-(3,4,8,9-tetrahydro-6-methoxy-3,3,8,8-tetramethylfuro[2,3-h]isoquinolin-1-yl)benzamide The title compound was obtained using 4-(2-aminoethyl) pyridine by the method similar to that in Example 148. Yield:68%.

Melting point: 144–145° C. (ethyl acetate-diisopropyl ether).

$^1$H NMR (CDCl$_3$) δ 1.24 (6H, s), 1.30 (6H, s), 2.17 (2H, s), 2.68 (2H, s), 2.91 (2H, t, J=7.2 Hz), 3.70 (2H, q, J=7.2 Hz), 3.93 (3H, s), 6.62 (1H, s), 6.65 (1H, br s), 7.17 (2H, d, J=6.2 Hz), 7.41–7.50 (2H, m), 7.79 (1H, s), 7.81–7.87 (1H, m), 8.51 (2H, d, J=6.2 Hz).

Example 150

N-(2-Pyrimidinyl)-4-(3,4,8,9-tetrahydro-6-methoxy-3,3,8,8-tetramethylfuro[2,3-h]isoquinolin-1-yl)benzamide Dihydrochloride 4-(3,4,8,9-Tetrahydro-6-methoxy-3,3,8,8-tetramethylfuro[2,3-h]isoquinolin-1-yl) benzoyl chloride hydrochloride (0.30 g, 0.691 mmol) was added to a solution of 2-aminopyrimidine (72.3 mg, 0.760 mol) in pyridine (3 mL), and the mixture was stirred at room temperature for 2 hours. The reaction solution was combined with a saturated aqueous solution of sodium hydrogen carbonate, and extracted with ethyl acetate. The extract was washed with water, and then concentrated under reduced pressure. The residue was converted into a hydrochloride salt with 4 M solution of hydrogen chloride/ethyl acetate, and then concentrated under reduced pressure to obtain the title compound (0.29 g, Yield: 79%).

Amorphous.

$^1$H NMR (DMSO-d$_6$) δ 1.24 (6H, s), 1.48 (6H, s), 2.18 (2H, s), 3.20 (2H, s), 3.97 (3H, s), 7.11 (1H, s), 7.38–7.51 (1H, m), 7.83 (2H, d, J=8.0 Hz), 8.50 (2H, d, J=8.0 Hz), 8.92–9.98 (2H, m), 11.82 (1H, br s).

Example 151

N-Pyrazinyl-4-(3,4,8,9-tetrahydro-6-methoxy -3,3,8,8-tetramethylfuro[2,3-h]isoquinolin-1-yl)benzamide 4-(3,4,8,9-Tetrahydro-6-methoxy-3,3,8,8-tetramethylfuro[2,3-h]isoquinolin-1-yl)benzoyl chloride hydrochloride (0.30 g, 0.691 mmol) was added to a solution of aminopyrazine (72.3 mg, 0.760 mmol) in pyridine (3 mL) and the mixture was stirred at room temperature for 5 hours. The reaction solution was combined with a saturated aqueous solution of sodium hydrogen carbonate, and extracted with ethyl acetate. The extract was washed with water, and then concentrated under reduced pressure. The residue was subjected to a column chromatography on a basic silicas gel (ethyl acetate/methanol 19:1) to obtain the title compound (0.27 g, Yield: 86%).

Amorphous.

$^1$H NMR (DMSO-d$_6$) δ 1.27 (6H, s), 1.32 (6H, s), 2.21 (2H, s), 2.72 (2H, s), 3.93 (3H, s), 6.64 (1H, s), 7.58 (2H, d, J=8.4 Hz), 7.99 (2H, d, J=8.4 Hz), 8.27–8.33 (1H, m), 8.42 (1H, d, J=2.6 Hz), 8.61 (1H, br s), 9.75 (1H, d, J=1.6 Hz).

Example 152

N-(6-Chloro-3-pyridazinyl)-4-(3,4,8,9-tetrahydro-6-methoxy-3,3,8,8-tetramethylfuro[2,3-h]isoquinolin-1-yl) benzamide The title compound was obtained using 3-amino-6-chloropyridazine by the method similar to that in Example 151. Yield: 85%.

Amorphous.

$^1$H NMR (DMSO-d$_6$) δ 1.27 (6H, s), 1.33 (6H, s), 2.21 (2H, s), 2.71 (2H, s), 3.93 (3H, s), 6.64 (1H, s), 6.74 (1H, d, J=9.2 Hz), 7.25 (1H, d, J=9.2 Hz), 7.59 (2H, d, J=8.4 Hz), 8.00 (2H, d, J=8.4 Hz), 9.18 (1H, br 5).

Example 153

N-(4-Pyridinyl)-3-(3,4,8,9-tetrahydro-6-methoxy-3,3,8,8-tetramethylfuro[2,3-h]isoquinolin-1-yl)benzamide 3-(3,4,8,9-Tetrahydro-6-methoxy-3,3,8,8-tetramethylfuro[2,3-h]isoquinolin-1-yl)benzoyl chloride hydrochloride (0.50 g, 1.15 mmol) was added to a solution of 4-aminopyridine (0.119 g, 1.27 mmol) in pyridine (5 mL) and the mixture was stirred at 50° C. for 1 hour. The reaction solution was combined with a saturated aqueous solution of sodium hydrogen carbonate, and extracted with ethyl acetate. The extract was washed with water, and then concentrated under reduced pressure. The residue was recrystallized from ethyl acetate-diisopropyl ether to obtain the title compound (0.25 g, Yield: 48%).

Melting point: 175–176° C.

$^1$H NMR (CDCl$_3$) δ 1.27 (6H, s), 1.31 (6H, s), 2.22 (2H, s), 2.71 (2H, s), 3.93 (3H, s), 6.64 (1H, s), 7.48–7.58 (2H, m), 7.72–7.88 (2H, m), 8.00–8.06 (2H, m), 8.48–8.54 (2H, m), 9.71 (1H, br s).

Example 154

N-(3,5-Dichloro-4-pyridinyl)-3-(3,4,8,9-tetrahydro-6-methoxy-3,3,8,8-tetramethylfuro[2,3-h]isoquinolin-1-yl) benzamide A mixture of 3-(3,4,8,9-tetrahydro-6-methoxy-3,3,8,8-tetramethylfuro[2,3-h]isoquinolin-1-yl)benzoic acid hydrochloride (2.17 g, 5.22 mmol) and thionyl chloride (2 mL) was stirred at 70° C. for 1 hour. The reaction solution was concentrated under reduced pressure, and the residue was combined with toluene, and concentrated under reduced pressure again. A solution of 4-Amino-3,5-dichloropyridine (0.50 g, 3.07 mmol) in N,N-dimethylformamide (10 mL) was cooled with ice and sodium hydride (66% suspension in oil) (0.379 g, 10.4 mmol) was added to the solution. And then, the acid chloride which had been previously prepared was added thereto. The mixture was stirred at room temperature for 30 minutes, poured into ice water, and then extracted with ethyl acetate. The extract was washed with water, and then concentrated under reduced pressure. The residue was subjected to a column chromatography on a basic silica gel (ethyl acetate) to obtain the title compound (0.35 g, Yield: 22%).

Melting point: 227–228° C.

$^1$H NMR (CDCl$_3$) δ 1.21 (6H, s), 1.32 (6H, s), 2.23 (2H, s), 2.66 (2H, s), 3.93 (3H, s), 6.63 (1H, s), 7.52 (1H, t, J=7.8 Hz), 7.69 (1H, t, J=7.8 Hz), 8.00–8.06 (2H, m), 8.57 (2H, s), 9.02 (1H, br s).

Example 155
N-[3-(3,4,8,9-Tetrahydro-6-methoxy-3,3,8,8-tetramethylfuro[2,3-h]isoquinolin-1-yl)benzoyl]glycine Ethyl Ester Hydrochloride Triethylamine (5.86 mL, 42.0 mmol) was added to a solution of 3-(3,4,8,9-tetrahydro-6-methoxy-3,3,8,8-tetramethylfuro[2,3-h]isoquinolin-1-yl)benzoic acid hydrochloride (5.00 g, 12.0 mmol), glycine ethyl ester hydrochloride (1.85 g, 13.2 mmol) and 1-hydroxy-1H-benzotriazole monohydrate (2.03 g, 13.2 mmol) in N,N-dimethylformamide (30 mL). And then, 1-ethyl-3-(3-dimethylaminopropyl)carbodiimide hydrochloride (3.00 g, 15.6 mmol),was added thereto. The mixture was stirred at room temperature for 5 hours, and then poured into a saturated aqueous solution of sodium hydrogen carbonate. This was extracted with ethyl acetate, and then the extract was washed with water, and concentrated under reduced pressure. The residue was subjected to a column chromatography on a basic silica gel (hexane/ethyl acetate 1:1) to obtain a free base (5.05 g, Yield: 94%) of the title-compound.

$^1$H NMR (CDCl$_3$) δ 1.25 (6H, s), 1.30 (3H, t, J=7.2 Hz), 1.31 (6H, s), 2.17 (2H, s), 2.69 (2H, s), 3.93 (3H, s), 4.21–4.30 (4H, m), 6.62 (1H, s), 6.89–6.95 (1H, m), 7.42–7.55 (2H, m), 7.83–7.91 (2H, m).

An aliquot was converted into a hydrochloride salt with 4 M solution of hydrogen chloride/ethyl acetate, and then concentrated under reduced pressure to obtain the title compound.

Amorphous.

$^1$H NMR (DMSO-d$_6$) δ 1.21 (6H, s), 1.22 (3H, t, J=7.8 Hz), 1.47 (6H, s), 2.19 (2H, s), 2.78 (2H, s), 3.95 (3H, s), 4.03 (2H, t, J=6.2 Hz), 4.12 (2H, q, J=7.8 Hz), 7.12 (1H, s), 7.75–7.83 (2H, m), 8.16 (1H, s), 8.22–8.29 (1H, m), 9.28–9.35 (1H, m).

Example 156
N-[3-(3,4,8,9-Tetrahydro-6-methoxy-3,3,8,8-tetramethylfuro[2,3-h]isoquinolin-1-yl)benzoyl]glycine Hydrochloride 5 M aqueous solution of sodium hydroxide (5 mL) was added to a solution of N-[3-(3,4,8,9-tetrahydro-6-methoxy-3,3,8,8-tetramethylfuro[2,3-h]isoquinolin-1-yl)benzoyl] glycine ethyl ester (5.00 g, 11.1 mmol) in ethanol (20 mL) and the mixture was stirred at room temperature for 1 hour. 5 M hydrochloric acid (7.5 mL) was added to the reaction mixture and the mixture was concentrated under reduced pressure. The residue was combined with ethanol and filtered, and the filtrate was concentrated under reduced pressure, and this procedure was repeated 3 times. The residue was combined with diisopropyl ether, and a precipitate was recovered by filtration and dried to obtain the title compound (5.15 g, Yield: 98%).

Amorphous.

$^1$H NMR (DMSO-d$_6$) δ 1.23 (6H, s), 1.47 (6H, s), 2.21 (2H, s), 3.18 (2H, s), 3.95 (3H, s), 3.96–4.06 (2H, m), 7.12 (1H, s), 7.70–7.82 (2H, m), 8.18–8.28 (2H, m), 9.20–9.28 (1H, m).

Example 157
N-(2-Amino-2-oxoethyl)-3-(3,4,8,9-tetrahydro-6-methoxy-3,3,8,8-tetramethylfuro[2,3-h]isoquinolin-1-yl)benzamide 1-Ethyl-3-(3-dimethylaminopropyl)carbodiimide hydrochloride (0.422 g, 2.20 mmol) was added to a solution of N-[3-(3,4,8,9-tetrahydro-6-methoxy-3,3,8,8-tetramethylfuro[2,3-h]isoquinolin-1-yl)benzoyl]glycine hydrochloride (0.80 g, 1.69 mmol) and 1-hydroxy-1H-benzotriazole monohydrate (0.285 g, 1.86 mmol) in N,N-dimethylformamide (4 mL) and the mixture was stirred at room temperature for 5 hours. Conc. aqueous ammonia (1.7 mL) was added thereto, and the mixture was stirred at room temperature further for 1.5 hours. The reaction solution was combined with water, and extracted with ethyl acetate. The extract was washed with water, and then concentrated under reduced pressure. The residue was subjected to a column chromatography on a basic silica gel (ethyl acetate followed by ethyl acetate/methanol 19:1) to obtain the title compound (0.43 g, Yield: 58%). An aliquot was recrystallized from ethyl acetate-diisopropyl ether.

Melting point: 141–142° C.

$^1$H NMR (CDCl$_3$) δ 1.23 (6H, s), 1.30 (6H, s), 2.16 (2H, s), 2.67 (2H, s), 3.93 (3H, s), 4.08 (2H, d, J=5.0 Hz), 5.72 (1H, br s), 6.33 (1H, br s), 6.62 (1H, s), 7.43–7.55 (2H, m), 7.62–7.70 (1H, m), 7.89–7.99 (2H, m).

Example 158
N-[2-(Methylamino)-2-oxoethyl]-3-(3,4,8,9-tetrahydro-6-methoxy-3,3,8,8-tetramethylfuro[2,3-h]isoquinolin-1-yl)benzamide The title compound was obtained using a 40% solution of methylamine/methanol by the method similar to that in Example 157. Yield: 40%.

Melting point: 212–213° C. (ethyl acetate-hexane).

$^1$H NMR (CDCl$_3$) δ 1.23 (6H, s), 1.30 (6H, s), 2.16 (2H, s), 2.68 (2H, s), 2.83 (3H, d, J=4.8 Hz), 3.93 (3H, s), 4.05 (2H, d, J=4.8 Hz), 6.21 (1H, br s), 6.62 (1H, s), 7.42–7.55 (3H, m), 7.88–7.96 (2H, m).

Example 159
N-[2-Oxo-2-(phenylamino)ethyl]-3-(3,4,8,9-tetrahydro-6-methoxy-3,3,8,8-tetramethylfuro[2,3-h]isoquinolin-1-yl)benzamide Triethylamine (0.707 mL, 5.07 mmol) and amiline (0.170 mL, 1.86 mmol) were added to a solution of N-[3-(3,4,8,9-tetrahydro-6-methoxy-3,3,8,8-tetramethylfuro[2,3-h]isoquinolin-1-yl)benzoyl]glycine hydrochloride (0.80 g, 1.69 mmol) and 1-hydroxy-1H-benzotriazole monohydrate (0.285 g, 1.86 mmol) in N,N-dimethylformamide (4 mL). And then, 1-ethyl-3-(3-dimethylaminopropyl)carbodiimide hydrochloride (0.422 g, 2.20 mmol) was added thereto and the mixture was stirred at room temperature for 2 hours. The reaction mixture was combined with a saturated aqueous solution of sodium hydrogen carbonate, and extracted with ethyl acetate. The extract was washed with water, and then concentrated under reduced pressure. The residue was subjected to a column chromatography on a basic silica gel (hexane/ethyl acetate 1:1 followed by ethyl acetate/methanol 19:1) to obtain the title compound (0.30 g, Yield:35%).

Amorphous.

$^1$H NMR (DMSO-d$_6$) δ 1.23 (6H, s), 1.27 (6H, s), 2.14 (2H, s), 2.65 (2H, s), 3.93 (3H, s) 4.21 (2H, d, J=5.6 Hz), 6.62 (1H, s), 7.10 (1H, t, J=7.6 Hz), 7.26–7.41 (3H, m), 7.46–7.57 (3H, m), 7.87–7.94 (2H, m), 8.06–8.15 (1H, m), 8.90 (1H, s).

Example 160
N-[2-Oxo-2-[(4-pyridinylmethyl)amino]ethyl]-3-(3,4,8,9-tetrahydro-6-methoxy-3,3,8,8-tetramethylfuro[2,3-h]isoquinolin-1-yl)benzamide The title compound was obtained using 4-(aminomethyl)pyridine by the method similar to that in Example 159. Yield: 62%.

Melting point: 197–198° C. (ethyl acetate-diisopropyl ether).

$^1$H NMR (CDCl$_3$) δ 1.22 (6H, s), 1.29 (6H, s), 2.16 (2H, s), 2.67 (2H, s), 3.93 (3H, s), 4.12 (2H, d, J=5.4 Hz), 4.43

(2H, d, J=6.0 Hz), 6.62 (1H, s), 7.11–7.19 (3H, m), 7.41–7.50 (2H, m), 7.65–7.71 (1H, m), 7.84–7.91 (1H, m), 7.97 (1H, s), 8.48–8.55 (2H, m).

Example 161

N-[2-Oxo-2-[[2-(4-pyridinyl)ethyl]amino]ethyl]-3-[3,4,8,9-tetrahydro-6-methoxy-3,3,8,8-tetramethylfuro[2,3-h]isoquinolin-1-yl]benzamide The title compound was obtained using 4-(2-aminoethyl)pyridine by the method similar to that in Example 159. Yield: 82%.

Amorphous.

$^1$H NMR (CDCl$_3$) δ 1.20 (6H, s), 1.30 (6H, s), 2.17 (2H, s), 2.66 (2H, s), 2.81 (2H, t, J=6.0 Hz), 3.52 (2H, q, J=6.0 Hz), 3.92 (3H, s), 3.97 (2H, d, J=5.4 Hz), 6.61 (1H, s), 6.72–6.78 (1H, m), 7.10 (2H, d, J=6.2 Hz), 7.41–7.50 (2H, m), 7.76–7.81 (1H, m), 7.88–7.94 (1H, m), 7.98 (1H, s), 8.41–8.47 (2H, m).

Example 162

N-[2-(3-pyridinyl)ethyl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2 3-h]isoquinoline-1-yl)benzoic acid hydrochloride and 3-(2-aminoethyl)pyridine by the method similar to that in Example 159. Yield: 88%.

Amorphous.

$^1$H NMR (CDCl$_3$) δ 1.24 (6H, s), 1.30 (6H, s), 2.18 (2H, s), 2.68 (2H, s), 2.87–2.96 (2H, m), 3.69 (2H, q, J=6.6 Hz), 3.93 (3H, s), 6.62 (1H, s), 6.71 (1H, br s), 7.21–7.28 (1H, m), 7.43–7.48 (2H, m), 7.58–7.62 (1H, m), 7.80–7.86 (2H, m), 8.48–8.50 (2H, m).

Example 163

N-[2-(2-Pyridinyl)ethyl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 2-(2-aminoethyl)pyridine by the method similar to that in Example 159. Yield: 71%.

Amorphous.

$^1$H NMR (CDCl$_3$) δ 1.26 (6H, s), 1.27 (6H, s), 2.17 (2H, s), 2.70 (2H, s), 3.09 (2H, t, J=6.2 Hz), 3.85 (2H, q, J=6.2 Hz), 3.94 (3H, s), 6.64 (1H, s), 7.10–7.22 (2H, m), 7.40–7.51 (2H, m), 7.58–7.70 (2H, m), 7.80 (1H, m), 7.84–7.90 (1H, m), 8.42 (1H, d, J=4.4 Hz).

Example 164

N-[3-(4-Pyridinyl)propyl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 4-(3-aminopropyl)pyridine by the method similar to that in Example 159. Yield: 63%.

Melting point: 175–176° C. (ethyl acetate-diisopropyl ether).

$^1$H NMR (CDCl$_3$) δ 1.23 (6H, s), 1.29 (6H, s), 1.82–1.99 (2H, m), 2.16 (2H, s), 2.62–2.72 (4H, m), 3.41–3.50 (2H, m), 3.92 (3H, s), 6.60–6.65 (1H, m), 7.13 (2H, d, J=6.0 Hz), 7.43–7.46 (2H, m), 7.83–7.90 (2H, m), 8.50 (2H, d, J=6.0 Hz).

Example 165

N-[3-(3-Pyridinyl)propyl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 3-(3-aminopropyl)pyridine by the method similar to that in Example 159. Yield: 55%.

Melting point: 161–162° C. (ethyl acetate-diisopropyl ether).

$^1$H NMR (CDCl$_3$) δ 1.21 (6H, s), 1.29 (6H, s), 1.79–1.95 (2H, m), 2.14–2.18 (2H, m), 2.60–2.69 (4H, m), 3.38–3.49 (2H, m), 3.92 (3H, s), 6.61 (1H, s), 6.81–6.90 (1H, m), 7.18–7.24 (1H, m), 7.41–7.55 (3H, m), 7.86–7.93 (2H, m), 8.42–8.47 (2H, m).

Example 166

N-[3-(1H-Imidazol-1-yl)propyl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 1-(3-aminopropyl)imidazole by the method similar to that in Example 159. Yield: 70%.

Melting point: 104–106° C. (ethyl acetate-hexane).

$^1$H NMR (CDCl$_3$) δ 1.22 (6H, s), 1.30 (6H, s), 2.04 (2H, quintet, J=7.0 Hz), 2.18 (2H, s), 2.68 (2H, s), 3.36–3.47 (2H, m), 3.93 (3H, s), 4.01 (2H, t, J=7.0 Hz), 6.62 (1H, s), 6.90–6.97 (2H, m), 7.05 (1H, s), 7.44–7.50 (3H, m), 7.85–7.90 (2H, m).

Example 167

N-[2-[4-(Aminosulfonyl)phenyl]ethyl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 4-(2-aminoethyl)benzenesulfonamide by the method similar to that in Example 159. Yield: 85%.

Melting point: 138–139° C. (ethyl acetate-diisopropyl ether).

$^1$H NMR (CDCl$_3$) δ 1.21 (6H, s), 1.28 (6H, s), 2.15 (2H, s), 2.68 (2H, s), 2.91–2.98 (2H, m), 3.63–3.75 (2H, m), 3.93 (3H, s), 5.22 (2H, br s), 6.62 (1H, s), 6.78–6.84 (1H, m), 7.33 (2H, d, J=8.0 Hz), 7.46 (2H, d, J=4.8 Hz), 7.73–7.80 (3H, m), 7.83–7.89 (1H, m).

Example 168

N-(Hexahydro-2-oxo-1H-azepin-3-yl)-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 3-aminohexahydro-2-azepinone by the method similar to that in Example 159. Yield: 65%.

Melting point: 187–188° C. (ethyl acetate-hexane).

$^1$H NMR (CDCl$_3$) δ 1.25 (3H, s), 1.27 (3H, s), 1.30 (6H, s), 1.50–2.25 (6H, m), 2.16 (2H, s), 2.70 (2H, s), 3.18–3.40 (2H, m), 3.93 (3H, s), 4.68–4.77 (1H, m), 6.41 (1H, br s), 6.62 (1H, s), 7.41–7.49 (2H, m), 7.75–7.80 (1H, m), 7.88–7.96 (2H, m).

Example 169

N-(Hexahydro-5-oxo-1,4-thiazepin-6-yl)-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]

isoquinolin-1-yl)benzoic acid hydrochloride and 6-amino-1,4-thiazepin-5-one by the method similar to that in Example 159. Yield: 51%.

Melting point: 206–207° C. (ethyl acetate-diisopropyl ether).

$^1$H NMR (CDCl$_3$) δ 1.26 (6H, s), 1.29 (6H, s),2.14 (2H, s), 2.50–2.89 (3H, m), 2.71 (2H, s), 2.87–2.97 (1H, m), 3.58–3.83 (2H, m), 3.93 (3H, s), 5.05–5.13 (1H, m), 6.62 (1H, s), 6.80-6.88 (1H, m), 7.45–7.50 (2H, m), 7.89–7.96 (3H, m).

Example 170
N-[2-(4-Pyridinylamino)ethyl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 4-[(2-aminoethyl)amino]pyridine by the method similar to that in Example 159. Yield: 53%.

Amorphous.

$^1$H NMR (CDCl$_3$) δ 1.22 (6H, s), 1.29 (6H, s), 2.17 (2H, s), 2.66 (2H, s), 3.30–3.39 (2H, m), 3.60–3.70 (2H, m), 3.92 (3H, s), 5.12–5.18 (1H, m), 6.44 (2H, d, J=5.2 Hz), 6.62 (1H, s), 7.38–7.44 (3H, m), 7.82–7.90 (2H, m), 8.14 (2H, d, J=5.2 Hz).

Example 171
N-[2-(2-Pyridinylamino)ethyl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 2-[(2-aminoethyl)amino]pyridine by the method similar to that in Example 159. Yield: 33%.

Amorphous.

$^1$H NMR (CDCl$_3$) δ 1.27 (12H, s), 2.14 (2H, s), 2.71 (2H, s), 3.63 (4H, s), 3.93 (3H, s), 4.91 (1H, br s), 6.40–6.52 (2H, m), 6.64 (1H, s), 7.29–7.39 (1H, m), 7.43–7.48 (2H, m), 7.84 (1H, s), 7.90–7.99 (2H, m), 8.49 (1H, br s).

Example 172
N-[2-(Diethylamino)ethyl3–3-(3,4,8,9-tetrahydro-6-methoxy-3,3,8,8-tetramethylfuro[2,3-h]isoquinolin-1-yl)benzamide Dihydrochloride The title compound was obtained from N,N-diethylethylenediamine by the method similar to that in Example 155. Yield: 47%.

Amorphous.

$^1$H NMR (DMSO-d$_6$) δ 1.22 (6H, t, J=7.4 Hz), 1.24 (6H, s), 1.48 (6H, s), 2.20 (2H, s), 3.12–3.32 (4H, m), 3.62–3.81 (6H, m), 3.95 (3H, s), 7.12 (1H, s), 7.72–7.81 (2H, m), 8.25–8.34 (2H, m).

Example 173
N-(8-Methyl-8-azabicyclo[3.2.1]oct-3-yl)-3-(3,4,8,9-tetrahydro-6-methoxy-3,3,8,8-tetramethylfuro(2,3-h]isoquinolin-1-yl)benzamide Dihydrochloride The title compound was obtained using 3-amino-8-methyl-8-azabicyclo[3.2.1]octane by the method-similar to that in Example 155. Yield: 49%.

Amorphous.

$^1$H NMR (DMSO-d$_6$) δ 1.23 (6H, s), 1.43 (6H, s), 2.17–2.80 (14H, m), 2.96–3.22 (2H, m), 3.85 (2H, br s), 3.95 (3H, s), 7.12 (1H, s), 7.72–7.79 (2H, m), 8.14–8.19 (1H, m), 8.27 (1H, s).

Example 174
N-(1-Azabicyclo[2.2.2]oct-3-yl)-3-(3,4,8,9-tetrahydro-6-methoxy-3,3,8,8-tetramethylfuro[2,3-h]isoquinolin-1-yl)benzamide Dihydrochloride The title compound was obtained using 3-amino-1-azabicyclo[2.2.2]octane by the method similar to that in Example 155. Yield: 49%.

Amorphous.

$^1$H NMR (DMSO-d$_6$) δ 1.23 (6H, s), 1.48 (6H, s), 1.88–2.38 (7H, m), 3.18–3.83 (8H, m), 3.97 (3H, s), 4.27–4.48 (1H, m), 7.12 (1H, s), 7.70–7.78 (2H, m), 8.22–8.33 (1H, m), 8.43 (1H, s).

Example 175
N-(2-Amino-2-oxoethyl)-4-(3,4,8,9-tetrahydro-6-methoxy-3,3,8,8-tetramethylfuro[2,3-h]isoquinolin-1-yl)benzamide The title compound was obtained from-4-(3,4,8,9-tetrahydro-6-methoxy-3,3,8,8-tetramethylfuro[2,3-h]isoquinolin-1-yl)benzoic-acid hydrochloride and glycinamide hydrochloride by the method similar to that in Example 159. Yield: 31%.

Melting point: 135–136° C. (ethyl acetate-hexane).

$^1$H NMR (CDCl$_3$) δ 1.25 (6H, s), 1.31 (6H, s), 2.18 (2H, s), 2.70 (2H, s), 3.92 (3H, s), 4.13 (2H, d, J=5.0 Hz), 5.85 (1H, br s), 6.56–6.65 (2H, m), 7.44–7.57 (3H, m), 7.86 (2H, d, J=8.0 Hz).

Example 176
2-Methyl-N-[3-(3,4,8,9-tetrahydro-6-methoxy-3,3,8,8-tetramethylfuro[2,3-h]isoquinolin-1-yl)benzoyl]alanine Ethyl Ester Triethylamine (0.938 mL, 6.72 mmol) and 1-ethyl-3-(3-dimethylaminopropyl)carbodiimide hydrochloride (0.479 g, 2.50 mmol) were added to a solution of 3-(3,4,8,9-tetrahydro-6-methoxy-3,3,8,8-tetramethylfuro[2,3-h]isoquinolin-1-yl)benzoic acid hydrochloride (0.80 g, 1.92 mmol), 1-hydroxy-1H-benzotriazole monohydrate (0.324 g. 2.11 mmol), ethyl 2-aminoisobutyrate hydrochloride (0.355 g, 2.11 mmol) in N,N-dimethylformamide (4 mL) and the mixture was stirred at room temperature for 2 hours. The reaction mixture was combined with water, and extracted with ethyl acetate. The extract was washed with water, and then concentrated under reduced pressure. The residue was subjected to a column chromatography on a basic silica gel (ethyl acetate/methanol 1:1), and recrystallized from diisopropyl ether-hexane to obtain the title compound (0.63 g, Yield: 67).

Melting point: 114–115° C.

$^1$H NMR (CDCl$_3$) 1.26 (6H, s), 1.28 (3H, t, J=7.0 Hz), 1.30 (6H, s), 1.67 (6H, s), 2.17 (2H, s), 2.70 (2H, s), 3.93 (3H, s), 4.23 (2H, q, J=7.0 Hz), 6.62 (1H, s), 6.88 (1H, br s), 7.42–7.51 (2H, m), 7.81–7.91 (2H, m).

Example 177
2-Methyl-N-[3-(3,4,8,9-tetrahydro-6-methoxy-3,3,8,8-tetramethylfuro[2,3-h]isoquinolin-1-yl)benzoyl]alanine Hydrochloride 1 M aqueous solution of sodium hydroxide (8.0 mL) was added to a solution of 2-methyl-N-[3-(3,4,8,9-tetrahydro-6-methoxy-3,3,8,8-tetramethylfuro[2,3-h]isoquinolin-1-yl)benzoyl]alanine ethyl ester (2.60 g, 5.28 mmol) in ethanol (10 mL) and the mixture was stirred at room temperature for 12 hours. 1 M hydrochloric acid (13.5 mL) was added to the reaction mixture and the mixture was concentrated under reduced pressure. The residue was combined with ethanol and filtered, and the filtrate was concentrated under reduced pressure, and this procedure was repeated 3 times. The residue was crystallized from ethyl acetate to obtain the title compound (2.38 g, Yield: 90%).

Melting point: 197–201° C.

$^1$H NMR (DMSO-d$_6$) δ 1.24 (6H, br s), 1.49 (6H, s), 1.53 (6H, s), 2.22–2.30 (2H, m), 3.10–3.22 (2H, m), 3.95 (3H, s), 7.12 (1H, 5 5), 7.65–7.78 (2H, m), 8.16–8.22 (1H, m), 8.30 (1H, s), 8.90 (1H, m).

Example 178
N-(2-Amino-1,1-dimethyl-2-oxoethyl)-3-(3,4,8,9-tetrahydro-6-methoxy-3,3,8,8-tetramethylfuro[2,3-h]isoquinolin-1-yl)benzamide 1-Ethyl-3-(3-dimethylaminopropyl)carbodiimide hydrochloride (0.920 g, 4.80 mmol) was added to a solution of 2-methyl-N-[3-(3,4,8,9-tetrahydro-6-methoxy-3,3,8,8-tetramethylfuro[2,3-h]isoquinolin-1-yl)benzoyl]alanine hydrochloride (1.85 g, 3.69 mmol), 1-hydroxy-1H-benzotriazole monohydrate (0.622 g, 4.06 mmol) in N,N-dimethylformamide (20 mL) and the mixture was stirred at room temperature for 15 minutes. Conc. aqueous ammonia (3.7 mL) was added thereto and the mixture was stirred at room temperature further for 15 minutes. The reaction solution was combined with water, and extracted with ethyl acetate. The extract was washed with water, and then concentrated under reduced pressure. The residue was subjected to a column chromatography on a basic silica gel (ethyl acetate/hexane 9:1 followed by ethyl acetate/methanol 19:1), and then recrystallized from ethyl acetate-diisopropyl ether to obtain the title compound (1.05 g, Yield: 61%).

Melting point: 129–131° C.

$^1$H NMR (CDCl$_3$) δ 1.25 (6H, s), 1.31 (6H, s), 1.69 (6H, s), 2.19 (2H, s), 2.70 (2H, s), 3.93 (3H, s), 5.58 (1H, br s), 6.48 (1H, br s), 6.62 (1H, s), 7.11 (1H, s), 7.42–7.48 (2H, m), 7.86–7.90 (2H, m).

Example 179
N-Methyl-3-(3,4,8,9-tetrahydro-6-methoxy-3,3,8,8-tetramethylfuro[2,3-h]isoquinolin-1-yl)benzamide 1-Ethyl-3-(3-dimethylaminopropyl)carbodiimide hydrochloride (0.479 g, 2.50 mmol) was added to a solution of 3-(3,4,8,9-tetrahydro-6-methoxy-3,3,8,8-tetramethylfuro[2,3-h]isoquinolin-1-yl)benzoic acid hydrochloride (0.80 g, 1.92 mmol), 1-hydroxy-1H-benzotriazole monohydrate (0.324 g, 2.11 mmol) in N,N-dimethylformamide (4 mL) and the mixture was stirred at room temperature for 20 minutes. 40% solution of methylamine/methanol (1.0 mL) was added to the reaction mixture and the mixture was stirred at room temperature further for 2 hours. The reaction solution was combined with water, and extracted with ethyl acetate. The extract was washed with water, and then concentrated under reduced pressure. The residue was recrystallized from ethyl acetate-diisopropyl ether to obtain the title compound (0.39 g, Yield: 62%).

Melting point: 206–207° C.

$^1$H NMR (CDCl$_3$) δ 1.24 (6H, s), 1.29 (6H, s), 2.16 (2H, s), 2.67 (2H, s), 2.98 (3H, d, J=4.6 Hz), 3.93 (3H, s), 6.58–6.70 (1H, 20 m), 6.62 (1H, s), 7.40–7.48 (2H, m), 7.78 (1H, s), 7.83–7.90 (1H, m).

(Alternative Synthetic Method)

A mixture of 1-(2,3-dihydro-7-methoxy-2,2-dimethyl-5-benzofuranyl)-2-methyl-1-propanol (1.13 g, 4.50 mmol), 3-cyano-N-methylbenzamide (0.60 g, 3.75 mmol), acetic acid (4 mL) and toluene (6 mL) was cooled with ice, and conc. sulfuric acid (0.519 mL, 9.75 mmol) was added thereto. The mixture was stirred at 80° C. for 1 hour, and then the reaction solution was allowed to cool to room temperature, and combined with water. This was washed with diethyl ether, and then the aqueous layer was basified with conc. aqueous ammonia, and extracted with ethyl acetate. The extract was washed with water, and concentrated under reduced pressure. The residue was crystallized from ethyl acetate-hexane to obtain 0.79 g of the material. This was recrystallized from ethyl acetate to obtain the title compound (0.61 g, Yield: 42%).

Melting point: 202–203° C.

Example 180
N-Ethyl-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and a 70% aqueous solution of ethylamine by the method similar to that in Example 157. Yield: 58%.

Melting point: 186–187° C. (ethyl acetate-diisopropyl ether).

$^1$H NMR (CDCl$_3$) δ 1.24 (3H, t, J=5.4 Hz), 1.25 (6H, s), 1.30 (6H, s), 2.17 (2H, s), 2.69 (2H, s), 3.41–3.55 (2H, m), 3.93 (3H, s), 6.38–6.45 (1H, m), 6.62 (1H, s), 7.42–7.48 (2H, m), 7.78 (1H, s), 7.85–7.91 (1H, m).

Example 181
3,4,8,9-Tetrahydro-6-methoxy-3,3,8,8-tetramethyl-N-phenyl-1-furo[2,3-h]isoquinolinamine Phosphorus pentoxide (0.68 g, 2.41 mmol) was added to a solution of N-[2-(2,3-dihydro-7-methoxy-2,2-dimethyl-5-benzofuranyl)-1,1-dimethylethyl]-N'-phenylurea (0.68 g, 1.85 mmol) in phosphorus oxychloride (3 mL) and the mixture was stirred at 80° C. for 10 minutes. The reaction mixture was added to an excessive saturated aqueous solution of sodium hydrogen carbonate, and the mixture was extracted with ethyl acetate. The extract was washed with water, and then concentrated under reduced pressure. The residue was subjected to a column chromatography on a silica gel (hexane/ethyl acetate 3:2) to obtain the title compound (0.34 go Yield: 52%). An aliquot was recrystalized from hexane-ethyl acetate.

Melting point: 135–136° C.

$^1$H NMR (CDCl$_3$) δ 1.17 (6H, s), 1.51 (6H, s), 2.79 (2H, s), 3.53 (2H, s), 3.91 (3H, s), 4.59 (1H, br s), 6.52 (1H, s), 6.88–6.93 (2H, m), 6.95–7.04 (1H, m), 7.29–7.37 (2H, m).

Example 182
3,4,8,9-Tetrahydro-6-methoxy-N-(4-methoxyphenyl)-3,3,8,8-tetramethyl-1-furo[2,3-h]isoquinolinamine A mixture of N-[2-(2,3-dihydro-7-methoxy-2,2-dimethyl-5-benzofuranyl)-1,1-dimethylethyl]-N'-(4-methoxyphenyl)urea (1.00 g, 2.51 mmol), phosphorus oxychloride (1.92 g, 12.6 mmol) and toluene (10 mL) was stirred at room temperature for 2 hours, and at 80° C. further for 30 minutes. The reaction mixture was poured into excessive aqueous solution of sodium hydroxide, and extracted with ethyl acetate. The extract was washed with water, and then concentrated under reduced pressure. The residue was subjected to a column chromatography on a silica gel (hexane/ethyl acetate 2:3) to obtain the title compound (0.50 g, Yield: 52%). An aliquot was recrystallized from hexane-ethyl acetate.

Melting point: 139–140° C.

$^1$H NMR (CDCl$_3$) δ 1.17 (6H, s), 1.51 (6H, s), 2.78 (2H, s), 3.53 (2H, s), 3.80 (3H, s), 3.90 (3H, s), 4.62 (1H, br s), 6.52 (1H, s), 6.81–6.93 (4H, m).

Example 183
3,4,8,9-Tetrahydro-6-methoxy-3,3,8,8-tetramethyl-1-(1-piperidinyl)furo[2,3-h]isoquinoline Hydrochloride A free base of the title compound was obtained from N-[2-(2,3-dihydro-7-methoxy-2,2-dimethyl-5-benzofuranyl)-1,1-dimethylethyl]-1-piperidinecarboxamide by the method similar to that in Example 182. This was dissolved in ethanol. 4 M solution of hydrogen chloride/ethyl acetate was added to the reaction mixture and the mixture was concentrated under reduced pressure. The residue was recrystallized from ethanol-diethyl ether to obtain the title compound. Yield: 20%.

Melting point: 137–139° C.

$^1$H NMR (DMSO-d$_6$) δ 1.22 (6H, s), 1.42 (6H, s), 1.64(6H, s), 2.86 (2H, s), 3.12 (2H, s), 3.42–3.75 (4H, m), 3.86 (3H, s), 6.96 (1H, s), 9.31 (1H, s).

Example 184
8',9'-Dihydro-6'-methoxy-8',8'-dimethyl-1'-phenylspiro[cyclohexane-1,3 (4'H)-furo[2,3-h]isoquinoline] Hydrochloride Conc. sulfuric acid (0.333 mL, 6.24 mmol) was added to a solution of 5-(cyclohexylidenemethyl)-2,3-dihydro-7-methoxy-2,2-dimethylbenzofuran (0.85 g, 3.12 mmol) and benzonitrile (0.350 mL, 3.43 mmol) in acetic acid (4 mL) and the mixture was stirred at 80° C. for 10 minutes. The reaction solution was added to an aqueous solution of sodium hydroxide, and the mixture was extracted with ethyl acetate. The extract was washed with water, and then concentrated under reduced pressure. The residue was subjected to a column chromatography on a silica gel (hexane/ethyl acetate 3:1) to obtain a free base (0.54 g, Yield: 46%) of the title compound as an oil. This was dissolved in ethanol. 4 M solution of hydrogen chloride/ethyl acetate was added to the mixture and the mixture was concentrated under reduced pressure. The residue was precipitated from ethanol-diisopropyl ether to obtain the title compound (0.51 g, Yield: 40%).

Amorphous.

$^1$H NMR (DMSO-d$_6$) δ 1.22 (6H, s), 1.25–1.85 (10H, m), 2.15 (2H, s), 3.31 (2H, s), 3.94 (3H, s), 7.19 (1H, s), 7.58–7.80 (5H, m).

Example 185
8',9'-Dihydro-6'-methoxy-1'-(4-methoxyphenyl)-8',8'-dimethylspiro[cyclohexane-1,3'(4'H)-furo[2,3-h]isoquinoline]Hydrochloride The title compound was obtained using 4-methoxybenzonitrile by the method similar to that in Example 184. Yield: 45%.

Amorphous.

$^1$H NMR (DMSO-d$_6$) δ 1.25 (6H, s), 1.32–1.80 (10H, m), 2.31 (2H, s), 3.33 (2H, s), 3.88 (3H, s), 3.92 (3H, s), 7.14 (1H, s), 7.16 (2H, d, J=8.6 Hz), 7.55 (2H, d, J=8.6 Hz).

Example 186
3,4,8,9-Tetrahydro-3,3,8,8-tetramethyl-6-(1-methylethoxy)-1-phenylfuro[2,3-h]isoquinoline Hydrochloride A free base of the title compound was obtained from 3,4,8,9-tetrahydro-3,3,8,8-tetramethyl-1-phenyl-6-furo[2,3-h]isoquinolinol and 2-iodopropane by the method similar to that in Example 99. This was dissolved in hexane and 4 M solution of hydrogen chloride/ethyl acetate was added thereto. The mixture was concentrated under reduced pressure, and crystallized from hexane-ethyl acetate to obtain the title compound. Yield: 71%.

Melting point: 154–155° C.

$^1$H NMR (DMSO-d$_6$) δ 1.22 (6H, s), 1.33 (6H, d, J=6.0 Hz), 1.44 (6H, s), 2.15 (2H, s), 3.15 (2H, s), 4.82–4.95 (1H, m), 7.10 (1H, s), 7.62–7.77 (5H, m).

Example 187
6-(Cyclopentyloxy)-3,4,8,9-tetrahydro-3,3,8,8-tetramethyl-1-phenylfuro[2,3-h]isoquinoline The title compound was obtained from 3,4,8,9-tetrahydro-3,3,8,8-tetramethyl-1-phenyl-6-furo[2,3-h]isoquinolinol and bromocyclopentane by the method similar to that in Example 99. Yield: 43%.

Melting point: 73–74° C. (hexane).

$^1$H NMR (CDCl$_3$) δ 1.24 (6H, s), 1.28 (6H, s), 1.55–2.00 (8H, m), 2.15 (2H, s), 2.66 (2H, s), 4.84–4.92 (1H, m), 6.59 (1H, s), 7.38 (5H, s).

Example 188
3,4,8,9-Tetrahydro-3,3,8,8-tetramethyl-1-phenylfuro[2,3-h]isoquinolin-6-yl Acetate Hydrochloride Acetic anhydride (2 mL) was added to a solution of 3,4,8,9-tetrahydro-3,3,8,8-tetramethyl-1-phenyl-6-furo[2,3-h]isoquinolinol (567 mg, 1.76 mmol) in pyridine (2 mL) and the mixture was stirred at room temperature for 12 hours. A saturated aqueous solution of sodium hydrogen carbonate was poured into the reaction mixture, which was then extracted twice with ethyl acetate. The combined organic layer was washed with water and brine, dried over magnesium sulfate, filtered, and concentrated under reduced pressure. The residue was subjected to a column chromatography on a silica gel (hexane/ethyl acetate 3:1) to obtain a free base of the title compound. This was dissolved in ethyl acetate, combined with 4 M solution of hydrogen chloride/ethyl acetate, concentrated under reduced pressure, and crystallized from hexane-ethyl acetate to obtain the title compound (533 mg, Yield: 76%).

Melting point: 155–165° C.

1H NMR (DMSO-d$_6$) δ 1.23 (6H, s), 1.45 (6H, s), 2.23 (2H, s), 2.31 (3H, s), 3.16 (2H, s), 7.22 (1H, s), 7.66–7.80 (5H, m).

Example 189
3,4,8,9-Tetrahydro-3,3,8,8-tetramethyl-1-phenylfuro[2,3-h]isoquinolin-6-yl Benzoate Hydrochloride The title compound was obtained from benzoyl chloride by the method similar to that in Example 188. Yield: 75%.

Melting point: 160–165° C. (ethyl acetate).

$^1$H NMR (DMSO-d$_6$) δ 1.23 (6H, s), 1.47 (6H, s), 2.28 (2H, s), 3.18 (2H, s), 7.34 (1H, s), 7.60–7.85 (8H, m), 8.14 (2H, d, J=7.4 Hz).

Example 190
6-Butoxy-3,4,8,9-tetrahydro-3,3,8,8-tetramethyl-1-phenylfuro[2,3-h]isoquinoline Sodium hydride (66% suspension in oil) (61 mg, 1.69 mmol) and 1-iodobutane (0.19 mL, 1.65 mmol) were added sequentially to a solution of 3,4,8,9-tetrahydro-3,3,8,8-tetramethyl-1-phenyl-6-furo[2,3-h]isoquinolinol (495 mg, 1.54 mmol) in N,N-dimethylformamide (5 mL) and the mixture was stirred at room temperature for 2 hours. The reaction mixture was poured into water, and extracted twice with ethyl acetate. The combined organic layer was washed with water (twice) and a brine, dried over magnesium sulfate, filtered, and concentrated under reduced pressure. The residue was subjected to a column chromatography on a silica gel (hexane/ethyl acetate 5:1 followed by 3:1), and recrystallized from hexane to obtain the title compound (357 mg, Yield: 61%).

Melting point: 99–101° C.

$^1$H NMR (CDCl$_3$) δ 0.98 (3H, t, J=7.4 Hz), 1.25 (6H, s), 1.29 (6H, s), 1.39–1.58 (2H, m), 1.68–1.90 (2H, m), 2.17 (2H, s), 2.67 (2H, s), 4.10 (2H, t, J=7.0 Hz), 6.60 (1H, s), 7.38 (5H, s).

Example 191
3,4,8,9-Tetrahydro-3,3,8,8-tetramethyl-1-phenyl-6-propoxyfuro[2,3-h]isoquinoline Hydrochloride A free base of the title compound was obtained using 1-iodopropane by the method similar to that in Example 190. This was dissolved in ethyl acetate, combined with 4 M solution of hydrogen chloride/ethyl acetate, and concentrated under reduced pressure to obtain the title compound. Yield: 91%.

Amorphous.

$^1$H NMR (DMSO-d$_6$) δ 0.97 (3H, t, J=7.3 Hz), 1.23 (6H, s), 1.44 (6H, s), 1.68–1.88 (2H, m), 2.16 (2H, s), 3.15 (2H, s), 4.14 (2H, t, J=6.8 Hz), 7.10 (1H, s), 7.60–7.80 (5H, m).

Example 192
3,4,8,9-Tetrahydro-3,3,8,8-tetramethyl-1-phenyl-6-(phenylmethoxy)furo[2,3-h]isoquinoline The title compound was obtained using benzyl bromide by the method similar to that in Example 190. Yield: 74%.

Melting point: 129–131° C. (diethyl ether-hexane).

$^1$H NMR (CDCl$_3$) δ 1.22 (6H, s), 1.31 (6H, s), 2.18 (2H, s), 2.62 (2H, s), 5.23 (2H, s), 6.60 (1H, s), 7.30–7.48 (10H, m).

Example 193
3,4,8,9-Tetrahydro-3,3,8,8-tetramethyl-1-phenyl-6-(2-pyridinylmethoxy)furo[2,3-h]isoquinoline Dihydrochloride A free base of the title compound was obtained using 2-(chloromethyl)pyridine hydrochloride by the method similar to that in Example 190. This was dissolved in ethyl acetate, combined with 4 M solution of hydrogen chloride/ethyl acetate, concentrated under reduced pressure, and crystallized from ethanol-ethyl acetate to obtain the title compound. Yield: 90%.

Melting point: 170–210° C.

$^1$H NMR (CDCl$_3$) δ 1.33 (6H, s), 1.69 (6H, s), 2.25 (2H, s), 3.05 (2H, s), 5.92 (2H, s), 7.09 (1H, s), 7.57–7.74 (5H, m), 7.85–7.95 (1H, m), 8.20 (1H, d, J=76 Hz), 8.42–8.56 (1H, m), 8.75 (1H, d, J=4.8 Hz).

Example 194
3,4,8,9-Tetrahydro-3,3,8,8-tetramethyl-1-phenyl-6-(3-pyridinylmethoxy)furo[2,3-h]isoquinoline The title compound was obtained from 3-(chloromethyl)pyridine hydrochloride by the method similar to that in Example 190. Yield: 85%.

Melting point: 112–115° C. (hexane).

$^1$H NMR (CDCl$_3$) δ 1.31 (6H, s), 1.32 (6H, s), 2.19 (2H, s), 2.70 (2H, s), 5.26 (2H, s), 6.64 (1H, s), 7.33 (1H, d, J=7.4, 4.8 Hz), 7.43 (5H, s), 7.80 (1H, dd, J=7.4, 1.6 Hz), 8.59 (1H, dd, J=4.8, 1.6 Hz), 8.68 (1H, d, J=1.6 Hz).

Example 195
3,4,8,9-Tetrahydro-3,3,8,8-tetramethyl-1-phenyl-6-(4-pyridinylmethoxy)furo[2,3-h]isoquinoline The title compound was obtained from 4-(chloromethyl)pyridine hydrochloride by the method similar to that in Example 190. Yield: 79%.

Melting point: 122–124° C. (hexane).

$^1$H NMR (CDCl$_3$) δ 1.22 (6H, s), 1.32 (6H, s), 2.19 (2H, s), 2.61 (2H, s), 5.25 (2H, s), 6.53 (1H, s), 7.36 (2H, d, J=6.2 Hz), 7.38 (5H, s), 8.61 (2H, d, J=6.2 Hz).

Example 196
3,4,8,9-Tetrahydro-3,3,8,8-tetramethyl-1-phenyl-6-[(3-phenyl-2-propenyl)oxy]furo[2,3-h]isoquinoline The title compound was obtained using cinnamyl chloride by the method similar to that in Example 190. Yield: 78%.

Melting point: 121–123° C. (hexane-diethyl ether).

$^1$H NMR (DMSO-d$_6$) δ 1.13 (6H, s), 1.21 (6H, s), 2.18 (2H, s), 2.63 (2H, s), 4.78 (2H, d, J=6.0 Hz), 6.45–6.59 (1H, m), 6.78 (1H, d, J=16.8 Hz), 6.88 (1H, s), 7.28–7.52 (10H, m).

Example 197
3,4,8,9-Tetrahydro-3,3,8,8-tetramethyl-1-phenyl-6-(3-phenylpropoxy)furo[2,3-h]isoquinoline Hydrochloride A free base of the title compound was obtained using 1-bromo-3-phenylpropane by the method similar to that in Example 190. This was dissolved in ethyl acetate, combined with 4 M solution of hydrogen chloride/ethyl acetate, concentrated under reduced pressure, and crystallized from hexane to obtain the title compound. Yield: 89%.

Melting point: 165–180° C.

$^1$H NMR (DMSO-d$_6$) δ 1.24 (6H, s), 1.45 (6H, s), 2.02–2.16 (2H, m), 2.17 (2H, s), 2.74 (2H, t, J=8.0 Hz), 3.14 (2H, s), 4.19 (2H, t, J=6.0 Hz), 7.07 (1H, s), 7.18–7.38 (5H, m), 7.63–7.80 (5H, m), 12.68 (1H, br s).

Example 198
3,4,8,9-Tetrahydro-3,3,8,8-tetramethyl-1-phenyl-6-[(5-phenylpentyl)oxy]furo[2,3-h]isoquinoline The title compound was obtained using 1-bromo-5-phenylpentane by the method similar to that in Example 190. Yield: 79%.

Melting point: 104–106° C. (hexane).

$^1$H NMR (CDCl$_3$) δ 1.25 (6H, s), 1.29 (6H, s), 1.45–1.94 (6H, m), 2.17 (2H, s), 2.64 (2H, t, J=7.8 Hz), 2.67.(2H, s), 4.09 (2H, t, J=6.8 Hz), 6.58 (1H, s), 7.17–7.35 (5H, m), 7.38 (5H, s).

Example 199
Ethyl (3,4,8,9-tetrahydro-3,3,8,8-tetramethyl-1-phenylfuro[2,3-h]isoquinolin-6-yl) carbonate hydrochloride A free base of the title compound was obtained using ethyl chloroformate by the method similar to that in Example 190. This was dissolved in ethyl acetate, combined with 4 M solution of hydrogen chloride/ethyl acetate, concentrated under reduced pressure, and crystallized from hexane-ethyl acetate to obtain the title compound. Yield: 71%.

Melting point: 144–147° C.

$^1$H NMR (DMSO-d$_6$) δ 1.24 (6H, s), 1.29 (3H, t, J=8 7.1 Hz), 1.45 (6H, s), 2.25 (2H, s), 3.16 (2H, s), 4.28 (2H, q, J=7.1 Hz), 7.33 (1H, s), 7.65–7.80 (5H, m).

Example 200
3,4,8,9-Tetrahydro-3,3,8,8-tetramethyl-1-phenyl-6-[(1-phenyl-1H-tetrazol-5-yl)oxy]furo[2,3-h]isoquinoline The title compound was obtained using 5-chloro-1-phenyl 1H-tetrazole by the method similar to that in Example 190. Yield: 88%.

Melting point: 191–193° C. (diethyl ether).

$^1$H NMR (CDCl$_3$) δ 1.24 (6H, s), 1.27 (6H, s), 2.24 (2H, s), 2.71 (2H, s), 7.09 (1H, s), 7.41 (5H, s), 7.50–7.62 (3H, m), 7.82–7.88 (2H, m).

Example 201
6-(Fluoromethoxy)-3,4,8,9-tetrahydro-3,3,8,8-tetramethyl-1-phenylfuro[2,3-h]isoquinoline The title compound was obtained using bromofluoromethane by the method similar to that in Example 190. Yield: 75%.

Melting point: 120–122° C. (hexane-diethyl ether).

$^1$H NMR (CDCl$_3$) δ 1.26 (6H, s), 1.31 (6H, s), 2.21 (2H, s), 2.69 (2H, s), 5.80 (2H, d, J=54.2 Hz), 6.85 (1H, s), 7.40 (5H, s).

Example 202
2-[[(3,4,8,9-Tetrahydro-3,3,8,8-tetramethyl-1-phenylfuro[2,3-h]isoquinolin-6-yl)oxy]methyl]-1H-isoindole-1,3(2H)-dione The title compound was obtained using N-(bromomethyl)phthalimide by the method similar to that in Example 190. Yield: 92%.

Melting point: 191–193° C. (diethyl ether).
$^1$H NMR (CDCl$_3$) δ 1.20 (6H, s), 1.24 (6H, s), 2.16 (2H, s), 2.62 (2H, s), 5.73 (2H, s), 6.77 (1H, s), 7.38 (5H, s), 7.75–7.79 (2H, m), 7.89–7.94 (2H, m).

Example 203
[(3,4,8,9-Tetrahydro-3,3,8,8-tetramethyl-1-phenylfuro[2,3-h]isoquinolin-6-yl)oxy]acetic Acid Methyl Ester The title compound was obtained using methyl bromoacetate by the method similar to that in Example 190. Yield: 72%.

Melting point: 82–84° C. (hexane-diethyl ether).
$^1$H NMR (CDCl$_3$) δ 1.24 (6H, s), 1.29 (6H, s), 2.17 (2H, s), 2.65 (2H, s), 3.81 (3H, s), 4.78 (2H, s), 6.57 (1H, s), 7.38 (5H, s).

Example 204
2-[(3,4,8,9-Tetrahydro-3,3,8,8-tetramethyl-1-phenylfuro[2,3-h]isoquinolin-6-yl)oxy]acetamide 5 M solution of ammonia/methanol (7 mL) was added to a mixture of [(3,4,8,9-tetrahydro-3,3,8,8-tetramethyl-1-phenylfuro[2,3-h]isoquinolin-6-yl)oxy]acetic acid methyl ester (501 mg, 1.27 mmol) and sodium cyanide (6.2 mg, 0.127 mmol) and the mixture was stirred in sealed tube at 45° C. for 5 hours. ethanol was distilled off under reduced pressure, and water was poured into the residue, which was then extracted twice with ethyl acetate. The combined organic layer was washed with brine, dried over magnesium sulfate, filtered, and concentrated under reduced pressure. The resultant crystals were washed with diethyl ether to obtain the title compound (409 mg, Yield: 85%).

Melting point: 117–119° C.
$^1$H NMR (CDCl$_3$) δ 1.25 (6H, s), 1.30 (6H, s), 2.20 (2H, s), 2.68 (2H, s), 4.62 (2H, s), 5.63 (1H, br s), 6.63 (1H, s), 6.80 (1H, br s), 7.39 (5H, s).

Example 205
[(3,4,8,9-Tetrahydro-3,3,8,8-tetramethyl-1-phenylfuro[2,3-h]isoquinolin-6-yl)oxy]acetate Hydrochloride.

2 M aqueous solution of sodium hydroxide (3.13 mL, 6.26 mmol) was added to a solution of [(3,4,8,9-tetrahydro-3,3,8,8-tetramethyl-1-phenylfuro[2,3-h]isoquinolin-6-yl)oxy]acetic acid methyl ester (1.23 g, 3.13 mmol) in methanol (6 mL) and the mixture was stirred at room temperature for 4 hours. Methanol was distilled off under reduced pressure, and water was poured into the residue, which was then neutralized with 2 M hydrochloric acid. 4 M solution of hydrogen chloride/ethyl acetate (1.17 mL, 4.68 mmol) was added to the mixture and the mixture was concentrated under reduced pressure. The residue was dissolved in methanol, and the insolubles were filtered off, and mother liquor was concentrated under reduced pressure. The same procedure was repeated twice, and then the title compound (1.17 g, Yield: 90%) was obtained.

Amorphous.
$^1$H NMR (CDCl$_3$) δ 1.29 (6H, s), 1.54 (6H, s), 2.18 (2H, s), 2.93 (2H, s), 4.66 (2H, s), 6.66 (1H, s), 7.48–7.70 (5H, m).

Example 206
N-Methyl-2-[(3,4,8,9-tetrahydro-3,3,8,8-tetramethyl-1-phenylfuro[2,3-h]isoquinolin-6-yl)oxy]acetamide Hydrochloride.

N,N'-Carbonyldiimidazole (187 mg, 1.15 mmol) was added to a solution of [(3,4,8,9-tetrahydro-3,3,8,8-tetramethyl-1-phenylfuro[2,3-h]isoquinolin-6-yl)oxy] acetate hydrochloride (435 mg, 1.05 mmol) in N,N-dimethylformamide (4 mL) and the mixture was stirred at room temperature for 2 hours. Methylamine hydrochloride (78 mg, 1.15 mmol) and triethylamine (0.32 mL, 2.31 mmol) were added, and the mixture was stirred at room temperature further for 5 hours. Ice water was poured into the reaction mixture, which was then extracted twice with ethyl acetate. The combined organic layer was washed twice with brine, dried over magnesium sulfate, filtered, and concentrated under reduced pressure. The residue was subjected to a column chromatography on a silica gel (hexane/ethyl acetate 1:1 followed by ethyl acetate) to obtain a free base of the title compound. This was dissolved in ethyl acetate, combined with 4 M solution of hydrogen chloride/ethyl acetate, and concentrated under reduced pressure to obtain the title compound (330 mg, Yield: 73%).

Amorphous.
$^1$H NMR (DMSO-d$_6$) δ 1.24 (6H, s), 1.44 (6H, s), 2.17 (2H, s), 2.66 (3H, d, J=4.8 Hz), 3.13 (2H, s), 4.72 (2H, s), 6.99 (1H, s), 7.63–7.80 (5H, m), 8.17 (1H, q, J=4.8 Hz).

Example 207
N,N-Dimethyl-2-[(3,4,8,9-tetrahydro-3,3,8,8-tetramethyl-1-phenylfuro[2,3-h]isoquinolin-6-yl)oxylacetamide Triethylamine (0.22 mL, 1.60 mmol) was added to a solution of [(3,4,8,9-tetrahydro-3,3,8,8-tetramethyl-1-phenylfuro[2,3-h]isoquinolin-6-yl)oxy]acetic acid hydrochloride (604 mg, 1.45 mmol) in tetrahydrofuran (6 mL) and the mixture was stirred at room temperature for 3 minutes. N,N'-carbonyldiimidazole (259 mg, 1.60 mmol) was added to the reaction mixture and the mixture was stirred at room temperature for 2 hours. 2 M solution of dimethylamine/tetrahydrofuran (0.80 mL, 1.60 mmol) was added to the reaction mixture and the mixture was stirred at room temperature for 1 hour. Water was poured into the mixture, which was then extracted twice with ethyl acetate. The combined organic layer was washed with brine, dried over sodium sulfate, filtered, and concentrated under reduced pressure. The residue was crystallized from ethyl acetate-diethyl ether to obtain the title compound (422 mg, Yield: 72%).

Melting point: 120–140° C.
$^1$H NMR (CDCl$_3$) δ 1.26 (6H, s), 1.29 (6H, s), 2.17 (2H, s), 2.69 (2H, s), 2.99 (3H, s), 3.10 (3H, s), 4.83 (2H, s), 6.67 (1H, s), 7.39 (5H, s).

Example 208
2-[(3,4,8,9-Tetrahydro-3,3,8,8-tetramethyl-1-phenylfuro[2,3-h]isoquinolin-6-yl)oxylethanamine Sodium hydride (66% suspension in oil) (142 mg, 3.92 mmol) was added to a solution of 3,4,8,9-tetrahydro-3,3,8,8-tetramethyl-1-phenyl-6-furo[2,3-h]isoquinolinol (1.20 g, 3.73 mmol) in N,N-dimethylformamide (6 mL) and the mixture was stirred at room temperature for 15 minutes. N-(2-Bromoethyl)phthalimide (949 mg, 3.73 mmol) was added to the reaction mixture, and the mixture was stirred at room temperature for 1 hour, and then at 60° C. for 3 hours. N-(2-bromoethyl)phthalimide (949 mg, 3.73 mmol) and potassium carbonate (542 mg, 3.92 mmol) were added at room temperature, and the mixture was stirred at 50° C. for 3 hours. Water was poured into the reaction mixture, which was then extracted twice with ethyl acetate. The combined organic layer was washed twice with water and brine, dried over sodium sulfate, filtered, and concentrated under reduced pressure. The residue was subjected to a column chromatography on a silica gel (hexane/ethyl acetate 50:1 followed by ethyl acetate) to obtain 2-[2-[(3,4,8,9-tetrahydro-3,3,8,8-tetramethyl-1-phenylfuro[2,3-h]isoquinolin-6-yl)oxy]ethyl]-1H-isoindole-1,3(2H)-dione (707 mg, Yield: 38%).
$^1$H NMR (CDCl$_3$) δ 1.21 (6H, s), 1.22 (6H, s), 2.13 (2H, s), 2.62 (2H, s), 4.12 (2H, t, J=6.4 Hz), 4.39 (2H, t, J=6.4

Hz), 6.70 (1H, s), 7.35–7.37 (5H, m), 7.70–7.75 (2H, m), 7.84–7.88 (2H, m).

2-[2-[(3,4,8,–9-tetrahydro-3,3,8,8-tetramethyl-1-phenylfuro[2,3-h]isoquinolin-6-yl)oxy]ethyl]-1H-isoindole-1,3(2H)-dione (708 mg, 1.42 mmol) was dissolved in ethanol (7 mL), hydrazine monohydrate (0.072 mL, 1.50 mmol) was added thereto, and the mixture was stirred at 80° C. for 1.5 hours. The insolubles were removed by filtration, and the filtrate was concentrated under reduced pressure. A dilute aqueous solution of sodium hydroxide was poured into the residue, which was then extracted twice with ethyl acetate. The combined organic layer was washed with brine, dried over sodium sulfate, filtered, and concentrated under reduced pressure. The residue was subjected to a column chromatography on a silica gel (hexane/ethyl acetate 3:1 followed by ethyl acetate), and crystallized from hexane-diethyl ether to obtain the title compound (56 mg, Yield: 11%).

Melting point: 77–79° C.

$^1$H NMR (CDCl$_3$) δ 1.24 (6H, s), 1.30 (6H, s), 2.18 (2H, s), 2.67 (2H, s), 3.11 (2H, t, J=5.3 Hz), 4.08–4.18 (2H, m), 6.63 (1H, s), 7.38 (5H, s).

Example 209
2-[(3,4,8,9-Tetrahydro-3,3,8,8-tetramethyl-1-phenylfuro[2,3-h]isoquinolin-6-yl)oxy]ethanol 2-Bromoethanol (0.11 mL, 1.57 mmol) and potassium carbonate (217 mg, 1.57 mmol) were added to a solution of 3,4,8,9-tetrahydro-3,3,8,8-tetramethyl-1-phenyl-6-furo[2,3-h]isoquinolinol (459 mg, 1.43 mmol) in N,N-dimethylformamide (4.5 mL), and the mixture was stirred at 60° C. for 36 hours. Water was poured into the reaction mixture, which was then extracted twice with ethyl acetate. The combined organic layer was washed with water and brine (twice), dried over sodium sulfate, filtered, and concentrated under reduced pressure. The residue was subjected to a column chromatography on a basic silica gel (hexane/ethyl acetate 3:1 followed by 1:1), and crystallized from hexane-diethyl ether to obtain the title compound (366 mg, Yield: 70%).

Melting point: 90–92° C.

$^1$H NMR (CDC$_{13}$) δ 1.25 (6H, s), 1.30 (611, s), 2.19 (2H, s), 2.67 (2H, s), 3.92–3.98 (2H, m), 4.21 (2H, t, J=4.4 Hz), 6.65 (1H, s), 7.39 (5H, s).

Example 210
6-(2-Fluoroethoxy)-3,4,8,9-tetrahydro-3,3,8,8-tetramethyl-1-phenylfuro[2,3-h]isoquinoline The title compound was obtained using 1-bromo-2-fluoroethane by the method similar to that in Example 209. Yield: 56%.

Melting point: 77–79° C. (diethyl ether-hexane).

$^1$H NMR (CDCl$_3$) δ 1.25 (6H, s), 1.30 (6H, s), 2.18 (2H, s), 2.67 (2H, s), 4.29–4.47 (2H, m), 4.64–4.92 (2H, m), 6.65 (1H, s), 7.39 (5H, s).

Example 211
Dimethylcarbamothioic acid O-(3,4,8,9-tetrahydro-3,3,8,8-tetramethyl-1-phenylfuro[2,3-h]isoquinolin-6-yl) Ester The title compound was obtained using dimethylthiocarbamoyl chloride by the method, similar to that in Example 209. Quantitative.

Amorphous.

$^1$H NMR (CDCl$_3$) δ 1.25 (6H, s), 1.27 (6H, s), 2.19 (2H, s), 2.69 (2H, s), 3.34 (3H, s), 3.45 (3H, s), 6.76 (1H, s), 7.35–7.47 (5H, m).

Example 212
Dimethylcarbamothioic acid O-(3,4,8,9-tetrahydro-3,3,8,8-tetramethyl-1-phenylfuro[2,3-h]isoquinolin-6-yl)ester Hydrochloride Dimethylcarbamothioic acid O-(3,4,8,9-tetrahydro-3,3,8,8-tetramethyl-1-phenylfuro[2,3-h]isoquinolin-6-yl)ester (902 mg, 2.21 mmol) was dissolved in ethyl acetate and combined with 4 M hydrogen chloride/ethyl acetate solution (0.55 mL). The resultant mixture was concentrated under reduced pressure to obtain crystals, which were washed with diethyl ether to obtain the title compound (946 mg, yield: 96%).

Melting point: 170–180° C.

$^1$H NMR (DMSO-d$_6$) δ 1.22 (6H, s), 1.46 (6H, s), 2.22 (2H, s), 3.18 (2H, s), 3.30 (3H, s), 3.36 (3H, s), 7.17 (1H, s), 7.66–7.82 (5H, m).

Example 213
Dimethylcarbamothioic acid S-(3,4,8,9-tetrahydro-3,3,8,8-tetramethyl-1-phenylfuro[2,3-h]isoquinolin-6-yl)ester Hydrochloride Dimethylcarbamothioic acid O-(3,4,8,9-tetrahydro-3,3,8,8-tetramethyl-1-phenylfuro[2,3-h]isoquinolin-6-yl)ester (4.92 g, 12.0 mmol) was stirred at 190° C. for 24 hours. The reaction mixture was subjected to a column chromatography on a silica gel (hexane/ethyl acetate 5:1 followed by 3:1) to obtain a free base of the title compound.

$^1$H NMR (CDCl$_3$) δ 1.25 (6H, s), 1.29 (6H, s), 2.21 (2H, s), 2.68 (2H, s), 3.05 (3H, br s), 3.10 (3H, br s), 7.11 (1H, s), 7.40 (5H, s).

This was dissolved in ethyl acetate, combined with 4 M hydrogen chloride/ethyl acetate solution, concentrated under reduced pressure, crystallized from hexane-diethyl ether to obtain the title compound.(404 mg, yield: 8.2%).

Melting point: 146–148° C.

$^1$H NMR (DMSO-d$_6$) δ 1.23 (6H, s), 1.45 (6H, s), 2.25 (2H, s), 2.94 (3H, s), 3.06 (3H, s), 3.15 (2H, s), 7.40 (1H, s), 7.66–7.77 (5H, s).

Example 214
3,4,8,9-Tetrahydro-3,3,8,8-tetramethyl-6-(methylthio)-1-phenylfuro[2,3-h]isoquinoline Hydrochloride A solution of dimethylcarbamothioic acid S-(3,4,8,9-tetrahydro-3,3,8,8-tetramethyl-1-phenylfuro [2,3-h]isoquinolin-6-yl)ester (539 mg, 1.32 mmol) in 10% aqueous solution of potassium hydroxide (5 mL) was heated under reflux for 1 hour. Water was poured into the reaction mixture, which was neutralized with 2 M hydrochloric acid and extracted twice with ethyl acetate. The combined organic layer was washed with brine, dried over sodium sulfate, filtered and concentrated under reduced pressure to obtain 3,4,8,9-tetrahydro-3,3,8,8-tetramethyl-1-phenyl-6-furo[2,3-h]isoquinolinethiol (434 mg).

This was dissolved in N,N-dimethylformamide (5 mL), sodium hydride (66% dispersion in oil) (57 mg, 1.58 mmol) was added thereto, and the mixture was stirred at room temperature for 20 minutes. While cooling in ice, iodomethane (0.098 mL, 1.58 mmol) was added thereto, and the mixture was stirred at room temperature for 1 hour. Water was poured into the reaction mixture, which was extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 10:1 followed by 5:1) to obtain a free base of the title compound. This was dissolved in ethyl acetate, combined with 4 M hydrogen chloride/ethyl acetate solution, concentrated under reduced pressure to obtain the title compound (287 mg, yield: 56%).

Amorphous.

$^1$H NMR (DMSO-d$_6$) δ 1.24 (6H, s), 1.45 (6H, s), 2.20 (2H, s), 2.57 (3H, s), 3.17 (2H, s), 7.20 (1H, s), 7.64–7.80 (5H, m).

Example 215

6-Chloro-3,4,8,9-tetrahydro-3,3,8,8-tetramethyl-1-phenylfuro(2,3-h]isoquinoline Hydrochloride Phosphorus oxychloride (0.44 mL, 4.67 mmol) was added to a solution of 3,4,8,9-tetrahydro-3,3,8,8-tetramethyl-1-phenyl-6-furo[2,3-h]isoquinolinol (1.00 g, 3.11 mmol) in N,N-dimethylformamide (1 mL) and the mixture was stirred at 90° C. for 15 hours and then at 130° C. for 3 hours. The reaction mixture was poured into 2 M aqueous solution of sodium hydroxide and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 100:1 followed by 30:1) to obtain a free base of the title compound. This was dissolved in ethyl acetate, combined with 4 M hydrogen chloride/ethyl acetate solution, concentrated under reduced pressure, crystallized from hexane-ethyl acetate to obtain the title compound (380 mg, yield: 33%).

Melting point: 165–167° C.

$^1$H NMR (CDCl$_3$) δ 1.36 (6H, s), 1.71 (6H, s), 2.31 (2H, s), 3.01 (2H, s), 7.21 (1H, s), 7.55–7.75 (5H, m).

Example 216

6-Chloro-3,4,8,9-tetrahydro-3,3,8,8-tetramethyl-1-[3-(4-pyridinyl)phenyl]furo[2,3-h]isoquinoline Dihydrochloride The title compound was obtained from 3,4,8,9-tetrahydro-3,3,8,8-tetramethyl-1-[3-(4-pyridinyl)phenyl]-6-furo[2,3-h]isoquinolinol by the method similar to that in EXAMPLE 215. Yield: 30%.

Melting point: 145–155C (ethanol-ethyl acetate).

1H NMR (DMSO-d$_6$) δ 1.27 (6H, s), 1.50 (6H, s), 2.40 (2H, s), 3.17 (2H, s), 7.51 (1H, s), 7.85–7.87 (2H, m), 8.37–8.39 (2H, m), 8.47 (2H, d, J=6.3 Hz), 9.13 (2H, d, J=6.3 Hz).

Example 217

3,4,8,9-Tetrahydro-N,3,3,8,8-pentamethyl-1-phenyl-6-furo2,3-h]isoquinolinamine Hydrochloride 40% Methylamine/methanol solution (5 mL) was added to a mixture of 3,4,8,9-tetrahydro-6-methoxy-3,3,8,8-tetramethyl-1-phenylfuro[2,3-h]isoquinoline (518 mg, 1.54 mmol) and ammonium chloride (165 mg, 3.09 mmol) and the mixture was stirred in a sealed tube at 150° C. for 15 hours. Methanol was distilled off under reduced pressure, and water was poured into the residue, and the mixture was extracted twice with ethyl acetate. The combined organic layer was washed with water and brine, dried over magnesium sulfate, filtered and concentrated under reduced pressure. The residue was subjected to a column chromatography on a silica gel (hexane/ethyl acetate 3:1 followed by hexane/ethyl acetate/triethylamine 25:25:1) to obtain a free base of the title compound.

$^1$H NMR (CDCl$_3$) δ 1.26 (6H, s), 1.30 (6H, s), 2.16 (2H, s), 2.72 (2H, s), 2.93 (3H, s), 6.31 (1H, s), 7.40 (5H, s).

This was dissolved in ethyl acetate, combined with 4 M hydrogen chloride/ethyl acetate solution and concentrated under reduced pressure to obtain the title compound (376 mg, yield: 76%).

Amorphous.

$^1$H NMR (CDCl$_3$) δ 1.28 (6H, s), 1.67 (6H, s), 2.19 (2H, s), 2.96 (2H, s), 3.03 (3H, s), 6.35 (1H, s), 7.50–7.70 (5H, m).

Example 218

3,4,8,9-Tetrahydro-N,N,3,3,8,8-hexamethyl-1-phenyl-6-furo[2,3-h]isoquinolinamine Dihydrochloride A mixture of 3,4,8,9-tetrahydro-N,3,3,8,8-pentamethyl-1-phenyl-6-furo[2,3-h]isoquinolinamine (321 mg, 0.865 mmol), 37% aqueous solution of formaldehyde (0.14 mL, 1.90 mmol) and formic acid (0.16 mL, 4.33 mmol) was stirred at 60° C. for 1.5 hours and at 100° C. for 1 hour. The reaction mixture was neutralized with 2 M aqueous solution of sodium hydroxide and extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 100:1 followed by 10:1) to obtain a free base of the title compound. This was dissolved in ethyl acetate, combined with 4 M hydrogen chloride/ethyl acetate solution and crystallized from ethyl acetate to obtain the title compound (114 mg, yield: 31%).

Melting point: 105–115° C.

$^1$H NMR (DMSO-d$_6$) δ 1.22 (6H, s), 1.41 (6H, s), 2.05 (2H, s), 3.05 (2H, s), 3.16 (6H, s), 6.64 (1H, s), 7.53–7.73 (5H, m), 11.69 (1H, br s).

Example 219

N-Ethyl-3,4,8,9-tetrahydro-3,3,8,8-tetramethyl-1-phenyl-6-furo[2,3-h]isoquinolinamine Hydrochloride The title compound was obtained from 70% aqueous solution of ethylamine by the method similar to that in EXAMPLE 217. Yield: 21%.

Amorphous.

$^1$H NMR (DMSO-d$_6$) δ 1.24 (6H, s), 1.40 (6H, s), 1.70 (3H, t, J=7.4 Hz), 2.09 (2H, s), 3.04 (2H, s), 3.26–3.50 (2H, m), 6.59 (1H, s), 7.08 (1H, br s), 7.52–7.84 (5H, m), 11.37 (1H, br s).

Example 220

3,4,8,9-Tetrahydro-3,3,8,8-tetramethyl-1-phenyl-6-furo[2,3-h]isoquinolinamine

5 M Ammonia/methanol solution (40 mL) was added to a mixture of 3,4,8,9-tetrahydro-6-methoxy-3,3,8,8-tetramethyl-1-phenylfuro[2,3-h]isoquinoline (3.77 g, 11.2 mmol) and ammonium chloride (1.20 g, 22.5 mmol) and the mixture was stirred in a sealed tube at 150° C. for 24 hours. Methanol was distilled off under reduced pressure, and water was poured into the residue, which was neutralized with sodium hydrogen carbonate, and extracted three times with ethyl acetate. The combined organic layer was washed with brine dried over sodium sulfate, filtered, and concentrated under reduced pressure. The residue was subjected to a column chromatography on a basic silica gel (hexane/ethyl acetate 50:1 followed by 5:1) and crystallized from diethyl ether to obtain the title compound (1.58 g, yield: 44%).

Melting point: 158–162° C.

$^1$H NMR (CDCl$_3$) δ 1.26 (12H, s), 2.15 (2H, s), 2.63 (2H, s), 6.40 (1H, s), 7.36–7.44 (5H, m).

Example 221

N-(3,4,8,9-Tetrahydro-3,3,8,8-tetramethyl-1-phenylfuro[2,3-h]isoquinolin-6-yl)formamide A solution of formic acid (3 mL) and acetic anhydride (1 mL) was stirred at room temperature for 1.5 hours, and 3,4,8,9-tetrahydro-3,3,8,8-tetramethyl-1-phenyl-6-furo[2,3-h]isoquinolinamine (500 mg, 1.56 mmol) was added thereto and the mixture was stirred at room temperature for 2 hours. The reaction mixture was poured into 3.5 M aqueous solution of sodium hydroxide and extracted twice with ethyl acetate. The combined organic layer was washed with brine, dried over sodium sulfate, filtered and concentrated under reduced pressure to obtain the title compound (470 mg, yield: 87%).

Amorphous.

$^1$H NMR (CDCl$_3$) δ 1.26 (6H, s), 1.29 (6H, s), 2.22 (2H, s), 2.69 (0.6H, s), 2.73 (1.4H, s), 7.40 (6H, s), 8.03 (1H, s), 8.45 (1H, d, J=1.4 Hz).

Example 222
N-(3,4,8,9-Tetrahydro-3,3,8,8-tetramethyl-1-phenylfuro[2,3-]isoquinolin-6-yl)acetamide Acetic anhydride (2 mL) was added to a solution of 3,4,8,9-tetrahydro-3,3,8,8-tetramethyl-1-phenyl-6-furo[2,3-h]isoquinolinamine (542 mg, 1.69 mmol) in pyridine (3 mL) and the mixture was stirred at room temperature for 12 hours. Aqueous solution of sodium hydrogen carbonate was poured into the reaction mixture, and the mixture was extracted three times with ethyl acetate. The combined organic layer was washed with brine, dried over magnesium sulfate, filtered and concentrated under reduced pressure. The residue was subjected to a column chromatography on a basic silica gel (hexane/ethyl acetate 5:1) and crystallized from hexane-diethyl ether to obtain the title compound (445 mg, yield: 74%).

Melting point: 175–180° C.

$^1$H NMR (CDCl$_3$) δ 1.24 (6H, s), 1.28 (6H, s), 2.20 (2H, s), 2.22 (3H, s), 2.71 (2H, s), 7.32 (1H, s), 7.83 (5H, s), 8.04 (1H, br s).

Example 223
N-(3,4,8,9-Tetrahydro-3,3,8,8-tetramethyl-1-phenylfuro[2,3-h]isoquinolin-6-yl)methanesulfonamide While cooling in ice, methanesulfonyl chloride (0.22 mL, 2.74 mmol) was added to a solution of 3,4,8,9-tetrahydro-3,3,8,8-tetramethyl-1-phenyl-6-furo[2,3-h]isoquinolinamine (400 mg, 1.25 mmol) and triethylamine (0.38 mL, 2.74 mmol) in tetrahydrofuran (5 mL) and the mixture was stirred at room temperature for 2 hours. Water was poured into the reaction mixture, which was neutralized with 1 M aqueous solution of sodium hydroxide and extracted twice with ethyl acetate. The combined organic layer was washed with water and brine, dried over sodium sulfate, filtered and concentrated under reduced pressure. The residue was subjected to a column chromatography on a silica gel (hexane/ethyl acetate 5:1 followed by 1:1) and crystallized from diethyl ether to obtain the title compound (27 mg, yield: 5.4%).

Melting point: 175–177° C.

$^1$H NMR (CDCl$_3$) δ 1.25 (6H, s), 1.28 (6H, s), 2.21 (2H, s), 2.70 (2H, s), 3.06 (3H, s), 7.17 (1H, s), 7.39 (5H, s).

Example 224
N-(3,4,8,9-Tetrahydro-3,3,8,8-tetramethyl-1-phenylfuro[2,3-h]isoquinolin-6-yl)propanamide The title compound was obtained from 3,4,8,9-tetrahydro-3,3,8,8-tetramethyl-1-phenyl-6-furo[2,3-h]isoquinolinamine and propionyl chloride by the method similar to that in EXAMPLE 30. Yield: 57%.

Melting point: 129–131° C. (diethyl ether-hexane).

$^1$H NMR (CDCl$_3$) δ 1.24 (6H, s), 1.26 (3H, t, J=7.5 Hz), 1.28 (6H, s), 2.20 (2H, s), 2.44 (2H, q, J=7.5 Hz), 2.70 (2H, s), 7.31 (1H, s), 7.38 (5H, s), 8.07 (1H, br s).

Example 225
(3,4,8,9-Tetrahydro-3,3,8,8-tetramethyl-1-phenylfuro[2,3-h]isoquinolin-6-yl)carbamic Acid Ethyl Ester The title compound was obtained from 3,4,8,9-tetrahydro-3,3,8,8-tetramethyl-1-phenyl-6-furo[2,3-h]isoquinolinamine and ethyl chloroformate by the method similar to that in EXAMPLE 30. Yield: 3.2%.

Melting point: 92–94° C. (diethyl ether-hexane).

$^1$H NMR (CDCl$_3$) δ 1.24 (6H, s), 1.27 (6H, s), 1.33 (3H, t, J=7.1 Hz), 2.19 (2H, s), 2.70 (2H, s), 4.25 (2H, q, J=7.1 Hz), 6.81 (1H, s), 7.38 (5H, s), 7.70 (1H, br s).

Example 226
N-(3,4,8,9-Tetrahydro-3,3,8,8-tetramethyl-1-phenylfuro[2,3-h]isoquinolin-6-yl)glycine Ethyl Ester The title compound was obtained from 3,4,8,9-tetrahydro-3,3,8,8-tetramethyl-1-phenyl-6-furo[2,3-h]isoquinolinamine and ethyl bromoacetate by the method similar to that in EXAMPLE 209. Yield: 35%.

Melting point: 79–81° C. (diethyl ether-hexane).

$^1$H NMR (CDCl$_3$) δ 1.23 (6H, s), 1.26 (6H, s), 1.31 (3H, t, J=7.1 Hz), 2.15 (2H, s), 2.64 (2H, s), 3.98 (2H, d, J=5.8 Hz), 4.27 (2H, q, J=7.1 Hz), 4.52 (1H, t, J=5.8 Hz), 6.20 (1H, s), 7.37 (5H, s).

Example 227
N-(3,4,8,9-Tetrahydro-3,3,8,8-tetramethyl-1-phenylfuro[2,3-h]isoquinolin-6-yl)urea While cooling with ice, trifluoroacetic acid (0.34 mL, 4.43 mmol) was added to a suspension of 3,4,8,9-tetrahydro-3,3,8,8-tetramethyl-1-phenyl-6-furo[2,3-h]isoquinolinamine (346 mg, 1.08 mmol) and sodium cyanate (140 mg, 2.16 mmol) in toluene (5 mL) and the mixture was stirred at room temperature for 3 hours. 1 M aqueous solution of sodium hydroxide was poured into the mixture, and the mixture was extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 3:1 followed by 1:2), and the resultant crystals were washed with diethyl ether to obtain the title compound (178 mg, yield: 45%).

Melting point: 151–153° C.

$^1$H NMR (CDCl$_3$) δ 1.24 (6H, s), 1.26 (6H, s), 2.19 (2H, s), 2.70 (2H, s), 4.85 (2H, br s), 6.72 (1H, s), 7.37 (5H, s), 7.72 (1H, s).

Example 228
N-Methyl-N'-(3,4,8,9-tetrahydro-3,3,8,8-tetramethyl-1-phenylfuro[2,3-h]isoquinolin-6-yl)urea While cooling with ice, phenyl chloroformate (0.22 mL, 1.67 mmol) was added to a solution of 3,4,8,9-tetrahydro-3,3,8,8-tetramethyl-1-phenyl-6-furo[2,3-h]isoquinolinamine (485 mg, 1.51 mmol) and triethylamine (0.23 mL, 1.67 mmol) in N,N-dimethylformamide (6 mL) and the mixture was stirred at room temperature for 4 hours. Triethylamine (0.12 mL, 0.84 mmol) and phenyl chloroformate (0.11 mL, 0.84 mmol) were further added, and the mixture was stirred at room temperature further for 4 hours. Methylamine hydrochloride (305 mg, 4.53 mmol) and triethylamine (0.63 mL, 4.53 mmol) were added to the reaction mixture and the mixture was stirred at room temperature for 15 hours. Ice water was poured into the mixture and the mixture was extracted twice with ethyl acetate. The combined organic layer was washed with water (twice) and brine, dried over magnesium sulfate, filtered and concentrated under reduced pressure. The residue was subjected to a column chromatography on a basic silica gel (hexane/ethyl acetate 3:1 followed by 1:1) and crystallized from diethyl ether to obtain the title compound (305 mg, yield: 54%).

Melting point: 209–211° C.

$^1$H NMR (CDCl$_3$) δ 1.24 (6H, s), 1.25 (6H, s), 2.18 (2H, s), 2.69 (2H, s), 2.86 (3H, d, J=5.0 Hz), 4.86 (1H, br q, J=5.0 Hz), 6.41 (1H, s), 7.37 (5H, s), 7.75 (1H, s).

Example 229
2-[(3,4,8,9-Tetrahydro-6-methoxy-3,3,8,8-tetramethyl-1-phenylfuro[2,3-h]isoquinolin-5-yl)methyl]-1H-isoindol-1,3(2H)-dione 3,4,8,9-Tetrahydro-6-methoxy-3,3,8,8-tetramethyl-1-phenylfuro[2,3-h]isoquinoline (796 mg, 2.37 mmol) was dissolved in conc. sulfuric acid (3 mL), N-(hydroxymethyl)phthalimide (462 mg, 2.61 mmol) was added thereto and the mixture was stirred at room temperature for 2 hours. Water was poured into the reaction mixture, which was extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 8:1 followed by 5:1) and the resultant crystals were washed with diethyl ether to obtain the title compound (506 mg, yield: 43%).

Melting point: 193–195° C.
$^1$H NMR (CDCl$_3$) δ 1.25 (6H, s), 1.28 (6H, s), 2.12 (2H, s), 2.81 (2H, s), 3.96 (3H, s), 4.92 (2H, s), 7.37 (5H, s), 7.69–7.71 (2H, m), 7.81–7.85 (2H, m).

Example 230
3,4,8,9-Tetrahydro-6-methoxy-3,3,8,8-tetramethyl-1-phenyl-5-furo[2,3-h]isoquinolinemethanamine Hydrazine monohydrate (0.71 mL, 14.7 mmol) was added to a suspension of 2-[(3,4,8,9-tetrahydro-6-methoxy-3,3,8,8-tetramethyl-1-phenylfuro[2,3-h]isoquinolin-5-yl)methyl]-1H-isoindol-1,3(2H)-dione (6.94 g, 14.0 mmol) in ethanol (40 mL) and the mixture was heated under reflux for 3 hours. Diisopropyl ether was poured into the reaction mixture and the precipitated crystals were removed off by filtration. The filtrate was combined with 1 M aqueous solution of sodium hydroxide and water, and the organic layer was separated and the aqueous layer was extracted with ethyl acetate. The organic layer was washed with brine, dried over sodium sulfate, filtered and concentrated under reduced pressure. The residue was subjected to a column chromatography on a silica gel (ethyl acetate followed by ethyl acetate/triethylamine 50:1) and crystallized from hexane-diethyl ether to obtain the title compound (3.46 g, yield: 68%).

Melting point: 140–142° C.
$^1$H NMR (CDCl$_3$) δ 1.26 (6H, s), 1.28 (6H, s), 2.13 (2H, s), 2.71 (2H, s), 3.86 (2H, s), 3.97 (3H, s), 7.38 (5H, s).

Example 231
N-[(3,4,8,9-Tetrahydro-6-methoxy-3,3,8,8-tetramethyl-1-phenylfuro[2,3-h]isoquinolin-5-yl)methyl]formamide The title compound was obtained from 3,4,8,9-tetrahydro-6-methoxy-3,3,8,8-tetramethyl-1-phenyl-5-furo[2,3-h]isoquinolinemethanamine by the method similar to that in EXAMPLE 221. Yield: 84%.

Melting point: 205–208° C. (diethyl ether-hexane).
$^1$H NMR (CDCl$_3$) δ 1.23 (6H, s), 1.28(6H, s), 2.14 (2H, s), 2.79 (2H, s), 4.00 (3H, s), 4.53 (2H, d, J=5.4 Hz), 5.86 (1H, br 9). 7.37 (5H, s), 8.17 (1H, s).

Example 232
N-[(3,4,8,9-Tetrahydro-6-methoxy-3,3,8,8-tetramethyl-1-phenylfuro[2,3-h]isoquinolin-5-yl)methyl]acetamide The title compound was obtained from 3,4,8,9-tetrahydro-6-methoxy-3,3,8,8-tetramethyl-1-phenyl-5-furo[2,3-h]isoquinolinemethanamine by the method similar to that in EXAMPLE 30. Yield: 90%.

Melting point: 164–166° C. (diethyl ether-hexane).
$^1$H NMR (CDCl$_3$) δ 1.23 (6H, s), 1.28 (6H, s), 1.97 (3H, s), 2.14 (2H, s), 2.78 (2H, s), 3.99 (3H, s), 4.48 (2H, d, J=5.6 Hz), 5.74 (1H, br s), 7.38 (5H, s).

Example 233
N-[(3,4,8,9-Tetrahydro-6-methoxy-3,3,–8,8-tetramethyl-1-phenylfuro[2,3-h]isoquinolin-5-yl)methyl]urea The title compound was obtained from 3,4,8,9-tetrahydro-6-methoxy-3,3,8,8-tetramethyl-1-phenyl-5-furo[2,3-h]isoquinolinemethanamine by the method similar to that in EXAMPLE 227. Yield: 59%.

Melting point: 172–174° C. (diethyl ether-hexane).
$^1$H NMR (CDCl$_3$) δ 1.24 (6H, s), 1.27 (1.8H, s), 1.28 (4.2H, s), 1.58 (2H, s), 2.13 (0.6H, s), 2.14 (1.4H, s), 2.77 (2H, s), 3.98 (2.1H, s), 4.00 (0.9H, s), 4.38 (1.4H, d, J=5.8 Hz), 4.45–4.58 (1.4H, m), 4.46 (0.6H, d, J=5.8 Hz), 4.80–4.95 (0.6H, m), 7.33–7.38 (5H, m).

Example 234
5-Bromomethyl-3,4,8,9-tetrahydro-6-methoxy-3,3,8,8-tetramethyl-1-phenylfuro[2,3-h]isoquinoline Conc. sulfuric acid (3.39 mL, 63.6 mmol) was added to a suspension of 3,4,8,9-tetrahydro-6-methoxy-3,3,8,8-tetramethyl-1-phenylfuro[2,3-h]isoquinoline (7.12 g, 21.2 mmol), paraformaldehyde (94%) (1.02 g, 31.8 mmol) and sodium bromide (2.51 g, 24.4 mmol) in acetic acid (6.07 mL, 106 mmol) and the mixture was stirred at 90° C. for 5 hours. Ice water was poured into the reaction mixture, which was washed with diethyl ether, neutralized with con. aqueous ammonia, and extracted twice with ethyl acetate. The combined organic layer was washed with water and brine, dried over sodium sulfate, filtered and concentrated under reduced pressure. The residue was subjected to a column chromatography on a silica gel (hexane/ethyl acetate 7:1 followed by 5:1) to obtain the title compound (4.57 g, yield: 50%).

Amorphous.
$^1$H NMR (CDCl$_3$) δ 1.28 (12H, s), 2.14 (2H, s), 2.71 (2H, s), 4.03 (3H, s), 4.65 (2H, s), 7.38 (5H, s).

Example 235
3,4,8,9-Tetrahydro-6-methoxy-5-(methoxymethyl)-3,3,8,8-tetramethyl-1-phenylfuro[2,3-h]isoquinoline Hydrochloride 28% sodium methoxide/methanol-solution (0.91 mL, 4.73 mmol) was added to a solution of 5-bromomethyl-3,4,8,9-tetrahydro-6-methoxy-3,3,8,8-tetramethyl-1-phenylfuro[2,3-h]isoquinoline (1.84 g, 4.30 mmol) in methanol (10 mL) and the mixture was stirred at room temperature for 1 hour and then at 60° C. for 1 hour. Furthermore 28% sodium methoxide/methanol solution (1.82 mL, 9.46 mmol) was added to the mixture and the mixture was stirred at 60° C. for 1 hour. The reaction mixture was concentrated under reduced pressure, and the residue was combined with water and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 7:1) to obtain a free base of the title compound. This was dissolved in ethyl acetate, combined with 4 M hydrogen chloride/ethyl acetate solution (0.77 mL), and the resultant crystals were washed with ethyl acetate to obtain the title compound (1.16 g, yield: 65%).

Melting point: 143–145° C.
$^1$H NMR (DMSO-d$_6$) δ 1.26 (6H, s), 1.44 (6H, s), 2.16 (2H, s), 3.15 (2H, s), 3.29 (3H, s), 3.99 (3H, s), 4.50 (2H, s), 7.63–7.66 (5H, m).

Example 236
5-(Ethoxymethyl)-3,4,8,9-tetrahydro-6-methoxy-3,3,8,8-tetramethyl-1-phenylfuro[2,3-h]isoquinoline Hydrochloride Sodium acetate (143 mg, 1.75 mmol) and 2 M aqueous solution of sodium hydroxide (2 mL) were added to a solution of 5-bromomethyl-3,4,8,9-tetrahydro-6-methoxy-3,3,8,8-tetramethyl-1-phenylfuro[2,3-h]isoquinoline (374 mg, 0.873 mol) in ethanol (3 mL) and the mixture was stirred at 60° C. for 2 hours and then at 80° C. for 2 hours. Ice water was poured into the reaction mixture, which was extracted twice with ethyl acetate. The combined organic layer was washed with brine, dried over sodium sulfate, filtered, and concentrated under reduced pressure. The residue was subjected to a column chromatography on a silica gel (hexane/ethyl acetate 5:1) to obtain a free base of the title compound. This was dissolved in ethyl acetate, combined with 4 M hydrogen chloride/ethyl acetate solution, concentrated under reduced pressure and crystallized from diethyl ether to obtain the title compound (191 mg, yield: 51%).

Melting point: 137–139° C.

$^1$H NMR (DMSO-$d_6$) δ 1.14 (3H, t, J=7.2 Hz), 1.26 (6H, s), 1.44 (6H, s), 2.16 (2H, s), 3.16 (2H, s), 3.49 (2H, q, J=7.2 Hz), 3.99 (3H, s), 4.54 (2H, s), 7.63–7.78 (5H, m).

Example 237

3,4,8,9-Tetrahydro-6-methoxy-3,3,8,8-tetramethyl-1-phenyl-5-furo[2,3-h]isoquinolinemethanol A suspension of 5-bromomethyl-3,4,8,9-tetrahydro-6-methoxy-3,3,8,8-tetramethyl-1-phenylfuro[2,3-h]isoquinoline (289 mg, 0.675 mmol) and calcium carbonate (506 mg, 5.06 mmol) in 1,4-dioxane (3 mL) and water (3 mL) was stirred at 60° C. for 2 hours. Water was poured into the reaction mixture, which was extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 3:1) and crystallized from hexane-diethyl ether to obtain the title compound.(159 mg, yield: 65%).

Melting point: 160–163° C.

$^1$H NMR (CDCl$_3$) δ 1.25 (6H, s), 1.28 (6H, s), 1.97 (1H, t, J=6.0 Hz), 2.14 (2H, s), 2.75 (2H, s), 4.00 (3H, s), 4.74 (2H, d, J=6.0 Hz), 7.38 (5H, s).

Example 238

5-(Fluoromethyl)-3,4,8,9-tetrahydro-6-methoxy-3,3,8,8-tetramethyl-1-phenylfuro[2,3-h]isoquinoline Hydrochloride Potassium fluoride (spray dried material) (118 mg, 2.02 mmol) and 18-crown-6 (534 mg, 2.02 mmol) were added to a solution of 5-bromomethyl-3,4,8,9-tetrahydro-6-methoxy-3,3,8,8-tetramethyl-1-phenylfuro[2,3-h]isoquinoline (289 mg, 0.675 mmol) in acetonitrile (5 mL) and the mixture was stirred at 80° C. for 7 hours. Acetonitrile was distilled off under reduced pressure, and water was poured into the residue and the mixture was extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 10:1 followed by 5:1) to obtain a free base of the title compound. This was dissolved in ethyl acetate, combined with 4 M hydrogen chloride/ethyl acetate solution, crystallized from diethyl ether to obtain the title compound (230 mg, yield: 84%).

Melting point: 146–158° C.

$^1$H NMR (DMSO-$d_6$) δ 1.26 (6H, s), 1.45 (6H, s), 2.15–2.23 (2H, m), 3.22 (2H, s), 4.04 (3H, s), 5.57 (2H, d, J=48.0 Hz), 7.63–7.80 (5H, m).

Example 239

3,4,8,9-Tetrahydro-6-methoxy-3,3,5,8,8-pentamethyl-1-phenylfuro[2,3-h]isoquinoline Hydrochloride Tributyltin hydride (0.91 mL, 4.73 mmol) and 2,2'-azobis(isobutyronitrile) (11 mg, 0.0677 mmol) were added to a solution of 5-bromomethyl-3,4,8,9-tetrahydro-6-methoxy-3,3,8,8-tetramethyl-1-phenylfuro[2,3-h]isoquinoline (290 mg, 0.677 mmol) in chlorobenzene (3 mL) and the mixture was stirred at 80° C. for 2 hours. Chlorobenzene was distilled off under reduced pressure and the residue was subjected to a column chromatography on a basic silica gel (hexane/ethyl acetate 10:1) to obtain a free base of the title compound. This was dissolved in ethyl acetate, combined with 4 M hydrogen chloride/ethyl acetate solution, and crystallized from ethyl acetate to obtain the title compound (63 mg, yield: 24%).

Melting point: 138–140° C.

$^1$H NMR (DMSO-$d_6$) δ 1.24 (6H, s), 1.45 (6H, s), 2.12 (2H, s), 2.17 (3H, s), 3.08 (2H, s), 3.99 (3H, s), 7.58–7.76 (5H, m).

Example 240

3,4,8,9-Tetrahydro-6-methoxy-3,3,8,8-tetramethyl-1-phenyl-5-furo[2,3-h]isoquinolineacetonitrile A solution of potassium cyanide (143 mg, 2.20 mmol) in water (2.25 mL) was added to a solution of 5-bromomethyl-3,4,8,9-tetrahydro-6-methoxy-3,3,8,8-tetramethyl-1-phenylfuro[2,3-h]isoquinoline (947 mg, 2.20 mmol) in N,N-dimethylformamide (9.5 mL) and the mixture was stirred at room temperature for 3 hours. Water was poured into the reaction mixture, which was extracted twice with ethyl acetate. The combined organic layer was washed twice each with water and brine, dried over sodium sulfate, filtered and concentrated under reduced pressure. The residue was subjected to a column chromatography on a silica gel (hexane/ethyl acetate 5:1 followed by 3:1) and crystallized from hexane-diethyl ether to obtain the title compound (465 mg, yield: 56%).

Melting point: 95–96° C.

$^1$H NMR (CDCl$_3$) δ 1.28 (6H, s), 1.28 (6H, s), 2.15 (2H, s), 2.68 (2H, s), 3.74 (2H, s), 4.03 (3H, s), 7.38 (5H, s).

Example 241

3,4,8,9-Tetrahydro-6-methoxy-3,3,8,8-tetramethyl-1-phenyl-5-furo[2,3-h]isoquinolineacetic Acid Ethyl Ester Hydrochloride While cooling in ice, conc. sulfuric acid (2.34 mL, 43.8 mmol) was added to a solution of 3,4,8,9-tetrahydro-6-methoxy-3,3,8,8-tetramethyl-1-phenyl-5-furo[2,3-h]isoquinolineacetonitrile (4.01 g, 10.7 mmol) in ethanol (36 mL) and the mixture was heated under reflux for 60 hours. Ice water was poured into the reaction mixture, which was neutralized with conc. aqueous ammonia, and then extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 20:1 followed by 5:1) to obtain a free base of the title compound.

$^1$H NMR (CDCl$_3$) δ 1.23 (6H, s), 1.28 (6H, s), 1.28 (3H, t, J=7.1 Hz), 2.14 (2H, s), 2.59 (2H, s), 3.73 (2H, s), 3.92 (3H, s), 4.18 (2H, g, J=7.1 Hz), 7.38 (5H, s).

This was dissolved in ethyl acetate, combined with 4 M hydrogen chloride/ethyl acetate solution and concentrated under reduced pressure to obtain the title compound (2.58 g, yield: 53%).

Amorphous.

$^1$H NMR (DMSO-$d_6$) δ 1.21 (3H, t, J=7.0 Hz), 1.26 (6H, s), 1.42 (6H, s), 2.17 (2H, s), 3.08 (2H, s), 3.78 (2H, s), 3.96 (3H, s), 4.91 (2H, q, J=7.0 Hz), 7.63–7.80 (5H, m).

Example 242

3,4,8,9-Tetrahydro-6-methoxy-3,3,8,8-tetramethyl-1-phenyl-5-furo[2,3-h]isoquinolineacetic Acid

5 M aqueous solution of sodium hydroxide (2 mL) was added to a solution of 3,4,8,9-tetrahydro-6-methoxy-3,3,8,8-tetramethyl-1-phenyl-5-furo[2,3-h]isoquinolineacetic acid ethyl ester (750 mg, 1.78 mmol) in ethanol (5 mL) and the mixture was stirred at room temperature for 5 hours. Ethanol was distilled off under reduced pressure, and water was poured into the residue, and the mixture was washed with diisopropyl ether. The aqueous layer was adjusted at pH 3.5 with 2 M hydrochloric acid, combined with sodium chloride, and extracted three times with tetrahydrofuran. The combined organic layer was dried over sodium sulfate, filtered, concentrated under reduced pressure and crystallized from hexane-diethyl ether to obtain the title compound (176 mg, yield: 25%).

Melting point: 225–245° C.

$^1$H NMR (CDCl$_3$) δ 1.25 (6H, s), 1.27 (6H, s), 2.13 (2H, s), 2.61 (2H, s), 3.74 (2H, s), 3.94 (3H, s), 7.38 (5H, s).

Example 243

3,4,8,9-Tetrahydro-6-methoxy-3,3,8,8-tetramethyl-1-phenyl-5-furo[2,3-h]isoquinolineacetamide

N,N'-Carbonyldiimidazole (226 mg, 1.40 mmol) was added to a solution of 3,4,8,9-tetrahydro-6-methoxy-3,3,8,8-tetramethyl-1-phenyl-5-furo[2,3-h]isoquinolineacetic acid (499 mg, 1.27 mmol) in N,N-dimethylformamide (5 mL) and the mixture was stirred at room temperature for 10 minutes. Powdered ammonium chloride (75 mg, 1.40 mmol) and triethylamine (0.20 mL, 1.40 mmol) were added and stirred at room temperature for 1 hour and then at 60° C. for 4 hours. Ice water was poured into the reaction mixture, which was extracted twice with ethyl acetate. The combined organic layer was washed with water and brine (twice), dried over sodium sulfate, filtered and concentrated under reduced pressure. The resultant crystals were washed with diethyl ether to obtain the title compound (358 mg, yield: 72%).

Melting point: 171–176° C.

$^1$H NMR (CDCl$_3$) δ 1.27 (6H, s), 1.29 (6H, s), 2.15 (2H, s), 2.74 (2H, s), 3.65 (2H, s), 4.00 (3H, s), 5.22 (1H, br s), 5.80 (1H, br s), 7.40 (5H, s).

Example 244

3,4,8,9-Tetrahydro-6-methoxy-N,3,3,8,8-pentamethyl-1-phenyl-5-furo[2,3-h]isoquinolineacetamide

The title compound was obtained from methylamine hydrochloride by the method similar to that in EXAMPLE 243. Yield: 73%.

Melting point: 187–190° C. (hexane).

$^1$H NMR (CDCl$_3$) δ 1.23 (6H, s), 1.30 (611, s), 2.15 (2H, s), 2.69 (2H, s), 2.76 (3H, d, J=5.2 Hz), 3.63 (2H, s), 3.96 (3H, s), 5.63–5.75 (1H, br s), 7.38 (5H, s).

Example 245

2-[(3,4,8,9-Tetrahydro-6-hydroxy-3,3,8,8-tetramethyl-1-phenylfuro[2,3-h]isoquinolin-5-yl)methyl]-1H-isoindol-1,3 (2H)-dione

The title compound was obtained from 3,4,8,9-tetrahydro-3,3,8,8-tetramethyl-1-phenyl-6-furo[2,3-h]isoquinolinol by the method similar to that in EXAMPLE 229. Yield: 16%.

Melting point: 239–242° C. (diethyl ether-hexane).

$^1$H NMR (CDCl$_3$) δ 1.28 (12H, s), 2.15 (2H, s), 2.98 (2H, s), 4.94 (2H, s), 7.35 (5H, s), 7.73–7.77 (2H, m), 7.86–7.91 (2H, m), 8.08 (1H, br s).

Example 246

3,4,8,9-Tetrahydro-6-hydroxy-3,3,8,8-tetramethyl-1-phenyl-5-furo[2,3-h]isoquinolinemethanol

While cooling in ice, 3,4,8,9-tetrahydro-3,3,8,8-tetramethyl-1-phenyl-6-furo[2,3-h]isoquinolinol (200 mg, 0.622 mmol) was added to a solution of chloromethylmethyl ether (0.052 mL, 0.684 mmol) and aluminum chloride (91 mg, 0.684 mmol) in 1,2-dichloroethane (2 mL) and the mixture was stirred at room temperature for 5 hours. The reaction mixture was poured into ice water, washed with diethyl ether, neutralized with 5 M aqueous solution of sodium hydroxide and extracted twice with ethyl acetate. The combined organic layer was washed with water and brine, dried over sodium sulfate, filtered and concentrated under reduced pressure. The residue was subjected to a column chromatography on a silica gel (hexane/ethyl acetate/triethylamine 25:25:1 followed by ethyl acetate/triethylamine 50:1) and crystallized from hexane-ethyl acetate to obtain the title compound (31 mg, yield: 14%).

Melting point: 210–230° C.

$^1$H NMR (CDCl$_3$) δ 1.28 (6H, s), 1.32 (6H, s), 2.13 (2H, s), 2.77 (2H, s), 4.84 (2H, s), 7.34–7.44 (5H, m).

Example 247

1-(2-Bromophenyl)-3,4,8,9-tetrahydro-6-methoxy-3,3,8,8-tetramethylfuro[2,3-h]isoquinoline Hydrochloride

While cooling in ice, conc. sulfuric-acid (2.52 mL, 47.3 mmol) was added to a solution of 2-bromobenzonitrile (3.92 g, 21.5 mmol) in toluene (12 mL) and acetic acid (12 mL). And then, a solution of 2,3-dihydro-7-methoxy-2,2-dimethyl-5-(2-methyl-1-propenyl)benzofuran (5.00 g, 21.5 mmol) in toluene (12 mL) was added thereto and the mixture was stirred at 80° C. for 1 hour. Ice water was poured into the reaction mixture, and the aqueous layer was separated and neutralized with conc. aqueous ammonia and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 20:1 followed by 10:1) to obtain a free base of the title compound.

$^1$H NMR (CDCl$_3$) δ 1.23 (3H, s), 1.29 (3H, s), 1.33 (3H, s), 1.38 (3H, s), 2.00 (1H, d, J=16.1 Hz), 2.17 (1H, d, J=16.1 Hz), 2.68 (1H, d, J=15.7 Hz), 2.80 (1H, d, J=15.7 Hz), 3.91 (3H, s), 6.60 (1H, s), 7.17–7.42 (3H, m), 7.56 (1H, d, J=8.0 Hz).

This was dissolved in ethyl acetate, combined with 4 M hydrogen chloride/ethyl acetate solution and concentrated under reduced pressure to obtain the title compound (3.27 g. yield: 34%).

Amorphous.

$^1$H NMR (DMSO-d$_6$) δ 1.21 (3H, s), 1.24 (3H, s), 1.47 (3H, s), 1.50 (3H, s), 1.99 (1H, d, J=16.4 Hz), 2.12 (1H, d, J=16.4 Hz), 3.11 (1H, d, J=17.2 Hz), 3.29 (1H, d, J=17.2 Hz), 3.95 (3H, s), 7.14 (1H, s), 7.56–7.68 (3H, m), 7.89–7.93 (1H, m).

Example 248

1-[3-(2-Furanyl)phenyl]-3,4,8,9-tetrahydro-6-methoxy-3,3,8,8-tetramethylfuro[2,3-h]isoquinoline

Dichlorobis(triphenylphosphine)palladium(II) (53 mg, 0.0750 mmol) and copper (I) iodide (14 mg, 0.0750 mmol) were added to a suspension of 1-(3-bromophenyl)-3,4,8,9-tetrahydro-6-methoxy-3,3,8,8-tetramethylfuro[2,3-h]isoquinoline (622 mg, 1.50 mmol) and tributyl-2-furanyltin (590 mg, 1.65 mmol) in tetrahydrofuran (6 mL) and the mixture was heated under reflux for 24 hours, and tributyl-2-furanyltin (590 mg, 1.65 mmol) was added thereto and the mixture was heated under reflux for 15 hours. The insolubles were filtered off and the filtrate was concentrated under reduced pressure. The residue was subjected to a column chromatography on a basic silica gel (hexane/ethyl acetate 100:1 followed by 10:1) and crystallized-from diethyl ether-hexane to obtain the title compound (114 mg, yield: 19%).

Melting point: 126–128° C.

$^1$H NMR (CDCl$_3$) δ 1.27 (6H, s), 1.30 (6H, s), 2.27 (2H, s), 2.71 (2H, s), 3.93 (3H, s), 6.46–6.49 (1H, m), 6.63 (1H, s), 6.68 (1H, d, J=3.4 Hz), 7.31–7.47 (3H, m), 7.69–7.74(2H, m).

Example 249

3,4,8,9-Tetrahydro-6-methoxy-3,3,8,8-tetramethyl-1-[4-(2-pyridinyl)phenyl]furo[2,3-h]isoquinolin The title compound was obtained from 1-(4-bromophenyl)-3,4,8,9-tetrahydro-6-methoxy-3,3,8,8-tetramethylfuro[2,3-h]isoquinoline and tributyl-2-pyridinyltin by the method similar to that in EXAMPLE 248. Yield: 50%.

Melting point: 127–129° C. (hexane).

$^1$H NMR (CDCl$_3$) δ 1.26 (6H, s), 1.30 (6H, s), 2.32 (2H, s), 2.70 (2H, s), 3.93 (3H, s), 6.62 (1H, s), 7.22–7.30 (1H, m), 7.52 (2H, d, J=8.4 Hz), 7.76–7.79 (2H, m), 8.04 (2H, d, J=8.4 Hz), 8.72 (1H, d, J=4.8 Hz).

Example 250

3,4,8,9-Tetrahydro-6-methoxy-3,3,8,8-tetramethyl-1-[2-(2-pyridinyl)phenyl]furo[2,3-h]isoquinoline The title compound was obtained from 1-(2-bromophenyl)-3,4,8,9-tetrahydro-6-methoxy-3,3,8,8-tetramethylfuro[2,3-h]isoquinoline and tributyl-2-pyridinyltin by the method similar to that in EXAMPLE 248. Yield: 9.5%.

Melting point: 120–122° C. (hexane-diethyl ether).

$^1$H NMR (CDCl$_3$) δ 1.13 (3H, s), 1.17 (3H, s), 1.25 (3H, s), 1.28 (3H, s), 1.98 (1H, d, J=16.2 Hz), 2.42 (1H, d, J=16.2 Hz), 2.64 (2H, s), 3.85 (3H, s), 6.45 (1H, s), 6.99–7.06 (1H, m), 7.35–7.50 (5H, m), 7.65–7.70 (1H, m), 8.41–8.44 (1H, m).

Example 251

3,4,8,9-Tetrahydro-6-methoxy-3,3,8,8-tetramethyl-1-[3-(2-pyridinyl)phenyl]furo[2,3-h]isoquinoline The title compound was obtained from tributyl-2-pyridinyltin by the method similar to that in EXAMPLE 248. Yield: 60%.

Melting point: 137–139° C. (diethyl ether-hexane).

$^1$H NMR (CDCl$_3$) δ 1.28 (12H, s), 2.28 (2H, s), 2.71 (2H, s), 3.93 (3H, s), 6.63 (1H, s), 7.20–7.25 (1H, m), 7.42–7.55 (2H, m), 7.74–7.77 (2H, m), 8.03–8.07 (2H, m), 8.69 (1H, d, J=5.0 Hz).

Example 252

3,4,8,9-Tetrahydro-6-methoxy-3,3,8,8-tetramethyl-1-[3-(2-thienyl)phenyl]furo[2,3-h]isoquinoline The title compound was obtained from tributyl-2-thienyltin by the method similar to that in EXAMPLE 248. Yield: 37%.

Melting point: 172–175° C. (diethyl ether-hexane).

$^1$H NMR (CDCl$_3$) δ 1.28 (6H, s), 1.31 (6H, s), 2.28 (2H, s), 2.72 (2H, s), 3.94 (3H, s), 6.63 (1H, s), 7.06–7.10 (1H, m), 7.29–7.44 (4H, m), 7.62–7.69 (2H, m).

Example 253

3,4,8,9-Tetrahydro-6-methoxy-3,3,8,8-tetramethyl-1-[3-(5-pyrimidinyl)phenyl]furo[2,3-h]isoquinoline Sodium (431 mg, 18.8 mmol) was added to a solution of naphthalene (2.20 g, 17.1 mmol) in 1,2-dimethoxyethane (20 mL) and the mixture was stirred at room temperature for 1.5 hours. While cooling in ice, chlorotrimethyltin (2.91 g, 14.6 mmol) was added to the mixture and after 10 minutes, 5-bromopyrimidine (2.0 g, 12.6 mmol) was added thereto and the mixture was stirred at room temperature for 2 hours. 1,2-Dimethoxyethane was distilled off under reduced pressure, and water was poured into the residue, and the mixture was extracted twice with diethyl ether. The combined organic layer was washed twice with water and then with brine, dried over sodium sulfate, filtered, concentrated under reduced pressure to obtain a mixture of trimethyl-5-pyrimidinyltin, naphthalene and 5-bromopyrimidine.

This mixture was used to obtain the title compound by the method similar to that in EXAMPLE 248. Yield: 32%.

Melting point: 141–143° C. (diethyl ether-hexane).

$^1$H NMR (CDCl$_3$) δ 1.28 (6H, s), 1.31 (6H, s), 2.25 (2H, s), 2.73 (2H, s), 3.94 (3H, s), 6.64 (1H, s), 7.46–7.67 (4H, m), 8.99 (2H, s), 9.22 (1H, s).

Example 254

3,4,8,9-Tetrahydro-6-methoxy-3,3,8,8-tetramethyl-1-[2-(4-pyridinyl)phenyl]furo [2,3-h]isoquinoline A solution of sodium carbonate (236 mg, 2.23 mol) in water (2 mL) and tetrakis(triphenylphosphine)palladium(0) (66 mg, 0.0567 mmol) were added to a solution of 1-(2-bromophenyl)-3,4,8,9-tetrahydro-6-methoxy-3,3,8,8-tetramethylfuro[2,3-h]isoquinoline (558 mg, 1.35 mmol) and 4-pyridinylboronic acid (248 mg, 2.02 mmol) in 1,2-dimethoxyethane (6 mL) and ethanol (2 mL) and the mixture was stirred at 80° C. for 24 hours under nitrogen atmosphere. Water was poured into the reaction mixture, which was extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 20:1 followed by 3:1) and crystallized from diethyl ether-hexane to obtain the title compound (200 mg, yield: 36).

Melting point: 187–189° C.

$^1$H NMR (CDCl$_3$) δ 1.09 (3H, s), 1.25 (3H, s), 1.28 (6H, s), 1.94 (1H, d, J=16.3 Hz), 2.13 (1H, d, J=16.3 Hz), 2.60 (2H, s), 3.84 (3H, s), 6.44 (1H, s), 7.24 (2H, d, J=6.2 Hz), 7.36–7.52 (4H, m), 8.44 (2H, d, J=6.2 Hz).

Example 255

3,4,8,9-Tetrahydro-6-methoxy-3,3,8,8-tetramethyl-1-[4-(4-pyridinyl)phenyl]furo[2,3-h]isoquinoline Dihydrochloride By the method similar to that In EXAMPLE 254 and starting from 1-(4-bromophenyl)-3,4,8,9-tetrahydro-6-methoxy-3,3,8,8-tetramethylfuro[2,3-h]isoquinoline, a free base of the title compound was obtained. This was dissolved in ethyl acetate, combined with 4 M hydrogen chloride/ethyl acetate solution, concentrated under reduced pressure and crystallized from ethanol-ethyl acetate to obtain the title compound. Yield: 51%.

Melting point: 115–117° C.

$^1$H NMR (DMSO-d$_6$) δ 1.23 (6H, s), 1.48 (6H, s), 2.70 (2H, s), 3.19 (2H, s), 3.96 (3H, s), 7.13 (1H, s), 7.86 (2H, d, J=8.4 Hz), 8.27 (2H, d, J=8.4 Hz), 8.35 (2H, d, J=6.6 Hz), 8.96 (2H, d, J=6.6 Hz).

Example 256

3,4,8,9-Tetrahydro-6-methoxy-3,3,8,8-tetramethyl-1-[3-(3-pyridinyl)phenyl]furo[2,3-h]isoquinoline The title compound was obtained from 1-(3-bromophenyl)-3,4,8,9-tetrahydro-6-methoxy-3,3,8,8-tetramethylfuro[2,3-h]isoquinoline and 3-(diethylboryl)pyridine by the method similar to that in EXAMPLE 254. Yield: 70%.

Melting point: 116–117° C. (hexane-diethyl ether).
$^1$H NMR (CDCl$_3$) δ 1.27 (6H, s), 1.30 (6H, s), 2.25 (2H, s), 2.72 (2H, s), 3.93 (3H, s), 6.63 (1H, s), 7.33–7.63 (5H, m), 7.85–7.93 (1H, m), 8.58–8.61 (1H, m), 8.87 (1H, d, J=2.6 Hz).

Example 257

3,4,8,9-Tetrahydro-6-methoxy-3,3,8,8-tetramethyl-1-[4-(3-pyridinyl)phenyl]furo[2,3-h]isoquinoline Dihydrochloride By the method similar to that in EXAMPLE 254 and starting from 1-(4-bromophenyl)-3,4,8,9-tetrahydro-6-methoxy-3,3,8,8-tetramethylfuro[2,3-h]isoquinoline and 3-(diethylboryl)pyridine, a free base of the title compound was obtained. This was dissolved in ethyl acetate, combined with 4 M hydrogen chloride/ethyl acetate solution, concentrated under reduced pressure to obtain the title compound. Yield: 84%.
Amorphous.
$^1$H NMR (DMSO-d$_6$) δ 1.22 (6H, s), 1.48 (6H, s), 2.29 (2H, s), 3.19 (2H, s), 3.95 (3H, s), 7.13 (1H, s), 7.82 (2H, d, J=8.4 Hz), 7.92–7.99 (1H, m), 8.16 (2H, d, J=8.4 Hz), 8.74 (1H, d, J=7.8 Hz), 8.87 (1H, d, J=5.0 Hz), 9.31 (1H, s).

Example 258

1-[3-(Benzofuran-2-yl)phenyl]-3,4,8,9-tetrahydro-6-methoxy-3,3,8,8-tetramethylfuro[2,3-h]isoquinoline The title compound was obtained from 1-(3-bromophenyl)-3,4,8,9-tetrahydro-6-methoxy-3,3,8,8-tetramethylfuro[2,3-h]isoquinoline and 2-benzofuranylboronic acid by the method similar to that in EXAMPLE 254. Yield: 74%.
Melting point: 160–161° C. (hexane-diethyl ether).
$^1$H NMR (CDCl$_3$) δ 1.29 (12H, s), 2.29 (2H, s), 2.32 (2H, s), 3.94 (3H, s), 6.65 (1H, s), 7.07 (1H, s), 7.23–7.33 (2H, m), 7.37–7.61 (4H, m), 7.88–7.93 (2H, m).

Example 259

3'-(3,4,8,9-Tetrahydro-6-methoxy-3,3,8,8-tetramethylfuro[2,3-h]isoquinolin-1-yl)[1,1'-biphenyl]-4-amine The title compound was obtained from 1-(3-bromophenyl)-3,4,8,9-tetrahydro-6-methoxy-3,3,8,8-tetramethylfuro[2,3-h]isoquinoline and 4-(1,3,2-dioxaborynan-2-yl)aniline by the method similar to that in EXAMPLE 254. Yield: 49%.
Melting point: 224–225° C. (ethyl acetate).
$^1$H NMR (CDCl$_3$) δ 1.26 (6H, s), 1.29 (6H, s), 2.26 (2H, s), 2.70 (2H, s), 3.72 (2H, br s), 3.93 (3H, s), 6.62 (1H, s), 6.74 (2H, d, J=8.8 Hz), 7.30–7.57 (4H, m), 7.43 (2H, d, J=8.8 Hz).

Example 260

N-[3'-(3,4,8,9-Tetrahydro-6-methoxy-3,3,8,8-tetramethylfuro[2,3-h]isoquinolin-1-yl)[1,1'-biphenyl]-4-yl]acetamide The title compound was obtained from 3'-(3,4,8,9-tetrahydro-6-methoxy-3,3,8,8-tetramethylfuro[2,3-h]isoquinolin-1-yl)[1,1'-biphenyl]-4-amine by the method similar to that in EXAMPLE 30. Yield: 82%.
Melting point: 224–225° C. (diethyl ether-hexane).
$^1$H NMR (CDCl$_3$) δ 1.27 (6H, s), 1.29 (6H, s), 2.18 (3H, s), 2.25 (2H, s), 2.71 (2H, s), 3.93 (3H, s), 6.62 (1H, s), 7.32–7.60 (9H, m).

Example 261

N-[3'-(3,4,8,9-tetrahydro-6-methoxy-3,3,8,8-tetramethylfuro[2,3-h]isoquinolin-1-yl)[1,1'-biphenyl]-4-yl]methanesulfonamide The title compound was obtained from 3'-(3,4,8,9-tetrahydro-6-methoxy-3,3,8,8-tetramethylfuro[2,3-h]isoquinolin-1-yl)[1,1'-biphenyl]-4-amine and methanesulfonyl chloride by the method similar to that in EXAMPLE 222. Yield: 81%.
Melting point: 228–230° C. (diethyl ether-hexane).
$^1$H NMR (CDCl$_3$) δ 1.30 (12H, s), 2.25 (2H, s), 2.73 (2H, s), 2.89 (3H, s), 3.93 (3H, s), 6.63 (1H, s), 7.22–7.57 (8H, m).

Example 262

3'-(3,4,8,9-Tetrahydro-6-methoxy-3,3,8,8-tetramethylfuro[2,3-h]isoquinolin-1-yl)[1,1'-biphenyl]-3-amine dihydrochloride By the method similar to that in EXAMPLE 254 and starting from 1-(3-bromophenyl)-3,4,8,9-tetrahydro-6-methoxy-3,3,8,8-tetramethylfuro[2,3-h]isoquinoline and 3-aminophenylboronic acid hydrate, a free base of the title compound was obtained.
$^1$H NMR (CDCl$_3$) δ 1.26 (6H, s), 1.30 (6H, s), 2.25 (2H, s), 2.71 (2H, s), 3.72 (2H, br s), 3.93 (3H, s), 6.62 (1H, s), 6.62–6.70 (1H, m), 6.92 (1H, t, J=1.8 Hz), 6.96–7.03 (1H, m), 7.20 (1H, t, J=7.8 Hz), 7.32–7.48 (2H, m), 7.54–7.62 (2H, m).

This was dissolved in ethyl acetate, combined with 4 M hydrogen chloride/ethyl acetate solution and concentrated under reduced pressure to obtain the title compound. Yield: 86%.
Amorphous.
$^1$H NMR (DMSO-d$_6$) δ 1.21 (3H, s), 1.25 (3H, s), 1.45 (3H, s), 1.50 (3H, s), 2.17–2.35 (2H, m), 3.08–3.30 (2H, m), 3.95 (3H, s), 7.12 (1H, s), 7.25–7.80 (8H, m).

Example 263

N-[3'-(3,4,8,9-Tetrahydro-6-methoxy-3,3,8,8-tetramethylfuro[2,3-h]isoquinolin-1-yl)[1,1'-biphenyl]-3-yl]acetamide The title compound was obtained from 3'-(3,4,8,9-tetrahydro-6-methoxy-3,3,8,8-tetramethylfuro[2,3-h]isoquinolin-1-yl)[1,1'-biphenyl]-3-amine by the method similar to that in EXAMPLE 30. Yield: 64%.
Melting point: 217–218° C. (ethanol).
$^1$H NMR (CDCl$_3$) δ 1.26 (6H, s), 1.30 (6H, s), 2.17 (3H, s), 2.25 (2H, s), 2.70 (2H, s), 3.93 (3H, s), 6.62 (1H, s), 7.32–7.66 (9H, m).
(Alternative Synthetic Method)
The title compound was obtained from 1-(3-bromophenyl)-3,4,8,9-tetrahydro-6-methoxy-3,3,8,8-tetramethylfuro[2,3-h]isoquinoline and 3-acetamidobenzenboronic acid by the method similar to that in EXAMPLE 254. Yield: 87%.

Example 264

2-Methyl-N-[3'-(3,4,8,9-tetrahydro-6-methoxy-3,3,8,8-tetramethylfuro[2,3-h]isoquinolin-1-yl)[1,1'-biphenyl]-3-yl]alanine Ethyl Ester Hydrochloride By the method similar to that in EXAMPLE 209 and starting from 3'-(3,4,8,9-tetrahydro-6-methoxy-3,3,8,8-tetramethylfuro[2,3-h]isoquinolin-1-yl)[1,1'-biphenyl]-3-amine and ethyl 2-bromoisobutyrate, a free base of the title compound was obtained. This was dissolved in ethyl acetate, combined with 4 M hydrogen chloride/ethyl acetate solution, concentrated under reduced pressure to obtain the title compound. Yield: 62%.
Amorphous.
$^1$H NMR (DMSO-d$_6$) δ 1.07 (3H, t, J=7.0 Hz), 1.21 (6H, s), 1.48 (12H, s), 2.15–2.32 (2H, m), 3.19 (2H, s), 3.96 (3H, s), 4.07 (2H, q, J=7.2 Hz), 6.50–7.92 (9H, m), 12.68 (1H, br s).

Example 265
N-[3'-(3,4,8,9-Tetrahydro-6-methoxy-3,3,8,8-tetramethylfuro[2,3-h]isoquinolin-1-yl)[1,1'-biphenyl]-3-yl]urea Hydrochloride By the method similar to that in EXAMPLE 227 and starting from 3'-(3,4,8,9-tetrahydro-6-methoxy-3,3,8,8-tetramethylfuro[2,3-h]isoquinolin-1-yl)[1,1'-biphenyl]-3-amine, a free base of the title compound was obtained. This was dissolved in ethyl acetate, combined with 4 M hydrogen chloride/ethyl acetate solution, concentrated under reduced pressure to obtain the title compound. Yield: 76%.

Amorphous.

$^1$H NMR (DMSO-d$_6$) δ 1.21 (6H, s), 1.47 (6H, s), 2.27 (2H, s), 3.19 (2H, s), 3.95 (3H, s), 6.00 (2H, br s), 7.12 (1H, s), 7.31–7.98 (8H, m), 8.92 (1H, s), 12.63 (1H, br s).

Example 266
2,2,2-Trifluoro-N-[3'-(3,4,8,9-tetrahydro-6-methoxy-3,3,8,8-tetramethylfuro[2,3-h]isoquinolin-1-yl)[1,1'-biphenyl]-3-yl]acetamide The title compound was obtained from 3'-(3,4,8,9-tetrahydro-6-methoxy-3,3,8,8-tetramethylfuro[2,3-h]isoquinolin-1-yl)[1,1'-biphenyl]-3-amine and trifluoroacetic anhydride by the method similar to that in EXAMPLE 222. Yield. 58%.

Melting point: 222–224° C. (diethyl ether). $^1$H NMR (CDCl$_3$) δ 1.26 (6H, s), 1.29 (6H, s), 2.23 (2H, s), 2.68 (2H, s), 3.93 (3H, s), 6.62 (1H, s), 7.34–7.69 (8H, m), 8.67 (1H, br s).

Example 267
N-[3'-(3,4,8,9-Tetrahydro-6-methoxy-3,3,8,8-tetramethylfuro[2,3-h]isoquinolin-1-yl)[1,1'-biphenyl]-3-yl]methanesulfonamide The title compound was obtained from 3'-(3,4,8,9-tetrahydro-6-methoxy-3,3,8 8-tetramethylfuro[2,3-h]isoquinolin-1-yl)[1,1'-biphenyl]-3-amine and methanesulfonyl chloride by the method similar to that in EXAMPLE 222. Yield: 54%.

Melting point: 141–143° C. (diethyl ether-ethyl acetate).
$^1$H NMR (CDCl$_3$) δ 1.30 (12H, s), 2.24 (2H, s), 2.73 (2H, s), 2.98 (3H, s), 3.94 (3H, s), 6.64 (1H, s), 7.36–7.66 (8H, m).

Example 268
N-Methyl-N-[3'-(3,4,8,9-tetrahydro-6-methoxy-3,3,8,8-tetramethylfuro[2,3-h]isoquinolin-1-yl)[1,1'-biphenyl]-3-yl]methanesulfonamide Hydrochloride By the method similar to that in EXAMPLE 190 and starting from N-[3'-(3,4,8,9-tetrahydro-6-methoxy-3,3,8,8-tetramethylfuro[2,3-h]isoquinolin-1-yl)[1,1'-biphenyl]-3-yl]methanesulfonamide and iodomethane, a free base of the title compound was obtained. This was dissolved in ethyl acetate, combined with 4 M hydrogen chloride/ethyl acetate solution, concentrated under reduced pressure to obtain the title compound. Yield: 85%.

Amorphous.

$^1$H NMR (DMSO-d$_6$) δ 1.21 (3H, s), 1.25 (3H, s), 1.45 (3H, s), 1.51 (3H, s), 2.18–2.37 (2H, m), 2.89 (3H, s), 3.07–3.29 (2H, m), 3.32 (3H, s), 3.95 (3H, s), 7.12 (1H, s), 7.48–7.62 (3H, m), 7.74–7.83 (3H, m), 8.00 (1H, s), 8.08 (1H, d, J=7.8 Hz).

Example 269
α,α-Dimethyl-4-(3,4,8,9-tetrahydro-6-methoxy-3,3,8,8-tetramethylfuro[2,3-h]isoquinolin-1-yl)benzeneacetonitrile While cooling in ice, sodium hydride (66% dispersion in oil) (4.33 g, 119 mmol) was added to a solution of 4-cyanobenzeneacetonitrile (7.70 g, 54.2 mmol) in N,N-dimethylformamide (68 mL) and the mixture was stirred at room temperature for 15 minutes. While cooling in ice, iodomethane (7.43 mL, 119 mmol) was added to the mixture and the mixture was stirred at room temperature for 2 hours. The reaction mixture was poured into ice water, and extracted twice with ethyl acetate. The combined organic layer was washed with water (twice) and brine, dried over magnesium sulfate, filtered and concentrated under reduced pressure. The residue was subjected to a column chromatography on a silica gel (hexane/ethyl acetate 5:1) and the resultant crystals were washed with hexane to obtain 4-cyano-α,α-dimethylbenzeneacetonitrile (4.76 g, yield: 52%).

$^1$H NMR (CDCl$_3$) δ 1.75 (6H, s), 7.61 (2H, d, J=8.6 Hz), 7.71 (2H, d, J=8.6 Hz).

Using this and by the method similar to that in EXAMPLE 17, the title, compound was obtained. Yield: 7.8%.

Melting point: 122–123° C. (disopropyl ether-hexane).
$^1$H NMR (CDCl$_3$) δ 1.25 (6H, s), 1.33 (6H, s), 1.74 (6H, s), 2.22 (2H, s), 2.69 (2H, s), 3.93 (3H, s), 6.62 (1H, s), 7.43 (2H, d, J=8.8 Hz), 7.50 (2H, d, J=8.8 Hz).

Example 270
α,α-Dimethyl-4-(3,4,8,9-tetrahydro-6-methoxy-3,3,8,8-tetramethylfuro[2,3-h]isoquinolin-1-yl)benzeneacetamide After separating a nitrile form by a column chromatography in EXAMPLE 269 followed by elution with ethyl acetate, the resultant crystals were washed with diusopropyl ether to obtain the title compound. Yield: 9.6%.

Melting point: 180–182° C.
$^1$H NMR (CDCl$_3$) δ 1.25 (6H, s), 1.31 (6H, s), 1.62 (6H, s), 2.21 (2H, s), 2.69 (2H, s), 3.93 (3H, s), 5.17 (2H, br s), 6.62 (1H, s), 7.42 (4H, s).

Example 271
α,α-Dimethyl-4-(3,4,8,9-tetrahydro-6-methoxy-3,3,8,8-tetramethylfuro[2,3-h]isoquinolin-1-yl)benzeneacetic Acid Ethyl Ester The title compound was obtained from α,α-Dimethyl-4-(3,4,8,9-tetrahydro-6-methoxy-3,3,8,8-tetramethylfuro[2,3-h]isoquinolin-1-yl)benzeneacetonitrile by the method similar to that in EXAMPLE 241. Yield: 43%.

Melting point: 150–151° C. (hexane).
$^1$H NMR (CDCl$_3$) δ 1.16 (3H, t, J=7.0 Hz), 1.24 (6H, s), 1.30 (6H, s), 1.57 (6H, s), 2.19 (2H, s), 2.68 (2H, s), 3.92 (3H, s), 4.10 (2H, q, J=7.0 Hz), 6.60 (1H, s), 7.34 (4H, s).

Example 272
N,α,α-Trimethyl-4-(3,4,8,9-tetrahydro-6-methoxy-3,3,8,8-tetramethylfuro[2,3-h]isoquinolin-1-yl)benzeneacetamide The title compound was obtained from α,α-Dimethyl-4-(3,4,8,9-tetrahydro-6-methoxy-3,3,8,8-tetramethylfuro[2,3-h]isoquinolin-1-yl)benzeneacetamide and iodomethane by the method similar to that in EXAMPLE 190. Yield: 31%.

Melting point: 160–162° C. (hexane-diethyl ether).
$^1$H NMR (CDCl$_3$) δ 1.25 (6H, s), 1.31 (6H, s), 1.60 (6H, s), 2.20 (2H, s), 2.69 (3H, d, J=4.6 Hz), 2.69 (2H, s), 3.93 (3H, s), 5.10 (1H, br s), 6.62 (1H, s), 7.39 (4H, s).

Example 273
N-[2-Methyl-2-[4-(3,4,8,9-tetrahydro-6-methoxy-3,3,8,8-tetramethylfuro[2,3-h]isoquinolin-1-yl)phenyl]propanoyl]glycine Ethyl Ester Ethyl bromoacetate (0.23 mL, 2.04 mmol) and potassium tert-butoxide (230 mg, 2.04 mmol) were added to a solution of α,α-dimethyl-4-(3,4,8,9-tetrahydro-6-methoxy-3,3,8,8- tetramethylfuro[2,3-h]isoquinolin-1-yl)benzeneacetamide (782 mg, 1.85 mmol) in N,N-dimethylformamide (7 mL) and the mixture was stirred at room temperature for 2 hours. Water was poured into the reaction mixture, which was extracted twice with ethyl acetate. The combined organic layer was washed twice with water and with brine, dried over sodium sulfate, filtered and concentrated under reduced pressure. The residue was subjected to a column chromatography on a basic silica gel (hexane/ethyl acetate 3:1 followed by ethyl acetate) and the resultant crystals were washed with diethyl ether-hexane to obtain the title compound (63 mg, yield; 6.7%).

Melting point: 133–138° C.

$^1$H NMR (CDCl$_3$) δ 1.24 (6H, s), 1.26 (3H, t, J=7.1 Hz), 1.32 (6H, s), 1.61 (6H, s), 2.25 (2H, s), 2.68 (2H, s), 3.92 (3H, s), 3.93 (2H, d, J=5.2 Hz), 4.15 (2H, q, J=7.1 Hz), 5.67 (1H, br s), 6.61 (1H, s), 7.42 (4H, s).

Example 274

α,α-Dimethyl-3-(3,4,8,9-tetrahydro-6-methoxy-3,3,8,8-tetramethylfuro[2,3-h]isoquinolin-1-yl)benzeneacetic Acid Ethyl Ester Hydrochloride By the method similar to that in EXAMPLE 17 and starting from 3-cyano-α,α-dimethylbenzeneacetic acid ethyl ester, a free base of the title compound was obtained $^1$H NMR (CDCl$_3$) δ 1.16 (3H, t, J=7.0 Hz), 1.25 (6H, br s), 1.30 (6H, s), 1.55 (6H, s), 2.15 (2H, s), 2.70 (2H, s), 3.92 (3H, s), 4.10 (2H, q, J=7.0 Hz), 6.61 (1H, s), 7.22–7.38 (4H, m).

This was dissolved in ethyl acetate, combined with 4 M hydrogen chloride/ethyl acetate solution, concentrated under reduced pressure, and crystallized from ethyl acetate to obtain. the title compound. Yield: 12%.

Melting point: 143–145° C.

$^1$H NMR (DMSO-d$_6$) δ 1.10 (3H, t, J=7.0 Hz), 1.21 (6H, s), 1.41 (3H, s), 1.45 (3H, s), 1.53 (6H, s), 2.10 (2H, s), 3.14 (2H, s), 3.94 (3H, s), 4.08 (2H, q, J=7.0 Hz), 7.09 (1H, s), 7.48–7.65 (4H, m).

Example 275

α,α-Dimethyl-3-(3,4,8,9-tetrahydro-6-methoxy-3,3,8,8-tetramethylfuro[2,3-h]isoquinolin-1-yl)benzeneacetic Acid Sodium Salt 5 M aqueous solution of sodium hydroxide (4 mL) was added to a solution of α,α-dimethyl-3-(3,4,8,9-tetrahydro-6-methoxy-3,3,8,8-tetramethylfuro[2,3-h]isoquinolin-1-yl) benzeneacetic acid ethyl ester (370 mg, 0.823 mmol) and α,α-Dimethyl-3-(3,4,8,9-tetrahydro-6-methoxy-3,3,8,8-tetramethylfuro[2,3-h]isoquinolin-1-yl)benzeneacetic acid ethyl ester hydrochloride (1.54 g, 3.17 mmol) in ethanol (8 mL) and the mixture was stirred at 70° C. for 7 hours. After distilling ethanol off under reduced pressure, the residue was combined with water-diethyl ether and the precipitated crystals were recovered by filtration to obtain the title compound (423 mg, yield: 24%).

Melting point: 153–155° C.

$^1$H NMR (DMSO-d()) δ 1.13 (6H, s), 1.20 (6H, s), 1.34 (6H, s), 2.22 (2H, s), 2.62 (2H, s), 3.80 (3H, s), 6.78 (1H, s), 7.12–7.41 (4H, m).

Example 276

α,α-Dimethyl-3-(3,4,8,9-tetrahydro-6-methoxy-3,3,8,8-tetramethylfuro[2,3-h]isoquinolin-1-yl)benzeneacetic Acid A mother liquor after filtration of the sodium salt in EXAMPLE 275 was concentrated under reduced pressure. The residue was combined with water, adjusted at pH 5.5 with 2 M hydrochloric acid, and extracted twice with tetrahydrofuran. The combined organic layer was dried over sodium sulfate, filtered and concentrated under reduced pressure to obtain the title compound. Yield: 49%.

Amorphous.

$^1$H NMR (CDCl$_3$) δ 1.27 (6H, s), 1.32 (6H, br 5), 1.47 (6H, s), 2.08 (2H, s), 2.74 (2H, br s), 3.92 (3H, s), 6.60 (1H, s), 7.12–7.37 (4H, m).

Example 277

N,α,α-Trimethyl-3-(3,4,8,9-tetrahydro-6-methoxy-3,3,8,8-tetramethylfuro[2,3-h]isoquinolin-1-yl)benzeneacetamide Hydrochloride The title compound was obtained from α,α-dimethyl-3-(3,4,8,9-tetrahydro-6-methoxy-3,3,8,8-tetramethylfuro[2.3-h]isoquinolin-1-yl)benzeneacetic acid by the method similar to that in EXAMPLE 206. Yield: 55%.

Amorphous.

$^1$H NMR (DMSO-d$_6$) δ 1.22–1.50 (18H, m), 2.02–2.24 (2H, m), 2.55 (3H, d, J=4.4 Hz), 2.97–3.40 (2H, m), 3.94 (3H, s), 7.09 (1H, s), 7.45–7.69 (4H, m), 8.06 (1H, br s).

Example 278

α,α-Dimethyl-N-(4-pyridinylmethyl)-3-(3,4,8,9-tetrahydro-6-methoxy-3,3,8,8-tetramethylfuro[2,3-h]isoquinolin-1-yl) benzeneacetamide Dihydrochloride The title compound was obtained from α,α-dimethyl-3-(3,4,8,9-tetrahydro-6-methoxy-3,3,8,8-tetramethylfuro[2,3-h]isoquinolin-1-yl)benzeneacetic acid and 4-(aminomethyl) pyridine by the method similar to that in EXAMPLE 206. Yield: 49%.

Amorphous.

$^1$H NMR (DMSO-d$_6$) δ 1.17 (6H, s), 1.45 (6H, s), 1.60 (6H, s), 2.05–2.25 (2H, m), 3.05–3.30 (2H, m), 3.95 (3H, s), 4.33–4.50 (2H, m), 7.10 (1H, s), 7.49–7.69 (7H, m), 8.48–8.58 (1H, m), 8.68–8.71 (2H, m), 9.05 (1H, br s).

Example 279

1-[4-(Bromomethyl)phenyl]-3,4,8,9-tetrahydro-6-methoxy-3,3,8,8-tetramethylfuro[2,3-h]isoquinoline The title compound was obtained from 4-cyanobenzyl bromide by the method similar to that in EXAMPLE 17. Yield: 27%.

Amorphous.

$^1$H NMR (CDCl$_3$)δ 1.24 (6H, s), 1.32 (6H, s), 2.21 (2H, s), 2.68 (2H, s), 3.92 (3H, s), 4.53 (2H, s), 6.60 (1H, s), 7.34–7.42 (4H, m).

Example 280

4-(3,4,8,9-Tetrahydro-6-methoxy-3,3,8,8-tetramethylfuro [2,3-h]isoquinolin-1-yl)benzeneacetonitrlle The title compound was obtained from 1-[4-(bromomethyl)phenyl]-3,4,8,9-tetrahydro-6-methoxy-3,3,8, 8-tetramethylfuro[2,3-h]isoquinoline by the method similar to that in EXAMPLE 240. Yield: 13%.

Melting point: 182–184° C. (hexane-diethyl ether).

$^1$H NMR (CDCl$_3$) δ 1.24 (6H, s), 1.33 (6H, s), 2.21 (2H, s), 2.69 (2H, s), 3.80 (2H, s), 3.93 (3H, s), 6.62 (1H, s), 7.36 (2H, d, J=8.3 Hz), 8.44 (2H, d, J=8.3 Hz).

Example 281

4-(3,4,8,9-Tetrahydro-6-methoxy-3,3,8,8-tetramethylfuro [2,3-h]isoquinolin-1-yl)benzeneacetic Acid Ethyl Ester Hydrochloride While cooling in ice, conc. sulfuric acid (0.18 mL, 3.58 mmol) was added to a solution of 4-(3,4,8,9-tetrahydro-6-methoxy-3,3,8,8-tetramethylfuro[2,3-h]isoquinolin-1-yl) benzeneacetonitrile (671 mg, 1.19 mmol) in ethanol (7 mL) and the mixture was heated under reflux for 24 hours. Ice water was poured into the reaction mixture, which was washed with diisopropyl ether and the aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 10:1 followed by 5:1) followed by a column chromatography on a silica gel (hexane/ethyl acetate 3:1) to obtain a free base of the title compound. This was dissolved in ethyl acetate, combined with 4 M hydrogen chloride/ethyl acetate solution, concentrated under reduced pressure and crystallized from ethyl acetate-ethanol to obtain the title compound (406 mg, yield: 50%).

Melting point: 104–106° C.

$^1$H NMR (DMSO-d4) δ 1.19 (3H, t, J=7.2 Hz), 1.22 (6H, s), 1.44 (6H, s), 2.20 (2H, s), 3.16 (2H, s), 3.86 (2H, s), 3.94 (3H, s), 4.10 (2H, q, J=7.2 Hz), 7.10 (1H, s), 7.52–7.62 (4H, m), 12.60 (1H, br s).

Example 282

2-[[[3-(3,4,8,9-tetrahydro-6-methoxy-3,3,8,8-tetramethylfuro[2,3-h]isoquinolin-1-yl)phenyl]amino]methylene]-1,3-propanedioic Acid Diethyl Ester 2-(Chloromethylene)malonic acid diethyl ester (1.0 g, 4.84 mmol) and triethylamine (0.72 mL, 5.18 mmol) were added to a solution of 3-(3,4,8,9-tetrahydro-6-methoxy-3,3,8,8-tetramethylfuro[2,3-h]isoquinolin-1-yl)benzenamine (1.76 g, 5.03 mmol) in toluene (3.5 mL) and stirred at 85° C. for 3 hours. Water was poured into the reaction mixture, which was extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 10:1. followed by 5:1) and crystallized from diethyl ether-hexane to obtain the title compound (905 mg, yield: 36%).

Melting point: 115–117° C.

1H NMR (CDCl$_3$) δ 1.33 (12H, s), 1.33 (3H, t, J=7.2 Hz), 1.38 (3H, t, J=7.2 Hz), 2.24 (2H, s), 2.70 (2H, s), 3.93 (3H, s), 4.25 (2H, q, J=7.2 Hz), 4.31 (2H, q, J=7.2 Hz), 6.62 (1H, s), 7.10–7.41 (4H, m), 8.57 (1H, d, J=13.7 Hz), 11.09 (1H, d, J=13.7 Hz).

Example 283

N-Ethyl-3-(3,4,8,9-tetrahydro-6-methoxy-3,3,8,8-tetramethylfuro[2,3-h]isoquinolin-1-yl)benzenamine Triethylamine (0.50 mL, 3.55 mmol) was added to a solution of 3-(3,4,8,9-tetrahydro-6-methoxy-3,3,8,8-tetramethylfuro[2,3-h]isoquinolin-1-yl)benzenamine (1.21 g, 3.45 mmol) and (Z)-3-iodo-2-propenamide (654 mg, 3.32 mmol) in toluene (2.5 mL) and the mixture was stirred at 60° C. for 2 hours and then at 80° C. for 6 hours. The reaction mixture was extracted with 2 M hydrochloric acid, and the aqueous layer was neutralized with conc. aqueous ammonia, and extracted twice with ethyl acetate. The combined organic layer was washed with. brine, dried over sodium sulfate, filtered, and concentrated under reduced pressure. The residue was subjected to a column chromatography on a basic silica gel (hexane/ethyl acetate 5:1 followed by 3:1) and crystallized from hexane to obtain the title compound (178 mg, yield: 14%).

Melting point: 109–111° C.

$^1$H NMR (CDCl$_3$) δ 1.23 (6H, s), 1.24 (3H, t, J=7.2 Hz), 1.32 (6H, s), 2.35 (2H, s), 2.67 (2H, s), 3.16 (2H, q, J=7.2 Hz), 3.66 (1H, br s), 3.91 (3H, s), 6.59 (1H, s), 6.63–6.69 (3H, m), 7.11–7.19 (1H, m).

Example 284

N-[3-(3,4,8,9-Tetrahydro-6-methoxy-3,3,8,8-tetramethylfuro[2,3-h]isoquinolin-1-yl)phenyl]-3-pyridinamine Tris(dibenzylideneacetone)dipalladium (0) (65 mg, 0.0707 mmol) was added to a suspension of 3-(3,4,8,9-tetrahydro-6-methoxy-3,3,8,8-tetramethylfuro[2,3-h]isoquinolin-1-yl)benzenamine (1.23 g, 3.46 mmol), 3-bromopyridine (0.32 mL, 3.43 mmol), sodium-tert-butoxide (411 mg, 4.81 mmol) and 2,2'-bis(diphenylphosphino)-1,1'-binaphthyl (98 mg, 0.141 mol) in toluene (30.5 mL) and the mixture was stirred at 110° C. for 24 hours. Water was poured into the reaction mixture, which was extracted twice with ethyl acetate. The combined organic layer was washed with brine, dried over magnesium sulfate, filtered and concentrated under reduced pressure. The residue was subjected to a column chromatography on a basic silica gel (hexane/ethyl acetate 3:1 followed by 1:1) and crystallized from hexane-diethyl ether to obtain the title compound (796 mg, yield: 54%).

Melting point: 204–205° C.

$^1$H NMR (CDCl$_3$) δ 1.24 (6H, s), 1.34 (6H, s), 2.34 (2H, s), 2.69 (2H, s), 3.92 (3H, s), 5.79 (1H, s), 6.61 (1H, s), 6.97 (1H, d, J=7.6 Hz), 7.11–7.43 (5H, m), 8.11 (1H, dd, J=4.8, 1.4 Hz), 8.40 (1H, d, J=2.8 Hz).

Example 285

N-(3-Pyridinyl)-N-[3-(3,4,8,9-tetrahydro-6-methoxy-3,3,8,8-tetramethylfuro[2,3-h]isoquinolin-1-yl)phenyl]acetamide While cooling in ice, sodium hydride (66% dispersion in oil) (57 mg, 1.57 mmol) was added to a solution of N-[3-(3,4,8,9-tetrahydro-6-methoxy-3,3,8,8-tetramethylfuro[2,3-h]isoquinolin-1-yl)phenyl]-3-pyridinamine (513 mg, 1.20 mmol) in N,N-dimethylformamide (5 mL) and the mixture was stirred at room temperature for 20 minutes under reduced pressure. And then, while cooling in ice, acetyl chloride (0.11 mL, 1.50 mmol) was added thereto and the mixture was stirred at room temperature for 15 hours. Ice water was poured into the reaction mixture, which was extracted twice with ethyl acetate. The combined organic layer was washed with water (twice) and brine, dried over sodium sulfate, filtered and concentrated under reduced pressure. The residue was subjected to a column chromatography on a basic silica gel (hexane/ethyl acetate 1:1 followed by 1:2) to obtain a mixture of the starting material and the title compound. This was subjected to the similar reactions and work-ups and subjected to a column chromatography on a silica gel (hexane/ethyl acetate 3:1) and crystallized from diethyl ether to obtain the title compound (176 mg, yield: 31%).

Melting point: 157–158° C.

$^1$H NMR (CDCl$_3$) δ 1.23 (6H, s), 1.24 (6H, s), 2.09 (5H, s), 2.68 (2H, s), 3.91 (3H, s), 7.09 (1H, s), 7.25–7.67 (6H, m), 8.45–8.53 (2H, m).

Example 286

N-Methyl-N-[3-(3,4,8,9-tetrahydro-6-methoxy-3,3,8,8-tetramethylfuro[2,3-h]isoquinolin-1-yl)phenyl]-3-pyridinamine Trihydrochloride By the method similar to that in EXAMPLE 285 and using iodomethane, a free base of the title compound was obtained. This was dissolved in ethyl acetate, combined with 4 M hydrogen chloride/ethyl acetate solution and concentrated under reduced pressure to obtain the title compound. Yield; 74%.

Amorphous.

$^1$H NMR (DMSO-d$_6$) δ 1.21 (6H, s), 1.46 (6H, s), 2.30 (2H, s), 3.16 (2H, s), 3.43 (3H, s), 3.94 (3H, s), 7.10 (1H, s), 7.45–7.86 (6H, m), 8.27–8.29 (2H, m).

Example 287
3-Pyridinyl[3-(3,4,8,9-tetrahydro-6-methoxy-3,3,8,8-tetramethylfuro[2,3-h]isoquinolin-1-yl)phenyl]carbamic Acid Ethyl Ester Dihydrochloride By the method similar to that in EXAMPLE 190 and starting from N-[3-(3,4,8,9-tetrahydro-6-methoxy-3,3,8,8-tetramethylfuro[2,3-h]isoquinolin-1-yl)phenyl]-3-pyridinamine and ethyl chloroformate, a free base of the title compound was obtained. This was dissolved in ethyl acetate, combined with 4 M hydrogen chloride/ethyl acetate solution and concentrated, under reduced pressure to -obtain the title compound. Yield: 29%.

Amorphous.

$^1$H NMR (DMSO-d$_6$) δ 1.15 (3H, t, J=7.0 Hz), 1.19 (6H, s), 1.41 (3H, s), 1.48 (3H, s), 1.98–2.28 (2H, m), 3.00–3.30 (2H, m), 3.93 (3H, s), 4.15 (2H, q, J=7.0 Hz), 7.09 (1H, s), 7.53–7.74 (5H, m), 7.95 (1H, d, J=8.0 Hz), 8.52 (1H, d, J=3.6 Hz), 8.67 (1H, d, J=2.2 Hz), 12.79 (1H, br s).

Example 288
N-(3-Pyridinyl)-N-[3-(3,4,8,9-tetrahydro-6-methoxy-3,3,8,8-tetramethylfuro[2,3-h]isoquinolin-1-yl)phenyl]urea Chlorosulfonyl isocyanate (0.075 mL, 0.865 mmol) was added to a solution of N-[3-(3,4,8,9-tetrahydro-6-methoxy-3,3,8,8-tetramethylfuro[2,3-h]isoquinolin-1-yl)phenyl]-3-pyridinamine (336 mg, 0.786 mmol) in tetrahydrofuran (3 mL) and the mixture was stirred at room temperature for 6 hours. Acetic acid (1 mL) and water (0.5 mL) were added to the reaction mixture and the mixture was stirred at room temperature further for 3 hours. The reaction mixture was neutralized with 5 M aqueous solution of sodium hydroxide and extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 1:2 followed by ethyl acetate) and crystallized from hexane-ethyl acetate to obtain the title compound (177 mg, yield: 48%).

Melting point: 168–169° C.

$^1$H NMR (CDCl$_3$) δ 1.24 (6H, br s), 1.26 (6H, s), 2.14 (2H, s), 2.69 (2H, s), 3.91 (3H, s), 4.74 (2H, br s), 6.60 (1H, s), 7.24–7.31 (2H, m), 7.39–7.53 (3H, m), 7.70–7.78 (1H, m), 8.40 (1H, dd, J=4.6, 1.3 Hz), 8.49 (1H, d, J=2.0 Hz).

Example 289
N-Phenyl-3-(3,4,8,9-tetrahydro-6-methoxy-3,3,8,8-tetramethylfuro[2,3-h]isoquinolin-1-yl)benzenamine Calcium carbonate (570 mg, 1.75 mmol), palladium (II) acetate (8.4 mg, 0.0375 mmol) and 2,2'-bis(diphenylphosphino)-1,1'-binaphthyl (35 mg, 0.0563 mmol) were added to a solution of 1-(3bromophenyl)-3,4,8,9-tetrahydro-6-methoxy-3,3,8,8-tetramethylfuro[2,3-h]isoquinoline (517 mg, 1.25 mmol) and aniline (0.04 mL, 1.50 mmol) in toluene (2.5 mL) and the mixture was stirred at 100° C. for 24 hours. Ice water was poured into the reaction mixture, which was extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 10:1 followed by 3:1) and crystallized from diethyl ether to obtain the title compound (226 mg, yield: 42%).

Melting point: 87–88° C.

$^1$H NMR (CDCl$_3$) δ 1.24 (6H, s), 1.34 (6H, s), 2.36 (2H, s), 2.68 (2H, s), 3.91 (3H, s), 5.74 (1H, s), 6.59 (1H, s), 6.89–7.30 (9H, m).

Example 290
N-Phenyl-N-[3-(3,4,8,9-tetrahydro-6-methoxy-3,3,8,8-tetramethylfuro[2,3-h]isoquinolin-1-yl)phenyl]acetamide Hydrochloride Triethylamine (0.18 mL, 1.28 mmol) and acetyl chloride (0.086 mL, 1.22 mmol) were added to a solution of N-phenyl-3-(3,4,8,9-tetrahydro-6-methoxy-3,3,8,8-tetramethylfuro[2,3-h]isoquinolin-1-yl)benzenamine (494 mg, 1.16 mmol) in N,N-dimethylformamide (2 mL) and the mixture was stirred at room temperature for 10 hours. Ice water was poured into the reaction mixture, which was extracted twice with ethyl acetate. The combined organic layer was washed with brine, dried over sodium sulfate, filtered, and concentrated under reduced pressure. The residue was subjected to a column chromatography on a basic silica gel (hexane/ethyl acetate 3:1) to obtain a free base of the title compound. This was dissolved in ethyl acetate, combined with 4 M hydrogen chloride/ethyl acetate solution, concentrated under reduced pressure to obtain the title compound (364 mg, yield: 62%).

Amorphous.

$^1$H NMR (DMSO-d$_6$) δ 1.56 (6H, s), 1.37 (3H, s), 1.51 (3H, s), 1.95 (3H, s), 2.50 (2H, s), 3.26 (2H, s), 3.93 (3H, s), 7.09 (1H, s), 7.30–7.80 (9H, m), 12.70 (1H, s).

Example 291
1-(3-Bromophenyl)-3,4,8,9-tetrahydro-6-methoxy-3,3,8,8-tetramethyl-4-furo[2,3-h]isoquinolinol Hydrochloride N-Bromosuccinimide (773 mg, 4.34 mmol) and 2,2'-azobis(isobutyronitrile) (79 mg, 0.483 mmol) were added to a solution of 1-(3bromophenyl)-3,4,8,9-tetrahydro-6-methoxy-3,3,8,8-tetramethylfuro[2,3-h]isoquinoline (2.00 g, 4.83 mmol) in carbon tetrachloride (20 mL) and the mixture was stirred at 60° C. for 6 hours. The reaction mixture was extracted twice with 2 M hydrochloric acid, and the combined aqueous layer was neutralized with conc. aqueous ammonia and extracted twice with ethyl acetate. The combined organic layer was washed with water and brine, dried over sodium sulfate, filtered and concentrated under reduced pressure. The residue was subjected to a column chromatography on a silica gel (hexane/ethyl acetate 5:1 followed by 1:2) to obtain a free base of the title compound.

$^1$H NMR (CDCl$_3$) δ 1.25 (3H, s), 1.30 (3H, s), 1.35 (3H, s), 1.36 (3H, s), 2.26 (2H, s), 3.96 (3H, s), 4.48 (1H, s), 6.96 (1H, s), 7.22–7.39 (2H, m), 7.50–7.62 (2H, m).

This was dissolved in ethyl acetate, combined with 4 M hydrogen chloride/ethyl acetate solution and crystallized from ethyl acetate to obtain the title compound (630 mg, yield: 31%).

Melting point: 190–192° C.

$^1$H NMR (DMSO-d$_6$) δ 1.24 (3H, s), 1.28 (3H, s), 1.34 (3H, s), 1.41 (3H, s), 2.26 (2H, s), 3.97 (3H, s), 4.56 (1H, br s), 6.17 (1H, s), 7.24 (1H, s), 7.59–7.62 (2H, m), 7.95–7.99 (2H, m).

Example 292
N-[3'-(3,4,8,9-Tetrahydro-4-hydroxy-6-methoxy-3,3,8,8-tetramethylfuro[2,3-h]isoquinolin-1-yl)[1,1'-biphenyl]-3-yl]acetamide The title compound was obtained from 1-(3bromophenyl)-3,4,8,9-tetrahydro-6-methoxy-3,3,8,8-tetramethyl-4-furo[2,3-h]isoquinolinol and 3-acetamidobenzeneboronic acid by the method similar to that in EXAMPLE 254. Yield: 64%.

Amorphous.

$^1$H NMR (CDCl$_3$) δ 1.25 (3H, s), 1.30 (6H, s), 1.33 (3H, s), 2.18 (3H, s), 2.26 (2H, s), 3.97 (3H, s), 4.45 (1H, s), 6.96 (1H, s), 7.23–7.63 (8H, m), 7.72 (1H, br s).

Example 293

N-[3'-(3,4,8,9-Tetrahydro-4-hydroxy-6-methoxy-3,3,8,8-tetramethylfuro[2,3-h]isoquinolin-1-yl)[1,1'-biphenyl]-3-yl]acetamide Hydrochloride The title compound was obtained from N-[3'-(3,4,8,9-tetrahydro-4-hydroxy-6-methoxy-3,3,8,8-tetramethylfuro[2,3-h]isoquinolin-1-yl)[1,1'-biphenyl]-3-yl]acetamide by the method similar to that in EXAMPLE 212. Yield: 88%.

Amorphous.

$^1$H NMR (DMSO-d$_6$) δ 1.21 (6H, s), 1.37 (3H, s), 1.45 (3H, s), 2.07 (3H, s), 2.32 (2H, s), 3.98 (3H, s), 4.61 (1H, br s), 6.18 (1H, br s), 7.26 (1H, s), 7.42–8.06 (8H, m), 10.19 (1H, s), 12.67 (1H, br s).

Example 294

N-[3'-(3,4,8,9-Tetrahydro-6-methoxy-3,3,8,8-tetramethyl-4-oxofuro[2,3-h]isoquinolin-1-yl)[1,1'-biphenyl]-3-yl]acetamide Manganese dioxide (1.04 g, 12.0 mmol) was added to a solution of N-[3'-(3,4,8,9-tetrahydro-4-hydroxy-6-methoxy-3,3,8,8-tetramethylfuro[2,3-h]isoquinolin-1-yl)[1,1'-biphenyl]-3-yl]acetamide (290 mg, 0.598 mmol) in chloroform (5 mL) and the mixture was stirred at room temperature for 6 hours. Inorganics were filtered off and the filtrate was concentrated under reduced pressure. The residue was subjected to a column chromatography on a silica gel (hexane/ethyl acetate 1:1 followed by 1:2) and crystallized from hexane-ethyl acetate to obtain the title compound (209 mg, yield: 72%).

Melting point: 210–212° C.

$^1$H NMR (CDCl$_3$) δ 1.34 (6H, s), 1.56 (6H, s), 2.20 (3H, s), 2.26 (2H, s), 4.00 (3H, s), 7.27–7.69 (8H, m), 7.84 (1H, s).

Example 295

5-[3-(3,4,8,9-Tetrahydro-6-methoxy-3,3,8,8-tetramethylfuro[2,3-h]isoquinolin-1-yl)phenyl]-2-pyridinamine A solution of sodium carbonate (198 mg, 1.86 mmol) in water (1 mL) and tetrakis(triphenylphosphine)palladium(0) (55 mg, 0.0475 mmol) were added to a solution of N-(5bromo-2-pyridinyl)acetamide (243 mg, 1.13 mmol) and 3-cyanophenylboronic acid (249 mg, 1.70 mmol) in 1,2-dimethoxyethane (2 mL) and ethanol (1 mL) and the mixture was stirred at 80° C. for 15 hours. Water was poured into the reaction mixture, which was extracted twice with tetrahydrofuran. The combined organic layer was washed with brine, dried over sodium sulfate, filtered, and concentrated under reduced pressure. The resultant crystals were washed with diethyl ether to obtain N-[5-(3-cyanophenyl)-2-pyridinyl]acetamide (205 mg, yield: 77%).

$^1$H NMR (CDCl$_3$) δ 2.25 (3H, s), 7.54–7.92 (5H, m), 8.02 (1H, br s), 8.32 (1H, d, J=8.0 Hz), 8.48 (1H, d, J=2.2 Hz).

Using this and by the method similar to that in EXAMPLE 17, the title compound was obtained. Yield: 11%.

Melting point: 165–168° C. (diethyl ether).

$^1$H NMR (CDCl$_3$) δ 1.27 (6H, s), 1.30 (6H, s), 2.26 (2H, s), 2.72 (2H, s), 3.93 (3H, s), 4.50 (2H, s), 6.57 (1H, dd, J=8.4, 0.8 Hz), 6.63 (1H, s), 7.32–7.56 (4H, m), 7.70 (1H, dd, J=8.4, 2.4 Hz), 8.34 (1H, d, J=1.8 Hz).

Example 296

N-[5-[3-(3,4,8,9-Tetrahydro-6-methoxy-3,3,8,8-tetramethylfuro[2,3-h]isoquinolin-1-yl)phenyl]-2-pyridinyl]acetamide From a mixture of 5-[3-(3,4,8,9-tetrahydro-6-methoxy-3,3,8,8-tetramethylfuro[2,3-h]isoquinolin-1-yl)phenyl]-2-pyridinamine obtained by the column chromatography in EXAMPLE 295 and N-[5-[3-(3,4,8,9-tetrahydro-6-methoxy-3,3,8,8-tetramethylfuro[2,3-h]isoquinolin-1-yl)phenyl]-2-pyridinyl]acetamide and by the method similar to that in EXAMPLE 222, the title compound was obtained. Yield: 8.9%.

Melting point: 208–209° C. (diethyl ether).

$^1$H NMR (CDCl$_3$) δ 1.27 (6H, s), 1.30 (6H, s), 2.23 (3H, s), 2.26 (2H, s), 2.72 (2H, s), 3.93 (3H, s), 6.63 (1H, s), 7.25 (1H, d, J=8.4 Hz), 7.38–7.58 (4H, m), 7.91–7.96 (2H, m), 8.51 (1H, d, J=1.4 Hz).

Example 297

N-[5-[3-(3,4,8,9-Tetrahydro-6-methoxy-3,3,8,8-tetramethylfuro[2,3-h]isoquinolin-1-yl)phenyl]-2-pyridinyl]methanesulfonamide Hydrochloride By the method similar to that in EXAMPLE 222 and starting from 5-13-(3,4,8,9-tetrahydro-6-methoxy-3,3,8,8-tetramethylfuro[2,3-h]isoquinolin-1-yl)phenyl-2-pyridinylamine and methanesulfonyl chloride, a free base of the title compound was obtained. This was dissolved in ethyl acetate, combined with 4 M hydrogen chloride/ethyl acetate solution, and concentrated under reduced pressure to obtain the title compound. Yield: 54%.

Amorphous.

$^1$H NMR (DMSO-d$_6$) δ 1.21 (6H, s), 1.45 (3H, s), 1.52 (3H, s), 2.26 (2H, s), 3.00–3.40 (5H, m), 3.95 (3H, s), 7.13–7.15 (2H, m), 7.58–7.78 (2H, m), 8.02–8.52 (6H, m).

Example 298

6-(Ethylthio)-3,4,8,9-tetrahydro-3,3,8,8-tetramethyl-1-phenylfuro[2,3-h]isoquinoline Hydrochloride By the method similar to that in EXAMPLE 17 and starting from 7-(ethylthio)-2,3-dihydro-2,2-dimethyl-5-(2-methyl-1-propenyl)benzofuran and benzonitrile, a free base of the title compound was, obtained. This was dissolved in ethyl acetate, combined with 4 M hydrogen chloride/ethyl acetate solution, and concentrated under reduced pressure to obtain the title compound. Yield: 32%.

Amorphous.

$^1$H NMR (DMSO-d$_6$) δ 1.23 (6H, s), 1.32 (3H, t, J=7.5 Hz), 1.45 (6H, s), 2.19 (2H, s), 3.12 (2H, q, J=7.5 Hz), 3.17 (2H, s), 7.23 (1H, s), 7.63–7.80 (5H, m).

Example 299

N-(4-Pyridinylmethyl)-4-(3,4,8,9-tetrahydro-6-methoxy-3,3,8,8-tetramethylfuro[2,3-h]isoquinolin-1-yl)benzenesulfonamide Dihydrochloride 4-(Aminomethyl)pyridine (851 mg, 7.87 mmol) was dissolved in pyridine (2 mL) and, while cooling in ice, 4-cyanobenzenesulfonyl chloride (1.75 g, 8.66 mmol) was added and the mixture was stirred at room temperature for 2 hours. The reaction mixture was combined with 2 M hydrochloric acid with cooling in ice, and washed with diethyl ether. The aqueous layer was adjusted at pH 8 with 5 M aqueous solution of sodium hydroxide and extracted twice with ethyl acetate. The combined organic layer was washed with brine dried over sodium sulfate. filtered, and concentrated under reduced pressure. The residue was subjected to a column chromatography on a basic silica gel (ethyl acetate) to obtain 4-cyano-N-(4-pyridinylmethyl)benzenesulfonamide (674 mg, yield: 31%).

$^1$H NMR (CDCl$_3$+DMSO-d$_6$2 drops) δ 4.12 (2H, d, J=5.4 Hz), 7.20 (2H, dd, J=4.4, 1.4 Hz), 7.74–7.80 (2H, m), 7.94–8.00 (2H, m), 8.08 (1H, br s), 8.50 (2H, dd, J=4.4, 1.8 Hz).

Using this and by the method similar to that in EXAMPLE 17, a free base of the title compound was obtained. This was dissolved in ethyl acetate, combined with 4 M hydrogen chloride/ethyl acetate solution, concentrated under reduced pressure and crystallized from ethanol-ethyl acetate to obtain the title compound. Yield: 18%.

Amorphous.

$^1$H NMR (DMSO-$d_6$) δ 1.24 (6H, s), 1.48 (6H, s), 2.16 (2H, s), 3.19 (2H, s), 3.95 (3H, s), 4.34 (2H, d, J=8 6.0 Hz), 7.12 (1H, s), 7.83–7.89 (4H, m), 8.08 (2H, d, J=8.4 Hz), 8.82 (2H, d, J=6.6 Hz), 9.07 (1H, t, J=6.0 Hz).

Example 300
N-Methyl-4-(3,4,8,9-tetrahydro-6-methoxy-3,3,8,8-tetramethylfuro[2,3-h]isoquinolin-1-yl)benzenesulfonamide Methylamine hydrochloride (1.05 g, 15.6 mmol) was dissolved in pyridine (4 mL), 4-cyanobenzenesulfonyl chloride (3.30 g, 16.4 mmol) was added thereto with cooling in ice, and the mixture was stirred at room temperature for 2 hours. The reaction mixture was combined with ice water, acidified with 1 M hydrochloric acid, and extracted twice with ethyl acetate. The combined organic layer was washed with water and brine, dried over magnesium sulfate, filtered and concentrated under reduced pressure. The residue was subjected to a column chromatography on a silica gel (hexane/ethyl acetate 3:1 followed by 1:1), and the resultant crystals were washed with diethyl ether to obtain 4-cyano-N-methylbenzenesulfonamide (1.54 g, yield: 56%).

$^1$H NMR (CDCl$_3$) δ 2.72 (3H, d, J=5.2 Hz), 4.50 (1H, q, J=5.2 Hz), 7.84 (2H, dd, J=6.6, 1.8 Hz), 7.99 (2H, dd, J=6.6, 1.8 Hz).

The title compound was obtained from this by the method similar to that in EXAMPLE 17. Yield: 26%.

Melting point: 146–148° C. (methanol-diethyl ether).

$^1$H NMR (CDCl$_3$) δ 1.26 (6H, s), 1.32 (6H, s), 2.17 (2H, s), 2.65 (3H, d, J=5.3 Hz), 2.71 (2H, s), 3.93 (3H, s), 4.43 (1H, q, J=5.3 Hz), 6.63 (1H, s), 7.57 (2H, d, J=8.3 Hz), 7.89 (2H, d, J=8.3 Hz).

Example 301
N-(2-Amino-2-oxoethyl)-N-methyl-4-(3,4,8,9-tetrahydro-6-methoxy-3,3,8,8-tetramethylfuro[2,3-h]isoquinolin-1-yl)benzenesulfonamide The title compound was obtained from N-methyl-4-(3,4,8,9-tetrahydro-6-methoxy-3,3,8,8-tetramethylfuro[2,3-h]isoquinolin-1-yl)benzenesulfonamide and 2bromoacetamide by the method similar to that in EXAMPLE 190. Yield: 35%.

Melting point: 115–117° C. (ethyl acetate-diethyl ether).

$^1$H NMR (CDCl$_3$) δ 1.26 (6H, s), 1.33 (6H, s), 2.14 (2H, s), 2.71 (2H, s), 2.84 (3H, s), 3.63 (2H, s), 3.93 (3H, s), 5.57 (1H, br s), 6.57 (1H, br s), 6.64 (1H, s), 7.62 (2H, d, J=8.4 Hz), 7.84 (2H, d, J=8.4 Hz).

Example 302
3,4,8,9-Tetrahydro-6-methoxy-3,3,8,8-tetramethyl-1-(6-quinolinyl)furo[2,3-h]isoquinoline Dihydrochloride A free base of the title compound was obtained from 6-quinolinecarbonitrile by the method similar to that in EXAMPLE 28. This was dissolved in ethyl acetate, combined with 4 M hydrogen chloride/ethyl acetate solution, concentrated under reduced pressure, and crystallized from ethanol-ethyl acetate to obtain the title compound. Yield: 37%.

Melting point: 182–184° C.

$^1$H NMR (DMSO-$d_6$) δ 1.17 (6H, s), 1.50 (6H, s), 2.18 (2H, s), 3.05–3.35 (2H, m), 3.87 (3H, s), 7.15 (1H, s), 7.86 (1H, dd, J=8.6, 4.4 Hz), 8.02 (1H, dd, J=8.8, 1.8 Hz), 8.36 (1H, d, J=8.8 Hz), 8.51 (1H, s), 8.78 (1H, d, J=8.0 Hz), 9.21 (1H, dd, J=4.4, 1.4 Hz).

Example 303
3,4,8,9-Tetrahydro-6-methoxy-3,3,8,8-tetramethyl-1-(7-quinolinyl)furo[2,3-h]isoquinoline A solution of 7-quinolinecarboxamide (1.21 g, 7.03 mmol) in chloroform (8 mL) was treated dropwise with phosphorus oxychloride (3.28 mL, 35.1 mmol), and stirred at 90° C. for 3 hours. The reaction mixture was poured into ice water, neutralized with conc. aqueous ammonia and extracted twice with ethyl acetate. The combined organic layer was washed with water and brine, dried over sodium sulfate, and concentrated under reduced pressure to obtain 7-quinolinecarbonitrile (984 mg, yield: 72%).

$^1$H NMR (CDCl$_3$) δ 7.57 (1H, dd, J=8.5, 4.1 Hz), 7.72 (1H, dd, J=8.4, 1.4 Hz), 7.94 (1H, d, J=8.4 Hz), 8.20–8.27 (1H, m), 8.50 (1H, s), 9.06 (1H, dd, J=4.2, 1.6 Hz).

The title compound was obtained from this by the method similar to that in EXAMPLE 28. Yield: 48%.

Melting point: 172–174° C. (diethyl ether).

$^1$H NMR (CDCl$_3$) δ 1.25 (6H, s), 1.29 (6H, s), 2.19 (2H, s), 2.74 (2H, s), 3.94 (3H, s), 6.65 (1H, s), 7.43 (1H, dd, J=8.2, 4.2 Hz), 7.61 (1H, dd, J=8.2, 1.6 Hz), 7.85 (1H, d, J=8.4 Hz), 8.15–8.21 (2H, m), 8.95 (1H, dd, J=4.2, 1.6 Hz).

Example 304
N-Methyl-3-(3,4,8,9-tetrahydro-6-methoxy-3,3,8,8-tetramethylfuro[2,3-h]isoquinolin-1-yl)benzenamine The title compound was obtained from 3-(methylamino) benzonitrile by the method similar to that in EXAMPLE 28. Yield: 22%.

Melting point: 105–107° C. (diethyl ether-hexane).

$^1$H NMR (CDCl$_3$) δ 1.24 (6H, s), 1.32 (6H, s), 2.35 (2H, s), 2.68 (2H, s), 2.84 (3H, s), 3.73 (1H, br s), 3.92 (3H, s), 6.59 (1H, s), 6.63–6.70 (3H, m), 7.13–7.21 (1H, m).

Example 305
3,4,8,9-Tetrahydro-3,3,6,8,8-pentamethyl-1-phenylfuro[2,3-h]isoquinoline Hydrochloride Phosphorus oxychloride (1.10 mL, 11.8 mmol) was added to a solution of 2,3-dihydro-2,2,7-trimethyl-5-(2-methyl-1-propenyl)benzofuran (1.02 g, 1.94 mmol) and benzamide (1.14 g, 9.43 mmol) in toluene (10 mL) and the mixture was stirred at 60° C. for 2 hours, and then at 90° C. for 3 hours. The reaction. mixture was poured into water, and the aqueous layer was separated, neutralized by 5 M aqueous solution of sodium hydroxide, and extracted twice with ethyl acetate. The combined organic layer was washed with brine, dried over magnesium sulfate, filtered and concentrated under reduced pressure. The residue was subjected to a column chromatography on a basic silica gel (hexane/ethyl acetate 100:1 followed by 10:1) to obtain a free base of the title compound. This was dissolved in hexane, combined with 4 M hydrogen chloride/ethyl acetate solution, and concentrated under reduced pressure to obtain the title compound (65 mg, yield: 3.9%).

Amorphous.

$^1$H NMR (DMSO-$d_6$) δ 1.23 (6H, s), 1.43 (6H, s), 2.19 (2H, s), 2.21 (3H, s), 3.11 (2H, s), 7.16 (1H, s), 7.64–7.80 (5H, m).

Example 306
1-(4-Cyclohexylphenyl)-3,4,8,9-tetrahydro-6-methoxy-3,3,8,8-tetramethylfuro[2,3-h]isoquinoline Hydrochloride A free base of the title compound was obtained from 4-cyclohexylbenzonitrile by the method similar to that in EXAMPLE 1. This was dissolved in ethanol, combined with 3.3 M solution of hydrogen chloride/ethanol, and concentrated under reduced pressure. The resultant residue was crystallized from ethyl acetate to obtain the title compound. Yield: 21%.

Melting point: 213–214° C.

$^1$H NMR (CDCl$_3$) δ 1.23–1.54 (12H, m), 1.69–1.96(10H, m), 2.54–2.68 (1H, m), 2.28 (2H, s), 3.00 (2H, s), 4.01 (3H, s), 6.74 (1H, s), 7.39 (2H, d, J=8.3 Hz), 7.68 (2H, d, J=8.3 Hz).

Example 307

3,4,8,9-Tetrahydro-6-methoxy-3,3,8,8-tetramethyl-1-(4-phenoxyphenyl)furo[2,3-h]isoquinoline Hydrochloride The title compound was obtained from 4-phenoxybenzonitrile by the method similar to that in EXAMPLE 306. Yield: 19%.

Melting point: 198–199° C. (ethyl acetate-hexane).

$^1$H NMR (CDCl$_3$) δ 1.39 (6H, s), 1.68 (6H, s), 2.40 (2H, s), 3.00 (2H, s), 4.02 (3H, s), 6.74 (1H, s), 7.12 (4H, d, J=8.7 Hz), 7.18–7.26 (1H, m), 7.42 (2H, t, J=8.2 Hz), 7.75 (2H, d, J=8.7 Hz).

Example 308

3,4,8,9-Tetrahydro-6-methoxy-3,3,8,8-tetramethyl-1-(2-naphthyl)furo[2,3-h]isoquinoline Hydrochloride The title compound was obtained from β-naphthonitrile by the method similar to that in EXAMPLE 306. Yield: 37%.

Melting point: 158–160° C. (ethyl acetate).

$^1$H NMR (CDCl$_3$) δ 1.29 (6H, s), 1.73 (6H, br s), 2.27 (2H, s), 3.05 (2H, br s), 4.03 (3H, s), 6.78 ($^1$H, s), 7.56–7.70 (3H, m), 7.90–8.09 (3H, m), 8.49 (1H, s).

Example 309

3,4,8,9-Tetrahydro-6-methoxy-3,3,8,8-tetramethyl-1-[4-(1-piperidinyl)phenyl]furo[2,3-h]isoquinoline Hydrochloride The title compound was obtained from 4-(1-piperidinyl)benzonitrile by the method similar to that in EXAMPLE 306. Yield: 18%.

Melting point: 188–190° C. (ethyl acetate-hexane).

$^1$H NMR (CDCl$_3$) δ 1.63 (6H, s), 1.68 (12H, br), 2.58 (2H, s), 2.93 (2H, s), 3.42 (4H, br), 4.00 (3H, s), 6.71 (1H, s), 6.93 (2H, d, J=8.4 Hz), 7.77 (2H, d, J=8.4 Hz).

Example 310

2,6-Bis(1,1-dimethylethyl)-4-(3,4,8,9-tetrahydro-6-methoxy-3,3,8,8-tetramethylfuro[2,3-h]isoquinolin-1-yl) phenol Hydrochloride The title compound was obtained from 3,5-bis(1,1-dimethylethyl)-4-hydroxybenzonitrile by the method similar to that in EXAMPLE 306. Yield: 50%.

Melting point: 211–213° C. (ethyl acetate-hexane).

$^1$H NMR (CDCl$_3$) δ 1.50 (18H, s), 1.69 (12H, s), 2.40 (2H, s), 2.98 (2H, s), 4.02 (3H, s), 5.90 (1H, s), 6.74 (1H, s), 7.53 (2H, s).

Example 311

3,4,8.9-Tetrahydro-6-methoxy-3,3,8,8-tetramethyl-1-(4-methyl-2-phenyl-1H-imidazol-5-yl)furo[2,3-h]isoquinoline Hydrochloride The title compound was obtained from 4-methyl-2-phenyl-1H-imidazol-5-carbonitrile by the method similar to that in EXAMPLE 306. Yield: 5%.

Melting point: 238–240° C. (ethyl acetate).

$^1$H NMR (CDCl$_3$) δ 1.35 (6H, br), 1.65 (6H, br), 2.29 (1H, br), 2.63 (1H, br), 2.71 (3H, br), 3.08 (2H, br), 4.01 (3H, s), 6.70 (1H, s), 7.22 (1H, br), 7.49 (2H, br), 7.90 (2H, br), 8.39 (1H, br).

Example 312

6-Methyl-3-(3,4,8,9-tetrahydro-6-methoxy-3,3,8,8-tetramethylfuro[2,3-h]isoquinolin-1-yl)-2(1H)-pyridinone Hydrochloride The title compound was obtained from 3-cyano-6-methyl-2(1H)-pyridinone by the method similar to that in EXAMPLE 306. Yield: 53%.

Melting point: 178–180° C. (ethyl acetate).

$^1$H NMR (CDCl$_3$) δ 1.33 (6H, s), 1.51 (6H, s), 1.62 (2H, br), 2.36 (3H, s), 2.58 (2H, br), 3.90 (3H, s), 6.06 (1H, d, J=7.3 Hz), 6.59 (1H, s), 7.72 (1H, d, J=7.3 Hz).

Example 313

1-Cyclopentyl-3,4,8,9-tetrahydro-6-methoxy-3,3,8,8-tetramethylfuro[2,3-h]isoquinoline Hydrochloride The title compound was obtained from cyclopentanecarbonitrile by the method similar to that in EXAMPLE 306. Yield: 20%.

Melting point: 197–198° C. (ethyl acetate).

$^1$H NMR (CDCl$_3$) δ 1.57 (6H, s), 1.65 (6H, s), 1.76 (2H, br), 2.05–2.30 (4H, m), 2.44–2.57 (2H, m), 2.88 (2H, s), 3.20–3.58 (3H, m), 4.00 (3H, s), 6.67 (1H, s).

Example 314

1-(4-Ethoxyphenyl)-3,4,8,9-tetrahydro-6-methoxy-3,3,8,8-tetramethylfuro[2,3-h]isoquinoline Hydrochloride The title compound was obtained from 4-ethoxybenzonitrile by the method similar to that in EXAMPLE 306. Yield: 57%.

Melting point: 158–160° C. (ethyl acetate).

$^1$H NMR (CDCl$_3$) δ 1.37 (6H, s), 1.46 (3H, t, J=7.0 Hz), 1.67 (6H, s), 2.41 (2H, s), 2.99 (2H, s), 4.02 (3H, s), 4.14 (2H, q, J=7.0 Hz), 6.74 (1H, s), 7.04 (2H, br d, J=6.1 Hz), 7.75 (2H, br d, J=6.1 Hz).

Example 315

3,4,8,9-Tetrahydro-6-methoxy-3,3,8,8-tetramethyl-1-[4-(1-methylethoxy)phenyl]furo[2,3-h]isoquinoline Hydrochloride The title compound was obtained from 4-(1-methylethoxy)benzonitrile by the method similar to that in EXAMPLE 306. Yield: 21%.

Melting point: 130–132° C. (ethyl acetate).

$^1$H NMR (CDCl$_3$) δ 1.38 (6H, s), 1.39 (6H, d, J=4.6 Hz), 1.66 (6H, s), 2.43 (2H, s), 2.97 (2H, s), 4.01 (3H, s), 4.65–4.75 (1H, m), 6.72 (1H, s), 7.02 (2H, d, J=8.3 Hz), 7.76 (2H, d, J=8.3 Hz).

Example 316

[4-(3,4,8,9-Tetrahydro-6-methoxy-3,3,8,8-tetramethylfuro[2,3-h]isoquinolin-1-yl)phenyl]methyl Acetate Hydrochloride The title compound was obtained from 4-cyanobenzyl acetate by the method similar to that in EXAMPLE 306. Yield: 24%.

Melting point: 184–186° C. (ethyl acetate).

$^1$H NMR (CDCl$_3$) δ 1.35 (6H, s), 1.68 (9H, br s), 2.30 (2H, s), 3.05 (2H, br s), 4.02 (3H, s), 4.74 (2H, s), 6.74 (1H, s), 7.59 (4H, br).

Example 317

3,4,8,9-Tetrahydro-6-methoxy-1-[4-[2-(4-methoxyphenyl)ethoxy]phenyl]3,3,8,8-tetramethylfuro[2,3-h]isoquinoline Hydrochloride The title compound was obtained from 4-[2-(4-methoxyphenyl)ethoxy]benzonitrile by the method similar to that in EXAMPLE 306. Yield: 35%.

Melting point: 198–200° C. (ethyl acetate).

¹H NMR (CDCl₃) δ.1.37 (6H, s), 1.66 (6H, s), 2.39 (2H, s), 2.98 (2H, s), 3.07 (2H, t, J=7.0 Hz), 3.81 (3H, s), 4.01 (3H, s), 4.23 (2H, t, J=7.0 Hz), 6.72 (1H, s), 6.88 (2H, d, J=8.6 Hz), 7.03 (2H, d, J=8.8 Hz), 7.22 (2H, d, J=8.6 Hz), 7.72 (2H, d, J=8.8 Hz).

Example 318

1-Cyclohexyl-3,4,8,9-tetrahydro-6-methoxy-3,3,8,8-tetramethylfuro[2,3-h]isoquinoline Hydrochloride The title compound was obtained from cyclohexanecarbonitrile by the method similar to that in EXAMPLE 306. Yield: 28%.

Melting point: 210–211° C. (ethyl acetate).

¹H NMR (CDCl₃) δ 1.25–1.40 (2H, m), 1.58 (6H, s), 1.65 (6H, s), 1.69–1.85 (6H, m), 1.96–2.07 (2H, m), 2.58–2.78 (2H,m), 2.88–3.04 (3H, m), 3.99 (3H, s), 6.67 (1H, s).

Example 319

3,4,8,9-Tetrahydro-6-methoxy-3,3,8,8-tetramethyl-1-(2-methylthiazol-4-yl)furo[2,3-h]isoquinoline The title compound was obtained from 2-methylthiazol-4-carbonitrile by the method similar to that in EXAMPLE 1. Yield: 5%.

Melting point: 127–128° C. (hexane).

¹H NMR (CDCl₃) δ 1.26 (6H, s), 1.37 (6H, s), 2.34 (2H, s), 2.70 (2H, s), 2.74 (3H, s), 3.91 (3H, s), 6.59 (1H, s), 7.37 (1H, s).

Example 320

1-(3-Fluorophenyl)-3,4,8,9-tetrahydro-6-methoxy-3,3,8,8-tetramethylfuro[2,3-h]isoquinoline Hydrochloride The title compound was obtained from 3-fluorobenzonitrile by the method similar to that in EXAMPLE 306. Yield: 47%.

Melting point: 198–199° C. (ethyl acetate-hexane).

¹H NMR (CDCl₃) δ 1.24 (6H, s), 1.33 (6H, s), 2.24 (2H, s), 2.69 (2H, s), 3.92 (3H, s), 6.62 (1H, s), 7.06–7.18 (3H, m), 7.30–7.41 (1H, m).

Example 321

1-(2,4-Difluorophenyl)-3,4,8,9-tetrahydro-6-methoxy-3,3,8,8-tetramethylfuro[2,3-h]isoquinolin The title compound was obtained from 2,4-difluorobenzonitrile by the method similar to that in EXAMPLE 1. Yield: 45%.

Melting point: 143–144° C. (hexane).

¹H NMR (CDCl₃) δ 1.14 (3H, s), 1.32 (3H, s), 1.38 (3H, s), 1.39 (3H, s), 2.17 (1H, d, J=15.8 Hz), 2.34 (1H, d, J=15.8 Hz), 2.63 (1H, d, J=15.6 Hz), 2.81 (1H, d, J=15.6 Hz), 3.92 (3H, s), 6.60 (1H, s), 6.77–7.00 (2H, m), 7.32–7.43 (1H, m).

Example 322

1-(3,5-Difluorophenyl)-3,4,8,9-tetrahydro-6-methoxy-3,3,8,8-tetramethylfuro[2,3-h]isoquinoline Hydrochloride The title compound was obtained from 3,5-difluorobenzonitrile by the method similar to that in EXAMPLE 306. Yield: 42%.

Melting point: 198–199° C. (ethyl acetate-hexane-diethyl ether).

¹H NMR (CDCl₃) δ 1.24 (6H, s), 1.36 (6H, s), 2.30 (2H, s), 2.69 (2H, s), 3.93 (3H, s), 6.62 (1H, s), 6.71–6.90 (1H, m), 6.93–6.98 (2H, m).

Example 323

1-(2,3-Dihydro-7-methoxy-5-benzofuranyl)-3,4,8,9-tetrahydro-6-methoxy-3,3,8,8-tetramethylfuro[2,3-h]isoquinoline The title compound was obtained from 7-methoxy-2,3-dihydro-5-benzofurancarbonitrile by the. method similar to that in EXAMPLE 1. Yield: 52%.

Melting point: 150–151° C. (hexane).

¹H NMR (CDCl₃) δ 1.22 (6H, s), 1.34 (6H, s), 2.35 (2H, s), 2.67 (2H, s), 3.23 (2H, t, J=8.8 Hz), 3.85 (3H, s), 3.92 (3H, s), 4.67 (2H, t, J=8.8 Hz), 6.60 (1H, s), 6.75 (1H, s), 6.93 (1H, s).

Example 324

N-[[4-(3,4,8,9-Tetrahydro-6-methoxy-3,3,8,8-tetramethylfuro[2,3-h]isoquinolin-1-yl)phenyl]methyl]methanesulfonamide Hydrochloride The title compound was obtained from N-[(4-cyanophenyl)methyl]methanesulfonamide by the method similar to that in EXAMPLE 306. Yield: 65%.

Melting point: 234–235° C. (ethyl acetate).

¹H NMR (DMSO-d₆) δ 1.23 (6H, s), 1.45 (6H, s), 2.21 (2H, s), 2.92 (3H, s), 3.17 (2H, s), 3.95 (3H, s), 4.33 (2H, d, J=3.8 Hz), 7.10 (1H, s), 7.61(4H, s), 7.84 (1H, br).

Example 325

3,4,8,9-Tetrahydro-6-methoxy-1-(6-methoxy-3-pyridinyl)-3,3,8,8-tetramethylfuro[2,3-h]isoquinoline Hydrochloride The title compound was obtained from 6-methoxy-3-pyridinecarbonitrile by the method similar to that in EXAMPLE 306. Yield: 6%.

Amorphous.

¹H NMR (CDCl₃) δ 1.23 (6H, s), 1.35 (6H, s), 2.33 (2H, s), 2.68 (2H, s), 3.93 (3H, s), 3.98 (3H, s), 6.62 (1H,as), 6.77 (1H, dd, J=8.4, 0.6 Hz), 7.63 (1H, dd, J=8.4, 2.2 Hz), 8.19 (1H, d, J=2.2 Hz).

Example 326

3,4,8,9-Tetrahydro-6-methoxy-3,3,8,8-tetramethyl-1-[3-(1-methylethoxy)phenyl]furo[2,3-h]isoquinoline Hydrochloride The title compound was obtained as a main product from 3-(1-methylethoxy)benzonitrile by the method similar to that in EXAMPLE 306. Yield: 26%.

Melting point: 191–193° C. (ethyl acetate-hexane-diethyl ether).

¹H NMR (CDCl₃) δ 1.24 (6H, s), 1.30–1.33 (12H, m), 2.26 (2H, s), 2.69 (2H, s), 3.92 (3H, s), 4.52–4.63 (1H, m), 6.60 (1H, s), 6.89–6.96 (3H, m), 7.27 (1H, t,J=7.4 Hz).

Example 327

3-(3,4,8,9-Tetrahydro-6-methoxy-3,3,8,8-tetramethylfuro[2,3-h]isoquinolin-1-yl)phenol The title compound was obtained as a by-product in EXAMPLE 326. Yield: 17%.

Melting point: 208–209° C. (hexane).

¹H NMR (CDCl₃) δ 1.23 (6H, s), 1.31 (6H, s), 2.28 (2H, s), 2.74 (2H, s), 3.93 (3H, s), 6.61–6.73 (3H, m), 6.85 (1H, t, J=2.2 Hz), 7.09 (1H, t, J=7.8 Hz).

Example 328

3,4,8,9-Tetrahydro-6-methoxy-1-(6-methoxybenzothiazol-2-yl)-3,3,8,8-tetramethylfuro[2,3-h]isoquinoline The title compound was obtained from 2-cyano-6-methoxybenzothiazole by the method similar to that in EXAMPLE 1. Yield: 18%.

Melting point: 170–171° C. (ethyl acetate-hexane).

¹H NMR (CDCl₃) δ 1.27 (6H, s), 1.38 (6H, s), 2.70 (2H, s), 2.79 (2H, s), 3.91 (3H, s), 3.92 (3H, s), 6.61 (1H, s), 7.11 (1H, dd, J=9.0, 2.5 Hz), 7.39 (1H, d, J=2.5 Hz), 7.93 (1H, d, J=9.0 Hz).

Example 329
3-(3,4,8,9-Tetrahydro-6-methoxy-3,3,8,8-tetramethylfuro[2,3-h]isoquinolin-1-yl)pyridine 1-oxide The title compound was obtained from 3-cyanopyridine 1-oxide by the method similar to that in EXAMPLE 1. Yield: 27%.

Melting point: 145–146° C. (ethyl acetate-hexane-diisopropyl ether).

$^1$H NMR (CDCl$_3$) δ 1.24 (6H, s), 1.37 (6H, s), 2.39 (2H, s), 2.70 (2H, s), 3.93 (3H, s), 6.63 (1H, s), 7.27–7.32 (2H, m), 8.22–8.26 (1H, m), 8.28 (1H, s).

Example 330
1-(6-Chloro-3-pyridinyl)-3,4,8,9-tetrahydro-6-methoxy-3,3,8,8-tetramethylfuro[2,3-h]isoquinoline The title compound was obtained from 6-chloronicotinonitrile by the method similar to that in EXAMPLE 1. Yield: 11%.

Melting point: 140–141° C. (hexane).

$^1$H NMR (CDCl$_3$) δ 1.25 (6H, s), 1.36 (6H, s), 2.28 (2H, s), 2.70 (2H, s), 3.93 (3H, s), 6.63 (1H, s), 7.38 (1H, d, J=7.8 Hz), 7.74 (1H, dd, J=7.8, 2.2 Hz), 8.42 (1H, d, J=2.0 Hz).

Example 331
2-[2-Oxo-5-(3,4,8,9-tetrahydro-6-methoxy-3,3,8,8-tetramethylfuro[2,3-h]isoquinolin-1-yl)-1(2H)-pyridinyl]-4-pyridinecarboxamide A solution of 1-(6-chloro-3-pyridinyl)-3,4,8,9-tetrahydro-6-methoxy-3,3,8,8-tetramethylfuro[2,3-h]isoquinoline (1.0 g, 2.7 mmol), 4-pyridinecarboxamide 1-oxide (2.9 g, 21 mmol), 25% solution of hydrogen bromide/acetic acid (2.0 mL) and acetic acid (6.0 mL) in toluene (10 mL) was heated under reflux for 30 hours. The reaction solution was cooled to room temperature, and then the reaction mixture was poured into water. After basifying by the addition of 8 M aqueous solution of sodium hydroxide, the organic material was extracted with ethyl acetate. The extract was washed with brine, dried over sodium sulfate, and then the solvent was distilled off under reduced pressure. The resultant residue was purified by a column chromatography on a basic silica gel (chloroform/methanol 100:1 followed by 20:1) to obtain the title compound (0.46 g, yield: 48%).

Amorphous.

$^1$H NMR (CDCl$_3$) δ 1.20 (6H, s), 1.46 (6H, s), 2.65 (2H, s), 2.88 (2H, s), 3.93 (3H, s), 6.03 (1H, br), 6.62 (1H, s), 6.70 (1H, d, J=9.2 Hz), 7.04 (1H, br), 7.61 (1H, dd, J=9.2, 2.6 Hz), 7.79 (1H, d, J=5.0 Hz), 8.08 (1H, d, J=3 2.6 Hz), 8.28 (1H, s), 8.65 (1H, d, J=5.0 Hz).

Example 332
1-(2-Pyridinyl)-5-(3,4,8,9-tetrahydro-6-methoxy-3,3,8,8-tetramethylfuro[2,3-h]isoquinolin-1-yl)-2(1H)-pyridinone The title compound was obtained from pyridine 1-oxide by the method similar to that in EXAMPLE 331. Yield: 47%.

Melting point: 203–204° C. (ethyl acetate-hexane).

$^1$H MMR (CDCl$_3$) δ 1.20 (6H, s), 1.46 (6H, s), 2.65 (2H, s), 2.90 (2H, s), 3.93 (3H, s), 6.62 (1H, s), 6.69 (1H, d, J=9.4 Hz), 7.33 (1H, td, J=5.8, 1.2 Hz), 7.57 (1H, dd, J=9.4, 2.6 Hz), 7.80–7.95 (2H, m), 8.06 (1H, d, J=2.2 Hz), 8.55 (1H, d, J=4.2 Hz).

Example 333
1-(4-Methyl-2-quinolinyl)-5-(3,4,8,9-tetrahydro-6-methoxy-3,3,8,8-tetramethylfuro[2,3-h]isoquinolin-1-yl)-2(1H)-pyridinone The title compound was obtained from 4-methylquinoline 1-oxide by the method similar to that in EXAMPLE 331. Yield: 51%.

Melting point: 212–213° C. (ethyl acetate-hexane-diisopropyl ether).

$^1$H NMR (CDCl$_3$) δ 1.21 (6H, s), 1.52 (6H, s), 2.65 (2H, s), 2.76 (3H, s), 2.99 (2H, br s), 3.93 (3H, s), 6.62 (1H, s), 6.74 (1H, d, J=8.8 Hz), 7.57–7.75 (4H, m), 8.00–8.09 (3H, m).

Example 334
1-(3-Methyl-2-quinolinyl)-5-(3,4,8,9-tetrahydro-6-methoxy-3,3,8,8-tetramethylfuro[2,3-h]isoquinolin-1-yl)-2(1H)-pyridinone The title compound was obtained from 3-methylquinoline 1-oxide by the method similar to that in EXAMPLE 331. Yield: 58%.

Melting point: 212–213° C. (ethyl acetate-hexane-diisopropyl ether)

$^1$H NMR (CDCl$_3$) δ 1.11 (3H, s), 1.30 (3H, s), 1.66 (6H, s), 2.42 (3H, s), 2.54–2.69 (2H, m), 2.73 (1H, d, J=16.2 Hz), 3.29 (1H, br d, J=16.2 Hz), 3.90 (3H, s), 6.58 (1H, s), 6.74 (1H, d, J=9.4 Hz), 7.53–7.83 (5H, m), 7.99 ($^1$H, d, J=8.0 Hz), 8.10 (1H, s).

Example 335
1-(7-Methyl-2-quinolinyl)-5-(3,4,8,9-tetrahydro-6-methoxy-3,3,8,8-tetramethylfuro[2,3-h]isoquinolin-1-yl)-2(1H)-pyridinone.

The title compound was obtained from 7-methylquinoline 1-oxide by the method similar to that in EXAMPLE 331. Yield: 6%.

Melting point: 232–233° C. (ethyl acetate-hexane).

$^1$H NMR (CDCl$_3$) δ 1.23 (6H, s), 1.58 (6H, s), 2.56 (2H, s), 2.58 (3H, s), 3.01 (2H, s), 3.93 (3H, s), 6.71 (1H, d, J=9.4 Hz), 6.93 (1H, s), 7.44 (1H, dd, J=8.4, 1.4 Hz), 7.72–7.88 (4H, m), 8.23 (1H, d, J=8.4 Hz), 8.31 (1H, d, J=1.8 Hz).

Example 336
2-[2-Oxo-5-(3,4,8,9-tetrahydro-6-methoxy-3,3,8,8-tetramethylfuro[2,3-h]isoquinolin-1-yl)-1(2H)-pyridinyl]-4-pyridinecarboxylic Acid Ethyl Ester Dihydrochloride A free base of the title compound was obtained from 4-pyridinecarboxylic acid ethyl ester 1-oxide by the method similar to that in EXAMPLE 331. This was dissolved in ethanol, combined with 3.3 M solution of hydrogen chloride/ethanol, and concentrated under reduced pressure to obtain the title compound. Yield: 36%.

Amorphous.

$^1$H NMR (CDCl$_3$) δ 1.20 (6H, s), 1.42 (3H, t, J=7.4 Hz), 1.46 (6H, s), 2.65 (2H, s), 2.89 (2H, s), 3.93 (3H, s), 4.44 (2H, q, J=7.4 Hz), 6.62 (1H, s), 6.71 (1H, d, J=9.3 Hz), 7.59 (1H, dd, J=9.3, 2.4 Hz), 7.89 (1H, dd, J=4.8, 1.4 Hz), 8.04 (1H, d, J=2.4 Hz), 8.47 (1H, s), 8.67 (1H, d, J=4.8 Hz).

Example 337
5-(3,4,8,9-Tetrahydro-6-methoxy-3,3,8,8-tetramethylfuro[2,3-h]isoquinolin-1-yl)-2(1H)-pyridinone A solution of 1-(6-chloro-3-pyridinyl)-3,4,8,9-tetrahydro-6-methoxy-3,3,8,8-tetramethylfuro[2,3-h]isoquinolin (4.0 g, 11 mmol) in 6 M hydrochloric acid (40 mL) was heated under reflux for 11.5 hours. The reaction solution was cooled to room temperature, basified by the addition of 8 M aqueous solution of sodium hydroxide, and then the organic material was extracted with ethyl acetate. The extract was washed with brine, dried over sodium sulfate, and then the solvent was distilled off under reduced pressure. The resultant residue was crystallized from ethyl acetate-hexane-diisopropyl ether to obtain the title compound (3.6 g, yield: 94%).

Melting point: 195–196° C.

¹H NMR (CDCl₃) δ 1.17 (6H, s), 1.38 (6H, s), 2.59 (2H, s), 2.61 (2H, s), 3.91 (3H, s), 6.31 (1H, br), 6.52 (1H, d, J=9.3 Hz), 6.58 (1H, s), 7.41 (1H, dd, J=9.3, 2.2 Hz), 7.68 (1H, d, J=2.2 Hz).

Example 338

1-Methyl-5-(3,4,8,9-tetrahydro-6-methoxy-3,3,8,8-tetramethylfuro[2,3-h]isoquinolin-1-yl)-2(1H)-pyridinone A solution of 5-(3,4,8,9-tetrahydro-6-methoxy-3,3,8,8-tetramethylfuro[2,3-h]isoquinolin-1-yl)-2(1H)-pyridinone (1.0 g, 2.8 mmol) and sodium hydride (60% in oil, 0.35 g, 8.8 mmol) in N,N-dimethylformamide (10 mL) was stirred at room temperature. for 15 minutes. Iodomethane (2.0 mL, 32 mmol) was added to the reaction mixture at room temperature and the mixture was stirred at room temperature for 9 hours. The reaction solution was poured into water, and basified by the addition of 1 M aqueous solution of sodium hydroxide, and then the organic material was extracted with ethyl acetate. The extract was washed with brine, dried over sodium sulfate, and then the solvent was distilled off under reduced pressure. The resultant residue was purified by a column chromatography on a basic silica gel (hexane/chloroform/ethyl acetate 2:1:1 followed by 1:2:2) to obtain crude crystals. The resultant crude crystals were recrystallized from ethyl acetate-hexane-diisopropyl ether to obtain the title compound (0.52 g, yield: 50%).

Melting point: 158–159° C.

¹H NMR (CDCl₃) δ 1.20 (6H, s), 1.41 (6H, s), 2.61 (2H, s), 2.65 (2H, s), 3.60 (3H, s), 3.93 (3H, s), 6.56 (1H, d, J=9.4 Hz), 6.61 (1H, s), 7.33 (1H, dd, J=9.4, 2.6 Hz), 7.59 (1H, d, J=2.6 Hz).

Example 339

1-(3-Pyridinylmethyl)-5-(3,4,8,9-tetrahydro-6-methoxy-3,3,8,8-tetramethylfuro[2,3-h]isoquinolin-1-yl)-2(1H)-pyridinone The title compound was obtained from 3-(chloromethyl)pyridine hydrochloride by the method similar to that in EXAMPLE 338. Yield: 38%.

Melting point: 247–248° C. (ethyl acetate-hexane).

¹H NMR (CDCl₃) δ 1.19 (6H, s), 1.33 (6H, s), 2.47 (2H, s), 2.64 (2H, s), 3.91 (3H, s), 5.18 (2H, s), 6.60 (1H, s), 6.65 (1H, d, J=9.4 Hz), 7.27–7.32 (1H, m), 7.42 (H, dd, J=9.4, 2.6 Hz), 7.51 (1H, d, J=2.2 Hz), 7.77 (1H, dd, J=7.6, 1.8 Hz), 8.57 (1H, dd, J=4.8. 1.4 Hz), 8.64 (1H, d, J=2.2 Hz).

Example 340

1-(4-Pyridinylmethyl)-5-(3,4,8,9-tetrahydro-6-methoxy-3,3,8,8-tetramethylfuro[2,3-h]isoquinolin-1-yl)-2(1H)-pyridinone The title compound was obtained from 4-(chloromethyl)pyridine hydrochloride by the method similar to that in EXAMPLE 338. Yield: 63%.

Melting point: 199–200° C. (ethyl acetate-diisopropyl ether).

¹H NMR (CDCl₃) δ 1.19 (6H, s), 1.35 (6H, s), 2.52 (2H, s), 2.64 (2H, s), 3.92 (3H, s), 5.17 (2H, s), 6.61 (1H, s), 6.68 (1H, d, J=9.8 Hz), 7.21 (2H, d, J=5.8 Hz), 7.45–7.48 (2H, m), 8.59 (2H, d, J=5.8 Hz).

Example 341

1-(2-Pyridinylmethyl)-5-(3,4,8,9-tetrahydro-6-methoxy-3,3,8,8-tetramethylfuro[2,3-h]isoquinolin-1-yl)-2(1H)-pyridinone The title compound was obtained from 2-(chloromethyl)pyridine hydrochloride by the method similar to. that in EXAMPLE 338. Yield: 72%.

Melting point: 191–192° C. (ethyl acetate-hexane).

¹H NMR (CDCl₃) δ 1.20 (6H, s), 1.35 (6H, s), 2.57 (2H, s), 2.65 (2H, s), 3.92 (3H, s), 5.22 (2H, s), 6.60 (1H, s), 6.61 (1H, d, J=9.0 Hz), 7.17–7.27 (1H, m), 7.42 (1H, dd, J=9.2, 2.2 Hz), 7.49 (1H, d, J=7.6 Hz), 7.67 (1H, dd, J=7.6, 1.8 Hz), 7.72 (1H, d, J=2.2 Hz), 8.52 (1H, d, J=4.8 Hz).

Example 342

1-(2-Quinolinylmethyl)-5-(3,4,8,9-tatrahydro-6-methoxy-3,3,8,8-tetramethylfuro[2,3-h]isoquinolin-1-yl)-2(1H)-pyridinone The title compound was obtained from 2-(chloromethyl)quinoline hydrochloride by the method similar to that in EXAMPLE 338. Yield: 54%.

Melting point: 210–211° C. (ethyl acetate-diisopropyl ether).

¹H NMR (CDCl₃) δ 1.19 (6H, s, 1.23 (6H, s), 2.53 (2H, s), 2.64 (2H, s), 3.91 (3H, s), 5.45 (2H, s), 6.59 (1H, s), 6.66 (1H, d, J=9.6 Hz), 7.37–7.50 (1H, m), 7.53–7.59 (2H, m), 7.65–7.73 (1H, m), 7.75 (1H, d, J=2.2 Hz), 7.81 (1H, d, J=8.0 Hz), 7.98 (1H, d, J=8.6 Hz), 8.15 (1H, d, J=8.8 Hz).

Example 343

1-(Phenylmethyl)-5-(3,4,8,9-tetrahydro-6-methoxy-3,3,8,8-tetramethylfuro[2,3-h]isoquinolin-1-yl)-2(1H)-pyridinone The title compound was obtained from benzyl bromide by the method similar to that in EXAMPLE 338. Yield: 38%.

Melting point: 216–217° C. (ethyl acetate-hexane-diisopropyl ether).

¹H NMR (CDCl₃) δ 1.18 (6H, s), 1.30 (6H, s), 2.44 (2H, s), 2.63 (2H, s), 3.91 (3H, s), 5.17 (2H, br s), 6.58 (1H, s), 6.66 (1H, d, J=9.8 Hz), 7.32 (5H, s), 7.38–7.43 (2H, m).

Example 344

2-Oxo-5-(3,4,8,9-tetrahydro-6-methoxy-3,3,8,8-tetramethylfuro[2,3-h]isoquinolin-1-yl)-1(2H)-pyridineacetamide Hydrochloride A solution of 5-(3,4,8,9-tetrahydro-6-methoxy-3,3,8,8-tetramethylfuro[2,3-h]isoquinolin-1-yl)-2(1H)-pyridinone (1.5 g, 4.3 mmol) and sodium hydride (60% in oil, 0.19 g, 4.8 mmol) in N,N-dimethylformamide (10 mL) was stirred at room temperature for 25 minutes. 2-Chloroacetamide (0.51 g, 5.5 mmol) was added to the reaction mixture at room temperature and the mixture was stirred at room temperature for 24 hours. The reaction solution was poured into water, basified by the addition of 1 M aqueous solution of sodium hydroxide, and then the organic material was extracted with ethyl acetate. The extract was washed with brine, dried over sodium sulfate, and then the solvent was distilled off under reduced pressure. The resultant residue was purified by a column chromatography on a basic silica gel (chloroform/methanol 50:1 followed by 20:1) to obtain crude crystals. 3.3 M solution of hydrogen chloride/ethanol (5.0 mL, 17 mmol) was added to the solution of the resultant crude crystals in ethanol (20 mL) and the mixture was stirred at room temperature for 10 minutes. The reaction solution was concentrated under reduced pressure to obtain the title compound (1.3 g, yield: 59%).

Amorphous.

¹H NMR (DMSO-d₆) δ 1.34 (6H, s), 1.40 (6H, s), 2.78 (2H, br), 3.08 (2H, s), 3.93 (3H, s), 4.60 (2H, br), 6.59 (1H, d, J=9.5 Hz), 7.06 (1H, s), 7.73 (1H, dd, J=9.5, 2.4 Hz), 7.76 (1H, s), 8.27 (1H, d, J=2.4 Hz), 8.33 (1H, s), 12.39 (1H, br).

Example 345

2-Oxo-5-(3,4,8,9-tetrahydro-6-methoxy-3,3,8,8-tetramethylfuro[2,3-h]isoquinolin-1-yl)-1(2H)-pyridineacetic Acid Ethyl Ester The title compound was obtained from ethyl bromoacetate by the method similar to that in Example 338. Yield: 17%.

Amorphous.

$^1$H NMR (CDCl$_3$) δ 1.20 (6H, s), 1.30 (3H, t, J=7.4 Hz), 1.42 (6H, s), 2.65 (2H, s), 2.73 (2H, s), 3.92 (3H, s), 4.25 (2H, q, J=7.4 Hz), 4.68 (2H, br), 6.60–6.65 (2H, m), 7.42–7.47 (2H, m).

Example 346
2-Oxo-N-(3-pyridinyl)-5-(3,4,8,9-tetrahydro-6-methoxy-3,3,8,8-tetramethylfuro[2,3-h]isoquinolin-1-yl)-1(2H)-pyridineacetamide A solution of 2-oxo-5-(3,4,8,9-tetrahydro-6-methoxy-3,3,8,8-tetramethylfuro[2,3-h]isoquinolin-1-yl)-1(2H)-pyridineacetic acid ethyl ester (1.4 g, 3.2 mmol) and 3-aminopyridine (0.58 g, 6.2 mmol) in decalin (10 mL) was stirred at 200° C. for 17 hours under argon atmosphere. The reaction solution was combined with 2 M hydrochloric acid, and washed with chloroform. The aqueous solution was basified with 8 M aqueous solution of sodium hydroxide, and then the organic material was extracted with ethyl acetate. The extract was washed with brine, dried over sodium sulfate, and then the solvent was distilled off under reduced pressure. The resultant residue was purified by a column chromatography on a basic silica gel (ethyl acetate/methanol 50:1 followed by 10:1) to obtain crude crystals. The resultant crude crystals were recrystallized from ethyl acetate-diisopropyl ether to obtain the title compound (0.20 g, yield: 13%).

Melting point: 276–277° C.

$^1$H NMR (CDCl$_3$) δ 1.21 (6H, s), 1.40 (6H, s), 2.66 (4H, s), 3.93 (3H, s), 4.78 (2H, br s), 6.62 (1H, s), 6.71 (1H, d, J=9.3 Hz), 7.18–7.27 (1H, m), 7.56 (1H, dd, J=9.3, 2.6 Hz), 7.69 (1H, d, J=2.2 Hz), 8.04–8.08 (1H, m), 8.33 (1H, dd, J=4.6, 1.4 Hz), 8.63 (1H, d, J=2.6 Hz), 9.65 (1H, s).

Example 347
N-(2-Hydroxyethyl)-2-oxo-5-(3,4,8,9-tetrahydro-6-methoxy-3,3,8,8-tetramethylfuro[2,3-h]isoquinolin-1-yl)-1(2H)-pyridineacetamide The title compound was obtained from 2-aminoethanol by the method similar to that in EXAMPLE 346. Yield: 59%.

Melting point: 133–134° C. (ethyl acetate-diisopropyl ether).

$^1$H NMR (CDCl$_3$) δ 1.20 (6H, s), 1.42 (6H, s), 2.65 (2H, s), 2.68 (2H, s), 3.41 (2H, m), 3.69 (2H, t, J=4.8 Hz), 3.92 (3H, s), 4.64 (2H, s), 6.61 (1H, s), 6.62 (1H, d, J=7.6 Hz) 7.37–7.48 (2H, m), 7.63 (1H, d, J=2.2 Hz).

Example 348
2-Oxo-5-(3,4,8,9-tetrahydro-6-methoxy-3,3,8,8-tetramethylfuro 2,3-h]isoquinolin-1-yl)-1(2H)-pyridineacetic acid 1,1-dimethylethyl Ester The title compound was obtained from tert-butyl bromoacetate by the method similar to that in EXAMPLE 338. Yield: 51%.

Amorphous.

$^1$H NMR (CDCl$_3$) δ 1.20 (6H, s), 1.42 (15H, s), 2.65 (2H, s), 2.72 (2H, s), 3.92 (3H, s), 4.65 (2H, br), 6.61–6.65 (2H, m), 7.40–7.48 (2H, m).

Example 349
2-Oxo-5-(3,4,8,9-tetrahydro-6-methoxy-3,3,8,8-tetramethylfuro[2,3-h]isoquinolin-1-yl)-1(2H)-pyridineacetic Acid Hydrochloride A solution of 2-oxo-5-(3,4,8,9-tetrahydro-6-methoxy-3,3,8,8-tetramethylfuro[2,3-h]isoquinolin-1-yl)-1(2H)-pyridineacetic acid 1,1-dimethylethyl ester (2.7 g, 5.8 mmol) in 6 M hydrochloric acid (30 mL) was heated under reflux for 1 hour. After cooling to room temperature, the reaction mixture was concentrated under reduced pressure. The resultant residue was crystallized from chloroform-diisopropyl ether to obtain the title compound (2.5 g, yield: 97%).

Melting point: 231–233° C. (decomposition).

$^1$H NMR (DMSO-d$_6$) δ 1.34 (6H, s), 1.39 (6H, s), 2.80 (2H, br), 3.08 (2H, s), 3.94 (3H, s), 4.71 (2H, s), 6.63 (1H, d, J=9.6 Hz), 7.07 (1H, s), 7.76 (1H, dd, J=9.6, 3.0 Hz), 8.33 (1H, d, J=3.0 Hz), 12.40 (1H, br).

Example 350
4-[[2-Oxo-5-(3,4,8,9-tetrahydro-6-methoxy-3,3,8,8-tetramethylfuro[2,3-h]isoquinolin-1-yl)-1(2H)-pyridinyl]methyl]benzoic Acid Methyl Ester The title compound was obtained from methyl 4-(bromomethyl)benzoate by the method similar to that in EXAMPLE 338. Yield: 62%.

Amorphous.

$^1$H NMR (CDCl$_3$) δ 1.18 (6H, s), 1.32 (6H, s), 2.47 (2H, s), 2.63 (2H, s), 3.91 (6H, s), 5.22 (2H, br s), 6.60 (1H, s), 6.67 (1H, d, J=9.8 Hz), 7.37–7.46 (4H, m), 8.01 (2H, d, J=8.4 Hz).

Example 351
N-(2-Hydroxyethyl)-4-[[2-oxo-5-(3,4,8,9-tetrahydro-6-methoxy-3,3,8,8-tetramethylfuro[2,3-h]isoquinolin-1-yl)-1(2H)-pyridinyl]methyl]benzamide Hydrochloride A solution of 4-[[2-oxo-5-(3,4,8,9-tetrahydro-6-methoxy-3,3,8 8-tetramethylfuro[2,3-h]isoquinolin-1-yl)-1(2H)-pyridinyl]methyl]benzoic acid methyl ester (1.0 g, 2.0 mmol) and 2-aminoethanol (2.0 mL, 33 mmol) in xylene (10 mL) was heated under reflux for 4 hours. The reaction solution was cooled to room temperature, and the solvent was distilled off under reduced pressure. The residue was combined with water, and the mixture was made alkaline with 1 M aqueous solution of sodium hydroxide, and then the organic material was extracted with ethyl acetate. The extract was washed with brine and dried over sodium sulfate, and then the solvent was distilled off under reduced pressure. The resultant residue was purified by a column chromatography on a basic silica gel (ethyl acetate/methanol 50:1 followed by 20:1) to obtain crude crystals. 3.3 M hydrogen chloride/ethanol solution (3.0 mL, 10 mmol) was added to a solution of the resultant crude crystals in ethanol (20 mL) and the mixture was stirred at room temperature for 10 minutes. The reaction solution was concentrated under reduced pressure, and the resultant residue was crystallized from chloroform-diisopropyl ether to obtain the title compound (1.1 g, Yield: 96%).

Melting point: 175–176° C.

$^1$H NMR (DMSO-d$_6$) δ 1.28 (6H, s), 1.42 (6H, s), 2.66 (2H, s), 3.09 (2H, s), 3.30–3.40 (2H, m), 3.50 (2H, t, J=5.6 Hz), 3.93 (3H, s), 5.24 (2H, br), 6.62 (1H, d, J=9.6 Hz), 7.07 (1H, s), 7.45 (2H, d, J=8.0 Hz), 7.67 (1H, dd, J=9.4, 2.2 Hz), 7.88 (2H, d, J=8.0 Hz), 8.51–8.57 (2H, m).

Example 352
4-[[2-Oxo-5-(3,4,8,9-tetrahydro-6-methoxy-3,3,8,8-tetramethylfuro[2,3-h]isoquinolin-1-yl)-1(2H)-pyridinyl]methyl]benzoic Acid Hydrochloride The title compound was obtained from 4-[[2-oxo-5-(3,4,8,9-tetrahydro-6-methoxy-3,3,8,8-tetramethylfuro[2,3-h]isoquinolin-1-yl)-1(2H)-pyridinyl]methyl]benzoic acid methyl ester by the method similar to that in EXAMPLE 349. Yield: 62%.

Amorphous.

1H NMR (DMSO-d$_6$) δ 1.27 (6H, s), 1.42 (6H, s), 2.65 (2H, s), 3.09 (2H, s), 3.93 (3H, s), 5.30 (2H, br), 6.64 (1H, d, J=9.6 Hz), 7.08 (1H, s), 7.49 (2H, d, J=8.4 Hz), 7.70 (1H, dd, J=9.6, 2.2 Hz), 7.93 (2H, d, J=8.4 Hz), 8.58 (1H, d, J=2.2 Hz), 12.62 (1H, br).

Example 353
4-[[2-Oxo-5-(3,4,8,9-tetrahydro-6-methoxy-3,3,8,8-tetramethylfuro[2,3-h]isoquinolin-1-yl)-1(2H)-pyridinyl]methyl]benzamide N,N-Dimethylformamide (0.1 mL) was added to a solution of 4-[[2-oxo-5-(3,4,8,9-tetrahydro-6-methoxy-3,3,8,8-tetramethylfuro[2,3-h]isoquinolin-1-yl)-1(2H)-pyridinyl]methyl]benzoic acid hydrochloride (1.6 g, 3.1 mmol) and oxalyl chloride (0.75 mL, 8.6 mmol) in tetrahydrofuran (50 mL) at room temperature and the reaction mixture was stirred at room temperature for 1 hour. The reaction solution was concentrated under reduced pressure. 6.3 M ammonia/ethanol solution (30 mL) was added to a solution of the resultant residue in tetrahydrofuran (50 mL) at room temperature, and the reaction mixture was stirred at room temperature for 1 hour. The reaction solution was concentrated under reduced pressure, and the residue was combined with water, and the organic material was extracted with chloroform. The extract was washed with brine and dried over sodium sulfate, and then the solvent was distilled off under reduced pressure. The resultant. residue was purified by a column chromatography on a basic silica gel (chloroform/methanol 50:1 followed by 20:1) to obtain crude crystals. The resultant crude crystals were recrystallized from ethyl acetate to obtain the title compound (0.44 g, Yield: 31%).

Melting point: 262–266° C.
$^1$H NMR (CDCl$_3$) δ 1.18 (6H, s), 1.33 (6H, s), 2.49 (2H, s), 2.63 (2H, s), 3.91 (3H, s), 5.21 (2H, s), 5.64 (1H, br), 6.08 (1H, br), 6.60 (1H, s), 6.66 (1H, d, J=9.0 Hz), 7.39–7.47 (4H, m), 7.79 (2H, d, J=8.0 Hz).

Example 354
N-Methyl-4-[[2-oxo-5-(3,4,8,9-tetrahydro-6-methoxy-3,3,8,8-tetramethylfuro[2,3-h]isoquinolin-1-yl)-1(2H)-pyridinyl]methyl]benzamide The title compound was obtained from a 40% methylamine/methanol solution by the method similar to that in. EXAMPLE 353. Yield: 41%.

Amorphous.
$^1$H NMR (CDCl$_3$) δ 1.18 (6H, s), 1.33 (6H, s), 2.49 (2H, s), 2.63 (2H, s), 3.00 (3H, d, J=5.2 Hz), 3.91 (3H, s), 5.20 (2H, br), 6.18 (1H, br), 6.59 (1H, s), 6.65 (1H, d, J=10 Hz), 7.36–7.46 (4H, m), 7.73 (2H, d, J=8.0 Hz).

Example 355
4-[[2-Oxo-5-(3,4,8,9-tetrahydro-6-methoxy-3,3,8,8-tetramethylfuro[2.3-h]isoquinolin-1-yl)-1(2H)-pyridinyl]methyl]-N-propylbenzamide The title compound was obtained from propylamine by the method similar to EXAMPLE 353. Yield: 57%.

Melting point: 193–195° C. (ethyl acetate-hexane-diisopropyl ether).
$^1$H NMR (CDCl$_3$) δ 0.97 (3H, t, J=7.2 Hz), 1.18 (6H, s), 1.33 (6H, s), 1.55–1.65 (2H, m), 2.48 (2H, s), 2.63 (2H, s), 3.41 (2H, q, J=7.2 Hz), 3.91 (3H, s), 5.20 (2H, s), 6.12 (1H, br), 6.59 (1H, s), 6.65 (1H, d, J=9.0 Hz), 7.37–7.45 (4H, m), 7.73 (2H, d, J=8.0 Hz).

Example 356
3,4,8,9-Tetrahydro-6-methoxy-3,3,8,8-tetramethyl-1-[4-(methylthio)phenyl]furo[2,3-h]isoquinoline Hydrochloride A solution of 4-(methylthio)benzonitrile (0.776 g, 5.20 mmol) in toluene (5 mL) and acetic acid (5 mi) was treated dropwise with conc. sulfuric acid (0.5 mL) with cooling in ice. The ice bath was removed, and a solution of 2,3-dihydro-7-methoxy-2,2-dimethyl-5-(2-methyl-1-propenyl)benzofuran (0.929 g, 4.00 mmol) in toluene (5 mL) was added and the mixture was stirred at 80° C. for 1 hour. The reaction mixture was combined with ice, and the aqueous layer was neutralized with conc. aqueous ammonia and extracted twice with ethyl acetate. The combined organic layer was washed with water and brine, dried over sodium sulfate, filtered and concentrated under reduced pressure. The residue was subjected to a column chromatography on a silica gel (hexane/ethyl acetate 2:1) to obtain a free base of the title compound. This was combined with 2.8 M hydrogen chloride/ethanol solution (7.4 mL) and the mixture was concentrated under reduced pressure. The residue was crystallized from diethyl ether, and recrystallized from ethyl acetate to obtain the title compound (0.72 g, Yield: 43%).

Melting point: 137–140° C.
$^1$H NMR (CDCl$_3$) δ 1.37 (6H, s), 1.67 (6H, s), 2.39 (2H, s), 2.55 (3H, s), 3.00 (2H, s), 4.02 (3H, s), 6.74 (1H, s), 7.36 (2H, d, J=8.2 Hz), 7.68 (2H, d, J=8.2 Hz).

Example 357
1-(2,3-Dihydro-5-benzofuranyl)-3,4,8,9-tetrahydro-6-methoxy-3,3,8,8-tetramethylfuro[2,3-h]isoquinoline Hydrochloride The title compound was obtained from 2,3-dihydro-5-benzofurancarbonitrile by the method similar to that in EXAMPLE 356. Yield: 51%.

Melting point: 144–148° C. (ethyl acetate).
$^1$H NMR (CDCl$_3$) δ 1.39 (6H, s), 1.65 (6H, s), 2.45 (2H, s), 2.98 (2H, s), 3.36 (2H, t, J=8.8 Hz), 4.01 (3H, s), 4.72 (2H, t, J=8.8 Hz), 6.73 (1H, s), 6.86 (1H, d, J=8.4 Hz), 7.32 (1H, dd, J=8.4, 1.8 Hz), 7.93 (1H, d, J=1.8 Hz).

Example 358
1-(1,3-Benzodioxol-5-yl)-3,4,8,9-tetrahydro-6-methoxy-3,3,8,8-tetramethylfuro[2,3-h]isoquinoline Hydrochloride The title compound was obtained from 1,3-benzodioxol-5-carbonitrile by the method similar to that in EXAMPLE 356. Yield: 44%.

Melting point: 156–160° C. (ethyl acetate).
$^1$H NMR (CDCl$_3$) δ 1.39 (6H, s), 1.65 (6H, s), 2.45 (2H, s), 2.99 (2H, s), 4.01 (3H, s), 6.11 (2H, s), 6.73 (1H, s), 6.97 (1H, d, J=8.0 Hz), 7.17 (1H, br s), 7.27–7.29 (1H, m).

Example 359
N,N-Dimethyl-4-(3,4,8,9-tetrahydro-6-methoxy-3,3,8,8-tetramethylfuro[2,3-h]isoquinolin-1-yl)benzenamine Hydrochloride The title compound was obtained from 4-(dimethylamino)benzonitrile by the method similar to that in Example 356. Yield: 24%.

Melting point: 165–168° C. (ethyl acetate-ethanol).
$^1$H NMR (CDCl$_3$) δ 1.40 (6H, s), 1.62 (6H, s), 2.58 (2H, s), 2.94 (2H, s), 3.10 (6H, s), 4.01 (3H, s), 6.73 (1H, s), 6.75 (2H, d, J=9.0 Hz), 7.77 (2H, d, J=9.0 Hz).

Example 360
1-[4-(3,4,8,9-Tetrahydro-6-methoxy-3,3,8,8-tetramethylfuro[2,3-h]isoquinolin-1-yl)phenyl]ethanone Hydrochloride The title compound was obtained from 4-acetylbenzonitrile by the method similar to that in EXAMPLE 356. Yield: 29%.

Melting point: 167–170° C. (ethyl acetate-ethanol).
$^1$H NMR (CDCl$_3$) δ 1.34 (6H, s), 1.71 (6H, s), 2.21 (2H, s), 2.69 (3H, s), 3.06 (2H, s), 4.03 (3H, s), 6.77 (1H, s), 7.80 (2H, d, J=8.2 Hz), 8.14 (2H, d, J=8.2 Hz).

Example 361
3,4,8,9-Tetrahydro-6-methoxy-3,3,8,8-tetramethyl-1-(2-thienyl)furo[2,3-h]isoquinoline Hydrochloride Title compound was obtained from 2-thiophenecarbonitrile by the method similar to that in EXAMPLE 356. Yield: 30%.

Melting point: 154–156° C. (ethyl acetate-ethanol).

1H NMR (CDCl$_3$) δ 1.41 (6H, s), 1.66 (6H, s), 2.59 (2H, s), 3.00 (2H, s), 4.02 (3H, s), 6.75 (1H, s), 7.29 (1H, br s), 7.82 (1H, d, J=4.6 Hz), 8.05 (1H, br s).

Example 362
3,4,8,9-Tetrahydro-6-methoxy-3,3,8,8-tetramethyl-1-[4-(trifluoromethyl)phenyl]furo[2,3-h]isoquinoline Hydrochloride The title compound was obtained from 4-(trifluoromethyl)benzonitrile by the method similar to that in EXAMPLE 356. Yield: 53%.

Melting point: 149–151° C. (ethyl acetate).

$^1$H NMR (CDCl$_3$) δ 1.35 (6H, s), 1.71 (6H, s), 2.19 (2H, s), 3.05 (2H, s), 4.03 (3H, s), 6.77 (1H, s), 7.84 (4H, s).

Example 363
1-(2,3-Dihydro-7-methoxy-2,2-dimethyl-5-benzofuranyl)-3,4,8,9-tetrahydro-6-methoxy-3,3,8,8-tetramethylfuro[2,3-h]isoquinoline Hydrochloride The title compound was obtained from 2,3-dihydro-7-methoxy-2,2-dimethyl-5-benzofurancarbonitrile by the method similar to that in EXAMPLE 356. Yield: 38%.

Melting point: 141–143° C. (diethyl ether-ethyl acetate).

$^1$H NMR (CDCl$_3$) δ 1.40 (6H, s), 1.56 (6H, s), 1.66 (6H, s), 2.50 (2H, s), 2.97 (2H, s), 3.08 (2H, s), 4.02 (3H, s), 4.06 (3H, s), 6.74 (1H, s), 7.12 (1H, br s), 7.46 (1H, br s).

Example 364
Bis[3,4,8,9-tetrahydro-6-methoxy-3,3,8,8-tetramethyl-1-[4-(phenylthio)phenyl]furo[2,3-h]isoquinoline] trihydrochloride The title compound was obtained from 4-(phenylthio)benzonitrile by the method similar to that in EXAMPLE 356. Yield: 48%.

Melting point: 130–132° C. (diethyl ether-ethyl acetate).

$^1$H NMR (CDCl$_3$) δ 1.37 (6H, s), 1.67 (6H, s), 2.35 (2H, s), 3.00 (2H, s), 4.01 (3H, s), 6.74 (1H, s), 7.27–7.63 (9H, m).

Example 365
3,4,8,9-Tetrahydro-6-methoxy-3,3,8,8-tetramethyl-1-[4-(1-methylethyl)phenyl]furo[2,3-h]isoquinoline Hydrochloride The title compound was obtained from 4-(1-methylethyl)benzonitrile by the method similar to that in EXAMPLE 356. Yield: 37%.

Melting point: 169–171° C. (ethyl acetate).

$^1$H NMR (CDCl$_3$) δ 1.31 (6H, d, J=6.8 Hz), 1.35 (6H, s), 1.69 (6H, s), 2.29 (2H, s), 2.95–3.08 (1H, m), 3.01 (2H, s), 4.02 (3H, s), 6.75 (1H, s), 7.42 (2H, d, J=8.4 Hz), 7.69 (2H, d, J=8.4 Hz).

Example 366
3,4,8,9-Tetrahydro-6-methoxy-3,3,8,8-tetramethyl-1-(5-methyl-2-thienyl)furo[2,3-h]isoquinoline Hydrochloride The title compound was obtained from 5-methyl-2-thiophenecarbonitrile by the method similar to that in EXAMPLE 356. Yield: 12%.

Melting point: 177–179° C. (ethyl acetate).

$^1$H NMR (CDCl$_3$) δ 1.39 (6H, s), 1.69 (6H, s), 2.30 (3H, s), 2.32 (2H, s), 3.02 (2H, s), 4.02 (3H, s), 6.73 (1H, s), 7.01 (1H, d, J=4.8 Hz), 7.60 (1H, d, J=4.8 Hz).

Example 367
3,4,8,9-Tetrahydro-6-methoxy-3,3,8,8-tetramethyl-1-[4-(trifluoromethoxy)phenyl]furo[2,3-h]isoquinoline Hydrochloride The title compound was obtained from-4-(trifluoromethoxy)benzonitrile by the method similar to that in EXAMPLE 356. Yield: 27%.

Melting point: 163–166° C. (ethyl acetate).

$^1$H NMR (CDCl$_3$) δ 1.36 (6H, s), 1.70 (6H, s), 2.25 (2H, s), 3.04 (2H, s), 4.03 (3H, s), 6.76 (1H, s), 7.41 (2H, d, J=8.4 Hz). 7.81 (2H, d, J=8.4 Hz).

Example 368
2-Methoxy-4-(3,4,8,9-tetrahydro-6-methoxy-3,3,8,8-tetramethylfuro[2,3-h]isoquinolin-1-yl)phenol A solution of 4-hydroxy-3-methoxybenzonitrile (0.895 g, 6.00 mmol) in toluene (5 mL) and acetic acid (5 mL) was treated dropwise with conc. sulfuric acid (0.6 mL) with cooling in ice. The ice bath was removed, and a solution of 2,3-dihydro-7-methoxy-2,2-dimethyl-5-(2-methyl-1-propenyl)benzofuran (1.16 g, 5.00 mmol) in toluene (5 mL) was added and stirred at 80° C. for 1 hour. The reaction mixture was combined with ice, and the aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a silica gel (hexane/ethyl acetate 2:1 followed by ethyl acetate) and recrystallized from ethyl acetate-hexane to obtain the title compound (0.92 g, Yield: 48%).

Melting point: 143–145° C.

$^1$H NMR (CDCl$_3$) δ 1.24 (6H, s), 1.33 (6H, s), 2.32 (2H, s), 2.55 (1H, br s), 2.68 (2H, s), 3.89 (3H, s), 3.92 (3H, s), 6.61 (1H, s), 6.86–6.92 (3H, m).

Example 369
1-(3,5-Dichloro-4-pyridinyl)-3,4,8,9-tetrahydro-6-methoxy-3,3,8,8-tetramethylfuro[2,3-h]isoquinoline The title compound was obtained from 3,5-dichloro-4-pyridinecarbonitrile by the method similar to that in EXAMPLE 368. Yield: 23%.

Melting point: 147–148° C. (hexane).

$^1$H NMR (CDCl$_3$) δ 1.34 (6H, s), 1.35 (6H, s), 2.19 (2H, s), 2.78 (2H, s), 3.92 (3H, s), 6.63 (1H, s), 8.56 (2H, s).

Example 370
1-(2-Furanyl)-3,4,8,9-tetrahydro-6-methoxy-3,3,8,8-tetramethylfuro[2,3-h]isoquinoline The title compound was obtained from 2-furonitrile by the method similar to that in EXAMPLE 368. Yield: 25%.

Melting point: 125–127° C. (hexane).

$^1$H NMR (CDCl$_3$) δ 1.23 (6H, s), 1.41 (6H, s), 2.51 (2H, s), 2.66 (2H, s), 3.92 (3H, s), 6.49 (1H, dd, J=3.4, 1.8 Hz), 6.58 (1H, s), 6.66 (1H, d, J=3.4 Hz), 7.48 (1H, d, J=1.8 Hz).

Example 371
2-(3,4,8,9-Tetrahydro-6-methoxy-3,3,8,8-tetramethylfuro[2,3-h]isoquinolin-1-yl)phenol The title compound was obtained from 2-cyanophenyl acetate by the method similar to that in EXAMPLE 368. Yield: 19%.

Melting point: 186–189° C. (ethyl acetate-hexane).

$^1$H NMR (CDCl$_3$) δ 1.22 (6H, s), 1.42 (6H, s), 2.64 (2H, s), 2.74 (2H, s), 3.94 (3H, s), 6.64 (1H, s), 6.75–6.84 (1H, m), 6.98–7.03 (1H, m), 7.24–7.32 (2H, m).

Example 372
3,4,8,9-Tetrahydro-6-methoxy-3,3,8,8-tetramethyl-1-(3-thienyl)furo[2,3-h]isoquinolin The title compound was obtained from 3-thiophenecarbonitrile by the method similar to that In EXAMPLE 368. Yield: 45%.

Melting point: 119–122° C. (hexane).

$^1$H NMR (CDCl$_3$) δ 1.23 (6H, s), 1.35 (6H, s), 2.36 (2H, s), 2.67 (2H, s), 3.92 (3H, s), 6.60 (1H, s), 7.11 (1H, dd, J=5.0, 1.2 Hz), 7.30–7.39 (2H, m).

Example 373
3,4,8,9-Tetrahydro-6-methoxy-3,3,8,8-tetramethyl-1-(3-methyl-2-thienyl)furo[2,3-h]isoquinoline The title compound was obtained from 3-methyl-2-thiophenecarbonitrile by the method similar to that in EXAMPLE 368. Yield: 23%.

Melting point: 195–197° C. (hexane-ethyl acetate).

$^1$H NMR (CDCl$_3$) δ 1.19 (6H, s), 1.40 (6H, s), 2.50 (3H, d, J=0.8 Hz), 2.63 (2H, s), 2.67 (2H, s), 3.92 (3H, s), 6.59 (1H, s), 6.67–6.69 (1H, m), 6.84 (1H, d, J=3.6 Hz).

Example 374
1-(2-Chloro-3-pyridinyl)-3,4,8,9-tetrahydro-6-methoxy-3,3,8,8-tetramethylfuro[2,3-h]isoquinoline The title compound was obtained from 2-chloro-3-pyridinecarbonitrile by the method similar to that in EXAMPLE 368. Yield: 29%.

Melting point: 159–160° C. (ethyl acetate-hexane).

$^1$H NMR (CDCl$_3$) δ 1.21 (3H, s), 1.30 (3H, s), 1.36 (3H, s), 1.39 (3H, s), 2.03 (1H, d, J=15.8 Hz), 2.25 (1H, d, J=15.8 Hz), 2.70 (1H, d, J=15.8 Hz), 2.81 (1H, d, J=15.8 Hz), 3.92 (3H, s), 6.62 (1H, s), 7.34 (1H, dd, J=7.2, 4.8 Hz), 7.69 (1H, dd, J=7.2, 1.8 Hz), 8.46 (1H, dd, J=4.8, 1.8 Hz).

Example 375
1-(2,6-Dichloro-4-methyl-3-pyridinyl)-3,4,8,9-tetrahydro-6-methoxy-3,3,8,8-tetramethylfuro[2,3-h]isoquinoline The title compound was obtained from 2,6-dichloro-4-methyl-3-pyridinecarbonitrile by the method similar to that in EXAMPLE 368. Yield: 25%.

Melting point: 97–101° C. (ethyl acetate-hexane).

$^1$H NMR (CDCl$_3$) δ 1.32 (3H, s), 1.33 (3H, s), 1.34 (3H, s), 1.37 (3H, s), 2.02 (1H, d, J=15.8 Hz), 2.19 (3H, s), 2.32 (1H, d, J=15.8 Hz), 2.74 (1H, d, J=15.8 Hz), 2.79 (1H, d, J=15.8 Hz), 3.92 (3H, s), 6.62 (1H, s), 7.20 (1H, s).

Example 376
3,4,8,9-Tetrahydro-6-methoxy-3,3,8,8-tetramethyl-1-pyrazinylfuro[2,3-h]isoquinolin The title compound was obtained from pyrazinecarbonitrile by the method similar to that in EXAMPLE 368. Yield: 6%.

Melting point: 154–155° C. (ethyl acetate-hexane).

$^1$H NMR (CDCl$_3$) δ 1.30 (6H, s), 1.34 (6H, s), 2.17 (2H, s), 2.74 (2H, s), 3.92 (3H, s), 6.62 (1H, s), 8.57 (1H, dd, J=2.6, 1.6 Hz), 8.64 (1H, d, J=2.6 Hz), 8.87 (1H, d, J=1.6 Hz).

Example 377
3,4,8,9-Tetrahydro-6-methoxy-3,3,8,8-tetramethyl-1-(4-nitrophenyl)furo[2,3-h]isoquinoline The title compound was obtained from 4-nitrobenzonitrile by the method similar to that in EXAMPLE 368. Yield: 42%.

Melting point: 152–153° C. (ethyl acetate-hexane).

$^1$H NMR (CDCl$_3$) δ 1.26 (6H, s), 1.33 (6H, s), 2.19 (2H, s), 2.71 (2H, s), 3.93 (3H, s), 6.64 (1H, s), 7.60 (2H, ddd, J=8.6, 2.2, 1.8 Hz), 8.27 (2H, ddd, J=8.6, 2.2, 1.8 Hz).

Example 378
3,4,8,9-Tetrahydro-6-methoxy-3,3,8,8-tetramethyl-1-[4-(methylsulfinyl)phenyl]furo[2,3-h]isoquinoline The title compound was obtained from 4-(methylsulfinyl)benzonitrile by the method similar to that in. EXAMPLE 368. Yield: 26%.

Melting point: 120–121° C. (ethyl acetate-hexane).

$^1$H NMR (CDCl$_3$) δ 1.26 (6H, s), 1.32 (6H, s), 2.19 (2H, s), 2.70 (2H, s), 2.72 (3H, s), 3.93 (3H, s), 6.63 (1H, s), 7.58 (2H, d, J=8.4 Hz), 7.70 (2H, d, J=8.4 Hz).

Example 379
3,4,8,9-Tetrahydro-6-methoxy-3,3,8,8-tetramethyl-1-[4-(methylsulfonyl)phenyl]furo[2,3-h]isoquinoline.

The title compound was obtained from 4-(methylsulfonyl)benzonitrile by the method similar to that in EXAMPLE 368. Yield: 52%.

Melting point: 189–190° C. (ethyl acetate-hexane).

$^1$H NMR (CDCl$_3$) δ 1.26 (6H, s), 1.33 (6H, s), 2.18 (2H, s), 2.71 (2H, s), 3.04 (3H, s), 3.93 (3H, s), 6.63 (1H, s), 7.63 (2H, d, J=8.4 Hz), 7.99 (2H, d, J=8.4 Hz).

Example 380
1-(3-Furanyl)-3,4,8,9-tetrahydro-6-methoxy-3,3,8,8-tetramethylfuro[2.3-h]isoquinoline The title compound was-obtained from 3-furonitrile by the method similar to that in EXAMPLE 368. Yield: 31%.

Melting point: 130–131° C. (ethyl acetate-hexane).

$^1$H NMR (CDCl$_3$) δ 1.21 (6H, s), 1.40 (6H, s), 2.65 (4H, s), 3.92 (3H, s), 6.46 (1H, dd, J=1.8, 0.8 Hz), 6.59 (1H, s), 7.44 (1H, dd, J=1.8, 1.4 Hz), 7.59 (1H, dd, J=1.4, 0.8 Hz).

Example 381
3,4,8,9-Tetrahydro-6-methoxy-3,3,8,8-tetramethyl-1-(3,4,5-trimethoxyphenyl)furo[2,3-h]isoquinoline The title compound was obtained from 3,4,5-trimethoxybenzonitrile by the method similar to that in EXAMPLE 368. Yield: 45%.

Melting point: 186–188° C. (ethyl acetate-hexane).

$^1$H NMR (CDCl$_3$) δ 1.25 (6H, s), 1.34 (6H, s), 2.34 (2H, s), 2.69 (2H, s), 3.84 (3H, s), 3.86 (6H, s), 3.93 (3H, s), 6.61–6.62 (3H, m).

Example 382
1-[2,2'-Bipyridin]-6-yl-5-(3,4,8,9-tetrahydro-6-methoxy-3,3,8,8-tetramethylfuro[2,3-h]isoquinolin-1-yl)-2(1H)-pyridinone A solution of 1-[2,2'-bipyridin]-6-yl-1,6-dihydro-6-oxo-3-pyridinecarbonitrile (2.06 g, 7.51 mmol) in toluene (10 mL) was treated dropwise with conc. sulfuric acid (10 mL) with cooling in ice. A solution of 2,3-dihydro-7-methoxy-2,2-dimethyl-5-(2-methyl-1-propenyl)benzofuran (1.45 g, 6.26 mmol) in toluene (10 mL) was added dropwise and the mixture was stirred at 0° C. for 10 minutes. The reaction mixture was combined with ice, and the aqueous layer was neutralized with conc. aqueous ammonia and extracted twice with ethyl acetate. The combined organic layer was washed with water and brine, dried over sodium sulfate, filtered and concentrated under reduced pressure. The residue was subjected to a column chromatography on a silica gel (1% methanol/ethyl acetate followed by 5%), recrystallized from ethyl acetate-hexane to obtain the title compound (0.43 g, Yield: 17%).

Melting point: 231–234° C.

$^1$H NMR (CDCl$_3$) δ 1.22 (6H, s), 1.42 (6H, s), 2.66 (2H, s), 2.89 (2H, s), 3.94 (3H, s), 6.62 (1H, s), 6.76 (1H, dd, J=9.2, 0.6 Hz), 7.32 (1H, ddd, J=7.2, 4.8, 1.0 Hz), 7.62 (1H, dd, J=9.2, 2.6 Hz), 7.80 (1H, ddd, J=8.0, 7.2, 1.0 Hz), 7.91–8.02 (2H, m), 8.09 (1H, dd, J=2.6, 0.6 Hz), 8.28 (1H, dt, J=8.0, 1.0 Hz), 8.44 (1H, dd, J=6.6, 2.2 Hz), 8.68 (1H, ddd, J=4.8, 1.8, 1.0 Hz).

Example 383
1-(8-Methyl-2-quinolinyl)-5-(3,4,8,9-tetrahydro-6-methoxy-3,3,8,8-tetramethylfuro[2,3-h]isoquinolin-1-yl)-2(1H)-pyridinone The title compound was obtained from 1,6-dihydro-1-(8-methyl-2-quinolinyl)-6-oxo-3-pyridinecarbonitrile by the method similar to that in EXAMPLE 382. Yield: 29%.

Melting point: 182–183° C. (ethyl acetate-hexane).

$^1$H NMR (CDCl$_3$) δ 1.22 (6H, s), 1.45 (6H, s), 2.66 (2H, s), 2.74 (3H, s), 2.88 (2H, s), 3.93 (3H, s), 6.62 ($^1$H, s), 6.74 (1H, dd, J=9.2, 0.8 Hz), 7.47 (1H, dd, J=7.6, 7.0 Hz), 7.56–7.62 (2H, m), 7.71 (1H, d, J=7.6 Hz), 7.92 (1H, d, J=8.8 Hz), 8.14 (1H, dd, J=2.6, 0.8 Hz), 8.23 (1H, d, J=8.8 Hz).

Example 384
1-(4-Methyl-2-pyridinyl)-5-(3,4,8,9-tetrahydro-6-methoxy-3,3,8,8-tetramethylfuro[2,3-h]isoquinolin-1-yl)-2(1H)-pyridinone A solution of 1,6-dihydro-1-(4-methyl-2-pyridinyl)-6-oxo-3-pyridinecarbonitrile (3.22 g, 15.2 mmol) in toluene (10 mL) was treated dropwise with conc. sulfuric acid (10 mL) with cooling in ice. A solution of 2,3-dihydro-7-methoxy-2,2-dimethyl-5-(2-methyl-1-propenyl)benzofuran (2.72 g, 11.7 mmol) in toluene (10 mL) was added dropwise, and the mixture was stirred at room temperature for 30 minutes. The reaction mixture was combined with ice, and the aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a silica gel (1% methanol/ethyl acetate followed by 5%) and further to a column chromatography on a basic silica gel (hexane/ethyl acetate 1:1), recrystallized from ethyl acetate-hexane to obtain the title compound (1.00 g, Yield; 19%).

Melting point: 161–162° C.

$^1$H NMR (CDCl$_3$) δ 1.19 (6H, s), 1.45 (6H, s), 2.44 (3H, s), 2.64 (2H, s), 2.89 (2H, s), 3.92 (3H, s), 6.60 (1H, s), 6.68 (1H, d, J=9.6 Hz), 7.13 (1H, ddd, J=5.2, 1.6, 0.8 Hz), 7.55 (1H, dd, J=9.6, 2.6 Hz), 7.70 (1H, d, J=1.6 Hz), 8.00 (1H, d, J=2.6 Hz), 8.38 (1H, d, J=5.2 Hz).

Example 385
4-(3,4,8,9-Tetrahydro-6-methoxy-3,3,8,8-tetramethylfuro[2,3-h]isoquinolin-1-yl)pyridine 1-oxide A solution of 4-cyanopyridine 1-oxide (1.26 g, 10.0 mmol) in toluene (5 mL) was treated dropwise with conc. sulfuric acid (5 mL) with cooling in ice. A solution of 2,3-dihydro-7-methoxy-2,2-dimethyl-5-(2-methyl-1-propenyl)benzofuran (1.63 g, 7.00 mmol) in toluene (5 mL) was added dropwise, and the mixture was stirred at 0° C. for 30 minutes and then at 80° C. for 30 minutes. The reaction mixture was combined with ice, and the aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a basic silica gel (ethyl acetate) and recrystallized from ethyl acetate-hexane to obtain the title compound (1.33 g, Yield: 54%).

Melting point: 197–199° C.

$^1$H NMR (CDCl$_3$) δ 1.23 (6H, s), 1.39 (6H, s), 2.41 (2H, s), 2.68 (2H, s), 3.94 (3H, s), 6.64 (1H, s), 7.38 (2H, d, J=7.0 Hz), 8.25 (2H, d, J=7.0 Hz).

Example 386
4-Methyl-1-[4-(3,4,8,9-tetrahydro-6-methoxy-3,3,8,8-tetramethylfuro[2,3-h]isoquinolin-1-yl)-2-pyridinyl]-2(1H)-quinolinone 25% hydrogen bromide/acetic acid solution (4 mL) was added to a solution of 4-(3,4,8,9-tetrahydro-6-methoxy-3,3,8,8-tetramethylfuro[2,3-h]isoquinolin-1-yl)pyridine 1-oxide (3.52 g, 10.0 mmol) and 2-chloro-4-methylquinoline (3.55 g, 20.0 mmol) in xylene (30 mL) and acetic acid (6 mL) and the mixture was heated under reflux for 4 hours. The reaction mixture was combined with ice water, and the aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 2:1) and recrystallized from ethyl acetate to obtain the title compound (2.46 g, Yield: 50%).

Melting point: 218–219° C.

$^1$H NMR (CDCl$_3$) δ 1.26 (6H, s), 1.40 (6H, s), 2.51 (3H, d, J=1.0 Hz), 2.57 (2H, br s), 2.68 (2H, s), 3.91 (3H, s), 6.59 (1H, s), 6.61 (1H, d, J=1.0 Hz), 6.64 (1H, dd, J=8.4, 1.2 Hz), 7.17–7.25 (1H, m), 7.29–7.38 (2H, m), 7.61 (1H, dd, J=5.2, 1.6 Hz), 7.70 (1H, dd, J=8.0, 1.4 Hz), 8.82 (1H,dd, J=5.2, 0.8 Hz).

Example 387
1-[4-(3,4,8,9-Tetrahydro-6-methoxy-3,3,8,8-tetramethylfuro[2,3-h]isoquinolin-1-yl)-2-pyridinyl]-2(1H)-pyridinone 25% hydrogen bromide/acetic acid solution (6 mL) was added to a solution of 4-(3,4,8,9-tetrahydro-6-methoxy-3,3,8,8-tetramethylfuro[2,3-h]isoquinolin-1-yl)pyridine 1-oxide (5.00 g, 14.2 mmol) and 2-chloropyridine (16.1 g, 142 mmol) in xylene (45 mL) and acetic acid (9 mL) and the mixture was heated under reflux for 8 hours. The reaction mixture was combined with ice water, and the aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a silica gel (ethyl acetate) followed by a column chromatography on a basic silica gel (hexane/ethyl acetate 1:1), and recrystallized from ethyl acetate to obtain the title compound (1.55 g, Yield: 25%).

Melting point: 223–224° C.

$^1$H NMR (CDCl$_3$) δ 1.25 (6H, s), 1.38 (6H, s), 2.54 (2H, br s), 2.69 (2H, s), 3.92 (3H, s), 6.24–6.32 (1H, m), 6.61 (1H, s), 6.61 (1H, ddd, J=9.2, 1.4, 0.8 Hz), 7.34–7.43 (2H, m), 7.78 (1H, ddd, J=6.8, 2.2, 0.8 Hz), 7.93 (1H, dd, J=1.4, 0.6 Hz), 8.61 (1H, dd, J=5.0, 0.6 Hz).

Example 388
4-(3,4,8,9-Tetrahydro-6-methoxy-3–3,8,8-tetramethylfuro[2,3-h]isoquinolin-1-yl)-2(1H)-pyridinone A solution of 4-(3,4,8,9-tetrahydro-6-methoxy-3,3,8,8-tetramethylfuro[2,3-h]isoquinolin-1-yl)pyridine 1-oxide (0.90 g. 2.55 mmol) in acetic anhydride (5 mL) was heated under reflux for 20 hours. The reaction mixture was dissolved in methanol (100 mL), conc. aqueous ammonia (20 mL) was added thereto and the mixture was stirred at room temperature for 30 minutes. The reaction solvent was concentrated and distilled off under reduced pressure, and the residue was combined with water. The organic material was extracted with chloroform, and the extract was washed with brine, dried over sodium sulfate, filtered and concentrated under reduced pressure. The residue was subjected to a column chromatography on a basic silica gel (chloroform followed by 2% methanol/chloroform), and recrystallized from ethyl acetate-hexane to obtain the title compound (0.52 g, Yield: 58%).

Melting point: 232–233° C.

$^1$H NMR (CDCl$_3$) δ 1.24 (6H, s), 1.40 (6H, s), 2.63 (2H, s), 2.69 (2H, s), 3.92 (3H, s), 6.35 (1H, dd, J=6.6, 1.4 Hz), 6.60 (1H, d, J=1.4 Hz), 6.61 (1H, s), 7.43 (1H, d, J=6.6 Hz), 11.42 (1H, br s).

Example 389
1-(4-Pyridinylmethyl)-4-(3,4,8,9-tetrahydro-6-methoxy-3,3,8,8-tetramethylfuro[2,3-h]isoquinolin-1-yl)-2(1H)-pyridinone Sodium hydride (60% dispersion in oil) (0.360 g, 9.00 mmol) was added to a suspension of 4-(3,4,8,9-tetrahydro-6-methoxy-3,3,8,8-tetramethylfuro[2,3-h]isoquinolin-1-yl)-2(1H)-pyridinone (1.06 g, 3.00 mmol) in N,N-dimethylformamide (15 mL) with cooling in ice and the mixture was stirred at room temperature for 30 minutes. 4-(Chloromethyl)pyridine hydrochloride (0.738 g, 4.50 mmol) was added to the mixture and the mixture was stirred at room temperature further for 1 hour. The reaction solvent was concentrated and distilled off under reduced pressure and the residue was combined with water. The organic material was extracted with ethyl acetate, washed with brine, dried over sodium sulfate, filtered and concentrated under reduced pressure. The residue was subjected to a column chromatography on a basic silica gel (hexane/ethyl acetate 1:1 followed by ethyl acetate), and recrystallized from ethyl acetate-hexane to obtain the title compound (0.41 g, Yield: 31%).

Melting point: 171–172° C.

$^1$H NMR (CDCl$_3$) δ 1.24 (6H, s), 1.40 (6H, s), 2.65 (2H, s), 2.67 (2H, s), 3.92 (3H, s), 5.18 (2H, br s), 6.28(1H, dd, J=7.0, 1.8 Hz), 6.61 (1H, s), 6.65 (1H, d, J=1.8 Hz), 7.18 (2H, d, J=6.0 Hz), 7.32 (1H, d, J=7.0 Hz), 8.58 (2H, d, J=6.0 Hz).

Example 390
1-(2-Methoxyethyl)-4-(3,4,8,9-tetrahydro-6-methoxy-3,3,8,8-tetramethylfuro[2,3-h]isoquinolin-1-yl)-2(1H)-pyridinone The title compound was obtained from 2bromoethyl methyl ether by the method similar to that in EXAMPLE 389. Yield: 38%.

Melting point: 85–87° C. (hexane-ethyl acetate).

$^1$H NMR (CDCl$_3$) δ 1.23 (6H, s), 1.39 (6H, s), 2.63 (2H, s), 2.67 (2H, s), 3.31 (3H, s), 3.66 (2H, t, J=5.0 Hz), 3.92 (3H, s), 4.15 (2H, br s), 6.18 (1H, dd, J=7.0, 1.8 Hz), 6.58 (1H, d, J=1.8 Hz), 6.60 (1H, s), 7.39 (1H, d, J=7.0 Hz).

Example 391
1-(2-Pyridinylmethyl)-4-(3,4,8,9-tetrahydro-6-methoxy-3,3,8,8-tetramethylfuro[2,3-h]isoquinolin-1-yl)-2(1H)-pyridinone The title compound was obtained from 2-(chloromethyl)pyridine hydrochloride by the method similar to that in EXAMPLE 389. Yield: 57%.

Melting point: 165–166° C. (ethyl acetate-hexane).

$^1$H NMR (CDCl$_3$) δ 1.22 (6H, s), 1.38 (6H, s), 2.63 (2H, s), 2.66 (2H, s), 3.91 (3H, s), 5.26 (2H, br s), 6.23 (1H, dd, J=7.0, 1.8 Hz), 6.58 (1H, d, J=1.8 Hz), 6.59 (1H, s), 7.18–7.25 (1H, m), 7.42 (1H, d, J=7.6 Hz), 7.58 (1H, d, J=7.0 Hz), 7.66 (1H, td, J=7.6, 1.8 Hz), 8.53 (1H, d, J=4.8 Hz).

Example 392
2-Oxo-4-(3,4,8,9-tetrahydro-6-methoxy-3,3,8,8-tetramethylfuro[2,3-h]isoquinolin-1-yl)-1(2H)-pyridineacetamide The title compound was obtained as a main product from 2-chloroacetamide by the method similar to that in EXAMPLE 389. Yield: 56%.

Melting point: 251–252° C. (ethyl acetate-methanol).

$^1$H NMR (CDCl$_3$) δ 1.13 (6H, s), 1.29 (6H, s), 2.61 (4H, s), 3.81 (3H, s), 4.55 (2H, s), 6.14 (1H, dd, J=7.0, 1.8 Hz), 6.22 (1H, d, J=1.8 Hz), 6.80 (1H, s), 7.20 (1H, br s), 7.61 (1H, d, J=7.0 Hz), 7.65 (1H, br s).

Example 393
N-(2-Amino-2-oxoethyl)-2-oxo-4-(3,4,8,9-tetrahydro-6-methoxy-3,3,8,8-tetramethylfuro[2,3-h]isoquinolin-1-yl)-1(2H)-pyridineacetamide Similarly to EXAMPLE 392, the title compound was obtained as a by-product. Yield: 10%.

Melting point: 166–168° C. (ethyl acetate).

$^1$H NMR (CDCl$_3$) δ 1.13 (6H, s), 1.29 (6H, s), 2.61 (4H, s), 3.68 (2H, d, J=5.6 Hz), 3.81 (3H, s), 4.63 (2H, s), 6.19 (1H, dd, J=6.8, 1.8 Hz), 6.25 (1H, d, J=1.8 Hz), 6.80 (1H, s), 7.14 (1H, br s), 7.30 (1H, br s), 7.66 (1H, d, J=6.8 Hz), 8.47 (1H, t, J=5.6 Hz).

Example 394
1-(3-Pyridinylmethyl)-4-(3,4,8,9-tetrahydro-6-methoxy-3,3,8,8-tetramethylfuro[2,3-h]isoquinolin-1-yl)-2(1H)-pyridinone The title compound was obtained from 3-(chloromethyl)pyridine hydrochloride by the method similar to that In EXAMPLE 389. Yield: 56%.

Melting point: 126–128° C. (ethyl acetate-hexane).

$^1$H NMR (CDCl$_3$) δ 1.22 (6H, s), 1.39 (6H, s), 2.63 (2H, s), 2.66 (2H, s), 3.92 (3H, s), 5.19 (2H, br s), 6.25 (1H, dd, J=6.8, 1.8 Hz), 6.60 (1H, s), 6.62 (1H, d, J=1.8 Hz), 7.28 (1H, dd, J=8.0, 4.8 Hz), 7.35 (1H, d, J=6.8 Hz), 7.72 (1H, d, J=8.0 Hz), 8.57 (1H, dd, J=4.8, 1.6 Hz), 8.61 (1H, d, J=1.6 Hz).

Example 395
1-Methyl-4-(3,4,8,9-tetrahydro-6-methoxy-3,3,8,8-tetramethylfuro[2,3-h]isoquinolin-1-yl)-2(1H)-pyridinone The title compound was obtained from iodomethane by the method similar to that in EXAMPLE 389. Yield: 62%.

Melting point: 180–181° C.

$^1$H NMR (CDCl$_3$) δ 1.22 (6H, s), 1.40 (6H, s), 2.64 (2H, s), 2.66 (2H, s), 3.58 (3H, s), 3.92 (3H, s), 6.23 (1H, dd, J=7.0, 1.8 Hz), 6.58 (1H, d, J=1.8 Hz), 6.60 (1H, s), 7.33 (1H, d, J=7.0 Hz).

Example 396
1-(2-Quinolinylmethyl)-4-(3,4,8,9-tetrahydro-6-methoxy-3,3,8,8-tetramethylfuro[2,3-h]isoquinolin-1-yl)-2(1H)-pyridinone The title compound was obtained from 2-(chloromethyl)quinoline hydrochloride by the method similar to that in EXAMPLE 389. Yield: 55%.

Melting point: 189–190° C. (ethyl acetate-hexane).

$^1$H NMR (CDCl$_3$) δ 1.22 (6H, s), 1.37 (6H, s), 2.65 (4H, s), 3.91 (3H, s), 5.47 (2H, br s), 6.24 (1H, dd, J=6.8, 1.8 Hz), 6.59 (1H, s), 6.63 (1H, d, J=1.8 Hz), 7.51 (1H, d, J=8.4 Hz), 7.49–7.59 (1H, m), 7.60 (1H, d, J=6.8 Hz), 7.68–7.77 (1H, m), 7.82 (1H, d, J=8.4 Hz), 8.03 (1H, d, J=8.4 Hz), 8.14 (1H, d, J=8.4 Hz).

Example 397
2-[2-[2-Oxo-4-(3,4,8, 9-tetrahydro-6-methoxy-3,3,8,8-tetramethylfuro[2,3-h]isoquinolin-1-yl)-1(2H)-pyridinyl]ethyl]-1H-isoindole-1,3(2H)-dione The title compound was obtained from N-(2-bromoethyl)phthalimide by the method similar to that in EXAMPLE 389. Yield: 14%.

Melting point: 226–228° C. (ethyl acetate-methanol).
$^1$H NMR (CDCl$_3$) δ 1.19 (6H, s), 1.50 (6H, s), 2.65 (2H, s), 2.71 (2H, s), 3.92 (3H, s), 4.13 (2H, br s), 4.26 (2H, br s), 6.15 (1H, dd, J=7.0, 1.8 Hz), 6.51 (1H, d, J=1.8 Hz), 6.58 (1H, s), 7.14 (1H, d, J=7.0 Hz), 7.72–7.84 (4H, m).

Example 398

1-[2-(Dimethylamino)ethyl]-4-(3,4,8,9-tetrahydro-6-methoxy-3,3,8,8-tetramethylfuro[2,3-h]isoquinolin-1-yl)-2(1H)-pyridinone The title compound was obtained from 2-(dimethylamino)ethyl chloride hydrochloride by the method similar to that in EXAMPLE 389. Yield: 9%.

Melting point: 111–113° C. (ethyl acetate-hexane).
$^1$H NMR (CDCl$_3$) δ 1.23 (6H, s), 1.38 (6H, s), 2.28 (6H, s), 2.62 (2H, t, J=6.6 Hz), 2.63 (2H, s), 2.67 (2H, s), 3.92 (3H, s), 4.05 (2H, t, J=6.6 Hz), 6.19 (1H, dd, J=7.0, 1.8 Hz), 6.56 (1H, d, J=1.8 Hz), 6.60 (1H, s), 7.35 (1H, d, J=7.0 Hz).

Example 399

1-(Phenylmethyl)-4-(3,4,8,9-tetrahydro-6-methoxy-3,3,8,8-tetramethylfuro[2,3-h]isoquinolin-1-yl)-2(1H)-pyridinone The title compound was obtained from benzyl bromide by the method similar to that in EXAMPLE 389. Yield: 68%.

Melting point: 170–172° C. (ethyl acetate-hexane).
$^1$H NMR (CDCl$_3$) δ 1.22 (6H, s), 1.38 (6H, s), 2.63 (2H, s), 2.66 (2H, s), 3.91 (3H, s), 5.18 (2H, br s), 6.19 (1H, dd, J=7.0, 1.8 Hz), 6.59 (1H, s), 6.62 (1H, d, J=1.8 Hz), 7.30–7.33 (6H, m).

Example 400

4-[[2-Oxo-4-(3,4,8,9-tetrahydro-6-methoxy-3,3,8,8-tetramethylfuro[2,3-h]isoquinolin-1-yl)-1(2H)-pyridinyl]methyl]benzoic Acid Methyl Ester The title compound was obtained from 4-(bromomethyl)benzoic acid methyl ester by the method similar to that in EXAMPLE 389. Yield: 73%.

Melting point: 193–194° C. (ethyl acetate-hexane).
$^1$H NMR (CDCl$_3$) δ 1.23 (6H, s), 1.39 (6H, s), 2.64 (2H, s), 2.67 (2H, s), 3.92 (6H, s), 5.23 (2H, br s), 6.24 (1H, dd, J=7.0, 1.8 Hz), 6.60 (1H, s), 6.63 (1H, d, J=1.8 Hz), 7.32 (1H, d, J=7.0 Hz), 7.36 (2H, d, J=8.4 Hz), 8.01 (2H, d, J=8.4 Hz).

Example 401

N-(2-Hydroxyethyl)-4-[[2-oxo-4-(3,4,8,9-tetrahydro-6-methoxy-3,3,8,8-tetramethylfuro[2,3-h]isoquinolin-1-yl)-1(2H)-pyridinyl]methyl]benzamide A solution of 4-[[2-oxo-4-(3,4,8,9-tetrahydro-6-methoxy-3,3,8,8-tetramethylfuro[2,3-h]isoquinolin-1-yl)-1(2H)-pyridinyl]methyl]benzoic acid methyl ester (1.32 g, 2.64 mmol) and 2-aminoethanol (2 mL, 33.1 mol) in xylene (10 mL) was heated under reflux for 7 hours. The reaction mixture was combined with ice water and extracted twice with chloroform. The combined organic layer was washed with water and brine, dried over sodium sulfate, filtered and concentrated under reduced pressure. The residue was subjected to a column chromatography on a basic silica gel (ethyl acetate/methanol 19:1 followed by 9:1), and recrystallized from ethyl acetate-methanol to obtain the title compound (0.81 g, Yield: 58%).

Melting point: 220–222° C.
$^1$H NMR (CDCl$_3$) δ 1.22 (6H, s), 1.40 (6H, s), 2.64 (2H, s), 2.66 (2H, s), 3.48–3.59 (3H, m), 3.76 (2H, t, J=5.0 Hz), 3.92 (3H, 8), 5.18 (2H, br s), 6.26 (1H, dd, J=7.0, 1.8 Hz), 6.60 (1H, s), 6.63 (1H, d, J=1.8 Hz), 7.07 (1H, br t, J=5.5 Hz), 7.30 (2H, d, J=8.4 Hz), 7.35 (1H, d, J=7.0 Hz), 7.74 (2H, d, J=8.4 Hz).

Example 402

4-[[2-Oxo-4-(3,4,8,9-tetrahydro-6-methoxy-3,3,8,8-tetramethylfuro[2,3-h]isoquinolin-1-yl)-1(2H)-pyridinyl]methyl]-N-(4-pyridinyl)benzamide 4-[[2-Oxo-4-(3,4,8,9-tetrahydro-6-methoxy-3,3,8,8-tetramethylfuro[2,3-h]isoquinolin-1-yl)-1(2H)-pyridinyl]methyl]benzoic acid methyl ester (2.78 g, 5.55 mol) was dissolved in 1 M aqueous solution of sodium hydroxide (30 mL) and the mixture was heated under reflux for 30 minutes. The reaction mixture was cooled to room temperature, and 2 M hydrochloric acid (30 mL) was added thereto. The solvent was concentrated and distilled off under reduced pressure, and diluted with ethanol. The resultant insolubles were filtered off, and ethanol was concentrated and distilled off under the reduced pressure. This procedure was repeated twice to obtain 4-[[2-oxo-4-(3,4,8,9-tetrahydro-6-methoxy-3,3,8,8-tetramethylfuro[2,3-h]isoquinolin-1-yl)-1(2H)-pyridinyl]methyl]benzoic acid hydrochloride (2.90 g, quantitative). 1-Ethyl-3-(3-dimethylaminopropyl)carbodiimide hydrochloride (0.483 g, 2.52 mmol) was added to a solution of the resultant 4-[[2-oxo-4-(3,4,8,9-tetrahydro-6-methoxy-3,3,8,8-tetramethylfuro[2,3-h]isoquinolin-1-yl)-1(2H)-pyridinyl]methyl]benzoic acid hydrochloride (1.20 g, 2.29 mmol), 4-aminopyridine (0.259 g, 2.75 mmol) and 1-hydroxy-1H-benzotriazole monohydrate (0.701 g, 4.58 mmol) in N,N-dimethylformamide (10 mL) with cooling in ice, and stirred at the same temperature for 1 hour and then at room temperature for 30 hours. The reaction solvent was concentrated and distilled off under reduced pressure, and to the residue an aqueous solution of sodium hydroxide was poured. The organic material was extracted with ethylacetate, and the extract was washed with brine, dried over sodium sulfate, filtered and concentrated under reduced pressure. The residue was subjected to a column chromatography on a basic silica gel (1% methanol/ethyl acetate followed by 2%) and recrystallized from ethyl acetate-hexane to obtain the title compound (0.15 g, Yield: 12%).

Melting point: 144–146° C.
$^1$H NMR (CDCl$_3$) δ 1.23 (6H, s), 1.39 (6H, s), 2.63 (2H, s), 2.67 (2H, s), 3.92 (3H, s), 5.20 (2H, br s), 6.29 (1H, dd, J=6.8, 1.8 Hz), 6.61 (2H, s), 7.32 (2H, d, J=8.4 Hz), 7.38 (1H, d, J=6.8 Hz), 7.70 (2H, dd, J=4.8, 1.8 Hz), 7.84 (2H, d, J=8.4 Hz), 8.51 (2H, dd, J=4.8, 1.8 Hz), 9.06 (1H, br s).

Example 403

2-Oxo-4-(3,4,8,9-tetrahydro-6-methoxy-3,3,8,8-tetramethylfuro[2,3-h]isoquinolin-1-yl)-1(2H)-pyridineacetic acid 1,1-dimethylethyl Ester The title compound was obtained from tert-butyl bromoacetate by the method similar to that in EXAMPLE 389. Yield: 80%.

Melting point: 166–168° C. (diethyl ether-hexane).
$^1$H NMR (CDCl$_3$) δ 1.23 (6H, s), 1.40 (6H, s), 1.49 (9H, s), 2.67 (2H, s), 2.68 (2H, s), 3.92 (3H, s), 4.57 (2H, s), 6.25 (1H, dd, J=7.0, 1.8 Hz), 6.59 (1H, d, J=1.8 Hz), 6.59 (1H, s), 7.25 (1H, d, J=7.0 Hz).

Example 404

2-Oxo-4-(3,4,8,9-tetrahydro-6-methoxy-3,3,8,8-tetramethylfuro[2,3-h]isoquinolin-1-yl)-1(2H)-pyridineacetic Acid Hydrochloride 2-Oxo-4-(3,4,8,9-tetrahydro-6-methoxy-3,3,8,8-tetramethylfuro[2,3-h]isoquinolin-1-yl)-1(2H)-pyridineacetic acid 1,1-dimethylethyl ester (10.1 g, 21.6 mmol) was dissolved in 6 M hydrochloric acid (25 mL) and the mixture was heated under reflux for 1 hour. The reaction solution was cooled to room temperature, and the reaction solvent was concentrated and distilled off under reduced pressure to obtain the title compound (9.60 g, 99%).

Amorphous.
$^1$H NMR (CDCl$_3$) δ 1.41 (6H, s), 1.53 (6H, s), 2.68 (2H, s), 2.98 (2H, s), 3.98 (3H, s), 4.71 (2H, br s), 6.24 (1H, br s), 6.35 (1H, d, J=7.0 Hz), 6.70 (2H, s), 7.72 (1H, d, J=7.0 Hz).

Example 405

2-Oxo-N-(3-pyridinyl)-4-(3,4,8,9-tetrahydro-6-methoxy-3,3,8,8-tetramethylfuro[2,3-h]isoquinolin-1-yl)-1(2H)-pyridineacetamide 1-Ethyl-3-(3-dimethylaminopropyl)carbodiimide hydrochloride (0.566 g, 2.95 mmol) was added to a solution of 2-oxo-4-(3,4,8,9-tetrahydro-6-methoxy-3,3,8,8-tetramethylfuro[2,3-h]isoquinolin-1-yl)-1(2H)-pyridineacetic acid hydrochloride (1.20 g, 2.68 mmol), 3-aminopyridine (0.303 g, 3.22 mmol) and 1-hydroxy-1H-benzotriazole monohydrate (0.821 g, 5.36 mmol) in N,N-dimethylformamide (10 mL) with cooling in ice, and the mixture was stirred at the same temperature for 1 hour and then at room temperature for 3 hours. The reaction solvent was concentrated and distilled off under reduced pressure, and to the residue an aqueous solution of sodium hydroxide was poured. The organic material was extracted with ethyl acetate, and the extract was washed with brine, dried over sodium sulfate, filtered and concentrated under reduced pressure. The residue was subjected to a column chromatography on a basic silica gel (5% methanol/ethyl acetate) and recrystallized from ethyl acetate-methanol to obtain the title compound (0.51 g, Yield: 39%).

Melting point: 251–253° C.

$^1$H NMR (CDCl$_3$) δ 1.23 (6H, s), 1.40 (6H, s), 2.63 (2H, s), 2.68 (2H, s), 3.93 (3H, s), 4.80 (2H, br s), 6.42 (1H, dd, J=7.0, 1.8 Hz), 6.62 (1H, s), 6.75 (1H, d, J=1.8 Hz), 7.20 (1H, dd, J=8.4, 4.6 Hz), 7.52 (1H, d, J=7.0 Hz), 7.94 (1H, ddd, J=8.4, 1.8, 1.4 Hz), 8.31 (1H, dd, J=4.6, 1.4 Hz), 8.64 (1H, d, J=1.8 Hz), 9.82 (1H, br s).

Example 406

2-Oxo-N-(5-quinolinyl)-4-(3,4,8,9-tetrahydro-6-methoxy-3,3,8,8-tetramethylfuro[2,3-h]isoquinolin-1-yl)-1(2H)-pyridineacetamide The title compound was obtained from 5-aminoquinoline by the method similar to that in EXAMPLE 405. Yield: 10%.

Melting point: 136–138° C. (ethyl acetate-hexane).

$^1$H NMR (CDCl$_3$) δ 1.22 (6H, s), 1.31 (6H, s), 2.59 (2H, s), 2.66 (2H, s), 3.92 (3H, s), 4.89 (2H, br s), 6.48 (1H, dd, J=6.8, 1.8 Hz), 6.61 (1H, s), 6.80 (1H, d, J=1.8 Hz), 7.47 (1H, dd, J=8.8, 4.0 Hz), 7.58 (1H, d, J=6.8 Hz), 7.70 (1H, t, J=8.4 Hz), 7.93 (1H, d, J=8.4 Hz), 8.21 (1H, d, J=8.8 Hz), 8.47 (1H, d, J=8.4 Hz), 8.93 (1H, dd, J=4.0, 1.2 Hz), 10.21 (1H, br s).

Example 407

1-(2-Quinolinyl)-5-(3,4,8,9-tetrahydro-6-methoxy-3,3,8,8-tetramethylfuro[2,3-h]isoquinolin-1-yl)-2(1H)-pyridinone 25% Hydrogen bromide/acetic acid solution (1 mL) was added to a solution of 1-(6-chloro-3-pyridinyl)-3,4,8,9-tetrahydro-6-methoxy-3,3,8,8-tetramethylfuro[2,3-h]isoquinoline (0.78 g, 2.10 mmol) and quinoline 1-oxide monohydrate (3.05 g, 21.0 mmol) in toluene (5 mL) and acetic acid (5 mL) and the mixture was heated under reflux for 20 hours. The reaction mixture was combined with ice water, and the aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 2:1) and recrystallized from ethyl acetate to obtain the title compound (0.41 g, Yield: 41%).

Melting point: 191–192° C.

$^1$H NMR (CDCl$_3$) δ 1.21 (6H, s), 1.52 (6H, s), 2.65 (2H, s), 2.98 (2H, s), 3.94 (3H, s), 6.62 (1H, s), 6.74 (1H, d, J=9.2 Hz), 7.55–7.63 (1H, m), 7.64 (1H, dd, J=9.2, 2.6 Hz), 7.69–7.77 (1H, m), 7.88 (1H, dd, J=8.0, 1.4 Hz), 7.92 (1H, d, J=8.8 Hz), 8.04 (1H, dd, J=8.0, 1.4 Hz), 8.12 (1H, d, J=2.2 Hz), 8.26 (1H, d, J=8.8 Hz).

Example 408

1-(1-Isoquinolinyl)-5-(3,4,8,9-tetrahydro-6-methoxy-3,3,8,8-tetramethylfuro[2,3-h]isoquinolin-1-yl)-2(1H)-pyridinone The title compound was obtained from isoquinoline 2-oxide by the method similar to that in EXAMPLE 407. Yield: 40%.

Melting point: 147–149° C. (ethyl acetate-hexane).

$^1$H NMR (CDCl$_3$) δ 1.16 (3H, s), 1.23 (3H, s), 1.41 (3H, s), 1.55 (3H, s), 2.63 (2H, s), 2.75 (1H, d, J=16.0 Hz), 3.22 (1H, d, J=16.0 Hz), 3.90 (3H, s), 6.58 (1H, s), 6.78 (1H, d, J=9.6 Hz), 7.62–7.80 (6H, m), 7.92 (1H, d, J=8.4 Hz), 8.46 (1H, d, J=5.8 Hz).

Example 409

1-[4-(3,4,8,9-Tetrahydro-6-methoxy-3,3,8,8-tetramethylfuro[2,3-h]isoquinolin-1-yl)-2-pyridinyl]-2(1H)-quinolinone A solution of 4-(3,4,8,9-tetrahydro-6-methoxy-3,3,8,8-tetramethylfuro[2,3-h]isoquinolin-1-yl)pyridine 1-oxide (0.95 g, 2.7 mmol), 2-chloroquinoline (1.8 g, 11 mmol), 25% hydrogen bromide/acetic acid solution (0.7 mL) and acetic acid (6.0 mL) in toluene (8.8 mL) was heated under reflux for 1 hour. The reaction solution was cooled to room temperature, and the reaction mixture was poured into water. After the mixture was made weakly alkaline with conc. aqueous ammonia, the organic material was extracted with ethyl acetate. The extract was washed with brine and dried over sodium sulfate, and then the solvent was distilled off under reduced pressure. The resultant residue was purified by a column chromatography on a basic silica gel (ethyl acetate/hexane 2:1 followed by 1:1) to obtain crude crystals. The resultant crude crystals were recrystallized from ethyl acetate-hexane to obtain the title compound (0.72 g, Yield: 56%).

Melting point: 190–191° C.

$^1$H NMR (DMSO-d$_6$) δ 1.18 (6H, s), 1.24 (6H, s), 2.51 (2H, s), 2.67 (2H, s), 3.80 (3H, s), 6.48 (1H, d, J=8.8 Hz), 6.68 (1H, d, J=9.6 Hz), 6.80 (1H, s), 7.26 (1H, t, J=7.2 Hz), 7.40–7.48 (2H, m), 7.64 (1H, dd, J=4.9, 1.6 Hz), 7.79 (1H, d, J=7.6 Hz), 8.05 (1H, d, J=9.6 Hz), 8.80 (1H, d, J=4.9 Hz).

Example 410

1,6-Dihydro-6-oxo-1-[4-(3,4,8,9-tetrahydro-6-methoxy-3,3,8,8-tetramethylfuro[2,3-h]isoquinolin-1-yl)-2-pyridinyl]-3-pyridinecarboxamide The title compound was obtained from 6-chloronicotinamide by the method similar to that in EXAMPLE 409. Yield: 31%.

Amorphous.

$^1$H NMR (CDCl$_3$) δ 1.26 (6H, s), 1.38 (6H, s), 2.05 (2H, s), 2.69 (2H, s), 3.93 (3H, s), 6.12 (2H, br), 6.59 (1H, d, J=9.6 Hz), 6.62 (1H, s), 7.42 (1H, d, J=5.0 Hz), 7.78 (1H, dd, J=9.6, 2.6 Hz), 7.90 (1H, s), 8.49 (1H, d, J=2.6 Hz), 8.59 (1H, d, J=5.0 Hz).

Example 411

1-(2-Chloro-4-pyridinyl)-3,4,8,9-tetrahydro-6-methoxy-3,3,8,8-tetramethylfuro[2,3-h]isoquinoline A solution of 4-(3,4,8,9-tetrahydro-6-methoxy-3,3,8,8-tetramethylfuro[2,3-h]isoquinolin-1-yl)pyridine 1-oxide (2.4 g, 6.8 mmol) in phosphorus oxychloride (20 mL, 210 mmol) was heated under reflux for 30 minutes. The reaction solution was cooled to room temperature, and then poured into ice water. After the mixture was made alkaline with an aqueous solution of sodium hydroxide, the organic material was extracted with ethyl acetate. The extract was washed with brine and dried over sodium sulfate, and then the solvent was distilled off under reduced pressure. The resultant residue was purified by a column chromatography on a basic silica gel (hexane/ethyl acetate 5:1 followed by 3:1) to obtain crude crystals. The crude crystals were recrystallized from ethyl acetate-hexane to obtain, as a main product, the title compound (0.84 g, Yield: 33%).

Melting point: 139–140° C.
$^1$H NMR (CDCl$_3$) δ 1.26 (6H, s), 1.37 (6H, s), 2.30 (2H, s), 2.70 (2H, s), 3.93 (3H, s), 6.64 (1H, s), 7.27 (1H, dd, J=5.2, 0.8 Hz), 7.43 (1H, d, J=0.8 Hz), 8.44 (1H, d, J=5.2 Hz).

Example 412
1-(3-Chloro-4-pyridinyl)-3,4,8,9-tetrahydro-6-methoxy-3,3,8,8-tetramethylfuro[2,3-h]isoquinoline Similarly to EXAMPLE 411, the title compound was obtained as a by-product. Yield: 8%.

Melting point: 126–128° C. (hexane).
$^1$H NMR (CDCl$_3$) δ 1.23 (3H, s), 1.30 (3H, s), 1.35 (3H, s), 1.38 (3H, s), 2.05 (2H, s), 2.69 (1H, d, J=15.7 Hz), 2.80 (1H, d, J=15.7 Hz), 3.92 (3H, s), 6.62 (1H, s), 7.31 (1H, d, J=4.8 Hz), 8.58 (1H, d, J=4.8 Hz), 8.63 (1H, s).

Example 413
2-[2-Oxo-4-(3,4,8,9-tetrahydro-6-methoxy-3,3,8,8-tetramethylfuro[2,3-h]isoquinolin-1-yl)-1(2H)-pyridinyl]-4-pyridinecarboxamide A solution of 1-(2-chloro-4-pyridinyl)-3,4,8,9-tetrahydro-6-methoxy-3,3,8,8-tetramethylfuro[2,3-h]isoquinoline (1.0 g, 2.7 mmol), 4-pyridinecarboxamide 1-oxide (2.9 g, 21 mmol), 25% hydrogen bromide/acetic acid solution (1.0 mL) and acetic acid (5.6 mL) in xylene (10 mL) was heated under reflux for 9 hours. The reaction solution was cooled to room temperature, and the reaction mixture was poured into water. After the mixture was made weakly alkaline with 8 M aqueous solution of sodium hydroxide, the organic material was extracted with ethyl acetate. The extract was washed with brine and dried over sodium sulfate, and then the solvent was distilled off under reduced pressure. The resultant residue was purified by a column chromatography on a basic silica gel (chloroform/methanol 50:1 followed by 20:1) to obtain crude crystals. The resultant crude crystals were recrystallized from ethyl acetate-diisopropyl ether to obtain the title compound (0.22 g, Yield: 17%).

Melting point: 174–175° C.
$^1$H NMR (CDCl$_3$) δ 1.26 (6H, s), 1.43 (6H, s), 2.69 (2H, s), 2.76 (2H, s), 3.93 (3H, s), 6.12 (1H, br), 6.43 (1H, d, J=7.3 Hz), 6.63 (1H, s), 6.68 (1H, s), 7.16–7.39 (1H, br), 7.78 (1H, d, J=4.4 Hz), 8.01 (1H, d, J=7.3 Hz), 8.33 (1H, s), 8.67 (1H, d, J=4.4 Hz).

Example 414
1-(2-Pyridinyl)-4-(3,4,8,9-tetrahydro-6-methoxy-3,3,8,8-tetramethylfuro[2,3-h]isoquinolin-1-yl)-2(1H)-pyridinone The title compound was obtained from pyridine 1-oxide by the method similar to that in EXAMPLE 413. Yield: 56%.

Amorphous.
$^1$H NMR (CDCl$_3$) δ 1.25 (6H, s), 1.42 (6H, s), 2.69 (2H, s), 2.78 (2H, s), 3.93 (3H, s), 6.39 (1H, dd, J=7.1, 1.8 Hz), 6.62–6.67 (2H, m), 7.30–7.37 (1H, m), 7.80–7.89 (1H, m), 7.96–8.00 (2H, m), 8.57–8.60 (1H, m).

Example 415
1-(2-Quinolinyl)-4-(3,4,8,9-tetrahydro-6-methoxy-3,3,8,8-tetramethylfuro[2,3-h]isoquinolin-1-yl)-2(1H)-pyridinone The title compound was obtained from quinoline 1-oxide by the method similar to that in EXAMPLE 413. Yield: 24%.

Melting point: 175–176° C. (ethyl acetate-hexane).
$^1$H NMR (CDCl$_3$) δ 1.26 (6H, s), 1.44 (6H, s), 2.70 (2H, s), 2.82 (2H, s), 3.94 (3H, s), 6.45 (1H, dd, J=7.4, 1.8 Hz), 6.63 (1H, s), 6.70 (1H, d, J=1.4 Hz), 7.61 (1H, td, J=7.6, 1.2 Hz), 7.77 (1H, td, J=8.4, 1.4 Hz), 7.90 (1H, d, J=8.4 Hz), 7.99–8.16 (3H, m), 8.27 (1H, d, J=8.8 Hz).

Example 416
3,4,8,9-Tetrahydro-6-methoxy-1-(4-methoxyphenyl)-3,3-dimethylfuro[2,3-h]isoquinoline The title compound was obtained from 4-aminonitrile and 2,3-dihydro-7-methoxy-5-(2-methyl-1-propenyl)benzofuran by the method similar to that in EXAMPLE 1. Yield: 49%.

Melting point: 147–148° C. (ethyl acetate-hexane).
$^1$H NMR (CDCl$_3$) δ 1.23 (6H, s), 2.46 (2H, t, J=8.8 Hz), 2.68 (2H, s), 3.87 (3H, s), 3.93 (3H, s), 4.37 (2H, t, J=8.8 Hz), 6.61 (1H, s), 6.91 (2H, d, J=8.7 Hz), 7.34 (2H, d, J=8.7 Hz).

Example 417
3,4,8,9-Tetrahydro-6-methoxy-3,3,9,9-tetramethyl-1-phenylfuro[2,3-h]isoquinoline The title compound was obtained from benzonitrile and 2,3-dihydro-7-methoxy-3,3-dimethyl-5-(2-methyl-1-propenyl)benzofuran by the method similar to that in EXAMPLE 1. Yield: 1.4%.

Melting point: 142–143° C. (hexane-diethyl ether).
$^1$H NMR (CDCl$_3$) δ 0.78 (6H, s), 1.18 (6H, s), 2.61 (2H, s), 3.93 (3H, s), 4.03 (2H, s), 6.65 (1H, s), 7.32–7.44 (5H, m).

Example 418
3,3-Diethyl-3,4,8,9-tetrahydro-6-methoxy-8,8-dimethyl-1-phenylfuro[2,3-h]isoquinoline Hydrochloride The title compound was obtained from benzonitrile and 5-(2-ethyl-1-butenyl)-2,3-dihydro-7-methoxy-2,2-dimethylbenzofuran by the method similar to that in EXAMPLE 306. Yield: 36%.

Melting point: 178–179° C. (ethyl acetate).
$^1$H NMR (CDCl$_3$) δ 1.07 (6H, t, J=7.8 Hz), 1.33 (6H, s), 1.94–2.18 (4H, m), 2.22 (2H, s), 3.07 (2H, s), 4.01 (3H, s), 6.76 (1H, s), 7.57–7.67 (5H, m).

Example 419
3,4,8,9-Tetrahydro-6-methoxy-3,3,8,8-tetramethyl-1-furo[2,3-h]isoquinolinecarboxylic Acid Methyl Ester The title compound was obtained from methyl cyanoformate by the method similar to that in EXAMPLE 1. Yield: 16%.

Melting point: 161–162° C. (chloroform-hexane).
$^1$H NMR (CDCl$_3$) δ 1.25 (6H, s), 1.49 (6H, s), 2.65 (2H, s), 2.94 (2H, s), 3.91 (3H, s), 3.93 (3H, s), 6.55 (1H, s).

Example 420
3,4,8,9-Tetrahydro-6-methoxy-3,3,8,8-tetramethyl-1-furo[2,3-h]isoquinolinecarboxylic Acid Hydrochloride 5 M aqueous solution of sodium hydroxide was added to a solution of 3,4,8,9-tetrahydro-6-methoxy-3,3,8,8-tetramethyl-1-furo[2,3-h]isoquinolinecarboxylic acid methyl ester (1.49 g, 4.69 mmol) in methanol (5 mL) and the mixture was stirred at 60° C. for 5 hours. The reaction solution was made acidic with 5 M hydrochloric acid, and concentrated under reduced pressure. The residue was combined with ethanol and the mixture was filtered, and the filtrate was concentrated under reduced pressure, and this procedure was repeated three times to obtain the title compound (1.50 g, Yield: 94%).

Amorphous.

$^1$H NMR (DMSO-$d_6$) δ 1.35 (6H, s), 1.41 (6H, s), 3.02 (2H, s), 3.17 (2H, s), 3.91 (3H, s), 6.99 (1H, s).

Example 421
3,4,8,9-Tetrahydro-6-methoxy-3,3,8,8-tetramethyl-N-[2-(4-pyridinyl)ethyl]-1-furo[2,3-h]isoquinolinecarboxamide The title compound was obtained from 3,4,8,9-tetrahydro-6-methoxy-3,3,8,8-tetramethyl-1-furo[2,3-h]isoquinolinecarboxylic acid hydrochloride and 4-(2-aminoethyl)pyridine by the method similar to that in Example 159. Yield: 42%.

Melting point: 160–161° C. (diisopropyl ether-hexane).

$^1$H NMR (CDCl$_3$) δ 1.15 (6H, s), 1.47 (6H, s), 2.59 (2H, s), 2.93 (2H, t, J=7.0 Hz), 3.02 (2H, s), 3.68 (2H, q, J=7.0 Hz), 3.89 (3H, s), 6.52 (1H, s), 6.93–7.02 (1H, m), 7.22 (2H, d, J=6.0 Hz), 8.55 (2H, d, J=6.0 Hz).

Example 422
3,4,8,9-Tetrahydro-6-methoxy-3,3,8,8-tetramethyl-N-phenyl-1-furo[2,3-h]isoquinolinecarboxamide The title compound was obtained from 3,4,8,9-tetrahydro-6-methoxy-3,3,8,8-tetramethyl-1-furo[2,3-h]isoquinolinecarboxylic acid hydrochloride and aniline by the method similar to that in EXAMPLE 159. Yield: 60%.

Melting point: 175–176° C. (ethyl acetate-hexane).

$^1$H NMR (CDCl$_3$) δ 1.22 (6H, s), 1.48 (6H, s), 2.63 (2H, s), 3.21 (2H, s), 3.91 (3H, s), 6.55 (1H, s), 7.14 (1H, t, J=7.4 Hz), 7.38 (2H, d, J=7.4 Hz), 7.68 (2H, d, J=7.4 Hz), 8.84 (1H, s).

Example 423
N-(1-Azabicyclo[2.2.2]oct-3-yl)-3,4,8,9-tetrahydro-6-methoxy-3,3,8,8-tetramethyl-1-furo[2,3-h]isoquinolinecarboxamide The title compound was obtained from 3,4,8,9-tetrahydro-6-methoxy-3,3,8,8-tetramethyl-1-furo[2,3-h]isoquinolinecarboxylic acid hydrochloride and 3-amino-1-azabicyclo[2.2.2]octane by the method similar to that in EXAMPLE 159. Yield: 60%.

Melting point: 139–142° C. (ethyl acetate-hexane).

$^1$H NMR (CDCl$_3$) δ 1.17 (3H, s), 1.19 (3H, s), 1.48 (6H, s), 1.62–1.86 (4H, m), 2.02–2.10 (1H, m), 2.58–2.66 (1H, m), 2.59 (2H, s), 2.80–2.98 (4H, m), 3.14 (2H, s), 3.35–3.49 (1H, m), 3.89 (3H, s), 3.97–4.08 (1H, m), 6.52 (1H, s), 6.96 (1H, d, J=7.2 Hz).

Example 424
3,4,8,9-Tetrahydro-6-methoxy-3,3-dimethyl-1-(2-thienyl)furo[2,3-h]isoquinoline The title compound was obtained from 2,3-dihydro-7-methoxy-5-(2-methyl-1-propenyl)benzofuran and 2-thiophenecarbonitrile by the method similar-to that in EXAMPLE 368. Yield: 23%.

Melting point: 122–125° C. (hexane).

$^1$H NMR (CDCl$_3$) δ 1.23 (6H, s), 2.67 (2H, s), 2.73 (2H, t, J=8.6 Hz), 3.93 (3H, s), 4.43 (2H, t, J=8.6 Hz), 6.60 (1H, s), 7.01–7.09 (2H, m), 7.35 (1H, dd, J=5.0, 1.4 Hz).

Example 425
3',4'-Dihydro-6'-methoxy-3',3'-dimethyl-1'-phenylspiro[cyclopentane-1,8'(9'H)-furo[2,3-h]isoquinoline]

A solution of benzonitrile (0.700 g, 6.50 mmol) in toluene (5 mL) and acetic acid (5 mL) was treated dropwise with conc. sulfuric acid (0.6 mL) with cooling in ice. The ice bath was removed, and a solution of 7-methoxy-5-(2-methyl-1-propenyl)spiro[benzofuran-2(3H),1'-cyclopentane] (1.29 g, 5.00 mmol) in toluene (5 mL) was added to the mixture and the mixture was stirred at 80° C. for 1 hour. The reaction mixture was combined with ice, and the aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 10:1) and recrystallized from ethyl acetate-hexane to obtain the title compound (0.87 g, Yield: 48%).

Melting point: 130–131° C.

$^1$H NMR (CDCl$_3$) δ 1.25 (6H, s), 1.43–2.05 (8H, m), 2.32 (2H, s), 2.69 (2H, s), 3.91 (3H, s), 6.60 (1H, s), 7.38 (5H, s).

Example 426
3',4'-Dihydro-6'-methoxy-3',3'-dimethyl-1'-(2-thienyl)spiro[cyclopentane-1,8'(9'H)-furo[2,3-h]isoquinoline]

The title compound was obtained from 2-thiophenecarbonitrile by the method similar to that in EXAMPLE 425. Yield: 28%.

Melting point: 142–143° C. (ethyl acetate-hexane).

$^1$H NMR (CDCl$_3$) δ 1.22 (6H, s), 1.54–2.10 (8H, m), 2.65 (2H, s), 2.67 (2H, s), 3.92 (3H, s), 6.59 (1H, s), 7.03 (1H, dd, J=5.0, 3.6 Hz), 7.07 (1H, dd, J=3.6, 1.4 Hz), 7.35 (1H, dd, J=5.0, 1.4 Hz).

Example 427
4-[3',4'-Dihydro-6'-methoxy-3',3'-dimethylspiro[cyclopentane-1,8'(9'H)-furo[2,3-h]isoquinoline]-1'-yl]pyridine 1-oxide The title compound was obtained from 4-cyanopyridine 1-oxide by the method similar to that in EXAMPLE 425. Yield: 12%.

Melting point: 205–207° C. (ethyl acetate-hexane).

$^1$H NMR (CDCl$_3$) δ 1.23 (6H, s), 1.47–2.09 (8H, m), 2.56 (2H, s), 2.67 (2H, s), 3.92 (3H, s), 6.62 (1H, s), 7.39 (2H, d, J=5.0 Hz), 8.24 (2H, d, J=5.0 Hz).

Example 428
8,8-Diethyl-3,4,8,9-tetrahydro-6-methoxy-3,3-dimethyl-1-phenylfuro[2,3-h]isoquinoline Hydrochloride A solution of benzonitrile (0.670 g, 6.50 mmol) in toluene (5 mL) and acetic acid (5 mL) was treated dropwise with conc. sulfuric acid (0.6 mL) with cooling in ice. The ice bath was removed, and a solution of 2,2-diethyl-2,3-dihydro-7-methoxy-5-(2-methyl-1-propenyl)benzofuran (1.30 g, 5.00 mmol) in toluene (5 mL) was added to the mixture and the mixture was stirred at 80° C. for 1 hour. The reaction mixture was combined with ice, and the aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 10:1) to obtain a free base of the title compound. This was combined with 3.35 M hydrogen chloride/ethanol solution (9.61 mL), and the mixture was concentrated under reduced pressure. The residue was crystallized from diethyl ether, and the crystals were recrystallized from ethyl acetate to obtain the title compound (0.69 g, Yield: 35%).

Melting point: 167–169° C.

$^1$H NMR (CDCl$_3$) δ 0.78 (6H, t, J=7.4 Hz), 1.58 (2H, q, J=7.4 Hz), 1.60 (2H, q, J=7.4 Hz), 1.70 (6H, s), 2.20 (2H, s), 3.02 (2H, s), 4.02 (3H, s), 6.73 (1H, s), 7.28–7.72 (5H, m).

Example 429

8,8-Diethyl-3,4,8,9-tetrahydro-6-methoxy-3,3-dimethyl-1-(2-thienyl)furo[2,3-h]isoquinoline Hydrochloride The title compound was obtained from 2-thiophenecarbonitrile by the method similar to that in EXAMPLE 428. Yield: 20%.

Melting point: 152–154° C. (ethyl acetate-diethyl ether).

$^1$H NMR (CDCl$_3$) δ 0.84 (6H, t, J=7.4 Hz), 1.60–1.72 (4H, m), 1.66 (6H, s), 2.56 (2H, s), 2.98 (2H, s), 4.02 (3H, s), 6.71 (1H, s), 7.29 (1H, dd, J=4.8, 3.8 Hz), 7.81 (1H, dd, J=4.8, 1.2 Hz), 8.06 (1H, dd, J=3.8, 1.2 Hz).

Example 430

4-(8,8-Diethyl-3,4,8,9-tetrahydro-6-methoxy-3,3-dimethylfuro[2,3-h]isoquinolin-1-yl)pyridine 1-oxide Hydrochloride The title compound was obtained from 4-cyanopyridine 1-oxide by the method similar to that in EXAMPLE 428. Yield: 4%.

Melting point: 184–186° C. (ethyl acetate).

$^1$H NMR (CDCl$_3$) δ 0.84 (6H, t, J=7.4 Hz), 1.60–1.73 (4H, m), 1.67 (6H, s), 2.43 (2H, s), 3.03 (2H, s), 4.04 (3H, s), 6.75 (1H, s), 7.74 (2H, d, J=6;8 Hz), 8.34 (2H, d, J=6.8 Hz).

Example 431

1-(6-Methyl-2-quinolinyl)-5-(3,4,8,9-tetrahydro-6-methoxy-3,3,8,8-tetramethylfuro[2,3-h]isoquinolin-1-yl)-2 (1H) pyridinone A solution of N-[2-(2,3-dihydro-7-methoxy-2,2-dimethyl-5-benzofuranyl)-1,1-dimethylethyl]-1,6-dihydro-1-(6-methyl-2-quinolinyl)-6-oxo-3-pyridinecarboxamide (0.70 g, 1.4 mmol) in phosphorus oxychloride (5.0 mL, 54 mmol) was heated under reflux for 4.5 hours. The reaction solution was cooled to room temperature, and the reaction mixture was poured into water. After the mixture was made weakly alkaline with 8 M aqueous solution of sodium hydroxide, and the organic material was extracted with ethyl acetate. The extract was washed with brine and dried over sodium sulfate, and then the solvent was distilled off under reduced pressure. The resultant residue was purified by a column chromatography on a basic silica gel (hexane/ethyl acetate 2:1 followed by 1:1) to obtain crude crystals. The resultant crude crystals were recrystallized from hexane-diisopropyl ether to obtain the title compound (0.13 g, Yield: 19%).

Melting point: 201–202° C. (hexane-diisopropyl ether).

$^1$H NMR (CDCl$_3$) δ 1.21 (6H, s), 1.51 (6H, s), 2.56 (3H, s), 2.65 (2H, s), 2.98 (2H, s), 3.94 (3H, s), 6.62 (1H, s), 6.73 (1H, d, J=9.4 Hz), 7.55 (1H, dd, J=8.8, 1.8 Hz), 7.61–7.67 (2H, m), 7.87 (1H, d, J=8.8 Hz), 7.92 (1H, d, J=8.6 Hz), 8.10 (1H, d, J=2.6 Hz), 8.16 (1H, d, J=8.8 Hz).

Example 432

1-(6-Chloro-3-pyridinyl)-3,4,8,9-tetrahydro-6-methoxy-3,3,8,8-tetramethylfuro[2,3-h]isoquinoline The title compound was obtained from 6-chloro-N-[2-(2,3-dihydro-7-methoxy-2,2-dimethyl-5-benzofuranyl)-1,1-dimethylethyl]-3-pyridinecarboxamide by the method similar to that in EXAMPLE 431. Yield: 40%.

$^1$H NMR (CDCl$_3$) δ 1.25 (6H, s), 1.36 (6H, s), 2.28 (2H, s), 2.70 (2H, s), 3.93 (3H, s), 6.63 (1H, s),7.38 (1H, d, J=7.8 Hz), 7.74 (1H, dd, J=7.8, 2.2 Hz), 8.42 (1H, d, J=2.0 Hz).

Example 433

[5-[3-(3,4,8,9-Tetrahydro-6-methoxy-3,3,8,8-tetramethylfuro[2,3-h]isoquinolin-1-yl)phenyl]-1H-tetorazol-1-yl]methyl 2,2-dimethylpropanoate 3-(1H-Tetrazol-5-yl)benzonitrile (0.587 g, 3.4 mmol) was suspended in toluene (5 mL) and acetic acid (5 mL). While cooling in ice, conc. sulfuric acid (0.4 mL) followed by a solution of 1-(2,3-dihydro-7-methoxy-2,2-dimethyl-5-benzofuranyl)-2-methyl-1-propanol (0.751 g, 3.0 mmol) in toluene were added thereto and the mixture was stirred at 80° C. for 3 hours. The reaction mixture was combined with ice water, followed by an aqueous solution of sodium hydrogen carbonate to adjust at pH 4, and then extracted three times with tetrahydrofuran. The extract was washed with brine, dried over sodium sulfate, filtered and concentrated under reduced pressure. The residue was dissolved in N,N-dimethylformamide (5 mL), potassium carbonate (1.11 g, 8.0 mmol) and chloromethyl pivalate (1.04 mL, 7.2 mmol) were added thereto and the mixture was stirred at room temperature for 18 hours. The reaction mixture was combined with ice, water and extracted twice with ethyl acetate. The extract was washed with brine dried over sodium sulfate, filtered, and concentrated under reduced pressure. The residue was subjected to a column chromatography on a silica gel, eluted with hexane/ethyl acetate (2:1) to collect the intended fraction, which was concentrated and recrystallized from diethyl ether/hexane (1:1) to obtain the title compound (0.122 g, yield: 7.8%).

Melting point: 134–136° C.

$^1$H NMR (CDCl$_3$) δ 1.22 (9H, s), 1.26 (6H, s), 1.29 (6H, s), 2.25 (2H, s), 2.72 (2H, s), 3.93 (3H, s), 6.52 (2H, s), 6.64 (1H, s), 7.5–8.3 (4H, m).

Example 434

5-[3-(3,4,8,9-Tetrahydro-6-methoxy-3,3,8,8-tetramethylfuro[2,3-h]isoquinolin-1-yl)phenyl]-1H-tetrazole-1-acetic Acid Sodium Salt 5-(3-Cyanophenyl)-1H-tetrazole-1-acetic acid methyl ester (0.730 g, 3.0 mmol) was dissolved in toluene (5 mL) and acetic acid (5 mL), and, while cooling in ice, conc. sulfuric acid (0.4 mL) followed by a solution of 1-(2,3-dihydro-7-methoxy-2,2-dimethyl-5-benzofuranyl)-2-methyl-1-propanol (0.751 g, 3.0 mmol) in toluene were added thereto and the mixture was stirred at 80° C. for 4 hours. The reaction mixture was combined with ice water, and washed with diethyl ether. The aqueous layer was combined with aqueous solution of sodium hydrogen carbonate to adjust at pH 7, and subjected to a column chromatography on a polystyrene gel [MCI GEL CHP20P (MITSUBISHI KASEI KOGYO)], eluted with ethanol/water (3:7) to collect the intended fraction, which was concentrated to remove ethanol, and then freeze-dried to obtain the title compound (0.68 g, Yield: 47%).

Melting point: 180° C.

$^1$H NMR (DMSO-d$_6$) δ 1.17 (6H, s), 1.19 (6H, s), 2.26 (2H, s), 2.67 (2H, s), 3.82 (3H, s), 4.97 (2H, s), 6.83 (1H, s), 7.4–8.2 (4H, m).

Example 435

3,4,8,9-Tetrahydro-6-methoxy-8,8-dimethyl-1-phenylfuro [2,3-h]isoquinoline Hydrochloride Phosphorus oxychloride (3.4 mL, 36 mmol) was added to a suspension of N-[2-(2,3-dihydro-7-methoxy-2,2-dimethyl-5-benzofuranyl)ethyl]benzamide (2.93 g, 9.00 mmol) in xylene (30 mL) and the mixture was heated under reflux for 5 hours, and then stirred at room temperature for 15 hours. The reaction mixture was cooled with ice, combined with 5 M solution of sodium hydroxide (35 mL) and poured into ice water (100 mL). The aqueous layer was extracted twice with diethyl ether, and the combined organic layer was extracted twice with 2 M hydrochloric acid. The combined aqueous layer was neutralized with 5 M aqueous solution of sodium hydroxide, and extracted three times with diethyl ether. The combined organic layer was washed with a brine, dried over sodium sulfate, filtered, and concentrated under reduced pressure. The residue was subjected to a column chromatography on a silica gel (hexane/ethyl acetate 2:1 followed by 1:2) to obtain a free base of the title compound. This was dissolved in ethyl acetate (15 mL), combined with 4 M hydrogen chloride/ethyl acetate solution (3 mL), and the precipitated solid was recovered by filtration and washed with diethyl ether to obtain the title compound (2.10 g, Yield: 68%).

Melting point: 213–215° C.

$^1$H NMR (CDCl$_3$) δ 1.36 (6H, s), 2.35 (2H, s), 3.08 (2H, t, J=7.3 Hz), 3.96–4.08 (2H, m), 4.02 (3H, s), 6.82 (1H, s), 7.54–7.77 (5H, m), 14.50–14.80 (1H, br).

Example 436

3,4,8,9-Tetrahydro-6-methoxy-3,8,8-trimethyl-1-phenylfuro[2,3-h]isoquinoline

The title compound was obtained from N-[2-(2,3-dihydro-7-methoxy-2,2-dimethyl-5-benzofuranyl)-1-methylethyl]benzamide by the method similar to that in EXAMPLE 431. Yield: 71%.

Melting point: 133–134° C. (hexane-diisopropyl ether).

$^1$H NMR (CDCl$_3$) δ 1.29 (3H, s), 1.35 (3H, s), 1.47 (3H, d, J=7.0 Hz), 2.17–2.25 (2H, m), 2.44–2.73 (2H, m), 3.47–3.66 (1H, m), 3.92 (3H, s), 6.65 (1H, s), 7.40 (5H, s).

Example 437

3,4,8,9-Tetrahydro-6-methoxy-3,8,8-trimethyl-1-(4-pyridinyl)furo[2,3-h]isoquinoline The title compound was obtained from N-[2-(2,3-dihydro-7-methoxy-2,2-dimethyl-5-benzofuranyl)-1-methylethyl]-4-pyridinecarboxamide by the method similar to that in EXAMPLE 431. Yield: 24%.

Melting point: 135–136° C. (hexane-diethyl ether).

$^1$H NMR (CDCl$_3$) δ 1.30 (3H, s), 1.37 (3H, s), 1.47 (3H, d, J=6.8 Hz), 2.19–2.37 (2H, m), 2.45–2.75 (2H, m), 3.51–3.66 (1H, m), 3.93 (3H, s), 6.67 (1H, s), 7.37 (2H, d, J=5.8 Hz), 8.68 (2H, d, J=5.8 Hz).

Example 438

3,4,8,9-Tetrahydro-6-methoxy-8,8-dimethyl-1-phenyl-3-furo[2,3-h]isoquinolinecarboxylic Acid Methyl Ester A mixture of α-(benzoylamino)-2,3-dihydro-7-methoxy-2,2-dimethyl-5-benzofuranpropanoic acid methyl ester (2.81 g, 7.33 mmol) and phosphorus oxychloride (15 mL) was stirred at 100° C. for 2.5 hours. The reaction mixture was concentrated under reduced pressure, and the residue was combined with ice and ethyl acetate. The resultant mixture was neutralized with conc. aqueous ammonia and the organic layer was separated, and the aqueous layer was extracted with ethyl acetate. The combined organic layer was washed twice with water, and then concentrated under reduced pressure. The residue was subjected to a column chromatography on a silica gel (hexane/ethyl acetate 2:1, 1:1 followed by 1:2) and crystallized from ethyl acetate-diisopropyl ether to obtain the title compound (1.41 g, Yield: 53%).

Melting point: 182–184° C.

$^1$H NMR (CDCl$_3$) δ 1.29 (3H, s), 1.35 (3H, s), 2.20 (1H, d, J=16.3 Hz), 2.31 (1H, d, J=16.3 Hz), 2.86–3.10 (2H, m), 3.82 (3H, s), 3.93 (3H, s), 4.24 (1H, dd, J=12.0, 6.6 Hz), 6.69 (1H, s), 7.35–7.51 (5H, m).

Example 439

N-[3'-(3,4,8,9-Tetrahydro-6-methoxy-3,3,8,8-tetramethylfuro[2,3-h]isoquinolin-1-yl)[1,1'-biphenyl]-4-yl]propanamide The title compound was obtained from 3'-(3,4,8,9-tetrahydro-6-methoxy-3,3,8,8-tetramethylfuro[2,3-h]isoquinolin-1-yl)[1,1'-biphenyl]-4-amine and propionyl chloride by the method similar to that in EXAMPLE 30. Yield: 92%.

Melting point: 176–184° C. (ethyl acetate-diethyl ether).

$^1$H NMR (CDCl$_3$) δ 1.20–1.32 (3H, m), 1.27 (6H, s), 1.29 (6H, s), 2.26 (2H, s), 2.40 (2H, g, J=7.6 Hz), 2.71 (2H, s), 3.93 (3H, s), 6.63 (1H, s), 7.26–7.68 (9H, m).

Example 440

N-[3'-(3,4,8,9-Tetrahydro-6-methoxy-3,3,8,8-tetramethylfuro[2,3-h]isoquinolin-1-yl)[1,1'-biphenyl]-4-yl]-2,2-dimethylpropanamide The title compound was obtained from 3'-(3,4,8,9-tetrahydro-6-methoxy-3,3,8,8-tetramethylfuro[2,3-h]isoquinolin-1-yl)[1,1'-biphenyl]-4-amine and trimethylacetyl chloride by the method similar to that in EXAMPLE 30. Yield: 68%.

Melting point: 189–193° C. (ethyl acetate-diethyl ether-hexane).

$^1$H NMR (CDCl$_3$) δ 1.27 (6H, s), 1.30 (6H, s), 1.34 (9H, s), 2.26 (2H, s), 2.71 (2H, s), 3.93 (3H, s), 6.63 (1H, s), 7.32–7.50 (3H, m), 7.53–7.70 (6H, m).

Example 441

2,2,2-Trifluoro-N-[3'-(3,4,8,9-tetrahydro-6-methoxy-3,3,8,8-tetramethylfuro[2,3-h]isoquinolin-1-yl)[1,1'-biphenyl]-4-yl]acetamide A solution of 3'-(3,4,8,9-tetrahydro-6-methoxy-3,3,8,8-tetramethylfuro[2,3-h]isoquinolin-1-yl)[1,1'-biphenyl]-4-amine (192 mg, 0.450 mmol) and triethylamine (82 μL, 0.59 mmol) in tetrahydrofuran (1 mL) was treated dropwise with trifluoroacetic anhydride (70 μL, 0.50 mmol) with cooling in ice, and stirred at the same temperature for 10 minutes. The reaction mixture was combined with water and a saturated aqueous solution of sodium hydrogen carbonate, and extracted twice with ethyl acetate. The combined organic layer was washed with brine, dried through sodium sulfate, and concentrated. The residue was crystallized from ethyl acetate-hexane to obtain the title compound (222 mg, Yield: 94%).

Melting point: 149–154° C.

$^1$H NMR (CDCl$_3$) δ 1.28 (6H, s), 1.32 (6H, br s), 2.02 (2H, s), 2.76 (2H, s), 3.94 (3H, s), 6.65 (1H, s), 7.29–7.59 (8H, m), 8.95–9.20 (1H, m).

Example 442

N-[3'-(3,4,8,9-Tetrahydro-6-methoxy-3,3,8,8-tetramethylfuro[2,3-h]isoquinolin-1-yl)[1,1-biphenyl]-4-yl]benzamide The title compound was obtained from 3'-(3,4,8,9-tetrahydro-6-methoxy-3,3,8,8-tetramethylfuro[2,3-h]isoquinolin-1-yl)[1,1'-biphenyl]-4-amine and benzoyl chloride by the method similar to that in EXAMPLE 30. Quantitative.

Melting point: 204–207° C. (ethyl acetate-hexane).

$^1$H NMR (CDCl$_3$) δ 1.27 (6H, s), 1.30 (6H, s), 2.27 (2H, s), 2.71 (2H, s), 3.93 (3H, s), 6.63 (1H, s), 7.34–7.38 (1H, m), 7.42–7.64 (8H, m), 7.67–7.73 (2H, m), 7.87–7.92 (2H, m), 7.94–8.07 (1H, m).

Example 443
[3'-(3,4,8,9-tetrahydro-6-methoxy-3,3,8,8-tetramethylfuro[2,3-h]isoquinolin-1-yl)[1,1'-biphenyl]-4-yl]carbamic Acid Methyl Ester A solution of sodium carbonate (72 mg, 0.68 mmol) in water (0.5 mL) was added to a solution of 3'-(3,4,8,9-tetrahydro-6-methoxy-3,3,8,8-tetramethylfuro[2,3-h]isoquinolin-1-yl)[1,1'-biphenyl]-4-amine (192 mg, 0.450 mmol) in tetrahydrofuran (1 mL), and while cooling in ice, methyl chloroformate (43 µL, 0.54 mmol) was added thereto, and the mixture was stirred at the same temperature for 15 minutes. The reaction mixture was combined with water, and extracted twice with ethyl acetate. The combined organic layer was washed with water and brine, dried over sodium sulfate, filtered and concentrated under reduced pressure. The residue was crystallized from ethyl acetate-diethyl ether to obtain the title compound (165 mg, Yield: 76%).

Melting point: 129–133° C.
$^1$H NMR (CDCl$_3$) δ 1.27 (6H, s), 1.30 (6H, s), 2.26 (2H, s), 2.71 (2H, s), 3.79 (3H, s), 3.93 (3H, s), 6.63 (1H, s), 6.69 (1H, br s), 7.34 (1H, dt, J=7.7, 1.5 Hz), 7.39–7.49 (3H, m), 7.52–7.63 (4H, m).

Example 444
N-[3'-(3,4,8,9-Tetrahydro-6-methoxy-3,3,8,8-tetramethylfuro[2,3-h]isoquinolin-1-yl)[1,1'-biphenyl]-4-yl]formamide Formic acid (0.5 ml) was treated dropwise with acetic anhydride (0.13 mL, 1.4 mmol) with cooling in ice, and the mixture was stirred at the same temperature for 30 minutes. 3'-(3,4,8,9-Tetrahydro-6-methoxy-3,3,8,8-tetramethylfuro[2,3-h]isoquinolin-1-yl)[1,1'-biphenyl]-4-amine (192 mg, 0.450 mmol) was added to the resultant solution and the mixture was stirred at room temperature for 1.5 hours. To a suspension of sodium hydrogen carbonate (1.85 g, 22.0 mmol) in water-ethyl acetate, the reaction mixture was added dropwise, and the mixture was extracted twice with ethyl acetate. The combined organic layer was washed with water and brine, dried over sodium sulfate, filtered and concentrated under reduced pressure. The residue was crystallized from ethyl acetate to obtain the title compound (196 mg, Yield: 96%).

Melting point: 129–133° C.
$^1$H NMR (CDCl$_3$) δ 1.24–1.32 (12H, m), 2.26 (2H, s), 2.73 (2H, s), 3.93 (3H, s), 6.63 (1H, s), 7.05–7.17 (1H, m), 7.32–7.64 (8H, m), 8.36 (0.6H, d, J=1.8 Hz), 8.72 (0.4H, d, J=11.2 Hz).

Example 445
2-(Acetylamino)-N-[3'-(3,4,8,9-tetrahydro-6-methoxy-3,3,8,8-tetramethylfuro[2,3-h]isoquinolin-1-yl)[1,1'-biphenyl]-4-yl]acetamide 1-Ethyl-3-(3-dimethylaminopropyl)carbodimide hydrochloride (100 mg, 0.522 mmol) was added to a solution of 3'-(3,4,8,9-tetrahydro-6-methoxy-3,3,8,8-tetramethylfuro[2,3-h]isoquinolin-1-yl)[1,1'-biphenyl]-4-amine (171 mg, 0.401 mmol), N-acetylglycine (52 mg, 0.44 mmol) and 1-hydroxy-1H-benzotriazole (68 mg, 0.44 mmol) in N,N-dimethylformamide (0.5 mL) and the mixture was stirred at room temperature for 16 hours. The reaction mixture was combined with water and a saturated aqueous solution of sodium hydrogen carbonate, and extracted twice with ethyl acetate. The combined organic layer was washed with water and brine, dried over sodium sulfate, filtered and concentrated under reduced pressure. The residue was recrystallized from chloroform-diethyl ether to obtain the title compound (182 mg, Yield: 86%).

Melting point: 218–221° C.
$^1$H NMR (CDCl$_3$) δ 1.28 (6H, s), 1.29 (6H, s), 2.10 (3H, s), 2.52 (2H, s), 2.73 (2H, s), 3.93 (3H, s), 4.08 (2H, d, J=5.4 Hz), 6.45–6.55 (1H, m), 6.63 (1H, s), 7.31–7.36 (1H, m), 7.43 (1H, t, J=7.7 Hz), 7.49–7.60 (6H, m), 8.73–8.87 (1H, m).

Example 446
N-Methyl-N'-[3'-(3,4,8,9-tetrahydro-6-methoxy-3,3,8,8-tetramethylfuro[2,3-h]isoquinolin-1-yl)[1,1'-biphenyl]-4-yl]urea A solution of 3'-(3,4,8,9-tetrahydro-6-methoxy-3,3,8,8-tetramethylfuro[2,3-h]isoquinolin-1-yl)[1,1'-biphenyl]-4-amine (171 mg, 0.401 mmol) in chloroform (1 mL) was treated dropwise with methyl isocyanate (26 µL, 0.44 mmol) and stirred at room temperature for 3.5 hours. The reaction mixture was concentrated under reduced pressure, and the residue was subjected to a column chromatography on a basic silica gel (ethyl acetate) to obtain the title compound (186 mg, Yield: 96%).

Amorphous.
$^1$H NMR (CDCl$_3$) δ 1.29 (12H, s), 2.25 (2H, s), 2.74 (2H, s), 2.77 (3H, d, J=4.5 Hz), 3.93 (3H, s), 5.05 (1H, br s), 6.64 (1H, s), 6.98 (1H, br s), 7.25–7.33 (3H, m), 7.38–7.45 (3H, m), 7.49–7.57 (2H, m).

Example 447
4-Oxo-4-[[3'-(3,4,8,9-tetrahydro-6-methoxy-3,3,8,8-tetramethylfuro[2,3-h]isoquinolin-1-yl)[1,1'-biphenyl]-4-yl]amino]butyric Acid A solution of succinic anhydride (45 mg, 0.45 mmol) in tetrahydrofuran (0.5 mL) was added to a solution of 3'-(3,4,8,9-tetrahydro-6-methoxy-3,3,8,8-tetramethylfuro[2,3-h]isoquinolin-1-yl)[1,1'-biphenyl]-4-amine (192 mg, 0.450 mmol) in tetrahydrofuran (1 mL) and the mixture was stirred at 50° C. for 2.5 hours. The reaction mixture was concentrated under reduced pressure, and the residue was subjected to a column chromatography on a silica gel (chloroform followed by chloroform/methanol 5:1) to obtain the title compound (219 mg, Yield: 92%).

Amorphous.
$^1$H NMR (CDCl$_3$) δ 1.26 (6H, s), 1.38 (6H, br s), 2.24 (2H, s), 2.46 (4H, br s), 2.81 (2H, s), 3.94 (3H, s), 6.65 (1H, s), 7.25–7.60 (7H, m), 7.61 (1H, s), 9.45–9.75 (1H, br).

Example 448
N-Methyl-N-[3'-(3,4,8,9-tetrahydro-6-methoxy-3,3,8,8-tetramethylfuro[2,3-h]isoquinolin-1-yl)[1,1'-biphenyl]-4-yl]acetamide The title compound was obtained from N-[3'-(3,4,8,9-tetrahydro-6-methoxy-3,3,8,8-tetramethylfuro[2,3-h]isoquinolin-1-yl)[1,1'-biphenyl]-4-yl]acetamide by the method similar to that in EXAMPLE 74. Yield: 79%

Amorphous.
$^1$H NMR (CDCl$_3$) δ 1.27 (6H, s), 1.30 (6H, s), 1.92 (3H, s), 2.26 (2H, s), 2.71 (2H, s), 3.29 (3H, s), 3.93 (3H, s), 6.63 (1H, s), 7.20–7.30 (2H, m), 7.34 (1H, dt, J=7.6, 1.5 Hz), 7.48 (1H, t, J=7.6 Hz), 7.58–7.69 (4H, m).

Example 449
3'-(6-Butoxy-3,4,8,9-tetrahydro-3,3,8,8-tetramethylfuro[2,3-h]isoquinolin-1-yl)[1,1'-blphenyl]-4-amine To a solution of 1-(3-bromophenyl)-6-butoxy-3,4,8,9-tetrahydro-3,3,8,8-tetramethylfuro[2,3-h]isoquinolne hydrochloride (493 mg, 1.00 mmol) in 1,2-dimethoxyethane (3 mL), ethanol (1.5 mL) and water (1.5 mL), sodium carbonate (265 mg, 2.50 mmol), 4-(4.4,5,5-tetramethyl-1,3,2-dioxaborolane-2-yl)aniline (263 mg, 1.20 mmol) and tetrakis(triphenylphosphine)palladium (0) (24 mg, 0.021 mmol) were added, and the mixture was stirred at 80° C. for 14 hours. The reaction mixture was combined with water, and washed twice with ethyl acetate. The combined organic layer was washed with water, and extracted twice with 0.5 M hydrochloric acid. The aqueous layer was neutralized with conc. aqueous ammonia, and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate, 3:1 followed by 2:1), and recrystallized from ethyl acetate-hexane to obtain the title compound (373 mg, Yield: 80%).

Melting point: 148–150° C.

$^1$H NMR (CDCl$_3$) δ 0.98 (3H, t, J=7.3 Hz), 1.26 (6H, s), 1.28 (6H, s), 1.38–1.60 (2H, m), 1.74–1.91 (2H, m), 2.24 (2H, s), 2.68 (2H, s), 3.72 (2H, br s), 4.10 (2H, t, J=6.9 Hz), 6.61 (1H, s), 6.74 (2H, d, J=8.4 Hz), 7.25–7.32 (1H, m), 7.35–7.47 (3H, m), 7.51–7.59 (2H, m).

Example 450

N-[3'-(6-Butoxy-3,4,8,9-tetrahydro-3,3,8,8-tetramethylfuro[2,3-h]isoquinolin-1-yl)[1,1'-biphenyl]-4-yl]acetamide The title compound was obtained from N-3'-(6-butoxy-3,4,8,9-tetrahydro-3,3,8,8-tetramethylfuro[2,3-h]isoquinolin-1-yl)[1,1'-biphenyl]-4-amine by the method similar to that in EXAMPLE 30. Yield: 95%.

Melting point: 202–204° C. (ethyl acetate-diethyl ether).

$^1$H NMR (CDCl$_3$) δ 0.98 (3H, t, J=7.4 Hz), 1.28 (12H, s), 1.38–1.59 (2H, m), 1.74–1.91 (2H, m), 2.15 (3H, s), 2.23 (2H, s), 2.70 (2H, s), 4.11 (2H, t, J=6.8 Hz), 6.62 (1H, s), 7.29–7.60 (8H, m), 7.72 (1H, br s).

Example 451

4-Amino-3'-(3,4,8,9-tetrahydro-6-methoxy-3,3,8,8-tetramethylfuro[2,3-h]isoquinolin-1-yl)[1,1'-biphenyl]-3-carboxylic Acid Methyl Ester A suspension of 1-(3-bromophenyl)-3,4,8,9-tetrahydro-6-methoxy-3,3,8,8-tetramethylfuro[2,3-h]isoquinoline (1.66 g, 4.01 mmol), 2-amino-5-(4,4,5,5-tetramethyl-1,3,2-dioxaborolan-2-yl)benzoic acid methyl ester (1.22 g, 4.40 mmol), sodium carbonate (637 mg, 6.01 mmol) and tetrakis(triphenylphosphine)palladium (0) (93 mg, 0.080 mmol) in 1,2-dimethoxyethane (12 mL), ethanol (6 mL) and water (6 mL) was stirred at 85° C. for 14 hours under nitrogen atmosphere. The reaction mixture was combined with water, and extracted twice with ethyl acetate. The combined organic layer was washed with water and brine, dried over sodium sulfate-basic silica gel (eluting with ethyl acetate), and concentrated under reduced pressure. The residue was subjected to a column chromatography on a basic silica gel (hexane/ethyl acetate, 3:1). The resultant material was dissolved in ethyl acetate, extracted twice with 0.5 M hydrochloric acid, neutralized with conc. aqueous ammonia, and extracted twice with ethyl acetate. The combined organic layer was washed twice with water, and concentrated under reduced pressure to obtain the title compound (1.85 g, yield: 95%).

Amorphous.

$^1$H NMR (CDCl$_3$) δ 1.27 (6H, s), 1.31 (6H, s), 2.28 (2H, s), 2.71 (2H, s), 3.89 (3H, s), 3.93 (3H, s), 5.79 (2H, br s), 6.63 (1H, s), 6.73 (1H, d, J=8.4 Hz), 7.32 (1H, dt, J=7.3, 1.5 Hz), 7.38–7.47 (1H, m), 7.51–7.59 (3H, m), 8.11 (1H, d, J=2.2 Hz).

Example 452

4-(Acetylamino)-3'-(3,4,8,9-tetrahydro-6-methoxy-3,3,8,8-tetramethylfuro[2,3-h]isoquinolin-1-yl)[1,1'-biphenyl]-3-carboxylic Acid Methyl Ester A solution of 4-amino-3'-(3,4,8,9-tetrahydro-6-methoxy-3,3,8,8-tetramethylfuro[2,3-h]isoquinolin-1-yl)[1,1'-biphenyl]-3-carboxylic acid methyl ester (1.43 g, 2.95 mmol) in pyridine (10 mL) was treated dropwise with acetic anhydride (0.28 mL, 3.0 mmol) with cooling in ice, and stirred at room temperature for 10 minutes and then at 60° C. for 1 hour. The same volume of acetic anhydride was added to the mixture, and the mixture was stirred at 100° C. for 2 hours. The reaction mixture was combined with water and a saturated aqueous solution of sodium hydrogen carbonate, and extracted with ethyl acetate. The combined organic layer was washed twice with water, and concentrated under reduced pressure. The residue was subjected to a column chromatography on a basic silica gel (hexane/ethyl acetate, 4:1 followed by 2:1), and recrystallized from ethyl acetate-hexane to obtain the title compound (1.12 g, yield: 72%).

Melting point: 116–119° C.

$^1$H NMR (CDCl$_3$) δ 1.27 (6H, s), 1.31 (6H, s), 2.26 (3H, s), 2.27 (2H, 's), 2.72 (2H, s), 3.93 (3H, s), 3.95 (3H, s), 6.63 (1H, s), 7.39 (1H, dt, J=7.3, 1.6 Hz), 7.47 (1H, td, J=7.3, 1.2 Hz), 7.56–7.64 (2H, m), 7.79 (1H, dd, J=8.8, 2.4 Hz), 8.26 (1H, d, J=2.4 Hz), 8.78 (1H, d, J=8.8 Hz), 11.07 (1H, br s).

Example 453

4-(Acetylamino)-3'-(3,4,8,9-tetrahydro-6-methoxy-3,3,8,8-tetramethylfuro[2,3-h]isoquinolin-1-yl)[1,1'-biphenyl]-3-carboxylic Acid 5 M aqueous solution of sodium hydroxide (0.52 mL, 2.6 mmol) was added to a solution of 4-(acetylamino)-3'-(3,4,8,9-tetrahydro-6-methoxy-3,3,8,8-tetramethylfuro[2,3-h]isoquinolin-1-yl)[1,1'-biphenyl]-3-carboxylic acid methyl ester (692 mg, 1.32 mmol) in methanol (5 mL) and the mixture was stirred at room temperature for 40 minutes and then heated under reflux for 10 minutes. The reaction mixture was concentrated under reduced pressure, combined with water (2 mL), and neutralized by adding 2 M hydrochloric acid (1.3 mL, 2.6 mmol) dropwise, and the precipitated powder was recovered by filtration, washed with water and diethyl ether to obtain the title compound (671 mg, quantitative).

Melting point: 181–186° C.

$^1$H NMR (DMSO-d$_6$) δ 1.20 (6H, s), 1.22 (6H, s), 2.14 (3H, s), 2.28 (2H, s), 2.76 (2H, s) 3.85 (3H, s), 6.88 (1H, s), 7.38 (1H, d, J=7.6 Hz), 7.55 (1H, t, J=7.6 Hz), 7.63 (1H, s), 7.81 (1H, d, J=7.6 Hz), 7.84–7.93 (1H, m), 8.24 (1H, d J=2.2 Hz), 8.55 (1H, d, J=8.8 Hz), 11.75 (1H, br s).

Example 454

N-[4'-(3,4,8,9-tetrahydro-6-methoxy-3,3,8,8-tetramethylfuro[2,3-h]isoquinolin-1-yl)[1,1'-biphenyl]-4-yl]acetamide 4'-(4,4,5,5-Tetramethyl-1,3,2-dioxaborolan-2-yl)acetanilide (116 mg, 0.444 mmol) and tetrakis(triphenylphosphine)palladium (0) (11 mg, 0.0095 mmol) were added to a suspension of 1-(4-bromophenyl)-3,4,8,9-tetrahydro-6-methoxy-3,3,8,8-tetramethylfuro[2,3-h]isoquinoline hydrochloride (181 mg, 0.402 mmol) and sodium carbonate (149 mg, 1.41 mmol) in 1,2-dimethoxyethane (1.2 mL), ethanol (0.6 mL) and water (0.6 mL) and the mixture was stirred at 85° C. for 15 hours under nitrogen atmosphere. The reaction mixture was combined with water, and washed twice with ethyl acetate The combined organic layer was washed with water and brine, and dried through sodium sulfate-basic silica gel (eluting with ethyl acetate) and then concentrated under reduced pressure. The residue was subjected to a column chromatography on a basic silica gel (hexane/ethyl acetate, 2:1 followed by 1:1), and crystallized from ethyl acetate-hexane to obtain the title compound (102 mg, yield: 54%).

Melting point: 128–132° C.

¹H NMR (CDCl₃) δ 1.26 (6H, s), 1.33 (6H, s), 2.21 (3H, s), 2.32 (2H, s), 2.70 (2H, s), 3.93 (3H, s), 6.62 (1H, s), 7.23 (1H, br s), 7.46 (2H, d, J=8.6 Hz), 7.56–7.64 (4H, m), 7.60 (2H, d, J=8.6 Hz).

Example 455

N-[4'-(3,4,8,9-Tetrahydro-6-methoxy-3,3,8,8-tetramethylfuro[2,3-h]isoquinolin-1-yl)[1,1'-biphenyl]-3-yl]acetamide The title compound was obtained from 3-acetamidobenzeneboronic acid by the method similar to that in EXAMPLE 454. Yield: 84%.

Amorphous.

¹H NMR (CDCl₃) δ 1.27 (6H, s), 1.33 (6H, s), 2.20 (3H, s), 2.31 (2H, s), 2.71 (2H, s), 3.93 (3H, s), 6.63 (1H, s), 7.3–7.66 (8H, m), 7.79 (1H, br s).

Example 456

3'-(3,4,8,9-Tetrahydro-6-methoxy-3,3,8,8-tetramethylfuro[2,3-h]isoquinolin-1-yl)[1,1'-biphenyl]-4-carboxylic Acid Ethyl Ester A suspension of 1-(3-bromophenyl)-3,4,8,9-tetrahydro-6-methoxy-3,3,8,8-tetramethylfuro[2,3-h]isoquinoline (2.81 g, 6.78 mmol), 4-(4,4,5,5-tetramethyl-1,3,2-dioxaborolan-2-yl)benzoic acid ethyl ester (2.25 g, 8.15 mmol), sodium carbonate (1.08 g, 10.2 mmol) and tetrakis(trlphenylphosphine)palladium (0) (157 mg, 0.136 mmol) in 1,2-dimethoxyethane (24 mL), ethanol (12 mL) and water (12 mL) was stirred at 80° C. for 14 hours under nitrogen atmosphere. The reaction mixture was combined with water and extracted twice with ethyl acetate. The combined organic layer was washed with water and brine, dried through sodium sulfate-basic silica gel (eluting with ethyl acetate), and concentrated under reduced pressure. The residue was subjected to a column chromatography on a basic silica gel (hexane/ethyl acetate, 10:1) to obtain the title compound (2.87 g, yield: 88%).

Amorphous.

¹H NMR (CDCl₃) δ 1.27 (6H, s), 1.30 (6H, s), 1.42 (3H, t, J=7.1 Hz), 2.26 (2H, s), 2.72 (2H, s), 3.93 (3H, s), 4.40 (2H, q, J=7.1 Hz), 6.63 (1H, s), 7.37–7.54 (2H, m), 7.62–7.71 (4H, m), 8.10 (2H, d, J=8.4 Hz).

Example 457

3'-(3,4,8,9-Tetrahydro-6-methoxy-3,3,8,8-tetramethylfuro[2,3-h]isoquinolin-1-yl) [1,1'-biphenyl]-4-carboxylic Acid 1 M aqueous solution of sodium hydroxide (20 mL, 20 mmol) was added to -a solution of 3-'-(3,4,8,9-tetrahydro-6-methoxy-3,3,8,8-tetramethylfuro[2,3-h]isoquinolin-1-yl)[1,1'-biphenyl]-4-carboxylic acid ethyl ester (2.74 g, 5.67 mmol) in ethanol (15 mL) and the mixture was stirred at 70° C. for 30 minutes. The reaction mixture was cooled with ice, combined with 1 M hydrochloric acid (20 mL, 20 mmol), saturated with sodium chloride, and then extracted three times with ethyl acetate. The combined organic layer was dried over sodium sulfate, filtered and concentrated under reduced pressure. The residue was crystallized from ethyl acetate-diethyl ether to obtain the title compound (2.26 g, yield: 87%).

Melting point: 161–165° C.

¹H NMR (DMSO-d₆) δ 1.17 (6H, s), 1.19 (6H, s), 2.26 (2H, s), 2.67 (2H, s), 3.82 (3H, s), 6.84 (1H, s), 7.40 (1H, d, J=7.7 Hz), 7.56 (1H, t, J=7.7 Hz), 7.67 (1H, s), 7.79–7.87 (3H, m), 8.03 (2H, d, J=8.4 Hz).

Example 458

3'-(3,4,8,9-Tetrahydro-6-methoxy-3,3,8,8-tetramethylfuro[2,3-h]isoqulnolin-1-yl)[1,1'-biphenyl]-4-carboxamide 1-ethyl-3-(3-dimethylaminopropyl)carbodiumide hydrochloride (200 mg, 1.04 mmol) was added to a suspension of 3'-(3,4,8,9-tetrahydro-6-methoxy-3,3,8,8-tetramethylfuro[2,3-h]isoquinolin-1-yl)[1,1'-biphenyl]-4-carboxylic acid (365 mg, 0.801 mmol) and 1-hydroxy-1H-benzotriazole ammonium salt (147 mg, 0.966 mmol) in N,N-dimethylformamide (1.5 mL) and the mixture was stirred at-room temperature for 15 hours. The reaction mixture was combined with water and saturated aqueous solution of sodium hydrogen carbonate, and extracted twice with ethyl acetate. The combined organic layer was washed with water and a brine, dried over sodium sulfate, filtered and concentrated under reduced pressure. The residue was crystallized from ethyl acetate-hexane to obtain the title compound (286 mg, yield: 79%).

Melting point: 134–137° C. (decomposition).

¹H NMR (CDCl₃) δ 1.27 (6H, s), 1.30 (6H, s), 2.25 (2H, s), 2.72 (2H, s), 3.93 (3H, s), 5.50–6.40 (2H, m), 6.63 (1H, s), 7.39–7.54 (2H, m), 7.61–7.63 (2H, m), 7.69 (2H, d, J=8.5 Hz), 7.88 (2H, d, J=8.5 Hz).

Example 459

N-Methyl-3'-(3,4,8,9-tetrahydro-6-methoxy-3,3,8,8-tetramethylfuro[2,3-h]isoquinolin-1-yl)[1,1'-biphenyl]-4-carboxamide 1-Ethyl-3-(3-dimethylaminopropyl)carbodlimide hydrochloride (200 mg, 1.04 mmol) was added to a suspension of 3'-(3,4,8,9-tetrahydro-6-methoxy-3,3,8,8-tetramethylfuro[2,3-h]isoquinolin-1-yl)[1,1'-biphenyl]-4-carboxylic acid (365 mg, 0.801 mmol), 40% methylamine/methanol solution (75 mg, 0.97 mmol) and 1-hydroxy-1H-benzotriazole (135 mg, 0.880 mmol) in N,N-dimethylformamide (1.5 mL) and the mixture was stirred at room temperature for 20 hours. The reaction mixture was combined with water and a saturated aqueous solution of sodium hydrogen carbonate, and extracted twice with ethyl acetate. The combined organic layer was washed with water and brine, dried through sodium sulfate-basic silica gel (eluting with ethyl acetate), and concentrated under reduced pressure. The residue was crystallized from ethyl acetate-hexane to obtain the title compound (317 mg, yield: 84%).

Melting point: 242–244° C.

¹H NMR (CDCl₃) δ 1.27 (6H, s), 1.30 (6H, s), 2.25 (2H, s), 2.72 (2H, s), 3.04 (3H, d, J=4.8 Hz), 3.93 (3H, s), 6.15–6.30 (1H, m), 6.63 (1H, s), 7.37–7.53 (2H, m), 7.59–7.70 (2H, m), 7.66 (2H, d, J=8.4 Hz), 7.82 (2H, d, J=8.4 Hz).

Example 460

N,N'-Dimethyl-3'-(3,4,8,9-tetrahydro-6-methoxy-3,3,8,8-tetramethylfuro[2,3-h]isoquinolin-1-yl)[1,1'-biphenyl]-4-carboxamide 1-Ethyl-3-(3-dimethylaminopropyl)carbodiimide hydrochloride (200 mg, 1.04 mmol) was added to a suspension of 3'(3,4,8,9-tetrahydro-6-methoxy-3,3,8,8-tetramethylfuro[2,3-h]isoquinolin-1-yl)[1,1'-biphenyl]-4-carboxylic acid (365 mg, 0.801 mmol), 2 M dimethylamine/tetrahydrofuran solution (0.48 mL, 0.96 mmol) and 1-hydroxy-1H-benzotriazole (135 mg, 0.880 mmol) in N,N-dimethylformamide (1.5 mL) and the mixture was stirred at room temperature for 17 hours. The reaction mixture was combined with water and a saturated aqueous solution of sodium hydrogen carbonate, and extracted twice with ethyl acetate. The combined organic layer was washed with water and brine, dried through sodium sulfate-basic silica gel (eluting with ethyl acetate), concentrated under reduced pressure to obtain the title compound (319 mg, yield: 83%).

Amorphous.

¹H NMR (CDCl₃) δ 1.27 (6H, s), 1.30 (6H, s), 2.25 (2H, s), 2.71 (2H, s), 3.03 (3H, br s), 3.12 (3H, br s), 3.93 (3H, s), 6.63 (1H, s), 7.36–7.53 (4H, m), 7.58–7.68 (4H, m).

Example 461

N-[3'-(3,4,8,9-Tetrahydro-6-hydroxy-3,3,8,8-tetramethylfuro[2,3-h]isoquinolin-1-yl)(1,1'-biphenyl]-4-yl]acetamide A suspension of 1-(3-bromophenyl)-3,4,8,9-tetrahydro-3,3,8,8-tetramethylfuro[2,3-h]isoquinolinol (1.40 g, 3.50 mmol), 4'-(4,4,5,5-tetramethyl-1,3,2-dioxaborolan-2-yl)acetanilide (1.01 g, 3.87 mmol), sodium carbonate (927 mg, 8.75 mmol) and tetrakis(triphenylphosphine)palladium (0) (81 mg, 0.070 mmol) in 1,2-dimethoxyethane (10 mL), ethanol (5 mL) and water (5 mL) was stirred at 80° C. for 14 hours under nitrogen atmosphere. The reaction mixture was combined with water, and extracted twice with ethyl acetate. The combined organic layer was washed with brine, dried through sodium sulfate-basic silica gel (eluting with ethyl acetate followed by ethyl acetate/methanol, 10:1) and concentrated under reduced pressure, and the precipitated powder was recovered by filtration, washed with ethyl acetate-diethyl ether mixture to obtain the title compound (921 mg, yield: 58%).

Melting point: 185–189° C.

$^1$H NMR (DMSO-d$_6$) δ 1.14 (6H, s), 1.19 (6H, s), 2.06 (3H, s), 2.23 (2H, s), 2.56 (2H, s), 6.56 (1H, s), 7.29 (1H, d, J=7.6 Hz), 7.42–7.77 (7H, m), 10.05 (1H, s).

Example 462

1-[4'-(Acetylamino)[1,1'-biphenyl]-3-yl]-3,4,8,9-tetrahydro-3,3,8,8-tetramethylfuro[2,3-h]isoquinolin-6-yl Trifluoromethanesulfonate The title compound was obtained from N-[3'-(3,4,8,9-tetrahydro-6-hydroxy-3,3,8,8-tetramethylfuro[2,3-h]isoquinolin-1-yl)[1,1'-biphenyl]-4-yl]acetamide by the method similar to that in EXAMPLE 95. Yield: 96%.

Amorphous $^1$H NMR (CDCl$_3$) δ 1.28 (6H, s), 1.29 (6H, s), 2.13–2.23 (3H, m), 2.30 (2H, s), 2.72 (2H, s), 6.95 (1H, s), 7.29–7.70 (9H, m).

Example 463

N-[3'-(3,4,8,9-Tetrahydro-3,3,8,8-tetramethylfuro[2,3-h]isoquinolin-1-yl)[1,1'-biphenyl]-4-yl]acetamide Formic acid (64 μL, 1.7 mmol) was added to a solution of 1-[4'-(acetylamino)[1,1'-biphenyl]-3-yl]-3,4,8,9-tetrahydro-3,3,8,8-tetramethylfuro[2,3-h]isoquinolin-6-yl trifluoromethanesulfonate (496 mg, 0.846 mmol), triethylamine (0.35 mL, 2.5 mmol), palladium (II) acetate (4.7 mg, 0.021 mmol) and triphenylphosphine (11 mg, 0.042 mmol) in N,N-dimethylformamide (1.5 mL) and the mixture was stirred at 60° C. for 4 hours under nitrogen atmosphere. The reaction mixture was combined with water and a saturated aqueous solution of sodium hydrogen carbonate, and extracted twice with ethyl acetate. The combined organic layer was washed with water and brine, dried through sodium sulfate-basic silica gel (eluting with ethyl acetate), and concentrated under reduced pressure. The residue was subjected to a column chromatography on a basic silica gel (hexane/ethyl acetate, 2:1 followed by 1:1), crystallized from ethyl acetate-hexane to obtain the title compound (294 mg, yield: 79%).

Melting point: 198–200° C.

$^1$H NMR (CDCl$_3$) δ 1.26 (6H, s), 1.28 (6H, s), 2.16 (3H, s), 2.24 (2H, s), 2.72 (2H, s), 6.76 (1H, d, J=7.8 Hz), 6.99 (1H, d, J=7.8 Hz), 7.35 (1H, dt, J=7.4, 1.4 Hz), 7.44 (1H, td, J=7.4, 1.0 Hz), 7.49–7.62 (7H, m).

Example 464

1-(3-Bromophenyl)-3,4,8,9-tetrahydro-3,3,8,8-tetramethyl-6-furo[2,3-h]isoquinolin-6-yl Trifluoromethanesulfonate The title compound was obtained from 1-(3-bromophenyl)-3,4,8,9-tetrahydro-3,3,8,8-tetramethylfuro[2,3-h]isoquinolinol by the method similar to that in EXAMPLE 95.

Quantitative.

A gum.

$^1$H NMR (CDCl$_3$) δ 1.25 (6H, s), 1.34 (6H, s), 2.29 (2H, s), 2.69 (2H, s), 6.95 (1H, s), 7.14–7.38 (2H, m), 7.53–7.60 (2H, m).

Example 465

3'-(3,4,8,9-Tetrahydro-3,3,8,8-tetramethylfuro[2,3-h]isoquinolin-1-yl)[1,1'-biphenyl]-4-amine Formic acid (0.73 mL, 19 mmol) was added to a solution of 1-(3-bromophenyl)-3,4,8,9-tetrahydro-3,3,8,8-tetramethylfuro[2,3-h]isoquinolin-6-yl trifluoromethanesulfonate (5.13 g, 9.64 mmol), triethylamine (4.0 mL, 29 mmol), palladium (II) acetate (54 mg, 0.24 mmol) and triphenylphosphine (126 mg, 0.480 mmol) in N,N-dimethylformamide (20 mL) and the mixture was stirred at 65° C. for 2 hours under nitrogen atmosphere. The reaction mixture was combined with water and saturated aqueous solution of sodium hydrogen carbonate, and extracted twice with ethyl acetate. The combined organic layer was washed with water and brine, dried through sodium sulfate-basic silica gel (eluting with ethyl acetate), and concentrated under reduced pressure. The residue was subjected to a column chromatography on a silica gel (hexane/ethyl acetate, 10:1) to obtain an oil containing 1-(3-bromophenyl)-3,4,8,9-tetrahydro-3,3,8,8-tetramethylfuro[2,3-h]isoquinoline.

This material, 4-(4,4,5,5-tetramethyl-1,3,2-dioxaborolan-2-yl)aniline (1.21 g, 5.52 mmol), sodium carbonate (795 mg, 7.50 mmol) and tetrakis(triphenylphosphine)palladium (0) (116 mg, 0.100 mol) were suspended in 1,2-dimethoxyethane (15 mL), ethanol (7 mL) and water (7 mL), and the mixture was stirred at 80° C. for 15 hours under nitrogen atmosphere. The reaction mixture was combined with water and extracted twice with ethyl acetate. The combined organic layer was washed with water and brine, dried through sodium sulfate-basic silica gel (eluting with ethyl acetate), and concentrated under reduced pressure. The residue was subjected to a column chromatography on a basic silica gel (hexane/ethyl acetate, 10:1 followed by 2:1), and crystallized from ethyl acetate-hexane to obtain the title compound (1.35 g, yield: 35%).

Melting point: 161–163° C.

$^1$H NMR (CDCl$_3$) δ 1.25 (12H, s), 2.24 (2H, s), 2.70 (2H, s), 3.73 (2H, br s), 6.74 (2H, d, J=8.4 Hz), 6.75 (1H, d, J=8.0 Hz), 6.98 (1H, d, J=8.0 Hz), 7.27–7.34 (1H, m), 7.36–7.48 (3H, m), 7.54–7.60 (2H, m).

Example 466

2,2,2-Trifluoro-N-[3'-(3,4,8,9-tetrahydro-3,3,8,8-tetramethylfuro[2,3-h]isoquinolin-1-yl) [1,1'-biphenyl]-4-yl]acetamide The title compound was obtained from 3'-(3,4,8,9-tetrahydro-3,3,8,8-tetramethylfuro[2,3-h]isoquinolin-1-yl)[1,1'-biphenyl]-4-amine by the method similar to that in EXAMPLE 441. Yield: 83%.

Melting point: 228–230° C. (ethyl acetate-hexane).

$^1$H NMR (CDCl$_3$) δ 1.25 (6H, s), 1.30 (6H, s), 2.19 (2H, s), 2.75 (2H, s), 6.78 (1H, d, J=7.9 Hz), 7.01 (1H, d, J=7.9 Hz), 7.31–7.62 (8H, m), 8.82 (1H, br s).

Example 467
4-[[[3-(3,4,8,9-Tetrahydro-6-methoxy-3,3,8,8-tetramethylfuro[2,3-h]isoquinolin-1-yl)phenyl]amino]carbonyl]benzoic Acid Methyl Ester Terephthaloyl monomethyl chloride (1.91 g, 9.62 mmol) was added to a solution of 3-(3,4,8,9-tetrahydro-6-methoxy-3,3,8,8-tetramethylfuro[2,3-h]isoquinolin-1-yl) benzenamine (2.81 g, 8.02 mmol) and triethylamine (1.5 mL, 11 mmol) in tetrahydrofuran (15 mL) with cooling in ice, and the mixture was stirred at room temperature for 10 minutes. The reaction mixture was combined with water, and extracted twice with ethyl acetate. The combined organic layer was washed with a saturated aqueous solution of sodium hydrogen carbonate, water and brine, dried through sodium sulfate-basic silica gel (elutlng with ethyl acetate), and concentrated under reduced pressure. The residue was subjected to a column chromatography on a basic silica gel (hexane/ethyl acetate, 2:1 followed by 1:1), and recrystallized from ethyl acetate-hexane to obtain the title compound (3.75 g, yield: 91%).

Melting point: 156–160° C.

$^1$H NMR (CDCl$_3$) δ 1.16 (6H, br s), 1.33 (6H, s), 2.34 (2H, s), 2.60 (2H, br s), 3.92 (3H, s), 3.96 (3H, s), 6.59 (1H, s), 7.13 (1H, d, J=7.7 Hz), 7.37 (1H, t, J=7.7 Hz), 7.56 (1H, t, J=1.8 Hz), 7.89–7.98 (3H, m), 8.12 (2H, d, J=7.8 Hz), 8.66 (1H, br s).

Example 468
4-[[[3-(3,4,8,9-Tetrahydro-6-methoxy-3,3,8,8-tetramethylfuro[2,3-h]isoquinolin-1-yl)phenyl]amino]carbonyl]benzoic Acid Hydrochloride 5 M aqueous solution of sodium hydroxide (0.50 mL, 2.5 mmol) was added to a solution of 4-[[[3-(3,4,8,9-tetrahydro-6-methoxy-3,3,8,8-tetramethylfuro[2,3-h]isoquinolin-1-yl) phenyl]amino]carbonyl]benzoic acid methyl ester (1.03 g, 2.01 mmol) in methanol (10 mL) and the mixture was stirred at room temperature for 1.5 hours and then heated under reflux for 1.5 hours. The reaction mixture was concentrated under reduced pressure, and treated dropwise with 1 M hydrochloric acid (5.0 mL, 5.0 mmol) with cooling in ice. Brine was added to the mixture, and the mixture was extracted twice with ethyl acetate-tetrahydrofuran mixture. The combined organic layer was dried over sodium sulfate, filtered and concentrated under reduced pressure to obtain the title compound (1.06 g, yield: 99%).

Amorphous.

$^1$H NMR (CDCl$_3$) δ 1.34 (6H, s), 1.62 (3H, br s), 1.73 (3H, br s), 2.26–2.54 (2H, m), 2.94–3.24 (2H, m), 3.98 (3H, s), 6.72 (1H, 8), 7.24 (1H, d, J=3 8.1 Hz), 7.47 (1H, t, J=8.1 Hz), 7.83 (2H, d, J=8.6 Hz), 7.90 (2H, d, J=8.6 Hz), 8.25 (1H, s), 8.35 (1H, d, J=8.1 Hz), 10.01 (1H, br s), 12.88 (1H, br s).

Example 469
N-Methyl-N'-[3-(3,4,8,9-tetrahydro-6-methoxy-3,3,8,8-tetramethylfuro[2,3-h]isoquinolin-1-yl)phenyl]-1,4-benzenedicarboxamide Triethylamine (0.17 mL, 1.2 mol) and 1-ethyl-3-(3-dimethylaminopropyl)carbodiimide hydrochloride (125 mg, 0.652 mmol) were added to a solution of 4-[[[3-(3,4,8,9-tetrahydro-6-methoxy-3,3,8,8-tetramethylfuro[2,3-h] isoquinolin-1-yl)phenyl]amino]carbonyl]benzoic acid hydrochloride (268 mg, 0.501 mmol), 40% methylamine/methanol solution (55 mg, 0.56 mmol) and 1-hydroxy-1H-benzotriazole (85 mg, 0.56 mmol) in N,N-dimethylformamide (1 mL) and the mixture was stirred at room temperature for 24 hours. The reaction mixture was combined with water, and extracted twice with chloroform-methanol mixture. The combined organic phase was washed with brine, dried through sodium sulfate-basic silica gel (eluting with ethyl acetate/methanol, 10:1) and concentrated under reduced pressure. The residue was recrystallized from chloroform-methanol-diethyl ether to obtain the title compound (215 mg, Yield: 84%).

Melting point: 310–312° C.

$^1$H NMR (DMSO-d$_6$) δ 1.15 (6H, s), 1.23 (6H, s), 2.33 (2H, br s), 2.64 (2H, s), 2.81 (3H, d, J=4.5 Hz), 3.82 (3H, s), 6.82 (1H, s), 7.08–7.12 (1H, m), 7.40 (1H, t, J=8.0 Hz), 7.77–7.81 (1H, m), 7.88–7.94 (1H, m), 7.95 (2H, d, J=8.3 Hz), 8.04 (2H, d, J=8.3 Hz), 8.57–8.63 (1H, m), 10.40 (1H, s).

Example 470
2-[(3,4,8,9-Tetrahydro-6-methoxy-3,8,8-trimethyl-1-phenylfuro[2,3-h]isoquinolin-3-yl)methyl]-1H-isoindole-1,3(2H)-dione A suspension of 3-(bromomethyl)-3,4,8,9-tetrahydro-6-methoxy-3,8,8-trimethyl-1-phenylfuro[2,3-h]isoquinoline (2.49 g, 6.01 mmol), potassium phthalimide (90%) (1.86 g, 9.0 mmol) in N,N-dimethylacetamide (25 mL) was heated under reflux for 2.5 hours under nitrogen atmosphere The reaction mixture was combined with water, and extracted twice with ethyl acetate. The combined organic layer was washed twice with water, and concentrated under reduced pressure. The residue was subjected to a column chromatography on a silica gel (hexane/ethyl acetate, 2:1), crystallized from ethyl acetate-hexane, and recrystallized from methanol-acetone-hexane to obtain the title compound (1.56 g, yield; 54%).

Melting point: 121–125° C.

$^1$H NMR (CDCl$_3$) δ 1.19 (3H, s), 1.22 (3H, s), 1.38 (3H, s), 1.97–2.19 (2H, m), 2.81 (1H, d, J=15.9 Hz), 3.02 (1H, d, J=15.9 Hz), 3.85 (1H, d, J=13.6 Hz), 3.86 (3H, s), 3.96 (1H, d, J=13.6 Hz), 6.54 (1H, s), 7.36–7.52 (5H, m), 7.61–7.80 (4H, m).

Example 471
3,4,8,9-Tetrahydro-6-methoxy-3,8,8-trimethyl-1-phenyl-3-furo[2,3-h]isoquinolinemethanamine Hydrazine monohydrate (0.25 mL, 5.2 mmol) was added to a suspension of 2-[(3,4,8,9-tetrahydro-6-methoxy-3,8,8-trimethyl-1-phenylfuro[2,3-h]isoquinolin-3-yl)methyl]-1H-isoindole-1,3(2H)-dione (2.08 g, 4.33 mmol) in ethanol (20 mL) and heated under reflux for 4 hours with adding the same amount of the hydrazine monohydrate after 2 hours and after 3 hours. The reaction mixture was combined with 1 M aqueous solution of sodium hydroxide (9.0 mL, 9.0 mmol), diluted with water, and extracted twice with ethyl acetate. The combined organic layer was washed twice with water, and concentrated under reduced pressure. The residue was subjected to a column chromatography on a basic silica gel (ethyl acetate/methanol, 100:1), and recrystallized from ethyl acetate-hexane to obtain the title compound (823 mg. Yield: 54%).

Melting point: 143–145° C.

$^1$H NMR (CDCl$_3$) δ 1.06 (3H, s), 1.29 (3H, s), 1.33 (3H, s), 2.16 (1H, d, J=16.5 Hz), 2.25 (1H, d, J=16.5 Hz), 2.49 (1H, d, J=15.4 Hz), 2.80 (1H, d, J=12.6 Hz), 2.89 (1H, d, J=12.6 Hz), 2.93 (1H, d, J=15.4 Hz), 3.92 (3H, s), 6.63 (1H, s), 7.39 (5H, s).

Example 472
(3,4,8,9-Tetrahydro-6-methoxy-8,8-dimethyl-1-phenylfuro[2,3-h]isoquinolin-3-yl)methyl Acetate Phosphorus oxychloride (9.4 mL 0.10 mol) was added to a suspension of 2-(benzoylamino)-3-(2,3-dihydro-7- methoxy-2,2-dimethyl-5-benzofuranyl)propyl acetate (3.34 g, 8.40 mmol) in acetonitrile (65 mL) and heated under reflux for 1.5 hours. Water was poured into the reaction mixture, which was neutralized with conc. aqueous ammonia with cooling in ice, and extracted twice with ethyl acetate. The combined organic layer was washed twice with water, and concentrated under reduced pressure. The residue was recrystallized from ethyl acetate-hexane to obtain the title compound (2.62 g, yield: 82%).

Melting point: 168–169° C.

$^1$H NMR (CDCl$_3$) δ 1.28 (3H, s), 1.36 (3H, s), 2.12 (3H, s), 2.19 (1H, d, J=8.1 Hz), 2.31 (1H, d, J=8.1 Hz), 2.52–2.79 (2H, m), 3.54–3.76 (1H, m), 3.93 (3H, s), 4.34 (1H, dd, J=11.0, 6.6 Hz), 4.54 (1H, dd, J=11.0, 6.2 Hz), 6.68 (1H, s), 7.42 (5H, s).

Example 473

3,4,8,9-Tetrahydro-6-methoxy-8,8-dimethyl-1-phenyl-3-furo[2,3-h]isoquinolinemethanol 5 M aqueous solution of sodium hydroxide (1.6 mL, 8.0 mmol) was added to a solution of (3,4,8,9-tetrahydro-6-methoxy-8,8-dimethyl-1-phenylfuro[2,3-h]isoquinolin-3-yl)methyl acetate (1.00 g, 2.64 mmol) in methanol (5 mL) and tetrahydrofuran (5 mL), and the mixture was stirred at room temperature for 10 minutes. The reaction mixture was combined with water, and extracted twice with ethyl acetate. The combined organic layer was washed twice with water, and concentrated under reduced pressure. The residue was recrystallized from ethyl acetate-diisopropyl ether to obtain the title compound (553 mg, yield: 62%).

Melting point: 156–158° C.

$^1$H NMR (CDCl$_3$) δ 1.28 (3H, s), 1.38 (3H, s), 2.21 (1H, d, J=8.1 Hz), 2.35 (1H, d, J=8.1 Hz), 2.51–2.70 (2H, m), 2.90–3.15 (1H, br), 3.36–3.57 (1H, m), 3.76 (1H, dd, J=10.7, 7.7 Hz), 3.87–4.03 (1H, m), 3.93 (3H, s), 6.68 (1H, s), 7.43 (5H, s).

Example 474

2-[(3,4,8,9-Tetrahydro-6-methoxy-8,8-dimethyl-1-phenylfuro[2,3-h]isoquinolin-3-yl)methyl]-1H-isoindole-1,3(2H)-dione A solution of 3,4,8,9-tetrahydro-6-methoxy-8,8-dimethyl-1-phenyl-3-furo[2,3-h]isoquinolinemethanol (793 mg, 2.35 mmol) in pyridine (10 mL) was cooled with ice, treated dropwise with methanesulfonyl chloride (0.22 mL, 2.8 mmol), stirred at the same temperature for 30 minutes, treated further with methanesulfonyl chloride (0.04 mL, 0.05 mmol), and stirred further for 30 minutes. The reaction mixture was combined with water and a saturated aqueous solution of sodium hydrogen carbonate, and extracted twice with ethyl acetate. The combined organic layer was washed twice with water and concentrated under reduced pressure. The residue was combined with toluene, and concentrated under reduced pressure again to obtain (3,4,8,9-tetrahydro-6-methoxy-8,8-dimethyl-1-phenylfuro[2,3-h]isoquinolin-3-yl)methyl methanesulfonate.

This was dissolved in N,N-dimethylformamlde, potassium phthalimide (90%, 725 mg, 3.5 mmol) was added thereto, and the mixture was stirred at 100° C. for 4.5 hours. The reaction mixture was combined with water, and extracted twice with ethyl acetate. The combined organic layer was washed twice with water, and concentrated under reduced pressure. The residue was crystallized from ethyl acetate-diisopropyl ether to obtain the title compound (337 mg, yield: 31%).

Melting point: 228–229° C.

$^1$H NMR (CDCl$_3$) δ 1.26 (3H, s), 1.34 (3H, s), 2.18 (1H, d, J=16.5 Hz), 2.32 (1H, d, J=16.5 Hz), 2.57–2.75 (2H, m), 3.78–4.15 (2H, m), 3.87 (3H, s), 4.24 (1H, dd, J=13.2, 5.4 Hz), 6.61 (1H, s), 7.34–7.48 (5H, m), 7.68–7.92 (4H, m).

Example 475

3,4,8,9-Tetrahydro-6-methoxy-8,8-dimiethyl-1-phenyl-3-furo[2,3-h]isoquinolinemethanamine Dithydrochloride Hydrazine monohydrate (84 μL, 1.7 mmol) was added to a suspension of 2-[(3,4,8,9-tetrahydro-6-methoxy-8,8-dimethyl-1-phenylfuro[2,3-h]isoquinolin-3-yl)methyl]-1H-isoindole-1,3(2H)-dione (350 mg, 0.750 mmol) in ethanol (4 mL) and the mixture was heated under reflux for 2.5 hours. The reaction mixture was combined with 1 M aqueous solution of sodium hydroxide, diluted with water, and extracted twice with ethyl acetate. The combined organic layer was washed twice with water, and concentrated under reduced pressure. The residue was subjected to a column chromatography on a basic ssilica gel (ethyl acetate followed by ethyl acetate/methanol, 10:1) to obtain 3,4,8,9-tetrahydro-6-methoxy-8,8-dimethyl-1-phenyl-3-furo[2,3-h]isoquinolinemethanamine (164 mg) as an amorphous material. This was dissolved in ethyl acetate (2 mL), combined with 0.8 M hydrogen chloride/methanol solution (1.8 mL, 1.4 mmol) and concentrated under reduced pressure. The residue was crystallized from ethanol-ethyl acetate to obtain the title compound (140 mg, yield: 46%).

Melting point: 192–194° C.

$^1$H NMR (DMSO-d$_6$) δ 1.22 (3H, s), 1.26 (3H, s), 2.26 (2H, s), 3.05–3.40 (4H, m), 3.80–4.50 (1H, m), 3.94 (3H, s), 7.10 (1H, s), 7.55–7.78 (5H, m), 8.35–8.65 (3H, m).

Example 476

N-[3'-(3,4,8,9-Tetrahydro-6-methoxy-3,3,8,8-tetramethyl-2-oxidofuro[2,3-h]isoquinolin-1-yl)[1,1'-biphenyl]-3-yl]acetamide The title compound was obtained from N-[3'-(1,2,3,4,8,9-hexahydro-6-methoxy-3,3,8,8-tetramethylfuro[2,3-h]isoquinolin-1-yl)[1.1'-biphenyl]-3-yl]acetamide by the method similar to that in EXAMPLE 110. Yield: 66%.

Melting point: 158–162° C. (methanol-diethyl ether).

$^1$H NMR (CDCl$_3$) δ 1.24 (3H, s), 1.28 (3H, s), 1.51 (6H, s), 2.04 (2H, s), 2.13 (3H, s), 3.09 (2H, s), 3.9 (3H s), 6.65 (1H, s), 7.27–7.53 (5H, m), 7.56–7.69 (3H, m), 7.69 (1H, br s).

Example 477

N-(3,5-Dichloro-1-oxido-4-pyridinyl)-3-(3,4,8,9-tetrahydro-6-methoxy-3,3,8,8-tetramethylfuro[2,3-h]isoquinolin-1-yl)benzamide Conc. sulfuric acid (0.393 mL, 7.38 mmol) was added to a mixture of 3-cyano-N-(3,5-dichloro-1-oxido-4-pyridinyl)benzamide (0.84 g, 2.84 mmol), 1-(2,3-dihydro-7-methoxy-2,2-dimethyl-5-benzofuranyl)-2-methyl-1-propanol (1.07 g, 4.26 mmol), acetic acid (7 mL) and toluene (10 mL) and the mixture was stirred at 80° C. for 1 hour. The reaction solution was cooled with ice, combined with water and washed with diethyl ether. The aqueous layer was made basic with aqueous ammonia and 1 M aqueous solution of sodium hydroxide, and washed with diisopropyl ether-diethyl ether (1:1). The aqueous layer was adjusted at pH 7 with 2 M hydrochloric acid, and extracted with ethyl acetate. The extract was washed with brine, dried over anhydrous magnesium sulfate, and concentrated under reduced pressure. The residue was subjected to a column chromatography on a silica gel (ethyl acetate followed by ethyl acetate/methanol, 23:2), and then crystallized from ethyl acetate to obtain the title compound (0.20 g, yield: 13%).

Melting point: 264–266° C.

$^1$H NMR (DMSO-d$_6$) δ 1.17 (6H, s), 1.22 (6H, s), 2.23 (2H, s), 2.67 (2H, s), 3.82 (3H, s), 6.84 (1H, s), 7.57–7.68 (2H, m), 8.01–8.09 (2H, m), 8.72 (2H, s), 10.58 (1H, br s).

Example 478
N-(2-Oxo-3-piperidinyl)-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and 3-amino-3,4,5,6-tetrahydro-2(1H)-pyridinone by the method similar to that in EXAMPLE 159. Yield: 63%

Amorphous.

$^1$H NMR (CDCl$_3$) δ 1.23 (3H, s), 1.28 (3H, s), 1.30 (6H, s), 1.58–1.80 (2H, m), 1.88–1.98 (2H, m), 2.18 (2H, s), 2.59–2.72 (3H, m), 3.27–3.38 (2H, m), 3.92 (3H, s), 4.40–4.50 (1H, m), 6.27 (1H, br s), 6.62 (1H, s), 7.33–7.36 (1H, m), 7.43–7.48 (1H, m), 7.88–7.95 (2H, m).

Example 479
(S)-N-[Hexahydro-2-oxo-1H-azepin-3-yl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and (S)-3-aminohexahydro-2H-azepin-2-one by the method similar to that in EXAMPLE 159. Yield: 65%.

Amorphous.

[α]D+23.1° (c 1.0, methanol)

$^1$H NMR (CDCl$_3$) δ 1.23 (3H, s), 1.30 (9H, s), 1.51–2.05 (6H, m), 2.16 (2H, s), 2.70 (2H, s), 3.20–3.38 (2H, m), 3.92 (3H, s), 4.68–4.78 (1H, m), 6.53 (1H, br s), 6.62 (1H, s), 7.42–7.51 (2H, m), 7.69–7.73 (1H, m), 7.88–7.92 (2H, m).

Example 480
(R)-N-[Hexahydro-2-oxo-1H-azepin-3-yl]-3-(3,4,8,9-tetrahydro-6-methoxy-3,3,8,8-tetramethylfuro[2,3-h]isoquinolin-1-yl)benzamide The title compound was obtained from 3-(3,4,8,9-tetrahydro-6-methoxy-3,3,8,8-tetramethylfuro[2,3-h]isoquinolin-1-yl)benzoic acid hydrochloride and (R)-3-aminohexahydro-2H-azepin-2-one by the method similar to that in EXAMPLE 159. Yield: 33%.

Amorphous.

[α]D–22.5° (c 1.0, methanol).

$^1$H NMR (CDCl$_3$) δ 1.23 (3H, s), 1.30 (9H, s), 1.51–2.25 (6H, m), 2.17 (2H, s), 2.70 (2H, s), 3.20–3.36 (2H, m), 3.92 (3H, s), 4.69–4.78 (1H, m), 6.29 (1H, br s), 6.62 (1H, s), 7.41–7.51 (2H, m), 7.69–7.73 (1H, m), 7.88–7.91 (2H, m).

Example 481
3-(6-Ethoxy-3,4,8,9-tetrahydro-3,3,8,8-tetramethylfuro[2,3-h]isoquinolin-1-yl)benzoic Acid Methyl Ester Conc. sulfuric acid (7.86 mL, 0.147 mol) was added to a mixture of 1-(7-ethoxy-2,3-dihydro-2,2-dimethyl-5-benzofuranyl)-2-methyl-1-propanol (15.0 g, 56.7 mmol), methyl 3-cyanobenzoate (9.14 g, 56.7 mmol), acetic acid (80 mL) and toluene (100 mL) and the mixture was stirred at 80° C. for 1 hour. The reaction mixture was cooled with ice and combined with water, and washed with diethyl ether. The aqueous layer was cooled with ice, made basic with conc. aqueous ammonium, and extracted with ethyl acetate. The extract was washed with water, and concentrated under reduced pressure. The residue was subjected to a column chromatography on a basic silica gel (hexane/ethyl acetate, 4:1) to obtain the title compound (9.00 g, yield: 39%).

Amorphous.

$^1$H NMR (CDCl$_3$) δ 1.25 (6H, s), 1.29 (6H, s), 1.47 (3H, t, J=7.0 Hz), 2.15 (2H, s), 2.68 (2H, s), 3.92 (3H, s), 4.18 (2H, q, J=7.0 Hz), 6.62 (1H, s), 7.47 (1H, t, J=8.0 Hz), 7.61 (1H, d, J=8.0 Hz), 8.05–8.08 (2H, m).

Example 482
3-(6-Ethoxy-3,4,8,9-tetrahydro-3,3,8,8-tetramethylfuro[2,3-h]isoquinolin-1-yl)benzoic Acid Hydrochloride 5 M aqueous solution of sodium hydroxide (12 mL) was added to a solution of 3-(6-ethoxy-3,4,8,9-tetrahydro-3,3,8,8-tetramethylfuro[2,3-h]isoquinolin-1-yl)benzoic acid methyl ester (8.80 g, 21.6 mmol) in methanol (40 mL) and the mixture was stirred at 50° C. for 12 hours. The reaction mixture was cooled with ice, combined with 5 M hydrochloric acid(17 mL), and concentrated under reduced pressure. The residue was combined with ethanol, filtered, and the filtrate was concentrated under reduced pressure repetitively for three times. The residue was crystallized from ethyl acetate to obtain the title compound (6.15 g, yield: 66%).

Melting point: 240–243° C.

$^1$H NMR (DMSO-d$_6$) δ 1.22 (6H, s), 1.37 (3H, t, J=7.0 Hz), 1.46 (6H, s), 2.02–2.25 (2H, m), 3.16 (2H, s), 4.24 (2H, q, J=7.0 Hz), 7.09 (1H, s), 7.76 (1H, t, J=7.8 Hz), 7.86 (1H, d, J=7.8 Hz), 8.16 (1H, s), 8.26 (1H, d, J=7.8 Hz).

Example 483
3-(6-Ethoxy-3,4,8,9-tetrahydro-3,3,8,8-tetramethylfuro[2,3-h]isoquinolin-1-yl)-N-methylbenzamide 1-Ethyl-3-(3-dimethylaminopropyl)carbodiimide hydrochloride (0.580 g, 3.03 mmol) was added to a suspension of 3-(6-ethoxy-3,4,8,9-tetrahydro-3,3,8,8-tetramethylfuro[2,3-h]isoquinolin-1-yl)benzoic acid hydrochloride (1.00 g, 2.33 mmol), 1-hydroxy-1H-benzotriazole monohydrate (0.392 g, 2.56 mmol) in N,N-dimethylformamide (10 mL) and the mixture was stirred at room temperature for 30 minutes. To this, 40% methylamine/methanol solution (1.2 mL) was added, and the mixture was stirred at room temperature further for 2 hours. The reaction solution was combined with water, and extracted with ethyl acetate. The extract was washed with water, and concentrated under reduced pressure. The residue was recrystallized from ethyl acetate-hexane to obtain the title compound (0.80 g, yield: 84%).

Melting point: 173–174° C.

$^1$H NMR (CDCl$_3$) δ 1.21 (6H, s), 1.28 (6H, s), 1.47 (3H, t, J=7.0 Hz), 2.13 (2H, s), 2.61 (2H, s), 2.94 (3H, d, J=5.2 Hz), 4.19 (2H, q, J=7.0 Hz), 6.60 (1H, s), 6.85–6.90 (1H, m), 7.38–7.44 (2H, m), 7.77 (1H, d, J=1.2 Hz), 7.85–7.90 (1 m).

Example 484
N-[2-Amino-2-oxoethyl]-3-(6-ethoxy-3,4,8,9-tetrahydro-3,3,8,8-tetramethylfuro[2,3-h]isoquinolin-1-yl)benzamide Triethylamine (0.810 mL, 5.83 mmol) was added to a suspension of 3-(6-ethoxy-3,4,8,9-tetrahydro-3,3,8,8-tetramethylfuro[2,3-h]isoquinolin-1-yl)benzoic acid hydrochloride (1.00 g, 2.33 mol) in tetrahydrofuran (10 mL) and the mixture was stirred at room temperature for 10 minutes. This was cooled with ice, treated dropwise with isobutyl chloroformate (0.362 mL, 2.80 mmol), and the mixture was stirred with cooling in ice for 45 minutes.

A solution of glycinamide hydrochloride (0.386 g, 3.50 mmol) dissolved in 2 M aqueous solution of sodium hydroxide (1.75 mL, 3.5 mmol) was added to the reaction mixture, and the mixture was stirred with cooling in ice for 3 hours. The reaction mixture was combined with an aqueous solution of sodium hydrogen carbonate, and extracted with ethyl acetate. The extract was washed with water, and concentrated under reduced pressure. The residue was crystallized from ethyl acetate-diethyl ether to obtain the title compound (0.82 g, yield: 75%).

Melting point: 127–128° C.

$^1$H NMR (CDCl$_3$) δ 1.22 (6H, s), 1.29 (6H, s), 1.47 (3H, t, J=7.0 Hz), 2.14 (2H, s), 2.64 (2H, s), 4.05 (2H, d, J=5.0

Hz), 4.18 (2H, q, J=7.0 Hz), 5.81 (1H, br s), 6.40 (1H, br s), 6.61 (1H, s), 7.41–7.50 (2H, m), 7.85–7.99 (3H, m).

Example 485

N-[3-(6-Ethoxy-3,4,8,9-tetrahydro-3,3,8,8-tetramethylfuro [2,3-h]isoquinolin-1-yl)benzoyl]-2-methylalanine Ethyl Ester Triethylamine (2.59 mL, 18.6 mmol) and 1-ethyl-3-(3-dimethylaminopropyl)carbodiimide hydrochloride (1.16 g, 6.05 mmol) were added to a solution of 3-(6-ethoxy-3,4,8, 9-tetrahydro-3,3,8,8-tetramethylfuro[2,3-h]isoquinolin-1-yl)benzoic acid hydrochloride (2.00 g, 4.65 mmol), 1-hydroxy-1H-benzotriazole monohydrate (0.784 g, 5.12 mmol) and ethyl 2-aminoisobutyrate hydrochloride (1.05 g, 6.05 mmol) in N,N-dimethylformamide (20 mL) and the mixture was stirred at room temperature for 3 hours. The reaction mixture was combined with water and extracted with ethyl acetate. The extract was washed with water, and concentrated under reduced pressure. The residue was recrystallized from ethyl acetate-hexane to obtain the title compound (1.82 g, yield: 77%).

Melting point: 155–156° C.
$^1$H NMR (CDCl$_3$) δ 1.24–1.30 (15H, m), 1.47 (3H, t, J=7.0 Hz), 1.66 (6H, s), 2.16 (2H, s), 2.68 (2H, s), 4.13–4.28 (4H, m), 6.61 (1H, s), 6.93 (1H, s), 7.42–7.50 (2H, m), 7.83–7.89 (2H, m).

Example 486

N-[3-(6-Ethoxy-3,4,8,9-tetrahydro-3,3,8,8-tetramethylfuro [2,3-h]isoquinolin-1-yl)benzoyl]-2-methylalanine Hydrochloride 5 M aqueous solution of sodium hydroxide (3.0 mL) was added to a solution of N-[3-(6-ethoxy-3,4,8,9-tetrahydro-3, 3,8,8-tetramethylfuro[2,3-h]isoquinolin-1-yl)benzoyl]-2-methylalanine ethyl ester (1.25 g, 2.47 mmol) in ethanol (7 mL) and the mixture was stirred at room temperature for 3 hours. The reaction solution was combined with 5 M hydrochloric acid (3.7 mL), and concentrated under reduced pressure. The residue was combined with ethanol and filtered, and the filtrate was concentrated under reduced pressure repetitively 3 times. The residue was crystallized from ethyl acetate to obtain the title compound (1.28 g, quantitative).

Melting point: 234–238° C.
$^1$H NMR (DMSO-d$_6$) δ 1.22 (12H, s), 1.34 (3H, t, J=6.9 Hz), 1.45 (6H, s), 2.19 (2H, s), 2.72 (2H, s), 4.12 (2H, q, J=6.9 Hz), 6.85 (1H, s), 7.51–7.53 (2H, m), 7.92–7.96 (2H, m), 8.61 (1H, s).

Example 487

N-(2-Amino-1,1-dimethyl-2-oxoethyl)-3-(6-ethoxy-3,4,8,9-tetrahydro-3,3,8,8-tetramethylfuro[2,3-h]isoquinolin-1-yl) benzamides A solution of N-[3-(6-ethoxy-3,4,8,9-tetrahydro-3,3,8,8-tetramethylfuro[2,3-h]isoquinolin-1-yl)benzoyl]-2-methylalanine hydrochloride (0.80 g, 1.55 mmol), 1-hydroxy-1H-benzotriazole ammonium salt (0.307 g, 2.02 mmol) in N,N-dimethylformamide (8 mL) was cooled with ice, 1-ethyl-3-(3-dimethylaminopropyl)carbodiimide hydrochloride (0.387 g, 2.02 mmol) was added thereto, and the mixture was stirred with cooling in ice for 30 minutes. Triethylamine (0.541 mL, 3.88 mmol) was added to the reaction mixture, and the mixture was stirred at room temperature for 4 hours. The reaction mixture was combined with a small amount of water, and concentrated under reduced pressure. The residue was combined with a saturated aqueous solution of sodium hydrogen carbonate, and extracted with ethyl acetate. The extract was washed with water, and concentrated under reduced pressure The residue was crystallized from ethyl acetate-hexane to obtain the title compound (0.50 g, yield: 68%).

Melting point: 204–206° C.
$^1$H NMR (CDCl$_3$) δ 1.25 (6H, s), 1.30 (6H, s), 1.47 (3H, t, J=6.9 Hz), 1.69 (6H, s), 2.17 (2H, s), 2.68 (2H, s), 4.18 (2H, q, J=6.9 Hz), 5.54 (1H, br s), 6.50 (1H, br s), 6.61 (1H, s), 7.07 (1H, s), 7.42–7.49 (2H, m), 7.85–7.89 (2H, m).

Example 488

3-(6-Ethoxy-3,4,8,9-tetrahydro-3,3,8,8-tetramethylfuro[2,3-h]isoquinolin-1-yl)benzenamine A mixture of 1-(7-ethoxy-2,3-dihydro-2,2-dimethyl-5-benzofuranyl)-2-methyl-1-propanol (11.2 g, 42.3 mmol), 3-aminobenzonitrile (5.00 g, 42.3 mmol), acetic acid (60 mL) and toluene (75 mL) was cooled with ice, conc. sulfuric acid (6.77 mL, 0.127 mol) was added thereto, and the mixture was stirred at 80° C. for 1 hour. The reaction solution was allowed to cool to room temperature, combined with water, and washed with diethyl ether. The aqueous layer was made basic with conc. aqueous ammonia, and then extracted with ethyl acetate. The extract was washed with water, and concentrated under reduced pressure. The residue was subjected to a column chromatography on a basic silica gel (hexane/ethyl acetate 2:1) to obtain the title compound (8.17 g, yield: 53%).

An oil.
$^1$H NMR (CDCl$_3$) δ 1.23 (6H, s), 1.32 (6H, s), 1.46 (3H, t, J=7.0 Hz), 2.32 (2H, s), 2.65 (2H, s), 3.70 (2H, br s), 4.16 (2H, q, J=7.0 Hz), 6.58 (1H, s), 6.70–7.21 (4H, m).

Example 489

N-[3-(6-Ethoxy-3,4,8,9-tetrahydro-3,3,8,8-tetramethylfuro [2,3-h]isoquinolin-1-yl)phenyl]methanesulfonamide A solution of 3-(6-ethoxy-3,4,8,9-tetrahydro-3,3,8,8-tetramethylfuro[2,3-h]isoquinolin-1-yl)benzenamine (0.73 g, 2.00 mmol) in pyridine (5 mL) was cooled with ice, treated dropwise with methanesulfonyl chloride (0.186 mL, 2.40 mmol), and the mixture was stirred with cooling in ice for 1 hour. The reaction solution was combined with a saturated aqueous solution of sodium hydrogen carbonate and extracted with ethyl acetate. The extract was washed with water and concentrated under reduced pressure. The residue was subjected to a column chromatography on a basic silica gel (ethyl acetate/methanol 97:3), crystallized from ethyl acetate-hexane to obtain the title compound (0.52 g, yield: 59%).

Melting point: 181–182° C.
$^1$H NMR (CDCl$_3$) δ 1.27 (6H br s), 1.32 (6H, s), 1.46 (3H, t, J=7.2 Hz), 2.23 (2H, s), 2.71 (2H, s), 2.77 (3H, s), 4.18 (2H, q, J=7.2 Hz), 6.60 (1H, s), 7.08–7.14 (1H, m), 7.22–7.35 (4H, m).

Example 490

N-[3-(6-Ethoxy-3,4,8,9-tetrahydro-3,3,8,8-tetramethylfuro [2,3-h]isoquinolin-1-yl)phenyl]-N-(methylsulfonyl) methanesulfonamide The title compound was obtained from 3-(6-ethoxy-3,4, 8,9-tetrahydro-3,3,8,8-tetramethylfuro[2,3-h]isoquinolin-1-yl)benzenamine and methanesulfonyl chloride by the method similar to that in EXAMPLE 30. Yield: 53%.

Melting point: 183–184° C. (ethyl acetate-hexane).
$^1$H NMR (CDCl$_3$) δ 1.25 (6H, s), 1.31 (6H, s), 1.46 (3H, t, J=10 6.9 Hz), 2.23 (2H, br s), 2.68 (2H, s), 3.40 (6H, s), 4.18 (2H, q, J=6.9 Hz), 6.61 (1H, s), 7.29 (1H, t, J=1.5 Hz), 7.35–7.40 (1H, m), 7.52 (1H, t, J=7.8 Hz), 7.61 (1H, dt, J=7.8 Hz, 1.5 Hz).

Example 491
N-[3-(6-Ethoxy-3,4,8,9-tetrahydro-3,3,8,8-tetramethylfuro[2,3-h]isoquinolin-1-yl)phenyl]-2-(methylthio)acetamide By the method similar to that in EXAMPLE 30, 3-(6-ethoxy-3,4,8,9-tetrahydro-3,3,8,8-tetramethylfuro[2,3-h]isoquinolin-1-yl)benzenamine and chloroacetyl chloride were employed to obtain 2-chloro-N-[3-(6-ethoxy-3,4,8,9-tetrahydro-3,3,8,8-tetramethylfuro[2,3-h]isoquinolin-1-yl)phenyl]acetamide. This was converted to the title compound by the method similar to that in EXAMPLE 38. yield: 50%.

Melting point: 162–163° C. (ethyl acetate-hexane).

$^1$H NMR (CDCl$_3$) δ 1.24 (6H, s), 1.32 (6H, s), 1.46 (3H, t, J=6.9 Hz), 2.19 (3H, s), 2.28 (2H, s), 2.67 (2H, s), 3.34 (2H, s), 4.18 (2H, q, J=6.9 Hz), 6.60 (1H, s), 7.12 (1H, d, J=7.2 Hz), 7.36 (1H, t, J=7.2 Hz), 7.43 (1H, s), 7.84 (1H, d, J=7.2 Hz), 8.82 (1H, s).

Example 492
N-[3-(6-Ethoxy-3,4,8,9-tetrahydro-3,3,8,8-tetramethylfuro[2,3-h]isoquinolin-1-yl)phenyl]-2-(methylsulfinyl)acetamide The title compound was obtained from N-[3-(6-ethoxy-3,4,8,9-tetrahydro-3,3,8,8-tetramethylfuro[2,3-h]isoquinolin-1-yl)phenyl]-2-(methylthio)acetamide by the method similar to that in EXAMPLE 39. Yield: 67%.

Melting point: 114–118° C. (ethyl acetate-hexane).

$^1$H NMR (CDCl$_3$) δ 1.13 (6H, s), 1.22 (6H, s), 1.33 (3H, t, J=7.0 Hz), 2.28 (2H, s), 2.62 (2H, s), 2.69 (3H, s), 3.73 (1H, d, J=12.8 Hz), 3.93 (1H, d, J=12.8 Hz), 4.09 (2H, q, J=7.0 Hz), 6.78 (1H, s), 7.06 (1H, d, J=7.6 Hz), 7.32–7.39 (1H, m), 7.61–7.65 (2H, m), 10.40 (1H, s).

Example 493
N-(Hydroxymethyl)-3-(3,4,8,9-tetrahydro-6-methoxy-3,3,8,8-tetramethylfuro[2,3-h]isoquinolin-1-yl)benzamide A suspension of 3-(3,4,8,9-tetrahydro-6-methoxy-3,3,8,8-tetramethylfuro[2,3-h]isoquinolin-1-yl)benzamide (0.50 g, 1.32 mmol), 37% formalin (1.07 g, 13.2 mmol) and potassium carbonate (0.365 g, 2.64 mmol) in acetonitrile (5 mL) was stirred at 60° C. for 3 hours, and then allowed to stand for 1 month. The reaction mixture was combined with a saturated aqueous solution of sodium hydrogen carbonate, and extracted with ethyl acetate. The extract was washed with water, and concentrated under reduced pressure. The residue was subjected to a column chromatography on a silica gel (ethyl acetate/methanol 19:1) to obtain the title compound (0.40 g, yield: 74%).

Amorphous.

$^1$H NMR (CDCl$_3$) δ 1.23 (6H, s), 1.29 (6H, s), 2.14 (2H, s), 2.65 (2H, s), 3.93 (3H, s), 4.87 (2H, d, J=6.2 Hz), 6.62 (1H, s), 7.39–7.48 (2H, m), 7.83–7.89 (2H, m), 8.05–8.11 (1H, m).

Example 494
N-Methyl-3-(3,4,8,9-tetrahydro-4-hydroxy-6-methoxy-3,3,8,8-tetramethylfuro[2,3-h]isoquinolin-1-yl)benzamide The title compound was obtained from N-methyl-3-(3,4,8,9-tetrahydro-6-methoxy-3,3,8,8-tetramethylfuro[2,3-h]isoquinolin-1-yl)benzamide by the method similar to that in EXAMPLE 291. yield: 35%.

Melting point: 215–216° C. (ethyl acetate).

$^1$H NMR (CDCl$_3$) δ 1.25 (6H, s), 1.29 (6H, s), 2.16 (2H, s), 2.95 (3H, d, J=4.4 Hz), 3.95 (3H, s), 4.44 (1H, s), 6.98 (1H, s), 7.18 (1H, br s), 7.42–7.50 (2H, m), 7.81 (1H, s), 7.87–7.91 (1H, m).

Example 495
N-Methyl-3-(3,4,8,9-tetrahydro-6-methoxy-3,3,8,8-tetramethyl-4-oxofuro[2,3-h]isoquinolin-1-yl)benzamide The title compound was obtained from N-methyl-3-(3,4,8,9-tetrahydro-4-hydroxy-6-methoxy-3,3,8,8-tetramethylfuro[2.3-h]isoquinolin-1-yl)benzamide by the method similar to that in EXAMPLE 294. Yield: 45%.

Melting point: 229–231° C. (ethyl acetate-diisopropyl ether).

$^1$H NMR (CDCl$_3$) δ 1.34 (6H, s), 1.52 (6H, s), 2.17 (2H, s), 3.00 (3H, d, J=4.8 Hz), 4.00 (3H, s), 6.36–6.48 (1H, m), 7.44–7.59 (3H, m), 7.78 (1H, s), 7.85–7.91 (1H, m).

Example 496
N-(2-Amino-1,1-dimethyl-2-oxoethyl)-3-(3,4,8,9-tetrahydro-4-hydroxy-6-methoxy-3,3,8,8-tetramethylfuro[2,3-h]isoquinolin-1-yl)benzamide The title compound was obtained from N-(2-amino-1,1-dimethyl-2-oxoethyl)-3-(3,4,8,9-tetrahydro-6-methoxy-3,3,8,8-tetramethylfuro[2,3-h]isoquinolin-1-yl)benzamide by the method similar to that in EXAMPLE 291. Yield: 64%.

Melting point: 155–158° C. (ethyl acetate).

$^1$H NMR (CDCl$_3$) δ 1.25–1.31 (12H, m), 1.69 (6H, s), 2.20 (2H, s), 3.96 (3H, s), 4.48 (1H, s), 5.82 (1H, br s), 6.77 (1H, br s), 7.03 (1H, s), 7.43–7.52 (3H, m), 7.91 (2H, s).

Example 497
N-(2-Amino-1,1-dimethyl-2-oxoethyl)-3-(3,4,8,9-tetrahydro-6-methoxy-3,3,8,8-tetramethyl-4-oxofuro[2,3-h]isoquinolin-1-yl)benzamide The title compound was obtained from N-(2-amino-1,1-dimethyl-2-oxoethyl)-3-(3,4,8,9-tetrahydro-4-hydroxy-6-methoxy-3,3,8,8-tetramethylfuro[2,3-h]isoquinolin-1-yl)benzamide by the method similar to that in EXAMPLE 294. yield: 52%.

Melting point: 180–181° C. (ethyl acetate).

$^1$H NMR (DMSO-d$_6$) 1.26 (6H, s), 1.41 (6H, s), 1.45 (6H, s), 2.24 (2H, s), 3.91 (3H, s), 6.85 (1H, br s), 7.19 (1H, br s), 7.47–7.55 (3H, m), 7.90–7.98 (2H, m), 8.29 (1H, br s).

Example 498
3-(Bromomethyl)-6-ethoxy-3,4,8,9-tetrahydro-3,8,8-trimethyl-1-phenylfuro(2,3-h)isoquinoline hydrochloride Benzonitrile (20 mL) was cooled to −5° C., aluminum chloride (2.38 g, 17.9 mmol) was added thereto and the mixture was stirred.

Immediately after adding 7-ethoxy-2,3-dihydro-2,2-dimethyl-5-(2-methyl-2-propenyl)benzofuran (2.20 g, 8.93 mmol), bromine (0.46 mL, 8.93 mmol) was added dropwise to the mixture, and the mixture was stirred at −5° C. for 1 hour and then at room temperature further for 3 hours. The reaction mixture was poured into 1 M hydrochloric acid, and washed with diisopropyl ether. The aqueous layer was made basic with conc. aqueous ammonia, and extracted with ethyl acetate. The extract was washed with water, and concentrated under reduced pressure. The residue was subjected to a column chromatography on a silica gel (hexane/ethyl acetate 17:3 followed by 7:3) to obtain 3-(bromomethyl)-6-ethoxy-3,4,8,9-tetrahydro-3,8,8-trimethyl-1-phenylfuro[2,3-h]isoquinoline (1.41 g, yield: 37%).

An oil.

$^1$H NMR (CDCl$_3$) δ 1.31 (6H, s), 1.34 (3H, s), 1.47 (3H, t, J=7.2 Hz), 2.18 (2H, s), 2.78 (1H, d, J=15.9 Hz), 2.93 (1H, d, J=15.9 Hz), 3.40 (1H, d, J=9.9 Hz), 3.55 (1H, d, J=9.9 Hz), 4.19 (2H, q, J=7.2 Hz), 6.65 (1H, s), 7.39 (5H, s).

This was converted into a hydrochloride salt which was triturated from diethyl ether to obtain the title compound (1.40 g, yield from 7-ethoxy-2.3-dihydro-2,2-dimethyl-5-(2-methyl-2-propenyl)benzofuran: 34%). An aliquot was crystallized from ethyl acetate.

Melting point: 156–159° C.

$^1$H NMR-(DMSO-$d_6$) δ 1.22 (3H, s), 1.24 (3H, s), 1.37 (3H, t, J=6.9 Hz), 1.59 (3H, s), 2.17 (2H, s), 3.35 (2H, s), 3.83 (1H, d, J=10.8 Hz), 3.92 (1H, d, J=10.8 Hz), 4.24 (2H, q, J=6.9 Hz), 7.11 (1H, s), 7.59–7.78 (5H, m).

Example 499

6-Ethoxy-3,4,8,9-tetrahydro-N,N,3,8,8-pentamethyl-3-furo[2,3-h]isoquinolinemethanamine Dihydrochloride A mixture of 3-(bromomethyl)-6-ethoxy-3,4,8,9-tetrahydro-3,8,8-trimethylfuro[2,3-h]isoquinoline hydrochloride (0.50 g, 1.08 mmol), 40% aqueous solution of methylamine (2 mL) and N,N-dimethylacetamide (3 mL) was stirred at 180° C. for 14 hours in a sealed tube. The reaction solution was combined with a saturated aqueous solution of sodium hydrogen carbonate, and extracted with ethyl acetate. The extract was washed with water, and concentrated under reduced pressure. The residue was subjected to a column chromatography on a silica gel (hexane/ethyl acetate 1:1 followed by hexane/ethyl acetate/triethylamine 92:5:3), and then to a column chromatography on a basic silica gel (hexane/ethyl acetate 4:1) to obtain 6-ethoxy-3,4,8,9-tetrahydro-N,N,3,8,8-pentamethyl-3-furo[2,3-h]isoquinolinemethanamine (0.22 g, yield: 52%).

An oil.

$^1$H NMR (CDCl$_3$) δ 1.22–1.32 (9H, m), 1.45 (3H, t, J=7.0 Hz), 2.18 (2H, s), 2.31 (6H, s), 2.35–2.51 (2H, m), 2.64 (1H, d, J=15.6 Hz), 2.97 (1H, d, J=15.6 Hz), 4.17 (2H, q, J=7.0 Hz), 6.62 (1H, s), 7.38 (5H, s).

This was converted into a hydrochloride salt, crystallized from ethyl acetate to obtain the title compound (0.20 g, yield from 3-(bromomethyl)-6-ethoxy-3,4,8,9-tetrahydro-3,8,8-trimethylfuro[2,3-h]isoquinoline hydrochloride: 40%).

Melting point: 145–147° C.

$^1$H NMR (DMSO-$d_6$) δ 1.23 (3H, s), 1.25 (3H, s), 1.38 (3H, t, J=6.9 Hz), 1.54–1.62 (3H, m), 2.11 (1H, d, J=16.2 Hz), 2.28 (1H, d, J=16.2 Hz), 2.91 (6H, s), 3.20 (2H, s), 3.60 (2H, s), 4.23 (2H, q, J=6.9 Hz), 7.03 (1H, s), 7.59–7.69 (5H, m).

Example 500

6-Ethoxy-N-ethyl-3,4,8,9-tetrahydro-N,3,8,8-tetramethyl-3-furo[2,3-h]isoquinolinemethanamine Dihydrochloride The title compound was obtained from 3-(bromomethyl)-6-ethoxy-3,4,8,9-tetrahydro-3,8,8-trimethylfuro[2,3-h]isoquinoline hydrochloride and N-ethylmethylamine by the method similar to that in EXAMPLE 499. Yield: 33%.

Melting point: 146–149° C. (ethyl acetate).

$^1$H NMR (DMSO-$d_6$) δ 1.23 (6H, s), 1.27 (3H, t, J=7.4 Hz), 1.38 (3H, t, J=6.8 Hz), 1.58 (3H, s), 2.13 (1H, d, J=16.4 Hz), 2.26 (1H, d, J=16.4 Hz), 2.89 (3H, s), 3.20–3.61 (6H, m), 4.23 (2H, q, J=6.8 Hz), 7.03 (1H, s), 7.60–7.65 (5H, m).

Example 501

O-[3-(3,4,8,9-Tetrahydro-6-methoxy-3,3,8,8-tetramethylfuro[2,3-h]isoquinolin-1-yl)phenyl] dimethylcarbamothioate Hydrochloride 3-(3,4,8,9-Tetrahydro-6-methoxy-3,3,8,8-tetramethylfuro[2,3-h]isoquinolin-1-yl)phenol (3.50 g, 9.96 mmol) was added to a solution of potassium hydroxide (587 mg, 10.5 mmol) in water (30 mL)-acetone (30 mL), and the mixture was stirred at room temperature for 20 minutes. With cooling in ice, N,N-dimethythiocarbamoyl chloride (1.42 g, 11.5 mmol) was added to the mixture, and the mixture was stirred at room temperature for 3 hours. Acetone was distilled off under reduced pressure, the mixture was made basic by adding 1 M aqueous solution of sodium hydroxide, and extracted twice with ethyl acetate. The combined organic layer was washed with 1 M aqueous solution of sodium hydroxide and brine, dried over sodium sulfate, filtered, and concentrated under reduced pressure. The residue was subjected to a column chromatography on a basic silica gel (hexane/ethyl acetate 5:1 followed by 3:1) to obtain 3.40 g of a free base of the title compound. 753 mg of them was dissolved in ethyl acetate, combined with 4 M hydrogen chloride/ethyl acetate solution, concentrated under reduced pressure, triturated from diethyl ether to obtain the title compound (745 mg, yield: 57%).

Amorphous.

$^1$H NMR (DMSO-$d_6$) δ 1.23 (6H, s), 1.41 (3H, s), 1.47 (3H, s), 2.05–2.75 (2H, m), 3.17 (2H, s), 3.20–3.50 (6H, m), 3.94 (3H, s), 7.09 (1H, s), 7.37–7.54 (3H, m), 7.67–7.74 (1H, m), 12.70 (1H, br s).

Example 502

2-[3-(3,4,8,9-Tetrahydro-6-methoxy-3,3,8,8-tetramethylfuro[2,3-h]isoquinolin-1-yl)phenoxy]acetamide Potassium tert-butoxide (380 mg, 3.37 mmol) was added to a solution of 3-(3,4,8,9-tetrahydro-6-methoxy-3,3,8,8-tetramethylfuro[2,3-h]isoquinolin-1-yl)phenol (215 mg, 0.612 mmol) in N,N-dimethylformamide (2 mL) with cooling in ice, and the mixture was stirred at room temperature for 1 hour. 2-Bromoacetamide (279 mg, 2.02 mmol) was added and the mixture was stirred at room temperature for 2 hours, and then stirred at 90° C. for 24 hours. Water was poured into the reaction mixture, which was then extracted twice with ethyl acetate. The combined organic layer was washed with 1 M aqueous solution of sodium hydroxide and brine, dried over sodium sulfate, filtered, and concentrated under reduced pressure. The residue was subjected to a column chromatography on a basic silica gel (hexane/ethyl acetate 1:2 followed by hexane/ethyl acetate/triethylamine 15:30:1), crystallized from diethyl ether-hexane to obtain the title compound (130 mg, yield: 52%).

Melting point: 172–174° C.

$^1$H NMR (CDCl$_3$) δ 1.25 (6H, s), 1.32 (6H, s), 2.24 (2H, br s), 2.69 (2H, s), 3.93 (3H, s), 4.53 (2H, s), 5.63 (1H, br s), 6.60 (1H, br s), 6.62 (1H s), 6.93–7.05 (3H, m), 7.29–7.37 (1H, m).

Example 503

N-Methyl-3-(3,4,8,9-tetrahydro-6-methoxy-3,3,8,8-tetramethylfuro[2,3-h]isoquinolin-1-yl)benzenesulfonamide Hydrochloride A suspension of 3-cyano-N-methylbenzenesulfonamide (2.10 g, 10.7 mmol) in acetic acid (10 mL)-toluene (17 mL) was treated with conc. sulfuric acid (1.2 mL, 22.5 mmol) with cooling in ice, 1-(2,3-dihydro-7-methoxy-2,2-dimethyl-5-benzofuranyl)-2-methyl-1-propanol (3.20 g, 12.8 mmol) was added thereto at room temperature, and the mixture was stirred at 80° C. for 1 hour. Ice water was poured into the reaction mixture, which was then washed with diethyl ether. The aqueous layer was neutralized with conc. aqueous ammonia, and extracted twice with ethyl acetate. The combined organic layer was washed with brine, dried over sodium sulfate, filtered, and concentrated under reduced pressure. The residue was subjected to a column chromatography on a silica gel (hexane/ethyl acetate 1:1 followed by hexane/ethyl acetate/triethylamine 25:25:1) to obtain a free base of the title compound. This was dissolved in ethyl acetate, combined with 4 M hydrogen chlorlde/ethyl acetate solution, concentrated under reduced pressure, and crystallized from ethanol-ethyl acetate to obtain the title compound (3.19 g, yield: 64%).

Melting point: 164–167° C.

$^1$H NMR (DMSO-$d_6$) δ 1.22 (6H, s), 1.46 (6H, br s), 2.13 (2H, s), 2.45 (3H, d, J=4.8 Hz), 3.04–3.30 (3H, m), 3.95 (3H, s), 7.11 (1H, s), 7.76–8.26 (4H, m).

Example 504
2-[(Methyl)[[(3,4,8,9-tetrahydro-6-methoxy-3,3,8,8-tetramethylfuro[2,3-h]isoquinolin-1-yl)phenyl]sulfonyl]amino]acetic Acid Ethyl Ester Hydrochloride Sodium hydride (66% dispersion in oil) (148 mg, 4.07 mmol) was added to a solution of N-methyl-3-(3,4,8,9-tetrahydro-6-methoxy-3,3,8,8-tetramethylfuro[2,3-h]isoquinolin-1-yl)benzenesulfonamide hydrochloride (900 mg, 1.94 mmol) in N,N-dimethylformamide (9 mL) with cooling in ice, and the mixture was stirred at room temperature for 30 minutes. With cooling in ice, ethyl bromoacetate (0.23 mL, 2.03 mmol) was added to the mixture and the mixture was stirred at room temperature for 5 hours. Water was poured into the reaction mixture, which was extracted twice with ethyl acetate. The combined organic layer was washed with water and brine, dried over sodium sulfate, filtered, and concentrated under reduced pressure. The residue was subjected to a column chromatography on a basic silica gel (hexane/ethyl acetate 3:1) to obtain a free base of the title compound. This was dissolved in ethyl acetate, combined with 4 M hydrogen chloride/ethyl acetate solution, concentrated under reduced pressure, crystallized from ethyl acetate to obtain the title compound (680 mg, yield: 64%).

Melting point: 122–125° C.

$^1$H NMR (DMSO-$d_6$) δ 1.17 (3H, t, J=7.0 Hz), 1.22 (6H, s), 1.46 (6H, br s), 2.17 (2H, s), 2.87 (3H, s), 3.17 (2H, s), 3.94 (3H, s), 4.06 (2H, q, J=7.0 Hz), 4.12 (2H, s), 7.11 (1H, s), 7.81–7.92 (2H, m), 8.09–8.13 (2H, m).

Example 505
2-[(Methyl)[[3-(3,4,8,9,-tetrahydro-6-methoxy-3,3,8,8-tetramethylfuro[2,3-h]isoquinolin-1-yl)phenyl]sulfonyl]amino]acetamide 5 M aqueous solution of sodium hydroxide (1.5 mL) was added to a solution of 2[-(methyl)-[[(3,4,8,9-tetrahydro-6-methoxy-3,3,8,8-tetramethylfuro[2,3-h]isoquinolin-1-yl)phenyl]sulfonyl]amino]acetic acid ethyl ester hydrochloride (464 mg, 0.842 mmol) in ethanol (1.5 mL) and the mixture was stirred at room temperature for 1 hour. After distilling ethanol off under reduced pressure, water was added and the mixture was adjusted at pH 6 with 5 M hydrochloric acid, and extracted twice with ethyl acetate-tetrahydrofuran. The combined organic layer was dried over sodium sulfate, filtered, concentrated under reduced pressure to obtain 2-[(methyl)[[3-(3,4,8,9-tetrahydro-6-methoxy-3,3,8,8-tetramethylfuro[2,3-h]isoquinolin-1-yl)phenyl]sulfonyl]amino] acetic acid (394 mg). 1-Ethyl-3-(3-dimethylaminopropyl)carbodiimide hydrochloride (199 mg, 1.04 mmol) and 1-hydroxy-1H-benzotriazole monohydrate (123 mg, 0.802 mmol) were added to a solution of the resultant acetic acid derivative (390 mg) in N,N-dimethylformamide (2 mL) and the mixture was stirred at room temperature for 30 minutes. After cooling with ice, conc. aqueous ammonia (0.5 mL) was added to the mixture, and the mixture was stirred at room temperature for 1 hour. Water was poured into the reaction mixture, which was then extracted twice with ethyl acetate-tetrahydrofuran. The combined organic layer was washed with a brine, dried over sodium sulfate, filtered, and concentrated under reduced pressure. The residue was subjected to a column chromatography on a basic silica gel (hexane/ethyl acetate 3:1), crystallized from ethyl acetate-hexane to obtain the title compound (55 mg, yield: 14%).

Melting point: 105–107° C.

$^1$H NMR (CDCl$_3$) δ 1.26 (6H, s), 1.33 (6H, s), 2.16 (2H, s), 2.72 (2H, s), 2.86 (3H, s), 3.66 (2H, s), 3.93 (3H, s), 5.58 (1H, br s), 6.58 (1H, br s), 6.64 (1H, s), 7.59–7.86 (4H, m).

Example 506
N-[3-[[[3-(3,4,8,9-Tetrahydro-6-methoxy-3,3,8,8-tetramethylfuro[2,3-h]isoquinolin yl)phenyl]sulfonyl]amino]phenyl]acetamide Hydrochloride A solution of N-[3[(3-cyanophenylsulfonyl)amino]phenyl]acetamide (1.39 g, 4.41 mmol) in acetic acid (5 mL)-toluene (8 mL) was treated dropwise with conc. sulfuric acid (0.52 mL, 9.70 mmol) with cooling in ice, and 1-(2,3-dihydro-7-methoxy-2,2-dimethyl-5-benzofuranyl)-2-methyl-1-propanol (1.32 g, 5.29 mmol) was added thereto at room temperature, and the mixture was stirred at 60° C. for 3 hours. Ice water was poured into the reaction mixture, which was washed with diethyl ether. The aqueous layer was neutralized with conc. aqueous ammonia, and extracted twice with ethyl acetate. The combined organic layer was washed with brine, dried over sodium sulfate, filtered and concentrated under reduced pressure. The residue was subjected to a column chromatography on a silica gel (hexane/ethyl acetate 1:2 followed by 1:3) to obtain a free base of the title compound. This was dissolved in ethyl acetate, combined with 4 M hydrogen chloride/ethyl acetate solution, concentrated under reduced pressure, triturated from diethyl ether to obtain the title compound (815 mg, yield: 48%).

Amorphous.

$^1$H NMR (DMSO-$d_6$) δ 1.09 (6H, s), 1.45 (6H, s), 1.73–2.00 (2H, m), 1.94 (3H, s), 3.17 (2H, s), 3.93 (3H, s), 6.65–6.78 (1H, m), 7.10–7.13 (3H, m), 7.66 (1H, s), 7.80–7.90 (2H, m), 8.05–8.20 (2H, m), 10.05 (1H, s), 10.58 (1H, s).

Example 507
2-[[[3-(3,4,8,9-Tetrahydro-6-methoxy-3,3,8,8-tetramethylfuro[2,3-h]isoquinolin-1-yl)phenyl]sulfonyl]amino]acetamide Hydrochloride A suspension of 2-[[(3-cyanobenzene)sulfonyl]amino]acetamide (180 mg, 0.752 mmol) in acetic acid (1 ml)-toluene (1.6 mL) was treated dropwise with conc. sulfuric acid (0.088 mL, 1.65 mmol) with cooling in ice, 1-(2,3-dihydro-7-methoxy-2,2-dimethyl-5-benzofuranyl)-2-methyl-1-propanol (226 mg, 0.903 mmol) was added thereto at room temperature, and the mixture was stirred at 60° C. for 2 hours. Water was poured into the reaction mixture, which was washed twice with diethyl ether. The aqueous layer was neutralized with conc. aqueous ammonia, and extracted twice with ethyl acetate. The combined organic layer was washed with brine, dried over sodium sulfate, filtered and concentrated under reduced pressure. The residue was subjected to a column chromatography on a silica gel (ethyl acetate followed by ethyl acetate/methanol 10:1) to obtain a free base of the title compound. This was dissolved in ethyl acetate, combined with 4 M hydrogen chloride/ethyl, acetate solution, concentrated under reduced pressure, triturated from diethyl ether to obtain the title compound (189 mg, yield: 50%).

Amorphous.

$^1$H NMR (DMSO-$d_6$) δ 1.22 (6H, s), 1.46 (6H, br s), 2.00–2.30(2H, m), 3.17 (2H, s), 3.30–3.60 (2H, m), 3.94 (3H, s), 7.10 (2H, s), 7.42 (1H, s), 7.80–7.87 (2H, m), 8.04 (1H, s), 8.11–8.25 (2H, m).

Example 508
N-(Hexahydro-2-oxo-1H-azepin-3-yl)-3-(3,4,8,9-tetrahydro-6-methoxy-3,3,8,8-tetramethylfuro[2,3-h]isoquinolin-1-yl)benzenesulfonamide Hydrochloride A suspension of 3-cyano-N-(hexahydro-2-oxo-1H-azepin-3-yl)benzenesulfonamide (360 mg, 1.23 mmol) in acetic acid (2 mL)-toluene (3.2 mL) was treated dropwise with conc. sulfuric acid (0.14 mL, 2.71 mmol) with cooling in ice, and stirred at room temperature for 5 minutes. 1-(2,3-dihydro-7-methoxy-2,2-dimethyl-5-benzofuranyl)-2-methyl-1-propanol (369 mg, 1.47 mmol) was added to the mixture, and the mixture was stirred at 65° C. for 3 hours. Water was poured into the reaction mixture, which was washed twice with diethyl ether. The aqueous layer was neutralized with conc. aqueous ammonia, and extracted twice with ethyl acetate. The combined organic layer was washed with brine, dried over sodium sulfate, filtered and concentrated under reduced pressure. The residue was subjected to a column chromatography on a basic silica gel (hexane/ethyl acetate 1:2) to obtain a free base of the title compound. This was dissolved in ethyl acetate, combined with 4 M hydrogen chloride/ethyl acetate solution, concentrated under reduced pressure, triturated with diethyl ether to obtain the title compound (270 mg, yield: 39%).

Amorphous.

$^1$H NMR (DMSO-$d_6$) δ 1.22 (6H, s), 1.44 (3H, s), 1.45–1.85 (4H, m), 1.47 (3H, s), 2.00–2.35 (2H, m), 2.90–3.15 (2H, m), 3.16 (2H, s), 3.39–3.45 (2H, m), 3.94 (3H, s), 4.00–4.15 (1H, m), 7.10 (1H, s), 7.65–7.90 (2H, m), 7.82 (2H, br s), 8.03–8.20 (2H, m).

Example 509

S-[3-(3,4,8,9-Tetrahydro-6-methoxy-3,3,8,8-tetramethylfuro[2,3-h]isoquinolin-1-yl)phenyl] dimethylcarbamothioate Hydrochloride A suspension of S-(3-cyanophenyl) dimethylcarbamothioate (637 mg, 3.09 mmol) in acetic acid (4 mL)-toluene (6.5 mL) was treated dropwise with conc. sulfuric acid (0.36 mL 6.80 mmol) with cooling in ice, 1-(2,3-dihydro-7-methoxy-2,2-dimethyl-5-benzofuranyl)-2-methyl-1-propanol (928 mg, 3.71 mmol) was added thereto at room temperature, and the mixture was stirred at 80° C. for 1 hour. Ice water was poured into the reaction mixture, which was then washed with diethyl ether. The aqueous layer was neutralized with conc. aqueous ammonia, and extracted twice with ethyl acetate. The combined organic layer was washed with brine, dried over sodium sulfate, filtered and concentrated under reduced pressure. The residue was subjected to a column chromatography on a basic silica gel (hexane/ethyl acetate 5:1 followed by 3:1) to obtain a free base of the title compound as an amorphous material.

$^1$H NMR (CDCl$_3$) δ 1.24 (6H, s), 1.33 (6H, s), 2.39 (2H, br s), 2.67 (2H, s), 3.03 (6H, br s), 3.91 (3H, s), 6.59 (1H, s), 7.38–7.58 (4H, m).

This was dissolved in ethyl acetate, combined with 4 M hydrogen chloride/ethyl acetate solution, concentrated under reduced pressure, triturated with diethyl ether to obtain the title compound (618 mg, yield: 42%).

Amorphous.

$^1$H NMR (DMSO-$d_6$) δ 1.23 (6H, s), 1.42 (3H, s), 1.45 (3H, s), 2.13 (1H, br d, J=15.8 Hz), 2.40–2.60 (1H, m), 2.94 (3H, s), 3.00–3.50 (2H, m), 3.05 (3H, s), 3.94 (3H, s), 7.09 (1H, s), 7.68–7.80 (4H, m).

Example 510

3,4,8,9-Tetrahydro-6-methoxy-3,3,8,8-tetramethyl-1-[3-(methylthio)phenyl]furo[2,3-h]isoquinoline Hydrochloride 28% sodium methoxide/methanol solution (2 mL) was added to a solution of S-[3-(3,4,8,9-tetrahydro-6-methoxy-3,3,8,8-tetramethylfuro[2,3-h]isoquinolin-1-yl)phenyl] dimethylcarbamothioate(1.12 g, 2.55 mmol) in N,N-dimethylformamide (10 mL) with cooling in ice, and the mixture was stirred at room temperature for 1 hour. Ice water was poured into the reaction mixture, which was neutralized with 5 M hydrochloric acid, and extracted three times with ethyl acetate. The combined organic layer was washed with brine, dried over sodium sulfate, filtered and concentrated under reduced pressure. The residue was dissolved in N,N-dimethylformamide (10 mL), sodium hydride (66% dispersion in oil) (93 mg, 2.55 mmol) was added thereto and the mixture was stirred at room temperature for 20 minutes. With cooling in ice, iodomethane (0.16 mL, 2.55 mmol) was added to the mixture and the mixture was stirred at room temperature for 2 hours. Water was poured into the reaction mixture which was extracted twice with ethyl acetate. The combined organic layer was washed with brine, dried over sodium sulfate, filtered and concentrated under reduced pressure. The residue was subjected to a column chromatography on a basic silica gel (hexane/ethyi acetate 10:1) to obtain a free base of the title compound as an amorphous material.

$^1$H NMR (CDCl$_3$) δ 1.25 (6H, s), 1.33 (6H, s), 2.24 (2H, s), 2.49 (3H, s), 2.69 (2H, s), 3.93 (3H, s), 6.61 (1H, s), 7.13–7.31 (4H, m).

This was dissolved in ethyl acetate, combined with 4 M hydrogen chloride/ethyl acetate solution, concentrated under reduced pressure, crystallized from ethyl acetate to obtain the title compound (247 mg, yield: 23%).

Melting point: 130–140° C.

$^1$H NMR (DMSO-$d_6$) δ 1.24 (6H, s), 1.44 (6H, s), 2.25 (2H, s), 2.55 (3H, s), 3.14 (2H, s), 3.94 (3H, s), 7.09 (1H, s), 7.31–7.35 (1H, m), 7.51–7.63 (3H, m).

Example 511

3,4,8,9-Tetrahydro-6-methoxy-3,3,8,8-tetramethyl-1-[3-(methylsulfinyl)phenyl]furo[2,3-h]isoquinoline Hydrochloride A solution of sodium metaperiodate (404 mg, 1.89 mmol) in water (2.5 mL) was added to a solution of 3,4,8,9-tetrahydro-6-methoxy-3,3,8,8-tetramethyl-1-[3-(methylthio)phenyl]furo[2,3-h]isoquinoline (288 mg, 0.755 mmol) in methanol (3.5 mL) and the mixture was stirred at room temperature for 1 hour. Water was poured into the reaction mixture, which was combined with sodium hydrogen carbonate, and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 2:1 followed by 1:1) to obtain a free base of the title compound. This was dissolved in ethyl acetate, combined with 4 M hydrogen chloride/ethyl acetate solution, concentrated under reduced pressure, triturated with diethyl ether to obtain the title compound (257 mg, yield: 78%).

Amorphous.

$^1$H NMR (DMSO-$d_6$) δ 1.22 (6H, s), 1.47 (6H, s), 2.15 (2H, s), 2.85 (3H, s), 3.17 (2H, s), 3.94 (3H, s), 7.11 (1H, s), 7.76–8.05 (4H, m).

Example 512

3,4,8,9-Tetrahydro-6-methoxy-3,3,8,8-tetramethyl-1-[3-(methylsulfonyl)phenyl]furo[2,3-h]isoquinoline Hydrochloride A solution of sodium metaperiodate (517 mg, 2.42 mmol) in water (2 mL) was added to a solution of 3,4,8,9-tetrahydro-6-methoxy-3,3,8,8-tetramethyl-1-[3-(methylthio)phenyl]furo[2,3-h]isoquinoline hydrochloride (202 mg, 0.483 mmol) in methanol (3 mL) and the mixture was stirred at 60° C. for 4 hours. Water was poured into the reaction mixture, which was combined with sodium hydrogen carbonate and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 3:1) to obtain a free base of the title compound. This was dissolved in ethyl acetate, combined with 4 M hydrogen chloride/ethyl acetate solution, concentrated under reduced pressure, crystallized from ethanol-ethyl acetate-diisopropyl ether to obtain the title compound (171 mg, yield: 79%).

Melting point: 141–145° C.

$^1$H NMR (DMSO-d$_6$) δ 1.22 (6H, s), 1.47 (6H, s), 2.14 (2H, s), 3.16 (2H, s), 3.34 (3H, s), 3.94 (3H, s), 7.11 (1H, s), 7.86–8.00 (2H, m), 8.23–8.27 (2H, m).

Example 513

2-[[3-(3,4,8,9-Tetrahydro-6-methoxy-3,3,8,8-tetramethylfuro[2,3-h]isoquinolin-1-yl)phenyl]thio]acetamide S-[3-(3,4,8,9-Tetrahydro-6-methoxy-3,3,8,8-tetramethylfuro[2,3-h]isoquinolin-1-yl)phenyl] dimethylcarbamothioate (1.62 g, 3.69 mmol) was added to a solution of 28% sodium methoxide/methanol solution (1.43 g, 7.39 mmol) in N,N-dimethylformamide (8 mL) with cooling in ice, and the mixture was stirred at room temperature for 30 minutes. Water was poured into the reaction mixture, which was extracted twice with ethyl acetate-tetrahydrofuran. The combined organic layer was washed with brine, dried over sodium sulfate, filtered and concentrated under reduced pressure. The residue was subjected to a column chromatography on a basic silica gel (hexane/ethyl acetate 1:2) to obtain an amorphous material (1.25 g). An Aliquot (369 mg) was crystallized from ethyl acetate-hexane to obtain the title compound (298 mg, yield: 64%).

Melting point: 118–120° C.

$^1$H NMR (CDCl$_3$) δ 1.27 (6H, s), 1.33 (6H, s), 2.20 (2H, s), 2.71 (2H, s), 3.66 (2H, s), 3.93 (3H, s), 5.44 (1H, br s), 6.62 (1H, s), 6.81 (1H, br s), 7.21–7.43 (4H, m).

Example 514

2-[[3-(3,4,8,9-Tetrahydro-6-methoxy-3,3,8,8-tetramethylfuro[2,3-h]isoquinolin-1-yl)phenyl]sulfinyl]acetamide Hydrochloride A solution of sodium metaperiodate (655 mg, 3.06 mmol) in water (2.5 mL) was added to a solution of 2-[[3-(3,4,8,9-tetrahydro-6-methoxy-3,3,8,8-tetramethylfuro[2,3-h]isoquinolin-1-yl)phenyl]thio]acetamide (401 mg, 0.945 mmol) in methanol (4 mL) and the mixture was stirred at room temperature for 3 hours. Water was poured into the reaction mixture, which was neutralized with sodium hydrogen carbonate, and extracted three times with ethyl acetate. The combined organic layer was washed with water and brine, dried over sodium sulfate, filtered and concentrated under reduced pressure The residue was subjected to a column chromatography on a basic silica gel (hexane/ethyl acetate 1:3 followed by ethyl acetate) to obtain a free base of the title compound. This was dissolved in ethyl acetate, combined with 4 M hydrogen chloride/ethyl acetate solution, concentrated under reduced pressure, triturated with diethyl ether to obtain the title compound (357 mg, yield: 794%).

Amorphous.

$^1$H NMR (DMSO-d$_6$) δ 1.23 (6H, s), 1.47 (6H, s), 2.17 (2H, s), 3.17 (2H, s), 3.80 (1H, br d, J=13.4 Hz), 3.94 (3H, s), 4.04 (1H, d, J=13.4 Hz), 7.10 (1H, s), 7.36 (1H, s), 7.75–8.03 (5H, m).

Example 515

2-[[3-(3,4,8,9-Tetrahydro-6-methoxy-3,3,8,8-tetramethylfuro[2,3-h]isoquinolin-1-yl)phenyl]sulfonyl]acetamide Hydrochloride A solution of sodium metaperiodate (1.22 g, 5.72 mmol) in water (4 mL) was added to a solution of 2-[[3-(3,4,8,9-tetrahydro-6-methoxy-3,3,8,8-tetramethylfuro[2,3-h]isoquinolin-1-yl)phenyl]thio]acetamide (486 mg, 1.14 mmol) in methanol (6 mL) and the mixture was stirred at 70° C. for 6 hours. Water was poured into the reaction mixture, which was combined with sodium hydrogen carbonate, and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 1:3) to obtain a free base of the title compound. This was dissolved in ethyl acetate, combined with 4 M hydrogen chloride/ethyl acetate solution, concentrated under reduced pressure, triturated with diethyl ether to obtain the title compound (370 mg, yield: 66%).

Amorphous.

$^1$H NMR (DMSO-d$_6$) δ 1.21 (6H, s), 1.47 (6H, s), 2.00–2.40 (2H, m), 3.17 (2H, s), 3.94 (3H, s), 4.30–4.60 (2H, m), 7.10 (1H, s), 7.35 (1H, s), 7.80 (1H, s), 7.84–7.98 (2H, m), 8.15–8.19 (2H, m).

Example 516

3-Chloro-N-[3-(3,4,8,9-tetrahydro-6-methoxy-3,3,8,8-tetramethylfuro[2,3-h]isoquinolin-1-yl)phenyl]-1-propanesulfonamide A solution of 3-(3,4,8,9-tetrahydro-6-methoxy-3,3,8,8-tetramethylfuro[2,3-h]isoquinolin-1-yl)benzenamine (729 mg, 2.08 mmol) and triethylamine (0.32 mL, 2.29 mmol) in tetrahydrofuran (7 mL) was treated dropwise with 3-chloropropanesulfonyl chloride (0.25 mL, 2.08 mmol) with cooling in ice, and stirred at room temperature for 3 hours. Ice water was poured into the reaction mixture, which was extracted twice with ethyl acetate. The combined organic layer was washed with brine, dried over sodium sulfate, filtered and concentrated under reduced pressure. The residue was subjected to a column chromatography on a silica gel (hexane/ethyl acetate 2:1 followed by hexane/ethyl acetate/triethylamine 25:25:1) to obtain an oil (820 mg). An aliquot (520 mg) was crystallized from ethyl acetate-hexane to obtain the title compound (453 mg, yield: 70%).

Melting point: 163–165° C.

$^1$H NMR (CDCl$_3$) δ 1.27 (6H, s), 1.33 (6H, s), 2.17–2.31 (2H, m), 2.24 (2H, s), 2.72 (2H, s), 3.12 (2H, t, J=6.5 Hz), 3.64 (2H, t, J=6.2 Hz), 3.93 (3H, s), 6.61 (1H, s), 7.12–7.39 (4H, m).

Example 517

2-[3-(3,4,8,9-Tetrahydro-6-methoxy-3,3,8,8-tetramethylfuro[2,3-h]isoquinolin-1-yl)phenyl]isothiazolidine 1,1-dioxide 1,8-Diazabicyclo[5.4.0]undec-7-ene (0.11 mL, 0.753 mmol) was added to a solution of 3-chloro-N-[3-(3,4,8,9-tetrahydro-6-methoxy-3,3,8,8-tetramethylfuro[2,3-h]isoquinolin-1-yl)phenyl]-1-propanesulfonamide (352 mg, 0.717 mmol) in toluene (3 mL) and the mixture was stirred at 110° C. for 1 hour. Water was poured into the reaction mixture. The mixture was neutralized with 1 M hydrochloric acid, and extracted twice with ethyl acetate. The combined organic layer was washed with brine, dried over sodium sulfate, filtered and concentrated under reduced pressure. The residue was crystallized from ethyl acetate-diethyl ether to obtain the title compound (112 mg, yield: 34%).

Melting point: 114–116° C.

$^1$H NMR (CDCl$_3$) δ 1.26 (6H, s), 1.33 (6H, s), 2.30 (2H, s), 2.45–2.60 (2H, m), 2.70 (2H, s), 3.38 (2H, t, J=7.5 Hz), 3.81 (2H, t, J=6.6 Hz), 3.92 (3H, s), 6.60 (1H, s), 7.24–7.27 (2H, m), 7.39–7.42 (2H, m).

Example 518

N,N-Dimethyl-N'-[3-(3,4,8,9-tetrahydro-6-methoxy-3,3,8,8-tetramethylfuro[2,3-h]isoquinolin-1-yl)phenyl]sulfamide Triethylamine (0.15 mL, 1.07 mol) and dimethylsulfamoyl chloride (0.10 mL, 0.970 mmol) were added to a solution of 3-(3,4,8,9-tetrahydro-6-methoxy-3,3,8,8-tetramethylfuro[2,3-h]isoquinolin-1-yl)benzenamine (340 mg, 0.970 mmol) in tetrahydrofuran (3 mL) with cooling in ice, and the mixture was heated under reflux for 15 hours. Water was poured into the reaction mixture, which was made basic by adding 1 M aqueous solution of sodium hydroxide, and extracted twice with ethyl acetate. The combined organic layer was washed with a brine, dried over magnesium sulfate, filtered, and concentrated under reduced pressure. The residue was subjected to a column chromatography on a basic silica gel (hexane/ethyl acetate 1:2), and crystallized from diethyl ether to obtain the title compound (226 mg, yield: 51%).

Melting point: 134–136° C.

$^1$H NMR (CDCl$_3$) δ 1.25 (6H, s), 1.32 (6H, s), 2.24 (2H, s), 2.70 (2H, s), 2.82 (6H, s), 3.92 (3H, s), 6.61 (1H, s), 7.09–7.13 (2H, m), 7.21–7.36 (2H, m).

Example 519

N-[3-(3,4,8,9-Tetrahydro-6-methoxy-3,3,8,8-tetramethylfuro[2,3-h]isoquinolin-1-yl)phenyl]-2-propanamide Triethylamine (0.47 mL, 3.36 mmol) and 3-chloropropionyl chloride (0.31 mL, 3.21 mmol) were added to a solution of 3-(3,4,8,9-tetrahydro-6-methoxy-3,3,8,8-tetramethylfuro[2,3-h]isoquinolin-1-yl)benzenamine (1.07 g, 3.05 mmol) in tetrahydrofuran (10 mL) with cooling in ice, and the mixture was stirred at the same temperature for 1.5 hours. Ice water was poured to the reaction mixture, which was extracted three times with ethyl acetate. The combined organic layer was washed with brine, dried over sodium sulfate, filtered and concentrated under reduced pressure. The residue was subjected to a column chromatography on a silica gel (hexane/ethyl acetate 1:1 followed by hexane/ethyl acetate/methanol 25:25:1), crystallized from diethyl ether-hexane to obtain ca. 1:1 mixture (1.12 g) of the title compound and 3-chloro-N-[3-(3,4,8,9-tetrahydro-6-methoxy-3,3,8,8-tetramethylfuro[2,3-h]isoquinolin-1-yl)phenyl]propanamide.

Potassium carbonate (220 mg, 1.59 mmol) and potassium iodide (22 mg, 0.133 mmol) were added to a solution of this substance in N,N-dimethylformamide (10 mL) and the mixture was stirred at 60° C. for 4 hours. Water was poured into the reaction mixture, which was extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 3:1), crystallized from diethyl ether-diisopropyl ether to obtain the title compound (419 mg, yield: 34%).

Melting point: 188–190° C.

$^1$H NMR (CDCl$_3$) δ 1.25 (6H, s), 1.32 (6H, s), 2.30 (2H, s), 2.68 (2H, s), 3.92 (3H, s), 5.74 (1H, dd, J=10.0, 1.6 Hz), 6.22 (1H, dd, J=16.9, 10.0 Hz), 6.41 (1H, dd, J=16.9, 1.6 Hz), 6.60 (1H, s), 7.07 (1H, d, J=8.0 Hz), 7.31 (1H, t, J=8.0 Hz), 7.44 (1H, s), 7.77 (1H, d, J=8.0 Hz), 7.96 (1H, s).

Example 520

4-Chloro-N-[3-(3,4,8,9-tetrahydro-6-methoxy-3,3,8,8-tetramethylfuro[2,3-h]isoquinolin-1-yl)phenyl]butanamide Triethylamine (0.81 mL, 5.81 mmol) and 4-chlorobutyryl chloride (0.62 mL, 5.54 mmol) were added to a solution of 3-(3,4,8,9-tetrahydro-6-methoxy-3,3,8,8-tetramethylfuro[2,3-h]isoquinolin-1-yl)benzenamine (1.85 g, 5.28 mmol) in tetrahydrofuran (15 mL) with cooling in ice, and the mixture was stirred at the same temperature for 1 hour. Ice water and an aqueous solution of sodium hydroxide were poured into the reaction mixture, which was extracted with ethyl acetate. The organic layer was washed with brine, dried over sodium sulfate, filtered and concentrated under reduced pressure. The residue was crystallized from diethyl ether-diisopropyl ether to obtain the title compound (2.25 g, yield: 94%).

Melting point: 146–148° C.

$^1$H NMR (CDCl$_3$) δ 1.25 (6H, s), 1.32 (6H, s), 2.10–2.23 (2H, m), 2.30 (2H, s), 2.52 (2H, t, J=7.1 Hz), 2.69 (2H, s), 3.65 (2H, t, J=6.0 Hz), 3.92 (3H, s), 6.60 (1H, s), 7.07 (1H, d, J=7.6 Hz), 7.31 (1H, t, J=7.6 Hz), 7.45 (1H, s), 7.77 (1H, d, J=7.6 Hz), 7.78 (1H, s).

Example 521

1-[3-(3,4,8,9-Tetrahydro-6-methoxy-3,3,8,8-tetramethylfuro[2,3-h]isoquinolin-1-yl)phenyl]-2-pyrrolidinone Hydrochloride Potassium carbonate (514 mg, 3.72 mmol) and potassium iodide (56 mg, 0.338 mmol) were added to a solution of 4-chloro-N-[3-(3,4,8,9-tetrahydro-6-methoxy-3,3,8,8-tetramethylfuro[2,3-h]isoquinolin-1-yl)phenyl]butanamide (1.54 g, 3.38 mmol) in N,N-dimethylformamide (10 mL) and the mixture was stirred at 60° C. for 2 hours and 80° C. for 5 hours. Water was poured into the reaction mixture, which was extracted twice with ethyl acetate. The combined organic layer was washed with water and brine, dried over sodium sulfate, filtered and concentrated under reduced pressure. The residue was subjected to a column chromatography on a silica gel (ethyl acetate followed by ethyl acetate/triethylamine 50:1) to obtain a free base of the title compound. This was dissolved in ethyl acetate, combined with 4 M hydrogen chloride/ethyl acetate solution, concentrated under reduced pressure, triturated with diethyl ether to obtain the title compound (941 mg, yield: 61%).

Amorphous.

$^1$H NMR (DMSO-d$_6$) δ 1.23 (6H, s), 1.44 (6H, s), 2.02–2.15 (2H, m), 2.20–2.40 (2H, m), 2.45–2.60 (2H, m), 3.14 (2H, s), 3.70–4.05 (2H, m), 3.94 (3H, s), 7.09 (1H, s), 7.35 (1H, d, J=8.0 Hz), 7.60–7.68 (1H, m), 7.90 (1H, s), 7.94 (1H, d, J=8.0 Hz).

Example 522

3-Chloro-2,2-dimethyl-N-[3-(3,4,8,9-tetrahydro-6-methoxy-3,3,8,8-tetramethylfuro[2,3-h]isoquinolin-1-yl)phenyl]propanamide Triethylamine (1.30 mL, 9.30 mmol) and 3-chloropivaloyl chloride (1.15 mL, 8.87 mmol) were added to a solution of 3-(3,4,8,9-tetrahydro-6-methoxy-3,3,8,8-tetramethylfuro[2,3-h]isoquinolin-1-yl)benzenamine (2.96 g, 8.45 mmol) in tetrahydrofuran (20 mL) with cooling in ice, and the mixture was stirred at room temperature for 30 minutes. Ice water was poured into the reaction mixture, which was extracted twice with ethyl acetate. The combined organic layer was washed with a brine, dried over sodium sulfate, filtered and concentrated under reduced pressure. The residue was crystallized from ethyl acetate-hexane to obtain the title compound (3.83 g, yield: 97%).

Melting point: 189–191° C.

$^1$H NMR (CDCl$_3$) δ 1.24 (6H, s), 1.32 (6H, s), 1.42 (6H, s), 2.31 (2H, s), 2.68 (2H, s), 3.70 (2H, s), 3.92 (3H, s), 6.61 (1H, s), 7.12 (1H, dd, J=7.6, 1.4 Hz), 7.35 (1H, t, J=7.6 Hz), 7.48 (1H, t, J=1.4 Hz), 7.55 (1H, br s), 7.81 (1H, dd, J=7.6, 1.4 Hz).

Example 523
3,3-Dimethyl-1-[3-(3,4,8,9-tetrahydro-6-methoxy-3,3,8,8-tetramethylfuro[2,3-h]isoquinolin-1-yl)phenyl]-2-azethidinone Hydrochloride Potassium carbonate (529 mg, 3.83 mmol) and potassium iodide (58 mg, 0.348 mmol) were added to absolution of 3-chloro-2,2-dimethyl-N-[3-(3,4,8,9-tetrahydro-6-methoxy-3,3,8,8-tetramethylfuro[2,3-h]isoquinolin-1-yl)phenyl]propanamide (1.63 g, 3.48 mmol) in N,N-dimethylformamide (15 mL) and the mixture was stirred at 70° C. for 3 hours. Ice water was added to the reaction mixture, which was extracted twice with ethyl acetate. The combined organic layer was washed with brine, dried over sodium sulfate, filtered and concentrated under reduced pressure. The residue was subjected to a column chromatography on a basic silica gel (hexane/ethyl acetate 5:1 followed by 3:1) to obtain a free base of the title compound. This was dissolved in ethyl acetate, combined with 4 M hydrogen chloride/ethyl acetate solution, concentrated under reduced pressure, crystallized from ethyl acetate-diisopropyl ether to obtain the title compound (1.50 g, yield: 92%).

Melting point: 191–193° C.

$^1$H NMR (DMSO-d$_6$) δ 1.24 (6H, s), 1.32 (6H, s), 1.44 (6H, s), 2.29 (2H, s), 3.14 (2H, s), 3.58 (2H, s), 3.94 (3H, s), 7.09 (1H, s), 7.29–7.31 (1H, m), 7.62–7.64 (3H, m).

Example 524
5-Oxo-N-[3-(3,4,8,9-tetrahydro-6-methoxy-3,3,8,8-tetramethylfuro[2,3-h]isoquinolin-1-yl)phenyl]-2-pyrrolidinecarboxamide Thionyl chloride (2.06 mL, 28.3 mmol) and N,N-dimthylformamide (1 drop) were added to a solution of D,L-pyroglutamic acid (3.65 g, 28.3 mmol) in toluene (16 mL) and the mixture was stirred at 50° C. for 40 minutes. After distilling the solvent off under reduced pressure, the residue was dissolved in N,N-dimethylformamide (10 mL) and 3-(3,4,8,9-tetrahydro-6-methoxy-3,3,8,8-tetramethylfuro[2,3-h]isoquinolin-1-yl)benzenamine (1.98 g, 5.66 mmol) and triethylamine (3.94 mL, 28.3 mmol) were added thereto, and the mixture was stirred at room temperature for 3 hours. An aqueous solution of sodium chloride was poured into the reaction mixture, which was extracted twice with ethyl acetate-tetrahydrofuran. The combined organic layer was washed with brine, dried over sodium sulfate, filtered and concentrated under reduced pressure. The residue was subjected to a column chromatography on a basic silica gel (ethyl acetate followed by ethyl acetate/methanol 30:1), and crystallized from ethyl acetate-hexane to obtain the title compound (1.57 g, yield: 60%).

Melting point: 145–147° C.

$^1$H NMR (CDCl$_3$) δ 1.23 (6H, s), 1.31 (6H, s), 2.27 (2H, s), 2.30–2.59 (4H, m), 2.67 (2H, s), 3.92 (3H, s), 4.20–4.30 (1H, m), 6.60 (1H, s), 6.94 (1H, s), 7.09 (1H, d, J=8.0 Hz), 7.23–7.37 (1H, m), 7.53 (1H, s), 7.74 (1H, d, J=8.0 Hz), 8.50 (1H, s).

Example 525
N-Methyl-5-oxo-N-[3-(3,4,8,9-tetrahydro-6-methoxy-3,3,8,8-tetramethylfuro[2,3-h]isoquinolin-1-yl)phenyl]-2-pyrrolidinecarboxamide Hydrochloride Thionyl chloride (0.51 mL, 7.04 mmol) and N,N-dimethylformamide (1 drop) were added to a solution of D,L-pyroglutamic acid (909 mg, 7.04 mmol) in toluene (4 mL) and the mixture was stirred at 50° C. for 40 minutes. After distilling the solvent off, the residue was dissolved in N,N-dimethylformamide (4 mL ), and N-methyl-3-(3,4,8,9-tetrahydro-6-methoxy-3,3,8,8-tetramethylfuro[2,3-h]isoquinolin-1-yl)benzenamine (493 mg, 1.35 mmol) and triethylamine (0.98 mL, 7.04 mmol) were added thereto with cooling in ice, and the mixture was stirred at room temperature for 3 hours. Brine was poured into the reaction mixture, which was extracted three times with ethyl acetate-tetrahydrofuran. The combined organic layer was washed with brine, dried over sodium sulfate, filtered and concentrated under reduced pressure. The residue was subjected to a column chromatography on a basic silica gel (ethyl acetate) to obtain a free base of the title compound. This was dissolved in ethyl acetate, combined with 4 M hydrogen chloride/ethyl acetate solution, concentrated under reduced pressure, triturated with di ethyl ether to obtain the title compound (516 mg, yield: 75%).

Amorphous.

$^1$H NMR (DMSO-d$_6$) δ 1.23 (6H, s), 1.47 (6H, s), 1.90–2.30 (4H, m), 2.19 (2H, s), 3.17 (2H, s), 3.25 (3H, s), 3.94 (3H, s), 4.00–4.15 (1H, m), 7.11 (1H, s), 7.55–7.85 (5H, m).

Example 526
2,6-Dichloro-N-[3-(3,4,8,9-tetrahydro-6-methoxy-3,3,8,8-tetramethylfuro[2,3-h]isoquinolin-1-yl)phenyl]-3-pyridinecarboxamide N,N'-Carbonyldiimidazole (160 mg, 0.989 mmol) was added to a solution of 2,6-dichloronicotinic acid (90%) (188 mg, 0.881 mmol) in N,N-dimethylformamide (2.5 mL) and the mixture was stirred at room temperature for 1 hour. 3-(3,4,8,9-Tetrahydro-6-methoxy-3,3,8 8-tetramethylfuro[2,3-h]isoquinolin-1-yl)benzenamine (347 mg, 0.989 mmol) was added to the mixture, and the mixture was stirred at room temperature for 1 hour and at 60° C. for 2 hours and 90° C. for 15 hours. Water was poured into the reaction mixture, which was extracted twice with ethyl acetate-tetrahydrofuran. The combined organic layer was washed with water and brine dried over sodium sulfate, filtered and concentrated under reduced pressure. The residue was subjected to a column chromatography on a basic silica gel (hexane/ethyl acetate 2:1 followed by 1:1), crystallized from ethyl acetate-hexane to obtain the title compound (95 mg, yield: 18).

Melting point; 130–132° C.

$^1$H NMR (CDCl$_3$) δ 1.23 (6H, s), 1.34 (6H, br s), 2.33 (2H, s), 2.69 (2H, s), 3.93 (3H, s), 6.61 (1H, s), 7.19 (1H, d, J=7.5 Hz), 7.37–7.43 (2H, m), 7.61 (1H, s), 7.84 (1H, d, J=7.5 Hz), 8.13 (1H, d, J=8.0 Hz), 8.56 (1H, s).

Example 527
N-[3-[[[[3-(3,4,8,9-Tetrahydro-6-methoxy-3,3,8,8-tetramethylfuro[2,3-h]isoquinolin-1-yl)phenyl]amino]carbonyl]amino]phenyl]acetamide Hydrochloride N,N'-Carbonyldiimidazole (151 mg, 0.933 mmol) was added to a solution of 3-(3,4,8,9-tetrahydro-6-methoxy-3,3,8,8-tetramethylfuro[2,3-h]isoquinolin-1-yl)benzenamine (327 mg, 0.933 mmol) in N,N-dimethylformamide (3 mL) and the mixture was stirred at room temperature for 1 hour. 3'-Aminoacetanilide (140 mg, 0.933 mmol) was added to the mixture and the mixture was stirred at room temperature for 3 hours. Ice water was poured into the reaction mixture, which was extracted three times with ethyl acetate. The combined organic layer was concentrated under reduced pressure. The residue was subjected to a column chromatography on a basic silica gel (hexane/ethyl acetate 1:2, ethyl acetate followed by ethyl acetate/methanol 20:1) to obtain a free base of the title compound. This was dissolved in ethyl acetate, combined with 4 M hydrogen chloride/ethyl acetate solution, concentrated under reduced pressure, triturated with diethyl ether to obtain the title compound (128 mg, yield: 24%).

Amorphous.

$^1$H NMR (DMSO-d$_6$) δ 1.24 (6H, s), 1.44 (6H, s), 2.02 (3H, s), 2.18–2.55 (2H, m), 3.15 (2H, br s), 3.94 (3H, s), 7.09 (1H, s), 7.13–7.23 (4H, m), 7.50–7.88 (4H, m), 9.30 (1H, s), 9.59 (1H, s), 9.93 (1H, s).

Example 528
[3-(3,4,8,9-Tetrahydro-6-methoxy-3,3,8,8-tetramethylfuro[2,3-h]isoquinolin-1-yl)phenyl]urea Sodium cyanate (121 mg, 1.87 mmol) and trifluoroacetic acid(0.36 mL, 4.67 mmol) were added to a solution of 3-(3,4,8,9-tetrahydro-6-methoxy-3,3,8,8-tetramethylfuro[2,3-h]isoquinolin-1-yl)benzenamine (327 mg, 0.933 mmol) in tetrahydrofuran (3 mL) with cooling in ice, and the mixture was stirred at room temperature for 1 hour. The reaction mixture was neutralized with 1 M aqueous solution of sodium hydroxide, and extracted twice with ethyl acetate. The combined organic layer was washed with a brine, dried over sodium sulfate, filtered and concentrated under reduced pressure. The residue was subjected to a column chromatography on a basic silica gel (ethyl acetate), crystallized from diisopropyl ether to obtain the title compound (303 mg, yield: 83%).

Melting point: 174–176° C.

$^1$H NMR (CDCl$_3$) δ 1.23 (6H, s), 1.32 (6H, s), 2.28 (2H, s), 2.70 (2H, s), 3.93 (3H, s), 4.89 (2H, br s), 6.60 (1H, s), 6.98 (1H, d, J=7.6 Hz), 7.25–7.33 (2H, m), 7.49 (1H, d, J=8.2 Hz), 7.55 (1H, s).

Example 529
N-Methyl-N-[3-(3,4,8,9-tetrahydro-6-methoxy-3,3,8,8-tetramethylfuro[2,3-h]isoquinolin-1-yl)phenyl]urea Sodium cyanate (125 mg, 1.92 mmol) and trifluoroacetic acid (0.37 mL, 4.80 mmol) were added to a solution of N-methyl-3-(3,4,8,9-tetrahydro-6-methoxy-3,3,8,8-tetramethylfuro[2,3-h]isoquinolin-1-yl)benzenamine (350 mg, 0.960 mmol) in tetrahydrofuran (3 mL) with cooling in ice, and stirred at room temperature for 1 hour. The reaction mixture was neutralized with 1 M aqueous solution of sodium hydroxide, and extracted twice with ethyl acetate. The combined organic layer was washed with a brine, dried over sodium sulfate, filtered and concentrated under reduced pressure. The residue was subjected to a column chromatography on a basic silica gel (hexane/ethyl acetate 1:2), crystallized from ethyl acetate-hexane to obtain the title compound (263 mg, yield: 67%).

Melting point: 108–109° C.

$^1$H NMR (CDCl$_3$) δ 1.26 (6H, s), 1.33 (6H, s), 2.22 (2H, s), 2.70 (2H, s), 3.28 (3H, s), 3.93 (3H, s), 4.42 (2H, br s), 6.62 (1H, s), 7.30–7.52 (4H, m).

Example 530
N-Methyl-N'-[3-(3,4,8,9-tetrahydro-6-methoxy-3,3,8,8-tetramethylfuro[2,3-h]isoquinolin-1-yl)phenyl]urea Phenyl chlorocarbonate (0.11 mL, 0.902 mmol) and triethylamine (0.13 mL, 0.902 mmol) were added to a solution of 3-(3,4,8,9-tetrahydro-6-methoxy-3,3,8,8-tetramethylfuro[2,3-h]isoquinolin-1-yl)benzenamine (316 mg, 0.902 mmol) in N,N-dimethylformamide (3 mL) and the mixture was stirred at room temperature for 1 hour. Methylamine hydrochloride (73 mg, 1.08 mmol) and triethylamine (0.31 mL, 2.26 mmol) were added to the mixture, and the mixture was stirred at room temperature for 2 hours and at 50° C. for 5 hours. Water was added to the reaction mixture, which was extracted three times with ethyl acetate. The combined organic layer was washed with brine, dried over sodium sulfate, filtered and concentrated under reduced pressure. The residue was subjected to a column chromatography on a basic silica gel (ethyl acetate followed by ethyl acetate/methanol 50:1), crystallized from ethyl acetate-diisopropyl ether to obtain the title compound (278 mg, yield: 76%).

Melting point: 125–127° C.

$^1$H NMR (CDCl$_3$) δ 1.24 (6H, s), 1.31 (6H, s), 2.29 (2H, s), 2.69 (2H, s), 2.74 (3H, d, J=4.4 Hz), 3.92 (3H, s), 5.13 (1H, br s), 6.60 (1H, s), 6.95 (1H, d, J=7.6 Hz), 7.02 (1H, s), 7.21–7.39 (2H, m).

Example 531
N-(2-Pyridinyl)-N'-[3-(3,4,8,9-tetrahydro-6-methoxy-3,3,8,8-tetramethylfuro[2,3-h]isoquinolin-1-yl)phenyl]urea Triethylamine (0.13 mL, 0.899 mmol) and phenyl chlorocarbonate (0.11 mL, 0.899 mmol) were added to a solution of 3-(3,4,8,9-tetrahydro-6-methoxy-3,3,8,8-tetramethylfuro[2,3-h]isoquinolin-1-yl)benzenamine (315 mg, 0.899 mmol) in N,N-dimethylformamide (3 mL) with cooling in ice, and the mixture was stirred at room temperature for 40 minutes. 2-Aminopyridine (93 mg, 0.989 mmol) was added to the mixture and the mixture was stirred at room temperature for 2 hours and at 60° C. for 2 hours. Ice water was poured into the reaction mixture, which was extracted twice with ethyl acetate. The combined organic layer was washed with water and brine, and concentrated under reduced pressure. The residue was subjected to a column chromatography on a basic silica gel (hexane/ethyl acetate 1:1 followed by 1:2), crystallized from diisopropyl ether to obtain the title compound (166 mg, yield: 39%).

Melting point: 189–191° C.

$^1$H NMR (CDCl$_3$) δ 1.27 (6H, s), 1.32 (6H, s), 2.35 (2H, s), 2.71 (2H, s), 3.93 (3H, s), 6.62 (1H, s), 6.81 (1H, d, J=8.0 Hz), 6.91–6.97 (1H, m), 7.09 (1H, d, J=7.6 Hz), 7.36 (1H, t, J=8.0 Hz), 7.56–7.66 (2H, m), 7.81 (1H, d, J=7.6 Hz), 8.25–8.28 (2H, m), 11.91 (1H, s).

Example 532
N-(2-Chloroethyl)-N'-[3-(3,4,8,9-tetrahydro-6-methoxy-3,3,8,8-tetramethylfuro[2,3-h]isoquinolin-1-yl)phenyl]urea 2-Chloroethyl isocyanate (0.12 mL, 1.48 mmol) was added to a solution of 3-(3,4,8,9-tetrahydro-6-methoxy-3,3,8,8-tetramethylfuro[2,3-h]isoquinolin-1-yl)benzenamine (519 mg, 1.48 mmol) in N,N-dimethylformamide (5 mL) and the mixture was stirred at room temperature for 3 hours. An aqueous solution of sodium chloride was poured into the reaction mixture, which was extracted three times with ethyl acetate. The combined organic layer was washed with brine, dried over sodium sulfate, filtered and concentrated under reduced pressure. The residue was subjected to a column chromatography on a basic silica gel (hexane/ethyl acetate 1:1 followed by ethyl acetate), crystallized from diethyl ether to obtain the title compound (477 mg, yield: 71%).

Melting point: 147–150° C.

$^1$H NMR (CDCl$_3$) δ 1.26 (6H, s), 1.32 (6H, s), 2.30 (2H, s), 2.71 (2H, s), 3.45–3.63 (4H, m), 3.92 (3H, s), 5.68 (1H, t, J=5.2 Hz), 6.60 (1H, s), 6.95 (1H, d, J=7.8 Hz), 7.20 (1H, s), 7.24 (1H, t, J=7.8 Hz), 7.42 (1H, d, J=7.8 Hz), 7.59 (1H, s).

Example 533
1-[3-(3,4,8,9-Tetrahydro-6-methoxy-3,3,8,8-tetramethylfuro[2,3-h]isoquinolin-1-yl)phenyl]-2-imidazolidinone Potassium tert-butoxide (86 mg, 0.770 mmol) was added to a solution of N-(2-chloroethyl)-N'-[3-(3,4,8,9-tetrahydro-6-methoxy-3,3,8,8-tetramethylfuro[2,3-h]isoquinolin-1-yl)phenyl]urea (351 mg, 0.770 mmol) in N,N-dimethylformamide (3 mL) with cooling in ice, and the mixture was stirred at room temperature for 4 hours. Water was poured into the reaction mixture, which was extracted twice with ethyl acetate. The combined organic layer was washed with brine, dried over sodium sulfate, filtered and concentrated under reduced pressure. The resultant crystals were washed with diisopropyl ether to obtain the title compound (251 mg, yield: 78%).

Melting point: 225–227° C.

$^1$H NMR (CDCl$_3$) δ 1.24 (6H, s), 1.32 (6H, s), 2.30 (2H, br s), 2.68 (2H, s), 3.57 (2H, t, J=8.1 Hz), 3.92 (3H, s), 3.99 (2H, t, J=8.1 Hz), 4.60 (1H, s), 6.60 (1H, s), 7.05 (1H, d, J=7.8 Hz), 7.35 (1H, t, J=7.8 Hz), 7.35 (1H, s), 7.80 (1H, d, J=7.8 Hz).

Example 534

N,N'-Dimethyl-N-[3-(3,4,8,9-tetrahydro-6-methoxy-3,3,8,8-tetramethylfuro[2,3-h]isoquinolin-1-yl)phenyl]sulfamide Hydrochloride Chlorosulfonyl isocyanate (0.14 mL, 1.57 mmol) was added to a solution of 2-methyl-2-propanol (0.15 mL, 1.57 mmol) in tetrahydrofuran (3 mL) with cooling in ice and the mixture was stirred at room temperature for 30 minutes. With cooling in ice, 3-(3,4,8,9-tetrahydro-6-methoxy-3,3,8,8-tetramethylfuro[2,3-h]isoquinolin-1-yl)benzenamine (500 mg, 1.43 mmol) and triethylamine (0.24 mL, 1.72 mmol) were added to the mixture and the mixture was stirred at room temperature for 2 hours. Ice water was poured into the reaction mixture, which was extracted three times with ethyl acetate-tetrahydrofuran. The combined organic layer was washed with brine, dried over sodium sulfate, filtered and concentrated under reduced pressure. The residue was subjected to a column chromatography on a silica gel (hexane/ethyl acetate 2:1 followed by 1:1) to obtain [[[3-(3,4,8,9-tetrahydro-6-methoxy-3,3,8,8-tetramethylfuro[2,3-h]isoquinolin-1-yl)phenyl]amino]sulfonyl]carbamic acid 1,1-dimethylethyl ester (510 mg, yield: 67%) as crystals.

$^1$H NMR (CDCl$_3$) δ 1.27 (6H, s), 1.33 (6H, s), 1.41 (9H, s), 2.22 (2H, s), 2.71 (2H, s), 3.93 (3H, s), 6.62 (1H, s), 7.21–7.41 (4H, m).

Sodium hydride (66% dispersion in oil) (36 mg, 0.991 mmol) was added to a solution of the resultant carbamic acid derivative (500 mg, 0.944 mmol) in N,N-dimethylformamide (5 mL) with cooling in ice, and the mixture was stirred at room temperature for 30 minutes. With cooling in ice, iodomethane (0.06 mL, 0.991 mmol) was added to the mixture and the mixture was stirred at room temperature for 3 hours. Water was poured into the reaction mixture, and extracted twice with ethyl acetate. The combined organic layer was washed with water and brine, dried over sodium sulfate, filtered and concentrated under reduced pressure. The residue was subjected to a column chromatography on a silica gel (hexane/ethyl acetate 2:1) to obtain an about 1:1 mixture of (methyl)[[[3-(3,4,8,9-tetrahydro-6-methoxy-3,3,8,8-tetramethylfuro[2,3-h]isoquinolin-1-yl) phenyl]amino]sulfonyl]carbamic acid 1,1-dimethylethyl ester and (methyl)[[(methyl)[3-(3,4,8,9-tetrahydro-6-methoxy-3,3,8,8-tetramethylfuro[2,3-h]isoquinolin-1-yl) phenyl]amino]sulfonyl]carbamic acid 1,1-dimethylethyl ester (379 mg).

4 M hydrogen chloride/ethyl acetate solution (3 mL) was added to the resultant mixture (370 mg) and the mixture was stirred at room temperature for 1 hour. Water was poured into the reaction mixture, which was neutralized with 5 M aqueous solution of sodium hydroxide, and then extracted with ethyl acetate. The organic layer was washed with a brine, dried over sodium sulfate, filtered and concentrated under reduced pressure. The residue was subjected to a column chromatography, on a basic silica gel (hexane/ethyl acetate 1:1) to obtain a free base of the title compound. This was dissolved in ethyl acetate, combined with 4 M hydrogen chloride/ethyl acetate solution, concentrated under reduced pressure, triturated with diethyl ether to obtain the title compound (129 mg, yield: 28%).

Amorphous.

$^1$H NMR (DMSO-d$_6$) δ 1.19 (6H, s), 1.40 (3H, s), 1.45 (3H, s), 1.97–2.50 (2H, m), 2.51 (3H, d, J=4.8 Hz), 3.14 (2H, s), 3.15 (3H, s), 3.91 (3H, s), 7.06 (1H, s), 7.43–7.67 (4H, m).

Example 535

N-Methyl-N'-[3-(3,4,8,9-tetrahydro-6-methoxy-3,3,8,8-tetramethylfuro[2,3-h]isoquinolin-1-yl)phenyl]sulfamide After separating N,N'-dimethyl form in the column chromatography in Example 534, followed by elution with hexane/ethyl acetate 1:2 followed by crystallization from diethyl ether, the title compound was obtained (85 mg, yield: 21%).

Melting point: 135–136° C.

$^1$H NMR (CDCl$_3$) δ 1.28 (6H, s), 1.33 (6H, br s), 2.25 (2H, s), 2.60 (3H, s), 2.72 (2H, s), 3.93 (3H, s), 5.86 (1H, br s), 6.62 (1H, s), 7.03–7.14 (2H, m), 728–7.39 (2H, m).

Example 536

N-[3-(3,4,8,9-Tetrahydro-6-methoxy-3,3,8,8-tetramethylfuro[2,3-h]isoquinolin-1-yl)phenyl]sulfamide Hydrochloride 4 M hydrogen chloride/ethyl acetate solution (3 mL) was added to [[[3-(3,4,8,9-Tetrahydro-6-methoxy-3,3,8,8-tetramethylfuro[2,3-h]isoquinolin-1-yl)phenyl]amino] sulfonyl]carbamic acid 1,1-dimethylethyl ester (539 mg, 1.02 mmol) and the mixture was stirred at room temperature for 3 hours. The reaction mixture was neutralized with 5 M aqueous solution of sodium hydroxide, and extracted with ethyl acetate. The organic layer was washed with brine, dried over sodium sulfate, filtered and concentrated under reduced pressure. The residue was subjected to a column chromatography on a basic silica gel (hexane/ethyl acetate 1:1 followed by ethyl acetate) to obtain a free base Of the title compound. This was dissolved in ethyl acetate, combined with 4 M hydrogen chloride/ethyl acetate solution, concentrated under reduced pressure, and crystallized from ethanol-diusopropyl ether to obtain the title compound (333 mg, yield: 70%)

Melting point: 191–194° C.

$^1$H NMR (DMSO-d$_6$) δ 1.22 (6H, s), 1.41 (3H, s), 1.47 (3H, s), 2.00–2.55 (2H, m), 3.00–3.40 (2H, m), 3.94 (3H, s), 7.09 (1H, s), 7.18–7.59 (6H, m), 9.99 (1H, s).

Example 537

5-[3-(3,4,8,9-Tetrahydro-6-methoxy-3,3,8,8-tetramethylfuro[2,3-h]isoquinolin-1-yl)phenyl]-1,2,5-thiadiazolidine-2-carboxylate 1,1-dimethylethyl Ester 1,1-dioxide Sodium hydride (66% dispersion in oil) (45 mg, 1.24 mmol) was added to a solution of [[[3-(3,4,8,9-tetrahydro-6-methoxy-3,3,8,8-tetramethylfuro[2,3-h]isoquinolin-1-yl) phenyl]amino]sulfonyl]carbamic acid 1,1-dimethylethyl ester (312 mg, 0.589 mmol) in N,N-dimethylformamide (3 mL) and the mixture was stirred at room temperature for 30 minutes. With cooling in ice, 1,2-dibromoethane (0.051 mL, 0.589 mmol) was added to the mixture and the mixture was stirred at room temperature for 3.5 hours. Water was poured into the reaction mixture, which was extracted twice with ethyl acetate. The combined organic layer was washed with water and a brine, dried over sodium sulfate, filtered and concentrated under reduced pressure. The residue was subjected to a column chromatography on a basic silica gel (hexane/ethyl acetate 3:1 followed by 2:1, recrystallized from diisopropyl ether to obtain the title compound (133 mg, yield: 41%).

Melting point: 157–159° C.

$^1$H NMR (CDCl$_3$) δ 1.24 (6H, s), 1.32 (6H, s), 1.56 (9H, s), 2.26 (2H, br s), 2.69 (2H, s), 3.78–3.85 (2H, m), 3.92 (3H, s), 3.92–3.99 (2H, m), 6.60 (1H, s), 7.32–7.36 (2H, m), 7.44–7.46 (2H, m).

Example 538

2-[3-(3,4,8,9-Tetrahydro-6-methoxy-3,3,8,8-tetramethylfuro[2,3-h]isoquinolin-1-yl)phenyl]-1,2,5-thiadiazolidine 1,1-dioxide 4 M hydrogen chloride/ethyl acetate solution (10 mL) was added to 5-[3-(3,4,8,9-Tetrahydro-6-methoxy-3,3,8,8-tetramethylfuro[2,3-h]isoquinolin-1-yl)phenyl]-1,2,5-thiadiazolidine-2-carboxylic acid 1,1-dimethylethyl ester 1,1-dioxide (1.30 g, 2.34 mmol) and the mixture was stirred at room temperature for 2 hours. The reaction mixture was neutralized with 2 M aqueous solution of sodium hydroxide, and extracted twice with ethyl acetate. The combined organic layer was washed with a brine, dried over sodium sulfate, filtered and concentrated under reduced pressure. The crystals of the residue were washed with diisopropyl ether to obtain the title compound (922 mg, yield: 87%).

Melting point: 145–147° C.

$^1$H NMR (CDCl$_3$) δ 1.32 (12H, s), 2.22 (2H, s), 2.72 (2H, s), 3.18 (2H, br s), 3.64–3.80 (2H, br), 3.93 (3H, s), 6.61 (1H, s), 7.04–7.07 (2H, m), 7.39 (1H, t, J=7.6 Hz), 7.59 (1H, d, J=7.6 Hz).

Example 539

[5-[3-(3,4,8,9-Tetrahydro-6-methoxy-3,3,8,8-tetramethylfuro[2,3-h]isoquinolin-1-yl)phenyl]-1,2,5-thiadiazolidine-2-acetamide 1,1-dioxide Potassium tert-butoxide (77 mg, 0.687 mmol) was added to a solution of 2-[3-(3,4,8,9-tetrahydro-6-methoxy-3,3,8,8-tetramethylfuro[2,3-h]isoquinolin-1-yl)phenyl]-1,2,5-thiadiazolidine 1,1-dioxide (313 mg, 0.687 mmol) in N,N-dimethylformamide (3 mL) and the mixture was stirred at room temperature for 30 minutes. 2-Bromoacetamide (95 mg, 0.687 mmol) was added to the mixture and the mixture was stirred at room temperature for 2 hours, and 2-bromoacetamide (95 mg, 0.687 mmol) was further added and the mixture was stirred at room temperature for 1 hour. Water was poured into the reaction mixture, which was extracted three times with ethyl acetate. The combined organic layer was washed with brine, dried over sodium sulfate, filtered and concentrated under reduced pressure. The residue was subjected to a column chromatography on a basic silica gel (ethyl acetate, ethyl acetate/triethylamine 50:1 followed by ethyl acetate/methanol/triethylamine 50:1:1), crystallized from ethyl acetate-diisopropyl ether to obtain the title compound (206 mg, yield: 59%).

Melting point: 206–208° C.

$^1$H NMR (CDCl$_3$) δ 1.25 (6H, s), 1.32 (6H, s), 2.26 (2H, br s), 2.69 (2H, s), 3.65 (2H, t, J=6.6 Hz), 3.85 (2H, s), 3.92 (2H, t, J=6.6 Hz), 3.92 (3H, s), 5.63 (1H, br s), 6.61 (1H, s), 6.62 (1H, br s), 7.26–7.30 (2H, m), 7.38–7.45 (2H, m).

Example 540

5-[3-(3,4,8,9-Tetrahydro-6-methoxy-3,3,8,8-tetramethylfuro[2,3-h]isoquinolin-1-yl)phenyl]-1,2,5-thiadiazolidine-2-acetic Acid Ethyl Ester 1,1-dioxide Potassium tert butoxide (695 mg, 6.19 mmol) was added to a solution of 2-[3-(3,4,8,9-tetrahydro-6-methoxy-3,3,8,8-tetramethylfuro[2,3-h]isoquinolin-1-yl)phenyl]-1,2,5-thiadiazolidine 1,1-dioxide (1.88 g, 4.13 mmol) in N,N-dimethylformamide (15 mL) and the mixture was stirred at room temperature for 30 minutes. Ethyl bromoacetate (0.46 mL, 4.13 mmol) was added to the mixture, and the mixture was stirred at room temperature for 1 hour. Water was poured into the reaction mixture, which was extracted three times with ethyl acetate. The combined organic layer was washed with brine, dried over sodium sulfate, filtered and concentrated under reduced pressure. The residue was subjected to a column chromatography on a basic silica gel (hexane/ethyl acetate 3:1 followed by 1:1), crystallized from diethyl ether to obtain the title compound (583 mg, yield: 26%).

Melting point: 153–155° C.

$^1$H NMR (CDCl$_3$) δ 1.25 (6H, s), 1.31 (3H, t, J=7.0 Hz), 1.32 (6H, s), 2.27 (2H, s), 2.69 (2H, s), 3.73 (2H, t, J=6.2 Hz), 3.92 (2H, t, J=6.2 Hz), 3.92 (5H, s), 4.25 (2H, q, J=7.0 Hz), 6.60 (1H, s), 7.23–7.27 (2H, m), 7.41–7.43 (2H, m).

Example 541

2-[(2-Oxo-3-pyrrolidinyl)amino]-N-[3-(3,4,8,9-tetrahydro-6-methoxy-3,3,8,8-tetramethylfuro[2,3-h]isoquinolin-1-yl)phenyl]acetamide Dihydrochloride D,L-3-Amino-2-pyrrolidinone (83 mg, 0.825 mmol), potassium carbonate (114 mg, 0.825 mmol) and potassium iodide (13 mg, 0.0750 mmol) were added to a solution of 2-chloro-N-[3-(3,4,8,9-tetrahydro-6-methoxy-3,3,8,8-tetramethylfuro[2,3-h]isoquinolin-1-yl)phenyl]acetamide (320 mg, 0.750 mmol) in N,N-dimethylformamide (3 mL) and the mixture was stirred at 60° C. for 1 hour. An aqueous solution of sodium chloride was poured into the reaction mixture, which was extracted twice with ethyl acetate-tetrahydrofuran. The combined organic layer was washed with brine, dried over sodium sulfate, filtered and concentrated under reduced pressure. The residue was subjected to a column chromatography on a basic silica gel (ethyl acetate/methanol 10:1 followed by ethyl acetate/methanol/triethylamine 50:5:1) to obtain a free base of the title compound. This was dissolved in ethyl acetate, combined with 4 M hydrogen chloride/ethyl acetate solution, concentrated under reduced pressure, crystallized from ethanol-ethyl acetate-diisopropyl ether to obtain the title compound (245 mg, yield: 58%).

Melting point: 181–184° C.

$^1$H NMR (DMSO-d$_6$) δ 1.24 (6H, s), 1.44 (6H, s), 2.10–2.42 (4H, m), 3.16–3.30 (4H, m), 3.94 (3H, s), 4.01–4.33 (3H, m), 7.10 (1H, s), 7.37 (1H, d, J=8.0 Hz), 7.65 (1H, t, J=8.0 Hz), 7.86 (1H, s), 7.87 (1H, d, J=8.0 Hz), 8.40 (1H, s), 9.40–10.00 (2H, m), 11.32 (1H, s).

Example 542

2-[Acetyl(2-oxo-3-pyrrolidinyl)amino]-N-[3-(3,4,8,9-tetrahydro-6-methoxy-3,3,8,8-tetramethylfuro[2,3-h]isoquinolin-1-yl)phenyl]acetamide Hydrochloride D,L-3-Amino-2-pyrrolidinone (87 mg, 0.871 mmol), potassium carbonate (120 mg, 0.871 mmol) and potassium iodide (13 mg, 0.0792 mmol) were added to a solution of 2-chloro-N-[3-(3,4,8,9-tetrahydro-6-methoxy-3,3,8,8-tetramethylfuro[2,3-h]isoquinolin-1-yl)phenyl]acetamide (338 mg, 0.792 mmol) in N,N-dimethylformamide (3 mL) and the mixture was stirred at 60° C. for 2.5 hours. With cooling in ice, acetyl chloride (0.12 mL, 0.174 mmol) and triethylamine (0.36 mL, 2.61 mmol) were added to the mixture, and the mixture was stirred at room temperature for 2 hours. Water was poured into the reaction mixture, which was extracted twice with ethyl acetate. The combined organic layer was washed with brine, dried over sodium sulfate, filtered and concentrated under reduced pressure. The residue was subjected to a column chromatography on a basic silica gel (ethyl acetate/methanol 50:1 followed by 10:1) to obtain a free base of the title compound. This was dissolved in ethyl acetate, combined with 4 M hydrogen chloride/ethyl acetate solution, concentrated under reduced pressure, crystallized from ethanol-diisopropyl ether to obtain the title compound (167 mgyield: 37%).

Melting point: 197–200° C.

$^1$H NMR (DMSO-$d_6$) δ 1.22 (6H, s), 1.42 (6H, s), 1.96 (3H, s), 2.05–2.33 (4H, m), 3.10–3.58 (4H, m), 3.94 (3H, s), 4.15–4.81 (3H, m), 7.10 (1H, s), 7.29 (0.5H, d, J=7.6 Hz), 7.35 (0.5H, d, J=7.6 Hz), 7.55–7.67 (1H, m), 7.70–8.05 (1H, m), 7.98 (1H, s), 8.12 (0.5H, s), 8.19 (0.5H, s), 10.49 (0.5H, s), 11.23 (0.5H, s).

Example 543

2-[Methyl(2-oxo-3-pyrrolidinyl)amino]-N-[3-(3,4,8,9-tetrahydro-6-methoxy-3,3,8,8-tetramethylfuro[2,3-h] isoquinolin-1-yl)phenyl]acetamide Potassium carbonate (89 mg, 0.645 mmol) and iodomethane (0.021 mL, 0.338 mmol) were added to a solution of 2-[(2-oxo-3-pyrrolidinyl)amino]-N-[3-(3,4,8,9-tetrahydro-6-methoxy-3,3,8,8-tetramethylfuro[2,3-h] isoquinolin-1-yl)phenyl]acetamide dihydrochloride (173 mg, 0.307 mmol) in N,N-dimethylformamide (1.5 mL) with cooling in ice, and the mixture was stirred at room temperature for 2 hours. Brine was poured into the reaction mixture, which was extracted twice with ethyl acetate-tetrahydrofuran. The combined organic layer was washed with brine, dried over sodium sulfate, filtered and concentrated under reduced pressure. The residue was subjected to a column chromatography on a basic silica gel (hexane/ethyl acetate/triethylamine 30:1:1), crystallized from ethyl acetate-diethyl ether to obtain the title compound (4mg, yield: 3%).

Melting point: 112–114° C.

$^1$H NMR (CDCl$_3$) δ 1.23 (3H, s), 1.27 (3H, s), 1.32 (6H, s), 2.05–2.45 (2H, m), 2.30 (2H, s), 2.50 (3H, s), 2.68 (2H, s), 3.29 (2H, s), 3.32–3.42 (2H, m), 3.55–3.64 (1H, m), 3.92 (3H, s), 5.64 (1H, s), 6.60 (1H, s), 7.07 (1H, d, J=8.0 Hz), 7.34 (1H, t, J=8.0 Hz), 7.54 (1H, s), 7.89 (1H, d, J=8.0 Hz), 9.67 (1H, s).

Example 544

3-(6-Ethoxy-3,4,8,9-tetrahydro-3,3,8,8-tetramethylfuro[2,3-h]isoquinolin-1-yl)benzoic Acid Ethyl Ester A solution of ethyl 3-cyanobenzoate (27.6 g, 157 mmol) in acetic acid (90 mL)-toluene (150 mL) was treated dropwise with conc. sulfuric acid (17.6 mL, 330 mmol) with cooling in ice, and 1-(7-ethoxy-2,3-dihydro-2,2-dimethyl-5-benzofuranyl)-2-methyl-1-propanol (50.0 g, 189 mmol) was added thereto at room temperature, and the mixture was stirred at 65° C. for 1 hour. Ethanol (105 mL) was added dropwise to the mixture and the mixture was stirred at 75° C. for 40 minutes. Water was poured into the reaction mixture, and the organic phase was separated and extracted with 2 M hydrochloric acid. The combined aqueous layer was neutralized with conc. aqueous ammonia, and extracted twice with ethyl acetate (I). The combined organic layer was washed with 0.5 M aqueous solution of sodium hydroxide (II), water and brine, dried over sodium sulfate, filtered and concentrated under reduced pressure. The residue was crystallized from hexane to obtain the title compound (11.8 g, yield: 18%).

Melting-point: 97–100° C.

$^1$H NMR (CDCl$_3$) δ 1.25 (6H, s), 1.30 (6H, s), 1.39 (3H, t, J=7.1 Hz), 1.47 (3H, t, J=7.1 Hz), 2.15 (2H, s), 2.68 (2H, s), 4.19 (2H, q, J=7.1 Hz), 4.38 (2H, q, J=7.1 Hz), 6.62 (1H, s), 7.47 (1H, ddd, J=7.5, 7.4, 1.2 Hz), 7.61 (1H, ddd, J=7.4, 1.8, 1.2 Hz), 8.06–8.10 (2H, m).

Example 545

3-(6-Ethoxy-3,4,8,9-tetrahydro-3,3,8,8-tetramethylfuro[2,3-h]isoquinolin-1-yl)benzoic Acid The aqueous layers in EXAMPLE 544 ((I) and (II)) were combined, neutralized with 5 M hydrochloric acid, and extracted three times with ethyl acetate-tetrahydrofuran. The combined organic layer was concentrated under reduced pressure, crystallized from ethyl acetate to obtain the title compound (2.77 g, yield: 5%).

Melting point: 137–139° C.

$^1$H NMR (CDCl$_3$) δ 1.28 (12H, s), 1.49 (3H, t, J=7.1 Hz), 2.17 (2H, s), 2.66–3.10 (2H, br), 4.23 (2H, q, J=7.1 Hz), 6.65 (1H, s), 7.33–7.41 (2H, m), 7.94–7.97 (1H, m), 8.27 (1H, s).

Example 546

3-(6-Ethoxy-3,4,8,9-tetrahydro-3,3,8,8-tetramethylfuro[2,3-h]isoquinolin-1-yl)benzenamine Dihydrochloride 3-(6-Ethoxy-3,4,8,9-tetrahydro-3,3,8,8-tetramethylfuro [2,3-h]isoquinolin-1-yl)benzenamine (9.36 g, 25.7 mmol) was dissolved in ethyl-acetate, 4 M hydrogen chloride/ethyl acetate solution was added thereto, and the mixture was concentrated under reduced pressure, crystallized from ethanol-ethyl acetate to obtain the title compound (4.47 g, yield: 40%).

Melting point: 240° C. (decomposition).

$^1$H NMR (DMSO-$d_6$) δ 1.26 (6H, s), 1.37 (3H, t, J=7.0 Hz), 1.42 (6H, s), 2.10–2.55 (2H, m), 3.00–3.30 (2H, m), 4.23 (2H, q, J=7.0 Hz), 6.99–7.07 (3H, m), 7.19 (1H, d, J=7.6 Hz), 7.44 (1H, dd, J=8.2, 7.6 Hz).

Example 547

[[4-[[[3-(6-Ethoxy-3,4,8,9-tetrahydro-3,3,8,8-tetramethylfuro[2,3-h]isoquinolin-1-yl)phenyl]amino] carbonyl]phenyl]methyl]phosphonic Acid Diethyl Ester Hydrochloride 1-Hydroxy-1H-benzotriazole monohydrate (327 mg, 2.13 mmol), triethylamine (0.95 mL, 6.79 mmol) and 1-ethyl-3-(3-dimethylaminopropyl)carbodiimide hydrochloride (483 mg, 2.52 mmol) were added to a solution of 3-(6-ethoxy-3,4,8,9-tetrahydro-3,3,8,8-tetramethylfuro[2,3-h]isoquinolin-1-yl)benzenamine dihydrochloride (850 mg, 1.94 mmol) and 4-[(diethoxyphosphinyl)methyl]benzoic acid (529 mg, 1.94 mmol) in N,N-dimethylformamide (6 mL) and the mixture was stirred at room temperature for 7 hours. 4-[(Diethoxyphosphinyl)methyl]benzoic acid (211 mg, 0.776 mmol) was added to the mixture and the mixture was stirred under the same condition for 12 hours. Ice water was poured into the reaction mixture, which was extracted three times with ethyl acetate. The combined organic layer was washed with brine, dried over sodium sulfate, filtered and concentrated under reduced pressure. The residue was subjected to a column chromatography on a basic silica gel (hexane/ethyl acetate 1:1 followed by ethyl acetate) to obtain a free base of the title compound. This was dissolved in ethyl acetate, combined with 4 M hydrogen chloride/ethyl acetate solution, concentrated under reduced pressure, crystallized from ethanol-diisopropyl ether to obtain the title compound (682 mg, yield: 54%).

Melting point: 190–191° C.

$^1$H NMR (DMSO-$d_6$-$D_2O$ (1 drop)) δ 1.18 (6H, t, J=7.1 Hz), 1.25 (6H, s), 1.38 (3H, t, J=7.0 Hz), 1.42 (6H, s), 2.20–2.32 (1H, m), 2.40–2.53 (1H, m), 3.00–3.30 (2H, m), 3.35 (2H, d, J=21.9 Hz), 3.91–4.03 (4H, m), 4.25 (2H, q, J=7.0 Hz), 7.09 (1H, s), 7.36 (1H, d, J=7.7 Hz), 7.44 (2H, dd, J=8.3, 2.3 Hz), 7.64 (1H, t, J=7.7 Hz), 7.94 (2H, d, J=8.3 Hz), 8.06 (1H, d, J=7.7 Hz), 8.09 (1H, s), 10.59 (1H, s).

Example 548

6-(Ethylsulfinyl)-3,4,8,9-tetrahydro-3,3,8,8-tetramethyl-1-phenylfuro[2,3-h]isoquinoline A solution of sodium metaperiodate (434 mg, 2.03 mmol) in water (2.5 mL) was added to a solution of 6-(ethylthio)-3,4,8,9-tetrahydro-3,3,8,8-tetramethylfuro[2,3-h]isoquinoline hydrochloride (326 mg, 0.811 mmol) in methanol (3.5 mL) and the mixture was stirred at room temperature for 2 hours. Water was poured into the reaction mixture, which was combined with sodium hydrogen carbonate, and extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 5:1), crystallized from diisopropyl ether-hexane to obtain the title compound (168 mg, yield: 54%).

Melting point: 146–147° C.

$^1$H NMR (CDCl$_3$) δ 1.20–1.30 (15H, m), 2.19 (2H, s), 2.77 (2H, s), 2.82–3.18 (2H, m), 7.41–7.42 (6H, m).

Example 549

3-[3,4,8,9-Tetrahydro-3,3,8,8-tetramethyl-6-(propylthio)furo[2,3-h]isoquinolin-1-yl]benzoic Acid Ethyl Ester 1.57 M n-butyllithium/hexane solution (42.3 mL, 66.4 mmol) was treated dropwise successively with a solution of N,N,N',N'-tetramethylethylenediamine (10.0 mL, 66.4 mmol) in tetrahydrofuran (15 mL), a solution of 7-bromo-2,3-dihydro-2,2-dimethyl-5-(2-methy-1-proenyl)benzofuran (4.68 g, 16.6 mmol) in tetrahydrofuran (15 mL) and a solution of n-propyl disulfide (20 g, 133 mmol) in tetrahydrofuran (15 mL) at −78° C., and the mixture was allowed to warm to room temperature while stirring for 15 hours. The reaction mixture was poured into a saturated aqueous solution of ammonium chloride, and extracted twice with ethyl acetate. The combined organic layer was washed with brine, dried over magnesium sulfate, filtered and concentrated under reduced pressure. The residue was subjected to a column chromatography on a silica gel (hexane followed by hexane/ethyl acetate 50:1) to obtain an about 15:2 mixture of 2,3-dihydro-2,2-dimethyl-5-(2-methyl-1-propenyl)-7-(propylthio)benzofuran and 2,3-dihydro-2,2-dimethyl-5-(2-methyl-1-propenyl)benzofuran (4.11 g).

A suspension of the resultant mixture (1.01 g) and ethyl 3-cyanobenzoate (601 mg, 3.43 mmol) in acetic acid (2 mL)-toluene (4.5 mL) was treated dropwise with conc. sulfuric acid (0.38 mL, 7.20 mmol) with cooling in ice, and stirred at 60° C. for 1 hour. Ethanol (2.1 mL 34.9 mmol) was added dropwise to the mixture, and the mixture was stirred at the same temperature for 30 minutes. Ice water was poured into the reaction mixture, which was neutralized with sodium hydrogen carbonate, and extracted twice with ethyl acetate. The combined organic layer was washed with brine, dried over sodium sulfate, filtered and concentrated under reduced pressure. The residue was subjected to a column chromatography on a basic silica gel (hexane/ethyl acetate 50:1 followed by 10:1), and subjected again to a column chromatography on a silica gel (hexane/ethyl acetate 10:1 followed by 5:1), crystallized from hexane to obtain the title compound (136 mg, yield: 9%). The mother liquor was crystallized from hexane to obtain the second crystal of the title compound (78 mg, yield: 5%).

Melting point: 83–84° C.

$^1$H NMR (CDCl$_3$) δ 1.05 (3H, t, J=7.3 Hz), 1.25 (6H, s), 1.29 (6H, s), 1.39 (3H, t, J=7.2 Hz), 1.64–1.76 (2H, m), 2.16 (2H, s), 2.68 (2H, s), 2.95 (2H, t, J=7.2 Hz), 4.39 (2H, q, J=7.2 Hz), 6.92 (1H, s), 7.48 (1H, dd, J=7.8, 7.2 Hz), 7.62 (1H, d, J=7.8 Hz), 8.07–8.10 (2H, m).

Example 550

3-[6-(Ethylthio)-3,4,8,9-tetrahydro-3,3,8,8-tetramethylfuro[2,3-h]isoquinolin-1-yl]benzoic Acid Isopropyl Ester To a suspension of 7-(ethylthio)-2,3-dihydro-2,2-dimethyl-5-(2-methyl-1-propenyl)benzofuran (811 mg, 3.21 mmol) and isopropyl 3-cyanobenzoate (552 mg, 2.92 mmol) in acetic acid (3 mL)-toluene (6 mL) was treated dropwise with conc. sulfuric acid (0.33 mL, 6.13 mmol) with cooling in ice, and stirred at 70° C. for 1.5 hours. Ice water was poured into the reaction mixture, which was neutralized with sodium hydrogen carbonate and extracted twice with ethyl acetate. The combined organic layer was washed with a brine, dried over sodium sulfate, filtered and concentrated under reduced pressure. The residue was subjected to a column chromatography on a silica gel (hexane/ethyl acetate 10:1) and crystallized from pentane to obtain the title compound (86 mg, yield: 7%).

Melting point:. 108–110° C.

$^1$H NMR (CDCl$_3$) δ 1.26 (6H, s), 1.92 (6H, s), 1.34 (3H, t, J=7.5 Hz), 1.36 (6H, d, J=6.3 Hz), 2.17 (2H, s), 2.69 (2H, s), 3.00 (2H, q, J=7.5 Hz), 5.20–5.33 (1H, m), 6.94 (1H, s), 7.48 (1H, t, J=7.8 Hz), 7.61 (1H, dd, J=7.8, 1.5 Hz), 8.04 (1H, t, J=1.5 Hz), 8.09 (1H, dd, J=7.8, 1.5 Hz).

Example 551

3-[5-(Cyanomethyl)-3,4,8,9-tetrahydro-6-methoxy-3,3,8,8-tetramethylfuro[2,3-h]isoquinolin-1-yl]benzoic Acid Methyl Ester Hydrochloride Paraformaldehyde (94%) (841 mg, 26.3 mmol), sodium bromide (2.98 g, 29.0 mmol) and conc. sulfuric acid (2.11 mL, 39.6 mmol) were added to a solution of 3-[3,4,8,9-tetrahydro-6-methoxy-3,3,8,8-tetramethylfuro[2,3-h]isoquinolin-1-yl]benzoic acid methyl ester (4.99 g, 12.7 mmol) in acetic acid (6.5 mL) and the mixture was stirred at 100° C. for 11 hours. Methanol was added dropwise at 75° C., and the mixture was stirred at the same temperature for 3 hours. Water was poured into the reaction mixture, which was washed with diisopropyl ether, neutralized with sodium hydrogen carbonate, and extracted twice with ethyl acetate. The combined organic layer was washed with 1 M aqueous solution of sodium hydroxide and a brine, dried over sodium sulfate, filtered and concentrated under reduced pressure. The residue was subjected to a column chromatography on a silica gel (hexane/ethyl acetate 5:1) to obtain 3-[5-(bromomethyl)-3,4,8,9-tetrahydro-6-methoxy-3,3,8,8-tetramethylfuro[2,3-h]isoquinolin-1-yl]benzoic acid methyl ester (1.30 g, yield: 21%) as an amorphous material.

$^1$H NMR (CDCl$_3$) δ 1.28 (6H, s), 1.29 (6H, s), 2.12 (2H, s), 2.72 (2H, s), 3.92 (3H, s), 4.05 (3H, s), 4.64 (2H, s), 7.48 (1H, t, J=7.9 Hz), 7.61 (1H, dd, J=7.9, 1.6 Hz), 8.06 (1H, d, J=1.6 Hz), 8.08 (1H, dd, J=7.9, 1.6 Hz).

A solution of potassium cyanide (174 mg, 2.67 mmol) in water (2.5 mL) was added to a solution of the resultant bromo-derivative (1.30 g, 2.67 mmol) in N,N-dimethylformamide (8 mL) and the mixture was stirred at room temperature for 1 hour. Ice water was poured into the reaction mixture, which was extracted twice with ethyl acetate. The combined organic layer was washed with brine, dried over sodium sulfate, filtered and concentrated under reduced pressure. The residue was subjected to a column chromatography on a basic silica gel (hexane/ethyl acetate 10:1 followed by 5:1) to obtain a free base of the title compound. This was dissolved in ethyl acetate, combined with 4 M hydrogen chloride/ethyl acetate solution, concentrated under reduced pressure, crystallized from ethyl acetate to obtain the title compound (926 mg, yield: 74%).

Melting point: 186–188° C.

$^1$H NMR (DMSO-$_6$) δ 1.25 (6H, s), 1.45 (6H, s), 2.15 (2H, s), 3.19 (2H, s), 3.91 (3H, s), 4.02 (2H, s), 4.07 (3H, s), 7.78 (1H, t, J=7.6 Hz), 7.89 (1H, d, J=7.6 Hz), 8.21 (1H, s), 8.28 (1H, d, J=7.6 Hz).

Example 552

3-[5-(Cyanomethyl)-3,4,8,9-tetrahydro-6-methoxy-3,3,8,8-tetramethylfuro[2,3-h]isoquinolin-1-yl]benzoic Acid Hydrochloride The title compound was obtained from 3-[5-(cyanomethyl)-3,4,8,9-tetrahydro-6-methoxy-3,3,8,8-tetramethylfuro[2,3-h]isoquinolin-1-yl]benzoic acid methyl ester hydrochloride by the method similar to that in EXAMPLE 80. Quantitative.

Melting point: 182–184° C. (acetone-ethyl acetate).

$^1$H NMR (DMSO-d$_6$) δ 1.25 (6H, s), 1.45 (6H, s), 2.16 (2H, s), 3.19 (2H, s), 4.02 (2H, s), 4.07 (3H, s), 7.75 (1H, t, J=7.8 Hz), 7.87 (1H, d, J=7.8 Hz), 8.18 (1H, s), 8.26 (1H, d, J=7.8 Hz).

Example 553

3-[5-(Cyanomethyl)-3,4,8,9-tetrahydro-6-methoxy-3,3,8,8-tetramethylfuro[2,3-h]isoquinolin-1-yl]-N-methylbenzamide Hydrochloride N,N'-Carbonyldiimidazole (118 mg, 0.728 mmol) was added to a solution of 3-[5-(cyanomethyl)-3,4,8,9-tetrahydro-6-methoxy-3,3,8,8-tetramethylfuro[2,3-h]isoquinolin-1-yl]benzoic acid hydrochloride (331 mg, 0.728 mmol) in N,N-dimethylformamide (3 mL) and the mixture was stirred at room temperature for 40 minutes. Triethylamine (0.11 mL, 0.801 mmol) and methylamine hydrochloride (54 mg, 0.801 mmol) were added to the mixture, and the mixture was stirred at room temperature for 4 hours. Ice water was poured into the reaction mixture, which was extradted twice with ethyl acetate. The combined organic layer was washed with 1 M aqueous solution of sodium hydroxide, water and brine, dried over sodium sulfate, filtered and concentrated under reduced pressure. The residue was subjected to a column chromatography on a basic silica gel (hexane/ethyl acetate 1:1) to obtain a free base of the title compound. This was dissolved in ethyl acetate, combined with 4 M hydrogen chloride/ethyl acetate solution, concentrated under reduced pressure, crystallized from ethyl acetate to obtain the title compound (139 mg, yield: 41%).

Melting point: 160–162° C.

$^1$H NMR (DMSO-d$_6$) δ 1.26 (6H, s), 1.45 (6H, s), 2.18 (2H, s), 2.81 (3H, d, J=4.0 Hz), 3.18 (2H, s), 4.02 (2H, s), 4.07 (3H, s), 7.67–7.74 (2H, m), 8.12–8.19 (2H, m), 8.77 (1H, br s).

Example 554

3-[5-(Cyanomethyl)-3,4,8,9-tetrahydro-6-methoxy-3,3,8,8-tetramethylfuro[2,3-h]isoquinolin-1-yl]-N-(hexahydro-2-oxo-1H-azepin-3-yl)benzamide Triethylamine (0.10 mL, 0.743 mmol) and N,N'-carbonyldiimidazole (120 mg, 0.743 mmol) were added to a solution of 3-[5-(cyanomethyl)-3,4,8,9-tetrahydro-6-methoxy-3,3,8,8-tetramethylfuro[2,3-h]isoquinolin-1-yl]benzoic acid hydrochloride (338 mg, 0.743 mmol) in N,N-dimethylformamide (3 mL) and the mixture was stirred at room temperature for 40 minutes. 3-Aminohexahydro-2H-azepin-2-one (101 mg, 0.784 mmol) was added to the mixture and the mixture was stirred at room temperature for 4.5 hours. Ice water was poured into the reaction mixture, which was extracted twice with ethyl acetate. The combined organic layer was washed with 1 M aqueous solution of sodium hydroxide, water and a brine, dried over sodium sulfate, filtered and concentrated under reduced pressure. The residue was subjected to a column chromatography on a basic silica gel (hexane/ethyl acetate 1:2), crystallized from ethyl acetate to obtain the title compound (206 mg yield: 52% )

Melting point: 130–132° C.

$^1$H NMR (CDCl$_3$) δ 1.28 (12H, s), 1.48–1.70 (2H, m), 1.80–2.30 (4H, m), 2.13 (2H, s), 2.69 (2H, s), 3.25–3.40 (2H, m), 3.74 (2H, s), 4.04 (3H, s), 4.69–4.77 (1H, m), 6.15 (1H, br s), 7.47–7.49 (2H, m), 7.71 (1H, d, J=5.6 Hz), 7.88–7.95 (2H, m).

Example 555

N-[3-[5-(Cyanomethyl)-3,4,8,9-tetrahydro-6-methoxy-3,3,8,8-tetramethylfuro[2,3-h]isoquinolin-1-yl]benzoyl]-2-methylalanine Ethyl Ester 1-Hydroxy-1H-benzotriazole monohydrate (829 mg, 5.41 mmol), triethylamine (2.40 mL, 17.2 mmol) and 1-ethyl-3-(3-dimethylaminopropyl)carbodiimlde hydrochloride (1.23 g, 6.40 mmol) were added to a solution of 3-[5-(cyanomethyl)-3,4,8,9-tetrahydro-6-methoxy-3,3,8,8-tetramethylfuro[2,3-h]isoquinolin-1-yl]benzoic acid hydrochloride (2.24 g, 4.92 mmol) and ethyl 2-aminoisobutyrate hydrochloride (907 mg, 5.41 mmol) in N,N-dimethylformamide (10 mL) and the mixture was stirred at room temperature for 1.5 hours. Ice water was poured into the reaction mixture, which was extracted three times with ethyl acetate. The combined organic layer was washed with 0.5 M aqueous solution of sodium hydroxide and a brine, dried over sodium sulfate, filtered and concentrated under reduced pressure. The residue was subjected to a column chromatography on a basic silica gel (hexane/ethyl acetate 3:1 followed by 2:1), crystallized from ethyl acetate-diethyl ether to obtain the title compound (1.50 g, yield: 57%).

Melting point: 126–128° C.

$^1$H NMR (CDCl$_3$) δ 1.29 (3H, t, J=7.0 Hz), 1.29 (12H, s), 1.68 (6H, s), 2.13 (2H, s), 2.69 (2H, s), 3.75 (2H, s), 4.04 (3H, s), 4.24 (2H, q, J=7.0 Hz), 6.89 (1H, s), 7.46–7.48 (2H, m), 7.81–7.89 (2H, m).

Example 556

N-[3-[5-(Cyanomethyl)-3,4,8,9-tetrahydro-6-methoxy-3,3,8,8-tetramethylfuro[2,3-h]isoquinolin-1-yl]benzoyl]-2-methylalanine Hydrochloride 5 M aqueous solution of sodium hydroxide (2 mL) was added to a solution of N-[3-[5-(cyanomethyl)-3,4,8,9-tetrahydro-6-methoxy-3,3,8,8-tetramethylfuro[2,3-h]isoquinolin-1-yl]benzoyl]-2-methylalanine ethyl ester (1.05 g, 1.98 mmol) in ethanol (8 mL) and the mixture was stirred at room temperature for 1 hour. The reaction mixture was made acidic with 5 M hydrochloric acid, and the solvent was distilled off. The residue was dissolved in methanol, and the insolubles were filtered off. The filtrate was concentrated under reduced pressure, and this procedure was repeated three times. The residue was crystallized from acetone-ethyl acetate to obtain the title compound (1.04 g, yield: 97%).

Melting point: 191–194° C.

$^1$H NMR (DMSO-d$_6$) δ 1.27 (6H, br s), 1.42 (6H, br s), 1.48 (6H, s), 2.24 (2H, s), 3.05–3.30 (2H, m), 3.95–4.13 (5H, m), 7.65–7.80 (2H, m), 8.18–8.30 (2H, m), 8.80 (1H, s).

Example 557
N-(2-Amino-2-oxoethyl)-3-[5-(cyanomethyl)-3,4,8,9-tetrahydro-6-methoxy-3,3,8,8-tetramethylfuro[2,3-h]isoquinolin-1-yl]benzamide Hydrochloride 1-Hydroxy-1H-benzotriazole monohydrate (377 mg, 2.46 mmol), triethylamine (1.09 mL, 7.84 mmol) and 1-ethyl-3-(3-dimethylaminopropyl)carbodiimide hydrochloride (559 mg, 2.91 mmol) were added to a solution of 3-[5-(cyanomethyl)-3,4,8,9-tetrahydro-6-methoxy-3,3,8,8-tetramethylfuro[2,3-h]isoquinolin-1-yl]benzoic acid hydrochloride (1.02 g, 2.24 mmol) and glycinamide hydrochloride (248 mg, 2.24 mmol) in N,N-dimethylformamide (6 mL) and the mixture was stirred at room temperature for 6 hours. Water was poured into the reaction mixture, which was extracted three times with ethyl acetate. The combined organic layer was washed with brine, dried over sodium sulfate, filtered and concentrated under reduced pressure. The residue was subjected to a column chromatography on a basic silica gel (ethyl acetate/methanol 100:1) to obtain a free base of the title compound. This was dissolved in ethyl acetate, combined with 4 M hydrogen chloride/ethyl acetate solution, concentrated under reduced pressure, triturated with diethyl ether to obtain the title compound (425 mg, yield: 37%).
Amorphous.
$^1$H NMR (DMSO-$d_6$) δ 1.27 (6H, s), 1.46 (6H, s), 2.22 (2H, s), 3.20 (2H, s), 3.85 (2H, d, J=3.8 Hz), 4.03 (2H, s), 4.08 (3H, s), 7.09 (1H, s), 7.47 (1H, s), 7.74–7.80 (2H, m), 8.18–8.25 (2H, m), 8.99 (1H, s).

Example 558
N-(2-Amino-1,1-dimethyl-2-oxoethyl)-3-[5-(cyanomethyl)-3,4,8,9-tetrahydro-6-methoxy-3,3,8,8-tetramethylfuro[2,3-h]isoquinolin-1-yl]benzamide 1-Hydroxy-1H-benzotriazole ammonium salt (176 mg, 1.16 mmol) and 1-ethyl-3-(3-dimethylaminopropyl)carbodiimide hydrochloride (240 mg, 1.25 mmol) were added to a solution of N-[3-[5-(cyanomethyl)-3,4,8,9-tetrahydro-6-methoxy-3,3,8,8-tetramethylfuro[2,3-h]isoquinolin-1-yl]benzoyl]-2-methylalanine hydrochloride (521 mg, 0.965 mmol) in N,N-dimethylformamide (5 mL) and the mixture was stirred at room temperature for 10 minutes. Triethylamine (0.40 mL, 2.90 mmol) was added to the mixture and the mixture was stirred at room temperature for 3 hours. Ice water was poured into the reaction mixture, which was extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 1:2 followed by ethyl acetate), crystallized from ethyl acetate-diisopropyl ether to obtain the title compound (323 mg, yield: 67%).
Melting point: 217–219° C.
$^1$H NMR (CDCl$_3$) δ 1.29 (12H, s), 1.71 (6H, s), 2.14 (2H, s), 2.69 (2H, s), 3.74 (2H, s), 4.04 (3H, s), 5.44 (1H, br s), 6.42 (1H, br s), 7.26–7.27 (1H, m), 7.47–7.48 (2H, m), 7.84–7.89 (2H, m).

Example 559
3-[5-(Cyanomethyl)-3,4,8,9-tetrahydro-6-methoxy-3,3,8,8-tetramethylfuro[2,3-h]isoquinolin-1-yl]-N-[1,1-dimethyl-2-oxo-2-[(2-oxo-3-pyrrolidinyl)amino]ethyl]benzamide 1-Hydroxy-1H-benzotriazole monohydrate (138 mg, 0.904 mmol), triethylamine (0.29 mL, 2.06 mmol) and 1-ethyl-3-(3-dimethylaminopropyl)carbodiimide hydrochloride (205 mg, 1.07 mmol) were added to a solution of N-[3-[5-(cyanomethyl)-3,4,8,9-tetrahydro-6-methoxy-3,3,8,8-tetramethylfuro[2,3-h]isoquinolin-1-yl]benzoyl]-2-methylalanine hydrochloride (444 mg, 0.822 mmol) and D,L-3-amino-2-pyrrolidinone (82 mg, 0.822 mmol) in N,N-dimethylformamide (4 mL) and the mixture was stirred at room temperature for 6 hours. Ice water was poured into the reaction mixture, which was extracted three times with ethyl acetate. The combined organic layer was washed with brine, dried over sodium sulfate, filtered and concentrated under reduced pressure. The residue was subjected to a column chromatography on a basic silica gel (ethyl acetate/methanol 100:1 followed by 10:1), and the resultant crystals were washed with diisopropyl ether to obtain the title compound (157 mg, yield: 33%).
Melting point: 137–139° C.
$^1$H NMR (CDCl$_3$) δ 1.29 (12H, s), 1.70 (3H, s), 1.72 (3H, s), 1.94–2.08 (1H, m), 2.14 (2H, s), 2.69 (2H, s), 2.70–2.85 (1H, m), 3.16–3.45 (2H, m), 3.75 (2H, s), 4.04 (3H, s), 4.26–4.34 (1H, m), 5.99 (1H, s), 6.91 (1H, d, J=3.6 Hz), 7.13 (1H, s), 7.44–7.49 (2H, m), 7.87 (2H, s).

Example 560
3,4,8,9-Tetrahydro-6-methoxy-3,3,8,8-tetramethyl-1-phenyl-5-furo[2,3-h]-isoquinolinecarboxaldehyde Hydrochloride Manganese dioxide (4.90 g, 56.4 mmol) was added to a solution of 3,4,8,9-tetrahydro-6-methoxy-3,3,8,8-tetramethyl-5-furo[2,3-h]isoquinolinemethanol (1.03 g, 2.82 mmol) in chloroform (15 mL) and the mixture was stirred at room temperature for 2 hours, and at 50° C. for 15 hours. Inorganic salts were filtered off and the filtrate was concentrated under reduced pressure. The residue was subjected to a column chromatography on a silica gel (hexane/ethyl acetate 5:1) to obtain a free base of the title compound. This was dissolved in ethyl acetate, combined with 4 M hydrogen chloride/ethyl acetate solution, concentrated under reduced pressure, crystallized from ethyl acetate-hexane to obtain the title compound (344 mg, yield: 31%).
Melting point: 136–139° C.
$^1$H NMR (DMSO-$d_6$) δ 1.29 (6H, s), 1.43 (6H, s), 2.24 (2H, s), 3.40 (2H, s), 4.14 (3H, s), 7.60–7.82 (5H, m), 10.42 (1H, s).

Example 561
3,4,8,9-Tetrahydro-6-methoxy-3,3,8,8-tetramethyl-1-phenyl-5-furo[2,3-h]isoquinolinecarbonitrile Hydroxylamine hydrochloride (30 mg, 0.4.35 mmol) was added to a solution of 3,4,8,9-tetrahydro-6-methoxy-3,3,8,8,-tetramethyl-1-phenyl-5-furo[2,3-h]isoquinolinecarboxaldehyde hydrochloride (116 mg, 0.290 mmol) in formic acid (1 mL) and the mixture was stirred at 100° C. for 3 hours. Water was poured into the reaction mixture, which was neutralized with conc. aqueous ammonia and extracted twice with ethyl acetate. The combined organic layer was washed with water and brine, dried over sodium sulfate, filtered and concentrated under reduced pressure. The residue was subjected to a column chromatography on a silica gel (hexane/ethyl acetate 5:1), and the resultant crystals were washed with diisopropyl ether-hexane to obtain the title compound (55 mg, yield: 53%).
Melting point: 166–168° C.
$^1$H NMR (CDCl$_3$) δ 1.27 (6H, s), 1.30 (6H, s), 2.19 (2H, s), 2.87 (2H, s), 4.13 (3H, s), 7.35–7.43 (5H, m).

Example 562
3-[5-(Cyanomethyl)-6-ethoxy-3,4,8,9-tetrahydro-3,3,8,8-tetramethylfuro[2,3-h]isoquinolin-1-yl]benzoic Acid Ethyl Ester Hydrochloride Paraformaldehyde (94%) (613 mg, 19.2 mmol), sodium bromide (2.17 g, 21.1 mmol) and conc. sulfuric acid (1.71 mL, 32.0 mmol) were added to a solution of 3-(6-ethoxy-3,4,8,9-tetrahydro-3,3,8,8-tetramethylfuro[2,3-h]isoquinolin-1-yl)benzoic acid (5.03 g, 12.8 mmol) in acetic acid (10 mL) and the mixture was stirred at 105° C. for 14 hours. Paraformaldehyde (94%) (409 mg, 12.8 mmol), sodium bromide (1.45 g, 14.1 mmol) and conc. sulfuric acid (0.68 mL, 12.8 mmol) were further added to the mixture and the mixture was stirred at 115° C. for 10 hours. The reaction mixture was adjusted at pH 8 with 5 M aqueous solution of sodium hydroxide, and extracted with ethyl acetate. The organic layer was washed with brine, dried over sodium sulfate, filtered and concentrated under reduced pressure. The residue was dissolved in ethanol (12 mL) and thionyl chloride (0.65 mL, 8.94 mmol) was added thereto with cooling in ice, and the mixture was stirred at room temperature for 24 hours. The solvent was distilled off under reduced pressure, and the residue was combined with water, neutralized with sodium hydrogen carbonate, and extracted twice with ethyl acetate. The combined organic layer was washed with brine, dried over sodium sulfate, filtered and concentrated under reduced pressure. The residue was subjected to a column chromatography on a silica gel (hexane/ethyl acetate 5:1) to obtain 3-[5-(bromomethyl)-6-ethoxy-3,4,8,9-tetrahydro-3,3,8,8-tetramethylfuro[2,3-h]isoquinolin-1-yl]benzoic acid ethyl ester (170 mg, yield: 3%) as an oil.

$^1$H NMR (CDCl$_3$) δ 1.27 (6H, s), 1.28 (6H, s), 1.37–1.42 (6H, m), 2.12 (2H, s), 2.77 (2H, s), 4.31 (2H, q, J=7.1 Hz), 4.39 (2H, q, J=7.1 Hz), 4.76 (2H, s), 7.48 (1H, t, J=7.8 Hz), 7.61 (1H, dd, J=7.8, 1.5 Hz), 8.05–8.07 (1H, m), 8.09 (1H, dt, J=7.8, 1.5 Hz).

A solution of sodium cyanide (18 mg, 0.362 mmol) in water (0.5 mL) was added to absolution of the resultant bromo-derivative (170 mg, 0.330 mmol) in N,N-dimethylformamide (0.7 mL) and the mixture was stirred at room temperature for 1 hour and at 60° C. for 2 hours. Water was poured into the reaction mixture, which was extracted twice with ethyl acetate. The combined organic layer was washed with brine, dried over sodium sulfate, filtered and concentrated under reduced pressure. The residue was subjected to a column chromatography on a silica gel (hexane/ethyl acetate 3:1) to obtain a free base of the title compound. This was dissolved in ethyl acetate, combined with 4 M hydrogen chloride/ethyl acetate solution, concentrated under reduced pressure, crystallized from ethyl acetate to obtain the title compound (111 mg, yield: 68%).

Melting point: 126–128° C.

$^1$H NMR (DMSO-d$_6$) δ 1.25 (6H, s), 1.30–1.37 (6H, m), 1.44 (6H, s), 2.16 (2H, s), 3.16 (2H, s), 4.01 (2H, s), 4.33–4.47 (4H, m), 7.73–7.90 (2H, m), 8.18–8.29 (2H, m).

Example 563

(S)-N-(2-Oxo-3-azetidinyl)-3-(3,4,8,9-tetrahydro-6-methoxy-3,3,8,8-tetramethylfuro[2,3-h]isoquinolin-1-yl)benzamide 3-(3,4,8,9-Tetrahydro-6-methoxy-3,3,8,8-tetramethylfuro[2,3-h]isoquinolin-1-yl)benzoic acid hydrochloride (0.25 g, 0.6 mmol) was dissolved in N,N-dimethylformamide (3 mL), N-ethyldiisopropylamine (0.104 mL, 0.6 mmol) was added thereto, and the mixture was stirred for 5 minutes N,N'-Carbonyldiimidazole (0.107 g, 0.66 mmol) was added to the mixture and the mixture was stirred at room temperature for 30 minutes. (S)-3-Amino-2-azetidinone (0.057 g, 0.66 mmol) was added to the reaction mixture and the mixture was stirred at room temperature for 15 hours. Ice water was added to the reaction mixture, which was extracted twice with ethyl acetate. The extract was washed with an aqueous solution of sodium chloride, dried over sodium sulfate, filtered, and concentrated under reduced pressure The residue was subjected to a column chromatography on a silica gel, eluted with ethyl acetate/methanol/triethylamine (95:5:1) to collect the intended fraction, which was concentrated to obtain the title compound (0.171 g, yield: 63%). The title compound was recrystallized from diethyl ether.

Melting point: 154–157° C.

$^1$H NMR (CDCl$_3$) δ 1.29 (6H, s), 1.31 (6H, s), 2.16 (2H, s), 2.61 (2H, s), 3.22 (1H, br), 3.60 (1H, t, J=5 Hz), 3.93 (3H, s), 5.10 (1H, br), 6.32 (1H, br), 6.61 (1H, s), 7.4–8.0 (4H, m), 8.03 (1H, br).

Example 564

N-(2-Oxo-3-pyrrolidinyl)-3-(3,4,8,9-tetrahydro-6-methoxy-3,3,8,8-tetramethylfuro[2,3-h]isoquinolin-1-yl)benzamide 3-(3,4,8,9-Tetrahydro-6-methoxy-3,3,8,8-tetramethylfuro[2,3-h]isoquinolin-1-yl)benzoic acid hydrochloride (0.25 g, 0.6 mmol) was dissolved in N,N-dimethylformamide (3 mL), N-ethyldiisopropylamine (0.104 mL, 0.6 mmol) followed by N,N'-carbonyldiimidazole (0.107 g, 0.66 mmol) were added thereto, and the mixture was stirred at room temperature for 1 hour. 3-Amino-2-pyrrolidinone (0.067 g, 0.66 mmol) was added to the reaction mixture and the mixture was stirred at room temperature for 15 hours. Ice water was added to the reaction mixture, which was extracted twice with ethyl acetate. The extract was washed with an aqueous solution of sodium chloride, dried over sodium sulfate, filtered and concentrated under reduced pressure. The residue was subjected to a column chromatography on a silica gel, eluted with ethyl acetate/methanol (10:1) to collect the intended fraction, which was concentrated to obtain the title compound (0.184 g, yield: 66%). The title compound was recrystallized from diethyl ether.

Melting point: 191–193° C.

$^1$H NMR (CDCl$_3$) δ 1.26 (6H, s), 1.30 (6H, s), 1.7–2.3 (2H, m), 2.15 (2H, s), 2.70 (2H, s), 3.2–3.5 (2H, m), 3.93 (3H, s), 4.62 (1H, br), 6.62 (1H, s), 7.00 (1H, br), 7.4–8.0 (4H, m), 7.70 (1H, br).

Example 565

3,4,8,9-Tetrahydro-6-methoxy-4,4,8,8-tetramethyl-1-phenylfuro[2,3-h]isoquinoline N-[2-(2,3-Dihydro-7-methoxy-2,2-dimethyl-5-benzofuranyl)-2-methylpropyl]benzamide (0.269 g, 0.76 mmol) was suspended in phosphorus oxychloride (3.5 g, 22.8 mol) and the mixture was stirred at 100–105° C. for 2 hours. After cooling to room temperature, the reaction mixture was poured into an aqueous solution of sodium carbonate while cooling in ice with stirring, adjusted at pH 7 and extracted twice with ethyl acetate. The extract was washed with an aqueous solution of sodium chloride, dried over magnesium sulfate, filtered and concentrated under reduced pressure. The residue was subjected to a column chromatography on a silica gel, eluted with hexane/ethyl acetate/triethylamine (67:33:1) to collect the intended fraction, which was concentrated to obtain the title compound (0.175 g, yield: 68%). The title compound was recrystallized from diethyl ether/hexane (1:2).

Melting point: 137–139° C.

$^1$H NMR (CDCl$_3$) δ 1.28 (6H, s), 1.32 (6H, s), 2.26 (2H, s), 3.63 (2H, s), 3.95 (3H, s), 6.79 (1H, s), 7.42 (5H, s).

Example 566

3-(3,4,8,9-tetrahydro-6-methoxy-4,4,8,8-tetramethylfuro[2,3-h]isoquinolin-1-yl)benzonitrile 3-Cyano-N-[2-(2,3-dihydro-7-methoxy-2,2-dimethyl-5-benzofuranyl)-2-methylpropyl]benzamide (0.955 g, 2.52 mmol) was suspended in phosphorus oxychloride (11.6 g, 75.6 mmol) and the mixture was stirred at 100–105° C. for 2 hours. After cooling to room temperature, the reaction mixture was poured into an aqueous solution of potassium carbonate while cooling in ice with stirring, and adjusted at pH 7 and extracted twice with ethyl acetate. The extract was washed with an aqueous solution of sodium chloride, dried over magnesium sulfate, filtered and concentrated under reduced pressure. The residue was subjected to a column chromatography on a silica gel, eluted with hexane/ethyl acetate (3:2) to collect the intended fraction, which was concentrated to obtain the title compound (0.65 g, yield: 71%). The title compound was recrystallized from diethyl ether.

Melting point: 178–180° C.
$^1$H NMR (CDCl$_3$) δ 1.24 (6H, s), 1.27 (6H, s), 2.23 (2H, s), 3.64 (2H, s), 3.96 (3H, s), 6.81 (1H, s), 7.4–7.9 (4H, m).

Example 567

3-(3,4,8,9-Tetrahydro-6-methoxy-4,4,8,8-tetramethylfuro[2,3-h]isoquinolin-1-yl)benzamide 3-(3,4,8,9-Tetrahydro-6-methoxy-4,4,8,8-tetramethylfuro[2,3-h]isoquinolin-1-yl)benzonitrile (0.446 g, 1.23 mmol) was dissolved in methanol (7 mL), 1 M aqueous solution of sodium hydroxide (1.97 mL) and 30% aqueous solution of hydrogen peroxide (0.28 mL) were added thereto with cooling in ice, and the mixture was stirred at room temperature for 20 hours. Methanol was distilled off under reduced pressure, and the residue was diluted with water and extracted twice with ethyl acetate. The extract was washed with an aqueous solution of sodium chloride, dried over magnesium sulfate, filtered and concentrated under reduced pressure. The residue was recrystallized from ethyl acetate to obtain the title compound (0.275 g, yield: 59%).

Melting point: 191–193° C.
$^1$H NMR (CDCl$_3$) δ 1.28 (6H, s), 1.31 (6H, s), 2.24 (2H, s), 3.63 (2H, s), 3.95 (3H, s), 5.85 (1H, br), 6.35 (1H, br), 6.81 (1H, s), 7.4–7.9 (4H, m).

Example 568

3,4,8,9-Tetrahydro-6-methoxy-4,4,8,8-tetramethyl-1-furo[2,3-h]isoquinolinecarboxylic Acid Ethyl Ester Ethyl [[2-(2,3-dihydro-7-methoxy-2,2-dimethyl-5-benzofuranyl)-2-methylpropyl]amino]oxoacetate (0.510 g, 0.76 mmol) was dissolved in phosphorus oxychloride (6.72 g, 43.8 mmol) and stirred at 100–105° C. for 3 hours. After cooling to room temperature, the reaction mixture was poured into 2 M aqueous solution of sodium hydroxide (30 mL) while cooling in ice with stirring, adjusted at pH 5 with sodium hydrogen carbonate, and extracted twice with ethyl acetate. The extract was washed with an aqueous solution of sodium chloride, dried over sodium sulfate, filtered and concentrated under reduced pressure. The residue was subjected to a column chromatography on a silica gel, eluted with hexane/ethyl acetate (2:1) to collect the intended fraction, which was concentrated to obtain the title compound (0.286 g, yield: 68%). The title compound was recrystallized from diethyl ether/hexane (1:1).

Melting point: 117–121° C.
$^1$H NMR (CDCl$_3$) δ 1.23 (6H, s), 1.26 (3H, t, J=7 Hz), 1.49 (6H, s), 2.99 (2H, s), 3.61 (2H, s), 3.94(3H, s), 4.12 (2H, q, J=7 Hz), 6.75 (1H, s).

Example 569

1-(3-Bromophenyl)-3,4,8,9-tetrahydro-6-methoxy-4,4,8,8-tetramethylfuro[2,3-h]isoquinoline Phosphorus oxychloride (3.3 mL, 35 mmol) was added to a suspension of 3-bromo-N-[2-(2,3-dihydro-7-methoxy-2,2-dimethyl-5-benzofuranyl)-2-methylpropyl]benzamide (1.28 g, 2.96 mmol) in toluene (25 mL) and the mixture was heated under reflux for 3.5 hours. The reaction mixture was poured into ice water, and neutralized with 5 M aqueous solution of sodium hydroxide with cooling in ice. The organic layer was separated, and the aqueous layer was extracted with toluene. The combined organic layer was washed twice with water, and concentrated under reduced pressure. The residue was subjected to a column chromatography on a silica gel (hexane/ethyl acetate 4:1 followed by 2:1) and recrystallized from hexane to obtain the title compound (741 mg, yield: 60%).

Melting point: 127–129° C.
$^1$H NMR (CDCl$_3$) δ 1.26 (6H, s), 1.35 (6H, s) 2.31 (2H, s), 3.63 (2H, s), 3.95 (3H, s), 6.79 (1H, s), 7.28 (1H, t, J=7.7 Hz), 7.38 (1H, dt, J=7.7, 1.6 Hz), 7.55 (1H, dt, J=7.7, 1.6 Hz), 7.61 (1H, t, H=1.6 Hz).

Example 570

3'-(3,4,8,9-Tetrahydro-6-methoxy-4,4,8,8-tetramethylfuro[2,3-h]isoquinolin-1-yl)[1,1'-biphenyl]-4-amine A suspension of 1-(3-bromophenyl)-3,4,8,9-tetrahydro-6-methoxy-4,4,8,8-tetramethylfuro[2,3-h]isoquinoline (607 mg, 1.46 mmol), 4-(4,4,5,5-tetramethyl-1,3,2-dioxaborolan-2-yl)amine (353 mg, 1.61 mmol), sodium carbonate (388 mg, 3.66 mmol) and tetrakis(triphenylphosphine)palladium (0) (34 mg, 0.029 mmol) in 1,2-dimethoxyethane (4.5 mL), ethanol (2 ml) and water (1.5 mL) was stirred at 80° C. for 14 hours under nitrogen atmosphere. The reaction mixture was combined with water, and extracted twice with ethyl acetate. The combined organic layer was washed with water and brine, dried through sodium sulfate-basic silica gel (eluting with ethyl acetate), and concentrated under reduced pressure. The residue was subjected to a column chromatography on a basic silica gel(hexane/ethyl acetate 10:1 followed by 1:1), recrystallized from methanol-diethyl ether to obtain the title compound (400 mg, yield: 64%).

Melting point: 232–234° C.
$^1$H NMR (CDCl$_3$) δ 1.29 (6H, s), 1.30 (6H, s), 2.34 (2H, s), 3.64 (2H, s), 3.73 (2H, br s), 3.96 (3H, s), 6.74 (2H, d, J=8.4 Hz), 6.81 (1H, s), 7.32 (1H, dt, J=7.7, 1.5 Hz), 7.37–7.49 (3H, m), 7.56–7.63 (2H, m).

Example 571

N-[3'-(3,4,8,9-Tetrahydro-6-methoxy-4,4,8,8-tetramethylfuro[2,3-h]isoquinolin-1-yl)[1,1'-biphenyl]-4-yl]acetamide By the method similar to that in Example 30, 3'-(3,4,8,9-tetrahydro-6-methoxy-4,4,8,8-tetramethylfuro[2,3-h]isoquinolin-1-yl)[1,1'-biphenyl]-4-amine was employed to obtain the title compound. yield: 57%.

Melting point: 223–227° C. (ethyl acetate-diethyl ether).
$^1$H NMR. (CDCl$_3$) δ 1.29 (6H, s), 1.31 (6H, s), 2.15–2.21 (3H, m), 2.33 (2H, s), 3.65 (2H, s), 3.96 (3H, s), 6.81 (1H, s), 7.26–7.65 (9H, m).

Example 572

1-(3-Bromophenyl)-3,4,8,9-tetrahydro-4,4,8,8-tetramethyl-6-furo[2,3-h]isoquinolinol 48% Hydrobromic acid (50 mL) was added to 1-(3-Bromophenyl)-3,4,8,9-tetrahydro-6-methoxy-4,4,8,8-tetramethylfuro[2,3-h]isoquinoline (4.73 g, 11.4 mmol) and the mixture was heated under reflux for 22 hours. The reaction mixture was cooled with ice, neutralized with conc. aqueous ammonia, and extracted twice with ethyl acetate. The combined organic layer was washed twice with water, and concentrated under reduced pressure. The residue was crystallized from ethyl acetate-diethyl ether to obtain the title compound (3.96 g, yield: 87%).

Melting point: 230–235° C.

<sup>1</sup>H NMR (CDCl<sub>3</sub>) δ 1.21 (6H, s), 1.32 (6H, s), 2.29 (2H, s), 3.59 (2H, s), 6.74 (1H, s), 7.27 (1H, t, J=7.8 Hz), 7.40 (1H, dt, J=7.8, 1.6 Hz), 7.55 (1H, dt, J=7.8, 1.6 Hz), 7.60 (1H, t, J=1.6 Hz).

Example 573
[3'-(3,4,8,9-Tetrahydro-6-hydroxy-4,4,8,8-tetramethylfuro[2,3-h]isoquinolin-1-yl)[1,1'-biphenyl]-4-yl]carbamic Acid Phenylmethyl Ester A suspension of 1-(3-bromophenyl)-3,4,8,9-tetrahydro-4,4,8,8-tetramethyl-6-furo[2,3-h]isoquinolinol (2.40 g, 6.00 mmol), [4-(4,4,5,5-tetramethyl-1,3,2-dioxaborolan-2-yl)phenyl]carbamic acid phenylmethyl ester (2.54 g, 7.19 mmol), sodium carbonate (1.59 g, 15.0 mmol) and tetrakis(triphenylphosphine)palladium(0) (139 mg, 0.120 mmol) in 1,2-dimethoxyethane (20 mL), ethanol (10 mL) and water (10 mL) was stirred at 85° C. for 16 hours under nitrogen atmosphere. The reaction mixture was combined with ethyl acetate and water, and the organic layer was separated, and the aqueous layer was extracted with ethyl acetate. The combined organic layer was washed with brine, dried through sodium sulfate-silica gel (eluting with ethyl acetate), and concentrated under reduced pressure. The residue was subjected to a column chromatography on a basic silica gel (hexane/ethyl acetate 1:2 followed by ethyl acetate), crystallized from ethyl acetate-chloroform to obtain the title compound (2.63 g, yield: 80%).

Melting point: 161–165° C.

$^1$H NMR (DMSO-d$_6$) δ 1.15 (6H, s), 1.19 (6H, s), 2.25 (2H, s), 3.48 (2H, s), 5.17 (2H, s), 6.74 (1H, s), 7.31–7.75 (13H, m), 9.74 (1H, s), 9.91 (1H, s).

Example 574
[3'-[3,4,8,9-Tetrahydro-4,4,8,8-tetramethyl-6-[[(trifluoromethyl)sulfonyl]oxy]furo[2,3-h]isoquinolin-1-yl][1,1'-biphenyl]-4-yl]carbamic Acid Phenylmethyl Ester The title compound was obtained from [3'-(3,4,8,9-tetrahydro-6-hydroxy-4,4,8,8-tetramethylfuro[2,3-h]isoquinolin-1-yl)[1,1'-biphenyl]-4-yl]carbamic acid phenylmethyl ester by the method similar to that in EXAMPLE 95. Yield: 92%.

Amorphous.

$^1$H NMR (CDCl$_3$) δ 1.28 (6H, s), 1.30 (6H, s), 2.37.(2H, s), 3.70 (2H, s), 5.22 (2H, s), 6.80 (1H, br s), 7.08 (1H, s), 7.31–7.51 (9H, m), 7.57 (2H, d, J=8.7 Hz), 7.62–7.68 (2H, m).

Example 575
[3'-(3,4,8,9-Tetrahydro-4,4,8,8-tetramethylfuro[2,3-h]isoquinolin-1-yl)[1,1'-biphenyl]-4-yl]carbamic Acid Phenylmethyl Ester Formic acid (0.30 mL, 8.0 mmol) was added to a solution of [3'-[3,4,8,9-tetrahydro-4,4,8,8-tetramethyl-6-[[(trifluoromethyl)sulfonyl]oxy]furo[2,3-h]isoquinolin-1-yl][1,1'-biphenyl]-4-yl]carbamic acid phenylmethyl ester (2.74 g, 4.04 mmol), triethylamine (1.7 mL, 12 mmol), palladium acetate (II) (23 mg, 0.10 mmol) and triphenylphosphine (53 mg, 0.20 mmol) in N,N-dimethylformamide (8 mL) and the mixture was stirred at 70° C. for 4 hours under nitrogen atmosphere. The reaction mixture was combined with water and a saturated aqueous solution of sodium hydrogen carbonate, and extracted twice with ethyl acetate. The combined organic layer was washed twice with water, and concentrated under reduced pressure. The residue was subjected to a column chromatography on a basic silica gel (hexane/ethyl acetate 2:1), crystallized from ethyl acetate-diethyl ether to obtain the title compound (1.72 g, yield: 80%).

Melting point: 126–129° C.

$^1$H NMR (CDCl$_3$) δ 1.27 (6H, s), 1.28 (6H, s), 2.32 (2H, s), 3.68 (2H, s), 5.22 (2H, s), 6.77 (1H, br s), 6.83 (1H, d, J=8.4 Hz), 7.19 (1H, d, J=8.4 Hz), 7.31–7.50 (9H, m), 7.55–7.68 (4H, M)

Example 576
3'-(3,4,8,9-Tetrahydro-4,4,8,8-tetramethylfuro[2,3-h]isoquinolin-1-yl)[1,1'-biphenyl]-4-amine Dihydrobromide 25% Hydrobromic acid/acetic acid solution (7 mL) was added to a solution of [3'-(3,4,8,9-tetrahydro-4,4,8,8-tetramethylfuro[2,3-h]isoquinolin-1-yl) 1,1'-biphenyl]-4-yl] carbamic acid phenylmethyl ester (1.90 g, 3.58 mmol) in chloroform (20 mL) and the mixture was stirred at room temperature for 3 hours. The reaction mixture was concentrated under reduced pressure, and the residue was combined with diethyl ether, and the solid was recovered by filtration to obtain the title compound (1.97 g, 99%).

Melting point: 206–210° C.

$^1$H NMR (DMSO-d$_6$) δ 1.21 (3H, s), 1.25 (3H, s), 1.37 (6H, s), 2.25–2.50 (2H. m), 3.70–3.90 (2H, m), 7.15–7.32 (2H, m), 7.27 (1H, d, J=8.4 Hz), 7.50 (1H, d, J=8.4 Hz), 7.62–7.70 (1H, m), 7.72–7.85 (3H, m), 8.05–8.07 (1H, m), 8.08 (1H, d, J=7.8 Hz).

Example 577
N-[3'-(3,4,8,9-Tetrahydro-4,4,8,8-tetramethylfuro[2,3-h]isoquinolin-1-yl) [1,1'-biphenyl]-4-yl]acetamide A solution of sodium carbonate (t185 mg, 1.75 mmol) in water (1 mnL) was added to a suspension of 3'-(3,4,8,9-tetrahydro-4,4,8,8-tetramethylfuro[2,3-h]isoquinolin-1-yl)[1,1'-biphenyl]-4-amine dihydrobromide (279 mg, 0.500 mmol) in tetrahydrofuran (1 mL). The resultant mixture was cooled with ice, treated dropwise with acetyl chloride (46 μL, 0.65 mmol), and stirred at the same temperature for 15 minutes. The reaction mixture was combined with water, and extracted twice with chloroform. The combined organic layer was washed with brine, dried over sodium sulfate, filtered and concentrated under reduced pressure. The residue was crystallized from ethyl acetate-diethyl ether to obtain the title compound (149 mg, 68%).

Melting point: 246–249° C.

$^1$H NMR (CDCl$_3$) δ 1.27 (6H, s), 1.29 (6H, s), 2.19 (3H, s), 2.32 (2H, s), 3.68 (2H, s), 6.83 (1H, d, J=8.1 Hz), 7.19 (1H, d, J=8.1 Hz), 7.36–7.43 (2H, m), 7.47 (1H, t, J=7.5 Hz), 7.57 (4H, s), 7.61–7.68 (2H, m).

Example 578
N-[3'-(3,4,8,9-Tetrahydro-4,4,8,8-tetramethylfuro[2,3-h]isoquinolin-1-yl)[1,1'-biphenyl]-4-yl]propanamide The title compound was obtained from propionyl chloride by the method similar to that in EXAMPLE 577. Yield: 56%.

Melting point: 215–218° C. (ethyl acetate-diethyl ether).

$^1$H NMR (CDCl$_3$) δ 1.23–1.31 (3H, m), 1.27 (6H, s), 1.29 (6H, s), 2.32 (2H, s), 2.41 (2H, q, J=7.5 Hz), 3.68 (2H, s), 6.83 (1H, d, J=8.1 Hz), 7.19 (1H, d, J=8.1 Hz), 7.20–7.27 (1H, m), 7.37–7.42 (1H, m), 7.47 (1H, t, J=7.5 Hz), 7.59 (4H, s), 7.62–7.68 (2H, m).

Example 579
N-[3'-(3,4,8,9-Tetrahydro-4,4,8,8-tetramethylfuro(2,3-h]isoquinolin-1-yl)[1,1'-biphenyl]-4-yl]formamide Formic acid (0.5 mL) was treated dropwise with acetic anhydride (0.14 mL, 1.5 mmol) with cooling in ice, and stirred at the same temperature for 1.5 hours. The resultant solution was added dropwise to a solution of 3'-(3,4,8,9-tetrahydro-4,4,8,8-tetramethylfuro[2,3-h]isoquinolin-1-yl)

[1,1'-biphenyl]-4-amine dihydrobromide (279 mg, 0.500 mmol) and sodium formate (75 mg, 1.1 mmol) in formic acid (0.5 mL), and the mixture was stirred at room temperature for 1.5 hours. The reaction mixture was added dropwise to a suspension of sodium hydrogen carbonate (3.1 g, 37 mmol) in water-ethyl acetate, and the organic layer was separated, and the aqueous layer was extracted with ethyl acetate. The combined organic layer was washed with brine, dried over sodium sulfate, filtered and concentrated under reduced pressure. The residue was crystallized from ethyl acetate-hexane to obtain the title compound (147 mg, yield: 69%).

Melting point: 197–199° C.

$^1$H NMR (CDCl$_3$) δ 1.27 (6H, s), 1.29 (6H, s), 2.32 (2H, s), 3.69 (2H, s), 6.84 (1H, d, J=8.4 Hz), 7.13 (1H, d, J=8.7 Hz), 7.20 (1H, d, J=8.4 Hz), 7.38–7.69 (8H, m), 8.38 (0.55H, d, J=1.8 Hz), 8.73 (0.45H, d, J=11.1 Hz).

Example 580

3'-(6-Hydroxy-4,4,8,8-tetramethyl-3,4,8,9-tetrahydrofuro2,3-h]isoquinolin-1-yl)[1,1'-biphenyl]-4-carboxylic Acid Ethyl Ester The title compound was obtained from 1-(3-bromophenyl)-3,4,8,9-tetrahydro-4,4,8,8-tetramethyl-6-furo[2,3-h]isoquinolinol and 4-(4,4,5,5-tetramethyl-1,3,2-dioxaborolan-2-yl)benzoic acid ethyl ester by the method similar to that in EXAMPLE 461. Yield: 52%.

Melting point: 214–217° C. (ethyl acetate-diethyl ether).

$^1$H NMR (CDCl$_3$) δ 1.21 (6H, s), 1.28 (6H, s), 1.41 (3H, t, J=7.2 Hz), 2.32 (2H, s), 3.60 (2H, s), 4.40 (2H, g, J=7.2 Hz), 6.73 (1H, s), 7.38–7.54 (2H, m), 7.63–7.77 (2H, m), 7.68 (2H, d, J=8.4 Hz), 8.09 (2H, d, J=8.4 Hz).

Example 581

[3'-[3,4,8,9-tetrahydro-4,4,8,8-tetramethyl-6-[[(trifluoromethyl)sulfonyl]oxy]furo[2,3-h]isoquinolin-1-yl][1,1'-biphenyl]-4-carboxylic Acid Ethyl Ester The title compound was obtained from 3'-(6-hydroxy-4,4,8,8-tetramethyl-3,4,8,9-tetrahydrofuro[2,3-h]isoquinolin-1-yl)[1,1'-biphenyl]-4-carboxylic acid ethyl ester by the method similar to that in EXAMPLE 95. Yield: 97%.

Melting point: 147–149° C. (ethyl acetate-hexane).

$^1$H NMR (CDCl$_3$) δ 1.29 (6H, s), 1.31 (6H, s), 1.42 (3H, t, J=7.2 Hz), 2.38 (2H, s), 3.72 (2H, br s), 4.41 (2H, q, J=7.2 Hz), 7.10 (1H, s), 7.42–7.48 (1H, m), 7.50–7.57 (1H, m), 7.67–7.76 (4H, m), 8.12 (2H, d, J=8.1 Hz).

Example 582

3'-(3,4,8,9-Tetrahydro-4,4,8,8-tetramethylfuro[2,3-h]isoquinolin-1-yl)[1,1'-biphenyl]-4-carboxylic Acid Ethyl Ester The title compound was obtained from [3'-(3,4,8,9-tetrahydro-4,4,8,8-tetramethyl-6-[[(trifluoromethyl)sulfonyl]oxy]furo[2,3-h]isoquinolin-1-yl][1,1'-biphenyl]-4-carboxylic acid ethyl ester by the method similar to that in EXAMPLE 575. Yield: 75%.

Melting point: 144–149° C. (hexane).

$^1$H NMR (CDCl$_3$) δ 1.28 (6H, s), 1.29 (6H, s), 1.42 (3H, t, J=7.1 Hz), 2.32 (2H, s), 3.69 (2H, s), 4.40 (2H, q, J=7.1 Hz), 6.84 (1H, d, J=3 8.4 Hz), 7.20 (1H, d, J=8.4 Hz), 7.47 (1H, dt, J=7.6, 1.7 Hz), 7.52 (1H, td, J=7.6, 0.6 Hz), 7.67–7.76 (4H, m), 8.08–8.13 (2H, m).

Example 583

3'-(3,4,8,9-Tetrahydro-4,4,8,8-tetramethylfuro[2,3-h]isoquinolin-1-yl)[1,1'-biphenyl]-4-carboxylic Acid 1 M aqueous solution of sodium hydroxide (10 mL) was added to a suspension of 3'-(3,4,8,9-tetrahydro-4,4,8,8-tetramethylfuro[2,3-h]isoquinolin-1-yl)[1,1'-biphenyl]-4-carboxylic acid ethyl ester (1.30 g, 2.87 mmol) in ethanol (15 ml) and the mixture was stirred at 70° C. for 45 minutes the reaction mixture was cooled with ice, treated dropwise with 1 M hydrochloric acid (10 mL), and extracted twice with chloroform. The combined organic layer was washed with brine, combined with a small amount of methanol, dried over sodium sulfate, filtered, and concentrated under reduced pressure. The residue was crystallized from chloroform-ethyl acetate to obtain the title compound (1.19 g, yield: 97%).

Melting point: 286–291° C.

$^1$H NMR (DMSO-d$_6$) δ 1.19 (6H, s), 1.21 (6H, s), 2.28 (2H, s), 3.58 (2H, s), 6.86 (1H, d, J=8.3 Hz), 7.24 (1H, d, J=8.3 Hz), 7.44 (1H, dt, J=7.6, 1.4 Hz), 7.58 (1H, t, J=7.6 Hz), 7.74 (1H, t, J=1.4 Hz), 7.87–7.88 (3H, m), 8.03 (2H, d, J=8.4 Hz), 12.80–13.05 (1H, br).

Example 584

3'-(3,4,8,9-Tetrahydro-4,4,8,8-tetramethylfuro[2,3-h]isoquinolin-1-yl)[1,1'-biphenyl]-4-carboxamide 1-Ethyl-3-(3-dimethylaminopropyl)carbodiimide hydrochloride (125 mg, 0.652 mmol) was added to a suspension of 3'-(3,4,8,9-tetrahydro-4,4,8,8-tetramethylfuro[2,3-h]isoquinolin-1-yl)[1,1'-biphenyl]-4-carboxylic acid (213 mg, 0.501 mmol) and 1-hydroxy-1H-benzotriazole ammonium salt (92 mg, 0.60 mmol) in N,N-dimethylformamide (1 mL) and the mixture was stirred at room temperature for 15 hours. Triethylamine (0.16 mL, 1.1 mmol) was added to the resultant mixture and the mixture was stirred at room temperature for 2 hours. The reaction mixture was combined with water and extracted twice with ethyl acetate-tetrahydrofuran mixture. The combined organic layer was washed with brine, dried through sodium sulfate-basic silica gel (eluting with ethyl acetate), and concentrated under reduced pressure. The resultant solid was washed with ethyl acetate-hexane to obtain the title compound (89.5 mg, yield: 42%).

Melting point: 284–296° C.

$^1$H NMR (DMSO-d$_6$) δ 1.19 (6H, s), 1.21 (6H, s), 2.29 (2H, s), 3.58 (2H, s), 6.86 (1H, d, J=8.1 Hz), 7.24 (1H, d, J=8.1 Hz), 7.36–7.45 (2H, m), 7.57 (1H, t, J=7.7 Hz), 7.73 (1H, t, J=1.5 Hz), 7.79 (2H, d, J=8.6 Hz), 7.81–7.87 (1H, m), 7.97 (2H, d, J=8.6 Hz), 8.04 (1H, br s).

Example 585

N-Methyl-3'-(3,4,8,9-tetrahydro-4,4,8,8-tetramethylfuro[2,3-h]isoquinolin-1-yl)[1,1'-biphenyl]-4-carboxamide The title compound was obtained from 3'-(3,4,8,9-tetrahydro-4,4,8,8-tetramethylfuro[2,3-h]isoquinolin-1-yl)[1,1'-biphenyl]-4-carboxylic acid by the method similar to that in EXAMPLE 459. Yield: 70%.

Melting point: 242–244° C. (ethyl acetate-hexane).

$^1$H NMR (CDCl$_3$) δ 1.27 (6H, s), 1.29 (6H, s), 2.32 (2H, s), 3.05 (3H, d, J=4.8 Hz), 3.69 (2H, s), 6.15–6.25 (1H, m), 6.84 (1H, d, J=8.4 Hz), 7.20 (1H, d, J=8.4 Hz), 7.46 (1H, dt, J=7.7, 1.5 Hz), 7.47–7.54 (1H, m), 7.66–7.74 (4H, m), 7.83 (2H, d, J=8.4 Hz).

Example 586

3-(3,4,8,9-Tetrahydro-3,3,8,8-tetramethyl-6-(propylthio)furo[2,3-h]isoquinolin-1-yl)benzoic Acid A solution of an about 15:2 mixture of 2,3-dihydro-2,2-dimethyl-5-(2-methyl-1-propenyl)-7-(propylthio)benzofuran and 2,3-dihydro-2,2-dimethyl-5-(2-methyl-1-propenyl)benzofuran obtained in EXAMPLE 549 (3.10 g) and isopropyl 3-cyanobenzoate (1.83 g, 9.65 mmol) in acetic acid (6 mL)-toluene (13 mL) was treated dropwise with conc. sulfuric acid (1.80 mL, 33.7 mmol) with cooling in ice, and stirred at 60° C. for 1.5 hours. Isopropyl alcohol (11.7 mL) was added dropwlse to the mixture, and the mixture was heated under ref lux for 5 hours. Ice water was poured into the reaction mixture, which was neutralized with sodium hydrogen carbonate, and extracted twice with ethyl acetate. The combined organic layer was washed with brine, dried over sodium sulfate, filtered and concentrated under reduced pressure. The residue was dissolved in N,N-dimethylformamide (20 mL), potassium carbonate (668 mg, 4.83 mmol) and 2-iodopropane (0.48 mL, 4.83 mmol) were added thereto, and the mixture was stirred at room temperature for 15 hours. Water was poured into the reaction mixture, which was extracted twice with ethyl acetate. The combined organic layer was washed with water and brine, dried over sodium sulfate, filtered and concentrated under reduced pressure. The residue was subjected to a column chromatography on a silica gel (hexane/ethyl acetate 10:1 followed by 5:1) to obtain 3-(3,4,8,9-tetrahydro-3,3,8,8-tetramethyl-6-propylthiofuro(2,3-h]isoquinolin-1-yl) benzoic acid 1-methylethyl ester (1.00 g, yield: 22%) as an oil.

The resultant ester derivative (1.00 g, 2.15 mmol) was dissolved in methanol (4 mL), 5 M aqueous solution of sodium hydroxide (2 mL) was added thereto, and the mixture was stirred at room temperature for 15 hours. The reaction mixture was adjusted at pH 4.5 with 5 M hydrochloric acid, combined with sodium chloride, and extracted twice with ethyl acetate. The combined organic layer was washed with brine, dried over magnesium sulfate, filtered and concentrated under reduced pressure. The residue was crystallized from ethyl acetate-diisopropyl ether to obtain the title compound (153 mg, yield: 17%).

Melting point: 206–208° C.

$^1$H NMR (CDCl$_3$) δ 1.11 (3H, t, J=7.5 Hz), 1.25 (6H, s), 1.51 (3H, s), 1.74–1.86 (2H, m), 1.91 (3H s), 2.05–2.17 (2H, m), 2.83–3.04 (1H, m), 3.04 (2H, t, J=7.2 Hz), 3.30–3.50 (1H, m), 6.97 (1H, s), 7.60–7.72 (2H, m), 8.00 (1H, d, J=3 7.5 Hz), 8.12 (1H, d, J=7.8 Hz).

Example 587
N-(2-Amino-1,1-dimethyl-2-oxoethyl)-3-(3,4,8,9-tetrahydro-3,3,8,8-tetramethyl-6-(propylthio)furo[2,3-h] isoquinolin-1-yl)benzamide 1-Hydroxy-1H-benzotriazole monohydrate (280 mg, 1.83 mmol), triethylamine (0.58 mL, 4.15 mmol) and 1-ethyl-3-(3-dimethylaminopropyl)carbodiimide hydrochloride (414 mg, 2.16 mmol) were added to a solution of 3-(3,4,8,9-tetrahydro-3,3,8,8-tetramethyl-6-propylthiofurot2,3-h] isoquinolin-1-yl)benzoic acid (703 mg, 1.66 mmol) and 2-amino-2-methylpropanamide hydrochloride (254 mg, 1.83 mmol) in N,N-dimethylformamide (4 mL) and the mixture was stirred at room temperature for 4 hours. Water was poured into the reaction mixture, which was extracted twice with ethyl acetate. The combined organic layer was washed with water and brine, dried over sodium sulfate, filtered and concentrated under reduced pressure. The residue was subjected to a column chromatography on a basic silica gel (hexane/ethyl acetate 1:2 followed by ethyl acetate), and the resultant crystals were washed with diisopropyl ether to obtain the title compound (478 mg, yield: 57%).

Melting point: 195–197° C.

$^1$H NMR (CDCl$_3$) δ 1.05 (3H, t, J=7.2 Hz), 1.25 (6H, s), 1.30 (6H, s), 1.62–1.78 (2H, m), 1.71 (6H, s), 2.17 (2H, s), 2.68 (2H, s), 2.95 (2H, t, J=7.3 Hz), 5.49 (1H, br s), 6.43 (1H, br s), 6.92 (1H, s), 6.96 (1H, s), 7.43–7.52 (2H, m), 7.85–7.89 (2H, m).

Example 588
3,4,8,9-Tetrahydro-5,6-dimethoxy-3,3,8,8-tetramethyl-1-phenylfuro[2,3-h]isoquinoline Hydrochloride A solution of 2,3-dihydro-6,7-dimethoxy-2,2-dimethyl-5-(2-methyl-1-propenyl)benzofuran (220 mg, 0.839 mmol) and benzonitrile (0.086 mL, 0.839 mmol) in acetic acid (0.4 mL)-toluene (1 mL) was treated dropwise with conc. sulfuric acid (0.11 mL, 2.10 mmol) with cooling in ice, and stirred at 80° C. for 40 minutes. Ice water was poured into the reaction mixture, which was washed with diisopropyl ether. The aqueous layer was neutralized with conc. aqueous ammonia, and extracted with ethyl acetate. The combined organic layer was washed twice with brine, dried over sodium sulfate, filtered and concentrated under reduced pressure. The residue was subjected to a column chromatography on a basic silica gel (hexane/ethyl acetate 10:1 followed by 5:1) to obtain a free base of the title compound.

$^1$H NMR (CDCl$_3$) δ 1.25 (6H, s), 1.29 (6H, s), 2.13 (2H, s), 2.69 (2H, s), 3.83 (3H, s), 3.99 (3H, s), 7.38 (5H, s).

This was dissolved in ethyl acetate, 4 M hydrogen chloride/ethyl acetate solution was added thereto, and the mixture was concentrated under reduced pressure crystallized from ethyl acetate diisopropyl ether to obtain the title compound (6 mg, yield: 2%).

Melting point: 155–157° C.

The compounds produced in EXAMPLES described above are indicated in Tables 1 to 22 shown below.

TABLE 1

| ex. | R$^1$ | additive |
|---|---|---|
| 1 | phenyl | — |
| 2 | naphthyl | — |
| 3 | 4-hydroxyphenyl | — |
| 4 | 4-methoxyphenyl | — |
| 5 | 2-methoxyphenyl | — |

TABLE 1-continued
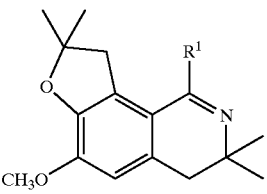
| ex. | R¹ | additive |
|---|---|---|
| 6 | 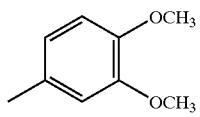 | — |
| 7 | 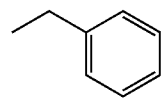 | — |
| 8 | 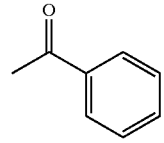 | — |
| 9 | 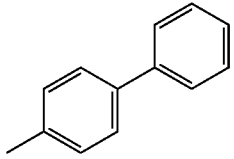 | — |
| 10 | 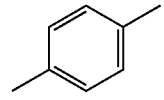 | — |
| 11 | 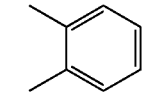 | HCl |
| 12 | 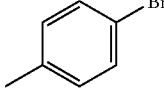 | HCl |
| 13 | 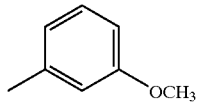 | HCl |
| 14 | CH₃ | — |
| 15 | 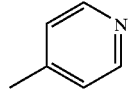 | — |
| 16 | 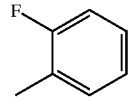 | HCl |
TABLE 1-continued
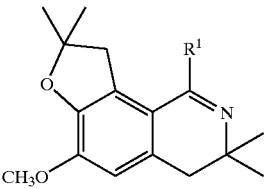
| ex. | R¹ | additive |
|---|---|---|
| 17 | 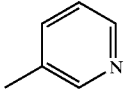 | — |
| 18 | 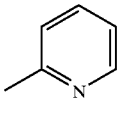 | — |
| 19 | 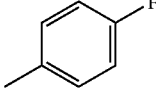 | — |
| 20 | 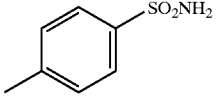 | — |
| 21 | 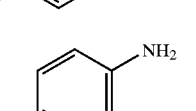 | — |
| 24 | 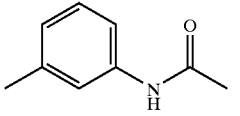 | — |
| 25 | | — |
| 27 | | — |
| 28 | | — |
| 29 | | 2HCl |
| 30 | | — |

TABLE 1-continued
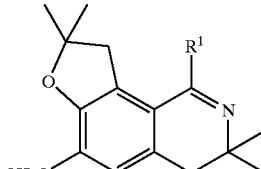
| ex. | R¹ | additive |
|---|---|---|
| 31 | 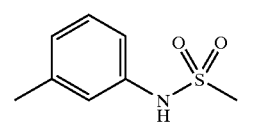 | — |
| 32 | 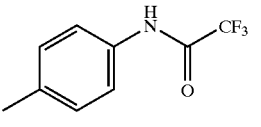 | — |
| 33 | 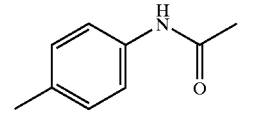 | — |
| 34 | 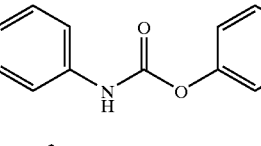 | — |
| 35 | 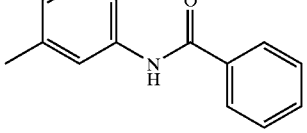 | — |
| 36 | 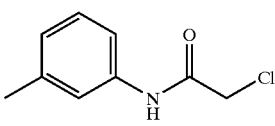 | — |
| 37 | 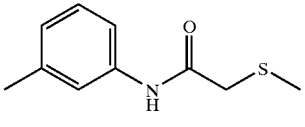 | — |
| 38 | 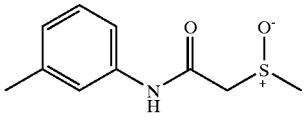 | — |
| 39 | 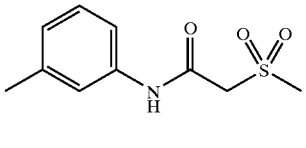 | — |
| 40 | 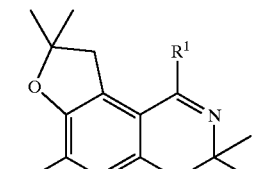 | — |
TABLE 1-continued
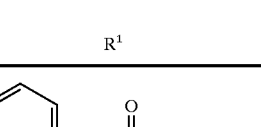
| ex. | R¹ | additive |
|---|---|---|
| 41 | 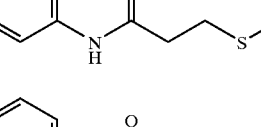 | — |
| 42 | 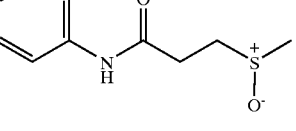 | — |
| 43 | 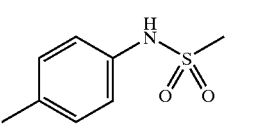 | — |
| 44 | 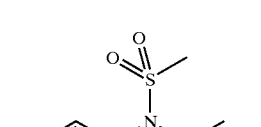 | — |
| 45 | 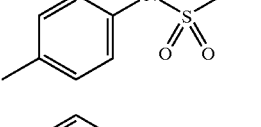 | — |
| 46 | 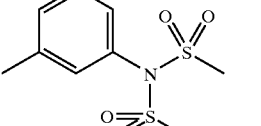 | — |
| 47 | 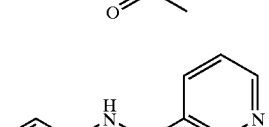 | — |
| 48 | 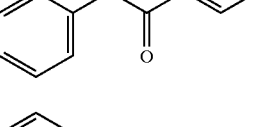 | — |

TABLE 2

| ex. | R¹ | additive |
|---|---|---|
| 49 | N-(4-methylphenyl)isonicotinamide | — |
| 50 | N-(3-methylphenyl)nicotinamide | — |
| 51 | methyl N-(3-methylphenyl)-N-(nicotinoyl)glycinate | — |
| 52 | N-methyl-N-(3-methylphenyl)nicotinamide | — |
| 53 | N-(3-methylphenyl)-N-(pyridin-3-yl)benzamide | — |
| 54 | N-(3-methylphenyl)-N-(pyridin-3-ylmethyl)amine | 3HCl |
| 55 | methyl N-(methylsulfonyl)-N-(3-methylphenyl)glycinate | — |
| 56 | N'-(dimethylaminomethylene)-3-[N-(methylsulfonyl)-N-(3-methylphenyl)amino]propanesulfonamide | — |
| 57 | 3-[N-(methylsulfonyl)-N-(3-methylphenyl)amino]propanesulfonamide | HCl |
| 58 | 2-[N-(methylsulfonyl)-N-(3-methylphenyl)amino]acetamide | — |
| 59 | 2-[N-(3-methylphenyl)carbamoyl]benzoic acid | — |
| 60 | 2-(3-methylphenyl)-1H-isoindole-1,3(2H)-dione | — |
| 61 | 6-(3-methylphenyl)-5H-pyrrolo[3,4-b]pyridine-5,7(6H)-dione | — |

TABLE 2-continued

[Structure: 2,2,8,8-tetramethyl-4-methoxy-dihydrofuro-isoquinoline with R¹ substituent]

| ex. | R¹ | additive |
|-----|-----|----------|
| 62 | 2-(m-tolyl)-1,3-dioxo-pyrrolo[3,4-c]pyridine | — |
| 63 | N-(m-tolyl)-1-Boc-piperidine-4-carboxamide | — |
| 64 | N-(m-tolyl)-piperidine-4-carboxamide | 2HCl |
| 65 | N-(m-tolyl)-2-(pyridin-4-yl)acetamide | — |
| 66 | N-(m-tolyl)-2-(pyridin-3-yl)acetamide | — |
| 67 | N-(m-tolyl)-2-(pyridin-2-yl)acetamide | — |
| 68 | 1-(4-((diethoxyphosphoryl)methyl)phenyl)-2-(m-tolyl)ethanone | HCl |
| 69 | N-(m-tolyl)-4-((phosphono)methyl)benzamide | — |
| 70 | N-(m-tolyl)-2-methyl-2-(trifluoroacetamido)propanamide | HCl |
| 71 | 2-amino-2-methyl-N-(m-tolyl)propanamide | — |
| 72 | 3-(m-tolyl)-5,5-dimethylimidazolidine-2,4-dione | — |
| 73 | 3-(m-tolyl)imidazolidine-2,4-dione | — |
| 74 | 1-methyl-3-(m-tolyl)imidazolidine-2,4-dione | — |
| 75 | methyl 2-(3-(m-tolyl)-2,5-dioxoimidazolidin-1-yl)acetate | — |
| 76 | N-methyl-2-(3-(m-tolyl)-2,5-dioxoimidazolidin-1-yl)acetamide | — |

TABLE 2-continued

[Structure: 2,2,8,8-tetramethyl-5-methoxy-furo-isoquinoline core with R¹ substituent]

| ex. | R¹ | additive |
|---|---|---|
| 77 | 3-phenylphenyl (biphenyl-3-yl, methyl-substituted) | — |
| 78 | 3-(pyridin-4-yl)phenyl, methyl-substituted | — |
| 79 | 3-(quinolin-2-yl)phenyl, methyl-substituted | — |
| 80 | 3-methylbenzoic acid (m-CO₂H) | HCl |
| 81 | 4-methylbenzoic acid (p-CO₂H) | HCl |

TABLE 3

[Structure: 2,2,8,8-tetramethyl-5-methoxy-furo-isoquinoline core with R¹ substituent]

| ex. | R¹ | additive |
|---|---|---|
| 83 | 4-methyl-N-(4-methoxyphenyl)benzamide | — |
| 84 | 4-methylbenzamide (p-CONH₂) | — |
| 85 | 4-methyl-N-methylbenzamide (p-CONHCH₃) | — |
| 86 | 3-methylbenzamide (m-CONH₂) | — |
| 88 | 4-methyl-N-phenylbenzamide | HCl |
| 89 | 4-methyl-N,N-dimethylbenzamide (p-CON(CH₃)₂) | HCl |
| 90 | 3-methyl-N-[4-(diethoxyphosphorylmethyl)phenyl]benzamide | — |
| 123 | 3-methyl-nitrobenzene (m-NO₂) | — |
| 139 | 4-methylbenzoyl chloride (p-COCl) | HCl |
| 140 | 3-methylbenzoyl chloride (m-COCl) | HCl |
| 141 | 4-methyl-N-(pyridin-4-yl)benzamide | 2HCl |

TABLE 3-continued
| ex. | R¹ | additive |
|---|---|---|
| 142 | 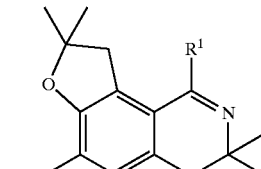 | 2HCl |
| 143 | 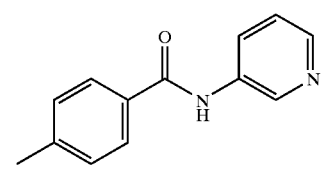 | 2HCl |
| 144 | 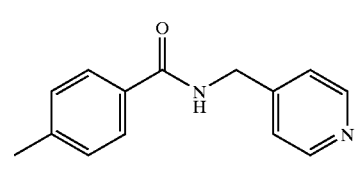 | 2HCl |
| 145 | 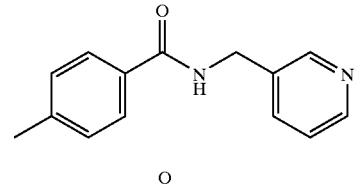 | 2HCl |
| 146 | 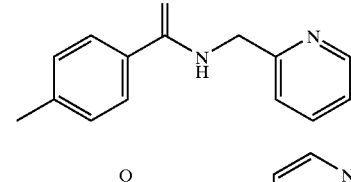 | 2HCl |
| 147 | 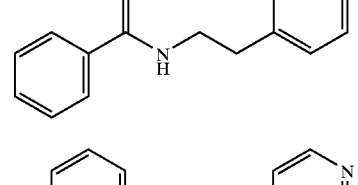 | 2HCl |
| 148 | 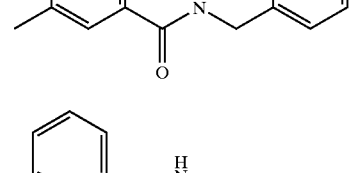 | — |
| 149 | 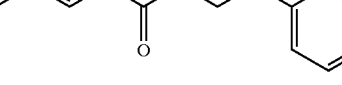 | — |
| 150 | 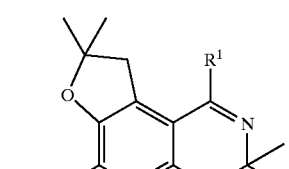 | 2HCl |
| 151 | 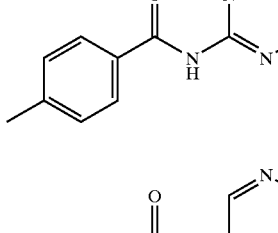 | — |
| 152 | 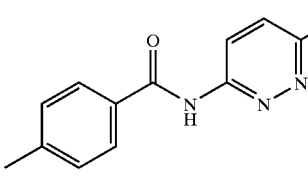 | — |
| 153 | 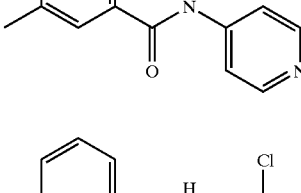 | — |
| 154 | 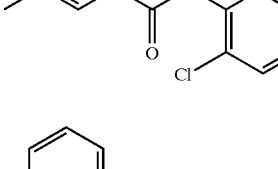 | — |
| 155 | 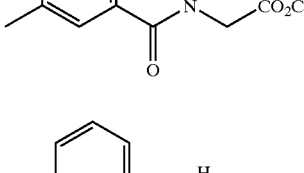 | HCl |
| 156 | 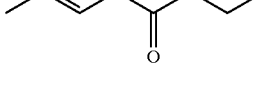 | HCl |

TABLE 4
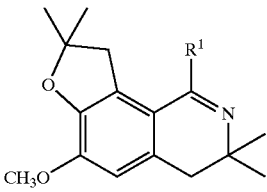
| ex. | R¹ | additive |
|---|---|---|
| 157 | 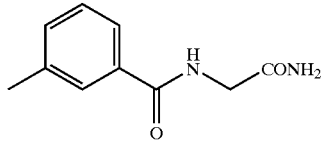 | — |
| 158 | 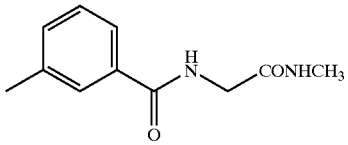 | — |
| 159 | 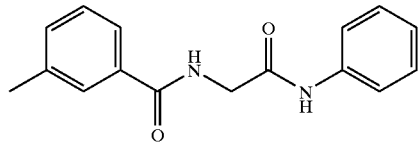 | — |
| 160 | 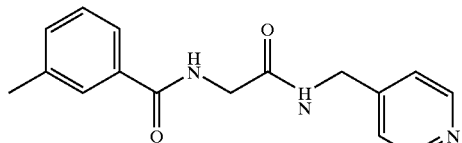 | — |
| 161 | 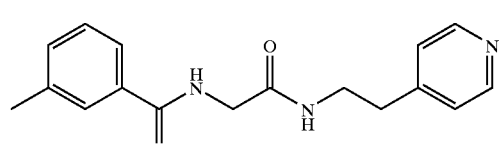 | — |
| 162 | 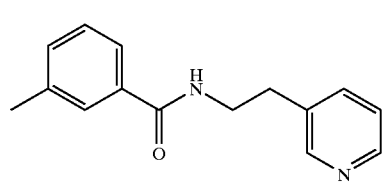 | — |
| 163 | 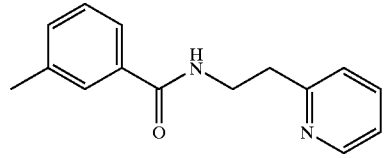 | — |
| 164 | 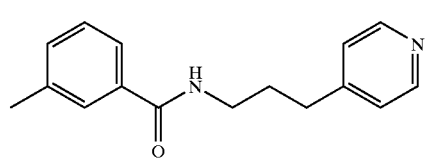 | — |

TABLE 4-continued
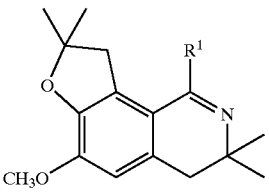
| ex. | R¹ | additive |
|---|---|---|
| 165 | 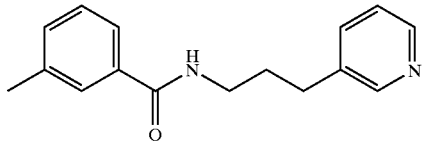 | — |
| 166 | 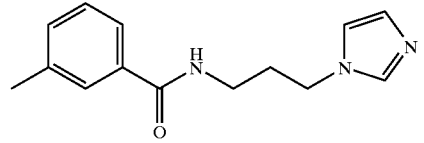 | — |
| 167 | 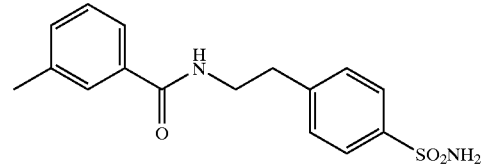 | — |
| 168 | 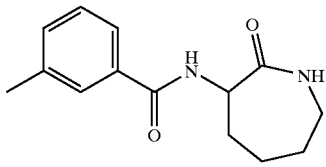 | — |
| 169 | 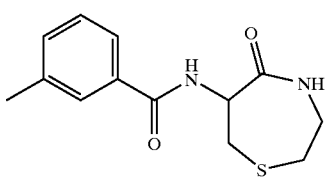 | — |
| 170 | 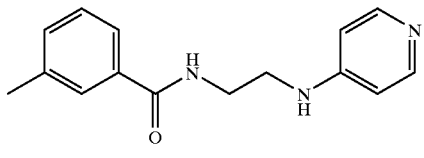 | — |
| 171 | 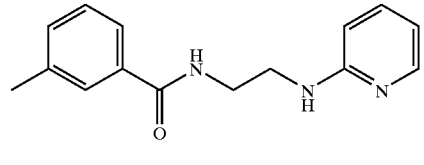 | — |
| 172 | 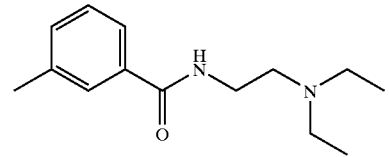 | 2HCl |

TABLE 4-continued
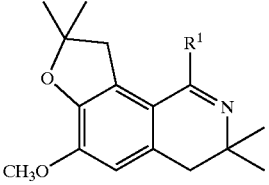
| ex. | R¹ | additive |
|---|---|---|
| 173 | 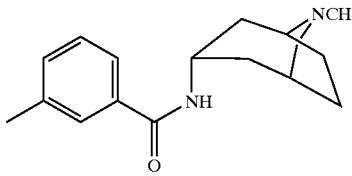 | 2HCl |
| 174 | 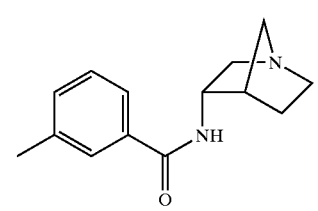 | 2HCl |
| 175 | 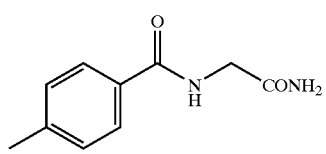 | — |
| 176 | 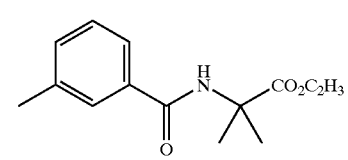 | — |
| 177 | 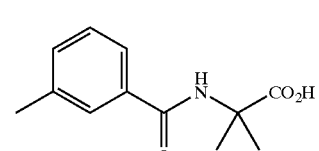 | HCl |
| 178 | 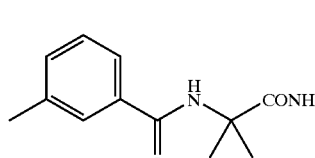 | — |
| 179 | 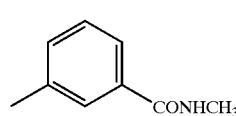 | — |
| 180 | 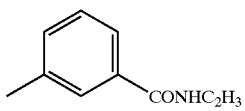 | — |

TABLE 4-continued
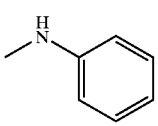
| ex. | R¹ | additive |
|---|---|---|
| 181 | 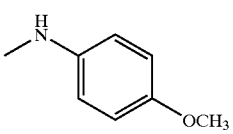 | — |
| 182 | 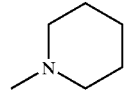 | — |
| 183 | 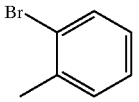 | HCl |
| 247 | 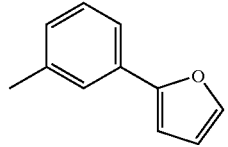 | HCl |
| 248 | 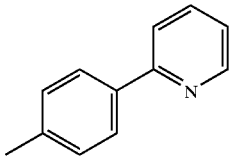 | — |
| 249 | 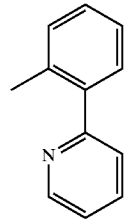 | — |
| 250 | 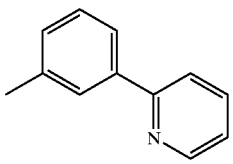 | — |
| 251 | | — |

TABLE 4-continued
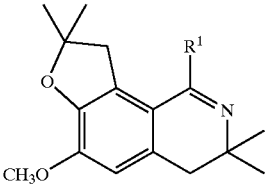
| ex. | R¹ | additive |
|---|---|---|
| 252 | 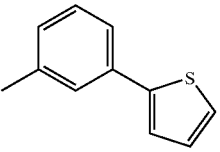 | — |
| 253 | 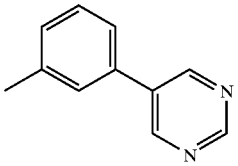 | — |
| 254 | 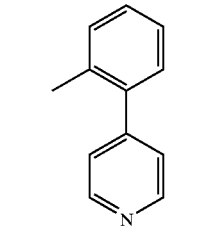 | — |
| 255 | 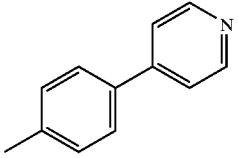 | 2HCl |
TABLE 5
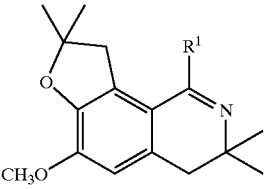
| ex. | R¹ | additive |
|---|---|---|
| 256 | 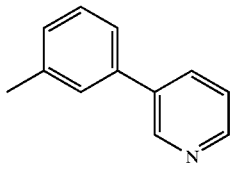 | — |
TABLE 5-continued
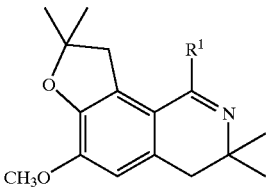
| ex. | R¹ | additive |
|---|---|---|
| 257 | 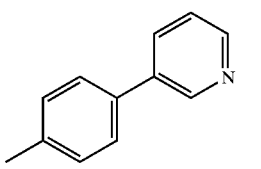 | 2HCl |

TABLE 5-continued
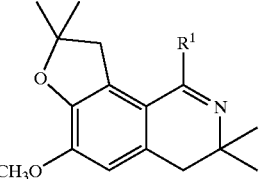
| ex. | R¹ | additive |
|---|---|---|
| 258 | 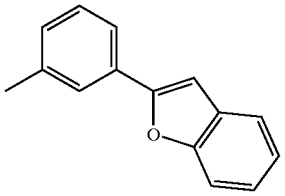 | — |
| 259 | 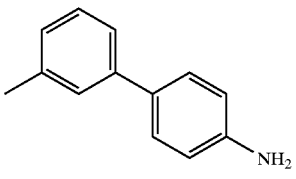 | — |
| 260 | 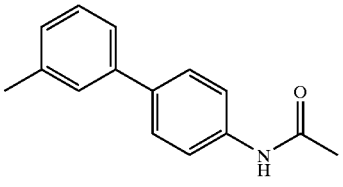 | — |
| 261 | 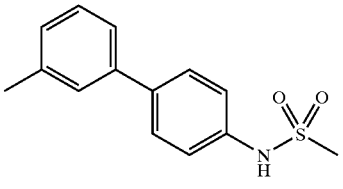 | — |
| 262 | 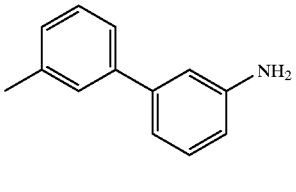 | 2HCl |
| 263 | 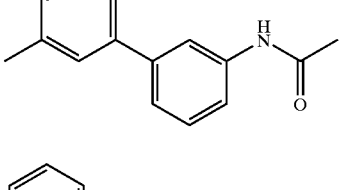 | — |
| 264 | 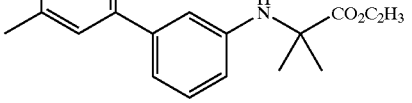 | HCl |
| 265 | 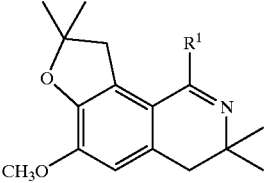 | HCl |
| 266 | 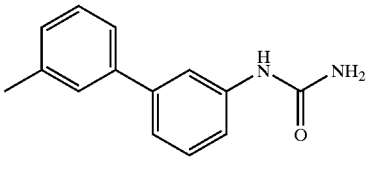 | — |
| 267 | 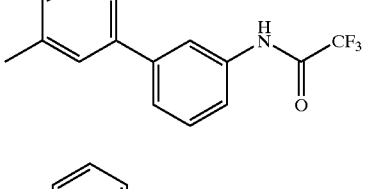 | — |
| 268 | 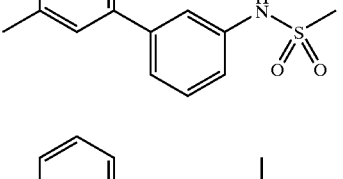 | HCl |
| 269 | 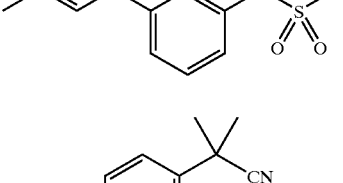 | — |
| 270 | 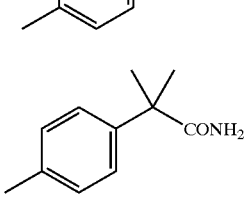 | — |
| 271 | 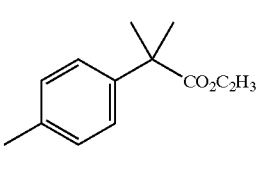 | — |
| 272 | 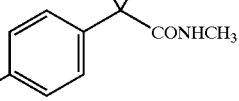 | — |

TABLE 5-continued

| ex. | R¹ | additive |
|---|---|---|
| 273 | (2-(4-methylphenyl)-2-methylpropanoyl)aminoacetic acid ethyl ester group | — |
| 274 | ethyl 2-(3-methylphenyl)-2-methylpropanoate group | HCl |
| 275 | sodium 2-(3-methylphenyl)-2-methylpropanoate group | — |
| 276 | 2-(3-methylphenyl)-2-methylpropanoic acid group | — |
| 277 | N-methyl 2-(3-methylphenyl)-2-methylpropanamide group | HCl |
| 278 | N-(pyridin-4-ylmethyl) 2-(3-methylphenyl)-2-methylpropanamide group | 2HCl |
| 279 | 4-methylbenzyl bromide group | — |
| 280 | 4-methylbenzyl CH group | — |
| 281 | ethyl 2-(4-methylphenyl)acetate group | HCl |

TABLE 5-continued

| ex. | R¹ | additive |
|---|---|---|
| 282 | diethyl 2-((3-methylphenyl)amino)methylene malonate group | — |
| 283 | N-ethyl-3-methylaniline group | — |
| 284 | N-(3-methylphenyl)-pyridin-3-amine group | — |
| 285 | N-acetyl-N-(3-methylphenyl)-pyridin-3-amine group | — |
| 286 | N-(3-methylphenyl)-N-(pyridin-3-yl) amine group | 3HCl |
| 287 | ethyl N-(3-methylphenyl)-N-(pyridin-3-yl) carbamate group | 2HCl |
| 288 | N-(3-methylphenyl)-N-(pyridin-3-yl) urea group | — |
| 289 | N-(3-methylphenyl)-aniline group | — |
| 290 | N-methyl-N-oxide-(3-methylphenyl)(phenyl)methylamine group | HCl |

TABLE 5-continued

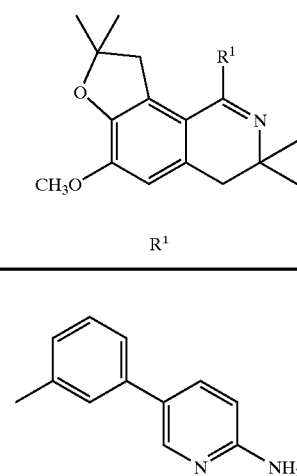

| ex. | R¹ | additive |
|---|---|---|
| 295 | (3-methylphenyl)-5-(2-aminopyridyl) | — |

TABLE 6

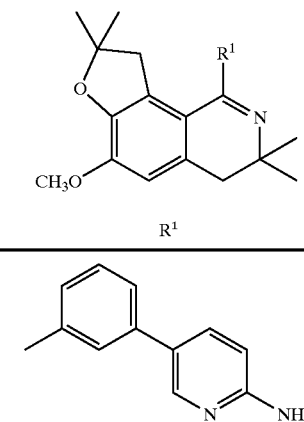

| ex. | R¹ | additive |
|---|---|---|
| 296 | (3-methylphenyl)-5-(2-aminopyridyl) | — |
| 297 | (3-methylphenyl)-5-(2-methanesulfonamidopyridyl) | HCl |
| 299 | 4-methylphenyl-SO₂-N(CH₃)-CH₂-(4-pyridyl) | 2HCl |
| 300 | 4-methylphenyl-SO₂NHCH₃ | — |
| 301 | 4-methylphenyl-SO₂-N(CH₃)-CH₂-CONH₂ | — |

TABLE 6-continued

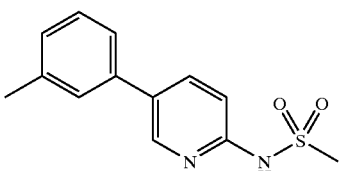

| ex. | R¹ | additive |
|---|---|---|
| 302 | 6-methylquinolinyl | 2HCl |
| 303 | 7-methylquinolinyl | — |
| 304 | 3-methylphenyl-NHCH₃ | — |
| 306 | 4-methylphenyl-cyclohexyl | HCl |
| 307 | 4-methylphenyl-O-phenyl | HCl |
| 308 | 6-methylnaphthyl | HCl |
| 309 | 4-methylphenyl-piperidinyl | HCl |
| 310 | 2,6-di-C₄H₃-4-methylphenol | HCl |
| 311 | 4,5-dimethyl-2-phenylimidazole | HCl |
| 312 | 3,6-dimethyl-2-pyridone | HCl |

TABLE 6-continued
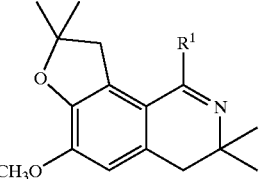
| ex. | R¹ | additive |
|---|---|---|
| 313 | 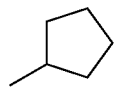 | HCl |
| 314 | 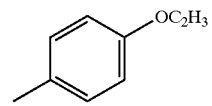 | HCl |
| 315 | 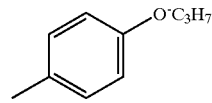 | HCl |
| 316 | 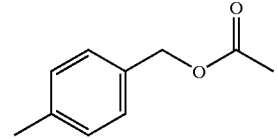 | HCl |
| 317 | 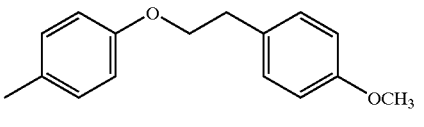 | HCl |
| 318 | 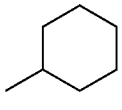 | HCl |
| 319 | 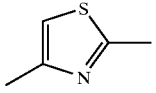 | — |
| 320 | 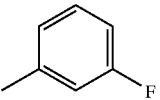 | HCl |
| 321 | 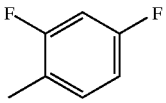 | — |
TABLE 6-continued
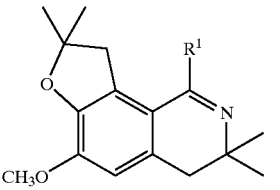
| ex. | R¹ | additive |
|---|---|---|
| 322 | 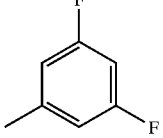 | HCl |
| 323 | 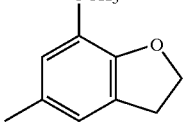 | — |
| 324 | 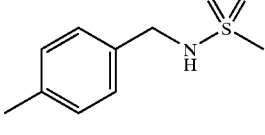 | HCl |
| 325 | 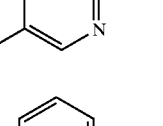 | HCl |
| 326 | 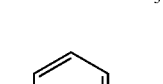 | HCl |
| 327 | 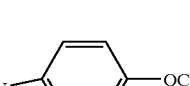 | — |
| 328 | 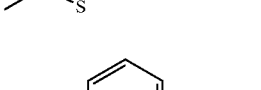 | — |
| 329 | 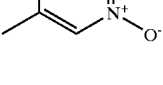 | — |
| 330 | 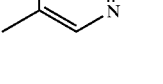 | — |

TABLE 6-continued

[Structure: 2,2-dimethyl-8,8-dimethyl-methoxy furo-isoquinoline core with R¹ substituent]

| ex. | R¹ | additive |
|---|---|---|
| 331 | 1-(5-methyl-2-oxopyridin-1(2H)-yl)-pyridine-4-carboxamide (N-linked via pyridin-2-yl) | — |
| 332 | 1-(pyridin-2-yl)-5-methylpyridin-2(1H)-one | — |
| 333 | 1-(4-methylquinolin-2-yl)-5-methylpyridin-2(1H)-one | — |
| 334 | 1-(3-methylquinolin-2-yl)-5-methylpyridin-2(1H)-one | — |
| 335 | 1-(7-methylquinolin-2-yl)-5-methylpyridin-2(1H)-one | — |
| 336 | ethyl 2-(5-methyl-2-oxopyridin-1(2H)-yl)pyridine-4-carboxylate | 2HCl |

TABLE 7

[Structure: same core]

| ex. | R¹ | additive |
|---|---|---|
| 337 | 5-methylpyridin-2(1H)-one (NH) | — |
| 338 | 1,5-dimethylpyridin-2(1H)-one | — |
| 339 | 5-methyl-1-(pyridin-3-ylmethyl)pyridin-2(1H)-one | — |
| 340 | 5-methyl-1-(pyridin-4-ylmethyl)pyridin-2(1H)-one | — |
| 341 | 5-methyl-1-(pyridin-2-ylmethyl)pyridin-2(1H)-one | — |
| 342 | 5-methyl-1-(quinolin-2-ylmethyl)pyridin-2(1H)-one | — |
| 343 | 1-benzyl-5-methylpyridin-2(1H)-one | — |
| 344 | 2-(5-methyl-2-oxopyridin-1(2H)-yl)acetamide | HCl |
| 345 | ethyl 2-(5-methyl-2-oxopyridin-1(2H)-yl)acetate | — |
| 346 | 2-(5-methyl-2-oxopyridin-1(2H)-yl)-N-(pyridin-3-yl)acetamide | — |
| 347 | 2-(5-methyl-2-oxopyridin-1(2H)-yl)-N-(2-hydroxyethyl)acetamide | — |

TABLE 7-continued
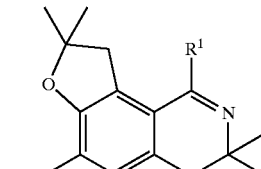
| ex. | R¹ | additive |
|---|---|---|
| 348 | 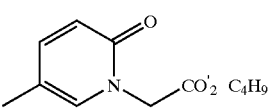 | — |
| 349 | 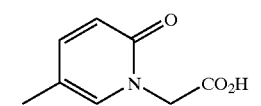 | HCl |
| 350 | 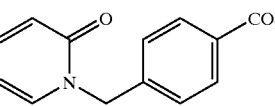 | — |
| 351 | 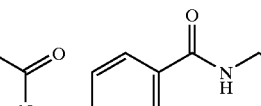 | HCl |
| 352 | 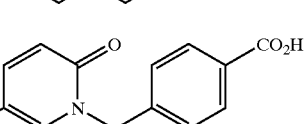 | HCl |
| 353 | 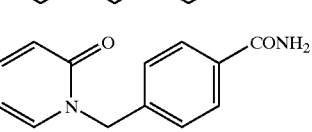 | — |
| 354 | 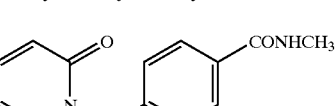 | — |
| 355 | 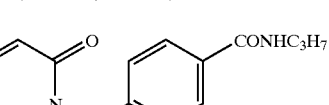 | — |
| 356 | 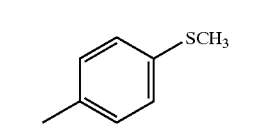 | HCl |
| 357 | 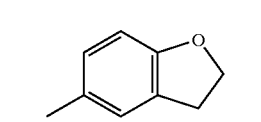 | HCl |
| 358 | 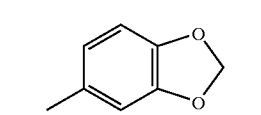 | HCl |
TABLE 7-continued
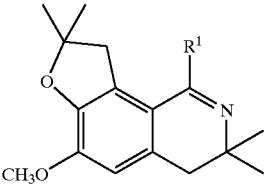
| ex. | R¹ | additive |
|---|---|---|
| 359 | 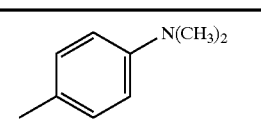 | HCl |
| 360 | 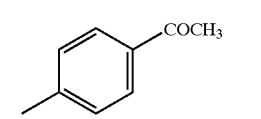 | HCl |
| 361 | 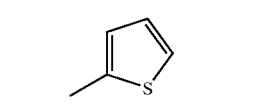 | HCl |
| 362 | 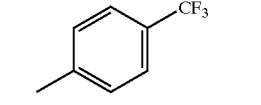 | HCl |
| 363 | 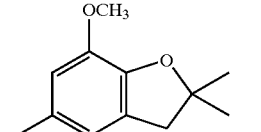 | HCl |
| 364 | 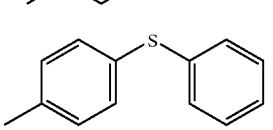 | 1.5 HCl |
| 365 | 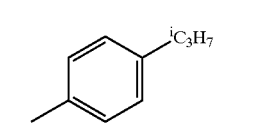 | HCl |
| 366 | 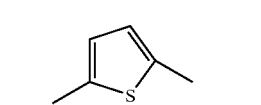 | HCl |
| 367 | 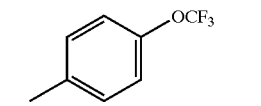 | HCl |
| 368 | 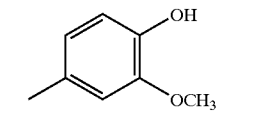 | — |
| 369 | 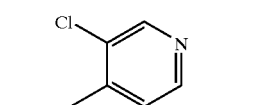 | — |

TABLE 7-continued
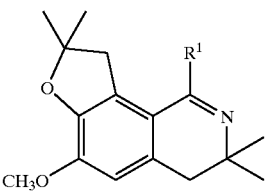
| ex. | R¹ | additive |
|---|---|---|
| 370 | 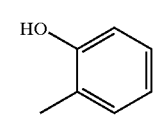 | — |
| 371 | 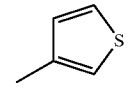 | — |
| 372 | 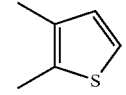 | — |
| 373 | 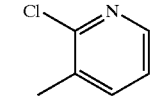 | — |
| 374 | 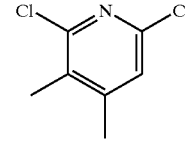 | — |
| 375 | 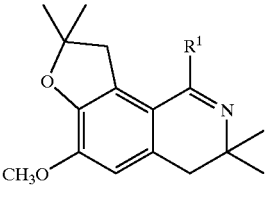 | — |
TABLE 8
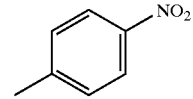
| ex. | R¹ | additive |
|---|---|---|
| 376 | 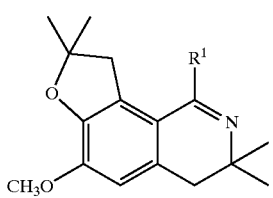 | — |
| 377 | 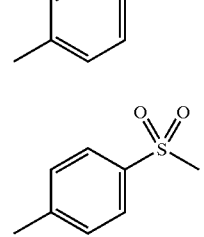 | — |
| 378 | 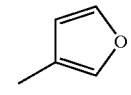 | — |
| 379 | 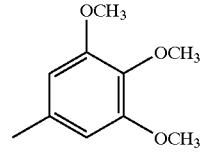 | — |
| 380 | 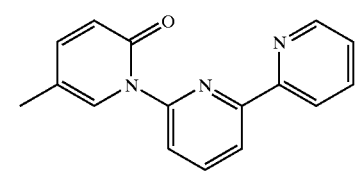 | — |
| 381 | 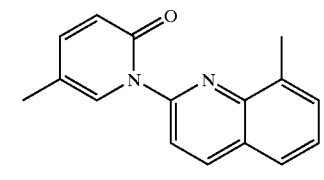 | — |
| 382 | 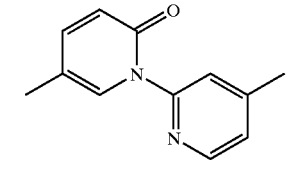 | — |
| 383 | | — |
| 384 | | — |
| 385 | 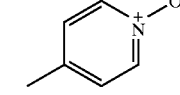 | — |

TABLE 8-continued
| ex. | R¹ | additive |
|---|---|---|
| 386 | 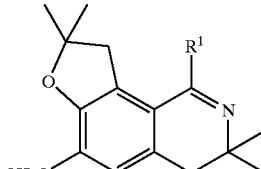 | — |
| 387 | 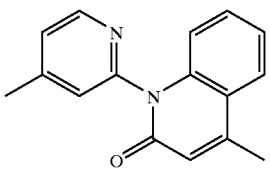 | — |
| 388 | 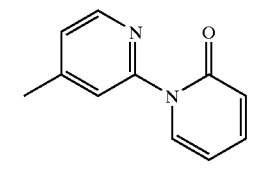 | — |
| 389 | 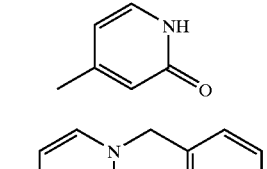 | — |
| 390 | 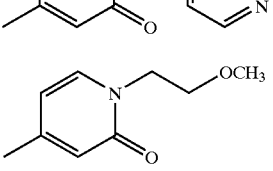 | — |
| 391 | 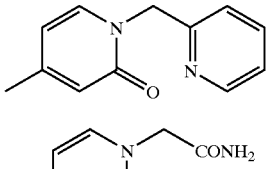 | — |
| 392 | 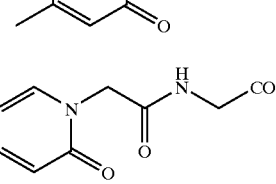 | — |
| 393 | 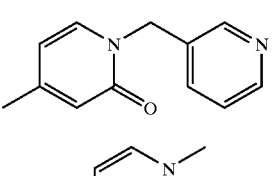 | — |
| 394 | 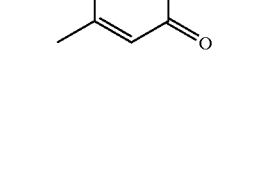 | — |
| 395 |  | — |
TABLE 8-continued
| ex. | R¹ | additive |
|---|---|---|
| 396 | 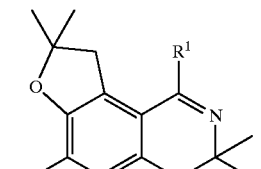 | — |
| 397 | 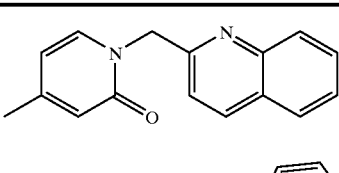 | — |
| 398 | 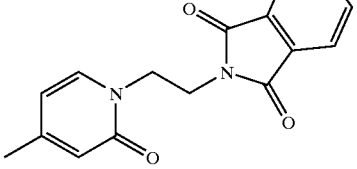 | — |
| 399 | 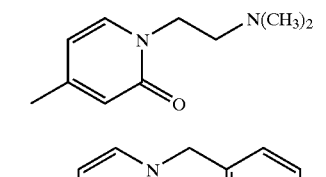 | — |
| 400 | 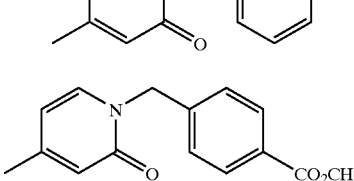 | — |
| 401 | 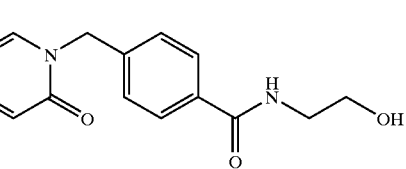 | — |
| 402 | 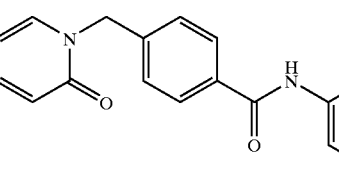 | — |
| 403 | 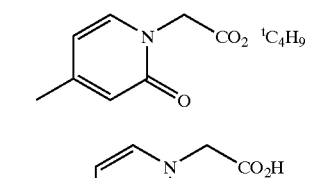 | — |
| 404 | 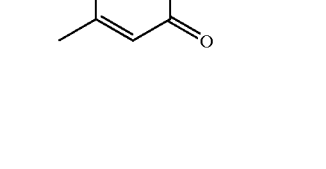 | HCl |

TABLE 8-continued
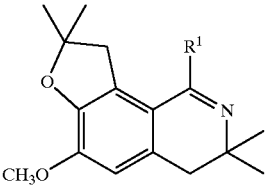
| ex. | R¹ | additive |
|---|---|---|
| 405 | 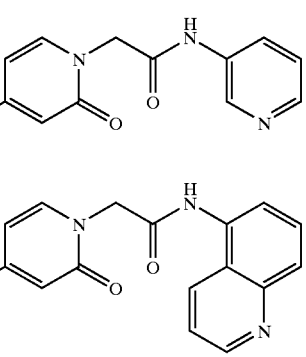 | — |
| 406 | 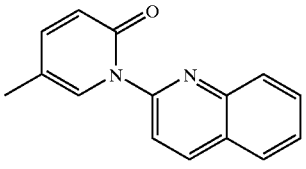 | — |
| 407 | 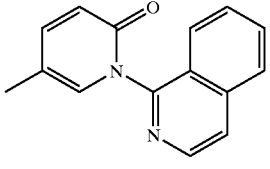 | — |
| 408 | 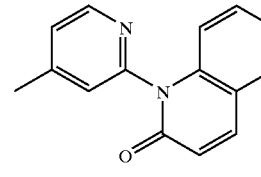 | — |
TABLE 9
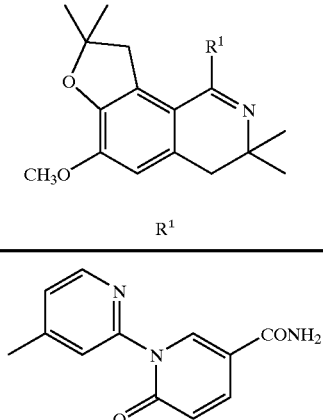
| ex. | R¹ | additive |
|---|---|---|
| 409 | 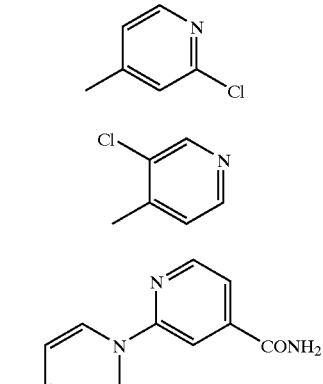 | — |
TABLE 9-continued
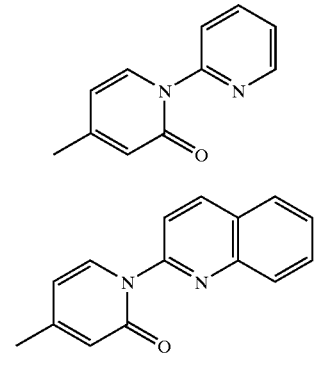
| ex. | R¹ | additive |
|---|---|---|
| 410 | 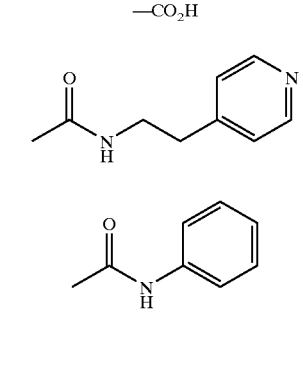 | — |
| 411 | 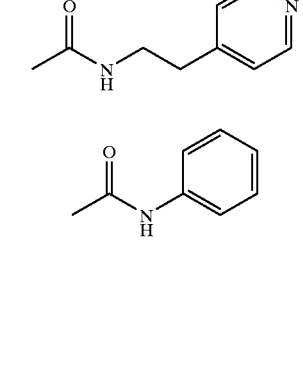 | — |
| 412 | 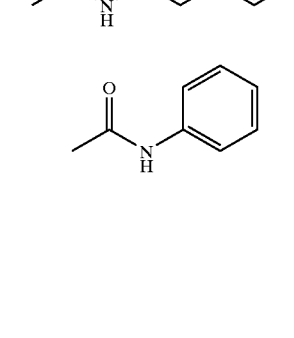 | — |
| 413 | 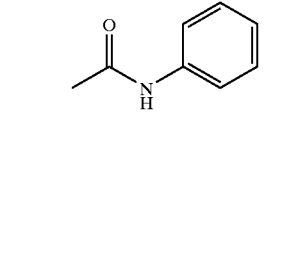 | — |
| 414 | 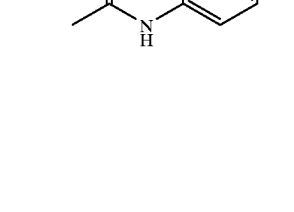 | — |
| 415 |  | — |
| 419 | —CO₂CH₃ | — |
| 420 | —CO₂H | HCl |
| 421 |  | — |
| 422 |  | — |

TABLE 9-continued
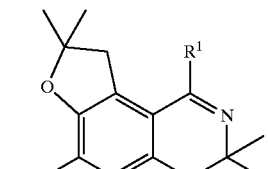
| ex. | R¹ | additive |
|---|---|---|
| 423 | 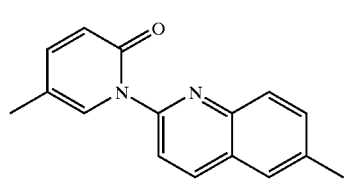 | — |
| 431 | 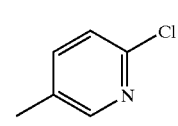 | — |
| 432 | 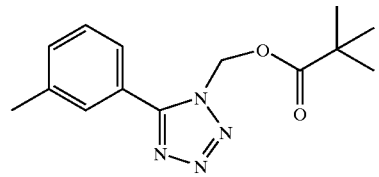 | — |
| 433 | 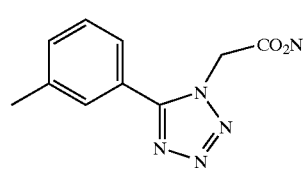 | — |
| 434 | 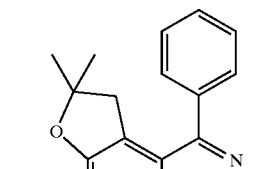 | — |
TABLE 10
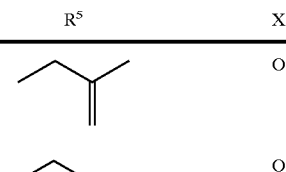
| ex. | R⁵ | X | additive |
|---|---|---|---|
| 22 | —C₂H₅ | O | — |
| 91 | —H | O | HBr |
| 92 | —H | O | — |
| 95 | —SO₂CF₃ | O | — |
| 96 | —SO₂CF₃ | O | HCl |
| 97 | —H | bond | HCl |
| 107 | —C₂H₃ | O | HCl |
TABLE 10-continued
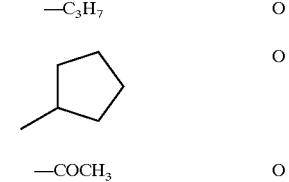
| ex. | R⁵ | X | additive |
|---|---|---|---|
| 136 |  | O | HCl |
| 138 |  | O | HCl |
| 186 | —C₃H₇ | O | HCl |
| 187 |  | O | — |
| 188 | —COCH₃ | O | HCl |
| 189 |  | O | HCl |
| 190 | —C₄H₉ | O | — |
| 191 | —C₃H₇ | O | HCl |
| 192 |  | O | — |
| 193 |  | O | 2HCl |
| 194 |  | O | — |
| 195 |  | O | — |
| 196 |  | O | — |
| 197 |  | O | HCl |

TABLE 10-continued

| ex. | R⁵ | X | additive |
|---|---|---|---|
| 198 | -(CH₂)₅-phenyl | O | — |
| 199 | —CO₂C₂H₅ | O | HCl |
| 200 | 1-phenyl-1H-tetrazol-5-yl-methyl | O | — |
| 201 | —CH₂F | O | — |
| 202 | N-ethylphthalimide | O | — |
| 203 | —CH₂CO₂CH₃ | O | — |
| 204 | —CH₂CONH₂ | O | — |
| 205 | —CH₂CO₂H | O | HCl |
| 206 | —CH₂CONHCH₃ | O | HCl |
| 207 | —CH₂CON(CH₃)₂ | O | — |
| 208 | —CH₂CH₂NH₂ | O | — |
| 209 | —CH₂CH₂OH | O | — |
| 210 | —CH₂CH₂F | O | — |
| 211 | C(=S)N(CH₃)₂ (methyl) | O | — |
| 212 | C(=S)N(CH₃)₂ (methyl) | O | HCl |
| 213 | C(=O)N(CH₃)₂ (methyl) | S | HCl |
| 214 | —CH₃ | S | HCl |
| 215 | —Cl | bond | HCl |
| 217 | —CH₃ | NH | HCl |
| 218 | —CH₃ | NCH₃ | 2HCl |
| 219 | —C₂H₅ | NH | HCl |
| 220 | —H | NH | — |
| 221 | —CHO | NH | — |
| 222 | —COCH₃ | NH | — |

TABLE 10-continued

| ex. | R⁵ | X | additive |
|---|---|---|---|
| 223 | —SO₂CH₃ | NH | — |
| 224 | —COC₂H₅ | NH | — |
| 225 | —CO₂C₂H₅ | NH | — |
| 226 | —CH₂CO₂C₂H₅ | NH | — |
| 227 | —CONH₂ | NH | — |
| 228 | —CONHCH₃ | NH | — |
| 296 | —C₂H₅ | S | HCl |
| 305 | —CH₃ | bond | HCl |

TABLE 11

| ex. | R¹ | R⁵ | X | additive |
|---|---|---|---|---|
| 23 | 4-methoxyphenyl (OCH₃) | —C₂H₅ | O | |
| 26 | 4-methyl-phenyl-CO₂CH₃ | —C₂H₅ | O | — |
| 82 | 4-methyl-phenyl-CO₂H | —C₂H₅ | O | HCl |
| 87 | 4-methyl-phenyl-CONH₂ | —CH₂H₅ | O | — |
| 93 | 4-methyl-phenyl-OH | —H | O | HBr |
| 94 | 3-bromo-methylphenyl | —H | O | — |

TABLE 11-continued

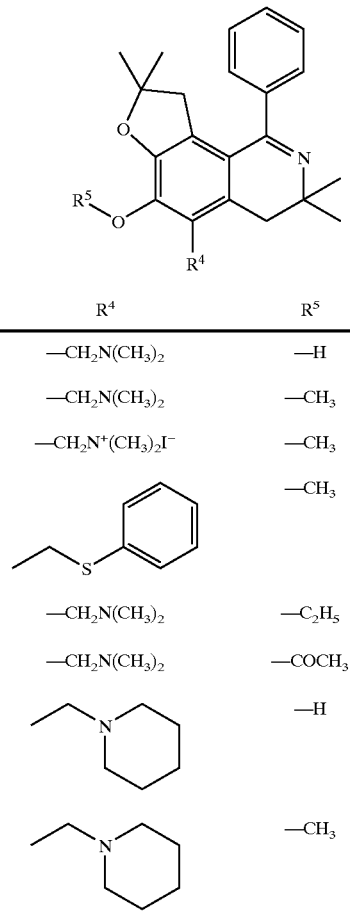

| ex. | R¹ | R⁵ | X | additive |
|---|---|---|---|---|
| 98 | 3-(pyridin-4-yl)phenyl | —H | O | — |
| 99 | 3-(pyridin-4-yl)phenyl | —C₃H₇ | O | — |
| 100 | 3-(pyridin-4-yl)phenyl | —CH₂CONH₂ | O | — |
| 101 | 3-bromophenyl | —CH₂H₅ | O | — |
| 102 | 3-bromophenyl | —C₂H₅ | O | HCl |
| 103 | 3-bromophenyl | —C₄H₉ | O | — |
| 104 | 3-bromophenyl | —C₄H₉ | O | HCl |
| 105 | 3-(pyridin-4-yl)phenyl | —C₄H₉ | O | — |
| 106 | 3-(pyridin-4-yl)phenyl | —C₂H₅ | O | — |
| 124 | 3-nitrophenyl | —H | O | — |
| 216 | 3-(pyridin-4-yl)phenyl | —Cl | bond | 2HCl |

TABLE 12

| ex. | R⁴ | R⁵ | additive |
|---|---|---|---|
| 113 | —CH₂N(CH₃)₂ | —H | — |
| 114 | —CH₂N(CH₃)₂ | —CH₃ | — |
| 115 | —CH₂N⁺(CH₃)₂I⁻ | —CH₃ | — |
| 116 | —CH₂S-phenyl (ethylthio-phenyl) | —CH₃ | HCl |
| 117 | —CH₂N(CH₃)₂ | —C₂H₅ | — |
| 118 | —CH₂N(CH₃)₂ | —COCH₃ | — |
| 119 | 1-ethylpiperidinyl | —H | — |
| 120 | 1-ethylpiperidinyl | —CH₃ | 2HCl |

TABLE 12-continued

[Structure: 2,2-dimethyl-furan fused to dihydroisoquinoline with 8,8-dimethyl, 10-phenyl; R⁵O- and R⁴ substituents on aromatic ring]

| ex. | R⁴ | R⁵ | additive |
|---|---|---|---|
| 121 | *N-ethylpiperidine* | —C₂H₅ | — |
| 122 | *N-ethylpiperidine* | —COCH₃ | 2HCl |
| 132 | —ⁱC₃H₇ | —H | — |
| 133 | —ⁱC₃H₇ | —CH₃ | HCl |
| 134 | —ⁱC₃H₇ | —C₂H₅ | HCl |
| 135 | —ⁱC₃H₇ | —COCH₃ | HCl |
| 137 | *2-methyl-1-butene group* | —H | — |
| 229 | *N-ethylphthalimide* | —CH₃ | — |
| 230 | —CH₂NH₂ | —CH₃ | — |
| 231 | *N-ethylformamide* | —CH₃ | — |
| 232 | *N-ethylacetamide* | —CH₃ | — |

TABLE 12-continued

| ex. | R⁴ | R⁵ | additive |
|---|---|---|---|
| 233 | *N-ethylurea (EtNHC(O)NH₂)* | —CH₃ | — |
| 234 | —CH₂Br | —CH₃ | — |
| 235 | —CH₂OCH₃ | —CH₃ | HCl |
| 236 | —CH₂OC₂H₅ | —CH₃ | HCl |
| 237 | —CH₂OH | —CH₃ | — |
| 238 | —CH₂F | —CH₃ | HCl |
| 239 | —CH₃ | —CH₃ | HCl |
| 240 | —CH₂CN | —CH₃ | — |
| 241 | —CH₂CO₂C₂H₅ | —CH₃ | HCl |
| 242 | —CH₂CO₂H | —CH₃ | — |
| 243 | —CH₂CONH₂ | —CH₃ | — |
| 244 | —CH₂CONHCH₃ | —CH₃ | — |
| 245 | *N-ethylphthalimide* | —H | — |
| 246 | —CH₂OH | —H | — |

TABLE 13

[Structure: bicyclic furan-fused dihydroisoquinoline core with 2,2-dimethyl dihydrofuran, R⁵O-, R⁴, R¹, and gem-dimethyl groups on the nitrogen-containing ring]

| ex. | R¹ | R⁴ | R⁵ | additive |
|---|---|---|---|---|
| 125 | 3-methyl-nitrobenzene (m-tolyl-NO₂) | N-ethylpiperidine (CH₂-piperidine) | —H | — |
| 126 | 3-methyl-nitrobenzene | N-ethylpiperidine | —C₂H₅ | — |
| 127 | 3-methyl-aniline (m-tolyl-NH₂) | N-ethylpiperidine | —C₂H₅ | — |
| 128 | 2-[(m-tolyl)carbamoyl]benzoic acid | N-ethylpiperidine | —C₂H₅ | — |
| 129 | N-(m-tolyl)phthalimide | N-ethylpiperidine | —C₂H₅ | — |
| 130 | N-(m-tolyl)methanesulfonamide | N-ethylpiperidine | —C₂H₅ | — |
| 131 | N-(m-tolyl)-N-(methylsulfonyl)methanesulfonamide | N-ethylpiperidine | —C₂H₅ | — |

TABLE 14
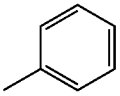
| ex. | R¹ | R² | R³ | R⁶ | R⁷ | R⁸ | R⁹ | additive |
|---|---|---|---|---|---|---|---|---|
| 109 | 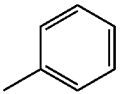 | —CH₂Br | —CH₃ | —CH₃ | —CH₃ | —H | —H | — |
| 184 | 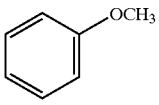 | —(CH₂)₅— | | —CH₃ | —CH₃ | —H | —H | HCl |
| 185 | 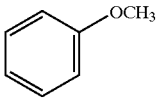 | —(CH₂)₅— | | —CH₃ | —CH₃ | —H | —H | HCl |
| 416 | 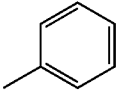 | —CH₃ | —CH₃ | —H | —H | —H | —H | — |
| 417 | 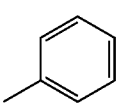 | —CH₃ | —CH₃ | —H | —H | —CH₃ | —CH₃ | — |
| 418 | 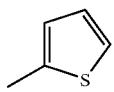 | —C₂H₅ | —C₂H₅ | —CH₃ | —CH₃ | —H | —H | HCl |
| 424 | 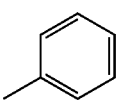 | —CH₃ | —CH₃ | —H | —H | —H | —H | — |
| 425 | 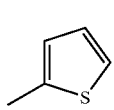 | —CH₃ | —CH₃ | —(CH₂)₄— | | —H | —H | — |
| 426 | 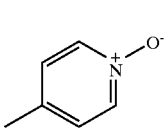 | —CH₃ | —CH₃ | —(CH₂)₄— | | —H | —H | — |
| 427 | 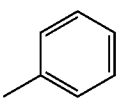 | —CH₃ | —CH₃ | —(CH₂)₄— | | —H | —H | — |
| 428 | 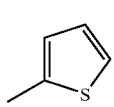 | —CH₃ | —CH₃ | —C₂H₅ | —C₂H₅ | —H | —H | HCl |
| 429 |  | —CH₃ | —CH₃ | —C₂H₅ | —C₂H₅ | —H | —H | HCl |

TABLE 14-continued

| ex. | R¹ | R² | R³ | R⁶ | R⁷ | R⁸ | R⁹ | additive |
|---|---|---|---|---|---|---|---|---|
| 430 | 4-pyridyl N-oxide | —CH₃ | —CH₃ | —C₂H₅ | —C₂H₅ | —H | —H | HCl |
| 435 | phenyl | —H | —H | —CH₃ | —CH₃ | —H | —H | HCl |
| 436 | phenyl | —CH₃ | —H | —CH₃ | —CH₃ | —H | —H | — |
| 437 | 4-pyridyl | —CH₃ | —H | —CH₃ | —CH₃ | —H | —H | — |
| 438 | phenyl | —CO₂CH₃ | —H | —CH₃ | —CH₃ | —H | —H | — |

TABLE 15

| ex. | R¹ | R⁵ | Y | n | additive |
|---|---|---|---|---|---|
| 108 | phenyl | —CH₃ | —CH(OH)— | 0 | — |
| 110 | phenyl | —C₂H₅ | —CH₂— | 1 | — |
| 111 | phenyl | —CH₃ | —CH₂— | 1 | — |
| 112 | 4-CONH₂-phenyl | —C₂H₅ | —CH₂— | 1 | — |

TABLE 15-continued

| ex. | R¹ | R⁵ | Y | n | additive |
|---|---|---|---|---|---|
| 291 | (3-bromophenyl) | —CH₃ | —CH(OH)— | 0 | HCl |
| 292 | (3'-methylbiphenyl-3-yl-NHC(O)CH₃) | —CH₃ | —CH(OH)— | 0 | — |
| 293 | (3'-methylbiphenyl-3-yl-NHC(O)CH₃) | —CH₃ | —CH(OH)— | 0 | HCl |
| 294 | (3'-methylbiphenyl-3-yl-NHC(O)CH₃) | —CH₃ | —C(=O)— | 0 | — |

TABLE 16

| ex. | R¹ | additive |
|---|---|---|
| 439 | (3'-methylbiphenyl-4-yl-NHC(O)CH₂CH₃) | — |
| 440 | (3'-methylbiphenyl-4-yl-NHC(O)C(CH₃)₃) | — |

TABLE 16-continued

[Structure: 2,2,8,8-tetramethyl-5-methoxy-2,7,8,8a-tetrahydrofuro[2,3-h]isoquinoline with R¹ substituent]

| ex. | R¹ | additive |
|---|---|---|
| 441 | 3'-methyl-biphenyl-4-yl-NHC(O)CF₃ | — |
| 442 | 3'-methyl-biphenyl-4-yl-NHC(O)Ph | — |
| 443 | 3'-methyl-biphenyl-4-yl-NHC(O)OCH₃ | — |
| 444 | 3'-methyl-biphenyl-4-yl-NHCHO | — |
| 445 | 3'-methyl-biphenyl-4-yl-NHC(O)CH₂NHC(O)CH₃ | — |
| 446 | 3'-methyl-biphenyl-4-yl-NHC(O)NHCH₃ | — |
| 447 | 3'-methyl-biphenyl-4-yl-NHC(O)CH₂CH₂CO₂H | — |
| 448 | 3'-methyl-biphenyl-4-yl-N(CH₃)C(O)CH₃ | — |
| 451 | 3'-methyl-4-amino-3-(methoxycarbonyl)biphenyl | — |
| 452 | 3'-methyl-4-acetamido-3-(methoxycarbonyl)biphenyl | — |
| 453 | 3'-methyl-4-acetamido-3-carboxybiphenyl | — |
| 454 | 4'-methyl-biphenyl-4-yl-NHC(O)CH₃ | — |

TABLE 16-continued
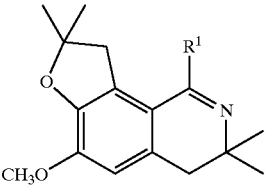
| ex. | R¹ | additive |
|---|---|---|
| 455 | 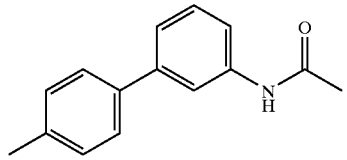 | — |
| 456 | 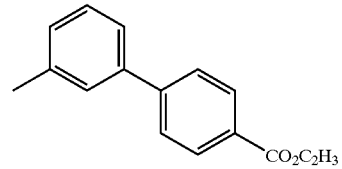 | — |
| 457 | 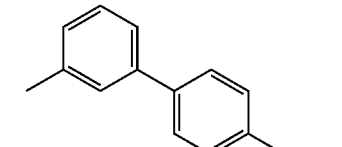 | — |
| 458 | 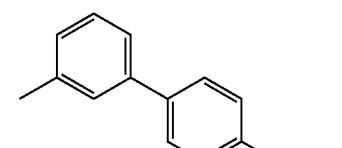 | — |
| 459 | 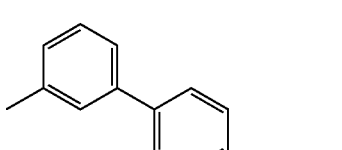 | — |
| 460 | 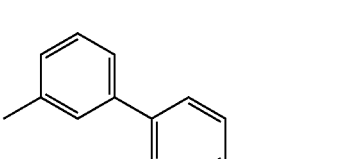 | — |
| 467 | 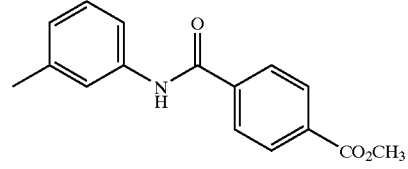 | — |
TABLE 16-continued
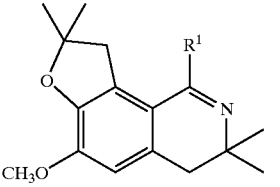
| ex. | R¹ | additive |
|---|---|---|
| 468 | 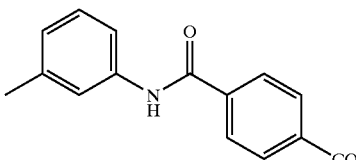 | HCl |
| 469 | 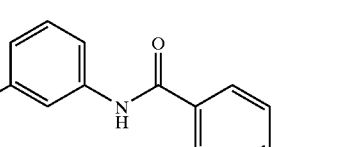 | — |
| 477 | 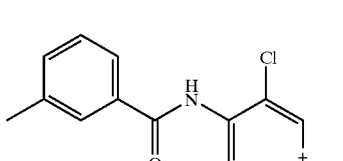 | — |
| 478 | 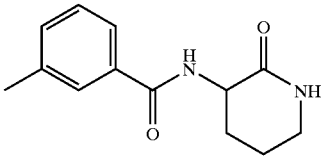 | — |
| 479 | 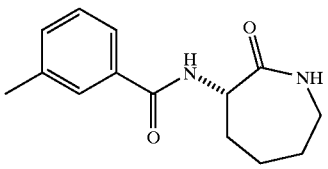 | — |
| 480 | 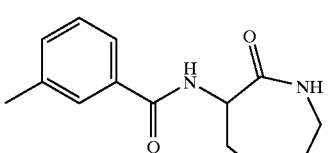 | — |
| 493 | 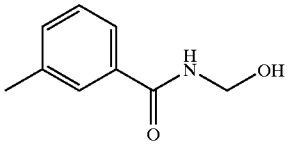 | — |

TABLE 16-continued

[Structure: 2,2-dimethyl-dihydrofuran fused bicyclic with CH3O and R¹ substituent, with N in ring and gem-dimethyl]

| ex. | R¹ | additive |
|---|---|---|
| 501 | 3-methylphenyl-O-C(=S)-N(CH3)2 | HCl |
| 502 | 3-methylphenyl-O-CH2-CONH2 | — |
| 503 | 3-methylphenyl-SO2NHCH3 | HCl |
| 504 | 3-methylphenyl-SO2-N(CH3)-CH2-CO2C2H5 | HCl |
| 505 | 3-methylphenyl-SO2-N(CH3)-CH2-CONH2 | — |

TABLE 17

[Structure: same bicyclic scaffold with R¹]

| ex. | R¹ | additive |
|---|---|---|
| 506 | 3-methylphenyl-SO2-NH-(3-acetamidophenyl) | HCl |
| 507 | 3-methylphenyl-SO2-NH-CH2-CONH2 | HCl |

TABLE 17-continued

[Structure: same bicyclic scaffold with R¹]

| ex. | R¹ | additive |
|---|---|---|
| 508 | 3-methylphenyl-SO2-NH-(3-oxo-azepan-2-yl) | HCl |
| 509 | 3-methylphenyl-S-C(=O)-NHCH3 | HCl |
| 510 | 3-methylphenyl-SCH3 | HCl |
| 511 | 3-methylphenyl-S(+)(CH3)-O(−) | HCl |
| 512 | 3-methylphenyl-S(=O)2-CH3 | HCl |
| 513 | 3-methylphenyl-S-CH2-CONH2 | — |
| 514 | 3-methylphenyl-S(+)(O−)-CH2-CONH2 | HCl |
| 515 | 3-methylphenyl-SO2-CH2-CONH2 | HCl |
| 516 | 3-methylphenyl-NH-SO2-CH2CH2-Cl | — |

TABLE 17-continued

| ex. | R¹ | additive |
|---|---|---|
| 517 | 3-methylphenyl-N-(isothiazolidine 1,1-dioxide) | — |
| 518 | 3-methylphenyl-NH-S(O)₂-N(CH₃)₂ | — |
| 519 | 3-methylphenyl-NH-C(O)-CH=CH₂ | — |
| 520 | 3-methylphenyl-NH-C(O)-CH₂CH₂CH₂Cl | — |
| 521 | 3-methylphenyl-N-(2-oxopyrrolidin-1-yl) | HCl |
| 522 | 3-methylphenyl-NH-C(O)-C(CH₃)₂-CH₂Cl | — |
| 523 | 3-methylphenyl-N-(3,3-dimethyl-2-oxoazetidin-1-yl) | HCl |
| 524 | 3-methylphenyl-NH-C(O)-(5-oxopyrrolidin-2-yl) | — |
| 525 | 3-methylphenyl-N(CH₃)-C(O)-(5-oxopyrrolidin-2-yl) | HCl |
| 526 | 3-methylphenyl-NH-C(O)-(2,6-dichloropyridin-3-yl) | — |
| 527 | 3-methylphenyl-NH-C(O)-NH-(3-acetamidophenyl) | HCl |
| 528 | 3-methylphenyl-NH-C(O)-NH₂ | — |
| 529 | 3-methylphenyl-N(CH₃)-C(O)-NH₂ | — |
| 530 | 3-methylphenyl-NH-C(O)-NH-CH₃ | — |
| 531 | 3-methylphenyl-NH-C(O)-NH-(pyridin-2-yl) | — |
| 532 | 3-methylphenyl-NH-C(O)-NH-CH₂CH₂Cl | — |
| 533 | 3-methylphenyl-N-(2-oxoimidazolidin-1-yl) | — |

TABLE 17-continued
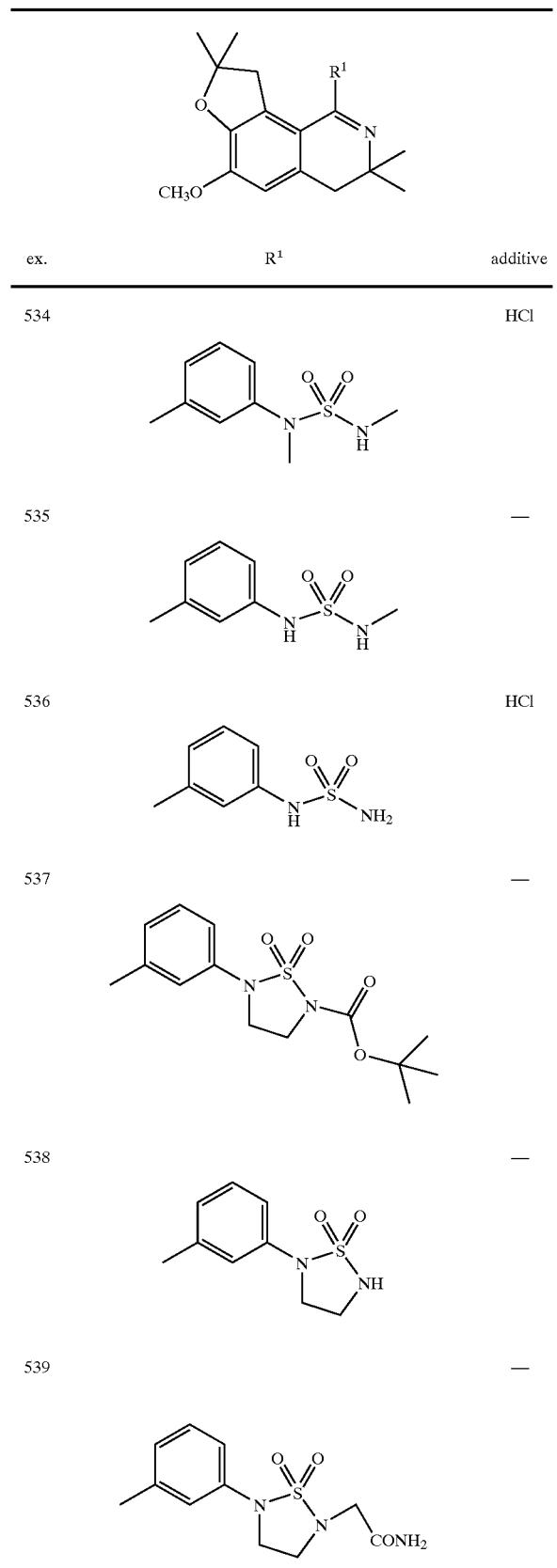
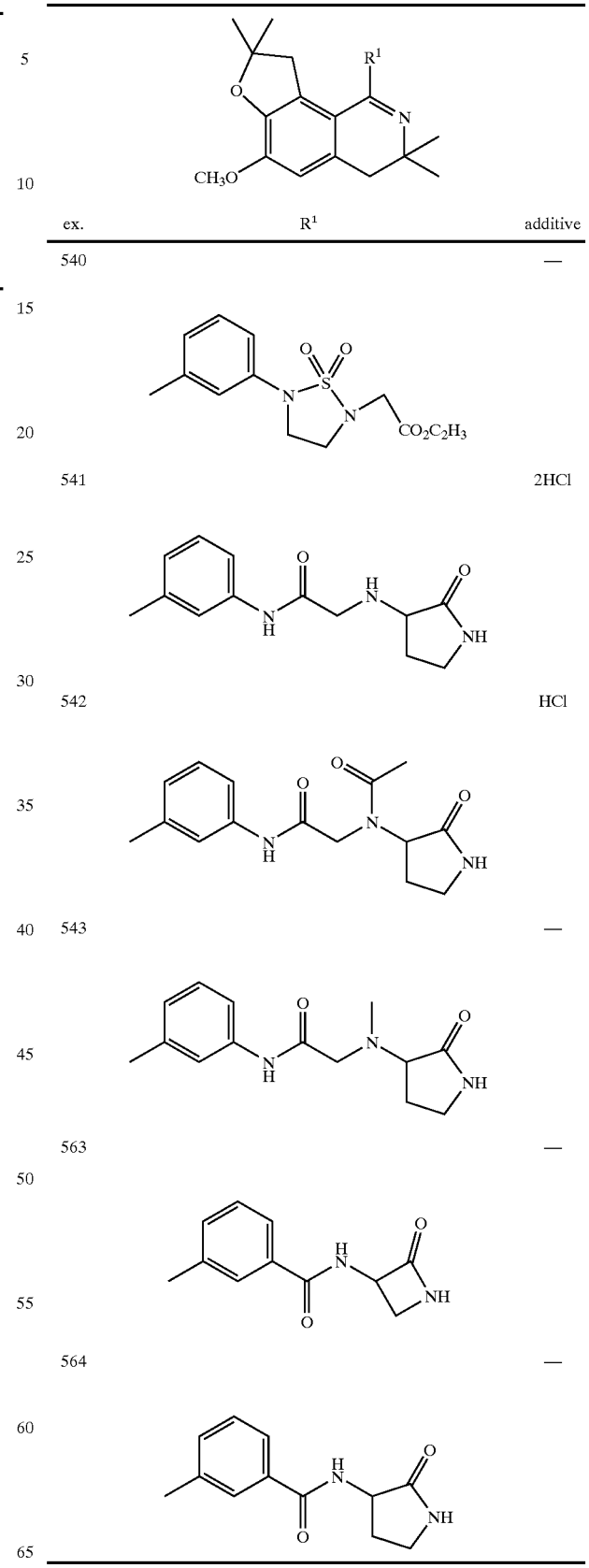

TABLE 18
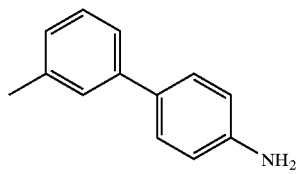
| ex. | R¹ | R⁵ | X | additive |
|---|---|---|---|---|
| 449 | 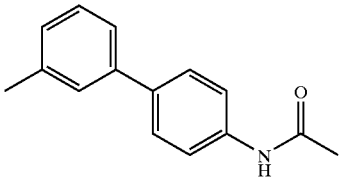 | —C$_4$H$_9$ | O | — |
| 450 | 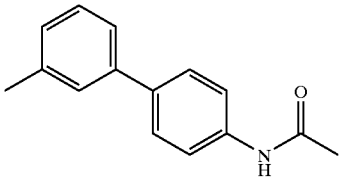 | —C$_4$H$_9$ | O | — |
| 461 | 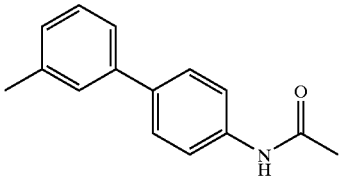 | —H | O | — |
| 462 | 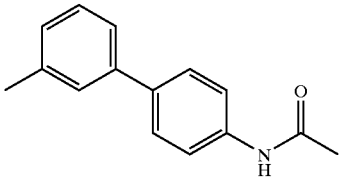 | —SO$_2$CF$_3$ | O | — |
| 463 | 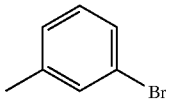 | —H | bond | — |
| 464 | 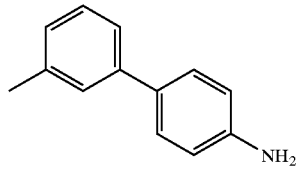 | —SO$_2$CF$_3$ | O | — |
| 465 | 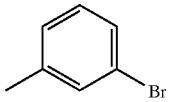 | —H | bond | — |
| 466 | | —H | bond | — |

TABLE 18-continued
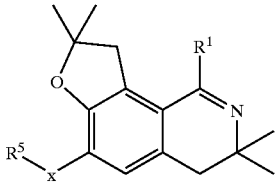
| ex. | R¹ | R⁵ | X | additive |
|---|---|---|---|---|
| 481 | 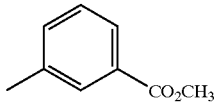 | —C₂H₅ | O | — |
| 482 | 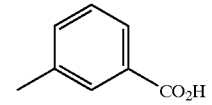 | —C₂H₅ | O | HCl |
| 483 | 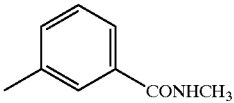 | —C₂H₅ | O | — |
| 484 | 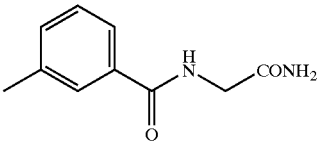 | —C₂H₅ | O | — |
| 485 | 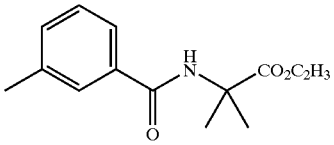 | —C₂H₅ | O | — |
| 486 | 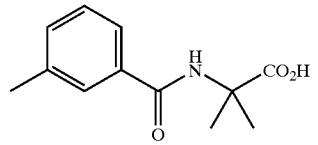 | —C₂H₅ | O | HCl |
| 487 | 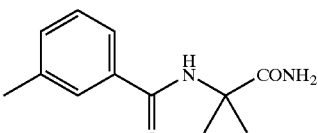 | —C₂H₅ | O | — |
| 488 | 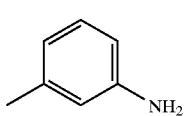 | —C₂H₅ | O | — |
| 489 | 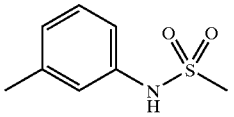 | —C₂H₅ | O | — |

TABLE 18-continued

| ex. | R¹ | R⁵ | X | additive |
|---|---|---|---|---|
| 490 | 3-methylphenyl-N(SO₂CH₃)₂ | —C₂H₅ | O | — |
| 491 | 3-methylphenyl-NHC(O)CH₂SCH₃ | —C₂H₅ | O | — |
| 492 | 3-methylphenyl-NHC(O)CH₂S⁺(O)CH₃ | —C₂H₅ | O | — |
| 544 | 3-methylphenyl-CO₂C₂H₅ | —C₂H₅ | O | — |
| 545 | 3-methylphenyl-CO₂H | —C₂H₅ | O | — |
| 546 | 3-methylphenyl-NH₂ | —C₂H₅ | O | 2HCl |
| 547 | 3-methylphenyl-NHC(O)-(4-phenyl)-CH₂P(O)(OC₂H₃)(OC₂H₃) | —C₂H₅ | O | HCl |
| 548 | 3-methylphenyl | —C₂H₅ | S⁺(—O) | — |
| 549 | 3-methylphenyl-CO₂C₂H₅ | —C₃H₇ | S | — |

TABLE 18-continued

Structure: 2,2,8,8-tetramethyl-furano-dihydroisoquinoline core with R¹ at position adjacent to N, and R⁵–X– substituent on aromatic ring.

| ex. | R¹ | R⁵ | X | additive |
|-----|----|----|---|----------|
| 550 | 3-methylphenyl with CO₂C₂H₇ | —C₂H₅ | S | — |
| 586 | 3-methylphenyl with CO₂H | —C₃H₇ | S | — |
| 587 | 3-methylphenyl-C(=O)NH–C(CH₃)₂–CONH₂ | —C₃H₇ | S | — |

TABLE 19

Structure: 2,2-dimethyl-furano-dihydroisoquinoline core with phenyl at R¹ position, R⁵O– on aromatic ring, R² and R³ on saturated carbon.

| ex. | R² | R³ | R⁵ | additive |
|-----|----|----|----|----------|
| 470 | N-ethylphthalimide | —CH₃ | —CH₃ | — |
| 471 | —CH₂CH₂NH₂ | —CH₃ | —CH₃ | — |
| 472 | —CH₂CH₂OC(=O)CH₃ | —H | —CH₃ | — |
| 473 | —CH₂CH₂OH | —H | —CH₃ | — |
| 474 | N-ethylphthalimide | —H | —CH₃ | — |
| 475 | —CH₂CH₂NH₂ | —H | —CH₃ | 2HCl |
| 498 | —CH₂CH₂Br | —CH₃ | —C₂H₅ | HCl |
| 499 | —CH₂CH₂N(CH₃)₂ | —CH₃ | —C₂H₅ | 2HCl |
| 500 | —CH₂CH₂N(C₂H₅)₂ | —CH₃ | —C₂H₅ | 2HCl |

TABLE 20
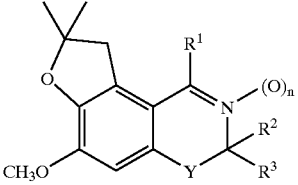
| ex. | R¹ | R² | R³ | Y | n | additive |
|---|---|---|---|---|---|---|
| 476 | 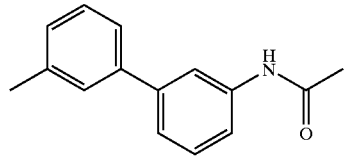 | —CH₃ | —CH₃ | —CH₂— | 1 | — |
| 494 | 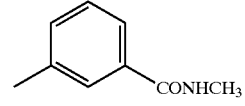 | —CH₃ | —CH₃ | —CH(OH)— | 0 | — |
| 495 | 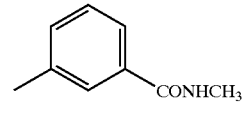 | —CH₃ | —CH₃ | —C(=O)— | 0 | — |
| 496 | 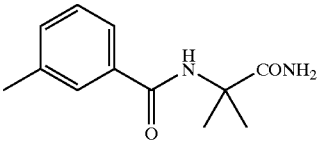 | —CH₃ | —CH₃ | —CH(OH)— | 0 | — |
| 497 | 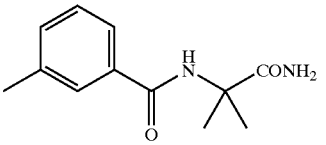 | —CH₃ | —CH₃ | —C(=O)— | 0 | — |
| 565 | 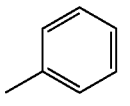 | —H | —H | —C(CH₃)₂— | 0 | — |
| 566 | 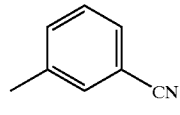 | —H | —H | —C(CH₃)₂— | 0 | — |
| 567 | 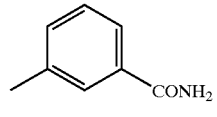 | —H | —H | —C(CH₃)₂— | 0 | — |
| 568 | —CO₂C₂H₅ | —H | —H | —C(CH₃)₂— | 0 | — |
| 569 | 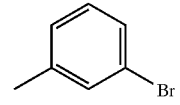 | —H | —H | —C(CH₃)₂— | 0 | — |

TABLE 20-continued
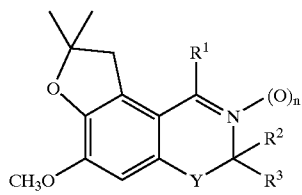
| ex. | R¹ | R² | R³ | Y | n | additive |
|---|---|---|---|---|---|---|
| 570 | ![biphenyl-NH2 with methyl] | —H | —H | —C(CH₃)₂— | 0 | — |
| 571 | ![biphenyl-NHAc with methyl] | —H | —H | —C(CH₃)₂— | 0 | — |
TABLE 21
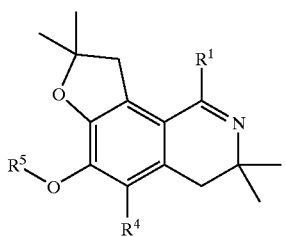
| ex. | R¹ | R⁴ | R⁵ | additive |
|---|---|---|---|---|
| 551 | ![3-methylphenyl-CO₂CH₃] | —CH₂CN | —CH₃ | HCl |
| 552 | ![3-methylphenyl-CO₂H] | —CH₂CN | —CH₃ | HCl |
| 553 | ![3-methylphenyl-CONHCH₃] | —CH₂CN | —CH₃ | HCl |
| 554 | ![3-methylbenzamide-azepanone] | —CH₂CN | —CH₃ | — |

TABLE 21-continued

| ex. | R¹ | R⁴ | R⁵ | additive |
|---|---|---|---|---|
| 555 | (3-methylbenzamido)-C(CH₃)₂-CO₂C₂H₅ | —CH₂CN | —CH₃ | — |
| 556 | (3-methylbenzamido)-C(CH₃)₂-CO₂H | —CH₂CN | —CH₃ | HCl |
| 557 | (3-methylbenzamido)-CH₂-CONH₂ | —CH₂CN | —CH₃ | HCl |
| 558 | (3-methylbenzamido)-C(CH₃)₂-CONH₂ | —CH₂CN | —CH₃ | — |
| 559 | (3-methylbenzamido)-C(CH₃)₂-C(O)NH-(2-oxopyrrolidin-3-yl) | —CH₂CN | —CH₃ | — |
| 560 | 3-methylphenyl | —CHO | —CH₃ | HCl |
| 561 | 3-methylphenyl | —CN | —CH₃ | — |
| 562 | 3-methyl-5-(CO₂C₂H₅)phenyl | —CH₂CN | —C₂H₃ | HCl |
| 563 | 3-methylphenyl | —OCH₃ | —CH₃ | HCl |

TABLE 22
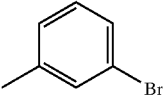
| ex. | R¹ | R⁵ | X | additive |
|---|---|---|---|---|
| 572 | 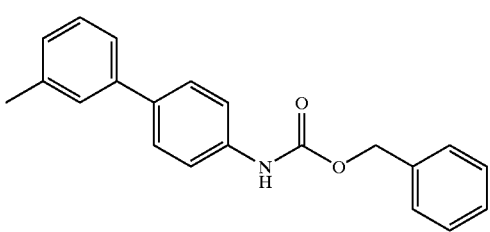 | —H | O | — |
| 573 | 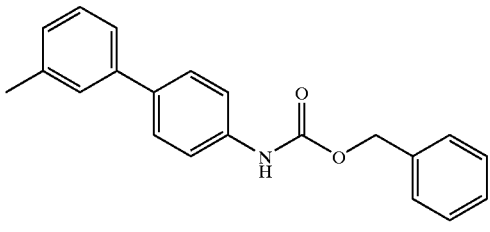 | —H | O | — |
| 574 | 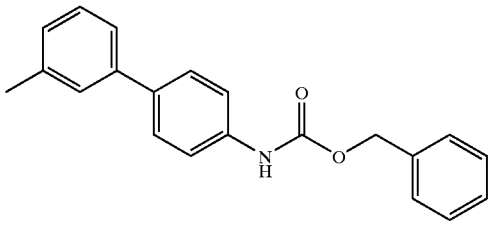 | —SO₂CF₃ | O | — |
| 575 | 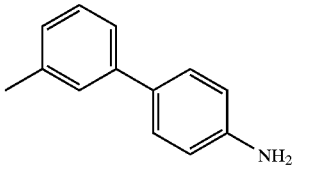 | —H | bond | — |
| 576 | 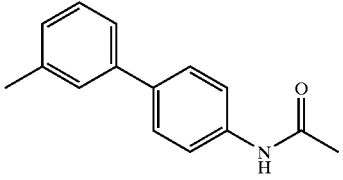 | —H | bond | 2HBr |
| 577 | | —H | bond | — |

TABLE 22-continued

| ex. | R¹ | R⁵ | X | additive |
|---|---|---|---|---|
| 578 | 3'-methylbiphenyl-4-yl-NHC(O)CH₂CH₃ | —H | bond | — |
| 579 | 3'-methylbiphenyl-4-yl-NHCHO | —H | bond | — |
| 580 | 3'-methylbiphenyl-4-yl-CO₂C₂H₅ | —H | O | — |
| 581 | 3'-methylbiphenyl-4-yl-CO₂C₂H₅ | —SO₂CF₃ | O | — |
| 582 | 3'-methylbiphenyl-4-yl-CO₂C₂H₅ | —H | bond | — |
| 583 | 3'-methylbiphenyl-4-yl-CO₂H | —H | bond | — |
| 584 | 3'-methylbiphenyl-4-yl-CONH₂ | —H | bond | — |

TABLE 22-continued

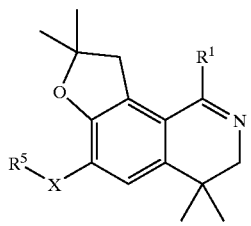

| ex. | R¹ | R⁵ | X | additive |
|---|---|---|---|---|
| 585 | (3-methylbiphenyl-4-CONHCH₃) | —H | bond | — |

Formulation Example 1

| | |
|---|---|
| (1) Compound of Example 1 | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of the compound obtained in Example 1, 60.0 mg of lactose and 35.0 mg of a corn starch was granulated using 0.03 ml of 10% aqueous solution of gelatin (3.0 mg as gelatin) through a 1 mm mesh sieve, dried at 40° C. and then sieved again. The resultant granule was combined with 2.0 mg of magnesium stearate and then compressed. The resultant core was coated with a sugar coating comprising sucrose, titanium dioxide, talc and gum arabic in an aqueous suspension. The resultant coated tablet was imparted with a gloss with a beeswax to obtain a coated tablet.

Formulation Example 2

| | |
|---|---|
| (1) Compound of Example 1 | 10.0 mg |
| (2) Lactose | 70.0 mg |
| (3) Corn starch | 50.0 mg |
| (4) Soluble starch | 7.0 mg |
| (5) Magnesium stearate | 3.0 mg |

10.0 mg of the compound obtained in Example 1 and 3.0 mg of magnesium stearate were granulated using 0.07 mL of an aqueous solution of a soluble starch (7.0 mg as soluble starch), dried, and then combined with 70.0 mg of lactose and 50.0 mg of a corn starch. The mixture was compressed into a tablet.

Formulation Example 3

| | |
|---|---|
| (1) Compound of Example 11 | 5.0 mg |
| (2) Sodium chloride | 20.0 mg |
| (3) Distilled water | to 2 mL |

5.0 mg of the compound obtained in Example 11 and 20.0 mg of sodium chloride were dissolved in distilled water and water was then added to make the entire volume 2.0 mL. The solution was filtered, and filled aseptically in a 2 mL ampoule. The ampoule was sterilized, sealed, whereby obtaining an injection solution.

Formulation Example 4

In a fluidized bed granulating drier (FD-5S, KK POW-REX Corporation), 1500 g of the compound obtained in Example 1, 2025 g of lactose and 556.5 g of corn starch were mixed homogeneously, and then an aqueous solution in which 126 g of hydroxypropyl cellulose was dissolved was sprayed in the drier to effect a granulation, after which the mixture was dried in the fluidized bed granulating drier. The resultant granule was ground using a power mill and sieved through a 1.5 mm punching screen to obtain a sized granule. 3927 g of this sized granule was combined with 210 g of sodium croscarmellose and 63 g of magnesium stearate, and mixed in a tumbler mixer to obtain a granule to be compacted into tablets. This granule was compacted into 300 mg tablets using a 6.5 mm frame in a tablet compacting machine. The resultant plain tablet was coated with a solution containing hydroxypropylmethyl cellulose 2910 (TC-5) and macrogol 6000 dissolved therein and titanium oxide and iron(III) oxide dispersed therein to obtain about 13500 film-coated tablets each containing 100 mg whose composition is shown below.

| Composition | Content (mg) |
|---|---|
| Tablet formulation: | |
| (1) Compound of Example 1 | 100.0 |
| (2) Lactose | 135.0 |
| (3) Corn starch | 37.1 |
| (4) Sodium croscarmellose | 15.0 |
| (5) Hydroxypropyl cellulose | 8.4 |
| (6) Magnesium stearate | 4.5 |
| Total (plain tablet) | 300.0 |
| Film-coated tablet composition: | |
| (1) Plain tablet 300.0 | |

-continued

| Composition | Content (mg) |
|---|---|
| (Film component) | |
| (2) Hydroxypropylmethyl cellulose 2910 | 7.485 |
| (3) Macrogol 6000 | 1.5 |
| (4) Titanium oxide | 1.0 |
| (5) iron(III) oxide | 0.015 |
| Total | 310.0 |

Formulation Example 5

According to the method described in Formulation Example 4, about 13500 film-coated tablets having the formulation shown below each containing 25 mg of the compound obtained in Example 1 were obtained.

| Composition | Content (mg) |
|---|---|
| Tablet formulation: | |
| (1) Compound of Example 1 | 25.0 |
| (2) Lactose | 210.0 |
| (3) Corn starch | 37.1 |
| (4) Sodium croscarmellose | 15.0 |
| (5) Hydroxypropyl cellulose | 8.4 |
| (6) Magnesium stearate | 4.5 |
| Total (plain tablet) | 300.0 |
| Film-coated formulation: | |
| (1) Plain tablet | 300.0 |
| (Film components) | |
| (2) Hydroxypropyl cellulose 2910 | 7.485 |
| (3) Macrogol 6000 | 1.5 |
| (4) Titanium oxide | 1.0 |
| (5) iron(III) oxide | 0.015 |
| Total | 310.0 |

Formulation Example 6

According to the method described in Formulation Example 4, about 13500 film-coated tablets having the formulation shown below each containing 5 mg of the compound obtained in Example 1 were obtained.

| Composition | Content (mg) |
|---|---|
| Tablet formulation: | |
| (1) Compound of Example 1 | 5.0 |
| (2) Lactose | 230.0 |
| (3) Corn starch | 37.1 |
| (4) Sodium croscarmellose | 15.0 |
| (5) Hydroxypropyl cellulose | 8.4 |
| (6) Magnesium stearate | 4.5 |
| Total (plain tablet) | 300.0 |
| Film-coated formulation: | |
| (1) Plain tablet | 300.0 |

-continued

| Composition | Content (mg) |
|---|---|
| (Film components) | |
| (2) Hydroxypropyl cellulose 2910 | 7.485 |
| (3) Macrogol 6000 | 1.5 |
| (4) Titanium oxide | 1.0 |
| (5) iron(III) oxide | 0.015 |
| Total | 310.0 |

Formulation Example 7

According to the method described in Formulation Example 4, about 13500 film-coated tablets having the formulation shown below each containing 1 mg of the compound obtained in Example 1 were obtained.

| Composition | Content (mg) |
|---|---|
| Tablet formulation: | |
| (1) Compound of Example 1 | 1.0 |
| (2) Lactose | 234.0 |
| (3) Corn starch | 37.1 |
| (4) Sodium croscarmellose | 15.0 |
| (5) Hydroxypropyl cellulose | 8.4 |
| (6) Magnesium stearate | 4.5 |
| Total (plain tablet) | 300.0 |
| Film-coated formulation: | |
| (1) Plain tablet | 300.0 |
| (Film components) | |
| (2) Hydroxypropyl cellulose 2910 | 7.485 |
| (3) Macrogol 6000 | 1.5 |
| (4) Titanium oxide | 1.0 |
| (5) iron(III) oxide | 0.015 |
| Total | 310.0 |

Formulation Example 8

| | |
|---|---|
| White vaseline | 40 g |
| Cetanol | 10 g |
| Bleached beeswax | 5 g |
| Sorbitan sesquioleate | 5 g |
| LauroMOCROGOLD | 0.5 g |
| Methyl p-hydroxybenzoate | 0.1 g |
| Propyl p-hydroxybenzoate | 0.1 g |
| Purified water | Appropriate |

A topical wettable ointment having the composition shown above (100 g) was heated preliminarily at 70° C., and the solution was combined with a solution which was obtained by dissolving 1 g of the compound obtained in Example 1 in 20 mL of methanol with heating. At the same temperature, the mixture was stirred with heating for 10 minutes to remove residual methanol, and then cooled to room temperature to obtain a wettable ointment.

Experiment Example 1 Assay of Phosphodiesterase IV-inhibiting Effect (1) Human Brain-derived Phosphodiesterase 4D3-encoding Gene Cloning From a human brain cDNA library, a gene encoding phosphodiesterase 4D3 was cloned. Using 1 ng of brain QUICK-Clone™ cDNA (Clontech) as a template, each 20 pmol of a primer set: 5'-CCACGATAGCTGCTC-AAACAAGAG-3' (SEQ. ID. No.1) and 5'-ATAGAAACCCCAAGTCCAATAAAC-3' (SEQ. ID. No.2) which was prepared referring to the phosphodiesterase 4D3 gene base sequence reported by Nemoz et al (FEBS Letters 384, 97–102, 1996) was added to effect a PCR by a MiniCycler™ (MJ RESEARCH) using TaKaRa EX Taq (TAKARA) (reaction condition: 30 cycles of 0.5 minutes at 94° C., 0.5 minutes at 55° C. and 4 minutes at 72° C.). The resultant PCR product was subjected to an agarose gel electrophoresis and an about 2.4 kb DNA fragment was recovered. This fragment was made blunt using a Pfu DNA polymerase (STRATAGENE) and then a phosphodiesterase 4D3 gene was cloned using Zero Blunt PCR Cloning Kit (Invitrogen).

(2) Construction of E.coli Expression Vector

The plasmid obtained in Section (1) described above was digested with a restriction enzyme EcoRI (Takara) and subjected to an agarose gel electrophoresis to recover an about 2.4 kb DNA fragment. This DNA fragment was digested with a restriction enzyme EcoRI (Takara) and ligated with a pGEX4T-3 (Pharmacia) which had been treated with BAP (Takara). The resultant cDNA fragment had the base sequence represented by Sequence ID No.3, and the amino acid sequence represented by Sequence ID No.4 was found to be encoded by the 74th to the 2092nd bases of this base sequence. This cDNA fragment was transformed into an E.coli BL21 (FUNAKOSHI) using a ligation solution, whereby obtaining an Escherichia coli BL21/pPDE4D3 capable of expressing the phosphodiesterase 4D3 gene.

(3) Expression of Recombinant Human Brain-derived Phosphodiesterase 4D3 in Escherichia coli and Purification Thereof Using the Escherichia coli BL21/pPDE4D3 obtained in Section (2) described above, a recombinant human brain-derived phosphodiesterase 4D3 was obtained. The expression and purification of E. coli were in accordance with the protocol attached to GST Gene Fusion System (Pharmacia). As a result, 34 mg of an about 76 kDa recombinant human brain-derived phodiesterase 4D3 was obtained as a target substance from 1 L of the E. coli culture medium.

(4) Assay of Phosphodiesterase IV-inhibiting Effect

To a 96-well plate (OPTI plate, Packard), 10 μl of a buffer solution [0.5 M Tris-HCl (pH7.5), 83 mM $MgCl_2$, 17 mM EGTA], 10 μl of the recombinant human brain-derived phosphodiesterase 4D3 (0.0034 mg/mL) obtained in Section (1) described above, 65 μl of Ultrapure water, 5 μl of an inhibitor sample and 10 μl of [$^3$H]cAMP were added and reacted for 30 minutes at 30° C. After completing the reaction, 50 μl of SPA beads solution [18 mg/mL Yttrium silicate beads, 18 mM $ZnSO_4$] was added, allowed to stand at room temperature for about 20 minutes, and the radioactivity was counted using a scintillation counter (Topcount, Packard). The radioactivity observed in the presence of the recombinant human brain-derived phosphodiesterase 4D3 was 28245 cpm, which was in contrast with the control radioactivity (1020 cpm). This reaction underwent the inhibition of the phosphodiesterase activity in the presence of a phosphodiesterase IV inhibitor rolipram (BIOMOL Research Laboratories, Inc), and rolipram inhibited this enzymatic reaction by 50% at about 100 nM. This assay system was employed to determine the recombinant human brain-derived phosphodiesterase-inhibiting effect ($IC_{50}$) of each inventive compound. The results are shown in Table 23.

TABLE 23

| Example No. | PDE IV-inhibiting effect ($IC_{50}$, nM) |
|---|---|
| 39 | 19.4 |
| 45 | 9.36 |
| 149 | 40.1 |
| 157 | 82.0 |
| 179 | 124 |
| 180 | 123 |
| 263 | 13.7 |

Example 2 Inhibiting Effect on Antigen-induced Bronchoconstriction in Guinea Pigs (1) Preparation of Rabbit Anti-ovalbumin (OA) Serum A white rabbit (body weight: about 3 kg; New Zealand white: KITAYAMA LABES) was immunized by an intramuscular administration of 1.0 mL of an emulsion of 0.5 mL of a 10% OA (Grade III, Sigma) solution and 0.5 mL of Freund Complete Adjuvant (WAKO PURE CHEMICAL INDUSTRIES, LTD.). This procedure was conducted once every week repetitively 4 times in total. One week after the final immunization, the whole blood was sampled. The blood sample was allowed to stand at room temperature for 1 hour or longer, and then in a refrigeration room for a day. On the following day, the serum fraction was isolated and centrifuged (3000 rpm, 10 min.), and the supernatant was stored as an antiserum at −20° C.

(2) Antigen-induced Bronchoconstriction

The bronchoconstriction was measured by a modified Konzett-Rossler method. Each male Hartley guinea pig weighing 400 to 500 g (NIPPON SLC, Shizuoka) was anesthetized with ether, treated intravenously with 1.0 mL of a 8- to 16-fold diluted anti-OA serum, and subjected to an experiment after 16 to 24 hours. Under an anesthesia with urethane (1.2 g/kg ip) (Aldrich), a tracheal cannula was inserted, and gallamine triethiodide (1 mg/kg iv) (Sigma) was administered to arrest the spontaneous respiration. The animal was ventilated artificially using an artificial respirator (Harvard model 683) at 70 respirations/minutes, with each ventilation volume of 2 to 3 mL and initial load of 10 $cmH_2O$, and the intratracheal pressure was measured at the side arm of the tracheal cannula using a differential pressure type transducer. Mepyramine maleate (1.0 mg/kg) (Sigma) and propranolol (1.0 mg/kg) (Sigma) were administered intravenously 2 minutes after the administration of gallamine triethiodide, and after further 2 minutes the OA antigen (1.0 mg/kg) was administered intravenously to induce the bronchoconstriction.

A compound of Example was dissolved in 25% dimethylacetamide, 25% polyethylene glycol 400 and 50% physiological saline, and administered intravenously 5 minutes before the antigen challenge at a dose of 1 mg/kg. Percent inhibition was calculated based on the comparison with a control group (intravenous administration of a mixture of 25% dimethylacetamide, 25% polyethylene glycol 400 and 50% physiological saline). The % inhibition by each inventive compound is shown in Table 24.

TABLE 24

| Example No. | % inhibition in bronchoconstriction |
|---|---|
| 39 | 45 |
| 45 | 44 |
| 149 | 58 |
| 157 | 57 |
| 179 | 46 |

TABLE 24-continued

| Example No. | % inhibition in bronchoconstriction |
|---|---|
| 180 | 57 |
| 263 | 59 |

INDUSTRIAL APPLICABILITY

A furoisoquinoline derivative of the invention has an excellent phosphodiesterase (PDE) IV-inhibiting effect, and is useful as a prophylactic or therapeutic agent against an inflammation-induced disease, such as bronchial asthma, chronic obstructive pulmonary disease (COPD), rheumatoid arthritis, autoimmune disease and diabetes, etc.

What is claimed is:

1. A compound of the Formula:

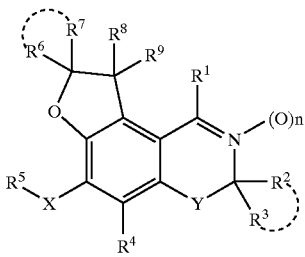

wherein $R^1$ is a hydrogen atom, optionally substituted hydrocarbon group, optionally substituted heterocyclic group or optionally substituted amino group, each of $R^2$ and $R^3$ is a hydrogen atom, optionally substituted hydrocarbon group or acyl group, and $R^2$ and $R^3$ may be taken together with the adjacent carbon atom to form an optionally substituted 3- to 8-membered ring, $R^4$ is a hydrogen atom, cyano group, optionally substituted hydrocarbon group, acyl group or optionally substituted hydroxy group, $R^5$ is (1) a hydrogen atom, (2) an optionally substituted hydrocarbon group, (3) an acyl group, (4) an optionally substituted heterocyclic group or (5) a halogen atom, each of $R^6$ and $R^7$ is a hydrogen atom or optionally substituted hydrocarbon group, and $R^6$ and $R^7$ may be taken together with the adjacent carbon atom to form an optionally substituted 3- to 8-membered ring, each of $R^8$ and $R^9$ is a hydrogen atom or optionally substituted hydrocarbon group, X is a bond, oxygen atom, optionally oxidized sulfur atom or optionally substituted nitrogen atom, Y is an optionally substituted methylene group or carbonyl group, and n is 0 to 1): or a salt or a prodrug thereof.

2. The compound according to claim 1, wherein each of $R^2$ and $R^3$ is a hydrogen atom, optionally substituted hydrocarbon group or acyl group, $R^2$ and $R^3$ may be taken together with the adjacent carbon atom to form an optionally substituted 3- to 8-membered homocyclic or heterocyclic group, $R^4$ is a hydrogen atom or optionally substituted hydrocarbon group, each of $R^6$ and $R^7$ is a hydrogen atom or optionally substituted hydrocarbon group, $R^6$ and $R^7$ may be taken together with the adjacent carbon atom to form an optionally substituted 3- to 8-membered homocyclic group, Y is methylene group which may have a hydroxy group or carbonyl group.

3. The compound according to claim 1 wherein $R^1$ is any of the following (i) to (iii):

(i) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from the group (hereinafter referred to as Substituent Group A) consisting of (1) a halogen atom, (2) a $C_{1-3}$ alkylenedioxy group, (3) a nitro group, (4) a cyano group, (5) an optionally halogenated $C_{1-6}$ alkyl group, (6) an optionally halogenated $C_{2-6}$ alkenyl group, (7) an optionally halogenated $C_{2-6}$ alkynyl group, (8) a $C_{3-6}$ cycloalkyl group, (9) a $C_{6-14}$ aryl group, (10) an optionally halogenated $C_{1-6}$ alkoxy group, (11) an optionally halogenated $C_{1-6}$ alkylthio group, (12) a hydroxy group, (13) an amino group, (14) a mono-$C_{1-6}$ alkylamino group, (15) a mono-$C_{6-14}$ arylamino group, (16) a di-$C_{1-6}$ alkylamino group, (17) a di-$C_{6-14}$ arylamino group, (18) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, (19) an acylamino group selected from formylamino, $C_{1-6}$ alkyl-carboxamido, $C_{6-14}$ aryl-carboxamido, $C_{1-6}$ alkoxy-carboxamido, $C_{1-6}$ alkylsulfonylamino and $C_{6-14}$ arylsulfonylaxnino, (20) an acyloxy group selected from $C_{1-6}$ alkyl-carbonyloxy, $C_{6-14}$ aryl-carbonyloxy, $C_{1-6}$ alkoxy-carbonyloxy, mono-$C_{1-6}$ alkyl-carbamoyloxy, di-$C_{1-6}$ alkyl-carbamoyloxy, $C_{6-14}$ aryl-carbamoyloxy and nicotinoyloxy, (21) a 4- to 14-membered heterocyclic group having, in addition to carbon atoms, 1 to 4 heteroatom(s) selected from nitrogen, sulfur and oxygen atoms, (22) a phosphono group, (23) a $C_{6-14}$ aryloxy group, (24) a di-$C_{1-6}$ alkoxy-phosphoryl group, (25) a $C_{6-14}$ arylthio group, (26) a hydrazino group, (27) an amino group, (28) an oxo group, (29) an ureido group, (30) a $C_{1-6}$ alkyl-ureido group, (31) a di-$C_{1-6}$-alkyl-ureido group, (32) an oxide group and (33) a group formed by binding 2 or 3 groups selected from (1) to (32) listed above, (ii) a 5- to 14-membered heterocyclic group having, in addition to carbon atoms, 1 to 4 heteroatom(s) selected from nitrogen, sulfur and oxygen atoms which may have 1 to 5 substituent(s) selected from Substituent Group A described above, (iii) an amino group which may have 1 or 2 substituent(s) selected from the following (ia) to (iiia):

(ia) a hydrogen atom, (iia) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (iiia) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbamoyl, mono-$C_{1-6}$ alkyl-carbamoyl, di-$C_{1-6}$ alkyl carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbanoyl, (5- or 6-membered heterocycle having, in addition to carbon atoms, 1 to 3 heteroatom(s) selected from nitrogen, sulfur and oxygen atoms)-thiocarbamoyl, mono-C 1-6 alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above;

each of $R^2$ and $R^3$ is any of the following (i) to (iii):

(i) a hydrogen atom, (ii) a $C_{1-6}$ alkyl group, $C_{2-6}$ alkenyl group, $C_{2-6}$ alkynyl group, $C_{34}$ cycloalkyl group, $C_{3-6}$ cycloalkenyl group, $C_{6-14}$ aryl group or $C_{7-16}$ aralkcyl group which may have 1 to 5 substituent(s) selected from Substituent Group A described above, (iii) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-14}$ aralkyl-carbonyl, $C_{6-14}$ aryloxy carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbamoyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{3-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfmo, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above;

$R^2$ and $R^3$ may be taken together with the adjacent carbon atom to form a $C_{3-8}$ cycloalkane or 3- to 8-membered heterocyclic ring which may have 1 to 3 substituent(s) selected from a $C_{1-6}$ alkyl, $C_{6-14}$ aryl, $C_{7-16}$ aralkyl, amino, mono-$C_{1-6}$ alkylamino, mono-$C_{6-14}$ arylamino, di-$C_{1-6}$ alkylamino, di-$C_{6-14}$ arylamino and 4- to 10-membered aromatic heterocyclic group;

$R^4$ is (i) a hydrogen atom, (ii) a cyano group, (iii) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (iv) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above, or, (v) a group represented by Formula: —$OR^4$ ($R^{4'}$ is <1> a hydrogen atom, <2> a $C_{1-6}$ alkyl group, $C_{2-6}$ alkenyl group, $C_2$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, or, <3> an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-14}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above);
$R^5$ is any of the following (i) to (v):
(i) a hydrogen atom,
(ii) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above,
(iii) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above,
(iv) a 5-to 14-membered heterocyclic ring containing 1to 4 heteroatom(s) selected from nitrogen, sulfur and oxygen atoms in addition to carbon atoms which may contain 1 to 5 substituent(s) selected from Substituent Group A described above,
(v) a halogen atom;
each of $R^6$ and $R^7$ is (i) a hydrogen atom, (ii) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above,
$R^6$ and $R^7$ may be taken together with the adjacent carbon atom to form a $C_{3-8}$ cycloalkane or 3- to 8-membered heterocyclic ring which may have 1 to 3 substituent(s) selected from $C_{1-6}$ alkyl, $C_{6-14}$ aryl, $C_{7-16}$ aralkyl, amino, mono-$C_{1-6}$ alkylamino, mono-$C_{6-14}$ arylamino, di-$C_{1-6}$ alkylamino, di-$C_{6-14}$ arylamino and 4- to 10-membered aromatic heterocyclic group;
each of $R^8$ and $R^9$ is (i) a hydrogen atom, (ii) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above;
X is (i) a bond, (ii) an oxygen atom, (iii) an optionally oxidized sulfur atom, (iv) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above,
(v) a nitrogen atom having an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above, or,
(vi) a 5- to 14-membered heterocyclic group containing 1 to 4 heteroatom(s) selected from nitrogen, sulfur and oxygen atoms in addition to carbon atoms which may contain 1 to 5 substituent(s) selected from Substituent Group A described above;
Y is <1> a methylene group which may have substituent(s) selected from Substituent Group A described above or <2> a carbonyl group;
n is 0 or 1.

4. The compound according to claim 1, wherein $R^1$ is (1) an optionally substituted aromatic hydrocarbon group, (2) an optionally substituted heterocyclic group, (3) an optionally substituted alicyclic hydrocarbon group or (4) a group represented by Formula: —L—$R^{1a}$ wherein L is methylene, carbonyl or an optionally substituted nitrogen atom, $R^{1a}$ is a hydrogen atom, optionally substituted aromatic group, optionally substituted hydroxy group or optionally substituted amino group.

5. The compound according to claim 4, wherein $R^1$ is any of the following (i) to (iv):
(i) a $C_{1-6}$ aryl group which may have 1 to 5 substituent(s) selected from Substituent Group A described above,
(ii) a 5- to 14-membered heterocyclic group containing 1 to 4 heteroatom(s) selected from nitrogen, sulfur and oxygen atoms in addition to carbon atoms which may contain 1 to 5 substituent(s) selected from Substituent Group A described above,

441

(iii) a $C_{3-6}$ cycloalkyl group which may have 1 to 5 substituent(s) selected from Substituent Group A described above,
(iv) a group represented by Formula —L—$R^{1a}$ wherein L is (a) a methylene, (b) a carbonyl or (c) a nitrogen atom which may be substituted by the following (ia) to (iiia):
(ia) a hydrogen atom,
(iia) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above,
(iiia) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-C, alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_6$, alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above,
$R^{1a}$ is (i) a hydrogen atom,
(ii) <1> a $C_{6-14}$ aryl group or <2> a 5- to 14-membered aromatic heterocyclic group containing 1 to 4 heteroatom(s) selected from 1 or 2 kind(s) of nitrogen, sulfur and oxygen atoms in addition to carbon atoms, both of which may contain 1 to 5 substituent(s) selected from Substituent Group A described above,
(iii) a hydroxy group which may have $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above,
(iv) an amino group which may be substituted by the following (ia) to (iiia):
(ia) a hydrogen atom, (iia) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above,
(iiia) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle

442 having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyithiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl.

6. The compound according to claim 1 wherein $R^1$ is a group represented by Formula:

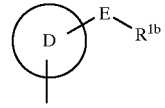

(wherein $R^{1b}$ is a hydrogen atom or an optionally substituted hydrocarbon group or optionally substituted heterocyclic group, Ring D is an optionally substituted aromatic hydrocarbon ring or optionally substituted heterocyclic group, E is a bond, methylene, oxygen atom, optionally oxidized sulfur atom, optionally substituted nitrogen atom or a group represented by Formula: —CS—O—, —CO—O, —S—CO, —(CH$_2$)$_k$—CO—, —NR$^{1C}$—CO—(CH$_2$)$_m$—, —NR$^{1C}$—SO$_2$—(CH$_2$)$_m$—, —SO$_2$—NR$^{1C}$—(CH$_2$)$_m$—, —O—CS—NR$^{1C}$—(CH$_2$)$_m$—, —NR$^{1C}$—CO—NR$^{1C}$—(CH$_2$)$_m$—, —NR$^{1C}$—CO—(CH$_2$)$_m$—NR$^{1C}$— wherein $R^{1C}$ is a hydrogen atom, optionally substituted alkyl group or acyl group, k is 0 or 1, m is an integer of 0 to 3.

7. The compound according to claim 6 wherein $R^{1b}$ is (i) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, or,
(ii) a 5- to 14-membered heterocyclic group containing 1 to 4 heteroatom(s) selected from nitrogen, sulfur and oxygen atoms in addition to carbon atoms which may contain 1 to 5 substituent(s) selected from Substituent Group A described above;
Ring D is (i) a $C_{6-14}$ aryl ring which may have 1 to 5 substituent(s) selected from Substituent Group A described above or (ii) a 5- to 14-membered heterocyclic ring containing 1 to 4 heteroatom(s) selected from nitrogen, sulfur and oxygen atoms in addition to carbon atoms which may contain 1 to 5 substituent(s) selected from Substituent Group A described above;
E is any of the following (i) to (viii):
(i) a bond, (ii) methylene, (iii) an oxygen atom, (iv) an optionally oxidized sulfur atom, (v) a $C_{1-6}$ alkyl group, $C_{2-6}$ alkenyl group, $C_{2-6}$ alkynyl group, $C_{3-6}$ cycloalkyl group, $C_{3-6}$ cycloalkenyl group, $C_{6-14}$ aryl group or $C_{7-16}$ aralkyl group which may have 1 to 5 substituent(s) selected from Substituent Group A described above, (vi) a nitrogen atom having an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbamoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkylthiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbamoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, (vii) a nitrogen atom having a 5- to 14-membered heterocyclic group containing 1 to 4 heteroatom(s) selected from nitrogen, sulfur and oxygen atoms in addition to carbon atoms which may contain 1 to 5 substituent(s) selected from Substituent Group A described above;

(viii) —CS—O, —CO—O—, —S—CO—, —$(CH_2)_k$—CO—, —$NR^{1C}$—CO—$(CH_2)_m$—, —$NR^{1C}$—$SO_2$—$(CH_2)_m$—, —$SO_2$—$NR^{1C}$—$(CH_2)_m$—, —O—CS—$NR^{1C}$—$CH_2)_m$—, —$NR^{1C}$—CO—$NR^{1C}$—$(CH_2)_m$—$NR^{1C}$— or —$NR^{1C}$—CO—$(CH_2)_m$—$NR^{1C}$— wherein $R^{1C}$ is (ia) a hydrogen atom, (iia) a $C_{1-6}$ alkyl group which may have 1 to 5 substituent(s) selected from Substituent Group A described above, or, (iiia) an acyl group selected from formyl, carboxy, carbamoyl, $C_{1-6}$ alkyl-carbonyl, $C_{3-6}$ cycloalkyl-carbonyl, $C_{1-6}$ alkoxy-carbonyl, $C_{6-14}$ aryl-carbonyl, $C_{7-16}$ aralkyl-carbonyl, $C_{6-14}$ aryloxy-carbonyl, $C_{7-16}$ aralkyloxy-carbonyl, (5- or 6-membered heterocycle having, in addition to carbon atoms, 1 to 3 heteroatom(s) selected from nitrogen, sulfur and oxygen atoms)-carbonyl, mono-$C_{1-6}$ alkyl-carbamoyl, di-$C_{1-6}$ alkyl-carbarnoyl, $C_{6-14}$ aryl-carbamoyl, (5- or 6-membered heterocycle having, in addition to carbon atoms, 1 to 3 heteroatom(s) selected from nitrogen, sulfur and oxygen atoms)-carbamoyl, $C_{1-6}$ alkyl-thiocarbonyl, $C_{3-6}$ cycloalkyl-thiocarbonyl, $C_{1-6}$ alkoxy-thiocarbonyl, $C_{6-14}$ aryl-thiocarbonyl, $C_{7-16}$ aralkyl-thiocarbonyl, $C_{6-14}$ aryloxy-thiocarbonyl, $C_{7-16}$ aralkyloxy-thiocarbonyl, (5- or 6-membered heterocycle having, in addition to carbon atoms, 1 to 3 heteroatom(s) selected from nitrogen, sulfur and oxygen atoms)-thiocarbonyl, thiocarbamoyl, mono-$C_{1-6}$ alkyl-thiocarbamoyl, di-$C_{1-6}$ alkyl-thiocarbamoyl, $C_{6-14}$ aryl-thiocarbamoyl, (5- or 6-membered heterocycle having, in addition to carbon atoms, 1 to 3 heteroatom(s) selected from nitrogen, sulfur and oxygen atoms)-thiocarbanoyl, mono-$C_{1-6}$ alkylsulfamoyl, di-$C_{1-6}$ alkylsulfamoyl, $C_{6-14}$ arylsulfamoyl, $C_{1-6}$ alkylsulfonyl, $C_{6-14}$ arylsulfonyl, $C_{1-6}$ alkylsulfinyl, $C_{6-14}$ arylsulfinyl, sulfino, sulfo, $C_{1-6}$ alkoxysulfinyl, $C_{6-14}$ aryloxysulfinyl, $C_{1-6}$ alkoxysulfonyl and $C_{6-14}$ aryloxysulfonyl, which may have 1 to 5 substituent(s) selected from Substituent Group A described above;

k is 0 or 1, m is an integer of 0 to 3).

8. The compound according to claim 6 wherein $R^{1b}$ is;

(1) a $C_{1-6}$ alkyl group [this $C_{1-6}$ alkyl group may have a substituent selected from a halogen atom, cyano, hydroxy, $C_{1-6}$ alkoxy-carbonyl, di-$C_{1-6}$ alkylamino, optionally halogenated $C_{1-6}$ alkyl-carbonyl-amino, carboxy, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, (5- to 6-membered heterocyclic ring containing 1 to 3 heteroatom(s) selected from nitrogen, sulfur and oxygen atoms in addition to carbon atoms)-$C_{1-6}$ alkyl-carbamoyl, $C_{1-6}$ alkylthio, $C_{1-6}$ alkylsulfinyl, $C_{1-6}$ alkylsulfonylamino, (5- to 6-membered heterocyclic ring containing 1 to 3 heteroatom(s) selected from nitrogen, sulfur and oxygen atoms in addition to carbon atoms)-$C_{1-6}$ alkylcarbamoyl, (5- to 6-membered heterocyclic ring containing 1 to 3 heteroatom(s) selected from nitrogen, sulfur and oxygen atoms in addition to carbon atoms)-amino, sulfamoyl-$C_{6-14}$ aryl, carboxy-$C_{6-14}$ aryl, $C_{1-6}$ alkoxy-carbonyl-$C_{6-14}$ aryl, carbamoyl-$C_{6-14}$ aryl, $C_{1-6}$ alkyl-carbamoyl-$C_{6-14}$ aryl which may have a hydroxy and (4- to 10-membered heterocyclic ring containing 1 to 3 heteroatom(s) selected from nitrogen, sulfur and oxygen atoms in addition to carbon atoms)-carbamoyl-$C_{6-14}$ aryl], (2) a $C_{3-6}$ cycloalkyl group, (3) a $C_{6-14}$ aryl group [this $C_{6-14}$ aryl group may have a substituent selected from $C_{1-6}$ alkoxy, amino, carboxy, optionally halogenated $C_{1-6}$ alkyl-carbonylamino, $C_{1-6}$ alkoxy-carbonylamino, formylamino, ureido, $C_{1-6}$ alkylsulfonylamino, ($C_{1-6}$ alkyl)($C_{1-6}$ alkylsulfonyl) amino, $C_{1-6}$ alkoxy-carbonyl-$C_{1-6}$ alkylamino, optionally $C_{1-6}$ alkyl-esterified phosphono-$C_{1-6}$ alkylamino, mono- or di-$C_{1-6}$ alkyl-carbamoyl and $C_{7-16}$ aralkyloxy-carbonylamino]or, (4) a 5- to 14-membered heterocyclic group containing 1 to 4 heteroatom(s) selected from nitrogen, sulfur and oxygen atoms in addition to carbon atoms [this heterocyclic group may be substituted by 1 or 2 substituent(s) selected from a halogen atom, $C_{1-6}$ alkyl, carboxy-$C_{1-6}$ alkyl, $C_{1-6}$ alkyl-carbonyloxy-$C_{1-6}$ alkyl, $C_{1-6}$ alkoxy-carbonyl, $C_{1-6}$ alkoxy-carbonyl-$C_{1-6}$ alkyl, $C_{1-6}$ alkyl-carbamoyl-$C_{1-6}$ alkyl, carbamoyl, oxo and 4- to 10-membered heterocyclic group containing 1 to 3 heteroatom(s) selected from nitrogen, sulfur and oxygen atoms in addition to carbon atoms];

Ring D is (i) a $C_{6-14}$ aryl ring or (ii) a 5- to 14-membered heterocyclic ring containing 1 to 4 heteroatom(s) selected from nitrogen, sulfur and oxygen atoms in addition to carbon atoms;

E is (I) a bond, (ii) methylene, (iii) O, (iv) S, (v) SO, (vi) $SO_2$, (vii) —NH—, (viii) —N($C_{1-6}$ alkyl)-, (ix) —N($C_{1-6}$ alkyl-carbonyl)-, (x) —N($C_{1-6}$ alkoxy-carbonyl)-, (xi) —N($C_{1-6}$ alkyl-sulfonyl)-, (xii) —CO—O—, (xiii) —S—CO—, (xiv) a group represented by Formula: —$(CH_2)_k$—CO wherein k is 0 or 1, (xv) —$NR^f$—CO—$(CH_2)_{m1}$— wherein $R^f$ is a hydrogen atom or $C_{1-6}$ alkoxy-carbonyl or $C_{1-6}$ alkyl group which may be substituted by a heterocyclic group containing 1 to 3 heteroatom(s) selected from nitrogen, oxygen, sulfur atoms and the like in addition to carbon atoms, and ml is an integer of 0 to 3, (xvi) a group represented by Formula —NR$^g$—SO$_2$—(CH$_2$)$_{m2}$— wherein R$^g$ is a hydrogen atom or $C_{1-6}$ alkyl-sulfonyl group and m2 is 0, (xvii) a group represented by Formula —SO$_2$—NR$^h$—(CH$_2$)$_{m3}$— wherein R$^h$ is a hydrogen atom or $C_{1-6}$ alkyl group and m3 is 0 or 1, (xviii) a group represented by Formula —O—CS—NR$^i$—(CH$_2$)$_{m4}$— wherein R$^i$ is a hydrogen atom or $C_{1-6}$ alkyl group and m4 is 0 or 1, (xix) a group represented by Formula —NR$^j$—CO—NR$^k$—(CH$_2$)$_{m5}$— wherein R$^j$ is a hydrogen atom or $C_{1-6}$ alkyl group, R$^k$ is a hydrogen atom or $C_{1-6}$ alkyl group and m5 is 0 or 1, (xx) a group represented by Formula —NR$^L$—CO—CH$_2$—(CH$_2$)$_{m6}$——NR$^m$— wherein R$^L$ is a hydrogen atom or $C_{1-6}$ alkyl group, R$^m$ is a hydrogen atom or $C_{1-6}$ alkyl group and m6 is 0 or 1.

9. The compound according to claim 1 wherein R$^1$ is a group represented by Formula

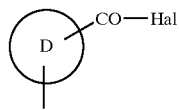

wherein Hal is a halogen atom and Ring D is an optionally substituted aromatic hydrocarbon ring or optionally substituted heterocyclic group.

10. The compound according to claim 1, wherein R$^1$ is a group represented by Formula:

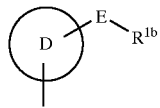

wherein R$^{1b}$ is a hydrogen atom or an optionally substituted hydrocarbon group or optionally substituted heterocyclic group, Ring D is an optionally substituted aromatic hydrocarbon ring or optionally substituted heterocyclic group, E is a bond, methylene, oxygen atom, optionally oxidized sulfur atom, optionally substituted nitrogen atom or a group represented by Formula: —CS—O—, —CO—O—, —S—CO—, —(CH$_2$)$_k$—CO—, —NR$^{1C}$—CO—(CH$_2$)$_m$—, —NR$^{1C}$—SO$_2$—(CH$_2$)$_m$—, —SO$_2$—NR$^{1C}$—(CH$_2$)$_m$—, —O—CS—NR$^{1C}$—(CH$_2$)$_m$—, —NR$^{1C}$—CO—NR$^{1C}$—(CH$_2$)$_m$—, —NR$^{1C}$—CO—(CH$_2$)$_m$—NR$^{1C}$— wherein R$^{1C}$ is a hydrogen atom, optionally substituted alkyl group or acyl group, k is 0 or 1, m is an integer of 0 to 3 or a group represented by Formula:

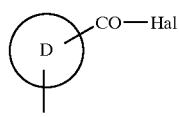

wherein Hal is a halogen atom each of R$^2$ and R$^3$ is a hydrogen atom or optionally substituted hydrocarbon group, and R$^2$ and R$^3$ may be taken together with the adjacent carbon atom to form an optionally substituted 3- to 8-membered ring, R$^4$ is a hydrogen atom, cyano group, optionally substituted hydrocarbon group, acyl group or a group represented by Formula: —OR$^{4'}$ wherein R$^{4'}$ a hydrogen atom, optionally substituted hydrocarbon group or acyl group, R$^5$ is an optionally substituted hydrocarbon group, each of R$^6$ and R$^7$ is an optionally substituted hydrocarbon group, R$^6$ and R$^7$ may be taken together with the adjacent carbon atom to form an optionally substituted 3- to 8-membered ring, each of R$^8$ and R$^9$ is a hydrogen atom, X is an oxygen atom or an optionally oxidized sulfur atom, Y is methylene which may have 1 or 2 $C_{1-6}$ alkyl group(s) and n is 0 or 1.

11. The compound according to claim 1 wherein R$^1$ is, (i) a $C_{6-14}$ aryl group which may have 1 to 3 substituent(s) selected from the following (1) to (23):

(1) a halogen atom, (2) a nitro group, (3) a $C_{1-6}$alkyl group [this $C_{1-6}$ alkyl group may have a substituent selected from a halogen atom, cyano, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, (5- or 6-membered heterocyclic ring containing 1 to 3 heteroatom(s) selected from nitrogen, sulfur and oxygen atoms in addition to carbon atoms)-$C_{1-6}$ alkyl-carbamoyl, $C_{1-6}$ alkylsulfonylamino, $C_{1-6}$ alkoxy-carbonyl and carboxy], (4) a $C_{3-6}$ cycloalkyl group, (5) a $C_{6-14}$ aryl group [this $C_{6-14}$ aryl group may have a substituent selected from amino, carboxy, $C_{1-6}$ alkoxy-carbonyl, carbamoyl, mono- or di-$C_{1-6}$ alkylcarbamoyl, formylamino, $C_{1-6}$ alkyl-carbonylamino which may have a halogen atom or carboxy, $C_{6-14}$ aryl-carbonylamino, $C_{1-6}$ alkoxy-carbonylammo, ureido, mono- or di-$C_{1-6}$ alkylureido, $C_{1-6}$ alkylsulfonylamino, ($C_{1-6}$ allcyl)($C_{1-6}$ alkylsulfonyl) amino, ($C_{1-6}$alkyl)($C_{1-6}$ alkyl-carbonyl) amino, $C_{1-6}$ alkoxy-carbonyl-$C_{1-6}$ alkylamino, $C_{6-14}$ aralkyloxy-carbonylamino, $C_{1-6}$ alkyl-carbonylamino-$C_{1-6}$ alkyl-carbonylamino, $C_{1-6}$ allcylthio-$C_{1-6}$ alkyl-carbonylamino, $C_{1-6}$ alkyl-sulfinyl-$C_{1-6}$ alkyl-carbonylamino, $C_{1-6}$ alkyl-sulfonyl-$C_{1-6}$ alkyl-carbonylamino, $C_{6-14}$ aryloxy-carbonylamino and hydroxy-$C_{1-6}$ alkyl-carbamoyl], (6) a $C_{1-6}$ alkoxy group which may have a halogen atom or $C_{1-6}$ alkoxy-$C_{6-14}$ aryl, (7) a $C_{6-14}$ aryloxy group, (8) a $C_{1-6}$ alkylthio group which may have a carbamoyl, (9) a $C_{1-6}$ alkylsulfinyl group which may have a carbamoyl,

(10) a $C_{6-14}$ arylthio group,

(11) a hydroxy group,

(12) a 5- to 14-membered heterocyclic group containing 1 to 4 heteroatom(s) selected from nitrogen, sulfur and oxygen atoms [this heterocyclic group may have a substituent selected from oxo, carboxy-$C_{1-6}$ alkyl, $C_{1-6}$ alkyl-carbonyloxy-$C_{1-6}$ alkyl, $C_{1-6}$ alkyl, $C_{1-6}$ alkoxy-carbonyl-$C_{1-6}$ alkyl, C,6 alkoxy-carbonyl, carbamoyl-$C_{1-6}$ alkyl and $C_{1-6}$ allcyl-carbamoyl-$C_{1-6}$ alkyl],

(13) a carboxy group,

(14) a group represented by Formula: —CO—Hal (wherein Hal is a halogen atom),

(15) a $C_{1-6}$ alkyl-carbonyl group,

(16) a $C_{1-6}$ alkyl-sulfonyl group,

(17) a $C_{1-6}$ alkoxy-carbonyl group,

(18) a sulfamoyl group [this sulfamoyl group may have 1 or 2 substituent(s) selected from $C_{1-6}$ alkyl, carbamoyl- $C_{1-6}$ alkyl, $C_{1-6}$ alkoxy-carbonyl-$C_{1-6}$ alkyl, (5- to 8-membered heterocyclic ring which may have an oxo group)-$C_{1-6}$ alkyl and $C_{1-6}$ alkyl-carbonylamino-$C_{6-14}$ aryl],

(19) a group represented by Formula: —NR$^a$R$^b$ [each of R$^a$ and R$^b$ is (i) a hydrogen atom, (ii) a $C_{1-6}$ alkyl, (iii) (5- or 6-membered heterocyclic ring containing 1 to 3 heteroatom(s) selected from nitrogen, sulfur and oxygen atoms in addition to carbon atoms)-$C_{1-6}$ alkyl, (iv) a $C_{1-6}$ alkoxy-carbonyl-$C_{1-6}$ alkyl, (v) a di-$C_{1-6}$ alkylamino-methylene-sulfamoyl-$C_{1-6}$ alkyl, (vi) a carbamoyl-$C_{1-6}$ alkyl, (vii) a sulfamoyl-$C_{1-6}$ alkyl, (viii) a $C_{1-6}$ alkyl-sulfonyl, (ix) a $C_{1-6}$ alkoxy-carbonyl, (x) a di-$C_{1-6}$ alkoxy-carbonyl-$C_{2-6}$ alkenyl, (xi) a $C_{6-14}$ aryl, (xii) a 5- or 6-membered heterocyclic group containing 1 to 3 heteroatom(s) selected from nitrogen, sulfur and oxygen atoms in addition to carbon atoms [this 5- or 6-membered heterocyclic group may have a substituent selected from amino, $C_{1-6}$ alkyl-carboxamido and $C_{1-6}$ alkyl-sulfonylamino], (xiii) an optionally halogenated-$C_{1-6}$ alkyl-carbonyl, (xiv) a $C_{1-6}$ alkylthio-$C_{1-6}$ alkyl-carbonyl, (xv) a $C_{1-6}$ alkylsulfinyl-$C_{1-6}$ alkyl-carbonyl, (xvi) a $C_{1-6}$ alkylsulfonyl-$C_{1-6}$ alkyl-carbonyl, (xvii) an amino-$C_{1-6}$ alkyl-carbonyl, (xviii) an optionally halogenated $C_{1-6}$ alkyl-carbonyl-amino-$C_{1-6}$ alkyl-carbonyl, (xix) a $C_{1-6}$ aryl-carbonyl, (xx) a carboxy-$C_{6-14}$ aryl-carbonyl, (xxi) an optionally $C_{1-6}$ alkyl-esterified phosphono-$C_{1-6}$ alkyl-$C_{1-6\ 14}$ aryl-carbonyl, (xxii) (5- or 6-membered heterocyclic ring containing 1 to 3 heteroatom(s) selected from nitrogen, sulfur and oxygen atoms in addition to carbon atoms which may have a halogen atom, oxy or a $C_{1-6}$ alkoxy-carbonyl)-carbonyl, (xxiii) (5- or 6-membered heterocyclic ring containing 1 to 3 heteroatom(s) selected from nitrogen, sulfur and oxygen atoms in addition to carbon atoms)-$C_{1-6}$ alkyl-carbonyl, (xxiv) a $C_{6-14}$ aryl-oxy-carbonyl, (xxv) a carboxy-$C_{1-6}$ alkyl, (xxvi) a carbamoyl, (xxvii) an optionally halogenated $C_{1-6}$ alkylcarbamoyl, (xxviii) a $C_{6-14}$ arylcarbamoyl which may have a $C_{1-6}$ alkyl-carbonylamino, (xxix) (5- or 6-membered heterocyclic ring containing 1 to 3 heteroatom(s) selected from nitrogen, sulfur and oxygen atoms in addition to carbon atoms)-carbamoyl, (xxx) a $C_{2-6}$ alkenyl-carbonyl, (xxxi) a (5- or 6-membered heterocyclic ring containing 1 to 3 heteroatom(s) selected from nitrogen, sulfur and oxygen atoms in addition to carbon atoms which may have an oxo group)-amino-$C_{1-6}$ alkyl-carbonyl, (xxxii) a (5- or 6-membered heterocyclic ring containing 1 to 3 heteroatom(s) selected from nitrogen, sulfur and oxygen atoms in addition to carbon atoms which may have an oxo group)($C_{1-6}$ alkyl) amino-$C_{1-6}$ alkyl-carbonyl, (xxxiii) a (5- or 6-membered heterocyclic ring containing 1 to 3 heteroatom(s) selected from nitrogen, sulfur and oxygen atoms in addition to carbon atoms which may have an oxo group)($C_{1-6}$ alkylcarbonyl) amino-$C_{1-6}$ alkyl-carbonyl, (xxxiv) a $C_{1-6}$ alkylthio-$C_{1-6}$ alkylcarbonyl (sulfur atom may be oxidized), (xxxv) an optionally halogenated $C_{1-6}$ alkylsulfonyl, (xxxvi) a sulfamoyl or (xxxvii) a $C_{1-6}$ alkylsulfamoyl],

(20) a group represented by Formula: —C(=O)NR$^c$R$^d$ [each of R$^c$ and R$^d$ is (i) a hydrogen atom, (ii) a $C_{1-6}$ alkyl, (iii) a (5- or 6-membered heterocyclic ring containing 1 to 3 heteroatom(s) selected from nitrogen, sulfur and oxygen atoms in addition to carbon atoms)-$C_{1-6}$ alkyl, (iv) a carboxy-$C_{145}$alkyl, (v) a $C_{1-6}$ alkoxy-carbonyl-$C_{1-6}$ alkyl, (vi) a di-$C_{1-6}$ alkylamino-$C_{1-6}$ alkyl, (vii) a carbamoyl-$C_{1-6}$ alkyl, (viii) a $C_{1-6}$ alkylcaxbamoyl-$C_{1-6}$ alkyl, (ix) (5- or 6-membered heterocyclic group containing 1 to 3 heteroatom(s) selected from nitrogen, sulfur and oxygen atoms in addition to carbon atoms)-$C_{1-6}$ alkylcarbamoyl-$C_{1-6}$ alkyl, (x) (5- or 6-membered heterocyclic group containing 1 to 3 heteroatom(s) selected from nitrogen, sulfur and oxygen atoms in addition to carbon atoms)-amino-$C_{1-6}$ alkyl, (xi) a sulfamoyl-$C_{6-14}$ aryl-$C_{1-6}$ alkyl, (xii) a $C_{6-14}$ aryl which may have a $C_{1-6}$ alkoxy, (xiii) an optionally $C_{1-6}$ alkyl-esterified phosphono-$C_{1-6}$ alkyl-$C_{6-14}$ aryl, (xiv) a 4- to 10-membered heterocyclic ring containing 1 to 3 heteroatom(s) selected from nitrogen, sulfur and oxygen atoms in addition to carbon atoms [this 4- to 10-membered heterocyclic group may have 1 to 2 substituent(s) selected from a halogen atom, $C_{1-6}$ alkyl and oxo], (xv) a $C_{6-14}$ aryl-carbamoyl-$C_{1-6}$ alkyl, (xvi) a hydroxy-$C_{1-6}$ alkyl or (xvii) a (5- or 6-membered heterocyclic ring containing 1 to 3 heteroatom(s) selected from nitrogen, sulfur and oxygen atoms in addition to carbon atoms which may have a oxo group)-carbamoyl-$C_{1-6}$ alkyl],

(21) a cyano group,

(22) a mono- or di-$C_{1-6}$ alkylcarbamoylthio group,

(23) a mono- or di-$C_{1-6}$ alkyithiocarbamoyloxy group;

(ii) a 5- to 14-membered heterocyclic group containing 1 to 4 heteroatom(s) selected from nitrogen, sulfur and oxygen atoms in addition to carbon atoms which may contain 1 to 3 substituent(s) selected from the following (1) to (8):

(1) a halogen atom, (2) a $C_{1-6}$ alkyl group [this alkyl may have a substituent selected from carboxy, $C_{1-6}$ alkoxy, $C_{1-6}$ alkoxy-carbonyl, mono-$C_{1-6}$ alkyl-amino, di-$C_{1-6}$ alkyl-amino, carbamoyl, $C_{1-6}$ alkyl-carbamoyl which may have a hydroxy, 4- to 10-membered heterocyclic group containing 1 to 3 heteroatom(s) selected from nitrogen, sulfur and oxygen atoms in addition to carbon atoms which may have oxo, (4- to 10-membered heterocyclic ring containing 1 to 3 heteroatom(s) selected from nitrogen, sulfur and oxygen atoms in addition to carbon atoms)-carbamoyl, carbamoyl-$C_{1-6}$ alkyl-carbamoyl], (3) a $C_{1-6}$ alkoxy group, (4) a $C_{6-14}$ aryl group, (5) a $C_{7-16}$ aralkyl group [this $C_{7-16}$ aralkyl group may have a substituent selected from carboxy, $C_{1-6}$ alkoxy-carbonyl, carbamoyl, $C_{1-6}$ alkyl-carbamoyl which may have a hydroxy, (4- to 10-membered heterocyclic ring containing 1 to 3 heteroatom(s) selected from nitrogen, sulfur and oxygen atoms in addition to carbon atoms)-carbamoyl], (6) a 4- to 10-membered heterocyclic group containing 1 to 3 heteroatom(s) selected from nitrogen, sulfur and oxygen atoms in addition to carbon atoms [this 4- to 10-membered heterocyclic group may have a substituent selected from a $C_{1-6}$ alkyl, $C_{1-6}$ alkoxy-carbonyl, carbamoyl, oxo, 4- to 10-membered heterocyclic group containing 1 to 3 heteroatom(s) selected from nitrogen, sulfur and oxygen atoms in addition to carbon atoms], (7) an oxo group, (8) an oxide group;

(iii) a $C_{3-6}$ cycloalkyl group; or, (iv) a group represented by Formula: —L'—R$^{1a}$ (L' is methylene, carbonyl or an optionally substituted nitrogen atom, $R^{1a'}$ is (1) a hydrogen atom, (2) a $C_{6-14}$ aryl group which may have 1 to 5 substituent(s) selected from a $C_{1-6}$ alkyl and $C_{1-6}$ alkoxy, (3) a hydroxy group which may be substituted by a $C_{1-6}$ alkyl group, (4) a $C_{1-6}$ alkyl-amino group which may be substituted by a 4- to 10-membered heterocyclic ring containing 1 to 3 heteroatom(s) selected from nitrogen, oxygen and sulfur atoms in addition to carbon atoms, (6) a $C_{6-14}$ aryl-amino group or (7) a (4- to 10-membered heterocyclic ring containing 1 to 3 heteroatom(s) selected from nitrogen, oxygen and sulfur atoms in addition to carbon atoms)-amino group), each of $R^2$ and $R^3$ is (1) a hydrogen atom, (2) a $C_{1-6}$ alkyl group which may be substituted by <1> a halogen atom, <2> a hydroxy group which may be substituted by a substituent selected from a $C_{1-6}$ alkyl, $C_{1-6}$ alkyl-carbonyl, $C_{1-6}$ alkylsulfonyl and $C_{7-16}$ aralkyl, <3> an amino group which may be substituted by 1 or 2 $C_{1-6}$ alkyl, $C_{3-6}$ alkyl-carbonyl and $C_{6-14}$ aryl-carbonyl, <4> a 4- to 10-membered heterocyclic group containing 1 to 3 heteroatom(s) selected from nitrogen, oxygen and sulfur atoms in addition to carbon atoms, <5> a thio group which may be substituted by $C_{1-6}$ alkyl, <6> a $C_{1-6}$ alkyl-sulfinyl group or <7> a $C_{1-6}$ alkyl-sulfonyl group, or (3) a $C_{1-6}$ alkoxy-carbonyl group, $R^2$ and $R^3$ may be taken together with the adjacent carbon atom to form a $C_{3-8}$ cycloalkane, $R^4$ is (i) a hydrogen atom, (ii) a cyano group, (iii) a $C_{1-6}$ alkyl group [this $C_{1-6}$ alkyl group may have a substituent selected from (1) a halogen atom, (2) a cyano group, (3) a $C_{1-6}$ alkoxy group, (4) a hydroxy group, (5) an amino group, (6) a mono-$C_{1-6}$ alkylamino group, (7) a di-$C_{1-6}$ alkylamino group, (8) a tri-$C_{1-6}$ alkylammonium group, (8) a 4- to 10-membered heterocyclic group containing 1 to 3 heteroatom(s) selected from nitrogen, sulfur and oxygen atoms in addition to carbon atoms which may have an oxo, (9) a $C_{6-14}$ arylthio, (10) an ureido, (11) a carboxy, (12) a carbamoyl, (13) a $C_{1-6}$ alkoxy-carbonyl, (14) a mono-$C_{1-6}$ alkyl-carbamoyl, (15) a formylamino and (16) a $C_{1-6}$ alkyl-carboxamide], (iv) a $C_{2-6}$ alkenyl group or (v) a formyl group;

X is a bond, oxygen atom, optionally oxidized sulfur atom, —NH— or —N(methyl)-, $R^5$ is, when X is a bond, then (i) a hydrogen atom, (ii) a $C_{1-6}$ alkyl group or (iii) a halogen atom, when X is an oxygen atom, then (i) a hydrogen atom, (ii) a $C_{1-6}$ alkyl group [this $C_{1-6}$ alkyl group may have a substituent selected from (1) a halogen atom, (2) a hydroxy group, (3) an amino group, (4) a carboxy, (5) a carbamoyl, (6) a $C_{1-6}$ alkoxy-carbonyl, (7) a mono-$C_{1-6}$ alkyl-carbamoyl, (8) a di-$C_{1-6}$ alkyl-carbamoyl, (9) a 4- to 10-membered heterocydic group containing 1 to 3 heteroatom(s) selected from nitrogen, sulfur and oxygen atoms in addition to carbon atoms], (iii) a $C_{2-6}$ alkenyl group [this $C_{2-6}$ alkenyl group may have a $C_{1-6}$ aryl], (iv) a $C_{2-6}$ alkynyl group, (v) a $C_{3-6}$ cycloalkyl group, (vi) a $C_{7-16}$ aralkyl group, (vii) a $C_{1-6}$ alkyl-carbonyl group, (viii) a $C_{6-14}$ aryl-carbonyl group, (ix) a $C_{1-6}$ alkoxy-carbonyl group, (x) a mono- or di-$C_{1-6}$ alkyl-thiocarbamoyl group, (xi) an optionally halogenated $C_{1-6}$ alkyl-sulfonyl group or (xii) a 4- to 10-membered heterocyclic group containing 1 to 4 heteroatom(s) selected from nitrogen, sulfur and oxygen atoms in addition to carbon atoms [this beterocyclic group may have a $C_{6-14}$ aryl], when X is an optionally oxidized sulfur, then (i) a $C_{1-6}$ alkyl group or (ii) a mono- or di-$C_{1-6}$ alkyl-carbamoyl group, when X is —NH— or —N(methyl)-, then (i) a hydrogen atom, (ii) a $C_{1-6}$ alkyl group [this $C_{1-6}$ alkyl group may have a $C_{1-6}$ alkoxy-carbonyl], (iii) formyl, (iv) a $C_{1-6}$ alkyl-carbonyl group, (v) a $C_{1-6}$ alkoxy-carbonyl group, (vi) a carbamoyl group, (vii) a mono- or di-$C_{1-6}$ alkyl-carbamoyl group or (viii) a $C_{1-6}$ alkyl-sulfonyl group, each of $R^6$ and $R^7$ is a hydrogen atom or $C_{1-6}$ alkyl group, $R^6$ and $R^7$ may be taken together with the adjacent carbon atom to form a $C_{3-8}$ cycloalkane, Each of $R^8$ and $R^9$ is a hydrogen atom or a $C_{1-6}$ alkyl group, Y is <1> a methylene group which may have 1 or 2 $C_{1-6}$ alkyl or hydroxy group or <2> a carbonyl group, n is 0 or 1.

12. The compound according to claim 2, wherein $R^1$ is, (i) a $C_{6-14}$ aryl group which may have 1 to 3 substituent(s) selected from the following (1) to (20):

(1) a halogen atom, (2) a nitro group, (3) a $C_{1-6}$ alkyl group [this $C_{1-6}$ alkyl group may have a substituent selected from a halogen atom, cyano, carbamoyl, $C_{1-6}$ alkyl-carbamoyl, $C_{1-6}$ alkyl-carbonyloxy, $C_{1-6}$ alkoxy-carbonyl-$C_{1-6}$ alkyl-carbamoyl, (5- or 6-membered heterocyclic ring containing 1 to 3 heteroatom(s) selected from nitrogen, sulfur and oxygen atoms in addition to carbon atoms)-$C_{1-6}$ alkyl-carbamoyl, $C_{1-6}$ alkylsulfonylamino, $C_{1-6}$ alkoxy-carbonyl and carboxy], (4) a $C_{3-6}$ cycloalkyl group, (5) a $C_{6-14}$ aryl group [this 06–14 aryl group may have a substituent selected from amino, optionally halogenated $C_{1-6}$ alkyl-carbonylamino, ureido, $C_{1-6}$ alkylsulfonylamino, ($C_{1-6}$ alkyl)($C_{1-6}$ alkylsulfonyl)amino, $C_{1-6}$ alkoxy-carbonyl-$C_{1-6}$ alkylamino], (6) a $C_{1-6}$ alkoxy group which may have a halogen atom or $C_{1-6}$ alkoxy-$C_{6-14}$ aryl, (7) a $C_{6-14}$ aryloxy group, (8) a $C_{1-6}$ alkylthio group, (9) a $C_{1-6}$ alkylsulfinyl group,

(10) a $C_{6-14}$ arylthio group,

(11) a hydroxy group,

(12) a 5- to 14-membered heterocyclic group containing 1 to 4 heteroatom(s) selected from nitrogen, sulfur and oxygen atoms [this heterocyclic group may have a substituent selected from oxo, carboxy-$C_{1-6}$ alkyl, $C_{1-6}$ alkyl-carbonyloxy-$C_{1-6}$ alkyl, $C_{1-6}$ alkoxy-carbonyl-$C_{1-6}$ alkyl, $C_{1-6}$ alkyl-carbamoyl-$C_{1-6}$ alkyl],

(13) a carboxy group,

(14) a group represented by Formula: —CO—Hal (Hal is a halogen atom),

(15) a $C_{1-6}$ alkyl-carbonyl group,

(16) a $C_{1-6}$ alkyl-sulfonyl group,

(17) a $C_{1-6}$ alkoxy-carbonyl group,

(18) a sulfamoyl group [this sulfamoyl group may have a substituent selected from $C_{1-6}$ alkyl, carbamoyl-$C_{1-6}$ alkyl, (5- or 6-membered heterocyclic ring containing 1 to 3 heteroatom(s) selected from nitrogen, sulfur and oxygen atoms in addition to carbon atoms)-$C_{1-6}$ alkyl],

(19) a group represented by Formula: —NR$^a$R$^b$ [each of R$^a$ and R$^b$ is (i) a hydrogen atom, (ii) a C$_{1-6}$ alkyl, (iii) a (5- or 6-membered heterocyclic ring containing 1 to 3 heteroatom(s) selected from nitrogen, sulfur and oxygen atoms in addition to carbon atoms)-C$_{1-6}$ alkyl, (iv) a C$_{1-6}$ alkoxy-carbonyl-C$_{1-6}$ alkyl, (v) a di-C$_{1-6}$ alkylamino-methylene-sulfamoyl-C$_{2-6}$ alkyl, (vi) a carbamoyl-C$_{1-6}$ alkyl, (vii) a sulfamoyl-C$_{1-6}$ alkyl, (viii) a C$_{1-6}$ alkyl-sulfonyl, (ix) a C$_{1-6}$ alkoxy-carbonyl, (x) a di-C$_{1-6}$ alkoxy-carbonyl-C$_{1-6}$ alkenyl, (xi) a C$_{6-14}$ aryl, (xii) a 5- or 6-membered heterocyclic group containing 1 to 3 heteroatom(s) selected from nitrogen, sulfur and oxygen atoms in addition to carbon atoms [this 5- or 6-membered heterocyclic group may have a substituent selected from amino, C$_{1-6}$ alkyl-carboxamido and C$_{1-6}$ alkyl-sulfonylamino], (xiii) an optionally halogenated C$_{1-6}$ alkyl-carbonyl, (xiv) a C$_{1-6}$ alkylthio-C$_{1-6}$ alkyl-carbonyl, (xv) a C$_{1-6}$ alkylsulfinyl-C$_{1-6}$ alkyl-carbonyl, (xvi) a C$_{1-6}$ alkylsulfonyl-C$_{1-6}$ alkyl-carbonyl, (xvii) an amino-C$_{1-6}$ alkyl-carbonyl, (xviii) an optionally halogenated C$_{1-6}$ alkyl-carbonyl-amino-C$_{1-6}$ alkyl-carbonyl, (xix) a C$_{6-14}$ aryl-carbonyl, (xx) a carboxy-C$_{6-14}$ aryl-carbonyl, (xxi) an optionally C$_{1-6}$ alkyl-esterified phosphono-C$_{1-6}$ alkyl-C$_{6-14}$ aryl-carbonyl, (xxii) a (5- or 6-membered heterocyclic ring containing 1 to 3 heteroatom(s) selected from nitrogen, sulfur and oxygen atoms in addition to carbon atoms)-carbonyl, (xxiii) a (5- or 6-membered heterocyclic ring containing 1 to 3 heteroatom(s) selected from nitrogen, sulfur and oxygen atoms in addition to carbon atoms which may have a C$_{1-6}$ alkoxy-carbonyl)-C$_{1-6}$ alkyl-carbonyl, (xxiv) a C$_{6-14}$ aryl-oxy-carbonyl, (xxv) a carboxy-C$_{1-6}$ alkyl or (xxvi) a carbamoyl],

(20) a group represented by Formula: —C(=O)NR$^c$R$^d$ [each of R$^c$ and R$^d$ is (i) a hydrogen atom, (ii) a C$_{1-6}$ alkyl, (iii) a (5- or 6-membered heterocyclic ring containing 1 to 3 heteroatom(s) selected from nitrogen, sulfur and oxygen atoms in addition to carbon atoms)-C$_{1-6}$ alkyl, (iv) a carboxy-C$_{1-6}$ alkyl, (v) a C$_{1-6}$ alkoxy-carbonyl-C$_{1-6}$ alkyl, (vi) a di-C$_{1-6}$ alkylamino-C$_{1-6}$ alkyl, (vii) a carbamoyl-C$_{1-6}$ alkyl, (viii) a C$_{1-6}$ alkylcarbamoyl-C$_{1-6}$ alkyl, (ix) a (5- or 6-membered heterocyclic group containing 1 to 3 heteroatom(s) selected from nitrogen, sulfur and oxygen atoms)-C$_{1-6}$ alkyl carbamoyl-C$_{1-6}$ alkyl, (x) a (5- or 6-membered heterocyclic group containing 1 to 3 heteroatom(s) selected from nitrogen, sulfur and oxygen atoms in addition to carbon atoms)-amino-C$_{1-6}$ alkyl, (xi) a sulfamoyl-C$_{6-14}$ aryl-C$_{1-6}$ alkyl, (xii) a C$_{6-14}$ aryl which may have a C$_{1-6}$ alkoxy, (xiii) a C$_{1-6}$ alkyl-C$_{1-14}$ aryl which have an optionally C$_{1-6}$ alkyl-esterified phosphono group, (xiv) a 4- to 10-membered heterocyclic ring containing to 3 heteroatom(s) selected from nitrogen, sulfur and oxygen atoms in addition to carbon atoms [this heterocyclic group may have 1 or 2 substituent(s) selected from a halogen atom, C$_{1-6}$ alkyl and oxo] or (xv) a C$_{6-14}$ aryl-carbamoyl-C$_{1-6}$ alkyl;

(ii) a 5- to 14-membered heterocyclic group containing 1 to 4 heteroatom(s) selected from nitrogen, sulfur and oxygen atoms in addition to carbon atoms which may contain 1 to 3 substituent(s) selected from the following (1) to (8):

(1) a halogen atom, (2) a C$_{1-6}$ alkyl group [this alkyl may have a substituent selected from carboxy, C$_{1-6}$ alkoxy, C$_{1-6}$ alkoxy-carbonyl, mono-C$_{1-6}$ alkyl-amino, di-C$_{1-6}$ alkyl-amino, carbamoyl, C$_{1-6}$ alkyl-carbamoyl which may have a hydroxy, 4- to 10-membered heterocyclic group containing 1 to 3 heteroatom(s) selected from nitrogen, sulfur and oxygen atoms in addition to carbon atoms which may have oxo, (4- to 10-membered heterocyclic ring containing 1 to 3 heteroatom(s) selected from nitrogen, sulfur and oxygen atoms in addition to carbon atoms)-carbamoyl, carbamoyl-C$_{1-6}$ alkyl-carbamoyl], (3) a C$_{1-6}$ alkoxy group, (4) a C$_{6-14}$ aryl group, (5) a C$_{7-16}$ aralkyl group [this C$_{7-16}$ aralkyl group may have a substituent selected from carboxy, C$_{1-6}$ alkoxy-carbonyl, carbamoyl, C$_{1-6}$ alkyl-carbamoyl which may have a hydroxy, (4- to 10-membered heterocyclic ring containing 1 to 3 heteroatom(s) selected from nitrogen, sulfur and oxygen atoms in addition to carbon atoms)-carbamoyl], (6) a 4- to 10-membered heterocyclic group containing 1 to 3 heteroatom(s) selected from nitrogen, sulfur and oxygen atoms in addition to carbon atoms [this 4- to 10-membered heterocyclic group may have a substituent selected from a C$_{1-6}$ alkyl, C$_{1-6}$ alkoxy-carbonyl, carbamoyl, oxo, 4- to 10-membered heterocyclic group containing 1 to 3 heteroatom(s) selected from nitrogen, sulfur and oxygen atoms in addition to carbon atoms], (7) an oxo group, (8) an oxide group;

(iii) a C$_{3-6}$ cycloalkyl group; or, (iv) a group represented by Formula: —L'—R$^{1a}$ (L' is methylene, carbonyl or —NH—, R$^{1a}$ is (1) a hydrogen atom, (2) a C$_{6-14}$ aryl group which may have 1 to 5 substituent(s) selected from a C$_{1-6}$ alkyl and C$_{1-6}$ alkoxy, (3) a hydroxy group which may be substituted by a C$_{1-6}$ alkyl group, (4) a C$_{1-6}$ alkyl-amino group which may be substituted by a 4- to 10-membered heterocyclic ring containing 1 to 3 heteroatom(s) selected from nitrogen, oxygen and sulfur atoms in addition to carbon atoms, (6) a C$_{6-14}$ aryl-amino group or (7) a (4- to 10-membered heterocyclic ring containing 1 to3 heteroatom(s) selected from nitrogen, oxygen and sulfur atoms in addition to carbon atoms)-amino group), each of R$^2$ and R$^3$ is (1) a hydrogen atom, (2) an optionally halogenated C$_{1-6}$ alkyl group or (3) a C$_{1-6}$ alkoxy-carbonyl group, R$^2$ and R$^3$ may be taken together with the adjacent carbon atom to form a C$_{3-8}$ cycloalkane, R$^4$ is (i) a hydrogen atom, (ii) a C$_{1-6}$ alkyl group [this C$_{1-6}$ alkyl group may have a substituent selected from (1) a halogen atom, (2) a cyano group, (3) a C$_{1-6}$ alkoxy group, (4) a hydroxy group, (5) an amino group, (6) a mono-C$_{1-6}$ alkylamino group, (7) a di-C$_{1-6}$ alkylamino group, (8) a tri-C$_{1-6}$ alkylammonium group, (9) a 4- to 10-membered heterocyclic group containing 1 to 3 heteroatom(s) selected from nitrogen, sulfur and oxygen atoms in addition to carbon atoms which may have an oxo, (10) a C$_{6-14}$ arylthio, (11) an ureido, (12) a carboxy, (13) a carbamoyl, (14) a C$_{1-6}$ alkoxy-carbonyl, (15) a mono-C$_{1-6}$ alkyl-carbamoyl, (16) a formylamino, (17) a C$_{1-6}$ alkyl-carboxamido] or (iii) a C$_{2-6}$ alkenyl group;

X is a bond, oxygen atom, sulfur atom, —NH— or —N(methyl)-,

R$^5$ is, when X is a bond, then (i) a hydrogen atom, (ii) a C$_{1-6}$ alkyl group or (iii) a halogen atom, when X is an oxygen atom, then (i) a hydrogen atom, (ii) a $C_{1-6}$ alkyl group [this $C_{1-6}$ alkyl group may have a substituent selected from (1) a halogen atom, (2) a hydroxy group, (3) an amino group, (4) a carboxy, (5) a carbamoyl, (6) a $C_{1-6}$ alkoxy-carbonyl, (7) a mono-$C_{1-6}$ alkyl-carbamoyl, (8) a di-$C_{1-6}$ alkyl-carbamoyl, (9) a 4- to 10-membered heterocyclic group containing 1 to 3 heteroatom(s) selected from nitrogen, sulfur and oxygen atoms in addition to carbon atoms which may have an oxo], (iii) a $C_{2-6}$ alkenyl group [this $C_{2-6}$ alkenyl group may have a $C_{6-14}$ aryl], (iv) a $C_{2-6}$ alkynyl group, (v) a $C_{3-6}$ cycloalkyl group, (vi) a $C_{7-16}$ aralkyl group, (vii) a $C_{1-6}$ alkyl-carbonyl group, (viii) a $C_{6-14}$ aryl-carbonyl group, (ix) a $C_{1-6}$ alkoxy-carbonyl group, (x) a mono- or di-$C_{1-6}$ alkyl-thiocarbamoyl group, (xi) an optionally halogenated $C_{1-6}$ alkyl-sulfonyl group or (xii) a 4- to 10-membered heterocyclic group containing 1 to 4 heteroatom(s) selected from nitrogen, sulfur and oxygen atoms in addition to carbon atoms [this heterocyclic group may have a $C_{6-14}$ aryl], when X is a sulfur, then (i) a $C_{1-6}$ alkyl group or (ii) a mono- or di-$C_{1-6}$ alkyl-carbamoyl group, when X is —NH— or —N(methyl)-, then (i) a hydrogen atom, (ii) a $C_{1-6}$ alkyl group [this $C_{1-6}$ alkyl group may have a $C_{1-6}$ alkoxy-carbonyl], (iii) formyl, (iv) a $C_{1-6}$ alkyl-carbonyl group, (v) a $C_{1-6}$ alkoxy-carbonyl group, (vi) a carbamoyl group, (vii) a mono- or di-$C_{1-6}$ alkyl-carbamoyl group or (viii) a $C_{1-6}$ alkyl-sulfonyl group, each of $R^6$ and $R^7$ is a hydrogen atom or $C_{1-6}$ alkyl group, $R^6$ and $R^7$ may be taken together with the adjacent carbon atom to form a $C_{3-8}$ cycloalkane, each of $R^8$ and $R^9$ is a hydrogen atom or a $C_{1-6}$ alkyl group, Y is a methylene group which may have a hydroxy group or carbonyl group, n is 0 or 1.

13. The compound according to claim 1, wherein each of $R^2$ and $R^3$ is a $C_{1-6}$ alkyl group.

14. The compound according to claim 1, wherein $R^4$ is a hydrogen atom.

15. The compound according to claim 1, wherein each of $R^6$ and $R^7$ is a $C_{1-6}$ alkyl group.

16. The compound according to claim 1, wherein each of $R^8$ and $R^9$ is a hydrogen atom.

17. The compound according to claim 1, wherein n is 0.

18. (i) 2-(methylsulfinyl)—N—[3-(3,4,8,9-tetrahydro-6-methoxy-3,3,8,8-tetramethylfuro[2,3-h]isoquinolin-1-yl)phenyl]acetamide, (ii) N-(methylsulfonyl)-N-[3-(3,4,8,9-tetrahydro-6-methoxy-3,3,8,8-tetramethylfuro[2,3-h]isoquinolin-1-yl)phenyl]methanesulfonamide, (iii) N-[2-(4-pyridinyl)ethyl]-3-(3,4,8,9-tetrahydro-6-methoxy-3,3,8,8-tetramethylfuro [2,3-h]isoquinolin-1-yl)benzamide, (iv) N-(2-amino-2-oxoethyl)-3-(3,4,8,9-tetrahydro-6-methoxy-3,3,8,8-tetramethylfuro[2,3-h]isoquinolin-1-yl)benzamide, (v)N-methyl-3-(3,4,8,9-tetrahydro-6-methoxy-3,3,8,8-tetramethylfuro[2,3-h]isoquinolin-1-yl)benzamide, (vi) N-ethyl-3-(3,4,8,9-tetrahydro-6-methoxy-3,3,8,8-tetramethylfuro[2,3-h]isoquinolin-1-yl)benzamide, (vii) N-[3'-(3,4,8,9-tetrahydro-6-methoxy-3,3,8,8-tetramethylfuro[2,3-h]isoquinolin-1-yl)[1,1'-biphenyl]-3-yl]acetamide, (viii) N-(2-amino-1,1-dimethyl-2-oxoethyl)-3-(3,4,8,9-tetrahydro-6-methoxy-3,3,8,8-tetramethylfuro[2,3-h]isoquinolin-1-yl)benzamide, (ix)3-(6-ethoxy-3,4,8,9-tetrahydro-3,3,8,8-tetramethylfuro[2,3-h]isoquinolin-1-yl)-N-methylbenzamide, (x) N-(2-amino-2-oxoethyl)-3-(6-ethoxy-3,4,8,9-tetrahydro-3,3,8,8-tetramethylfuro[2,3-h]isoquinolin-1-yl)benzamide, (xi) N-(2-amino-1,1-dimethyl-2-oxoethyl)-3-(6-ethoxy-3,4,8,9-tetrahydro-3,3,8,8-tetramethylfuro[2,3-h]isoquinolin-1-yl)benzamide, (xii)N-(3-(6-ethoxy-3 4,8,9-tetrahydro-3,3,8,8-tetramethylfuro[2,3-h]isoquinolin-1-yl)phenyl]methanesulfonamide, (xiii) N-(hydroxymethyl)-3-(3,4,8,9-tetrahydro-6-methoxy-3,3,8,8-tetramethylfuro[2,3-h]isoquinolin-1-yl)benzamide or its salts.

19. A prodrug of a compound according to claim 1.

20. A process for producing a compound according to claim 1, comprising: reacting a compound represented by Formula:

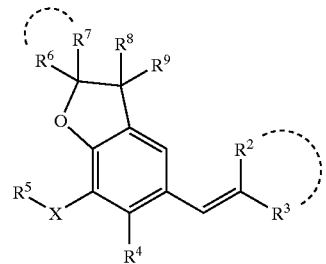

wherein each symbol is defined as described in claim 2 or a salt thereof with a compound represented by Formula: $R^1$—CN or Formula: $R^1$—$CONH_2$ wherein $R^1$ is defined as described in claim 2 or a salt thereof, or, reacting a compound represented by Formula:

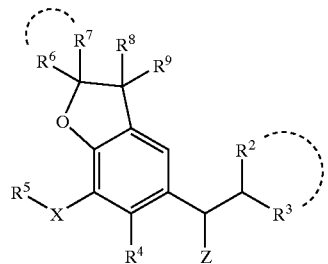

wherein Z is an optionally substituted hydroxy group or halogen atom, and other symbols are defined as described in claim 2 or a salt thereof with a compound represented by Formula: $R^1$—CN wherein $R^1$ is defined as described in claim 2 or a salt thereof.

21. A pharmaceutical composition comprising a compound according to claim 1 or a salt or prodrug thereof and a pharmaceutically acceptable carrier, excipient or diluent.

22. A pharmaceutical composition comprising (1) a compound according to claim 1 or a salt or prodrug thereof in combination with (2) a drug selected from antiasthma agents, antiallergic agents, anticholinergic agents, antiinflammatory agents, antibacterial agents, antifungal agents and antidiabetic agents.

23. A method for inhibiting a phosphodiesterase IV comprising administering an effective amount of the compound according to claim 1 or a salt or prodrug thereof to a mammal.

24. A method for treating inflammatory diseases comprising administering an effective amount of the compound according to claim 1 or a salt or prodrug thereof to a mammal.

25. A method for treating asthma, chronic obstructive pulmonary disease (COPD), rheumatoid arthritis, autoimmune disease or diabetes comprising administering an effective amount of the compound according to claim 1 or a salt or prodrug thereof to a mammal.

26. A method for treating inflammatory diseases comprising administering (1) an effective amount of the compound according to claim 1 or a salt or prodrug thereof in combination with (2) an effective amount of a drug selected from antiasthma agents, antiallergic agents, anticholinergic agents, antiinflammatory agents, antibacterial agents, antifungal agents and antidiabetic agents to a mammal.

27. A method for treating asthma, chronic obstructive pulmonary disease (COPD), rheumatoid arthritis, autoinimune disease or diabetes comprising administering (1) an effective amount of the compound according to claim 1 or a salt or prodrug thereof in combination with (2) an effective amount of a drug selected from antiasthma agents, antiallergic agents, anticholinergic agents, antiinflammatory agents, antibacterial agents, antifungal agents and antidiabetic agents to a mammal.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
ccacgatagc tgctcaaaca agag                                              24

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
atagaaaccc caagtccaat aaac                                              24

<210> SEQ ID NO 3
<211> LENGTH: 2435
<212> TYPE: DNA
<213> ORGANISM: Human
<220> FEATURE:
<221> NAME/KEY: CDS
<222> LOCATION: (74)..(2092)
<220> FEATURE:
<221> NAME/KEY: mat_peptide
<222> LOCATION: (74)..()

<400> SEQUENCE: 3
gaattcatct gtaaaaatca ctacatgtaa cgtaggagac aagaaaaata ttaatgacag        60
aagatctgcg aac atg atg cac gtg aat aat ttt ccc ttt aga agg cat         109
            Met Met His Val Asn Asn Phe Pro Phe Arg Arg His
              1               5                  10 tcc tgg ata tgt ttt gat gtg gac aat ggc aca tct gcg gga cgg agt        157
Ser Trp Ile Cys Phe Asp Val Asp Asn Gly Thr Ser Ala Gly Arg Ser
         15                  20                  25 ccc ttg gat ccc atg acc agc cca gga tcc ggg cta att ctc caa gca        205
Pro Leu Asp Pro Met Thr Ser Pro Gly Ser Gly Leu Ile Leu Gln Ala
     30                  35                  40
```

-continued

| | |
|---|---|
| aat ttt gtc cac agt caa cga cgg gag tcc ttc ctg tat cga tcc gac<br>Asn Phe Val His Ser Gln Arg Arg Glu Ser Phe Leu Tyr Arg Ser Asp<br>45                    50                      55                  60 | 253 |
| agc gat tat gac ctc tct cca aag tct atg tcc cgg aac tcc tcc att<br>Ser Asp Tyr Asp Leu Ser Pro Lys Ser Met Ser Arg Asn Ser Ser Ile<br>                    65                      70                      75 | 301 |
| gcc agt gat ata cac gga gat gac ttg att gtg act cca ttt gct cag<br>Ala Ser Asp Ile His Gly Asp Asp Leu Ile Val Thr Pro Phe Ala Gln<br>                      80                      85                      90 | 349 |
| gtc ttg gcc agt ctg cga act gta cga aac aac ttt gct gca tta act<br>Val Leu Ala Ser Leu Arg Thr Val Arg Asn Asn Phe Ala Ala Leu Thr<br>      95                      100                      105 | 397 |
| aat ttg caa gat cga gca cct agc aaa aga tca ccc atg tgc aac caa<br>Asn Leu Gln Asp Arg Ala Pro Ser Lys Arg Ser Pro Met Cys Asn Gln<br>110                    115                      120 | 445 |
| cca tcc atc aac aaa gcc acc ata aca gag gag gcc tac cag aaa ctg<br>Pro Ser Ile Asn Lys Ala Thr Ile Thr Glu Glu Ala Tyr Gln Lys Leu<br>125                    130                      135                      140 | 493 |
| gcc agc gag acc ctg gag gag ctg gac tgg tgt ctg gac cag cta gag<br>Ala Ser Glu Thr Leu Glu Glu Leu Asp Trp Cys Leu Asp Gln Leu Glu<br>                    145                      150                      155 | 541 |
| acc cta cag acc agg cac tcc gtc agt gag atg gcc tcc aac aag ttt<br>Thr Leu Gln Thr Arg His Ser Val Ser Glu Met Ala Ser Asn Lys Phe<br>                      160                      165                      170 | 589 |
| aaa agg atg ctt aat cgg gag ctc acc cat ctc tct gaa atg agt cgg<br>Lys Arg Met Leu Asn Arg Glu Leu Thr His Leu Ser Glu Met Ser Arg<br>175                    180                      185 | 637 |
| tct gga aat caa gtg tca gag ttt ata tca aac aca ttc tta gat aag<br>Ser Gly Asn Gln Val Ser Glu Phe Ile Ser Asn Thr Phe Leu Asp Lys<br>                    190                      195                      200 | 685 |
| caa cat gaa gtg gaa att cct tct cca act cag aag gaa aag gag aaa<br>Gln His Glu Val Glu Ile Pro Ser Pro Thr Gln Lys Glu Lys Glu Lys<br>205                    210                      215                      220 | 733 |
| aag aaa aga cca atg tct cag atc agt gga gtc aag aaa ttg atg cac<br>Lys Lys Arg Pro Met Ser Gln Ile Ser Gly Val Lys Lys Leu Met His<br>                    225                      230                      235 | 781 |
| agc tct agt ctg act aat tca agt atc cca agg ttt gga gtt aaa act<br>Ser Ser Ser Leu Thr Asn Ser Ser Ile Pro Arg Phe Gly Val Lys Thr<br>                    240                      245                      250 | 829 |
| gaa caa gaa gat gtc ctt gcc aag gaa cta gaa gat gtg aac aaa tgg<br>Glu Gln Glu Asp Val Leu Ala Lys Glu Leu Glu Asp Val Asn Lys Trp<br>                    255                      260                      265 | 877 |
| ggt ctt cat gtt ttc aga ata gca gag ttg tct ggt aac cgg ccc ttg<br>Gly Leu His Val Phe Arg Ile Ala Glu Leu Ser Gly Asn Arg Pro Leu<br>270                    275                      280 | 925 |
| act gtt atc atg cac acc att ttt cag gaa cgg gat tta tta aaa aca<br>Thr Val Ile Met His Thr Ile Phe Gln Glu Arg Asp Leu Leu Lys Thr<br>285                    290                      295                      300 | 973 |
| ttt aaa att cca gta gat act tta att aca tat ctt atg act ctc gaa<br>Phe Lys Ile Pro Val Asp Thr Leu Ile Thr Tyr Leu Met Thr Leu Glu<br>                    305                      310                      315 | 1021 |
| gac cat tac cat gct gat gtg gcc tat cac aac aat atc cat gct gca<br>Asp His Tyr His Ala Asp Val Ala Tyr His Asn Asn Ile His Ala Ala<br>                    320                      325                      330 | 1069 |
| gat gtt gtc cag tct act cat gtg cta tta tct aca cct gct ttg gag<br>Asp Val Val Gln Ser Thr His Val Leu Leu Ser Thr Pro Ala Leu Glu<br>335                    340                      345 | 1117 |
| gct gtg ttt aca gat ttg gag att ctt gca gca att ttt gcc agt gca<br>Ala Val Phe Thr Asp Leu Glu Ile Leu Ala Ala Ile Phe Ala Ser Ala<br>350                    355                      360 | 1165 |

```
ata cat gat gta gat cat cct ggt gtg tcc aat caa ttt ctg atc aat    1213
Ile His Asp Val Asp His Pro Gly Val Ser Asn Gln Phe Leu Ile Asn
365                 370                 375                 380 aca aac tct gaa ctt gcc ttg atg tac aat gat tcc tca gtc tta gag    1261
Thr Asn Ser Glu Leu Ala Leu Met Tyr Asn Asp Ser Ser Val Leu Glu
                385                 390                 395 aac cat cat ttg gct gtg ggc ttt aaa ttg ctt cag gaa gaa aac tgt    1309
Asn His His Leu Ala Val Gly Phe Lys Leu Leu Gln Glu Glu Asn Cys
400                 405                 410 gac att ttc cag aat ttg acc aaa aaa caa aga caa tct tta agg aaa    1357
Asp Ile Phe Gln Asn Leu Thr Lys Lys Gln Arg Gln Ser Leu Arg Lys
        415                 420                 425 atg gtc att gac atc gta ctt gca aca gat atg tca aaa cac atg aat    1405
Met Val Ile Asp Ile Val Leu Ala Thr Asp Met Ser Lys His Met Asn
430                 435                 440 cta ctg gct gat ttg aag act atg gtt gaa act aag aaa gtg aca agc    1453
Leu Leu Ala Asp Leu Lys Thr Met Val Glu Thr Lys Lys Val Thr Ser
445                 450                 455                 460 tct gga gtt ctt ctt ctt gat aat tat tcc gat agg att cag gtt ctt    1501
Ser Gly Val Leu Leu Leu Asp Asn Tyr Ser Asp Arg Ile Gln Val Leu
                465                 470                 475 cag aat atg gtg cac tgt gca gat ctg agc aac cca aca aag cct ctc    1549
Gln Asn Met Val His Cys Ala Asp Leu Ser Asn Pro Thr Lys Pro Leu
            480                 485                 490 cag ctg tac cgc cag tgg acg gac cgg ata atg gag gag ttc ttc cgc    1597
Gln Leu Tyr Arg Gln Trp Thr Asp Arg Ile Met Glu Glu Phe Phe Arg
        495                 500                 505 caa gga gac cga gag agg gaa cgt ggc atg gag ata agc ccc atg tgt    1645
Gln Gly Asp Arg Glu Arg Glu Arg Gly Met Glu Ile Ser Pro Met Cys
510                 515                 520 gac aag cac aat gct tcc gtg gaa aaa tca cag gtg ggc ttc ata gac    1693
Asp Lys His Asn Ala Ser Val Glu Lys Ser Gln Val Gly Phe Ile Asp
525                 530                 535                 540 tat att gtt cat ccc ctc tgg gag aca tgg gca gac ctc gtc cac cct    1741
Tyr Ile Val His Pro Leu Trp Glu Thr Trp Ala Asp Leu Val His Pro
                545                 550                 555 gac gcc cag gat att ttg gac act ttg gag gac aat cgt gaa tgg tac    1789
Asp Ala Gln Asp Ile Leu Asp Thr Leu Glu Asp Asn Arg Glu Trp Tyr
            560                 565                 570 cag agc aca atc cct cag agc ccc tct cct gca cct gat gac cca gag    1837
Gln Ser Thr Ile Pro Gln Ser Pro Ser Pro Ala Pro Asp Asp Pro Glu
        575                 580                 585 gag ggc cgg cag ggt caa act gag aaa ttc cag ttt gaa cta act tta    1885
Glu Gly Arg Gln Gly Gln Thr Glu Lys Phe Gln Phe Glu Leu Thr Leu
590                 595                 600 gag gaa gat ggt gag tca gac acg gaa aag gac agt ggc agt caa gtg    1933
Glu Glu Asp Gly Glu Ser Asp Thr Glu Lys Asp Ser Gly Ser Gln Val
605                 610                 615                 620 gaa gaa gac act agc tgc agt gac tcc aag act ctt tgt act caa gac    1981
Glu Glu Asp Thr Ser Cys Ser Asp Ser Lys Thr Leu Cys Thr Gln Asp
                625                 630                 635 tca gag tct act gaa att ccc ctt gat gaa cag gtt gaa gag gag gca    2029
Ser Glu Ser Thr Glu Ile Pro Leu Asp Glu Gln Val Glu Glu Glu Ala
            640                 645                 650 gta ggg gaa gaa gag gaa agc cag cct gaa gcc tgt gtc ata gat gat    2077
Val Gly Glu Glu Glu Glu Ser Gln Pro Glu Ala Cys Val Ile Asp Asp
        655                 660                 665 cgt tct cct gac acg taacagtgca aaactttca tgcctttttt tttttaagt     2132
Arg Ser Pro Asp Thr
```

-continued

```
                670
agaaaaattg tttccaaagt gcatgtcaca tgccacaacc acggtcacac ctcactgtca    2192
tctgccagga cgtttgttga acaaaactga ccttgactac tcagtccagc gctcaggaat    2252
atcgtaacca gttttttcac ctccatgttc atccgagcaa ggtggacatc ttcacgaaca    2312
gcgtttttaa caagatttca gcttggtaga gctgacaaag cagataaaat ctactccaaa    2372
ttattttcaa gagagtgtga ctcatcaggc agcccaaaag tttattggac ttggggtttc    2432
tat                                                                  2435
```

<210> SEQ ID NO 4
<211> LENGTH: 673
<212> TYPE: PRT
<213> ORGANISM: human

<400> SEQUENCE: 4

```
Met Met His Val Asn Asn Phe Pro Phe Arg Arg His Ser Trp Ile Cys
 1               5                  10                  15

Phe Asp Val Asp Asn Gly Thr Ser Ala Gly Arg Ser Pro Leu Asp Pro
                20                  25                  30

Met Thr Ser Pro Gly Ser Gly Leu Ile Leu Gln Ala Asn Phe Val His
            35                  40                  45

Ser Gln Arg Arg Glu Ser Phe Leu Tyr Arg Ser Asp Ser Asp Tyr Asp
        50                  55                  60

Leu Ser Pro Lys Ser Met Ser Arg Asn Ser Ser Ile Ala Ser Asp Ile
65                  70                  75                  80

His Gly Asp Asp Leu Ile Val Thr Pro Phe Ala Gln Val Leu Ala Ser
                85                  90                  95

Leu Arg Thr Val Arg Asn Asn Phe Ala Ala Leu Thr Asn Leu Gln Asp
            100                 105                 110

Arg Ala Pro Ser Lys Arg Ser Pro Met Cys Asn Gln Pro Ser Ile Asn
        115                 120                 125

Lys Ala Thr Ile Thr Glu Glu Ala Tyr Gln Lys Leu Ala Ser Glu Thr
    130                 135                 140

Leu Glu Glu Leu Asp Trp Cys Leu Asp Gln Leu Glu Thr Leu Gln Thr
145                 150                 155                 160

Arg His Ser Val Ser Glu Met Ala Ser Asn Lys Phe Lys Arg Met Leu
                165                 170                 175

Asn Arg Glu Leu Thr His Leu Ser Glu Met Ser Arg Ser Gly Asn Gln
            180                 185                 190

Val Ser Glu Phe Ile Ser Asn Thr Phe Leu Asp Lys Gln His Glu Val
        195                 200                 205

Glu Ile Pro Ser Pro Thr Gln Lys Glu Lys Glu Lys Lys Lys Arg Pro
    210                 215                 220

Met Ser Gln Ile Ser Gly Val Lys Lys Leu Met His Ser Ser Ser Leu
225                 230                 235                 240

Thr Asn Ser Ser Ile Pro Arg Phe Gly Val Lys Thr Glu Gln Glu Asp
                245                 250                 255

Val Leu Ala Lys Glu Leu Glu Asp Val Asn Lys Trp Gly Leu His Val
            260                 265                 270

Phe Arg Ile Ala Glu Leu Ser Gly Asn Arg Pro Leu Thr Val Ile Met
        275                 280                 285

His Thr Ile Phe Gln Glu Arg Asp Leu Leu Lys Thr Phe Lys Ile Pro
    290                 295                 300
```

-continued

```
Val Asp Thr Leu Ile Thr Tyr Leu Met Thr Leu Glu Asp His Tyr His
305             310             315             320

Ala Asp Val Ala Tyr His Asn Asn Ile His Ala Ala Asp Val Val Gln
            325             330             335

Ser Thr His Val Leu Leu Ser Thr Pro Ala Leu Glu Ala Val Phe Thr
            340             345             350

Asp Leu Glu Ile Leu Ala Ala Ile Phe Ala Ser Ala Ile His Asp Val
            355             360             365

Asp His Pro Gly Val Ser Asn Gln Phe Leu Ile Asn Thr Asn Ser Glu
    370             375             380

Leu Ala Leu Met Tyr Asn Asp Ser Ser Val Leu Glu Asn His His Leu
385             390             395             400

Ala Val Gly Phe Lys Leu Leu Gln Glu Glu Asn Cys Asp Ile Phe Gln
                405             410             415

Asn Leu Thr Lys Lys Gln Arg Gln Ser Leu Arg Lys Met Val Ile Asp
                420             425             430

Ile Val Leu Ala Thr Asp Met Ser Lys His Met Asn Leu Leu Ala Asp
            435             440             445

Leu Lys Thr Met Val Glu Thr Lys Lys Val Thr Ser Ser Gly Val Leu
    450             455             460

Leu Leu Asp Asn Tyr Ser Asp Arg Ile Gln Val Leu Gln Asn Met Val
465             470             475             480

His Cys Ala Asp Leu Ser Asn Pro Thr Lys Pro Leu Gln Leu Tyr Arg
            485             490             495

Gln Trp Thr Asp Arg Ile Met Glu Glu Phe Phe Arg Gln Gly Asp Arg
            500             505             510

Glu Arg Glu Arg Gly Met Glu Ile Ser Pro Met Cys Asp Lys His Asn
    515             520             525

Ala Ser Val Glu Lys Ser Gln Val Gly Phe Ile Asp Tyr Ile Val His
    530             535             540

Pro Leu Trp Glu Thr Trp Ala Asp Leu Val His Pro Asp Ala Gln Asp
545             550             555             560

Ile Leu Asp Thr Leu Glu Asp Asn Arg Glu Trp Tyr Gln Ser Thr Ile
            565             570             575

Pro Gln Ser Pro Ser Pro Ala Pro Asp Asp Pro Glu Glu Gly Arg Gln
            580             585             590

Gly Gln Thr Glu Lys Phe Gln Phe Glu Leu Thr Leu Glu Glu Asp Gly
    595             600             605

Glu Ser Asp Thr Glu Lys Asp Ser Gly Ser Gln Val Glu Glu Asp Thr
    610             615             620

Ser Cys Ser Asp Ser Lys Thr Leu Cys Thr Gln Asp Ser Glu Ser Thr
625             630             635             640

Glu Ile Pro Leu Asp Glu Gln Val Glu Glu Ala Val Gly Glu Glu
                645             650             655

Glu Glu Ser Gln Pro Glu Ala Cys Val Ile Asp Asp Arg Ser Pro Asp
            660             665             670

Thr
```